US012453706B2

(12) United States Patent
Klatte et al.

(10) Patent No.: US 12,453,706 B2
(45) **Date of Patent: *Oct. 28, 2025**

(54) BISPECIFIC STEALTH LIPID NANOPARTICLE COMPOSITIONS FOR CELL TARGETING

(71) Applicant: Generation Bio Co., Cambridge, MA (US)

(72) Inventors: Debra Klatte, Cambridge, MA (US); Lalita Oonthonpan, Cambridge, MA (US); Viktoriya Syrovatkina, Cambridge, MA (US); Anthony Joseph Perniciaro, Cambridge, MA (US); Salma Merchant, Cambridge, MA (US); Brandon Michael Johnston, Cambridge, MA (US)

(73) Assignee: Generation Bio Co., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 19/061,632

(22) Filed: Feb. 24, 2025

(65) Prior Publication Data

US 2025/0186358 A1 Jun. 12, 2025

Related U.S. Application Data

(63) Continuation of application No. PCT/US2024/052260, filed on Oct. 21, 2024, which (Continued)

(51) Int. Cl.
*A61K 9/00* (2006.01)
*A61K 9/51* (2006.01)
(Continued)

(52) U.S. Cl.
CPC .......... *A61K 9/5123* (2013.01); *A61K 9/5146* (2013.01); *A61K 47/6849* (2017.08);
(Continued)

(58) Field of Classification Search
CPC .................................................... A61K 9/5123
See application file for complete search history.

(56) References Cited

U.S. PATENT DOCUMENTS

2022/0175968 A1 6/2022 Stanton et al.
2022/0265857 A1 8/2022 Besin et al.

FOREIGN PATENT DOCUMENTS

CN 113908292 A 1/2022
WO 2022/216787 A2 10/2022
(Continued)

OTHER PUBLICATIONS

International Search Report and Written Opinion for Application No. PCT/US2024/52260, mailed Jan. 16, 2025, 20 pages.
(Continued)

*Primary Examiner* — Paul W Dickinson
(74) *Attorney, Agent, or Firm* — McCarter & English, LLP; Marcie B. Clarke

(57) ABSTRACT

The present disclosure provides bispecific stealth lipid nanoparticle (LNP) compositions engineered to target specific tissues or cell-types, e.g., hematopoietic stem cells, to modify the cells with therapeutic nucleic acid encapsulated in the LNP. The present disclosure also provides compositions and methods of making the LNPs and treatment using the same.

30 Claims, 66 Drawing Sheets

Specification includes a Sequence Listing.

Related U.S. Application Data is a continuation-in-part of application No. PCT/US2024/032646, filed on Jun. 5, 2024, and a continuation-in-part of application No. PCT/US2023/082078, filed on Dec. 1, 2023.

(60) Provisional application No. 63/705,914, filed on Oct. 10, 2024, provisional application No. 63/645,650, filed on May 10, 2024, provisional application No. 63/642,445, filed on May 3, 2024, provisional application No. 63/562,079, filed on Mar. 6, 2024, provisional application No. 63/545,474, filed on Oct. 24, 2023.

(51) Int. Cl.

| | |
|---|---|
| ***A61K 47/68*** | (2017.01) |
| ***A61K 47/69*** | (2017.01) |
| ***C07K 16/28*** | (2006.01) |
| ***C12N 15/88*** | (2006.01) |

(52) U.S. Cl.

CPC ...... *A61K 47/6929* (2017.08); *C07K 16/2809* (2013.01); *C07K 16/2896* (2013.01); *C12N 15/88* (2013.01); *C07K 2317/569* (2013.01); *C07K 2317/622* (2013.01)

(56) References Cited

FOREIGN PATENT DOCUMENTS

| | | | |
|---|---|---|---|
| WO | 2023/287861 | A2 | 1/2023 |
| WO | 2023/148277 | A1 | 8/2023 |
| WO | 2023/178422 | A1 | 9/2023 |
| WO | 2024/119074 | A1 | 6/2024 |

OTHER PUBLICATIONS

U.S. Appl. No. 19/058,352, filed Feb. 20, 2025, Pending.
U.S. Appl. No. 19/061,085, filed Feb. 24, 2025, Pending.
U.S. Appl. No. 19/063,950, filed Feb. 26, 2025, Pending.
International Search Report and Written Opinion for Application No. PCT/US2023/082078, dated Apr. 19, 2024, 15 pages.
International Search Report and Written Opinion for Application No. PCT/US2024/052277, dated Feb. 4, 2025, 20 pages.
International Search Report and Written Opinion for Application No. PCT/US2024/032646, dated Jan. 17, 2025, 26 pages.

100X INCREASE IN HEPATIC EXPRESSION WITH ADDITION OF HEPATOCYTE TARGETING GalNAc $(GalNAc)_3$
hASGPR (nM): 30.7
CD301 (nM): 7.6

SEQUENCE LISTING

Sequence total quantity: 33
SEQ ID NO: 1 moltype = AA length = 192
FEATURE Location/Qualifiers
source 1..192

```
                        mol_type = protein
                        organism = synthetic construct
SEQUENCE: 1
MKVEQAVETE PEPELRQQTE WQSGQRWELA LGRFWDYLRW VQTLSEQVQE ELLSSQVTQE  60
LRALMDETMK ELKAYKSELE EQLTPVAEET RARLSKELQA AQARLGADME DVCGRLVQYR  120
GEVQAMLGQS TEELRVRLAS HLRKLRKRLL RDADDLQKRL AVYQAGAREG AERGLSAIRE  180
RLGPLVEQGR VR                                                     192

SEQ ID NO: 2            moltype = AA  length = 198
FEATURE                 Location/Qualifiers
source                  1..198
                        mol_type = protein
                        organism = synthetic construct
SEQUENCE: 2
MKVEQAVETE PEPELRQQTE WQSGQRWELA LGRFWDYLRW VQTLSEQVQE ELLSSQVTQE  60
LRALMDETMK ELKAYKSELE EQLTPVAEET RARLSKELQA AQARLGADME DVCGRLVQYR  120
GEVQAMLGQS TEELRVRLAS HLRKLRKRLL RDADDLQKRL AVYQAGAREG AERGLSAIRE  180
RLGPLVEQGR VRHHHHHH                                               198

SEQ ID NO: 3            moltype = AA  length = 192
FEATURE                 Location/Qualifiers
source                  1..192
                        mol_type = protein
                        organism = synthetic construct
SEQUENCE: 3
MKVEQAVETE PEPELRQQTE WQSGQRWELA LGRFWDYLRW VQTLSEQVQE ELLSSQVTQE  60
LRALMDETMK ELKAYKSELE EQLTPVAEET RARLSKELQA AQARLGADME DVSGRLVQYR  120
GEVQAMLGQS TEELRVRLAS HLRKLRKRLL RDADDLQKRL AVYQAGAREG AERGLSAIRE  180
RLGPLVEQGR VR                                                     192

SEQ ID NO: 4            moltype = AA  length = 206
FEATURE                 Location/Qualifiers
source                  1..206
                        mol_type = protein
                        organism = synthetic construct
SEQUENCE: 4
MKVEQAVETE PEPELRQQTE WQSGQRWELA LGRFWDYLRW VQTLSEQVQE ELLSSQVTQE  60
LRALMDETMK ELKAYKSELE EQLTPVAEET RARLSKELQA AQARLGADME DVSGRLVQYR  120
GEVQAMLGQS TEELRVRLAS HLRKLRKRLL RDADDLQKRL AVYQAGAREG AERGLSAIRE  180
RLGPLVEQGR VRHHHHHHGG SSGSGC                                      206

SEQ ID NO: 5            moltype = AA  length = 4
FEATURE                 Location/Qualifiers
source                  1..4
                        mol_type = protein
                        organism = synthetic construct
SEQUENCE: 5
GGGS                                                              4

SEQ ID NO: 6            moltype = AA  length = 20
FEATURE                 Location/Qualifiers
source                  1..20
                        mol_type = protein
                        organism = synthetic construct
SEQUENCE: 6
GGGGSGGGGS GGGGSGGGGS                                             20

SEQ ID NO: 7            moltype = AA  length = 15
FEATURE                 Location/Qualifiers
source                  1..15
                        mol_type = protein
                        organism = synthetic construct
SEQUENCE: 7
GGGGSGGGGS GGGGS                                                  15

SEQ ID NO: 8            moltype = DNA  length = 16
FEATURE                 Location/Qualifiers
source                  1..16
                        mol_type = genomic DNA
                        organism = Adeno-associated virus
SEQUENCE: 8
gcgcgctcgc tcgctc                                                 16

SEQ ID NO: 9            moltype = DNA  length = 12
FEATURE                 Location/Qualifiers
source                  1..12
                        mol_type = other DNA
                        organism = synthetic construct
misc_difference         12
```

```
                        note = a, c, t, g, unknown or other
SEQUENCE: 9
ccaagctctt cn                                                12

SEQ ID NO: 10           moltype = AA  length = 10
FEATURE                 Location/Qualifiers
source                  1..10
                        mol_type = protein
                        organism = synthetic construct
SEQUENCE: 10
GGGGSGGGGS                                                   10

SEQ ID NO: 11           moltype = AA  length = 116
FEATURE                 Location/Qualifiers
source                  1..116
                        mol_type = protein
                        organism = synthetic construct
SEQUENCE: 11
QVQLKQSGAE LVRPGASVKL SCKASGYTFT DYYINWVKQR PGQGLEWIAR IYPGSGNTYY  60
NEKFKGKATL TAEKSSSTAY MQLSSLTSED SAVYFCARGV YYFDYWGQGT TLTVSS      116

SEQ ID NO: 12           moltype = AA  length = 108
FEATURE                 Location/Qualifiers
source                  1..108
                        mol_type = protein
                        organism = synthetic construct
SEQUENCE: 12
DIVMTQSQKF MSTSVGDRVS VTCKASQNVR TNVAWYQQKP GQSPKALIYS ASYRYSGVPD  60
RFTGSGSGTD FTLTISNVQS EDLADYFCQQ YNSYPRTFGG GTKLEIKR              108

SEQ ID NO: 13           moltype = AA  length = 281
FEATURE                 Location/Qualifiers
source                  1..281
                        mol_type = protein
                        organism = synthetic construct
SEQUENCE: 13
QVQLVQSGAE VKKPGSSVKV SCKASGGTFS SYAISWVRQA PGQGLEWMGG IIPMSGRTTY  60
AQKFQGRVTI TADESTSTAY MELSSLRSED TAVYYCARDY GPEAPDYGQS TSYFWYYAFD  120
PWGQGTLVTV SSGGGGSGGG GSGGGGSGGG GDIELTQPPS VSVSPGQTAS ITCSGDNIPS  180
YFVHWYQQKP GQAPVLVIYD DNDRPSGIPE RFSGSNSGNT ATLTISGTQA EDEADYYCSS  240
WDQDTVVFGG GTKLTVLGGG GSGGGGSDYK DDDDKGGGGS C                    281

SEQ ID NO: 14           moltype = AA  length = 132
FEATURE                 Location/Qualifiers
source                  1..132
                        mol_type = protein
                        organism = synthetic construct
SEQUENCE: 14
QVQLVQSGAE VKKPGSSVKV SCKASGGTFS SYAISWVRQA PGQGLEWMGG IIPMSGRTTY  60
AQKFQGRVTI TADESTSTAY MELSSLRSED TAVYYCARDY GPEAPDYGQS TSYFWYYAFD  120
PWGQGTLVTV SS                                                132

SEQ ID NO: 15           moltype = AA  length = 106
FEATURE                 Location/Qualifiers
source                  1..106
                        mol_type = protein
                        organism = synthetic construct
SEQUENCE: 15
DIELTQPPSV SVSPGQTASI TCSGDNIPSY FVHWYQQKPG QAPVLVIYDD NDRPSGIPER  60
FSGSNSGNTA TLTISGTQAE DEADYYCSSW DQDTVVFGGG TKLTVL                106

SEQ ID NO: 16           moltype = AA  length = 268
FEATURE                 Location/Qualifiers
source                  1..268
                        mol_type = protein
                        organism = synthetic construct
SEQUENCE: 16
DIQMTQSPSF LSASVGDRVT INCKASQNIN KYLDWYQQKH GEAPKLLIHY TNNLHTGIPS  60
RFSGSGSGTD YTLTISSLQP EDVATYFCLQ HSSRWTFGGG TKLELKGGGG SGGGGSGGGG  120
SGGGGEVQLV ESGGDLVQPG RSLKLSCIAS GFTFTNFWMT WIRQVSGKGL EWVASISSSG  180
GSIYYPDSVK DRFTISRDNA KNTLYLQMNS LRSEDTATYY CVKLHYYSGG GDAWGQGTSV  240
TVSSGGGGSG GGGSDYKDDD DKGGGGSC                                268

SEQ ID NO: 17           moltype = AA  length = 119
FEATURE                 Location/Qualifiers
source                  1..119
                        mol_type = protein
                        organism = synthetic construct
SEQUENCE: 17
```

```
EVQLVESGGD LVQPGRSLKL SCIASGFTFT NFWMTWIRQV SGKGLEWVAS ISSSGGSIYY  60
PDSVKDRFTI SRDNAKNTLY LQMNSLRSED TATYYCVKLH YYSGGGDAWG QGTSVTVSS   119

SEQ ID NO: 18          moltype = AA  length = 106
FEATURE                Location/Qualifiers
source                 1..106
                       mol_type = protein
                       organism = synthetic construct
SEQUENCE: 18
DIQMTQSPSF LSASVGDRVT INCKASQNIN KYLDWYQQKH GEAPKLLIHY TNNLHTGIPS  60
RFSGSGSGTD YTLTISSLQP EDVATYFCLQ HSSRWTFGGG TKLELK                106

SEQ ID NO: 19          moltype = AA  length = 268
FEATURE                Location/Qualifiers
source                 1..268
                       mol_type = protein
                       organism = synthetic construct
SEQUENCE: 19
EVQLVESGGD LVQPGRSLKL SCVASGFTFN NYWMTWIRQV PGKGLEWVAS ISSSGGSIYY  60
PDSVKDRFTI SRDNAKNTLF LQMNSLRSED TATYYCARLY YYSGGGDAWG QGTSVTVSSG  120
GGGSGGGGSG GGGSGGGGDI QMTQSPSFLS ASVGDRVTII CKASQDINKY LDWYQQKLGE  180
APKLLIYNTN NLHTGIPSRF SGSGSGTDYT LTISSLQPED VATYFCLQHI SRWTFGGGTK  240
LELKGGGGSG GGGSDYKDDD DKGGGGSC                                    268

SEQ ID NO: 20          moltype = AA  length = 119
FEATURE                Location/Qualifiers
source                 1..119
                       mol_type = protein
                       organism = synthetic construct
SEQUENCE: 20
EVQLVESGGD LVQPGRSLKL SCVASGFTFN NYWMTWIRQV PGKGLEWVAS ISSSGGSIYY  60
PDSVKDRFTI SRDNAKNTLF LQMNSLRSED TATYYCARLY YYSGGGDAWG QGTSVTVSS   119

SEQ ID NO: 21          moltype = AA  length = 106
FEATURE                Location/Qualifiers
source                 1..106
                       mol_type = protein
                       organism = synthetic construct
SEQUENCE: 21
DIQMTQSPSF LSASVGDRVT IICKASQDIN KYLDWYQQKL GEAPKLLIYN TNNLHTGIPS  60
RFSGSGSGTD YTLTISSLQP EDVATYFCLQ HISRWTFGGG TKLELK                106

SEQ ID NO: 22          moltype = AA  length = 278
FEATURE                Location/Qualifiers
source                 1..278
                       mol_type = protein
                       organism = synthetic construct
SEQUENCE: 22
EVKLLESGGG LVQPGGSLKL SCAASGFDFS RYWMSWVRQA PGKGLEWIGE INPTSSTINF  60
TPSLKDKVFI SRDNAKNTLY LQMSKVRSED TALYYCARGN YYRYGDAMDY WGQGTSVTVS  120
SAKGGGGSGG GGSGGGGSGG GGSDIALTQS PASLAVSLGQ RATISCRASK SVSTSGYSYL  180
HWYQQKPGQP PKLLIYLASN LESGVPARFS GSGSGTDFTL NIHPVEEEDA ATYYCQHSRE  240
LPFTFGSGTK LEIKGGGGSG GGGSDYKDDD DKGGGGSC                         278

SEQ ID NO: 23          moltype = AA  length = 123
FEATURE                Location/Qualifiers
source                 1..123
                       mol_type = protein
                       organism = synthetic construct
SEQUENCE: 23
EVKLLESGGG LVQPGGSLKL SCAASGFDFS RYWMSWVRQA PGKGLEWIGE INPTSSTINF  60
TPSLKDKVFI SRDNAKNTLY LQMSKVRSED TALYYCARGN YYRYGDAMDY WGQGTSVTVS  120
SAK                                                               123

SEQ ID NO: 24          moltype = AA  length = 111
FEATURE                Location/Qualifiers
source                 1..111
                       mol_type = protein
                       organism = synthetic construct
SEQUENCE: 24
DIALTQSPAS LAVSLGQRAT ISCRASKSVS TSGYSYLHWY QQKPGQPPKL LIYLASNLES  60
GVPARFSGSG SGTDFTLNIH PVEEEDAATY YCQHSRELPF TFGSGTKLEI K          111

SEQ ID NO: 25          moltype = AA  length = 267
FEATURE                Location/Qualifiers
source                 1..267
                       mol_type = protein
                       organism = synthetic construct
SEQUENCE: 25
```

-continued

```
QVQLKQSGAE LVRPGASVKL SCKASGYTFT DYYINWVKQR PGQGLEWIAR IYPGSGNTYY  60
NEKFKGKATL TAEKSSSTAY MQLSSLTSED SAVYFCARGV YYFDYWGQGT TLTVSSGGGG  120
SGGGGSGGGG SGGGGDIVMT QSQKFMSTSV GDRVSVTCKA SQNVRTNVAW YQQKPGQSPK  180
ALIYSASYRY SGVPDRFTGS GSGTDFTLTI SNVQSEDLAD YFCQQYNSYP RTFGGGTKLE  240
IKRGGGGSGG GGSDYKDDDD KGGGGSC                                      267

SEQ ID NO: 26          moltype = AA  length = 116
FEATURE                Location/Qualifiers
source                 1..116
                       mol_type = protein
                       organism = synthetic construct
SEQUENCE: 26
QVQLKQSGAE LVRPGASVKL SCKASGYTFT DYYINWVKQR PGQGLEWIAR IYPGSGNTYY  60
NEKFKGKATL TAEKSSSTAY MQLSSLTSED SAVYFCARGV YYFDYWGQGT TLTVSS      116

SEQ ID NO: 27          moltype = AA  length = 108
FEATURE                Location/Qualifiers
source                 1..108
                       mol_type = protein
                       organism = synthetic construct
SEQUENCE: 27
DIVMTQSQKF MSTSVGDRVS VTCKASQNVR TNVAWYQQKP GQSPKALIYS ASYRYSGVPD  60
RFTGSGSGTD FTLTISNVQS EDLADYFCQQ YNSYPRTFGG GTKLEIKR                108

SEQ ID NO: 28          moltype = AA  length = 274
FEATURE                Location/Qualifiers
source                 1..274
                       mol_type = protein
                       organism = synthetic construct
SEQUENCE: 28
DIQMTQSPSS LSASVGDRVT ITCRSSQGIR SDLGWYQQKP GKAPKLLIYD ASNLETGVPS  60
RFSGSGSGTD FTLTISSLQP EDFATYYCQQ ANGFPLTFGG GTKVEIKGGG GSGGGGSGGG  120
GSGGGGSEVQ LVQSGAEVKK PGESLKISCK GSGYSFTNYW IGWVRQMPGK GLEWMAIINP  180
RDSDTRYRPS FQGQVTISAD KSISTAYLQW SSLKASDTAM YYCARHGRGY EGYEGAFDIW  240
GQGTLVTVSS GGGGSGGGGS DYKDDDDKGG GGSC                              274

SEQ ID NO: 29          moltype = AA  length = 123
FEATURE                Location/Qualifiers
source                 1..123
                       mol_type = protein
                       organism = synthetic construct
SEQUENCE: 29
EVQLVQSGAE VKKPGESLKI SCKGSGYSFT NYWIGWVRQM PGKGLEWMAI INPRDSDTRY  60
RPSFQGQVTI SADKSISTAY LQWSSLKASD TAMYYCARHG RGYEGYEGAF DIWGQGTLVT  120
VSS                                                                123

SEQ ID NO: 30          moltype = AA  length = 107
FEATURE                Location/Qualifiers
source                 1..107
                       mol_type = protein
                       organism = synthetic construct
SEQUENCE: 30
DIQMTQSPSS LSASVGDRVT ITCRSSQGIR SDLGWYQQKP GKAPKLLIYD ASNLETGVPS  60
RFSGSGSGTD FTLTISSLQP EDFATYYCQQ ANGFPLTFGG GTKVEIK                107

SEQ ID NO: 31          moltype = AA  length = 274
FEATURE                Location/Qualifiers
source                 1..274
                       mol_type = protein
                       organism = synthetic construct
SEQUENCE: 31
DIQMTQSPSS LSASVGDRVT ITCRASQGIG SALAWYQQKP GKAPKLLIYD ASNLETGVPS  60
RFSGSGSGTD FTLTISSLQP EDFATYYCQQ LNGYPLTFGQ GTRLEIKGGG GSGGGGSGGG  120
GSGGGGSEVQ LVQSGAEVKK PGESLKISCK GSGYRFTTSW IGWVRQMPGK GLEWMGIIYP  180
GDSDTRYSPS FQGQVTISAD KSISTAYLQW SSLKASDTAM YYCARHGLGY NGYEGAFDIW  240
GQGTLVTVSS GGGGSGGGGS DYKDDDDKGG GGSC                              274

SEQ ID NO: 32          moltype = AA  length = 123
FEATURE                Location/Qualifiers
source                 1..123
                       mol_type = protein
                       organism = synthetic construct
SEQUENCE: 32
EVQLVQSGAE VKKPGESLKI SCKGSGYRFT TSWIGWVRQM PGKGLEWMGI IYPGDSDTRY  60
SPSFQGQVTI SADKSISTAY LQWSSLKASD TAMYYCARHG LGYNGYEGAF DIWGQGTLVT  120
VSS                                                                123

SEQ ID NO: 33          moltype = AA  length = 107
FEATURE                Location/Qualifiers
```

-continued

```
source                  1..107
                        mol_type = protein
                        organism = synthetic construct
SEQUENCE: 33
DIQMTQSPSS LSASVGDRVT ITCRASQGIG SALAWYQQKP GKAPKLLIYD ASNLETGVPS  60
RFSGSGSGTD FTLTISSLQP EDFATYYCQQ LNGYPLTFGQ GTRLEIK              107
```

BISPECIFIC STEALTH LIPID NANOPARTICLE COMPOSITIONS FOR CELL TARGETING

RELATED APPLICATIONS

The instant application claims priority to U.S. Provisional Application No. 63/545,474, filed on Oct. 24, 2023; PCT Application No. PCT/US2023/082078, filed Dec. 1, 2023; U.S. Provisional Application No. 63/562,079, filed Mar. 6, 2024; U.S. Provisional Application No. 63/642,445, filed May 3, 2024; U.S. Provisional Application No. 63/645,650, filed May 10, 2024; PCT Application No. PCT/US2024/032646, filed Jun. 5, 2024; and U.S. Provisional Application No. 63/705,914, filed Oct. 10, 2024. The entire contents of each of the foregoing applications are expressly incorporated by reference herein.

SEQUENCE LISTING

The application contains a Sequence Listing which has been submitted electronically in .XML format and is hereby incorporated by reference in its entirety. Said .XML copy, created on Feb. 24, 2025, is named “131698-17820.xml” and is 34,349 bytes in size. The sequence listing contained in this .XML file is part of the specification and is hereby incorporated by reference herein in its entirety.

TECHNICAL FIELD

The present disclosure relates to the field of gene and nucleic acid therapy, including compositions and methods of making lipid nanoparticles (LNPs) that encapsulate a therapeutic cargo for e.g., making genetically modified immune effector cells, e.g., hematopoietic stem cells or T cells.

BACKGROUND

Recent advances in immunotherapy in conjunction with cell and gene therapies have demonstrated remarkable efficacy in the treatment of cancer. The development of chimeric antigen receptor (CAR) T-cells has been a notable example of such therapeutic frontiers. Chimeric antigen receptors (CARs) are molecules that combine antibody-based specificity for disease-associated surface antigens with T cell receptor-activating intracellular domains with disease-directed cellular immune activity. This configuration allows T cells engineered to express a CAR to achieve MHC-independent primary activation through single chain Fv (scFv) antigen-specific extracellular regions fused to intracellular domains that provide T cell activation and co-stimulatory signals. Second and third generation CARs also provide appropriate co-stimulatory signals via CD28 and/or CD137 (4-1BB) intracellular activation motifs, which augment cytokine secretion and anti-tumor activity in a variety of solid tumor and leukemia models (Pinthus, et al., 2004, J Clin Invest 114(12): 1774-1781; Milone, et al., 2009, Mol Ther 17(8): 1453-1464; Sadelain, et al., 2009, Curr Opin Immunol 21(2):215-223). The benefit of bypassing the need for antigen presentation by MHC molecules to achieve cytotoxicity makes CAR T-cells an attractive therapeutic modality.

Adoptive cell transfer (ACT) therapy with T-cells transduced with CARs has shown promise in hematologic cancer trials. Among the CAR T-cell therapies currently available are brexucabtagene autoleucel (TECARTUS®), ciltacabtagene autoleucel (CARVYKTI®), axicabtagene ciloleucel (YESCARTA®) and tisagenlecleucel (KYMRIAH®), which have been approved by the Food and Drug Administration to treat acute lymphoblastic leukemia (ALL), multiple myeloma, large B-cell non-Hodgkin lymphomas, and advanced acute lymphoblastic leukemia, respectively. Other CAR T-cell therapies are being developed for blood cancers including chronic lymphocytic leukemia, other forms of lymphoma, and multiple myeloma.

Therapeutic CAR T-cells are prepared by first isolating native T-cells from a patient suffering from a cancer type that CAR T-cell is designed to target. The harvested T-cells are usually then infected with a virus encoding the CAR to target the patient’s cancer type. Once infected with the virus, the T-cells display both the appropriate antigen receptor, as well as the costimulatory molecules required to activate the T-cell against the targeted antigen. These T-cells are clonally expanded and then re-infused into the patient after pretreatment chemotherapy.

Despite remarkable efficacy in immunotherapy for cancer, CAR T-cell therapy has notable life-threatening adverse reactions. The most common severe reaction to CAR-T therapy is the cytokine release syndrome (CRS) which occurs after the hundreds of millions of infused T cells release cytokines in a positive feedback loop, causing a systematic inflammatory response syndrome with fevers, tachycardia, hypotension, and multiple organ system dysfunction. Over 75% of patients treated with CAR-T therapy develop CRS, with the greatest risk factor being a high tumor burden.

As an emerging technology, there is an urgent need in the art for improving on existing cell therapy, such as CAR-based therapies, that would allow for more effective, safe, and efficient transfer of therapeutic cargo to target cells like T-cells, B-cells, Natural Killer (NK) cells, dendritic cells, or hematopoietic stem cells (HSC) in vivo, in vitro or ex vivo.

SUMMARY

The present disclosure provides novel “stealth” LNP compositions that surpassingly exhibit physiological characteristics of prolonged blood circulation time (e.g., increased blood $t_{1/2}$) simultaneously with increased targeting capacity to specific cell-types (e.g., immune effector cells such as T-cells, B-cells, NK cells, and dendritic cells, or hematopoietic stem cells (HSC)), useful for creating genetically modified cells in vivo and/or ex vivo. The stealth LNPs can encapsulate various types of cargo, such as nucleic acids, e.g., nucleic acids encoding a desired therapeutic protein (e.g., a chimeric antigen receptor an enzyme, an antibody, etc.), or carrying a sequence for a gene/base editing template. The nucleic acid molecules can be various forms of double-stranded DNA, single-stranded DNA, partially single-stranded DNA, or RNA (e.g., mRNA, siRNA, gRNA).

In particular, the novel LNPs disclosed herein provide surprising and unexpected “stealth” properties as compared to previously known LNPs by, for example, providing steric stabilization (e.g., enhancing the stealth property of overall LNP characteristic in the circulation (e.g., the blood compartment) by minimizing interactions between opsonins present in the blood and the surface of the LNP). For example, a stealth LNP of the disclosure comprises a half-life ($t_{1/2}$) in blood in vivo of greater than 3 hours, greater than 4 hours, greater than 5 hours, greater than 6 hours, greater than 7 hours, greater than 8 hours, greater than 9 hours, greater than 10 hours, greater than 11 hours, greater than 12 hours, or greater than 24 hours. In contrast, prior to the instant disclosure, the half-life ($t_{1/2}$) in blood in vivo of LNPs was typically around 30 minutes.

Additionally, an optional helper lipid, if present in the stealth LNP of the disclosure, functions to increase the fusogenicity of the lipid bilayer of the LNP and to facilitate endosomal escape; the structural lipid of the LNP contributes to membrane integrity and stability of the LNP; and the lipid-anchored polymer of the LNP can inhibit aggregation of LNPs and provide steric stabilization (e.g., enhancing the stealth property of overall LNP characteristic in the circulation (e.g., the blood compartment) by minimizing interactions between opsonins present in the blood and the surface of the LNP).

Moreover, the present disclosure provides lipid-anchored polymers wherein the number of aliphatic carbons in the lipid portion of lipid-anchored polymer are crucial for slowing dissociation of the lipid-anchored polymer away from the LNP and allowing the LNP to remain intact and able to avoid non-specific fusion or removal within the first hour in the blood or plasma compartments. The present disclosure provides LNPs where at least one of the lipids in the lipid-anchored polymer contains 18 aliphatic carbons to anchor the lipid-anchored polymer more securely to the LNP.

The present disclosure further provides a "cell targeting stealth LNP" by combining the stealth characteristics described above with cell targeting of the LNP by conjugation of a targeting moiety to one of the lipid-anchored polymers in the LNP. In particular, the disclosed stealth cell targeting LNP compositions can further comprise a targeting moiety, wherein the targeting moiety binds to a hematopoietic stem cell (HSC) antigen, such as a single chain fragment variable (scFv) and/or single domain antibody (VHH) linked to the LNP, wherein the scFv or VHH is directed against an antigen present on the surface of a cell (e.g., a tumor cell, T-cell, hematopoietic stem cell (HSC), B-cell, NK cell, etc.), thereby providing targeting specificity to the stealth LNP to a desired tissue or cell-type. The stealth cell targeting LNPs described herein advantageously provide efficient covalent conjugation with minimal or no effects on blood pharmacokinetics (PK), particle size and stability as compared to unconjugated stealth LNPs.

It is a further finding of the present disclosure that DBCO mediated conjugation (via "Click chemistry") or maleimide conjugation (via thiol—maleimide reaction) between the targeting moiety (e.g., scFv or VHH) and the lipid-anchored polymer present on the surface of the stealth LNP resulted in robust linkages that maintained the physiochemical characteristics of the stealth LNPs and the resultant stealth LNPs comprising a targeting moiety effectively demonstrated highly increased specificity and targeting efficiency to a desired cell-type in vivo.

The present disclosure also provides a stealth LNP composition comprising a second lipid-anchored polymer having a reactive species, e.g., maleimide, azide, etc., that are capable of reacting with a targeting moiety functionalized with thiol (—SH) or dibenzocyclooctyne (DBCO) reactive species.

In one aspect, disclosed herein is a stealth lipid nanoparticle (LNP) comprising: (a) a therapeutic nucleic acid (TNA); (b) an ionizable lipid; (c) a sterol; (d) a first lipid-anchored polymer; (e) a second lipid-anchored polymer, wherein the second lipid-anchored polymer is conjugated to a first targeting moiety; and (f) a third lipid-anchored polymer, wherein the third lipid-anchored polymer is conjugated to a second targeting moiety, wherein the first targeting moiety and the second targeting moiety are different, and wherein the first lipid-anchored polymer, the second lipid-anchored polymer, and the third lipid-anchored polymer each comprise a lipid-linker and a hydrophilic polymer.

In one embodiment, the first, second, and third lipid-anchored polymers are the same. In one embodiment, the second lipid-anchored polymer and the third lipid-anchored polymer are the same. In one embodiment, the second lipid-anchored polymer and the third lipid-anchored polymer are the same, and wherein the first lipid-anchored polymer is different from the second and third lipid-anchored polymers. In one embodiment, the second lipid-anchored polymer and the third lipid-anchored polymer are different. In one embodiment, the first, second, and third lipid-anchored polymer are different.

In one embodiment, the first targeting moiety and the second targeting moiety are each tissue- and/or cell-type specific targeting moieties. In one embodiment, the first targeting moiety and the second targeting moiety each bind to a different tissue- and/or cell-type specific antigen. In one embodiment, the first targeting moiety and the second targeting moiety each bind to a different antigen on the same tissue and/or cell-type. In one embodiment, the first targeting moiety and the second targeting moiety each bind to antigens on different tissue- and/or cell-types.

In one embodiment, the tissue and/or cell-type is selected from the group consisting of a hematopoietic stem or progenitor cell (HSPC), a hematopoietic stem cell (HSC), a liver cell, a muscle cell, a retinal cell, a skin cell, a nerve cell, a brain cell, a kidney cell, an ovarian cell, a testicular cell, a uterine cell, an endocrine cell, a bone cell, an epithelial cell, an endothelial cell, and a lung cell. In one embodiment, at least one of the first targeting moiety and the second targeting moiety binds to a hematopoietic stem or progenitor cell (HSPC) specific antigen. In one embodiment, at least one of the first targeting moiety and the second targeting moiety binds to a hematopoietic stem cell (HSC) specific antigen. In one embodiment, the first targeting moiety and the second targeting moiety each bind to a different HSPC specific antigen. In one embodiment, the first targeting moiety and the second targeting moiety each bind to a different HSC specific antigen.

In one embodiment, each of the first and second targeting moieties binds to an antigen independently selected from the group consisting of CD45, CD46, CD135, CD90, CD117, CD133, ADAM8, ADAM28, ADGRE2, ASCT1, ASCT2, CALHN2, CD33, CD34, CD37, CD43, CD44, CD49f, CD71, CD79A, CD79B, CD84, CD105, CD110, CD123, CD126, CD131, CD133, CD146, CD164, CD184, CD244, CD300f, CD300LF, CD370, CSF3R, CSMD2, EFNA3, EPHB2, FASLG, GPI-80, GPR183, IGSF8, ITGA3, LAIR1, LILRA2, PTAFR, SELL, SLC2A5, TNFRSF8, and VCAM1. In one embodiment, at least one of the first and second targeting moieties binds to an antigen selected from the group consisting of CD45, CD117, and CD135. In one embodiment, the first targeting moiety binds to CD45. In one embodiment, the first targeting moiety binds CD45, and the second targeting moiety binds to CD117. In one embodiment, the first targeting moiety binds CD45, and the second targeting moiety binds to CD135.

In one embodiment, each of the first and second targeting moieties is independently selected from the group consisting of a protein, a nucleic acid, and a sugar. In one embodiment, at least one of the first and second targeting moieties is an antibody, an antibody fragment, or an antibody derivative. In one embodiment, the first and second targeting moieties are each independently an antibody, an antibody fragment, or an antibody derivative. In one embodiment, each antibody, antibody fragment, or antibody derivative is selected from the group consisting of a full-length antibody, an Fab, an Fab', a single-domain antibody, a single-chain antibody, and a variable heavy chain-only antibody (VHH). In one embodiment, each antibody, antibody fragment, or antibody derivative is an scFv. In one embodiment, each antibody, antibody fragment, or antibody derivative is a VHH. In one embodiment, each VHH is a nanobody.

In one embodiment, each targeting moiety is located on the exterior of the LNP. In one embodiment, at least one of the first and second targeting moieties is N-acetylgalactosamine (GalNAc) or a GalNAc derivative. In one embodiment, at least one of the first and second targeting moieties is an aptamer. In one embodiment, a first linker is present between the second lipid-anchored polymer and the first targeting moiety, and wherein a second linker is present between the third lipid-anchored polymer and the second targeting moiety. In one embodiment, the first targeting moiety is conjugated to the second lipid-anchored polymer via maleimide conjugation, and wherein the second targeting moiety is conjugated to the third lipid-anchored polymer via maleimide conjugation. In one embodiment, the first targeting moiety is conjugated to the second lipid-anchored polymer via maleimide conjugation, and wherein the second targeting moiety is conjugated to the third lipid-anchored polymer via click chemistry. In one embodiment, the first targeting moiety is conjugated to the second lipid-anchored polymer via click chemistry, and wherein the second targeting moiety is conjugated to the third lipid-anchored polymer via click chemistry. In one embodiment, the sterol is selected from the group consisting of cholesterol, beta-sitosterol, stigmasterol, beta-sitostanol, campesterol, brassicasterol, derivatives thereof, and combinations thereof. In one embodiment, the sterol is cholesterol. In one embodiment, the sterol is beta-sitosterol.

In one embodiment, the ionizable lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 2,2-dilinoleyl-4-(2-dimethylaminoethyl)-[1,3]-dioxolane (DLin-K-C2-DMA), (DC-Chol), Dioctadecyldimethylammonium Bromide (DDAB), a Saint lipid, SAINT-2, N-methyl-4-(dioleyl) methylpyridinium), 1,2-dimyristyloxypropyl-3-dimethylhydroxyethylammonium bromide (DMRIE), 1,2-dioleoyl-3-dimethyl-hydroxyethyl ammonium bromide (DORIE), 1,2-dioleoyloxypropyl-3-dimethylhydroxyethyl ammonium chloride (DORI), Di-alkylated Amino Acid (DILA2), C18: 1-norArg-C16), Dioleyldimethylammonium chloride (DODAC); 1-palmitoyl-2-oleoyl-sn-glycero-3-ethylphosphocholine (POEPC), 1,2-dimyristoleoyl-sn-glycero-3-ethylphosphocholine (MOEPC), Dioctadecyldimethylammonium bromide (DDAB), 1,2-dilinoleyloxy-3-dimethylaminopropane (DLinDMA), 2,2-dilinoleyl-4-(2-dimethylaminoethyl)-[1,3]-dioxolane (DLin-KC2-DMA), heptatriaconta-6,9,28,31-tetraen-19-yl-4-(dimethylamino) butanoate (DLin-MC3-DMA), 1,2-Dioleoyloxy-3-dimethylaminopropane (DODAP), 1,2-Dioleyloxy-3-dimethylaminopropane (DODMA), Morpholinocholesterol (Mo-CHOL), (R)-5-(dimethylamino)pentane-1,2-diyl dioleate hydrochloride (DODAPen-C1), (R)-5-guanidinopentane-1,2-diyl dioleate hydrochloride (DOPen-G), and (R)-N,N,N-trimethyl-4,5-bis(oleoyloxy)pentan-1-aminium chloride (DOTAPen), SMA102, L319, L369, L319, LPO1, SS-cleavable lipid, and combinations and mixtures thereof.

In one embodiment, the ionizable lipid is selected from the group consisting of the lipids set forth in Table 6, or a pharmaceutically acceptable salt thereof. In one embodiment, the ionizable lipid comprises Lipid No. 87 or a pharmaceutically acceptable salt or ester thereof, or a deuterated analogue thereof. In one embodiment, the first lipid-anchored polymer, the second lipid-anchored polymer, and the third lipid-anchored polymer each independently comprise a lipid comprising at least one hydrophobic tail. In one embodiment, the first lipid-anchored polymer, the second lipid-anchored polymer, and the third lipid-anchored polymer each independently comprise a lipid comprising at least two hydrophobic tails. In one embodiment, each hydrophobic tail comprises a carbon chain having at least 18 carbon atoms (C18). In one embodiment, each hydrophobic tail comprises a carbon chain having 18 to 22 carbon atoms (C18-C22). In one embodiment, each hydrophobic tail comprises a carbon chain having 18 carbon atoms (C18).

LIPID 87

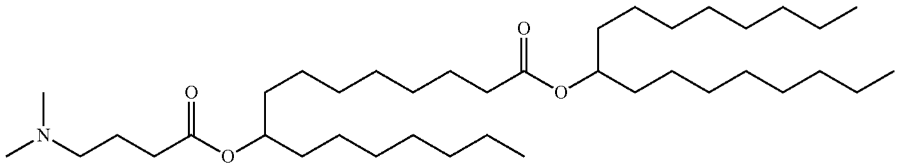

heptadecan-9-yl 9-((4-(dimethylamino)butanoyl)oxy)hexadecanoate 2,2-dilinoleyl-4-dimethylaminomethyl-[1,3]-dioxolane (DLin-K-DMA), DLin-MC3-DMA, N-[1-(2,3-dioleyloxy) propyl]-N,N,N-trimethylammonium chloride (DOTMA), N-[1-(2,3-dioleoyloxy)propyl]-N,N,N-trimethylammonium chloride (DOTAP), 1,2-dioleoyl-sn-glycero-3-ethylphosphocholine (DOEPC), 1,2-dilauroyl-sn-glycero-3-ethylphosphocholine (DLEPC), 1,2-dimyristoyl-sn-glycero-3-ethylphosphocholine (DMEPC), 1,2-dimyristoleoyl-sn-glycero-3-ethylphosphocholine (14:1), N1-[2-((1S)-1-[(3-aminopropyl)amino]-4-[di(3-amino-propyl)aminolbutylcarboxamidoiethyl]-3,4-di[oleyloxy]-benzamide (MVL5), Dioctadecylamido-glycylspermine (DOGS), 3b-[N—(N',N'-dimethylaminoethyl)carbamoyl] cholesterol In one embodiment, the first lipid-linker, the second lipid-linker, and the third lipid-linker are each independently selected from the group consisting of 1,2-dipalmitoyl-sn-glycero-3-phosphocholine (DPPC), 1-palmitoyl-2-oleoyl-glycero-3-phosphocholine (POPC), 1-palmitoyl-2-oleoyl-sn-glycero-3-phosphoethanolamine (POPE), 1-palmitoyl-2-oleoyl-sn-glycero-3-phospho-(1'-rac-glycerol) (POPG), 1,2-dipalmitoyl-sn-glycero-3-phosphoethanolamine (DPPE), 1,2-distearoyl-sn-glycero-3-phosphoethanolamine (DSPE), 1,2-dielaidoyl-sn-phosphatidylethanolamine (DEPE), 1-stearoyl-2-oleoyl-sn-glycero-3-phosphoethanolamine (SOPE), 1,2-dioleoyl-sn-glycero-3-phosphoglycerol (DOPG), 1,2-dipalmitoyl-sn-glycero-3-phosphoglycerol (DPPG), 18-1-trans PE, 1,2-dioleoyl-sn-glycero-3-phospho-L-serine (DOPS), 1,2-diphytanoyl-sn-glycero-3-phospho-ethanolamine (DPHyPE); and dioctadecylamine (DODA), distearoyl-rac-glycerol (DSG), 1,2-dipalmitoyl-rac-glycerol (DPG), and combinations and derivatives thereof. In one embodiment, the first lipid-linker, the second lipid-linker, and the third lipid-linker are each independently selected from the group consisting of DSPE, DSG, DODA, DPG, DOPE, and combinations and derivatives thereof. In one embodiment, the first lipid-anchored polymer, the second lipid-anchored polymer, and the third lipid-anchored polymer are each independently DSPE, DODA, DSG, or combinations thereof.

In one embodiment, the first lipid-anchored polymer, the second lipid-anchored polymer and the third lipid-anchored polymer each independently comprise a polymer selected from the group consisting of polyethylene glycol (PEG), polyglycerol (PG), polyoxazoline (POZ), poly(2-methacryloyloxyethyl phosphorylcholine) (PMPC), polyamide, and combinations thereof. In one embodiment, each polymer is PEG. In one embodiment, each PEG is selected from the group consisting of PEG5000, PEG2000, PEG2000-OMe, PEG3000, PEG3000-OMe, PEG3400, PEG3400-OMe, and PEG5000-OMe. In one embodiment, each polymer is polyglycerol (PG). In one embodiment, each PG comprises at least 5-60 glycerol units. In one embodiment, the first lipid-anchored polymer, the second lipid-anchored polymer, and the third lipid-anchored polymer each independently comprise DSPE, DODA, DSG, or combinations thereof. In one embodiment, the first lipid-anchored polymer, the second lipid-anchored polymer, and the third lipid-anchored polymer are each independently DSPE-PEG, DODA-PG, DSPE-PG, DODA-PEG, DSG-PEG, DSG-PG, or combinations thereof.

In one embodiment, the first lipid-anchored polymer, the second lipid-anchored polymer, and the third lipid-anchored polymer each comprise a different lipid-linker. In one embodiment, the first lipid-anchored polymer, the second lipid-anchored polymer, and the third lipid-anchored polymer each comprise the same lipid-linker. In one embodiment, the first lipid-anchored polymer, the second lipid-anchored polymer, and the third lipid-anchored polymer are different. In one embodiment, the first lipid-anchored polymer, the second lipid-anchored polymer, and the third lipid-anchored polymer are the same. In one embodiment, the second lipid-anchored polymer and the third lipid-anchored polymer and the same. In one embodiment, the first lipid-anchored polymer is different from the second and third lipid-anchored polymers. In one embodiment, the first lipid-anchored polymer, the second lipid-anchored polymer, and the third lipid-anchored polymer are each DSPE-PEG. In one embodiment, the first lipid-anchored polymer, the second lipid-anchored polymer, and the third lipid-anchored polymer are each DODA-PG.

In one embodiment, the stealth LNP disclosed herein further comprises a helper lipid. In one embodiment, the helper lipid is selected from the group consisting of distearoyl-sn-glycero-phosphoethanolamine (DSPE), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), monomethyl-phosphatidylethanolamine (such as 16-O-monomethyl PE), dimethyl-phosphatidylethanolamine (such as 16-O-dimethyl PE), 18-1-trans PE, 1-stearoyl-2-oleoyl-phosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoyl phosphatidylcholine (DMPC), dimyristoyl phosphatidylglycerol (DMPG), distearoylphosphatidylglycerol (DSPG), dierucoylphosphatidylcholine (DEPC), palmitoyloleyolphosphatidylglycerol (POPG), dielaidoyl-phosphatidylethanolamine (DEPE), 1,2-dilauroyl-sn-glycero-3-phosphoethanolamine (DLPE); 1,2-diphytanoyl-sn-glycero-3-phosphoethanolamine (DPHyPE); lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidicacid, cerebrosides, dicetylphosphate, lysophosphatidylcholine, dilinoleoylphosphatidylcholine, DODA, ceramide, and derivatives and combinations thereof. In one embodiment, the helper lipid is DSPC.

In one embodiment, the ionizable lipid is present at a molar percentage of about 30% to about 80%. In one embodiment, the sterol is present at a molar percentage of about 20% to about 50%. In one embodiment, the sterol is present at a molar percentage of about 35% to about 40%.

In one embodiment, the first lipid-anchored polymer, the second anchored polymer, and the third lipid-anchored polymer are present at a combined molar percentage of about 1% to about 8%. In one embodiment, the first lipid-anchored polymer, the second anchored polymer, and the third lipid-anchored polymer are present at a combined molar percentage of about 2% to about 5%. In one embodiment, the first lipid-anchored polymer, the second anchored polymer, and the third lipid-anchored polymer are present at a combined molar percentage of about 3%. In one embodiment, the first lipid-anchored polymer is present at a molar percentage of about 1% to about 7%. In one embodiment, the first lipid-anchored polymer is present at a molar percentage of about 1.5% to about 5%. In one embodiment, the first lipid-anchored polymer is present at a molar percentage of about 2% to about 3%. In one embodiment, the first lipid-anchored polymer is present at a molar percentage of about 2% to about 3%. In one embodiment, the first lipid-anchored polymer is present at a molar percentage of about 2.5%.

In one embodiment, the second lipid-anchored polymer and the third lipid-anchored polymer are present at a combined molar percentage of about 0.01% to about 1%. In one embodiment, the second lipid-anchored polymer and the third lipid-anchored polymer are present at a combined molar percentage of about 0.01% to about 0.75%. In one embodiment, the second lipid-anchored polymer and the third lipid-anchored polymer are present at a combined molar percentage of about 0.01% to about 0.5%. In one embodiment, the second lipid-anchored polymer and the third lipid-anchored polymer are present at a combined molar percentage of about 0.01% to about 0.4%. In one embodiment, the second lipid-anchored polymer and the third lipid-anchored polymer are present at a combined molar percentage of about 0.01% to about 0.3%. In one embodiment, the second lipid-anchored polymer and the third lipid-anchored polymer are present at a combined molar percentage of about 0.01% to about 0.25%.

In one embodiment, the second lipid-anchored polymer and the third lipid-anchored polymer are present at a combined molar percentage of about 0.02% to about 0.2%. In one embodiment, the second lipid-anchored polymer and the third lipid-anchored polymer are present at a combined molar percentage of about 0.1%. In one embodiment, the second lipid-anchored polymer is present at a molar percentage of about 0.02% to about 0.05%, and the third lipid-anchored polymer is present at a molar percentage of about 0.05% to about 0.1%. In one embodiment, the second lipid-anchored polymer is present at a molar percentage of about 0.025%, and the third lipid-anchored polymer is present at a molar percentage of about 0.075%. In one embodiment, the second lipid-anchored polymer and the third lipid-anchored polymer are present at a combined molar percentage of about 0.05%. In one embodiment, the second lipid-anchored polymer and the third lipid-anchored polymer are present at a combined molar percentage of about 0.15%. In one embodiment, the second lipid-anchored polymer and the third lipid-anchored polymer are present at a combined molar percentage of about 0.25%. In one embodiment, the second lipid-anchored polymer and the third lipid-anchored polymer are present at a combined molar percentage of about 0.3%. In one embodiment, the second lipid-anchored polymer and the third lipid-anchored polymer are present at a combined molar percentage of about 0.4%. In one embodiment, the second lipid-anchored polymer and the third lipid-anchored polymer are present at a combined molar percentage of about 0.5%. In one embodiment, the helper lipid is present at a molar percentage of about 2% to about 20%. In one embodiment, the helper lipid is present at a molar percentage of about 10%. In one embodiment, the stealth LNP disclosed herein further comprises an immunosuppressant.

In one embodiment, the nanoparticle has a total lipid to TNA ratio of about 10:1 to about 40:1. In one embodiment, the LNP has a diameter of about 40 nm to about 120 nm. In one embodiment, the LNP has a diameter of less than about 110 nm. In one embodiment, the LNP has a diameter of about 90 nm to about 110 nm. In one embodiment, the LNP is present in an LNP composition comprising a plurality of LNPs having an average diameter of about 40 nm to about 120 nm. In one embodiment, the LNP is present in an LNP composition comprising a plurality of LNPs having an average diameter of less than about 110 nm. In one embodiment, the LNP is present in an LNP composition comprising a plurality of LNPs having an average diameter of about 90 nm to about 110 nm.

In one embodiment, the TNA is selected from the group consisting of RNA, DNA, and derivatives and analogues thereof. In one embodiment, the TNA encodes a therapeutic gene and/or a therapeutic protein. In one embodiment, the TNA is selected from the group consisting of mRNA, siRNA, synthetic ribozymes, antisense RNA, and gRNA. In one embodiment, the TNA is mRNA. In one embodiment, the TNA is siRNA. In one embodiment, the TNA is selected from the group consisting of single-stranded-DNA (ssDNA), partially single-stranded DNA (partially ssDNA) and double-stranded DNA (dsDNA). In one embodiment, the TNA is ssDNA. In one embodiment, the TNA is linear ssDNA. In one embodiment, the TNA is partially ssDNA. In one embodiment, the TNA is dsDNA. In one embodiment, the TNA is a non-viral capsid-free DNA vector with covalently-closed ends (ceDNA vector). In one embodiment, the TNA is synthetically produced in a cell-free environment.

In one aspect, the disclosure provides a cell comprising a stealth LNP disclosed herein. In one embodiment, the cell is in vitro, ex vivo, or in vivo. In one embodiment, the cell is selected from the group consisting of a hematopoietic stem or progenitor cell (HSPC), a hematopoietic stem cell (HSC), a liver cell, a muscle cell, a retinal cell, a skin cell, a nerve cell, a brain cell, a kidney cell, an ovarian cell, a testicular cell, a uterine cell, an endocrine cell, a bone cell, an epithelial cell, an endothelial cell, and a lung cell. In one embodiment, the cell is a In one embodiment, cell. In one embodiment, the cell is an HSPC. In one embodiment, the cell is an HSC. In one embodiment, the cell is an autologous HSPC or HSC. In one embodiment, the cell is an allogeneic HSPC or HSC.

In one aspect, disclosed herein is a pharmaceutical composition comprising a stealth LNP disclosed herein or a cell disclosed herein. In one embodiment, the pharmaceutical composition disclosed herein further comprises a pharmaceutically acceptable excipient or carrier. In one embodiment, the pharmaceutical composition disclosed herein further comprises an immunosuppressant. In one embodiment, the pharmaceutical composition disclosed herein further comprises a tyrosine kinase inhibitor (TKI). In one embodiment, the tyrosine kinase inhibitor is a pharmaceutically acceptable salt of the TKI.

In one aspect, disclosed herein, is a method of treating a disease or disorder in a subject, comprising administering to the subject a therapeutically effective amount of the stealth LNP disclosed herein, the cell disclosed herein, and/or or the pharmaceutical composition disclosed herein. In one embodiment, the disease or disorder is a genetic disease or disorder. In one embodiment, the genetic disease or disorder is selected from the group consisting of sickle-cell anemia, melanoma, hemophilia A (clotting factor VIII (FVIII) deficiency) and hemophilia B (clotting factor IX (FIX) deficiency), cystic fibrosis (CFTR), familial hypercholesterolemia (LDL receptor defect), hepatoblastoma, Wilson disease, phenylketonuria (PKU), congenital hepatic porphyria, inherited disorders of hepatic metabolism, Lesch Nyhan syndrome, thalassaemias, xeroderma pigmentosum, Fanconi's anemia, retinitis pigmentosa, ataxia telangiectasia, Bloom's syndrome, retinoblastoma, mucopolysaccharide storage diseases (e.g., Hurler syndrome (MPS Type I), Scheie syndrome (MPS Type I S), Hurler-Scheie syndrome (MPS Type I H-S), Hunter syndrome (MPS Type II), Sanfilippo Types A, B, C, and D (MPS Types III A, B, C, and D), Morquio Types A and B (MPS IVA and MPS IVB), Maroteaux-Lamy syndrome (MPS Type VI), Sly syndrome (MPS Type VII), hyaluronidase deficiency (MPS Type IX)), Niemann-Pick Disease Types A/B, C1 and C2, Fabry disease, Schindler disease, GM2-gangliosidosis Type II (Sandhoff Disease), Tay-Sachs disease, Metachromatic Leukodystrophy, Krabbe disease, Mucolipidosis Type I, II/III and IV, Sialidosis Types I and II, Glycogen Storage disease Types I and II (Pompe disease), Gaucher disease Types I, II and III, cystinosis, Batten disease, Aspartylglucosaminuria, Salla disease, Danon disease (LAMP-2 deficiency), Lysosomal Acid Lipase (LAL) deficiency, neuronal ceroid lipofuscinoses (CLN1-8, INCL, and LINCL), sphingolipidoses, galactosialidosis, amyotrophic lateral sclerosis (ALS), Parkinson's disease, Alzheimer's disease, Huntington's disease, spinocerebellar ataxia, spinal muscular atrophy, Friedreich's ataxia, Duchenne muscular dystrophy (DMD), Becker muscular dystrophies (BMD), dystrophic epidermolysis bullosa (DEB), ectonucleotide pyrophosphatase 1 deficiency, generalized arterial calcification of infancy (GACI), Leber Congenital Amaurosis, Stargardt macular dystrophy (ABCA4), ornithine transcarbamylase (OTC) deficiency, Usher syndrome, age-related macular degeneration (AMD), alpha-1 antitrypsin deficiency, progressive familial intrahepatic cholestasis (PFIC) type I (ATP8B1 deficiency), type II (ABCB11), type III (ABCB4), or type IV (TJP2), and Cathepsin A deficiency.

In one embodiment, the disease or disorder is hemophilia A. In one embodiment, the disease or disorder is hemophilia B. In one embodiment, the disease or disorder is phenylketonuria (PKU). In one embodiment, the disease or disorder is Wilson disease. In one embodiment, the disease or disorder is Gaucher disease Types I, II and III. In one embodiment, the disease or disorder is Stargardt macular dystrophy. In one embodiment, the disease or disorder is LCA10. In one embodiment, the disease or disorder is Usher syndrome. In one embodiment, the disease or disorder is wet AMD.

In one embodiment, the disease or disorder is selected from the group consisting of: Sickle Cell Disease (SCD), Thalassemia, Pyruvate Kinase Deficiency (PKD), G6PD deficiency, Hereditary elliptocytosis, Familial Thrombocytosis, Polycythemia vera, Erythropoietic protoporphyria, Leukocyte Adhesion Deficiency, Hereditary spherocytosis, Paroxysmal noctunal hemoglobinuria (PNH), Red cell aplasia, HFE-related hemochromatosis, Diamond Blackfan Amenia, Fanconi Anemia, Hemophagocytic Lymphohistiocytosis, Thrombocytopenia Absent Radius (TAR) syndrome, Myelodysplastic Syndromes (MDS), Histiocytosis, Chronic Granulomatous Disease (CGD), Leukocytes Adhesion Deficiency (LAD), Myoloperoxidase Deficiency, Neutropenia, Glanzmann's Thrombasthenia, Bernard-Soulier Syndrome, Gray Platelet Syndrome, Storage Pool Deficiency, Hemoglobin E disease, Hemoglobin C disease, Hereditary stomatocytosis, Hereditary persistence of fetal hemoglobin (HPFH), Southeast Asian ovalocytosis, Rh-null disease, and Shwachman-Diamond Syndrome (SBDS). In some embodiments, the ctLNPs described herein may be used to produce a therapeutic protein (e.g., a secreted therapeutic protein) in an HSC cell to treat a disease such as Hemophilia A, Hemophilia B, Gaucher disease, Fabry disease, and MPS Types I and II. In one embodiment, the disease or disorder is SCD.

In one aspect, disclosed herein, is a method of delivering a therapeutic nucleic acid (TNA) to a subject, comprising administering a therapeutically effective amount of the stealth LNP disclosed herein, the cell disclosed herein, and/or the pharmaceutical composition disclosed herein to the subject.

In one aspect, disclosed herein, is a method of delivering a therapeutic gene and/or a therapeutic protein to a cell, wherein the therapeutic gene and/or therapeutic protein is encoded by a therapeutic nucleic acid (TNA), comprising contacting the cell with the stealth LNP disclosed herein and/or the pharmaceutical composition disclosed herein to the subject, thereby delivering the therapeutic gene and/or therapeutic protein to the cell.

In one aspect, disclosed herein, is a method of delivering a therapeutic gene to the nucleus of a cell comprising contacting the cell with stealth LNP disclosed herein, and/or the pharmaceutical composition disclosed herein to the subject, thereby delivering the therapeutic gene and/or therapeutic protein to the nucleus of the cell. In one embodiment, the cell is in vitro. In one embodiment, the cell is in vivo. In one embodiment, the cell is ex vivo. In one embodiment, the subject is a human.

In one aspect, disclosed herein, is a method for producing a stealth LNP comprising two or more targeting moieties, comprising: (a) providing a stealth LNP comprising: (i) a therapeutic nucleic acid (TNA); (ii) an ionizable lipid; (iii) a sterol; (iv) a first lipid-anchored polymer; (v) a second lipid-anchored polymer, wherein the second lipid-anchored polymer comprises a first reactive moiety; (vi) a third lipid-anchored polymer, wherein the third lipid-anchored polymer comprises a second reactive moiety; wherein the first lipid-anchored polymer, the second lipid-anchored polymer, and the third lipid-anchored polymer each comprise a lipid-linker and a hydrophilic polymer; (b) providing a first targeting moiety comprising a third reactive moiety, wherein the first reactive moiety and the third reactive moiety are capable of reacting to form a covalent linkage; (c) providing a second targeting moiety comprising a fourth reactive moiety, wherein the second reactive moiety and the fourth reactive moiety are capable of reacting to form a covalent linkage, wherein the first targeting moiety and the second targeting moiety are different; (d) contacting the stealth LNP of (a) with the first targeting moiety of (b) and the second targeting moiety of (c) under conditions sufficient to allow a reaction between the first reactive moiety and the third reactive moiety, and between the second reactive moiety and the fourth reactive moiety, thereby producing a stealth LNP comprising two or more targeting moieties.

In one embodiment, the second lipid-anchored polymer and the third lipid-anchored polymer are the same. In one embodiment, the first, second, and third lipid-anchored polymers are the same. In one embodiment, the second lipid-anchored polymer and the third lipid-anchored polymer are the same, and wherein the first lipid-anchored polymer is different from the second and third lipid-anchored polymers. In one embodiment, the second lipid-anchored polymer and the third lipid-anchored polymer are different. In one embodiment, the first, second, and third lipid-anchored polymer are different.

In one embodiment, the first reactive moiety and the second reactive moiety are the same. In one embodiment, the third reactive moiety and the fourth reactive moiety are the same. In one embodiment, the first reactive moiety and the second reactive moiety are different. In one embodiment, the third reactive moiety and the fourth reactive moiety are different. In one embodiment, the first reactive moiety and the second reactive moiety are located on the exterior of the LNP.

In one embodiment, the stealth LNP disclosed herein further comprises a covalent linker between the second lipid-anchored polymer and the second reactive moiety, and a covalent linker between the third lipid-anchored polymer and the third reactive moiety. In one embodiment, the first and second reactive moieties are both maleimide or both thiol. In one embodiment, the third and fourth reactive moieties are both maleimide or both thiol. In one embodiment, the first and second reactive moieties are both maleimide, and wherein the third and fourth reactive moieties are both thiol. In one embodiment, the first and second reactive moieties are both thiol, and wherein the third and fourth reactive moieties are both maleimide. In one embodiment, the first, second, third, and fourth reactive moieties are click chemistry reagents. In one embodiment, the first and second reactive moieties are both azide or both DBCO. In one embodiment, the first and second reactive moieties are both azide, and the third and fourth reactive moieties are both DBCO. In one embodiment, the first and second reactive moieties are both DBCO, and the third and fourth reactive moieties are both azide. In one embodiment, the first reactive moiety is maleimide, the third reactive moiety is thiol, the second reactive moiety is azide, and the fourth reactive moiety is DBCO. In one embodiment, the first reactive moiety is thiol, the third reactive moiety is maleimide, the second reactive moiety is azide, and the fourth reactive moiety is DBCO. In one embodiment, the first reactive moiety is maleimide, the third reactive moiety is thiol, the second reactive moiety is DBCO, and the fourth reactive moiety is azide. In one embodiment, the first reactive moiety is thiol, the third reactive moiety is maleimide, the second reactive moiety is DBCO, and the fourth reactive moiety is azide.

In one embodiment, the first targeting moiety and the second targeting moiety are each tissue- and/or cell-type specific targeting moieties. In one embodiment, the second targeting moiety each bind to a different tissue- and/or cell-type specific antigen. In one embodiment, the first targeting moiety and the second targeting moiety each bind to a different antigen on the same tissue and/or cell-type. In one embodiment, the first targeting moiety and the second targeting moiety each bind to antigens on different tissue- and/or cell-types. In one embodiment, the tissue and/or cell-type is selected from the group consisting of a hematopoietic stem or progenitor cell (HSPC), a hematopoietic stem cell (HSC), a liver cell, a muscle cell, a retinal cell, a skin cell, a nerve cell, a brain cell, a kidney cell, an ovarian cell, a testicular cell, a uterine cell, an endocrine cell, a bone cell, an epithelial cell, an endothelial cell, and a lung cell. In one embodiment, at least one of the first targeting moiety and the second targeting moiety binds to a hematopoietic stem or progenitor cell (HSPC) specific antigen. In one embodiment, at least one of the first targeting moiety and the second targeting moiety binds to a hematopoietic stem cell (HSC) specific antigen. In one embodiment, each of the first targeting moiety and the second targeting moiety binds to a different HSPC specific antigen. In one embodiment, each of the first targeting moiety and the second targeting moiety binds to a different HSC specific antigen.

In one embodiment, each of the first and second targeting moieties independently binds to an antigen selected from the group consisting of CD45, CD46, CD135, CD90, CD117, CD133, ADAM8, ADAM28, ADGRE2, ASCT1, ASCT2, CALHN2, CD33, CD34, CD37, CD43, CD44, CD49f, CD71, CD79A, CD79B, CD84, CD105, CD110, CD123, CD126, CD131, CD133, CD146, CD164, CD184, CD244, CD300f, CD300LF, CD370, CSF3R, CSMD2, EFNA3, EPHB2, FASLG, GPI-80, GPR183, IGSF8, ITGA3, LAIR1, LILRA2, PTAFR, SELL, SLC2A5, TNFRSF8, and VCAM1. In one embodiment, at least one of the first and second targeting moieties binds to an antigen selected from the group consisting of CD45, CD117, and CD135. In one embodiment, the first targeting moiety binds to CD45. In one embodiment, the first targeting moiety binds CD45, and the second targeting moiety binds to CD117. In one embodiment, the first targeting moiety binds CD45, and the second targeting moiety binds to CD135.

In one embodiment, each targeting moiety is independently selected from the group consisting of a protein, a nucleic acid, and a sugar. In one embodiment, at least one targeting moiety is an antibody, an antibody fragment, or an antibody derivative. In one embodiment, the first and second targeting moieties are each independently an antibody, an antibody fragment, or an antibody derivative. In one embodiment, each antibody, antibody fragment, or antibody derivative is selected from the group consisting of a full-length antibody, an Fab, an Fab', a single-domain antibody, a single-chain antibody, and a VHH. In one embodiment, each antibody, antibody fragment, or antibody derivative is an scFv. In one embodiment, each antibody, antibody fragment, or antibody derivative is a VHH. In one embodiment, each VHH is a nanobody. In one embodiment, at least one targeting moiety is N-acetylgalactosamine (GalNAc) or a GalNAc derivative. In one embodiment, at least one targeting moiety is an aptamer.

In one aspect, disclosed herein is a stealth lipid nanoparticle (LNP) comprising: (a) a therapeutic nucleic acid (TNA); (b) an ionizable lipid; (c) a sterol; (d) a first lipid-anchored polymer comprising a first hydrophilic polymer and a first lipid-linker, wherein the first lipid-linker comprises a first lipid comprising at least two hydrophobic tails, and wherein each hydrophobic tail comprises a carbon chain having 18 carbon atoms ($C_{18}$); (e) a second lipid-anchored polymer comprising a second hydrophilic polymer, a second lipid-linker, and a first reactive moiety conjugated to a first targeting moiety; wherein the second lipid-linker comprises a second lipid comprising at least two hydrophobic tails, wherein each hydrophobic tail comprises a carbon chain having 18 carbon atoms ($C_{18}$); and wherein the targeting moiety is a variable heavy chain-only antibody (VHH) or a single-chain antibody (scFv); and (f) a third lipid-anchored polymer comprising a third hydrophilic polymer, a third lipid-linker, and a second reactive moiety conjugated to a second targeting moiety; wherein the third lipid-linker comprises a third lipid comprising at least two hydrophobic tails, wherein each hydrophobic tail comprises a carbon chain having 18 carbon atoms ($C_{18}$); and wherein the second targeting moiety is a variable heavy chain-only antibody (VHH) or a single-chain antibody (scFv); wherein the first targeting moiety and the second targeting moiety are different; wherein the molecular weight of each of the second and third hydrophilic polymers is greater than the molecular weight of the first hydrophilic polymer; wherein the first lipid-anchored polymer, the second lipid-anchored polymer, and the third lipid-anchored polymer are present at a combined molar percentage of about 2% to about 5%, and wherein the second lipid-anchored polymer and the third lipid-anchored polymer are present at a combined molar percentage of about 0.01% to about 0.5%; optionally wherein the stealth LNP comprises about 5 to 400 total targeting moieties; and optionally comprising (f) a helper lipid.

In one embodiment, the first hydrophilic polymer, the second hydrophilic polymer, and the third hydrophilic polymer are each independently selected from the group consisting of polyethylene glycol (PEG), polyglycerol (PG), polyoxazoline (POZ), poly(2-methacryloyloxyethyl phosphorylcholine) (PMPC), polyamide, polysarcosine (pSar), and combinations thereof. In one embodiment, the first hydrophilic polymer, the second hydrophilic polymer, and the third hydrophilic polymer are each independently polyethylene glycol (PEG). In one embodiment, each PEG is independently selected from the group consisting of PEG5000, PEG2000, PEG2000-OMe, PEG3000, PEG3000-OMe, PEG3400, PEG3400-OMe, and PEG5000-OMe. In one embodiment, the second and third hydrophilic polymers are PEG5000. In one embodiment, the first hydrophilic polymer is PEG2000. In one embodiment, the first hydrophilic polymer, the second hydrophilic polymer, and the third hydrophilic polymer are the same. In one embodiment, the second and third hydrophilic polymers are the same, and wherein the first hydrophilic polymer is different from the second and third hydrophilic polymers.

In one embodiment, the second and third lipid-anchored polymers are present at a combined molar percentage of about 0.01% to about 0.3%. In one embodiment, the second and third lipid-anchored polymers are present at a combined molar percentage of about 0.05% to about 0.2%. In one embodiment, the second and third lipid-anchored polymers are present at a combined molar percentage of about 0.05% to about 0.1%. In one embodiment, the second and third lipid-anchored polymers are present at a combined molar percentage of about 0.08%. In one embodiment, the second and third lipid-anchored polymers are present at a combined molar percentage of about 0.1%. In one embodiment, the second and third lipid-anchored polymers are present at a combined molar percentage of about 0.2%. In one embodiment, the second and third lipid-anchored polymers are present at a combined molar percentage of about 0.3%. In one embodiment, the second and third lipid-anchored polymers are present at a combined molar percentage of about 0.4%. In one embodiment, the second and third lipid-anchored polymer are present at a combined molar percentage of about 0.5%. In one embodiment, the first, second, and third lipid-anchored polymers are present at a combined molar percentage of about 3%. In one embodiment, the first lipid-anchored polymer is present at a molar percentage of about 2% to about 3%. In one embodiment, the first lipid-anchored polymer is present at a molar percentage of about 2.5%.

In one embodiment, the second and third lipid-linkers are the same. In one embodiment, the second and third lipid-linkers are the same, and the first lipid-linker is different from the second and third lipid-linkers. In one embodiment, the first, second, and third lipid-linkers are the same.

In one embodiment, the first, second, and third lipid-linkers are each independently selected from the group consisting of 1,2-distearoyl-sn-glycero-3-phosphoethanolamine (DSPE), distearoyl-rac-glycerol (DSG), 1,2-dielaidoyl-sn-phosphatidylethanolamine (DEPE), 1-stearoyl-2-oleoyl-sn-glycero-3-phosphoethanolamine (SOPE), 1,2-dioleoyl-sn-glycero-3-phosphoglycerol (DOPG), 1,2-dielaidoyl-sn-glycero-3-phosphoethanolamine (18-1-trans PE), 1,2-dioleoyl-sn-glycero-3-phospho-L-serine (DOPS), dioctadecylamine (DODA), 1,2-dioleoyl-sn-glycero-3-phosphoethanolamine (DOPE), and combinations and derivatives thereof. In one embodiment, the first, second, and third lipid-linkers are each independently selected from the group consisting of DSPE, DSG, DEPE, SOPE, DOPG, 18-1-trans PE, DOPS, DODA, DOPE, and combinations thereof. In one embodiment, the molecular weight of each of the second and third hydrophilic polymers is at least about 10%, 15%, 20%, 25%, 30%, 35%, 40%, 45%, 47%, 50%, 55%, 60%, 65%, 70%, 75%, 80%, 85%, 90%, 95%, 100%, 110%, 120%, 130%, 140%, 150%, 160%, 170%, 180%, 190%, 200% or more greater than the molecular weight of the first hydrophilic polymer. In one embodiment, the molecular weight of each of the second and third hydrophilic polymers is at least about 40%, 45%, 47%, 50%, 55%, 60%, 65%, 70%, 75%, 80%, 85%, 90%, 95%, 100% or more greater than the molecular weight of the first hydrophilic polymer.

In one embodiment, the molecular weight of the first hydrophilic polymer is about 2000 Daltons (Da) to about 3400 Da. In one embodiment, the molecular weight of the first hydrophilic polymer is about 2000 Da or about 3400 Da. In one embodiment, the molecular weight of each of the second and third hydrophilic polymers is about 3400 Da to about 7000 Da. In one embodiment, the molecular weight of each of the second and third hydrophilic polymers is at least about 3400 Da, at least about 3500 Da, at least about 3600 Da, at least about 3700 Da, at least about 3800 Da, at least about 3900 Da, at least about 4000 Da, at least about 4100 Da, at least about 4200 Da, at least about 4300 Da, at least about 4400 Da, at least about 4500 Da, at least about 4600 Da, at least about 4700 Da, at least about 4800 Da, at least about 4900 Da, at least about 5000 Da, at least about 5100 Da, at least about 5200 Da, at least about 5300 Da, at least about 5400 Da, at least about 5500 Da, at least about 5600 Da, at least about 5700 Da, at least about 5800 Da, at least about 5900 Da, at least about 6000 Da, at least about 6100 Da, at least about 6200 Da, at least about 6300 Da, at least about 6400 Da, at least about 6500 Da, at least about 6600 Da, at least about 6700 Da, at least about 6800 Da, at least about 6900 Da, or at least about 7000 Da.

In one embodiment, the first targeting moiety and the second targeting moiety are each tissue- and/or cell-type specific targeting moieties. In one embodiment, the first targeting moiety and the second targeting moiety each bind to a different tissue- and/or cell-type specific antigen. In one embodiment, the first targeting moiety and the second targeting moiety each bind to a different antigen on the same tissue and/or cell-type. In one embodiment, the first targeting moiety and the second targeting moiety each bind to antigens on different tissue- and/or cell-types. In one embodiment, the tissue and/or cell-type is selected from the group consisting of a hematopoietic stem or progenitor cell (HSPC), a hematopoietic stem cell (HSC), a liver cell, a muscle cell, a retinal cell, a skin cell, a nerve cell, a brain cell, a kidney cell, an ovarian cell, a testicular cell, a uterine cell, an endocrine cell, a bone cell, an epithelial cell, an endothelial cell, and a lung cell. In one embodiment, at least one of the first targeting moiety and the second targeting moiety binds to a hematopoietic stem or progenitor cell (HSPC) specific antigen. In one embodiment, at least one of the first targeting moiety and the second targeting moiety binds to a hematopoietic stem cell (HSC) specific antigen. In one embodiment, each of the first targeting moiety and the second targeting moiety binds to a different HSPC specific antigen. In one embodiment, each of the first targeting moiety and the second targeting moiety binds to a different HSC specific antigen.

In one embodiment, each of the first and second targeting moieties independently binds to an antigen selected from the group consisting of CD45, CD46, CD135, CD90, CD117, CD133, ADAM8, ADAM28, ADGRE2, ASCT1, ASCT2, CALHN2, CD33, CD34, CD37, CD43, CD44, CD49f, CD71, CD79A, CD79B, CD84, CD105, CD110, CD123, CD126, CD131, CD133, CD146, CD164, CD184, CD244, CD300f, CD300LF, CD370, CSF3R, CSMD2, EFNA3, EPHB2, FASLG, GPI-80, GPR183, IGSF8, ITGA3, LAIR1, LILRA2, PTAFR, SELL, SLC2A5, TNFRSF8, and VCAM1. In one embodiment, at least one of the first and second targeting moieties binds to an antigen selected from the group consisting of CD45, CD117, and CD135. In one embodiment, the first targeting moiety binds to CD45. In one embodiment, the first targeting moiety binds CD45, and the second targeting moiety binds to CD117. In one embodiment, the first targeting moiety binds CD45, and the second targeting moiety binds to CD135.

In one embodiment, the stealth LNP comprises a total of at least 5 targeting moieties, at least 10 targeting moieties, at least 15 targeting moieties, at least 20 targeting moieties, at least 25 targeting moieties, at least 30 targeting moieties, at least 35 targeting moieties, at least 40 targeting moieties, at least 42 targeting moieties, at least 45 targeting moieties, at least 50 targeting moieties, at least 52 targeting moieties, at least 55 targeting moieties, at least 60 targeting moieties, at least 65 targeting moieties, at least 70 targeting moieties, at least 75 targeting moieties, at least 80 targeting moieties, at least 84 targeting moieties, at least 85 targeting moieties, at least 90 targeting moieties, at least 95 targeting moieties, at least 100 targeting moieties, at least 104 targeting moieties, at least 110 targeting moieties, at least 120 targeting moieties, at least 124 targeting moieties, at least 126 targeting moieties, at least 130 targeting moieties, at least 140 targeting moieties, at least 150 targeting moieties, at least 156 targeting moieties, at least 160 targeting moieties, at least 168 targeting moieties, at least 170 targeting moieties, at least 180 targeting moieties, at least 190 targeting moieties, at least 200 targeting moieties, at least 208 targeting moieties, at least 210 targeting moieties, at least 220 targeting moieties, at least 230 targeting moieties, at least 240 targeting moieties, at least 250 targeting moieties, at least 260 targeting moieties, at least 270 targeting moieties, at least 280 targeting moieties, at least 290 targeting moieties, at least 300 targeting moieties, at least 310 targeting moieties, at least 320 targeting moieties, at least 330 targeting moieties, at least 340 targeting moieties, at least 350 targeting moieties, at least 360 targeting moieties, at least 370 targeting moieties, at least 380 targeting moieties, at least 390 targeting moieties, or at least 400 targeting moieties per LNP.

In one embodiment, the stealth LNP comprises a total of fewer than 400 targeting moieties, fewer than 390 targeting moieties, fewer than 380 targeting moieties, fewer than 370 targeting moieties, fewer than 360 targeting moieties, fewer than 350 targeting moieties, fewer than 340 targeting moieties, fewer than 330 targeting moieties, fewer than 320 targeting moieties, fewer than 310 targeting moieties, fewer than 300 targeting moieties, fewer than 290 targeting moieties, fewer than 280 targeting moieties, fewer than 270 targeting moieties, fewer than 260 targeting moieties, fewer than 250 targeting moieties, fewer than 240 targeting moieties, fewer than 230 targeting moieties, fewer than 220 targeting moieties, fewer than 210 targeting moieties, fewer than 200 targeting moieties, fewer than 190 targeting moieties, fewer than 180 targeting moieties, fewer than 170 targeting moieties, fewer than 160 targeting moieties, fewer than 150 targeting moieties, fewer than 140 targeting moieties, fewer than 130 targeting moieties, fewer than 120 targeting moieties, fewer than 110 targeting moieties, fewer than 100 targeting moieties, fewer than 95 targeting moieties, fewer than 90 targeting moieties, fewer than 85 targeting moieties, fewer than 80 targeting moieties, fewer than 75 targeting moieties, fewer than 70 targeting moieties, fewer than 65 targeting moieties, fewer than 60 targeting moieties, fewer than 55 targeting moieties, fewer than 50 targeting moieties, fewer than 45 targeting moieties, fewer than 40 targeting moieties, fewer than 35 targeting moieties, fewer than 30 targeting moieties, fewer than 25 targeting moieties, fewer than 20 targeting moieties, fewer than 15 targeting moieties, or fewer than 10 targeting moieties per LNP.

In one embodiment, the stealth LNP comprises a total of about 5-400 targeting moieties, about 10-390 targeting moieties, about 20-380 targeting moieties, about 30-370 targeting moieties, about 40-360 targeting moieties, about 50-350 targeting moieties, about 60-340 targeting moieties, about 70-330 targeting moieties, about 80-320 targeting moieties, about 90-310 targeting moieties, about 100-300 targeting moieties, about 110-290 targeting moieties, about 120-280 targeting moieties, about 130-270 targeting moieties, about 140-260 targeting moieties, about 150-250 targeting moieties, about 160-249 targeting moieties, about 170-230 targeting moieties, about 180-220 targeting moieties, about 195-215 targeting moieties, about 200-210 targeting moieties, about 210-250 targeting moieties, about 250-300 targeting moieties, about 300-350 targeting moieties, or about 350-400 targeting moieties per LNP.

In one embodiment, the stealth LNP comprises a total of about 5-50 targeting moieties, about 50-100 targeting moieties, about 100-150 targeting moieties, about 150-200 targeting moieties, about 200-250 targeting moieties, about 250-300 targeting moieties, about 300-350 targeting moieties, or about 350-400 targeting moieties per LNP. In one embodiment, the stealth LNP comprises a total of about 5-100 targeting moieties, about 100-200 targeting moieties, about 200-300 targeting moieties, or about 300-400 targeting moieties per LNP. In one embodiment, the stealth LNP comprises a total of about 5-20 targeting moieties, about 20-40 targeting moieties, about 40-60 targeting moieties, about 60-80 targeting moieties, about 80-100 targeting moieties, about 100-120 targeting moieties, about 120-140 targeting moieties, about 140-160 targeting moieties, about 160-180 targeting moieties, about 180-200 targeting moieties, about 200-220 targeting moieties, about 220-240 targeting moieties, about 240-260 targeting moieties, about 260-280 targeting moieties, about 280-300 targeting moieties, about 200-320 targeting moieties, about 320-340 targeting moieties, about 340-360 targeting moieties, about 360-380 targeting moieties, or about 380-400 targeting moieties per LNP.

In one embodiment, the stealth LNP comprises a total of about 5-10 targeting moieties, about 10-20 targeting moieties, about 20-30 targeting moieties, about 30-40 targeting moieties, about 40-50 targeting moieties, about 50-60 targeting moieties, about 60-70 targeting moieties, about 70-80 targeting moieties, about 80-90 targeting moieties, about 90-100 targeting moieties, about 100-110 targeting moieties, about 110-120 targeting moieties, about 120-130 targeting moieties, about 130-140 targeting moieties, about 140-150 targeting moieties, about 150-160 targeting moieties, about 160-170 targeting moieties, about 170-180 targeting moieties, about 180-190 targeting moieties, about 190-200 targeting moieties, about 210-220 targeting moieties, about 220-230 targeting moieties, about 230-240 targeting moieties, about 240-250 targeting moieties, about 250-260 targeting moieties, about 260-270 targeting moieties, about 270-280 targeting moieties, about 280-290 targeting moieties, about 290-300 targeting moieties, about 300-310 targeting moieties, about 310-320 targeting moieties, about 320-330 targeting moieties, about 330-340 targeting moieties, about 340-350 targeting moieties, about 350-360 targeting moieties, about 360-370 targeting moieties, about 370-380 targeting moieties, about 380-390 targeting moieties, or about 390-400 targeting moieties per LNP. In one embodiment, the stealth LNP comprises a total of about 5, 10, 15, 20, 25, 30, 35, 40, 42, 45, 50, 52, 55, 60, 65, 70, 75, 80, 84, 85, 90, 95, 100, 104, 105, 110, 115, 120, 125, 126, 130, 135, 140, 145, 150, 155, 156, 160, 165, 168, 170, 175, 180, 185, 190, 195, 200, 205, 208, 210, 215, 220, 225, 230, 235, 240, 245, 250, 255, 260, 265, 270, 275, 280, 285, 290, 295, 300, 305, 310, 315, 320, 325, 330, 335, 340, 345, 340, 345, 350, 355, 360, 365, 370, 375, 380, 385, 390, 390, 395, or 400 targeting moieties per LNP.

In one embodiment, each targeting moiety is a VHH. In one embodiment, the stealth LNP comprises a total of about 20-400 VHH targeting moieties, about 30-350 VHH targeting moieties, about 40-300 VHH targeting moieties, about 50-250 VHH targeting moieties, or about 52-210 VHH targeting moieties per LNP. In one embodiment, the stealth LNP comprises a total of about 52, 104, 156, 208, 210, 220, 230, 240, 250, 260, 270, 280, 290, or 300 VHH targeting moieties per LNP. In one embodiment, each targeting moiety is an scFv. In one embodiment, the stealth LNP comprises a total of about 60-250 scFv targeting moieties, about 70-200 scFv targeting moieties, about 80-150 scFv targeting moieties, or about 84-125 scFv targeting moieties per LNP. In one embodiment, the stealth LNP comprises a total of about 84, 126, 168, or 210 scFv targeting moieties per LNP. In one embodiment, the stealth LNP comprises a total of about 126 scFv targeting moieties per LNP. In one embodiment, the first and second targeting moieties are present at a combined molar percentage of about 0.001% to about 0.1% In one embodiment, the first and second targeting moieties are present at a combined molar percentage of about 0.1% of total lipid, or wherein the first and second targeting moieties are present at a combined molar percentage of about 20% of the combined molar percentage of second and third lipid-anchored polymers.

In one embodiment, the sterol is selected from the group consisting of cholesterol, beta-sitosterol, stigmasterol, beta-sitostanol, campesterol, brassicasterol, derivatives thereof, and combinations thereof. In one embodiment, the sterol is cholesterol. In one embodiment, the sterol is present at a molar percentage of about 35% to about 40%. In one embodiment, the sterol is present at a molar percentage of about 37% to about 40%. In one embodiment, the sterol is present at a molar percentage of about 39% to about 40%.

In one embodiment, the ionizable lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), DLin-MC3-DMA, N-[1-(2,3-dioleyloxy)propyl]-N,N,N-trimethylammonium chloride (DOTMA), (dioleyl)methylpyridinium), 1,2-dimyristyloxypropyl-3-dimethylhydroxyethylammonium bromide (DMRIE), 1,2-dioleoyl-3-dimethyl-hydroxyethyl ammonium bromide (DORIE), 1,2-dioleoyloxypropyl-3-dimethylhydroxyethyl ammonium chloride (DORI), Di-alkylated Amino Acid (DILA2), C18:1-norArg-C16), Dioleyldimethylammonium chloride (DODAC), 1-palmitoyl-2-oleoyl-sn-glycero-3-ethylphosphocholine (POEPC), 1,2-dimyristoleoyl-sn-glycero-3-ethylphosphocholine (MOEPC), Dioctadecyldimethylammonium bromide (DDAB), 1,2-dilinoleyloxy-3-dimethylaminopropane (DLinDMA), 2,2-dilinoleyl-4-(2-dimethylaminoethyl)-[1,3]-dioxolane (DLin-KC2-DMA), heptatriaconta-6,9,28,31-tetraen-19-yl-4-(dimethylamino)butanoate (DLin-MC3-DMA), 1,2-Dioleoyloxy-3-dimethylaminopropane (DODAP), 1,2-Dioleyloxy-3-dimethylaminopropane (DODMA), Morpholinocholesterol (Mo-CHOL), (R)-5-(dimethylamino)pentane-1,2-diyl dioleate hydrochloride (DODAPen-C1), (R)-5-guanidinopentane-1,2-diyl dioleate hydrochloride (DOPen-G), and (R)-N,N,N-trimethyl-4,5-bis(oleoyloxy)pentan-1-aminium chloride (DOTAPen), SMA102, L369, L319, LPO1, SS-cleavable lipid, and combinations and mixtures thereof.

In one embodiment, the ionizable lipid is selected from the group consisting of the lipids set forth in Table 6, or a pharmaceutically acceptable salt thereof. In one embodiment, the ionizable lipid comprises Lipid No. 87 or a pharmaceutically acceptable salt or ester thereof, or a deuterated analogue thereof. In one embodiment, the ionizable lipid comprises Lipid No. 119 or a pharmaceutically acceptable salt or ester thereof, or a deuterated analogue thereof.

LIPID 87

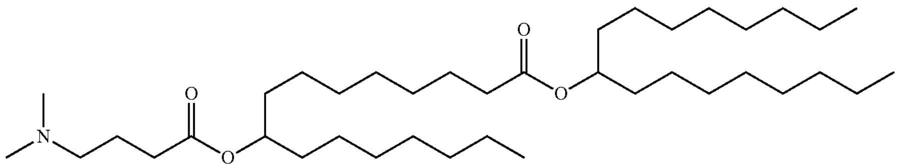

heptadecan-9-yl 9-((4-(dimethylamino)butanoyl)oxy)hexadecanoate

LIPID 119

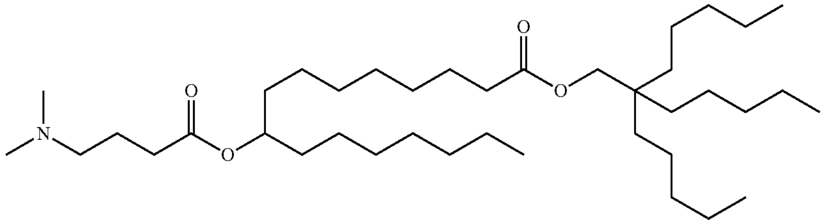

2,2-dipentylheptyl 9-((4-(dimethylamino)butanoyl)oxy)hexadecanoate

N-[1-(2,3-dioleoyloxy)propyl]-N,N,N-trimethylammonium chloride (DOTAP), 1,2-dioleoyl-sn-glycero-3-ethylphosphocholine (DOEPC), 1,2-dilauroyl-sn-glycero-3-ethylphosphocholine (DLEPC), 1,2-dimyristoyl-sn-glycero-3-ethylphosphocholine (DMEPC), 1,2-dimyristoleoyl-sn-glycero-3-ethylphosphocholine (14:1), N1-[2-((1S)-1-[(3-aminopropyl)amino]-4-[di(3-amino-propyl)aminolbutylcarboxamidoiethyl]-3,4-di[oleyloxy]-benzamide (MVL5), Dioctadecylamido-glycylspermine (DOGS), 3b-[N—(N',N'-dimethylaminoethyl)carbamoyl] cholesterol (DC-Chol), Dioctadecyldimethylammonium Bromide (DDAB), a Saint lipid, SAINT-2, N-methyl-4-

In one embodiment, the ionizable lipid is present at a molar percentage of about 40% to about 50%, or wherein the ionizable lipid is present at a molar percentage of about 45% to about 50%. In one embodiment, the stealth LNP herein disclosed further comprises a helper lipid. In one embodiment, the helper lipid is distearoylphosphatidylcholine (DSPC). In one embodiment, the helper lipid is selected from the group consisting of distearoyl-sn-glycero-phosphoethanolamine (DSPE), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), monomethyl-phosphatidylethanolamine (such as 16-O-monomethyl PE), dimethyl-phosphatidylethanolamine (such as 16-O-dimethyl PE), 18-1-trans PE, 1-stearoyl-2-oleoyl-phosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoyl phosphatidylcholine (DMPC), dimyristoyl phosphatidylglycerol (DMPG), distearoylphosphatidylglycerol (DSPG), dierucoylphosphatidylcholine (DEPC), palmitoyloleyolphosphatidylglycerol (POPG), dielaidoyl-phosphatidylethanolamine (DEPE), 1,2-dilauroyl-sn-glycero-3-phosphoethanolamine (DLPE); 1,2-diphytanoyl-sn-glycero-3-phosphoethanolamine (DPHyPE); lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidicacid, cerebrosides, dicetylphosphate, lysophosphatidylcholine, dilinoleoylphosphatidylcholine, DODA, ceramide, and derivatives and combinations thereof.

In one embodiment, the helper lipid is present at a molar percentage of about 10%. In one embodiment, the first and second reactive moieties are each independently selected from the group consisting of maleimide, thiol, azide, click chemistry reagent, and combinations thereof. In one embodiment, the first and second reactive moieties are both maleimide or both thiol. In one embodiment, the first and second reactive moieties are both maleimide, and wherein the third and fourth reactive moieties are both thiol. In one embodiment, the first and second reactive moieties are both thiol, and wherein the third and fourth reactive moieties are both maleimide. In one embodiment, the first reactive moiety is maleimide or thiol and the second reactive moiety is azide or DBCO. In one embodiment, the first and second reactive moieties are both azide, and wherein the third and fourth reactive moieties are both DBCO. In one embodiment, the first and second reactive moieties are both DBCO, and wherein the third and fourth reactive moieties are both azide. In one embodiment, neither of the first, second, third, nor fourth reactive moiety is azide or DBCO.

In one embodiment, the stealth LNP is present in an LNP composition comprising a plurality of LNPs having an average diameter of about 40 nm to about 120 nm. In one embodiment, the stealth LNP is present in an LNP composition comprising a plurality of LNPs having an average diameter of about 90 nm to about 110 nm.

In one embodiment, the TNA encodes a therapeutic protein. In one embodiment, the TNA is selected from the group consisting of mRNA, siRNA, synthetic ribozymes, antisense RNA, and gRNA. In one embodiment, the TNA is mRNA. In one embodiment, the TNA is siRNA. In one embodiment, the TNA is selected from the group consisting of single-stranded DNA (ssDNA), partially single-stranded DNA (partially ssDNA), and double-stranded DNA (dsDNA). In one embodiment, the TNA is ssDNA or partially single-stranded DNA. In one embodiment, the half-life ($t_{1/2}$) of the LNP in blood in vivo is greater than 3 hours. In one embodiment, the half-life ($t_{1/2}$) of the LNP in blood in vivo is greater than 4 hours. In one embodiment, the half-life ($t_{1/2}$) of the LNP in blood in vivo is between about 3 hours and about 48 hours. In one embodiment, the half-life ($t_{1/2}$) of the LNP in blood in vivo is between about 4 hours and about 48 hours.

In one aspect, disclosed herein is a stealth lipid nanoparticle (LNP) comprising: (a) a therapeutic nucleic acid (TNA); (b) an ionizable lipid; (c) cholesterol; (d) a first lipid-anchored polymer, wherein the first lipid-anchored polymer is DSG-PEG2000-OMe; (e) a second lipid-anchored polymer, wherein the second lipid-anchored polymer comprises DSPE-PEG5000-maleimide conjugated to a first targeting moiety, wherein the first targeting moiety is a variable heavy chain-only antibody (VHH) or a single-chain antibody (scFv); and (f) a third lipid-anchored polymer, wherein the third lipid-anchored polymer comprises DSPE-PEG5000-maleimide conjugated to a second targeting moiety, wherein the second targeting moiety is a variable heavy chain-only antibody (VHH) or a single-chain antibody (scFv); wherein the first targeting moiety and the second targeting moiety are different; wherein the first lipid-anchored polymer, the second lipid-anchored polymer, and the third lipid-anchored polymer are present at a combined molar percentage of about 2% to about 5%, and wherein the second lipid-anchored polymer and the third lipid-anchored polymer are present at a combined molar percentage of about 0.01% to about 0.5%; and optionally wherein the stealth LNP comprises a total of about 5 to 400 total targeting moieties.

In one embodiment, the stealth LNP, comprises: (a) a therapeutic nucleic acid (TNA); (b) about 57.5 mol % ionizable lipid; (c) about 39.5 mol % cholesterol; (d) about 2.8 mol % DSG-PEG2000-OMe; an (e) about 0.2 mol % DSPE-PEG5000-maleimide-VHH or 0.2 mol % DSPE-PEG5000-maleimide-scFv. In one embodiment, the stealth LNP further comprises (f) a helper lipid, optionally wherein the helper lipid is DSPC. In one embodiment, the stealth LNP comprises: (a) a therapeutic nucleic acid (TNA); (b) about 47.5 mol % ionizable lipid; (c) about 39.5 mol % cholesterol; (d) about 2.8 mol % DSG-PEG2000-OMe; (e) about 0.2 mol % DSPE-PEG5000-maleimide-VHH or 0.2 mol % DSPE-PEG5000-maleimide-scFv; and (f) about 10% DSPC. In one embodiment, the ionizable lipid is selected from the group consisting of the ionizable lipids set forth in Table 6. In one embodiment, the ionizable lipid is Lipid No. 87.

In one embodiment, the first targeting moiety and the second targeting moiety are each tissue- and/or cell-type specific targeting moieties. In one embodiment, the first targeting moiety and the second targeting moiety each bind to a different tissue- and/or cell-type specific antigen. In one embodiment, the first targeting moiety and the second targeting moiety each bind to a different antigen on the same tissue and/or cell-type. In one embodiment, the first targeting moiety and the second targeting moiety each bind to antigens on a different tissue- and/or cell-types. In one embodiment, the tissue and/or cell-type is selected from the group consisting of a hematopoietic stem or progenitor cell (HSPC), a hematopoietic stem cell (HSC), a liver cell, a muscle cell, a retinal cell, a skin cell, a nerve cell, a brain cell, a kidney cell, an ovarian cell, a testicular cell, a uterine cell, an endocrine cell, a bone cell, an epithelial cell, an endothelial cell, and a lung cell. In one embodiment, at least one of the first targeting moiety and the second targeting moiety binds to a hematopoietic stem or progenitor cell (HSPC) specific antigen. In one embodiment, at least one of the first targeting moiety and the second targeting moiety binds to a hematopoietic stem cell (HSC) specific antigen. In one embodiment, each of the first targeting moiety and the second targeting moiety binds to a different HSPC specific antigen. In one embodiment, each of the first targeting moiety and the second targeting moiety binds to a different HSC specific antigen.

In one embodiment, each of the first and second targeting moieties independently binds to an antigen selected from the group consisting of CD45, CD46, CD135, CD90, CD117, CD133, ADAM8, ADAM28, ADGRE2, ASCT1, ASCT2, CALHN2, CD33, CD34, CD37, CD43, CD44, CD49f, CD71, CD79A, CD79B, CD84, CD105, CD110, CD123, CD126, CD131, CD133, CD146, CD164, CD184, CD244, CD300f, CD300LF, CD370, CSF3R, CSMD2, EFNA3, EPHB2, FASLG, GPI-80, GPR183, IGSF8, ITGA3, LAIR1, LILRA2, PTAFR, SELL, SLC2A5, TNFRSF8, and VCAM1. In one embodiment, at least one of the first and second targeting moieties binds to an antigen selected from the group consisting of CD45, CD117, and CD135. In one embodiment, the first targeting moiety binds to CD45. In one embodiment, the first targeting moiety binds CD45, and the second targeting moiety binds to CD117. In one embodiment, the first targeting moiety binds CD45, and the second targeting moiety binds to CD135. In one embodiment, the first or second targeting moiety is an anti-CD117 scFv, optionally wherein the second targeting moiety is selected from the group consisting of L80CD117VH and L80CD117VL, L95CD117 scFv, L81CD117 scFv, L88CD117 scFv and L86CD117. In one embodiment, the first or second targeting moiety is an anti-CD45 scFv, optionally wherein the first targeting moiety is selected from the group consisting of L111-CD45 scFv (SEQ ID NO: 16), L112CD45 scFv (SEQ ID NO: 19) and L86CD45 scFv (SEQ ID NO: 28).

In one aspect, herein disclosed is a cell comprising the stealth LNP herein disclosed. In one embodiment, the cell is in vitro, ex vivo, or in vivo. In one embodiment, the cell is in vivo. In one embodiment, the cell is selected from the group consisting of a hematopoietic stem or progenitor cell (HSPC), a hematopoietic stem cell (HSC), a liver cell, a muscle cell, a retinal cell, a skin cell, a nerve cell, a brain cell, a kidney cell, an ovarian cell, a testicular cell, a uterine cell, an endocrine cell, a bone cell, an epithelial cell, an endothelial cell, and a lung cell. In one embodiment, the cell is a CD34+ cell. In one embodiment, the cell is a hematopoietic stem cell (HSC) or hematopoietic stem or progenitor cell (HSPC). In one embodiment, the cell is an HSPC. In one embodiment, the cell is an HSC.

In one aspect, herein disclosed is a pharmaceutical composition comprising the stealth LNP herein disclosed. In one aspect, herein disclosed is a pharmaceutical composition comprising the cell herein disclosed. In one embodiment, the pharmaceutical composition, herein disclosed, further comprises a pharmaceutically acceptable excipient or carrier.

In one aspect, herein disclosed is a method of treating a disease or disorder in a subject, comprising administering to the subject a therapeutically effective amount of the stealth LNP herein disclosed. In one aspect, herein disclosed is a method of treating a disease or disorder in a subject, comprising administering to the subject a therapeutically effective amount of the cell herein disclosed.

In one aspect, herein disclosed is a method of treating a disease or disorder in a subject, comprising administering to the subject a therapeutically effective amount of the pharmaceutical composition herein disclosed. In one embodiment, the disease or disorder is a genetic disease or disorder.

In one embodiment, the disease or disorder is selected from the group consisting of sickle cell disease, melanoma, hemophilia A (clotting factor VIII (FVIII) deficiency) and hemophilia B (clotting factor IX (FIX) deficiency), cystic fibrosis (CFTR), familial hypercholesterolemia (LDL receptor defect), hepatoblastoma, Wilson disease, phenylketonuria (PKU), congenital hepatic porphyria, inherited disorders of hepatic metabolism, Lesch-Nyhan syndrome, thalassaemias, xeroderma pigmentosum, Fanconi anemia, retinitis pigmentosa, ataxia telangiectasia, Bloom syndrome, retinoblastoma, mucopolysaccharide storage diseases (e.g., Hurler syndrome (MPS Type I), Scheie syndrome (MPS Type I S), Hurler-Scheie syndrome (MPS Type I H-S), Hunter syndrome (MPS Type II), Sanfilippo Types A, B, C, and D (MPS Types III A, B, C, and D), Morquio Types A and B (MPS IVA and MPS IVB), Maroteaux-Lamy syndrome (MPS Type VI), Sly syndrome (MPS Type VII), hyaluronidase deficiency (MPS Type IX)), Niemann-Pick Disease Types A/B, C1 and C2, Fabry disease, Schindler disease, GM2-gangliosidosis Type II (Sandhoff Disease), Tay-Sachs disease, Metachromatic Leukodystrophy, Krabbe disease, Mucolipidosis Type I, II/III and IV, Sialidosis Types I and II, Glycogen Storage disease Types I and II (Pompe disease), Gaucher disease Types I, II and III, cystinosis, Batten disease, Aspartylglucosaminuria, Salla disease, Danon disease (LAMP-2 deficiency), Lysosomal Acid Lipase (LAL) deficiency, neuronal ceroid lipofuscinoses (CLN1-8, INCL, and LINCL), sphingolipidoses, galactosialidosis, amyotrophic lateral sclerosis (ALS), Parkinson's disease, Alzheimer's disease, Huntington's disease, spinocerebellar ataxia, spinal muscular atrophy, Friedreich's ataxia, Duchenne muscular dystrophy (DMD), Becker muscular dystrophies (BMD), dystrophic epidermolysis bullosa (DEB), ectonucleotide pyrophosphatase 1 deficiency, generalized arterial calcification of infancy (GACI), Leber Congenital Amaurosis, Stargardt macular dystrophy (ABCA4), ornithine transcarbamylase (OTC) deficiency, Usher syndrome, age-related macular degeneration (AMD), alpha-1 antitrypsin deficiency, progressive familial intrahepatic cholestasis (PFIC) type I (ATP8B1 deficiency), type II (ABCB11), type III (ABCB4), or type IV (TJP2), and Cathepsin A deficiency.

In one embodiment, the disease or disorder is selected from the group consisting of Sickle Cell Disease (SCD), Thalassemia, Pyruvate Kinase Deficiency (PKD), G6PD deficiency, Hereditary elliptocytosis, Familial Thrombocytosis, Polycythemia vera, Erythropoietic protoporphyria, Leukocyte Adhesion Deficiency, Hereditary spherocytosis, Paroxysmal noctunal hemoglobinuria (PNH), Red cell aplasia, HFE-related hemochromatosis, Diamond Blackfan Amenia, Fanconi Anemia, Hemophagocytic Lymphohistiocytosis, Thrombocytopenia Absent Radius (TAR) syndrome, Myelodysplastic Syndromes (MDS), Histiocytosis, Chronic Granulomatous Disease (CGD), Leukocytes Adhesion Deficiency (LAD), Myoloperoxidase Deficiency, Neutropenia, Glanzmann's Thrombasthenia, Bernard-Soulier Syndrome, Gray Platelet Syndrome, Storage Pool Deficiency, Hemoglobin E disease, Hemoglobin C disease, Hereditary stomatocytosis, Hereditary persistence of fetal hemoglobin (HPFH), Southeast Asian ovalocytosis, Rh-null disease, Shwachman-Diamond Syndrome (SBDS), Hemophilia A, Hemophilia B, Gaucher disease, Fabry disease, and MPS Types I and II.

In one aspect, disclosed herein is a method for producing a stealth LNP, the method comprising: (i) providing an LNP comprising (a) a therapeutic nucleic acid (TNA); (b) an ionizable lipid; (c) a sterol; (d) a first lipid-anchored polymer comprising a first hydrophilic polymer and a first lipid-linker, wherein the first lipid-linker comprises a first lipid comprising at least two hydrophobic tails, and wherein each hydrophobic tail comprises a carbon chain having 18 carbon atoms (C18); (e) a second lipid-anchored polymer comprising a second hydrophilic polymer, a second lipid-linker, and a first reactive moiety; wherein the second lipid-linker comprises a second lipid comprising at least two hydrophobic tails, wherein each hydrophobic tail comprises a carbon chain having 18 carbon atoms (C18); (f) a third lipid-anchored polymer comprising a third hydrophilic polymer, a third lipid-linker, and a second reactive moiety; wherein the third lipid-linker comprises a third lipid comprising at least two hydrophobic tails, wherein each hydrophobic tail comprises a carbon chain having 18 carbon atoms (C18); wherein the molecular weight of the second hydrophilic polymer is greater than the molecular weight of the first hydrophilic polymer, and wherein the molecular weight of the third hydrophilic polymer is greater than the molecular weight of the first hydrophilic polymer; wherein the first lipid-anchored polymer, the second lipid-anchored polymer, and the third lipid-anchored polymer are present at a combined molar percentage of about 2% to about 5%, and wherein the second and third lipid-anchored polymers are present at a combined molar percentage of about 0.01% to about 0.5%; and optionally (f) a helper lipid; (ii) providing a first targeting moiety comprising a third reactive moiety, wherein the first targeting moiety is a variable heavy chain-only antibody (VHH) or a single-chain antibody (scFv), wherein the first reactive moiety and the third reactive moiety are capable of reacting to form a covalent linkage; (iii) providing a second targeting moiety comprising a fourth reactive moiety, wherein the second targeting moiety is a variable heavy chain-only antibody (VHH) or a single-chain antibody (scFv), wherein the second reactive moiety and the fourth reactive moiety are capable of reacting to form a covalent linkage, and wherein the first targeting moiety and the second targeting moiety are different; and (iv) contacting the LNP of (i) with the targeting moieties of (ii) and (iii) under conditions sufficient to allow a reaction between the first reactive moiety and the third reactive moiety and between the second reactive moiety and the fourth reactive moiety, resulting in a covalent linkage between the first reactive moiety and the second reactive moiety and a covalent linkage between the second reactive moiety and the fourth reactive moiety; thereby producing a stealth LNP.

In one embodiment, at least 90% of the first and second targeting moieties from (ii) and (iii) are conjugated to the stealth LNP. In one embodiment, at least 95% of the first and second targeting moieties from (ii) and (iii) are conjugated to the stealth LNP. In one embodiment, the size of the stealth LNP is less than 10% greater than the size of the LNP prior to conjugation with the first and second targeting moieties. In one embodiment, the first and second targeting moieties in steps (ii) (iii) are present at a combined molar percentage of about 0.001% to about 0.1%. In one embodiment, one of the first or second targeting moieties is an anti-CD117 scFv, optionally wherein the second targeting moiety is selected from the group consisting of L80CD117VH and L80CD117VL. L95CD117 scFv, L81CD117 scFv, L88CD117 scFv and L86CD117. In one embodiment, one of the first or targeting moieties is an anti-CD45 scFv, optionally wherein the first targeting moiety is selected from the group consisting of L111-CD45 scFv (SEQ ID NO: 16), L112-CD45 scFv (SEQ ID NO: 19) and L86-CD45 scFv (SEQ ID NO: 28).

In one aspect, disclosed herein is a method for producing a stealth LNP, the method comprising: (i) providing an LNP comprising (a) a therapeutic nucleic acid (TNA); (b) an ionizable lipid; (c) a sterol; (d) a first lipid-anchored polymer comprising a first hydrophilic polymer and a first lipid-linker, wherein the first lipid-linker comprises a first lipid comprising at least two hydrophobic tails, and wherein each hydrophobic tail comprises a carbon chain having 18 carbon atoms (C18); (e) a second lipid-anchored polymer comprising a second hydrophilic polymer, a second lipid-linker, and a first reactive moiety; wherein the second lipid-linker comprises a second lipid comprising at least two hydrophobic tails, wherein each hydrophobic tail comprises a carbon chain having 18 carbon atoms (C18); (e) a third lipid-anchored polymer comprising a third hydrophilic polymer, a third lipid-linker, and a second reactive moiety; wherein the third lipid-linker comprises a third lipid comprising at least two hydrophobic tails, wherein each hydrophobic tail comprises a carbon chain having 18 carbon atoms (C18); and optionally (f) a helper lipid; wherein the molecular weight of each of the second and third hydrophilic polymers is greater than the molecular weight of the first hydrophilic polymer; wherein the first, second, and third lipid-anchored polymers are present at a combined molar percentage of about 2% to about 5%, and wherein the second and third lipid-anchored polymers are present at a combined molar percentage of about 0.01% to about 0.5%; (ii) providing a first targeting moiety comprising a third reactive moiety, wherein the first targeting moiety is a variable heavy chain-only antibody (VHH) or a single-chain antibody (scFv), wherein the first reactive moiety and the third reactive moiety are capable of reacting to form a covalent linkage; (iii) providing a second targeting moiety comprising a fourth reactive moiety, wherein the second targeting moiety is a variable heavy chain-only antibody (VHH) or a single-chain antibody (scFv), wherein the second reactive moiety and the fourth reactive moiety are capable of reacting to form a covalent linkage, and wherein the first targeting moiety and the second targeting moiety are different; (iv) contacting the LNP of (i) with the first and second targeting moieties of (ii) and (iii) under conditions sufficient to allow a reaction between the first reactive moiety and the third reactive moiety and between the second reactive moiety and the fourth reactive moiety, resulting in a covalent linkage between the first reactive moiety and the third reactive moiety and between the second reactive moiety and the fourth reactive moiety; thereby producing a stealth LNP, optionally wherein the stealth LNP comprises about 5 to 400 targeting moieties.

In one embodiment, at least 90% of the first and second targeting moieties from (ii) and (iii) are conjugated to the stealth LNP. In one embodiment, at least 95% of the first and second targeting moieties from (ii) and (iii) are conjugated to the stealth LNP. In one embodiment, the size of the stealth LNP is less than 10% greater than the size of the LNP prior to conjugation with the first and second targeting moieties. In one embodiment, the first and second targeting moieties in steps (ii) and (iii) are present at a combined molar percentage of about 0.001% to about 0.1%.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

In some embodiments herein, the targeting moiety is also referred to as a ligand.

FIG. 5A shows whole blood PK of stealth LNP with mRNA cargo containing 0.3 mpk Trilink m1Ψ-mLuc. In a separate NHP study, the long circulating half-life of stealth LNPs and very low off-target delivery to the liver and spleen were demonstrated (FIG. 5B).

DETAILED DESCRIPTION

Figure 1:
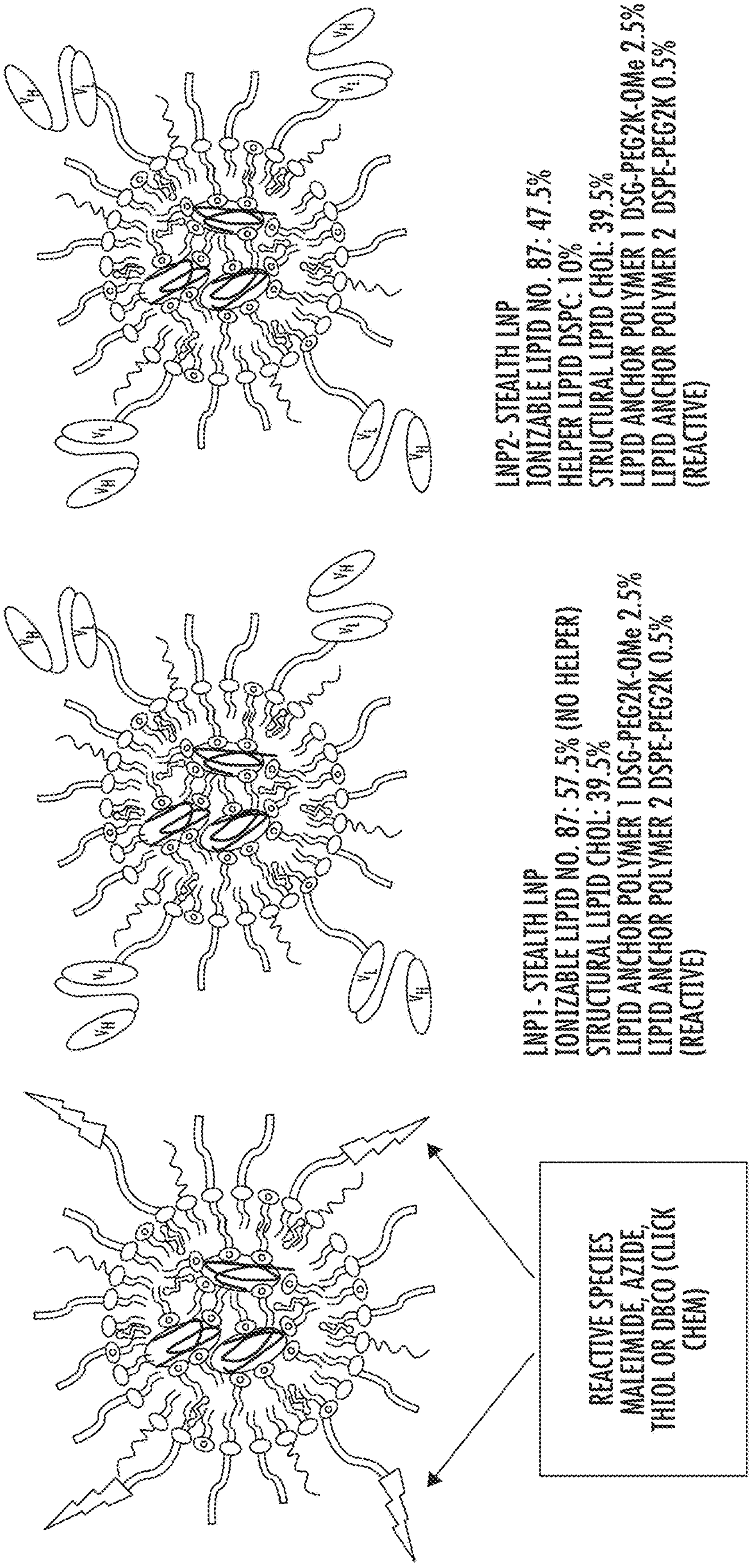
FIG. 1 shows a pictorial illustration of three different stealth LNPs of the present disclosure. The first is a stealth LNP showing the reactive species on the surface but not yet reacted to a targeting moiety. The middle LNP is a stealth LNP1 comprising 57.5 mol % ionizable lipid No. 87; 39.5 mol % cholesterol as structural lipid; 2.5 mol % of lipid-anchor polymer 1 (i.e., DSG-PEG2000-OMe); and 0.5% of lipid anchor polymer No. 2 (i.e., DSPE-PEG5000-Maleimide reactive species) bound to an scFv. The third stealth LNP on the right is 47.5 mol % ionizable lipid No. 87; 10 mol % helper lipid (i.e., DSPC); 39.5 mol % cholesterol structural lipid; 2.5 mol % lipid anchor No. 1 (i.e., DSP-PEG2000-OMe) and 0.5 mol % of lipid-anchor polymer No. 2 as DSPE-PEG5K-Maleimide reacted to an scFv targeting moiety.

The present disclosure provides novel bispecific "stealth" LNP compositions that surprisingly can induce improved expression of therapeutic nucleic acid cargoes by including two different targeting moieties in the same LNP. The bispecific stealth LNPs of the disclosure further exhibit physiological characteristics of prolonged blood circulation time (e.g., increased blood $t_{1/2}$) simultaneously with increased targeting capacity to specific cell-types (e.g., immune effector cells such as T-cells, B-cells, NK cells, and dendritic cells, or hematopoietic stem cells (HSC)), useful for creating genetically modified cells in vivo and/or ex vivo. The bispecific stealth LNPs can encapsulate various types of cargo, such as nucleic acids, e.g., nucleic acids encoding a desired therapeutic protein (e.g., a chimeric antigen receptor an enzyme, an antibody, etc.), or carrying a sequence for a gene/base editing template. The nucleic acid molecules can be various forms of double-stranded DNA, single-stranded DNA, partially single-stranded DNA, or RNA (e.g., mRNA, siRNA, gRNA).

In particular, the bispecific stealth LNPs disclosed herein take advantage of different properties of the antigens the bind to. For example, a stealth LNP may include one targeting moiety that binds to an abundant but slow-internalizing antigen, and a second targeting moiety that binds to a less-abundant, but faster-internalizing antigen. In another embodiment, inclusion of a second targeting moiety may overcome saturation of a single target antigen to provide improved cargo expression. Additionally, the novel bispecific LNPs disclosed herein provide surprising and unexpected "stealth" properties as compared to previously known LNPs by, for example, providing steric stabilization (e.g., enhancing the stealth property of overall LNP characteristic in the circulation (e.g., the blood compartment) by minimizing interactions between opsonins present in the blood and the surface of the LNP). For example, a stealth bispecific LNP of the disclosure comprises a half-life ($t_{1/2}$) in blood in vivo of greater than 3 hours. In other embodiments, a bispecific stealth LNP of the disclosure comprises a half-life ($t_{1/2}$) in blood in vivo of greater than 4 hours. In yet other embodiments, stealth LNP of the disclosure comprises a half-life ($t_{1/2}$) in blood in vivo of between about 3 hours and 48 hours, or between about 4 hours and 48 hours. In contrast, prior to the instant disclosure, the half-life ($t_{1/2}$) in blood in vivo of LNPs was typically around 30 minutes.

Additionally, an optional helper lipid, if present in the bispecific stealth LNP of the disclosure, functions to increase the fusogenicity of the lipid bilayer of the LNP and to facilitate endosomal escape; the structural lipid of the LNP contributes to membrane integrity and stability of the LNP; and the lipid-anchored polymer of the LNP can inhibit aggregation of LNPs and provide steric stabilization (e.g., enhancing the stealth property of overall LNP characteristic in the circulation (e.g., the blood compartment) by minimizing interactions between opsonins present in the blood and the surface of the LNP).

Moreover, the present disclosure provides lipid-anchored polymers wherein the number of aliphatic carbons in the lipid portion of lipid-anchored polymer are crucial for slowing dissociation of the lipid-anchored polymer away from the LNP and allowing the LNP to remain intact and able to avoid non-specific fusion or removal within the first hour in the blood or plasma compartments. The present disclosure provides LNPs where at least one of the lipids in the lipid-anchored polymer contains 18 aliphatic carbons to anchor the lipid-anchored polymer more securely to the LNP.

The present disclosure further provides a "bispecific cell targeting stealth LNP" by combining the stealth characteristics described above with cell targeting of the LNP by conjugation of two or more targeting moieties to the lipid-anchored polymers in the LNP. In particular, the disclosed stealth cell targeting LNP compositions can further comprise two or more targeting moieties such as a single chain fragment variable (scFv) and/or single domain antibody (VHH) linked to the LNP, wherein the scFv or VHH is directed against an antigen present on the surface of a cell (e.g., a tumor cell, T-cell, hematopoietic stem cell (HSC), B-cell, NK cell, etc.), thereby increasing the targeting specificity of the stealth LNP to a desired tissue or cell-type. The bispecific stealth targeting LNPs described herein advantageously provide efficient covalent conjugation with minimal or no effects on blood pharmacokinetics (PK), particle size and stability as compared to unconjugated stealth LNPs.

It is a further finding of the present disclosure that DBCO mediated conjugation (via "Click chemistry") or maleimide conjugation (via thiol—maleimide reaction) between the targeting moiety (e.g., scFv or VHH) and the lipid-anchored polymer present on the surface of the stealth LNP resulted in robust linkages that maintained the physiochemical characteristics of the stealth LNPs and the resultant stealth LNPs comprising a targeting moiety effectively demonstrated highly increased specificity and targeting efficiency to a desired cell-type in vivo.

The present disclosure also provides a bispecific stealth LNP composition comprising lipid-anchored polymers having a reactive species, e.g., maleimide, azide, etc., that are capable of reacting with a targeting moieties functionalized with thiol (—SH) or dibenzocyclooctyne (DBCO) reactive species.

Thus, the present disclosure provides bispecific stealth lipid nanoparticles (LNPs) and LNP compositions (e.g., pharmaceutical compositions) comprising a therapeutic nucleic acid (TNA), e.g., a gene expression vector such as closed-ended DNA (ceDNA), single stranded DNA vector, siRNA, or messenger RNA (mRNA); an ionizable lipid; a structural lipid, e.g., a sterol; and one or more types of lipid-anchored polymers comprising a hydrophilic polymer (e.g., PEG or polyglycerol); and a lipid-linker, e.g., a lipid moiety having at least one hydrophobic tail with 18 carbon atoms in a single aliphatic chain backbone and a linker connecting the polymer to the lipid moiety; with or without an optional "helper" lipid.

I. Definitions

The term "activation", as used herein, refers to the state of a T-cell that has been sufficiently stimulated to induce detectable cellular proliferation. Activation can also be associated with induced cytokine production, and detectable effector functions. The term "activated T cells" refers to, among other things, T-cells that are undergoing cell division.

The term "Chimeric Antigen Receptor" or "CAR" as used herein refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are contiguous with each other. In some embodiments, the set of polypeptides includes a dimerization switch that, upon the presence of a dimerization molecule, can couple the polypeptides to one another, e.g., can couple an antigen binding domain to an intracellular signaling domain. In some aspects, the stimulatory molecule is the zeta chain associated with the T cell receptor complex. In some aspects, the cytoplasmic signaling domain further comprises one or more functional signaling domains derived from at least one costimulatory molecule as defined below. In some aspects, the costimulatory molecule is chosen from the costimulatory molecules described herein, e.g., 4-1BB (i.e., CD137), CD27 and/or CD28. In some aspects, the CAR comprises a chimeric fusion protein comprising an extracellular antigen binding domain, a transmembrane domain and an intracellular signaling domain comprising a functional signaling domain derived from a stimulatory molecule. In some aspects, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In some aspects, the CAR comprises a chimeric fusion protein comprising an extracellular antigen binding domain, a transmembrane domain and an intracellular signaling domain comprising two functional signaling domains derived from one or more costimulatory molecule(s) and a functional signaling domain derived from a stimulatory molecule. In some aspects, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In some aspects, the CAR comprises an optional leader sequence at the amino-terminus (N-ter) of the CAR fusion protein. In some aspects, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane.

A CAR that comprises an antigen binding domain (e.g., a scFv, VHH, or TCR) that targets a specific tumor maker X, such as those described herein, is also referred to as XCAR.

The term "signaling domain" refers to the functional portion of a protein which acts by transmitting information within the cell to regulate cellular activity via defined signaling pathways by generating second messengers or functioning as effectors by responding to such messengers.

The term "antibody" as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules and a fragment.

The term "antibody fragment" refers to at least one portion of an antibody, which retains the ability to specifically interact with (e.g., by binding, steric hindrance, stabilizing/destabilizing, spatial distribution) an epitope of an antigen. Examples of antibody fragments include, but are not limited to, Fab, Fab', F(ab')2, Fv fragments, scFv antibody fragments, disulfide-linked Fvs (sdFv), an Fd fragment consisting of the VH and CHI domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23: 1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies).

The term "antigen" as used herein refers to any foreign substance which induces an immune response in the body.

The term "camelized" VH refers to an ISVD in which one or more amino acid residues in the amino acid sequence of a naturally occurring VH domain from a conventional four-chain antibody by one or more of the amino acid residues that occur at the corresponding position(s) in a VHH domain of a heavy chain antibody. Such "camelizing" substitutions may be inserted at amino acid positions that form and/or are present at the VH-VL interface, and/or at the so-called Camelidae hallmark residues, as defined herein (see also for example WO9404678 and Davies and Riechmann (1994 and 1996)). Reference is made to Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999).

The terms "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progenies will have precisely identical DNA content, due to deliberate or inadvertent mutations. Mutant progeny that has the same function or biological activity as screened for in the originally transformed cell are included. Where distinct designations are intended, it will be clear from the context.

The term "CDR area" refers to an antibody complementarity-determining region (CDR) as defined by any one of the methods commonly used for defining antibody CDRs and which may further include up to one amino acid N-terminal to the defined CDR or up to three amino acids C-terminal to the defined CDR.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "encoding" refers to the inherent property of specific sequences of nucleotides in a polynucleotide, such as a gene, a ceDNA, ssDNA or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "epitope", as used herein, is defined in the context of a molecular interaction between an antibody (e.g., IgG, scFv, VHH, etc.) and its corresponding "antigen" (Ag). Generally, "epitope" refers to the area or region on an Ag to which an antibody (e.g., IgG, scFv, VHH, etc.) specifically recognizes and binds, i.e., the area or region in physical contact with the antibody (e.g., IgG, scFv, VHH, etc.). Physical contact may be defined through distance criteria (e.g., a distance cutoff of 4 Å) for atoms in the human-like VHH and Ag molecules. The physical contacts and distance criteria between an antibody or other binding molecule and the target antigen can be determined through protein crystallography of the antibody-antigen complex.

The term "Fc domain" as used herein is the crystallizable fragment domain or region obtained from an antibody that comprises the $C_H2$ and $C_H3$ domains of an antibody. In an antibody, the two Fe domains are held together by two or more disulfide bonds and by hydrophobic interactions of the $C_H3$ domains. The Fc domain may be obtained by digesting an antibody with the protease papain.

The term "immunoglobulin single-chain variable domains" (abbreviated herein as "ISVD", and interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site.

Typically, in conventional immunoglobulins, a heavy chain variable domain (VH) and a light chain variable domain (VL) interact to form an antigen binding site. In the latter case, the complementarity determining region (CDR) areas of both VH and VL will contribute to the antigen binding site, i.e., a total of six CDRs will be involved in antigen binding site formation. In view of the above definition, the antigen-binding domain of a conventional four-chain antibody (such as an IgG, IgM, IgA, IgD or IgE molecule; known in the art) or of a Fab fragment, a $F(ab)_2$ fragment, an Fv fragment such as a disulfide linked Fv or a scFv fragment, or a diabody (all known in the art) derived from such conventional four-chain antibody, would normally not be regarded as an ISVD, as, in these cases, binding to the respective epitope of an antigen would normally not occur by one (single) immunoglobulin domain, but by a pair of (associating) immunoglobulin domains such as light and heavy chain variable domains, i.e., by a VH-VL pair of immunoglobulin domains, which jointly bind to an epitope of the respective antigen.

In contrast, ISVDs are capable of specifically binding to an epitope of the antigen without pairing with an additional immunoglobulin variable domain. The binding site of an ISVD is formed by a single VHH or VH domain. Hence, the antigen binding site of an ISVD is formed by no more than three CDRs. As such, the single variable domain may be a heavy chain variable domain sequence (e.g., a Vs-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit). An ISVD as used herein is selected from the group consisting of VHHs, human-like VHHs, and camelized VHS.

The term "NANOBODY" and "NANOBODIES" as used herein are registered trademarks of Ablynx N.V. The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

One or more lipid-anchored polymers of the lipid nanoparticles (LNP) of the disclosure may be chemically conjugated to a scFv or VHH directed to an epitope.

The portion of the CAR of the disclosure comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In some aspects, the antigen binding domain of a CAR composition of the disclosure comprises an antibody fragment.

In a further aspect, the CAR comprises an antibody fragment that comprises a scFv. The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), A1-Lazikani et al., (1997) JMB 273,927-948 ("Chothia" numbering scheme), or a combination thereof.

As used herein, the term "binding domain" or "antibody molecule" refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The portion of the CAR of the disclosure comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody, or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In some aspects, the antigen binding domain of a CAR composition of the disclosure comprises an antibody fragment. In a further aspect, the CAR comprises an antibody fragment that comprises a scFv.

The term "antibody heavy chain" as used herein refers to the larger of the two types of polypeptide chains present in antibody molecules in their naturally occurring conformations, and which normally determines the class to which the antibody belongs.

The term "antibody light chain" as used herein refers to the smaller of the two types of polypeptide chains present in antibody molecules in their naturally occurring conformations. Kappa (κ) and lambda (λ) light chains refer to the two major antibody light chain isotypes.

The term "recombinant antibody" as used herein refers to an antibody which is generated using recombinant DNA technology, such as, for example, an antibody expressed by a bacteriophage or yeast expression system. The term may also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" as used herein refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present disclosure includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample or might be macromolecule besides a polypeptide. Such a biological sample can include, but is not limited to, a tissue sample, a tumor sample, a cell or a fluid with other biological components.

The term "bispecific", as used herein in the context of a lipid nanoparticle (LNP), refers to an LNP having two targeting moieties each covalently bound to a lipid-anchored polymer. In some embodiments, bispecific LNPs described herein comprise two different antibodies or antibody fragments (e.g., VHH or scFv) each bound to a separate lipid lipid anchored polymer on the exterior of an LNP. In some embodiments, each targeting moiety may be conjugated to the same type of lipid-anchored polymer. In some embodiments, each targeting moiety may be conjugated to a different type of lipid-anchored polymer. In some embodiments, a bispecific LNP may comprise two targeting moieties that each bind to a different entigen on the same tissue- and/or cell-type. In some embodiments, a bispecific LNP may bind comprise one targeting moiety that binds to an antigen on one tissue- and/or cell type, and a second targeting moiety that binds to an antigen on different tissue- and/or cell-type. A bispecific LNP should not be understood to require a "bispecific antibody" (as described elsewhere herein), but it should also be understood that a bispecific LNP may include a bispecific antibody.

The term "anti-cancer effect" as used herein refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "autologous" as used herein refers to any material derived from the same individual to whom it is later to be re-introduced into the individual.

The term "allogeneic" as used herein refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The phrase "disease associated with expression of a tumor antigen as described herein" includes, but is not limited to, a disease associated with expression of a tumor antigen as described herein or condition associated with cells which express a tumor antigen as described herein including, e.g., proliferative diseases such as a cancer or malignancy or a precancerous condition such as a myelodysplasia, a myelodysplastic syndrome or a preleukemia; or a noncancer related indication associated with cells which express a tumor antigen as described herein. In some aspects, a cancer associated with expression of a tumor antigen as described herein is a hematological cancer. In some aspects, a cancer associated with expression of a tumor antigen as described herein is a solid cancer. Further diseases associated with expression of a tumor antigen described herein include, but not limited to, e.g., atypical and/or non-classical cancers, malignancies, precancerous conditions or proliferative diseases associated with expression of a tumor antigen as described herein. Non-cancer related indications associated with expression of a tumor antigen as described herein include, but are not limited to, e.g., autoimmune disease, (e.g., lupus), inflammatory disorders (allergy and asthma) and transplantation. In some embodiments, the tumor antigen-expressing cells express, or at any time expressed, mRNA encoding the tumor antigen. In an embodiment, the tumor antigen-expressing cells produce the tumor antigen protein (e.g., wild-type or mutant), and the tumor antigen protein may be present at normal levels or reduced levels. In an embodiment, the tumor antigen-expressing cells produced detectable levels of a tumor antigen protein at one point, and subsequently produced substantially no detectable tumor antigen protein.

The term "cancer" as used herein refers to a disease characterized by the uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "stimulation" refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

The term "stimulatory molecule" refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In some aspects, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or IT AM. Examples of an IT AM containing cytoplasmic signaling sequence that is of particular use in the disclosure includes, but is not limited to, those derived from CD3 zeta, common FcR gamma (FCERIG), Fe gamma RIla, FcR beta (Fc Epsilon Rib), CD3 gamma, CD3 delta, CD3 epsilon, CD79a, CD79b, DAP10, and DAP12. In a specific CAR of the disclosure, the intracellular signaling domain in any one or more CARS of the disclosure comprises an intracellular signaling sequence, e.g., a primary signaling sequence of CD3-zeta.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

The term "intracellular signaling domain," refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fe gamma Rlla, FcR beta (Fc Epsilon Rib), CD3 gamma, CD3 delta, CD3 epsilon, CD79a, CD79b, DAP10, and DAP12.

The term "zeta" or alternatively "zeta chain", "CD3-zeta" or "TCR-zeta" is defined as the protein provided as GenBank Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain, or functional derivatives thereof, that are sufficient to functionally transmit an initial signal necessary for T cell activation. In some aspects, the cytoplasmic domain of zeta comprises residues 52 through 164 of GenBank Acc. No. BAG36664.1 or the equivalent residues from a non-human species, e.g., mouse, rodent, monkey, ape and the like, which are functional orthologs thereof.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that contribute to an efficient immune response. Costimulatory molecules include but are not limited to an MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment or derivative thereof.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

"Immune effector function or immune effector response," as that term is used herein, refers to function or response, e.g., of an immune effector cell, which enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some versions contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "transfer vector" refers to a composition of matter which comprises an isolated nucleic acid (e.g., ceDNA, ssDNA, mRNA) and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. The term should also be construed to further include non-plasmid and non-viral compounds which facilitate transfer of nucleic acid into cells, such as, for example, a polylysine compound, liposome, lipid nanoparticle and the like. Examples of viral transfer vectors include, but are not limited to, adenoviral vectors, adeno-associated virus (AAV) vectors, retroviral vectors, lentiviral vectors, and the like.

The term "expression vector" as used herein refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including double stranded ceDNA, ssDNA, mRNA, cosmids, plasmids (e.g., naked or contained in liposomes or LNPs) and viruses (e.g., lentiviruses, retroviruses, adenoviruses, and adeno-associated viruses (AAVs)) that incorporate the recombinant polynucleotide.

The terms "homologous" or "identity" as used herein refers to the subunit sequence identity between two polymeric biological molecules, e.g., between two nucleic acid molecules, such as, two DNA molecules or two RNA molecules, or between two polypeptide molecules. When a subunit position in both of the two molecules is occupied by the same monomeric subunit, e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fe), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

The term "fully human" as used herein refers to an immunoglobulin, such as an antibody or antibody fragment, where the whole molecule is of human origin or consists of an amino acid sequence identical to a human form of the antibody or immunoglobulin.

The term "isolated" as used herein refers to altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell. In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

The terms "cancer associated antigen" and "tumor antigen" are used interchangeably herein and refer to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present disclosure include CARs comprising an antigen binding domain (e.g., antibody or antibody fragment) that binds to an MHC presented peptide. Normally, peptides derived from endogenous proteins fill the pockets of Major histocompatibility complex (MHC) class I molecules and are recognized by T cell receptors (TCRs) on CD8+T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al, J Virol. 2011 85(5): 1935-1942; Sergeeva et al., Blood, 2011 117(16): 4262-4272; Verma et al., J Immunol 2010 184(4):2156-2165; Willemsen et al., Gene Ther 2001 8(21): 1601-1608; Dao et al., Sci Transl Med 2013 5(176): 176ra33; Tassev et al., Cancer Gene Ther 2012 19(2):84-100). For example, TCR-like antibody can be identified from screening a library, such as a human scFv phage displayed library.

The term "tumor-supporting antigen" or "cancer-supporting antigen" interchangeably refer to a molecule (typically a protein, carbohydrate or lipid) that is expressed on the surface of a cell that is, itself, not cancerous, but supports the cancer cells, e.g., by promoting their growth or survival e.g., resistance to immune cells. Exemplary cells of this type include stromal cells and myeloid-derived suppressor cells (MDSCs). The tumor-supporting antigen itself need not play a role in supporting the tumor cells so long as the antigen is present on a cell that supports cancer cells.

The term "flexible polypeptide linker" or "linker" as used herein in the context of a scFv refers to a peptide linker that consists of amino acids such as glycine and/or serine residues used alone or in combination, to link variable heavy and variable light chain regions together. According to some embodiments, the flexible polypeptide linker is a Gly/Ser linker and comprises the amino acid sequence (Gly-Gly-Gly-Ser)n (SEQ ID NO:5), where n is a positive integer equal to or greater than 1. For example, n=1, n=2, n=3. n=4, n=5 and n=6, n=7, n=8, n=9 and n=10. According to some embodiments, the flexible polypeptide linkers include, but are not limited to, (Gly4 Ser)4 (SEQ ID NO:6) or (Gly4 Ser)3 (SEQ ID NO: 7). In another embodiment, the linkers include multiple repeats of (Gly2Ser), (GlySer) or (Gly3Ser) (SEQ ID NO: 5). Also included within the scope of the disclosure are linkers described in WO2012/138475, incorporated herein by reference).

As used herein, a 5' cap (also termed an RNA cap, an RNA 7-methylguanosine cap or an RNA m G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

The term "substantially purified" when referring to a cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cells that have been separated from the cells with which they are naturally associated in their natural state. In some aspects, the cells are cultured in vitro. In other aspects, the cells are not cultured in vitro.

The term "therapeutic" as used herein refers to a treatment. A therapeutic effect is obtained by reduction, suppression, remission, or eradication of a disease state.

The term "specifically binds" as used herein refers to an antibody, or a ligand, which recognizes and binds with a binding partner (e.g., a tumor antigen) protein or carbohydrate present in a sample, but which antibody or ligand does not substantially recognize or bind other molecules or non-binding partners in the sample.

"Membrane anchor" or "membrane tethering domain", as that term is used herein, refers to a polypeptide or moiety, e.g., a myristoyl group, sufficient to anchor an extracellular or intracellular domain to the plasma membrane.

The term "nucleic acid," as used herein, refers to a polymer containing at least two nucleotides (i.e., deoxyribonucleotides or ribonucleotides) in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. DNA may be in the form of minicircle, plasmid, bacmid, minigene, ministring DNA (linear covalently closed DNA vector), closed-ended linear duplex DNA (CELiD or ceDNA), single-stranded DNA (ssDNA), Doggybone™ DNA, dumbbell shaped DNA, minimalistic immunological-defined gene expression (MIDGE)-vector, viral vector or nonviral vectors. RNA may be in the form of small interfering RNA (siRNA), Dicer-substrate dsRNA, small hairpin RNA (shRNA), asymmetrical interfering RNA (aiRNA), microRNA (miRNA), mRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs and/or modified residues include, without limitation, phosphorothioates, phosphorodiamidate morpholino oligomer (morpholino), phosphoramidates, methyl phosphonates, chiral-methyl phosphonates, 2'-O-methyl ribonucleotides, locked nucleic acid (LNA™), and peptide nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated.

As used herein, the phrases "nucleic acid therapeutic", "therapeutic nucleic acid" and "TNA" are used interchangeably and refer to any modality of therapeutic using nucleic acids as an active component of therapeutic agent to treat a disease or disorder. As used herein, these phrases refer to RNA-based therapeutics and DNA-based therapeutics. Non-limiting examples of RNA-based therapeutics include mRNA, antisense RNA and oligonucleotides, ribozymes, aptamers, interfering RNAs (RNAi), Dicer-substrate dsRNA, small hairpin RNA (shRNA), asymmetrical interfering RNA (aiRNA), microRNA (miRNA) or guide RNA (gRNA). Non-limiting examples of DNA-based therapeutics include minicircle DNA, minigene, viral DNA (e.g., Lentiviral or AAV genome) or non-viral synthetic single stranded DNA vectors (ssDNA), closed-ended linear duplex DNA (ceDNA/CELiD), single-stranded DNA (ssDNA), plasmids, bacmids, DOGGYBONE™ DNA vectors, minimalistic immunological-defined gene expression (MIDGE)-vector, nonviral ministring DNA vector (linear-covalently closed DNA vector), or dumbbell-shaped DNA minimal vector ("dumbbell DNA"). TNA can be expressed or used as a template for gene or base editing.

As used herein, the term "AAV" or "adeno-associated virus" refer to single-stranded DNA parvoviruses that grow only in cells. Certain functions of AAV are provided only by co-infecting a helper virus. Thirteen serotypes of AAV have been identified. General information and review of AAV can be found, e.g., in Carter, 1989, Handbook of Parvoviruses, Vol. 1, p. 169-228, and Berns, 1990, Virology, pp. 1743-1764, Raven Press, (New York).

As used herein, the term "single-stranded (ss) synthetic DNA molecules", "single-stranded (ss) synthetic AAV vectors", "synthetic production of ssDNA molecules" and "synthetic production of ss AAV vectors" refer to a single-stranded (ss) synthetic DNA molecule (ssDNA), a single-stranded AAV vector and synthetic production methods thereof in an entirely cell-free environment. The production may involve one or more molecules in a manner that does not involve replication or other multiplication of the molecule by or inside of a cell or using a cellular extract. Synthetic production avoids contamination of the produced molecule with cellular contaminants, e.g., cellular proteins or cellular nucleic acid, viral protein or DNA, insect protein or DNA and further avoids unwanted cellular-specific modification of the molecule during the production process, e.g., methylation or glycosylation or other post-translational modification.

According to some embodiments, the 5' and/or 3' terminus of certain ssDNA molecules comprise inverted terminal repeats (ITRs) of about 145 nucleotides at both ends, or fragments thereof. The terminal 125 nucleotides in each ITR form a palindromic double-stranded T-shaped hairpin structure, in which the A-A' palindrome forms the stem, and the two smaller palindromes, B-B' and the C-C', form the cross-arms of the T. The other 20 nucleotides in ITR remain single-stranded and are called the D sequence. The D (−) sequence (also referred to herein as "the ssD(−) sequence") is at the 3' end, and the complementary D (+) sequence (also referred to herein as "the ssD(+) sequence") is at the 5' end. Second-strand DNA synthesis turns both ssD(−) and ssD(+) sequences into a double-stranded (ds) D(±) sequence, each of which comprises a D region and a D' region. Ling et al. J Virol. 2015 Jan. 15; 89(2):952-61, WO2016081927A2, incorporated by reference in its entirety herein, described ssD(+)-sequence-substituted ssAAV genomes. ssD(−) and ssD(+) have been reported to contain one or more transcription factor binding sites and to be required for packaging and replication (Ling et al. J Virol. 2015 Jan. 15; 89(2):952-61; WO2016081927A2, incorporated by reference in its entirety herein).

As used herein, the term "stem-loop structure" refers to a nucleic acid structure comprising at least one double-stranded region (referred to herein as a "stem") and at least one single-stranded region (referred to herein as a "loop"). In some embodiments, a stem-lop structure is a hairpin structure. In some embodiments, a stem-loop structure comprises more than one stem and more than one loop. In some embodiments, a loop is located at the end of a stem (such that a single loop connects the two strands of a duplex stem, e.g., as in a hairpin structure). In some embodiments, a loop may be located between two stems (which may be referred to herein as a "bulge" or a "bubble"), such that the loop connects two strands of different stems. In some embodiments, as described in more detail herein, a stem-loop structure may comprise more complex secondary structures comprising multiple stems and multiple loops. As used herein, the term "ceDNA" refers to capsid-free closed-ended linear double stranded (ds) duplex DNA for non-viral gene transfer, synthetic or otherwise. Detailed description of ceDNA is described in international application of PCT/US2017/020828, filed Mar. 3, 2017, the entire content of which is incorporated herein by reference. Certain methods for the production of ceDNA comprising various inverted terminal repeat (ITR) sequences and configurations using cell-based methods are described in Example 1 of international applications PCT/US18/49996, filed Sep. 7, 2018, and PCT/US2018/064242, filed Dec. 6, 2018, each of which is incorporated herein in its entirety by reference. Certain methods for the production of synthetic ceDNA vectors comprising various ITR sequences and configurations are described, e.g., in international application PCT/US2019/14122, filed Jan. 18, 2019, the entire content of which is incorporated herein by reference. According to some embodiments, ceDNA comprises one of more phosphorothioate-modified nucleotides.

"Nucleotides" contain a sugar deoxyribose (DNA) or ribose (RNA), a base, and a phosphate group. Nucleotides are linked together through the phosphate group.

"Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "interfering RNA" or "RNAi" or "interfering RNA sequence" as used herein includes single-stranded RNA (e.g., mature miRNA, ssRNAi oligonucleotides, ssDNAi oligonucleotides), double-stranded RNA (i.e., duplex RNA such as siRNA, Dicer-substrate dsRNA, shRNA, aiRNA, or pre-miRNA), a DNA-RNA hybrid (see, e.g., PCT Publication No. WO 2004/078941), or a DNA-DNA hybrid (see, e.g., PCT Publication No. WO 2004/104199) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized. The disclosures of each of the above patent documents are herein incorporated by reference in their entirety for all purposes.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. As used herein, the term "siRNA" includes RNA-RNA duplexes as well as DNA-RNA hybrids (see, e.g., PCT Publication No. WO 2004/078941).

The phrase "immunosuppressant" refers to a group of small molecules, monoclonal antibodies or polypeptide antagonists that inhibit protein kinases, such as tyrosine kinases. The term immunosuppressant also includes any drugs, including antibody and other protein drugs, which inhibit or prevent activity of the immune system such as in the case of allergic reactions, inflammation or autoimmune disorders, transplant rejection or graft versus host disease.

As used herein, the term "tyrosine kinase inhibitor" or "TKI" refers to a molecule that inhibits tyrosine kinase activity. A tyrosine kinase inhibitor may be, for example, a small molecule inhibitor, a biologic (such as a monoclonal antibody), or a large polypeptide molecule that inhibits the activity of, for example, IFN signaling and production pathways; or any other form of antagonist that can decrease expression or activity of a tyrosine kinase.

The phrase "anti-therapeutic nucleic acid immune response", "anti-transfer vector immune response", "immune response against a therapeutic nucleic acid", "immune response against a transfer vector", or the like refers to any undesired immune response against a therapeutic nucleic acid, viral or non-viral in its origin. In some embodiments, the undesired immune response is an antigen-specific immune response against the viral transfer vector itself. In some embodiments, the immune response is specific to the transfer vector which can be double stranded DNA, single stranded DNA, single stranded RNA, or double stranded RNA. In other embodiments, the immune response is specific to a sequence of the transfer vector. In other embodiments, the immune response is specific to the CpG content of the transfer vector.

By "decrease," "decreasing," "reduce," or "reducing" of an immune response by an immunosuppressant is intended to mean a detectable decrease of an immune response to a given immunosuppressant. The amount of decrease of an immune response by the immunosuppressant may be determined relative to the level of an immune response in the presence of an immunosuppressant. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or lower than the immune response detected in the presence of the immunosuppressant. A decrease in the immune response in the presence of an immunosuppressant is typically measured by a decrease in cytokine production (e.g., IFNα, IFNγ, TNFα, IL-1β, IL-2, IL-6, IL-8, IL-10, IL-12, or IL-18) by a responder cell in vitro or a decrease in cytokine production in the sera of a mammalian subject after administration of the interfering RNA.

As used herein, the term "responder cell" refers to a cell, preferably a mammalian cell, that produces a detectable immune response when contacted with an immunostimulatory therapeutic nucleic acid. Exemplary responder cells include, e.g., dendritic cells, macrophages, peripheral blood mononuclear cells (PBMCs), splenocytes, and the like. Exemplary responder cells can be human THP1 monocytes and murine RAW macrophage cells. Detectable immune responses can be readily measured in vitro by using various reporter constructs including interferon regulatory factor (IRF)-inducible reporter constructs using, e.g., THP1-Interferon stimulated gene (ISG) or RAW-ISG cells.

In vivo immune responses can be measured by determining production levels of cytokines or growth factors such as TNF-α, IFN-α, IFN-β, IFN-γ, IL-1α, IL-1β, IL-2, IL-3, IL-4, IL-5, IL-6, IL-8, IL-10, IL-12, IL-18, IP-10, TGF, VEGF, VEGFR or combinations thereof. Further, immune responses can be also measured by detecting levels of chemokine such as MCP-1, MIP-1α (CCL3), MIP-1β (CCL4), and Rantes (CCL5).

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

As used herein, the term "lipid particle" or "lipid nanoparticle" (LNP) refers to a lipid formulation that can be used to deliver a therapeutic agent such as therapeutic nucleic acid to a target site of interest (e.g., cell, tissue, organ, and the like). In some embodiments, the lipid nanoparticle of the disclosure is typically formed from an ionizable lipid (e.g., cationic lipid), sterol (e.g., cholesterol), a conjugated lipid (e.g., lipid-anchored polymer) that prevents aggregation of the particle, and optionally a helper lipid (e.g., non-cationic lipid). In some other embodiments, a therapeutic agent such as a therapeutic nucleic acid (TNA) may be encapsulated in the lipid particle, thereby protecting it from degradation. In yet other embodiments, an immunosuppressant can be optionally included in the nucleic acid containing lipid nanoparticles. In one embodiment, the lipid particle comprises a nucleic acid (e.g., ceDNA, ssDNA and/or mRNA). The present disclosure provides LNPs where at least one of the lipids in the lipid-anchored polymer contains either 18 or 20 aliphatic carbons to anchor the lipid-anchored polymer more securely to the LNP. In some embodiments, at least one lipid of the lipid-anchored polymer having at least 18 aliphatic carbons is useful for creating stealth LNPs. In another embodiment, at least one lipid of the lipid-anchored polymer having at least 20 aliphatic carbons is useful for creating stealth LNPs.

According to some embodiments, lipid particles of the disclosure typically have a mean diameter of from about 20 nm to about 90 nm, about 25 nm to about 80 nm, about 25 nm to about 75 nm, about 25 nm to about 70 nm, from about 30 nm to about 75 nm, from about 30 nm to about 70 nm, from about 35 nm to about 75 nm, from about 35 nm to about 70 nm, from about 40 nm to about 75 nm, from about 40 nm to about 70 nm, from about 45 nm to about 75 nm, from about 50 nm to about 75 nm, from about 50 nm to about 70 nm, from about 60 nm to about 75 nm, from about 60 nm to about 70 nm, from about 65 nm to about 75 nm, from about 65 nm to about 70 nm, or about 20 nm, about 25 nm, about 30 nm, about 35 nm, about 40 nm, about 45 nm, about 50 nm, about 51 nm, about 52 nm, about 53 nm, about 54 nm, about 55 nm, about 56 nm, about 57 nm, about 58 nm, about 59 nm about 60 nm, about 61 nm, about 62 nm, about 63 nm, about 64 nm, about 65 nm, about 66 nm, about 67 nm, about 68 nm, about 69 nm, about 70 nm, about 71 nm, about 72 nm, about 73 nm, about 74 nm, or about 75 nm (±3 nm) in size.

Generally, the LNPs of the disclosure have a mean diameter selected to provide an intended therapeutic effect. For example, the LNPs of the disclosure have a mean diameter that is compatible with a target organ, such that the LNPs of the disclosure are able to diffuse through the fenestrations of a target organ (e.g., liver) or a target cell subpopulation (e.g., hepatocytes).

According to some embodiments, the lipid particles of the disclosure typically have a mean diameter of less than about 100 nm, less than about 90 nm, less than about 80 nm, less than about 75 nm, less than about 70 nm, less than about 65 nm, less than about 60 nm, less than about 55 nm, less than about 50 nm, less than about 45 nm, less than about 40 nm, less than about 35 nm, less than about 30 nm, less than about 25 nm, less than about 20 nm in size.

As used herein, the term "cationic lipid" refers to any lipid that is positively charged at physiological pH. The cationic lipid in the lipid particles may comprise, e.g., one or more cationic lipids such as 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), "SS-cleavable lipid", or a mixture thereof. In some embodiments, a cationic lipid can also be an ionizable lipid, i.e., an ionizable cationic lipid. The term "cationic lipids" also encompasses lipids that are positively charged at any pH, e.g., lipids comprising quaternary amine groups, i.e., quaternary lipids. Any cationic lipid described herein comprising a primary, secondary or tertiary amine group may be converted to a corresponding quaternary lipid, for example, by treatment with chloromethane ($CH_3Cl$) in acetonitrile ($CH_3CN$) and chloroform ($CHCl_3$).

As used herein, the term "ionizable lipid" is meant to refer to a lipid, e.g., cationic lipid, having at least one protonatable or deprotonatable group, such that the lipid is positively charged at a pH at or below physiological pH (e.g., pH 7.4), and neutral at a second pH, preferably at or above physiological pH. It will be understood by one of ordinary skill in the art that the addition or removal of protons as a function of pH is an equilibrium process, and that the reference to a charged or a neutral lipid refers to the nature of the predominant species and does not require that all of the lipids be present in the charged or neutral form. Generally, ionizable lipids have a pKa of the protonatable group in the range of about 4 to about 7. In some embodiments, ionizable lipid may include "cleavable lipid" or "SS-cleavable lipid".

As used herein, the term "neutral lipid" is meant to refer to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

As used herein, the term "non-cationic lipid" is meant to refer to any amphipathic lipid as well as any other neutral lipid or anionic lipid.

As used herein, the term "cleavable lipid" or "SS-cleavable lipid" refers to an ionizable lipid comprising a disulfide bond cleavable unit. Cleavable lipids may include cleavable disulfide bond ("ss") containing lipid-like materials that comprise a pH-sensitive amine, e.g., a tertiary amine, and self-degradable phenyl ester. For example, a SS-cleavable lipid can be an ss-OP lipid (COATSOME® SS-OP), an ss-M lipid (COATSOME® SS-M), an ss-E lipid (COATSOME® SS-E), an ss-EC lipid (COATSOME® SS-EC), an ss-LC lipid (COATSOME® SS-LC), an ss-OC lipid (COATSOME® SS-OC), and an ss-PalmE lipid (see, for example, Formulae I-IV), or a lipid described by Togashi et al., (2018) Journal of Controlled Release "A hepatic pDNA delivery system based on an intracellular environment sensitive vitamin E-scaffold lipid-like material with the aid of an anti-inflammatory drug" 279:262-270. Additional examples of cleavable lipids are described in U.S. Pat. Nos. 9,708,628, and 10,385,030, the entire contents of which are incorporated herein by reference. In one embodiment, cleavable lipids comprise a tertiary amine, which responds to an acidic compartment, e.g., an endosome or lysosome for membrane destabilization and a disulfide bond that can be cleaved in a reducing environment, such as the cytoplasm. In one embodiment, a cleavable lipid is a cationic lipid. In one embodiment, a cleavable lipid is an ionizable cationic lipid. Cleavable lipids are described in more detail herein.

As used herein, "lipid encapsulated" refers to a lipid nanoparticle that provides an active agent or therapeutic agent, such as a nucleic acid (e.g., a ceDNA, non-viral ssDNA or mRNA), with full encapsulation, partial encapsulation, or both. In a preferred embodiment, the nucleic acid is fully encapsulated in the lipid nanoparticle (e.g., to form a lipid nanoparticle encapsulating nucleic acid). The term "lipid-anchored polymer" or "lipid polymer" or "lipid conjugate" refers to a conjugated lipid that inhibits aggregation of lipid particles. Such lipid conjugates include, but are not limited to, PEG-lipid conjugates such as PEG coupled to DSG (e.g., PEG-DSG conjugates), PEG coupled to DSPE (e.g., PEG-DSPE conjugates), and PEG conjugated to ceramides (see, e.g., U.S. Pat. No. 5,885,613), polyglycerol (PG)-lipid conjugate such as DODA-PG, and mixtures thereof. Examples of PG-lipid conjugates include DODA-PG45. Additional examples of POZ-lipid conjugates are described in PCT Publication No. WO 2010/006282. PEG, PG or POZ can be conjugated directly to the lipid or may be linked to the lipid via a linker moiety. Any linker moiety suitable for coupling the PEG, PG, or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes.

As used herein, the term "lipid-anchored polymer", which may be used herein interchangeably with the term "lipid conjugate" or "lipid polymer" refers to a molecule comprising a lipid moiety covalently attached to a hydrophilic polymer, optionally via a linker. Without wishing to be bound by a specific theory, it is believed that a lipid-anchored polymer can inhibit aggregation of LNPs and provide steric stabilization and prolonged blood half-life ($t_{1/2}$) in vivo. The lipid moiety with a linker ("lipid-linker" or "linker-lipid") conjugated to a hydrophilic polymer (e.g., PEG, PG, or POZ) include, but are not limited to, 1,2-distearoyl-sn-glycero-3-phosphoethanolamine (DSPE), 1,2-dielaidoyl-sn-phosphatidylethanolamine (DEPE), 1-stearoyl-2-oleoyl-sn-glycero-3-phosphoethanolamine (SOPE), 1,2-dioleoyl-sn-glycero-3-phosphoglycerol (DOPG), 1,2-dielaidoyl-sn-glycero-3-phosphoethanolamine (18-1-trans PE), 1,2-dioleoyl-sn-glycero-3-phospho-L-serine (DOPS), dioctadecylamine (DODA), distearoyl-rac-glycerol (DSG), 1,2-dioleoyl-sn-glycero-3-phosphoethanolamine (DOPE), and combinations and derivatives thereof. According to some embodiments of any of the above aspects and embodiments, the first lipid-linker and the second lipid-linker are each independently selected from the group consisting of DSPE, DEPE, SOPE, DOPG, 18-1-trans PE, DOPS, DSG, DODA, DOPE, and combinations thereof. For example, PEG2000 coupled to DSG is a lipid-anchored polymer PEG2000-DSG (or DSG-PEG2000). PEG coupled to DSPE is a lipid-anchored polymer PEG-DSPE (or DSPE- PEG2000 or DSPE-PEG500). An example of lipid-anchored PG polymer can include DODA-PG, wherein PG can be a multiunit ranging from about 5 to about 50 PG units.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" or "helper lipid" refers to any amphipathic lipid as well as any other neutral lipid or anionic lipid. The helper lipid can include, but are not limited to distearoylphosphatidylcholine (DSPC), 1,2-dioleoyl-sn-glycero-3-phosphocholine (DOPC), and 1,2-dioleoyl-sn-glycero-3-phosphoethanolamine (DOPE) and the like.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N-N-dialkylamino, 1,2-diacyloxy-3-aminopropane, and 1,2-dialkyl-3-aminopropane.

As used herein, the term "aqueous solution" refers to a composition comprising in whole, or in part, water.

As used herein, the term "organic lipid solution" refers to a composition comprising in whole, or in part, an organic solvent having a lipid.

"Systemic delivery," as used herein, refers to delivery of lipid particles that leads to a broad biodistribution of an active agent (e.g., CAR T) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

The term "off-target delivery", as used herein, refers to delivery of LNPs of the disclosure to non-target cells. After administration to a subject, an LNP may be delivered to a non-target cell and may result in expression of a therapeutic nucleic acid (TNA) in the non-target cell.

"Local delivery," as used herein, refers to delivery of an active agent such as ceDNA, ssDNA, mRNA, or an interfering RNA (e.g., siRNA) directly to a target site within an organism. For example, an agent can be locally delivered by direct injection into a disease site such as a tumor or other target site such as a site of inflammation or a target organ such as the liver, heart, pancreas, kidney, and the like.

As used herein, the term "ceDNA" refers to capsid-free closed-ended linear double stranded (ds) duplex DNA for non-viral gene transfer, synthetic or otherwise. Detailed description of ceDNA is described in International application of PCT/US2017/020828, filed Mar. 3, 2017, the entire contents of which are expressly incorporated herein by reference. Certain methods for the production of ceDNA comprising various inverted terminal repeat (ITR) sequences and configurations using cell-based methods are described in Example 1 of International applications PCT/US18/49996, filed Sep. 7, 2018, and PCT/US2018/064242, filed Dec. 6, 2018, each of which is incorporated herein in its entirety by reference. Certain methods for the production of synthetic ceDNA vectors comprising various ITR sequences and configurations are described, e.g., in International application PCT/US2019/14122, filed Jan. 18, 2019, the entire content of which is incorporated herein by reference. As used herein, the terms "ceDNA vector" and "ceDNA" are used interchangeably.

As used herein, the term "neDNA" or "nicked ceDNA" refers to a closed-ended DNA having a nick or a gap of 1-100 base pairs in a stem region or spacer region 5' upstream of an open reading frame (e.g., a promoter and transgene to be expressed).

As used herein, the terms "gap" and "nick" are used interchangeably and refer to a discontinued portion of synthetic DNA vector of the present disclosure, creating a stretch of single stranded DNA portion in otherwise double stranded ceDNA. The gap can be 1 nucleotide (nt) to 100 nucleotides (nt) long in length in one strand of a duplex DNA. Typical gaps, designed and created by the methods described herein and synthetic vectors generated by the methods can be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 bp long in length. Exemplified gaps in the present disclosure can be 1 nt to 10 nt long, 1 to 20 nt long, 1 to 30 nt long in length.

As used herein, the terms "inverted terminal repeat" or "ITR" are meant to refer to a nucleic acid sequence located at the 5' and/or 3' terminus of the ssDNA vectors disclosed herein, which comprises at least one stem-loop structure comprising a partial duplex and at least one loop. According to some embodiments, the ITR may be an artificial sequence (e.g., contains no sequences derived from a virus). The ITR may further comprise one stem-loop structure (e.g., a "hairpin"), or more than one stem-loop structure. For example, the ITR may comprise two stem-loop structures (e.g., a "hammerhead", "doggy-bone", or "dumbbell"), three stem-loop structures (e.g., "cruciform"), or more complex structures. The ITR may comprise an aptamer sequence or one or more chemical modifications.

According to some embodiments, the "ITR" can be artificially synthesized using a set of oligonucleotides comprising one or more desirable functional sequences (e.g., palindromic sequence). The ITR sequence can be an artificial AAV ITR, an artificial non-AAV ITR, or an ITR physically derived from a viral AAV ITR (e.g., ITR fragments removed from a viral genome). For example, the ITR can be derived from the family Parvoviridae, which encompasses parvoviruses and dependoviruses (e.g., canine parvovirus, bovine parvovirus, mouse parvovirus, porcine parvovirus, human parvovirus B-19), or the SV40 hairpin that serves as the origin of SV40 replication can be used as an ITR, which can further be modified by truncation, substitution, deletion, insertion and/or addition. Parvoviridae family viruses consist of two subfamilies: Parvovirinae, which infect vertebrates, and Densovirinae, which infect invertebrates. Dependoparvoviruses include the viral family of the adeno-associated viruses (AAV) which are capable of replication in vertebrate hosts including, but not limited to, human, primate, bovine, canine, equine and ovine species. Typically, ITR sequences can be derived not only from AAV, but also from Parvovirus, lentivirus, goose virus, B19, in the configurations of wildtype, "doggy bone" and "dumbbell shape", symmetrical or even asymmetrical ITR orientation. Although the ITRs are typically present in both 5' and 3' ends of an AAV vector, in a single-stranded DNA (ssDNA) molecule the ITR can be present in only one end of the linear vector. For example, the ITR can be present on the 5' end only. Some other cases, the ITR can be present on the 3' end only in a single-stranded DNA (ssDNA) molecule. For convenience herein, an ITR located 5' to ("upstream of") an expression cassette in a single-stranded DNA (ssDNA) molecule is referred to as a "5' ITR" or a "left ITR", and an ITR located 3' to ("downstream of") an expression cassette in a single-stranded DNA (ssDNA) molecule is referred to as a "3' ITR" or a "right ITR".

As used herein, a "wild-type ITR" or "WT-ITR" refers to the sequence of a naturally occurring ITR sequence in an AAV genome or other dependovirus that remains, e.g., Rep binding activity and Rep nicking ability. The nucleotide sequence of a WT-ITR from any AAV serotype may slightly vary from the canonical naturally occurring sequence due to degeneracy of the genetic code or drift, and therefore WT-ITR sequences encompasses for use herein include WT-ITR sequences as result of naturally occurring changes (e.g., a replication error).

As used herein, the term "substantially symmetrical WT-ITRs" or a "substantially symmetrical WT-ITR pair" refers to a pair of WT-ITRs within a synthetic AAV vector that are both wild type ITRs that have an inverse complement sequence across their entire length. For example, an ITR can be considered to be a wild-type sequence, even if it has one or more nucleotides that deviate from the canonical naturally occurring canonical sequence, so long as the changes do not affect the physical and functional properties and overall three-dimensional structure of the sequence (secondary and tertiary structures). In some aspects, the deviating nucleotides represent conservative sequence changes. As one non-limiting example, a sequence that has at least 95%, 96%, 97%, 98%, or 99% sequence identity to the canonical sequence (as measured, e.g., using BLAST at default settings), and also has a symmetrical three-dimensional spatial organization to the other WT-ITR such that their 3D structures are the same shape in geometrical space. The substantially symmetrical WT-ITR has the same A, C-C' and B-B' loops in 3D space. A substantially symmetrical WT-ITR can be functionally confirmed as WT by determining that it has an operable Rep binding site (RBE or RBE') and terminal resolution site (TRS) that pairs with the appropriate Rep protein. One can optionally test other functions, including transgene expression under permissive conditions.

As used herein, the phrases of "modified ITR" or "mod-ITR" or "mutant ITR" are used interchangeably and refer to an ITR with a mutation in at least one or more nucleotides as compared to the WT-ITR from the same serotype. The mutation can result in a change in one or more of A, C, C', B, B' regions in the ITR, and can result in a change in the three-dimensional spatial organization (i.e., its 3D structure in geometric space) as compared to the 3D spatial organization of a WT-ITR of the same serotype.

As used herein, the term "asymmetric ITRs" also referred to as "asymmetric ITR pairs" refers to a pair of ITRs within a single synthetic AAV genome that are not inverse complements across their full length. As one non-limiting example, an asymmetric ITR pair does not have a symmetrical three-dimensional spatial organization to their cognate ITR such that their 3D structures are different shapes in geometrical space. Stated differently, an asymmetrical ITR pair have the different overall geometric structure, i.e., they have different organization of their A, C-C' and B-B' loops in 3D space (e.g., one ITR may have a short C-C' arm and/or short B-B' arm as compared to the cognate ITR). The difference in sequence between the two ITRs may be due to one or more nucleotide addition, deletion, truncation, or point mutation. According to some embodiments, one ITR of the asymmetric ITR pair may be a wild-type AAV ITR sequence and the other ITR a modified ITR as defined herein (e.g., a non-wild-type or synthetic ITR sequence). In another embodiment, neither ITRs of the asymmetric ITR pair is a wild-type AAV sequence and the two ITRs are modified ITRs that have different shapes in geometrical space (i.e., a different overall geometric structure). In some embodiments, one mod-ITRs of an asymmetric ITR pair can have a short C-C' arm and the other ITR can have a different modification (e.g., a single arm, or a short B-B' arm etc.) such that they have different three-dimensional spatial organization as compared to the cognate asymmetric mod-ITR.

As used herein, the term "symmetric ITRs" refers to a pair of ITRs within a single stranded AAV genome that are mutated or modified relative to wild-type dependoviral ITR sequences and are inverse complements across their full length. Neither ITRs are wild type ITR AAV2 sequences (i.e., they are a modified ITR, also referred to as a mutant ITR), and can have a difference in sequence from the wild type ITR due to nucleotide addition, deletion, substitution, truncation, or point mutation. For convenience herein, an ITR located 5' to (upstream of) an expression cassette in a synthetic AAV vector is referred to as a "5' ITR" or a "left ITR", and an ITR located 3' to (downstream of) an expression cassette in a synthetic AAV vector is referred to as a "3' ITR" or a "right ITR".

As used herein, the terms "substantially symmetrical modified-ITRs" or a "substantially symmetrical mod-ITR pair" refers to a pair of modified-ITRs within a synthetic AAV that are both that have an inverse complement sequence across their entire length. For example, the modified ITR can be considered substantially symmetrical, even if it has some nucleotide sequences that deviate from the inverse complement sequence so long as the changes do not affect the properties and overall shape. As one non-limiting example, a sequence that has at least 85%, 90%, 95%, 96%, 97%, 98%, or 99% sequence identity to the canonical sequence (as measured using BLAST at default settings), and also has a symmetrical three-dimensional spatial organization to their cognate modified ITR such that their 3D structures are the same shape in geometrical space. Stated differently, a substantially symmetrical modified-ITR pair have the same A, C-C' and B-B' loops organized in 3D space. In some embodiments, the ITRs from a mod-ITR pair may have different reverse complement nucleotide sequences but still have the same symmetrical three-dimensional spatial organization—that is both ITRs have mutations that result in the same overall 3D shape. For example, one ITR (e.g., 5' ITR) in a mod-ITR pair can be from one serotype, and the other ITR (e.g., 3' ITR) can be from a different serotype, however, both can have the same corresponding mutation (e.g., if the 5'ITR has a deletion in the C region, the cognate modified 3'ITR from a different serotype has a deletion at the corresponding position in the C' region), such that the modified ITR pair has the same symmetrical three-dimensional spatial organization. In such embodiments, each ITR in a modified ITR pair can be from different serotypes (e.g., AAV1, 2, 3, 4, 5, 6, 7, 8, 9, 10, 11, and 12) such as the combination of AAV2 and AAV6, with the modification in one ITR reflected in the corresponding position in the cognate ITR from a different serotype. According to some embodiments, a substantially symmetrical modified ITR pair refers to a pair of modified ITRs (mod-ITRs) so long as the difference in nucleotide sequences between the ITRs does not affect the properties or overall shape and they have substantially the same shape in 3D space. As a non-limiting example, a mod-ITR that has at least 95%, 96%, 97%, 98% or 99% sequence identity to the canonical mod-ITR as determined by standard means well known in the art such as BLAST (Basic Local Alignment Search Tool), or BLASTN at default settings, and also has a symmetrical three-dimensional spatial organization such that their 3D structure is the same shape in geometric space. A substantially symmetrical mod-ITR pair has the same A, C-C' and B-B' loops in 3D space, e.g., if a modified ITR in a substantially symmetrical mod-ITR pair has a deletion of a C-C' arm, then the cognate mod-ITR has the corresponding deletion of the C-C' loop and also has a similar 3D structure of the remaining A and B-B' loops in the same shape in geometric space of its cognate mod-ITR.

As used herein, the term "flanking" refers to a relative position of one nucleic acid sequence with respect to another nucleic acid sequence. Generally, in the sequence ABC, B is flanked by A and C. The same is true for the arrangement A×B×C. Thus, a flanking sequence precedes or follows a flanked sequence but need not be contiguous with, or immediately adjacent to the flanked sequence. According to some embodiments, the term flanking refers to terminal repeats at each end of the linear single strand synthetic AAV vector.

As used herein, the term "spacer region" refers to an intervening sequence that separates functional elements in a vector or genome. In some embodiments, AAV spacer regions keep two functional elements at a desired distance for optimal functionality. In some embodiments, the spacer regions provide or add to the genetic stability of the vector or genome. In some embodiments, spacer regions facilitate ready genetic manipulation of the genome by providing a convenient location for cloning sites and a gap of design number of base pair. For example, in certain aspects, an oligonucleotide "polylinker" or "poly cloning site" containing several restriction endonuclease sites, or a non-open reading frame sequence designed to have no known protein (e.g., transcription factor) binding sites can be positioned in the vector or genome to separate the cis—acting factors, e.g., inserting a 6 mer, 12 mer, 18 mer, 24 mer, 48 mer, 86 mer, 176 mer, etc., for example, between the terminal resolution site and the upstream transcriptional regulatory element as in an AAV vector or genome.

As used herein, the terms "Rep binding site" ("RBS") and "Rep binding element" ("RBE") are used interchangeably and refer to a binding site for Rep protein (e.g., AAV Rep 78 or AAV Rep 68) which upon binding by a Rep protein permits the Rep protein to perform its site-specific endonuclease activity on the sequence incorporating the RBS. An RBS sequence and its inverse complement together form a single RBS. RBS sequences are well known in the art, and include, for example, 5'-GCGCGCTCGCTCGCTC-3' (SEQ ID NO: 8), an RBS sequence identified in AAV2.

As used herein, the terms "terminal resolution site" and "TRS" are used interchangeably herein and refer to a region at which Rep forms a tyrosine-phosphodiester bond with the 5' thymidine generating a 3'-OH that serves as a substrate for DNA extension via a cellular DNA polymerase, e.g., DNA pol delta or DNA pol epsilon. Alternatively, the Rep-thymidine complex may participate in a coordinated ligation reaction.

As used herein, the terms "sense" and "antisense" refer to the orientation of the structural element on the polynucleotide. The sense and antisense versions of an element are the reverse complement of each other.

As used herein, the term "synthetic AAV vector" and "synthetic production of AAV vector" refers to an AAV vector and synthetic production methods thereof in an entirely cell-free environment.

As defined herein, "reporter" refers to a protein that can be used to provide a detectable read-out. A reporter generally produces a measurable signal such as fluorescence, color, or luminescence. Reporter protein coding sequences encode proteins whose presence in the cell or organism is readily observed.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutically active substances is well known in the art. Supplementary active ingredients can also be incorporated into the compositions. The phrase "pharmaceutically-acceptable" refers to molecular entities and compositions that do not produce a toxic, an allergic, or similar untoward reaction when administered to a host.

As used herein, the term "in vivo" refers to assays or processes that occur in or within an organism, such as a multicellular animal. In some of the aspects described herein, a method or use can be said to occur "in vivo" when a unicellular organism, such as a bacterium, is used. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term "in vitro" refers to assays and methods that do not require the presence of a cell with an intact membrane, such as cellular extracts, and can refer to the introducing of a programmable synthetic biological circuit in a non-cellular system, such as a medium not comprising cells or cellular systems, such as cellular extracts.

As used herein, the term "promoter" refers to any nucleic acid sequence that regulates the expression of another nucleic acid sequence by driving transcription of the nucleic acid sequence, which can be a heterologous target gene encoding a protein or an RNA. Promoters can be constitutive, inducible, repressible, tissue-specific, or any combination thereof. A promoter is a control region of a nucleic acid sequence at which initiation and rate of transcription of the remainder of a nucleic acid sequence are controlled. A promoter can also contain genetic elements at which regulatory proteins and molecules can bind, such as RNA polymerase and other transcription factors. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the expression of transgenes in the synthetic AAV vectors disclosed herein. A promoter sequence may be bounded at its 3' terminus by the transcription initiation site and extends upstream (5' direction) to include the minimum number of bases or elements necessary to initiate transcription at levels detectable above background.

As used herein, the terms "expression cassette" and "expression unit" are used interchangeably and refer to a heterologous DNA sequence that is operably linked to a promoter or other DNA regulatory sequence sufficient to direct transcription of a transgene of a DNA vector, e.g., synthetic AAV vector. Suitable promoters include, for example, tissue specific promoters. Promoters can also be of AAV origin.

As used herein, "operably linked" refers to a juxtaposition wherein the components so described are in a relationship permitting them to function in their intended manner. For instance, a promoter is operably linked to a coding sequence if the promoter affects its transcription or expression. A promoter can be said to drive expression or drive transcription of the nucleic acid sequence that it regulates. The phrases "operably linked," "operatively positioned," "operatively linked," "under control," and "under transcriptional control" indicate that a promoter is in a correct functional location and/or orientation in relation to a nucleic acid sequence it regulates to control transcriptional initiation and/or expression of that sequence. An "inverted promoter," as used herein, refers to a promoter in which the nucleic acid sequence is in the reverse orientation, such that what was the coding strand is now the non-coding strand, and vice versa. Inverted promoter sequences can be used in various embodiments to regulate the state of a switch. In addition, in various embodiments, a promoter can be used in conjunction with an enhancer.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., DNA-targeting RNA) or a coding sequence (e.g., site-directed modifying polypeptide, or Cas9/Csn1 polypeptide) and/or regulate translation of an encoded polypeptide.

A promoter can be one naturally associated with a gene or sequence, as can be obtained by isolating the 5' non-coding sequences located upstream of the coding segment and/or exon of a given gene or sequence. Such a promoter can be referred to as "endogenous." Similarly, in some embodiments, an enhancer can be one naturally associated with a nucleic acid sequence, located either downstream or upstream of that sequence. In some embodiments, a coding nucleic acid segment is positioned under the control of a "recombinant promoter" or "heterologous promoter," both of which refer to a promoter that is not normally associated with the encoded nucleic acid sequence that it is operably linked to in its natural environment. Similarly, a "recombinant or heterologous enhancer" refers to an enhancer not normally associated with a given nucleic acid sequence in its natural environment. Such promoters or enhancers can include promoters or enhancers of other genes; promoters or enhancers isolated from any other prokaryotic, viral, or eukaryotic cell; and synthetic promoters or enhancers that are not "naturally occurring," i.e., comprise different elements of different transcriptional regulatory regions, and/or mutations that alter expression through methods of genetic engineering that are known in the art. In addition to producing nucleic acid sequences of promoters and enhancers synthetically, promoter sequences can be produced using recombinant cloning and/or nucleic acid amplification technology, including PCR, in connection with the synthetic biological circuits and modules disclosed herein (see, e.g., U.S. Pat. Nos. 4,683,202, 5,928,906, each incorporated herein by reference in its entirety). Furthermore, it is contemplated that control sequences that direct transcription and/or expression of sequences within non-nuclear organelles such as mitochondria, chloroplasts, and the like, can be employed as well.

As described herein, an "inducible promoter" is one that is characterized by initiating or enhancing transcriptional activity when in the presence of, influenced by, or contacted by an inducer or inducing agent. An "inducer" or "inducing agent," as defined herein, can be endogenous, or a normally exogenous compound or protein that is administered in such a way as to be active in inducing transcriptional activity from the inducible promoter. In some embodiments, the inducer or inducing agent, i.e., a chemical, a compound or a protein, can itself be the result of transcription or expression of a nucleic acid sequence (i.e., an inducer can be an inducer protein expressed by another component or module), which itself can be under the control or an inducible promoter. In some embodiments, an inducible promoter is induced in the absence of certain agents, such as a repressor. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

The term "subject" as used herein is intended to include living organisms in which an immune response can be elicited (e.g., mammals, human). Usually, the animal is a vertebrate such as, but not limited to a primate, rodent, domestic animal or game animal. Primates include but are not limited to, chimpanzees, cynomolgus monkeys, spider monkeys, and macaques, e.g., Rhesus. Rodents include mice, rats, woodchucks, ferrets, rabbits and hamsters. Domestic and game animals include, but are not limited to, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate or a human. A subject can be male or female. Additionally, a subject can be an infant or a child. In some embodiments, the subject can be a neonate or an unborn subject, e.g., the subject is in utero. Preferably, the subject is a mammal. The mammal can be a human, non-human primate, mouse, rat, dog, cat, horse, or cow, but is not limited to these examples. Mammals other than humans can be advantageously used as subjects that represent animal models of diseases and disorders. In addition, the methods and compositions described herein can be used for domesticated animals and/or pets. A human subject can be of any age, gender, race or ethnic group, e.g., Caucasian (white), Asian, African, black, African American, African European, Hispanic, Mideastern, etc. In some embodiments, the subject can be a patient or another subject in a clinical setting. In some embodiments, the subject is already undergoing treatment. In some embodiments, the subject is an embryo, a fetus, neonate, infant, child, adolescent, or adult. In some embodiments, the subject is a human fetus, human neonate, human infant, human child, human adolescent, or human adult. In some embodiments, the subject is an animal embryo, or non-human embryo or non-human primate embryo. In some embodiments, the subject is a human embryo.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state. In the context of the present disclosure, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present disclosure are derived from, cancers including but not limited to primary or metastatic melanoma, thymoma, lymphoma, sarcoma, lung cancer, liver cancer, non-Hodgkin's lymphoma, non-Hodgkin's lymphoma, leukemias, uterine cancer, cervical cancer, bladder cancer, kidney cancer and adenocarcinomas such as breast cancer, prostate cancer, ovarian cancer, pancreatic cancer, and the like.

As used herein, the term "host cell" includes any cell type that is susceptible to transformation, transfection, transduction, and the like with nucleic acid therapeutics of the present disclosure. As non-limiting examples, a host cell can be an immune stimulatory cell, such as a T-cell, B cells, dendritic cell, or a natural killer (NK) cell.

As used herein, the term "exogenous" refers to a substance present in a cell other than its native source. The term "exogenous" when used herein can refer to a nucleic acid (e.g., a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell.

As used herein, the term "sequence identity" refers to the relatedness between two nucleotide sequences. For purposes of the present disclosure, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al. et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows: (Identical Deoxyribonucleotides.times.100)/(Length of Alignment-Total Number of Gaps in Alignment). The length of the alignment is preferably at least 10 nucleotides, preferably at least 25 nucleotides more preferred at least 50 nucleotides and most preferred at least 100 nucleotides.

As used herein, the term "homology" or "homologous" as used herein is defined as the percentage of nucleotide residues in the homology arm that are identical to the nucleotide residues in the corresponding sequence on the target chromosome, after aligning the sequences and introducing gaps, if necessary, to achieve the maximum percent sequence identity. Alignment for purposes of determining percent nucleotide sequence homology can be achieved in various ways that are within the skill in the art, for instance, using publicly available computer software such as BLAST, BLAST-2, ALIGN, ClustalW2 or Megalign (DNASTAR) software. Those skilled in the art can determine appropriate parameters for aligning sequences, including any algorithms needed to achieve maximal alignment over the full length of the sequences being compared. In some embodiments, a nucleic acid sequence (e.g., DNA sequence), for example of a homology arm of a repair template, is considered "homologous" when the sequence is at least 70%, at least 75%, at least 80%, at least 85%, at least 90%, at least 91%, at least 92%, at least 93%, at least 94%, at least 95%, at least 96%, at least 97%, at least 98%, at least 99%, or more, identical to the corresponding native or unedited nucleic acid sequence (e.g., genomic sequence) of the host cell.

As used herein, the term "heterologous," as used herein, means a nucleotide or polypeptide sequence that is not found in the native nucleic acid or protein, respectively. A heterologous nucleic acid sequence may be linked to a naturally occurring nucleic acid sequence (or a variant thereof) (e.g., by genetic engineering) to generate a chimeric nucleotide sequence encoding a chimeric polypeptide. A heterologous nucleic acid sequence may be linked to a variant polypeptide (e.g., by genetic engineering) to generate a nucleotide sequence encoding a fusion variant polypeptide.

As used herein, a "vector" or "expression vector" is a replicon, such as plasmid, bacmid, phage, virus, virion, or cosmid, to which another DNA segment, i.e., an "insert" "transgene" or "expression cassette", may be attached so as to bring about the expression or replication of the attached segment ("expression cassette") in a cell. A vector can be a nucleic acid construct designed for delivery to a host cell or for transfer between different host cells. As used herein, a vector can be viral or non-viral in origin in the final form. However, for the purpose of the present disclosure, a "vector" generally refers to synthetic AAV vector or a nicked ceDNA vector. Accordingly, the term "vector" encompasses any genetic element that is capable of replication when associated with the proper control elements and that can transfer gene sequences to cells. In some embodiments, a vector can be a recombinant vector or an expression vector.

As used herein, the phrase "recombinant vector" means a vector that includes a heterologous nucleic acid sequence, or "transgene" that is capable of expression in vivo. It is to be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the term "expression" refers to the cellular processes involved in producing RNA and proteins and as appropriate, secreting proteins, including where applicable, but not limited to, for example, transcription, transcript processing, translation and protein folding, modification and processing. As used herein, the phrase "expression products" include RNA transcribed from a gene (e.g., transgene), and polypeptides obtained by translation of mRNA transcribed from a gene.

As used herein, the term "gene" means the nucleic acid sequence which is transcribed (DNA) to RNA in vitro or in vivo when operably linked to appropriate regulatory sequences.

Pharmacokinetic principles provide a basis for modifying a dosage regimen to obtain a desired degree of therapeutic efficacy with a minimum of unacceptable adverse effects. In situations where the drug's plasma concentration can be measured and related to therapeutic window, additional guidance for dosage modification can be obtained.

As used herein, the terms "treat," "treating," and/or "treatment" include abrogating, inhibiting, slowing or reversing the progression of a condition, ameliorating clinical symptoms of a condition, or preventing the appearance of clinical symptoms of a condition, obtaining beneficial or desired clinical results. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s). In one aspect of any of the aspects or embodiments herein, the terms "treat," "treating," and/or "treatment" include abrogating, inhibiting, slowing or reversing the progression of a condition, or ameliorating clinical symptoms of a condition.

Beneficial or desired clinical results, such as pharmacologic and/or physiologic effects include, but are not limited to, preventing the disease, disorder or condition from occurring in a subject that may be predisposed to the disease, disorder or condition but does not yet experience or exhibit symptoms of the disease (prophylactic treatment), alleviation of symptoms of the disease, disorder or condition, diminishment of extent of the disease, disorder or condition, stabilization (i.e., not worsening) of the disease, disorder or condition, preventing spread of the disease, disorder or condition, delaying or slowing of the disease, disorder or condition progression, amelioration or palliation of the disease, disorder or condition, and combinations thereof, as well as prolonging survival as compared to expected survival if not receiving treatment.

As used herein, the term "combination therapy" refers to treatment regimens for a clinical indication that comprise two or more therapeutic agents. Thus, the term refers to a therapeutic regimen in which a first therapy comprising a first composition (e.g., active ingredient) is administered in conjunction with a second therapy comprising a second composition (active ingredient) to a patient, intended to treat the same or overlapping disease or clinical condition. The first and second compositions may both act on the same cellular target, or discrete cellular targets. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for sequential administration of the therapies.

As used herein, the term "alkyl" refers to a saturated monovalent hydrocarbon radical of 1 to 20 carbon atoms (i.e., $C_{1-20}$ alkyl). "Monovalent" means that alkyl has one point of attachment to the remainder of the molecule. In one embodiment, the alkyl has 1 to 12 carbon atoms (i.e., $C_{1-12}$ alkyl) or 1 to 10 carbon atoms (i.e., $C_{1-10}$ alkyl). In one embodiment, the alkyl has 1 to 8 carbon atoms (i.e., $C_{1-8}$ alkyl), 1 to 7 carbon atoms (i.e., $C_{1-7}$ alkyl), 1 to 6 carbon atoms (i.e., $C_{1-6}$ alkyl), 1 to 4 carbon atoms (i.e., $C_{1-4}$ alkyl), or 1 to 3 carbon atoms (i.e., $C_{1-3}$ alkyl). Examples include, but are not limited to, methyl, ethyl, 1-propyl, 2-propyl, 1-butyl, 2-methyl-1-propyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. A linear or branched alkyl, such as a "linear or branched $C_{1-6}$ alkyl," "linear or branched $C_{1-4}$ alkyl," or "linear or branched $C_{1-3}$ alkyl" means that the saturated monovalent hydrocarbon radical is a linear or branched chain. As used herein, the term "linear" as referring to aliphatic hydrocarbon chains means that the chain is unbranched.

The term "alkylene" as used herein refers to a saturated divalent hydrocarbon radical of 1 to 20 carbon atoms (i.e., $C_{1-20}$ alkylene), examples of which include, but are not limited to, those having the same core structures of the alkyl groups as exemplified above. "Divalent" means that the alkylene has two points of attachment to the remainder of the molecule. In one embodiment, the alkylene has 1 to 12 carbon atoms (i.e., $C_{1-12}$ alkylene) or 1 to 10 carbon atoms (i.e., $C_{1-10}$ alkylene). In one embodiment, the alkylene has 1 to 8 carbon atoms (i.e., $C_{1-8}$ alkylene), 1 to 7 carbon atoms (i.e., $C_{1-7}$ alkylene), 1 to 6 carbon atoms (i.e., $C_{1-6}$ alkylene), 1 to 4 carbon atoms (i.e., $C_{1-4}$ alkylene), 1 to 3 carbon atoms (i.e., $C_{1-3}$ alkylene), ethylene, or methylene. A linear or branched alkylene, such as a "linear or branched $C_{1-6}$ alkylene," "linear or branched $C_{1-4}$ alkylene," or "linear or branched $C_{1-3}$ alkylene" means that the saturated divalent hydrocarbon radical is a linear or branched chain.

The term "alkenyl" refers to straight or branched aliphatic hydrocarbon radical with one or more (e.g., one or two) carbon-carbon double bonds, wherein the alkenyl radical includes radicals having "cis" and "trans" orientations, or by an alternative nomenclature, "E" and "Z" orientations.

"Alkenylene" as used herein refers to aliphatic divalent hydrocarbon radical of 2 to 20 carbon atoms (i.e., $C_{2-20}$ alkenylene) with one or two carbon-carbon double bonds, wherein the alkenylene radical includes radicals having "cis" and "trans" orientations, or by an alternative nomenclature, "E" and "Z" orientations. "Divalent" means that alkenylene has two points of attachment to the remainder of the molecule. In one embodiment, the alkenylene has 2 to 12 carbon atoms (i.e., $C_{2-16}$ alkenylene), 2 to 10 carbon atoms (i.e., $C_{2-10}$ alkenylene). In one embodiment, the alkenylene has 2 to four carbon atoms ($C_{2-4}$). Examples include, but are not limited to, ethylenylene or vinylene (—CH═CH—), allyl (—$CH_2$CH═CH—), and the like. A linear or branched alkenylene, such as a "linear or branched C2-6 alkenylene," "linear or branched $C_{2-4}$ alkenylene," or "linear or branched $C_{2-3}$ alkenylene" means that the unsaturated divalent hydrocarbon radical is a linear or branched chain.

"Cycloalkylene" as used herein refers to a divalent saturated carbocyclic ring radical having 3 to 12 carbon atoms as a monocyclic ring, or 7 to 12 carbon atoms as a bicyclic ring. "Divalent" means that the cycloalkylene has two points of attachment to the remainder of the molecule. In one embodiment, the cycloalkylene is a 3- to 7-membered monocyclic or 3- to 6-membered monocyclic. Examples of monocyclic cycloalkyl groups include, but are not limited to, cyclopropylene, cyclobutylene, cyclopentylene, cyclohexylene, cycloheptylene, cyclooctylene, cyclononylene, cyclodecylene, cycloundecylene, cyclododecylene, and the like. In one embodiment, the cycloalkylene is cyclopropylene.

The terms "heterocycle," "heterocyclyl," heterocyclic and "heterocyclic ring" are used interchangeably herein and refer to a cyclic group which contains at least one N atom has a heteroatom and optionally 1-3 additional heteroatoms selected from N and S, and are non-aromatic (i.e., partially or fully saturated). It can be monocyclic or bicyclic (bridged or fused). Examples of heterocyclic rings include, but are not limited to, aziridinyl, diaziridinyl, thiaziridinyl, azetidinyl, diazetidinyl, triazetidinyl, thiadiazetidinyl, thiazetidinyl, pyrrolidinyl, pyrazolidinyl, imidazolinyl, isothiazolidinyl, thiazolidinyl, piperidinyl, piperazinyl, hexahydropyrimidinyl, azepanyl, azocanyl, and the like. The heterocycle contains 1 to 4 heteroatoms, which may be the same or different, selected from N and S. In one embodiment, the heterocycle contains 1 to 3 N atoms. In another embodiment, the heterocycle contains 1 or 2 N atoms. In another embodiment, the heterocycle contains 1 N atom. A "4- to 8-membered heterocyclyl" means a radical having from 4 to 8 atoms (including 1 to 4 heteroatoms selected from N and S, or 1 to 3 N atoms, or 1 or 2 N atoms, or 1 N atom) arranged in a monocyclic ring. A "5- or 6-membered heterocyclyl" means a radical having from 5 or 6 atoms (including 1 to 4 heteroatoms selected from N and S, or 1 to 3 N atoms, or 1 or 2 N atoms, or 1 N atom) arranged in a monocyclic ring. The term "heterocycle" is intended to include all the possible isomeric forms. Heterocycles are described in Paquette, Leo A., *Principles of Modern Heterocyclic Chemistry* (W. A. Benjamin, New York, 1968), particularly Chapters 1, 3, 4, 6, 7, and 9*; The Chemistry of Heterocyclic Compounds, A Series of Monographs* (John Wiley & Sons, New York, 1950 to present), in particular Volumes 13, 14, 16, 19, and 28; and *J. Am. Chem. Soc.* (1960) 82:5566. The heterocyclyl groups may be carbon (carbon-linked) or nitrogen (nitrogen-linked) attached to the rest of the molecule where such is possible.

If a group is described as being "optionally substituted," the group may be either (1) not substituted, or (2) substituted. If a carbon of a group is described as being optionally substituted with one or more of a list of substituents, one or more of the hydrogen atoms on the carbon (to the extent there are any) may separately and/or together be replaced with an independently selected optional substituent.

Suitable substituents for an alkyl, alkylene, alkenylene, cycloalkylene, and heterocyclyl, are those which do not significantly adversely affect the biological activity of the molecule. Unless otherwise specified, exemplary substituents for these groups include linear, branched or cyclic alkyl, alkenyl or alkynyl having from 1 to 10 carbon atoms, aryl, heteroaryl, heterocyclyl, halogen, guanidinium [—NH(C≡NH)NH$_2$], —OR$_{100}$, NR$_{101}$R$_{102}$, —NO$_2$, —NR$_{101}$COR$_{102}$, —SR$_{100}$, a sulfoxide represented by —SOR$_{101}$, a sulfone represented by —SO$_2$R$_{101}$, a sulfonate —SO$_3$M, a sulfate —OSO$_3$M, a sulfonamide represented by —SO$_2$NR$_{101}$R$_{102}$, cyano, an azido, —COR$_{101}$, —OCOR$_{101}$, —OCONR$_{101}$R$_{102}$ and a polyethylene glycol unit (—OCH$_2$CH$_2$)$_n$R$_{101}$ wherein M is H or a cation (such as Na$^+$ or K$^+$); R$_{101}$, R$_{102}$ and R$_{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$_{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$_{104}$ is H or a linear or branched alkyl having 1 to 4 carbon atoms, wherein the alkyl, alkenyl, alkynyl, aryl, heteroaryl and heterocyclyl in the groups represented by R$_{100}$, R$_{101}$, R$_{102}$, R$_{103}$ and R$_{104}$ are optionally substituted with one or more (e.g., 2, 3, 4, 5, 6 or more) substituents independently selected from halogen, —OH, —CN, —NO$_2$, and unsubstituted linear or branched alkyl having 1 to 4 carbon atoms. Preferably, the substituent for the optionally substituted alkyl, alkylene, alkenylene, cycloalkylene, and heterocyclyl described above is selected from the group consisting of halogen, —CN, —NR$_{101}$R$_{102}$, —CF$_3$, —OR$_{100}$, aryl, heteroaryl, heterocyclyl, —SR$_{101}$, —SOR$_{101}$, —SO$_2$R$_{101}$, and —SO$_3$M. Alternatively, the suitable substituent is selected from the group consisting of halogen, —OH, —NO$_2$, —CN, C$_{1-4}$ alkyl, —OR$_{100}$, NR$_{101}$R$_{102}$, —NR$_{101}$COR$_{102}$, —SR$_{100}$, —SO$_2$R$_{101}$, —SO$_2$NR$_{101}$R$_{102}$, —COR$_{101}$, —OCOR$_{101}$, and —OCONR$_{101}$R$_{102}$, wherein R$_{100}$, R$_{101}$, and R$_{102}$ are each independently —H or C$_{1-4}$ alkyl.

"Halogen" as used herein refers to F, Cl, Br or I. "Cyano" is —CN.

"Amine" or "amino" as used herein interchangeably refers to a functional group that contains a basic nitrogen atom with a lone pair.

The term "pharmaceutically acceptable salt" as used herein refers to pharmaceutically acceptable organic or inorganic salts of an ionizable lipid of the disclosure. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ions.

As used herein the term "comprising" or "comprises" is used in reference to compositions, methods, processes, and respective component(s) thereof, that are essential to the processes, methods or compositions, yet open to the inclusion of unspecified elements, whether essential or not. The use of "comprising" indicates inclusion rather than limitation.

The term "consisting of" refers to compositions, methods, processes, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the disclosure.

As used in this specification and the appended claims, the singular forms "a," "an," and "the" include plural references unless the context clearly dictates otherwise. Thus, for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below.

The abbreviation, "e.g." is derived from the Latin exempli gratia and is used herein to indicate a non-limiting example. Thus, the abbreviation "e.g." is synonymous with the term "for example." Other than in the operating examples, or where otherwise indicated, all numbers expressing quantities of ingredients or reaction conditions used herein should be understood as modified in all instances by the term "about." The term "about" when used in connection with percentages can mean±1%. The present disclosure is further explained in detail by the following examples, but the scope of the disclosure should not be limited thereto.

Groupings of alternative elements or embodiments of the disclosure disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the disclosure.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. It should be understood that this disclosure is not limited in any manner to the particular methodology, protocols, and reagents, etc., described herein and as such can vary. The terminology used herein is for the purpose of describing particular embodiments only and is not intended to limit the scope of the present disclosure, which is defined solely by the claims.

II. Lipid Nanoparticles (LNPs)

Provided herein are bispecific lipid nanoparticles (LNPs) comprising a therapeutic nucleic acid (TNA); an ionizable lipid; a structural lipid (e.g., a sterol); one or more lipid-anchored polymers, e.g., a first lipid-anchored polymer, a second lipid-anchored polymer, and a third lipid-anchored polymer and, optionally, a helper lipid (e.g., DSPC). Also provided herein are bispecific LNPs consisting essentially of a therapeutic nucleic acid (TNA); an ionizable lipid; a structural lipid (e.g., a sterol); one or more lipid-anchored polymers, e.g., a first lipid-anchored polymer, a second lipid-anchored polymer, and a third lipid-anchored polymer and, optionally, a helper lipid (e.g., DSPC). Also provided herein are bispecific LNPs consisting of a therapeutic nucleic acid (TNA); an ionizable lipid; a structural lipid (e.g., a sterol); one or more lipid-anchored polymers, e.g., a first lipid-anchored polymer, a second lipid-anchored polymer, and a third lipid-anchored polymer, and DSPC. Also provided herein are bispecific LNPs comprising a therapeutic nucleic acid (TNA); an ionizable lipid; a structural lipid (e.g., a sterol); one or more lipid-anchored polymers (e.g., a first lipid-anchored polymer, a second lipid-anchored polymer, and a third lipid-anchored polymer), and no helper lipid (e.g., 0 mol % of helper lipid, like DSPC). In some embodiments, a bispecific LNP of the present disclosure does not comprise distearoylphosphatidylcholine (DSPC), or a salt or an ester thereof, or a deuterated analogue of any of the foregoing is present.

In particular, the present disclosure provides novel bispecific "stealth" LNPs that surprisingly exhibit improved therapeutic nucleic acid expression, as well as physiological characteristics of prolonged blood circulation time (e.g., increased blood $t_{1/2}$) simultaneously with increased targeting capacity to specific cell-types (e.g., immune effector cells such as T-cells, B-cells, NK cells, and dendritic cells, or hematopoietic stem cells (HSC)), useful for creating genetically modified cells in vivo and/or ex vivo. More specifically, the novel bispecific LNPs disclosed herein provide surprising and unexpected "stealth" properties as compared to previously known LNPs by, for example, providing steric stabilization (e.g., enhancing the stealth property of overall LNP characteristic in the circulation (e.g., the blood compartment) by minimizing interactions between opsonins present in the blood and the surface of the LNP). For example, a bispecific stealth LNP of the disclosure comprises a half-life ($t_{1/2}$) in blood in vivo of greater than 3 hours. In contrast, prior to the instant disclosure, the half-life ($t_{1/2}$) in blood in vivo of LNPs was typically around 30 minutes.

In one embodiment, the half-life ($t_{1/2}$) of the LNP in blood in vivo is greater than 3 hours. In one embodiment, the half-life ($t_{1/2}$) of the LNP in blood in vivo is greater than 4 hours. In one embodiment, the half-life ($t_{1/2}$) of the LNP in blood in vivo is greater than 5 hours. In one embodiment, the half-life ($t_{1/2}$) of the LNP in blood in vivo is greater than 6 hours. In one embodiment, the half-life ($t_{1/2}$) of the LNP in blood in vivo is greater than 7 hours. In one embodiment, the half-life ($t_{1/2}$) of the LNP in blood in vivo is greater than 8 hours. In one embodiment, the half-life ($t_{1/2}$) of the LNP in blood in vivo is greater than 9 hours. In one embodiment, the half-life ($t_{1/2}$) of the LNP in blood in vivo is greater than 10 hours. In one embodiment, the half-life ($t_{1/2}$) of the LNP in blood in vivo is greater than 11 hours. In one embodiment, the half-life ($t_{1/2}$) of the LNP in blood in vivo is greater than 12 hours. In one embodiment, the half-life ($t_{1/2}$) of the LNP in blood in vivo is greater than 14 hours. In one embodiment, the half-life ($t_{1/2}$) of the LNP in blood in vivo is greater than 16 hours. In one embodiment, the half-life ($t_{1/2}$) of the LNP in blood in vivo is greater than 18 hours. In one embodiment, the half-life ($t_{1/2}$) of the LNP in blood in vivo is greater than 20 hours. In one embodiment, the half-life ($t_{1/2}$) of the LNP in blood in vivo is greater than 22 hours. In one embodiment, the half-life ($t_{1/2}$) of the LNP in blood in vivo is greater than 24 hours. In one embodiment, the half-life ($t_{1/2}$) of the LNP in blood in vivo is greater than 28 hours. In one embodiment, the half-life ($t_{1/2}$) of the LNP in blood in vivo is greater than 32 hours. In one embodiment, the half-life ($t_{1/2}$) of the LNP in blood in vivo is greater than 36 hours. In one embodiment, the half-life ($t_{1/2}$) of the LNP in blood in vivo is greater than 40 hours. In one embodiment, the half-life ($t_{1/2}$) of the LNP in blood in vivo is greater than 44 hours. In one embodiment, the half-life ($t_{1/2}$) of the LNP in blood in vivo is greater than 48 hours.

In one embodiment, the half-life ($t_{1/2}$) of the LNP in blood in vivo is less than 72 hours. In one embodiment, the half-life ($t_{1/2}$) of the LNP in blood in vivo is less than 96 hours.

In one embodiment, the half-life ($t_{1/2}$) of the LNP in blood in vivo is between about 3 hours and about 48 hours. In one embodiment, the half-life ($t_{1/2}$) of the LNP in blood in vivo is between about 4 hours and about 48 hours. In one embodiment, the half-life ($t_{1/2}$) of the LNP in blood in vivo is between about 5 hours and about 48 hours. In one embodiment, the half-life ($t_{1/2}$) of the LNP in blood in vivo is between about 6 hours and about 48 hours. In one embodiment, the half-life ($t_{1/2}$) of the LNP in blood in vivo is between about 7 hours and about 48 hours. In one embodiment, the half-life ($t_{1/2}$) of the LNP in blood in vivo is between about 8 hours and about 48 hours. In one embodiment, the half-life ($t_{1/2}$) of the LNP in blood in vivo is between about 9 hours and about 48 hours. In one embodiment, the half-life ($t_{1/2}$) of the LNP in blood in vivo is between about 10 hours and about 48 hours. In one embodiment, the half-life ($t_{1/2}$) of the LNP in blood in vivo is between about 11 hours and about 48 hours. In one embodiment, the half-life ($t_{1/2}$) of the LNP in blood in vivo is between about 12 hours and about 48 hours. In one embodiment, the half-life ($t_{1/2}$) of the LNP in blood in vivo is between about 16 hours and about 48 hours. In one embodiment, the half-life ($t_{1/2}$) of the LNP in blood in vivo is between about 20 hours and about 48 hours. In one embodiment, the half-life ($t_{1/2}$) of the LNP in blood in vivo is between about 24 hours and about 48 hours. In one embodiment, the half-life ($t_{1/2}$) of the LNP in blood in vivo is between about 36 hours and about 48 hours. In one embodiment, the half-life ($t_{1/2}$) of the LNP in blood in vivo is between about 8 hours and about 36 hours. In one embodiment, the half-life ($t_{1/2}$) of the LNP in blood in vivo is between about 12 hours and about 36 hours. In one embodiment, the half-life ($t_{1/2}$) of the LNP in blood in vivo is between about 24 hours and about 36 hours.

A. Ionizable Lipids

In some embodiments, the ionizable lipid is present in the LNP provided by the present disclosure in an amount of about 20 mol % to about 70 mol %, about 20 mol % to about 65 mol %, about 20 mol % to about 60 mol %, about 20 mol % to about 55 mol %, about 20 mol % to about 50 mol %, about 25 mol % to about 70 mol %, about 25 mol % to about 65 mol %, about 25 mol % to about 60 mol %, about 25 mol % to about 55 mol %, about 25 mol % to about 50 mol %, about 30 mol % to about 70 mol %, about 30 mol % to about 65 mol %, about 30 mol % to about 60 mol %, about 30 mol % to about 55 mol %, about 30 mol % to about 50 mol %, about 35 mol % to about 70 mol %, about 35 mol % to about 65 mol %, about 35 mol % to about 60 mol %, about 35 mol % to about 55 mol %, about 35 mol % to about 50 mol %, 40 mol % to about 70 mol %, about 40 mol % to about 65 mol %, about 40 mol % to about 60 mol %, about 40 mol % to about 55 mol %, or about 40 mol % to about 50 mol %, of the total lipid present in the LNP.

In some embodiments, the LNPs provided by the present disclosure comprise an ionizable lipid. Exemplary ionizable lipids in the LNPs of the present disclosure are described in International Patent Application Publication Nos. WO2015/095340, WO2015/199952, WO2018/011633, WO2017/049245, WO2015/061467, WO2012/040184, WO2012/000104, WO2015/074085, WO2016/081029, WO2017/004143, WO2017/075531, WO2017/117528, WO2011/022460, WO2013/148541, WO2013/116126, WO2011/153120, WO2012/044638, WO2012/054365, WO2011/090965, WO2013/016058, WO2012/162210, WO2008/042973, WO2010/129709, WO2010/144740, WO2012/099755, WO2013/049328, WO2013/086322, WO2013/086373, WO2011/071860, WO2009/132131, WO2010/048536, WO2010/088537, WO2010/054401, WO2010/054406, WO2010/054405, WO2010/054384, WO2012/016184, WO2009/086558, WO2010/042877, WO2011/000106, WO2011/000107, WO2005/120152, WO2011/141705, WO2013/126803, WO2006/007712, WO2011/038160, WO2005/121348, WO2011/066651, WO2009/127060, WO2011/141704, WO2006/069782, WO2012/031043, WO2013/006825, WO2013/033563, WO2013/089151, WO2017/099823, WO2015/095346, and WO2013/086354, and US Patent Application Publication Nos. US2016/0311759, US2015/0376115, US2016/0151284, US2017/0210697, US2015/0140070, US2013/0178541, US2013/0303587, US2015/0141678, US2015/0239926, US2016/0376224, US2017/0119904, US2012/0149894, US2015/0057373, US2013/0090372, US2013/0274523, US2013/0274504, US2013/0274504, US2009/0023673, US2012/0128760, US2010/0324120, US2014/0200257, US2015/0203446, US2018/0005363, US2014/0308304, US2013/0338210, US2012/0101148, US2012/0027796, US2012/0058144, US2013/0323269, US2011/0117125, US2011/0256175, US2012/0202871, US2011/0076335, US2006/0083780, US2013/0123338, US2015/0064242, US2006/0051405, US2013/0065939, US2006/0008910, US2003/0022649, US2010/0130588, US2013/0116307, US2010/0062967, US2013/0202684, US2014/0141070, US2014/0255472, US2014/0039032, US2018/0028664, US2016/0317458, and US2013/0195920, the contents of all of which are incorporated herein by reference in their entirety.

Formula (A)

In some embodiments, the ionizable lipid in the LNPs of the present disclosure is represented by Formula (A):

(A)

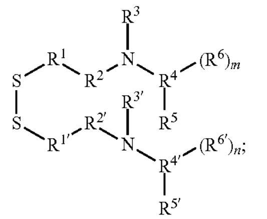

or a pharmaceutically acceptable salt thereof, wherein:

$R^1$ and $R^{1'}$ are each independently $C_{1-3}$ alkylene;

$R^2$ and $R^{2'}$ are each independently linear or branched $C_{1-6}$ alkylene, or C3-6 cycloalkylene;

$R^3$ and $R^{3'}$ are each independently optionally substituted $C_{1-6}$ alkyl or optionally substituted $C_{3-6}$ cycloalkyl;

or alternatively, when $R^2$ is branched $C_{1-6}$ alkylene and when $R^3$ is $C_{1-6}$ alkyl, $R^2$ and $R^3$, taken together with their intervening N atom, form a 4- to 8-membered heterocyclyl;

or alternatively, when $R^{2'}$ is branched $C_{1-6}$ alkylene and when $R^{3'}$ is $C_{1-6}$ alkyl, $R^{2'}$ and $R^3$, taken together with their intervening N atom, form a 4- to 8-membered heterocyclyl;

$R^4$ and $R^{4'}$ are each independently —CH, —$CH_2$CH, or —$(CH_2)_2$CH;

$R^5$ and $R^{5'}$ are each independently hydrogen, $C_{1-20}$ alkylene or $C_{2-20}$ alkenylene;

$R^6$ and $R^{6'}$, for each occurrence, are independently $C_{1-20}$ alkylene, $C_{3-20}$ cycloalkylene, or $C_{2-20}$ alkenylene; and m and n are each independently an integer selected from 1, 2, 3, 4, and 5.

In some embodiments, $R^2$ and $R^{2'}$ are each independently $C_{1-3}$ alkylene.

In some embodiments, the linear or branched $C_{1-3}$ alkylene represented by $R^1$ or $R^{1'}$, the linear or branched $C_{1-6}$ alkylene represented by $R^2$ or $R^{2'}$, and the optionally substituted linear or branched $C_{1-6}$ alkyl are each optionally substituted with one or more halo and cyano groups.

In some embodiments, $R^1$ and $R^2$ taken together are $C_{1-3}$ alkylene and $R^{1'}$ and $R^{2'}$ taken together are $C_{1-3}$ alkylene, e.g., ethylene.

In some embodiments, $R^3$ and $R^{3'}$ are each independently optionally substituted $C_{1-3}$ alkyl, e.g., methyl.

In some embodiments, $R^4$ and $R^{4'}$ are each —CH.

In some embodiments, $R^2$ is optionally substituted branched $C_{1-6}$ alkylene; and $R^2$ and $R^3$, taken together with their intervening N atom, form a 5- or 6-membered heterocyclyl. In some embodiments, $R^{2'}$ is optionally substituted branched $C_{1-6}$ alkylene; and $R^{2'}$ and $R^{3'}$, taken together with their intervening N atom, form a 5- or 6-membered heterocyclyl, such as pyrrolidinyl or piperidinyl.

In some embodiments, $R^4$ is —$C(R^a)_2CR^a$, or —$[C(R^a)_2]_2CR^a$ and $R^a$ is $C_{1-3}$ alkyl; and $R^3$ and $R^4$, taken together with their intervening N atom, form a 5- or 6-membered heterocyclyl. In some embodiments, $R^{4'}$ is —$C(R^a)_2CR^a$, or —$[C(R^a)_2]_2CR^a$ and $R^a$ is $C_{1-3}$ alkyl; and $R^{3'}$ and $R^{4'}$, taken together with their intervening N atom, form a 5- or 6-membered heterocyclyl, such as pyrrolidinyl or piperidinyl.

In some embodiments, $R^5$ and $R^{5'}$ are each independently $C_{1-10}$ alkylene or $C_{2-10}$ alkenylene. In one embodiment, $R^5$ and $R^{5'}$ are each independently $C_{1-8}$ alkylene or $C_{1-6}$ alkylene.

In some embodiments, $R^6$ and $R^{6'}$, for each occurrence, are independently $C_{1-10}$ alkylene, $C_{3-10}$ cycloalkylene, or $C_{2-10}$ alkenylene. In one embodiment, $C_{1-6}$ alkylene, $C_{3-6}$ cycloalkylene, or $C_{2-6}$ alkenylene. In one embodiment the $C_{3-10}$ cycloalkylene or the $C_{3-6}$ cycloalkylene is cyclopropylene. In some embodiments, m and n are each 3.

In some embodiments, the ionizable lipid in the LNPs of the present disclosure may be selected from any one of the lipids listed in Table 1 below, or a pharmaceutically acceptable salt thereof.

TABLE 1

| Exemplary ionizable lipids of Formula (A) | |
|---|---|
| Lipid No. | Structure and Name |
| 1 | 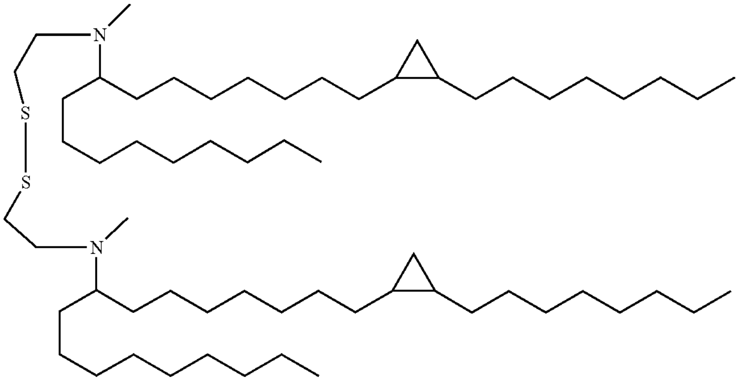 [SMILES: CCCCCCCCCC(CCCCCCCC1CC1CCCCCCCC)N(C)CCSSCCN(C)C(CCCCCCCCC)CCCCCCCC1CC1CCCCCCCC] |

TABLE 1-continued

| Exemplary ionizable lipids of Formula (A) | |
|---|---|
| Lipid No. | Structure and Name |
| | N,N'-(disulfanediylbis(ethane-2,1-diyl))bis(N-methyl-1-(2-octylcyclopropyl)heptadecan-8-amine) |
| 2 | 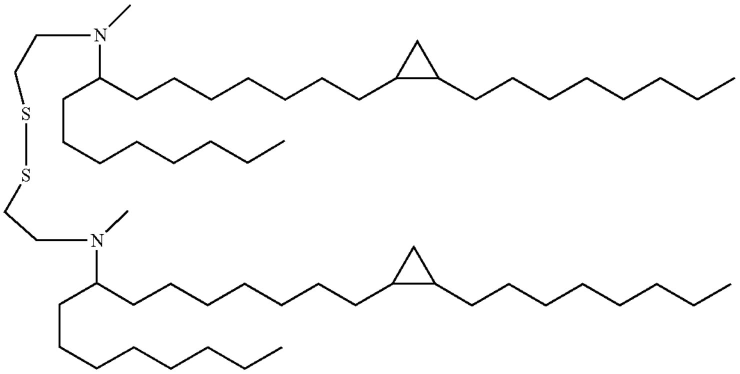 [SMILES: CCCCCCCCC1CC1CCCCCCCC(CCCCCCCC)N(C)CCSSCCN(C)C(CCCCCCCC)CCCCCCCC1CC1CCCCCCCC] N,N'-(disulfanediylbis(ethane-2,1-diyl))bis(N-methyl-1-(2-octylcyclopropyl)hexadecan-8-amine) |
| 3 | 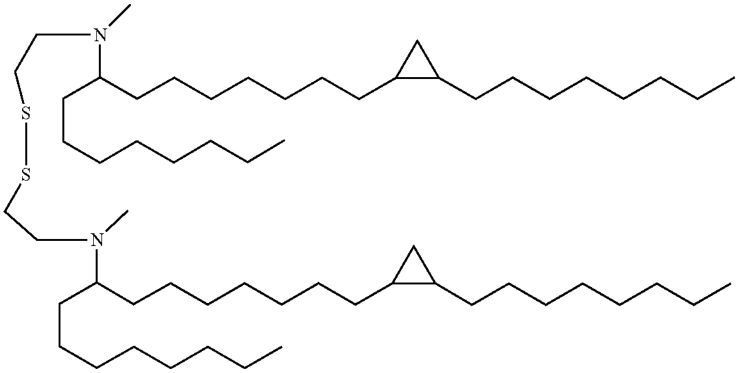 [SMILES: CCCCCCCCC1CC1CCCCCCCC(CCCCCCCC)N(C)CCSSCCN(C)C(CCCCCCCC)CCCCCCCC1CC1CCCCCCCC] N,N'-(disulfanediylbis(ethane-2,1-diyl))bis(N-methyl-1-(2-octylcyclopropyl)hexadecan-8-amine) |
| 4 | 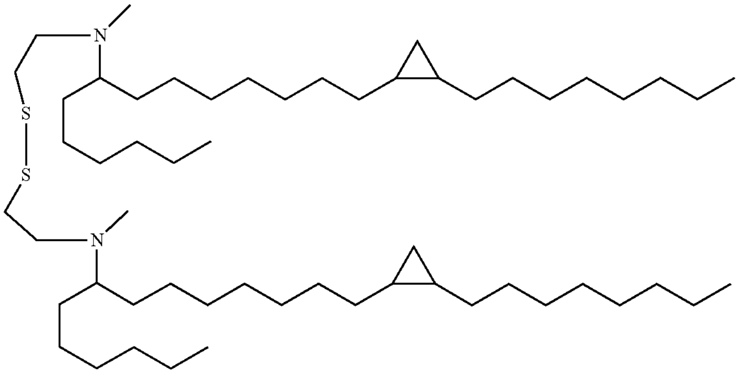 [SMILES: CCCCCCCCC1CC1CCCCCCCC(CCCCCC)N(C)CCSSCCN(C)C(CCCCCC)CCCCCCCC1CC1CCCCCCCC] N,N'-(disulfanediylbis(ethane-2,1-diyl))bis(N-methyl-14-(2-octylcyclopropyl)tetradecan-7-amine) |

TABLE 1-continued
| Exemplary ionizable lipids of Formula (A) | |
|---|---|
| Lipid No. | Structure and Name |
| 5 | 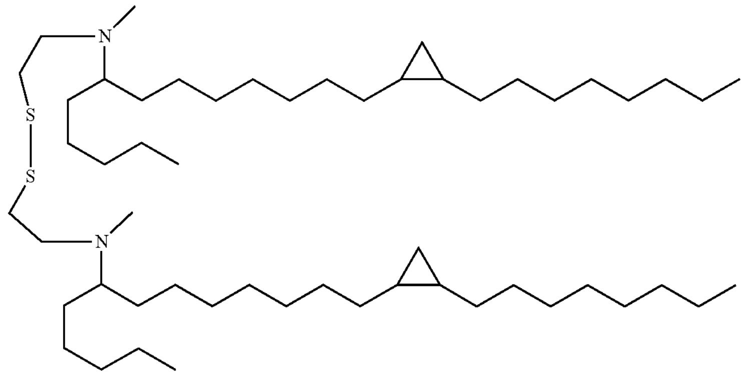 [SMILES: CCCCCCCCC1CC1CCCCCCCC(CCCCC)N(C)CCSSCCN(C)C(CCCCC)CCCCCCCC1CC1CCCCCCCC] N,N'-(disulfanediylbis(ethane-2,1-diyl))bis(N-methyl-13-(2-octylcyclopropyl)tridecan-6-amine) |
| 6 | 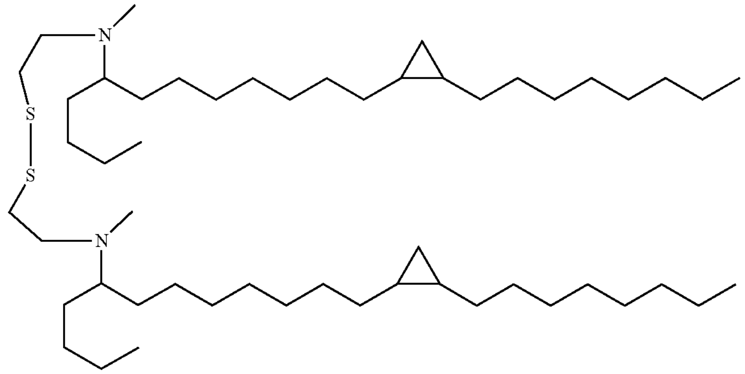 [SMILES: CCCCCCCCC1CC1CCCCCCCC(CCCC)N(C)CCSSCCN(C)C(CCCC)CCCCCCCC1CC1CCCCCCCC] N,N'-(disulfanediylbis(ethane-2,1-diyl))bis(N-methyl-12-(2-octylcyclopropyl)dodecan-5-amine) |
| 7 | 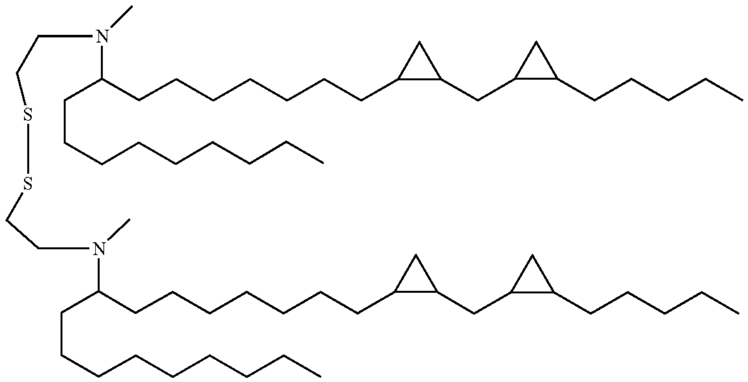 [SMILES: CCCCCCCCCC(CCCCCCCC1CC1CC1CC1CCCCC)N(C)CCSSCCN(C)C(CCCCCCCCC)CCCCCCCC1CC1CC1CC1CCCCC] N,N'-(disulfanediylbis(ethane-2,1-diyl))bis(N-methyl-1-(2-((2-pentylcyclopropyl)methyl)cyclopropyl)heptadecan-8-amine) |

TABLE 1-continued

| Exemplary ionizable lipids of Formula (A) | |
|---|---|
| Lipid No. | Structure and Name |
| 8 | 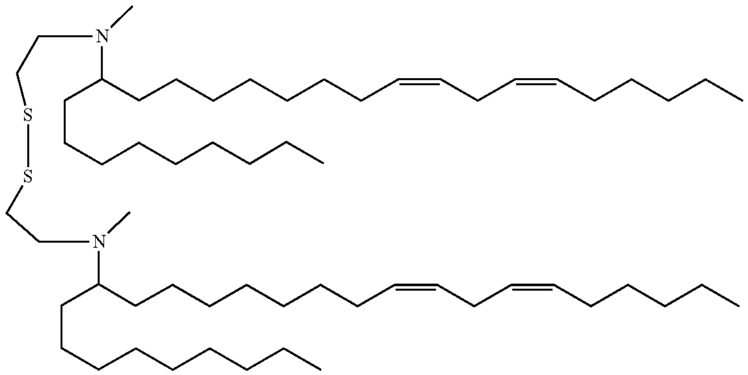 [SMILES: CCCCC/C=C\C/C=C\CCCCCCCC(CCCCCCCCC)N(C)CCSSCCN(C)C(CCCCCCC/C=C\C/C=C\CCCCC)CCCCCCCCC] (18Z,18'Z,21Z,21'Z)-N,N'-(disulfanediylbis(ethane-2,1-diyl))bis(N-methylheptacosa-18,21-dien-10-amine) |
| 9 | 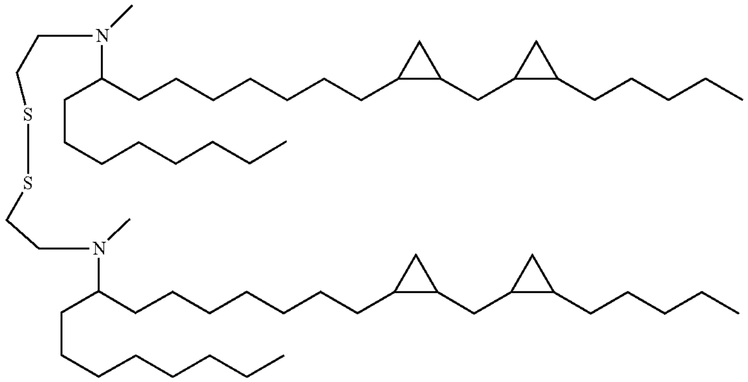 [SMILES: CCCCCCCCC(CCCCCCCC1CC1CC1CC1CCCCC)N(C)CCSSCCN(C)C(CCCCCCCC)CCCCCCCC1CC1CC1CC1CCCCC] N,N'-(disulfanediylbis(ethane-2,1-diyl))bis(N-methyl-1-(2-((2-pentylcyclopropyl)methyl)cyclopropyl)hexadecan-8-amine) |
| 10 | 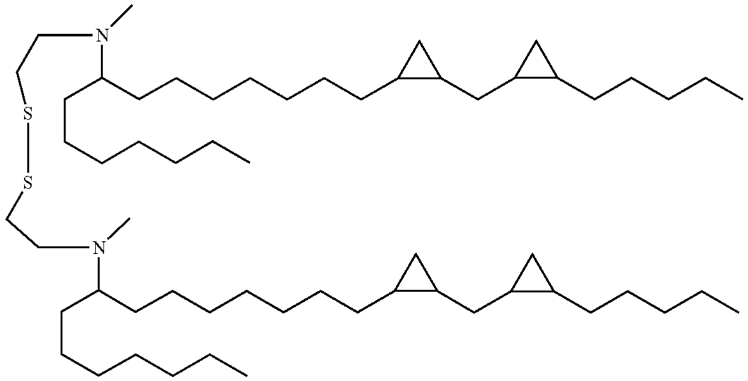 [SMILES: CCCCCCCC(CCCCCCCC1CC1CC1CC1CCCCC)N(C)CCSSCCN(C)C(CCCCCCC)CCCCCCCC1CC1CC1CC1CCCCC] N,N'-(disulfanediylbis(ethane-2,1-diyl))bis(N-methyl-1-(2-((2-pentylcyclopropyl)methyl)cyclopropyl)pentadecan-8-amine) |

TABLE 1-continued

| Exemplary ionizable lipids of Formula (A) | |
|---|---|
| Lipid No. | Structure and Name |
| 11 | 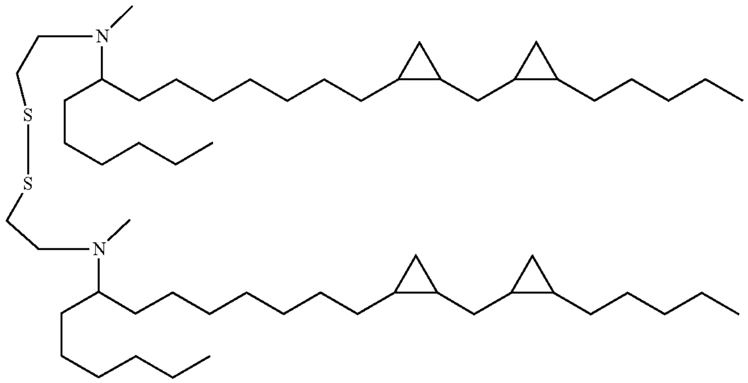 [SMILES: CCCCCCC(CCCCCCCC1CC1CC1CC1CCCCC)N(C)CCSSCCN(C)C(CCCCCC)CCCCCCCC1CC1CC1CC1CCCCC] N,N'-(disulfanediylbis(ethane-2,1-diyl))bis(N-methyl-14-(2-((2-pentylcyclopropyl)methyl)cyclopropyl)tetradecan-7-amine) |
| 12 | 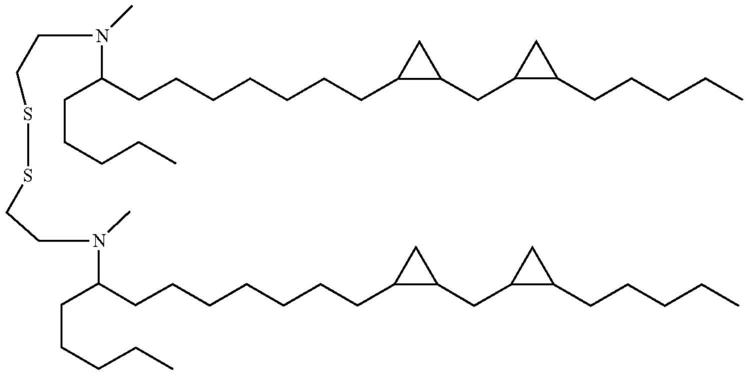 [SMILES: CCCCCC1CC1CC1CC1CCCCCCCC(CCCCC)N(C)CCSSCCN(C)C(CCCCC)CCCCCCCC1CC1CC1CC1CCCCC] N,N'-(disulfanediylbis(ethane-2,1-diyl))bis(N-methyl-13-(2-((2-pentylcyclopropyl)methyl)cyclopropyl)tridecan-6-amine) |
| 13 | 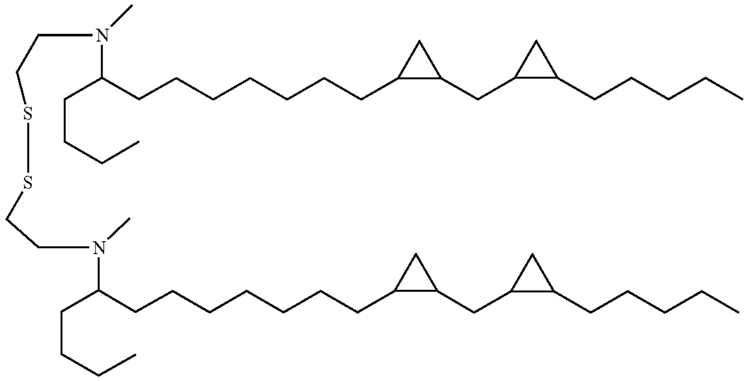 [SMILES: CCCCCC1CC1CC1CC1CCCCCCCC(CCCC)N(C)CCSSCCN(C)C(CCCC)CCCCCCCC1CC1CC1CC1CCCCC] N,N'-(disulfanediylbis(ethane-2,1-diyl))bis(N-methyl-12-(2-((2-pentylcyclopropyl)methyl)cyclopropyl)dodecan-5-amine) |

TABLE 1-continued
| Exemplary ionizable lipids of Formula (A) | |
|---|---|
| Lipid No. | Structure and Name |
| 14 | 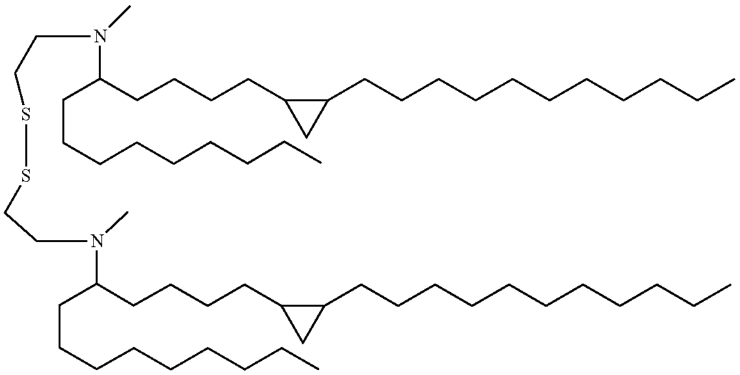 [SMILES: CCCCCCCCCCCC1CC1CCCCC(CCCCCCCCC)N(C)CCSSCCN(C)C(CCCCCCCCC)CCCCC1CC1CCCCCCCCCCC] N,N'-(disulfanediylbis(ethane-2,1-diyl))bis(N-methyl-1-(2-undecylcyclopropyl)tetradecan-5-amine) |
| 15 | 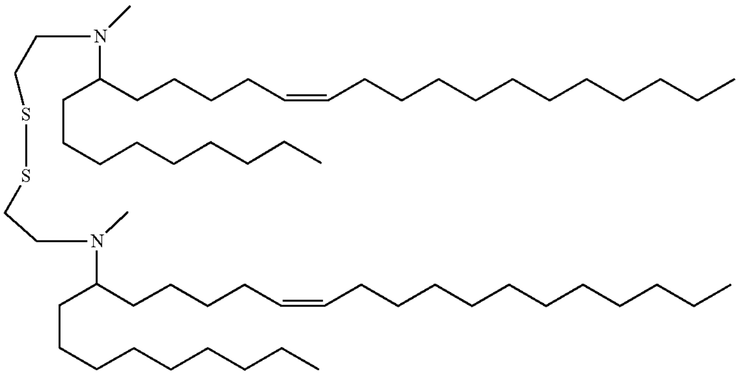 [SMILES: CCCCCCCCCCC/C=C\CCCCC(CCCCCCCCC)N(C)CCSSCCN(C)C(CCCC/C=C\CCCCCCCCCCC)CCCCCCCCC] (15Z,15'Z)-N,N'-(disulfanediylbis(ethane-2,1-diyl))bis(N-methylheptacos-15-en-10-amine) |
| 16 | 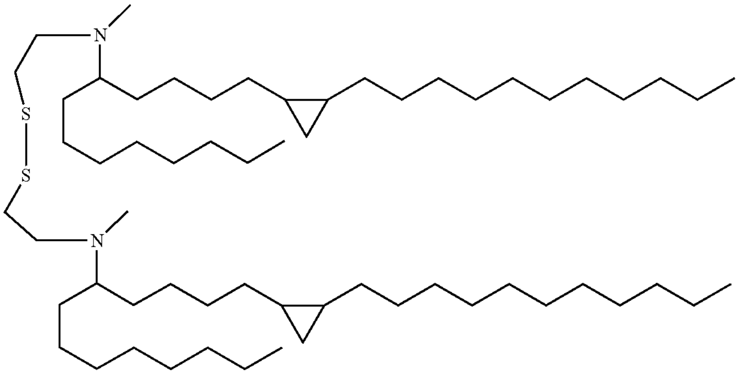 [SMILES: CCCCCCCCCCCC1CC1CCCCC(CCCCCCCC)N(C)CCSSCCN(C)C(CCCCCCCC)CCCCC1CC1CCCCCCCCCCC] N,N'-(disulfanediylbis(ethane-2,1-diyl))bis(N-methyl-1-(2-undecylcyclopropyl)tridecan-5-amine) |

TABLE 1-continued
| Exemplary ionizable lipids of Formula (A) | |
|---|---|
| Lipid No. | Structure and Name |
| 17 | 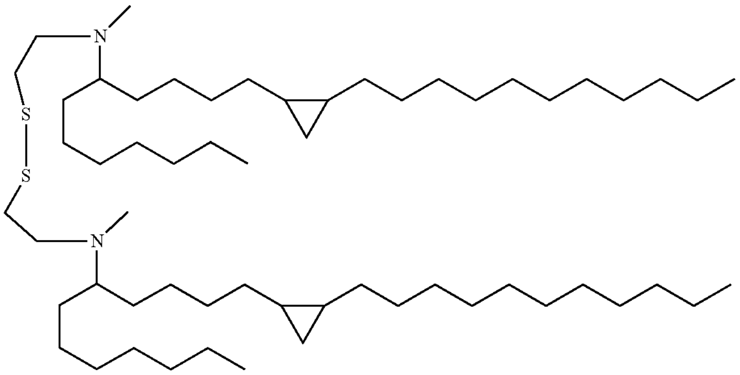 [SMILES: CCCCCCCCCCCC1CC1CCCCC(CCCCCCC)N(C)CCSSCCN(C)C(CCCCCCC)CCCCC1CC1CCCCCCCCCCC] N,N'-(disulfanediylbis(ethane-2,1-diyl))bis(N-methyl-1-(2-undecylcyclopropyl)dodecan-5-amine) |
| 18 | 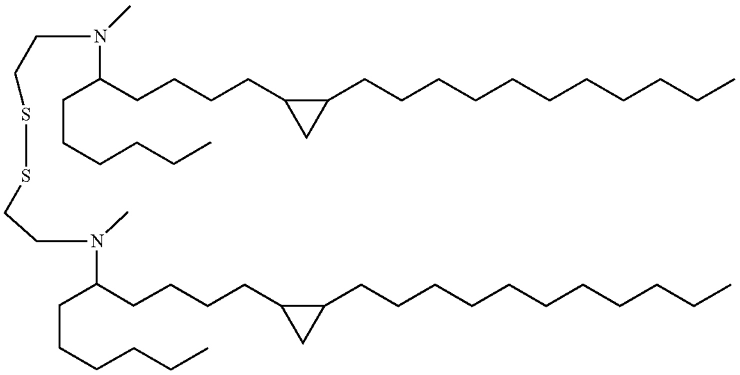 [SMILES: CCCCCCCCCCCC1CC1CCCCC(CCCCCC)N(C)CCSSCCN(C)C(CCCCCC)CCCCC1CC1CCCCCCCCCCC] N,N'-(disulfanediylbis(ethane-2,1-diyl))bis(N-methyl-1-(2-undecylcyclopropyl)undecan-5-amine) |
| 19 | 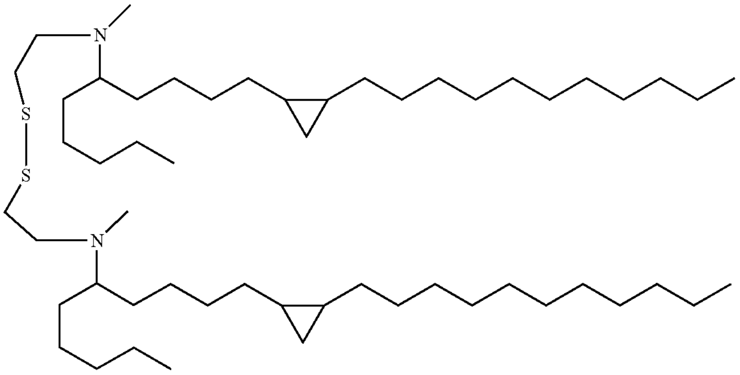 [SMILES: CCCCCCCCCCCC1CC1CCCCC(CCCCC)N(C)CCSSCCN(C)C(CCCCC)CCCCC1CC1CCCCCCCCCCC] N,N'-(disulfanediylbis(ethane-2,1-diyl))bis(N-methyl-1-(2-undecylcyclopropyl)decan-5-amine) |

TABLE 1-continued
| Exemplary ionizable lipids of Formula (A) | |
|---|---|
| Lipid No. | Structure and Name |
| 20 | 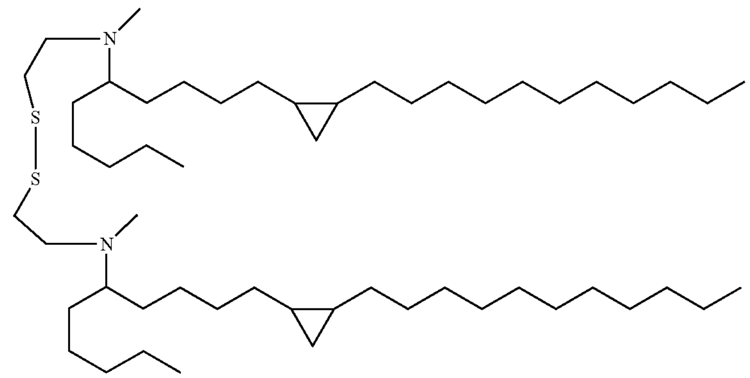 [SMILES: CCCCCCCCCCCC1CC1CCCCC(CCCCC)N(C)CCSSCCN(C)C(CCCCC)CCCCC1CC1CCCCCCCCCCC] N,N'-(disulfanediylbis(ethane-2,1-diyl))bis(N-methyl-1-(2-undecylcyclopropyl)decan-5-amine) |
| 21 | 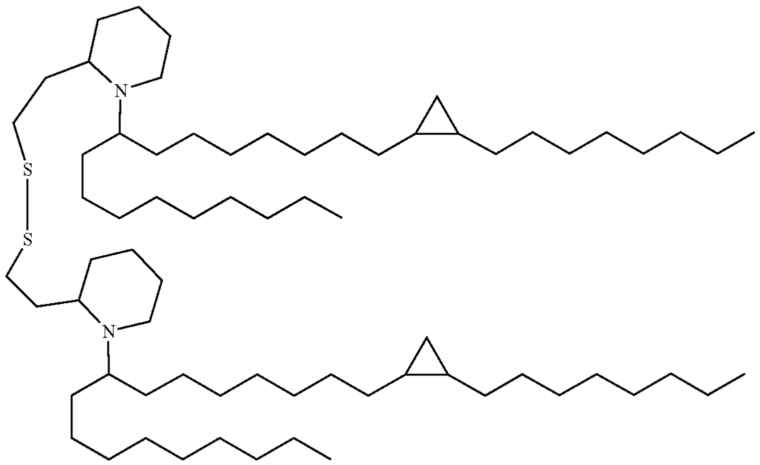 [SMILES: CCCCCCCCCC(CCCCCCCC1CC1CCCCCCCC)N1CCCCC1CCSSCCC1CCCCN1C(CCCCCCCCC)CCCCCCCC1CC1CCCCCCCC] 1,2-bis(2-(1-(1-(2-octylcyclopropyl)heptadecan-8-yl)piperidin-2-yl)ethyl)disulfane |
| 22 | 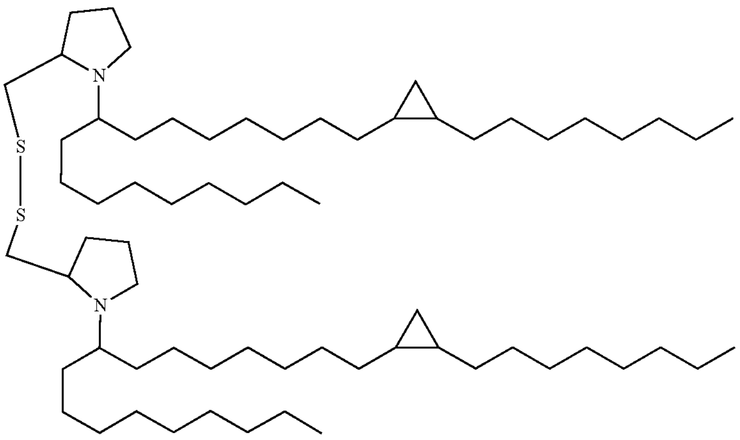 [SMILES: CCCCCCCCCC(CCCCCCCC1CC1CCCCCCCC)N1CCCC1CSSCC1CCCN1C(CCCCCCCCC)CCCCCCCC1CC1CCCCCCCC] 1,2-bis((1-(1-(2-octylcyclopropyl)heptadecan-8-yl)pyrrolidin-2-yl)methyl)disulfane |

TABLE 1-continued
| Exemplary ionizable lipids of Formula (A) | |
|---|---|
| Lipid No. | Structure and Name |
| 23 | 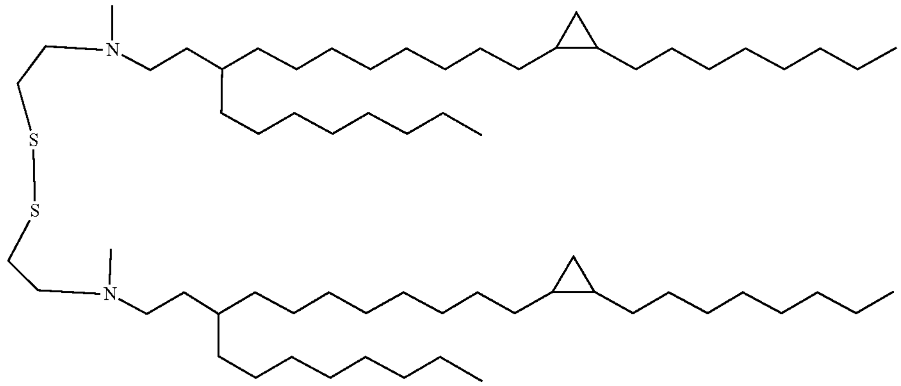 [SMILES: CCCCCCCCC(CCCCCCCCC1CC1CCCCCCCC)CCN(C)CCSSCCN(C)CCC(CCCCCCCC)CCCCCCCCC1CC1CCCCCCCC] N,N'-(disulfanediylbis(ethane-2,1-diyl))bis(N-methyl-3-octyl-11-(2-octylcyclopropyl)undecan-1-amine) |
| 24 | 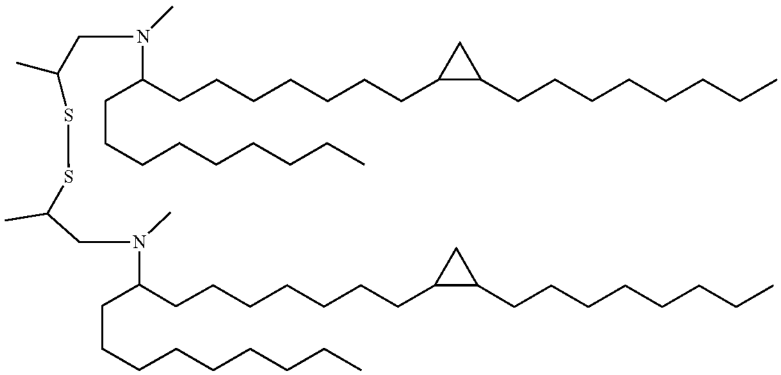 [SMILES: CCCCCCCCCC(CCCCCCCC1CC1CCCCCCCC)N(C)CC(C)SSC(C)CN(C)C(CCCCCCCCC)CCCCCCCC1CC1CCCCCCCC] N,N'-(disulfanediylbis(propane-2,1-diyl))bis(N-methyl-1-(2-octylcyclopropyl)heptadecan-9-amine) |
| 25 | 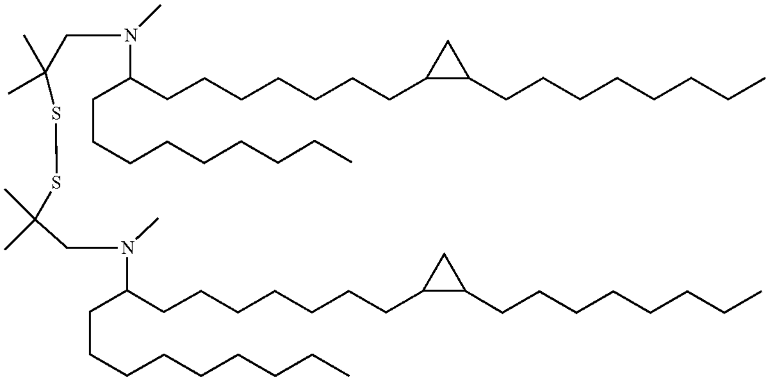 [SMILES: CCCCCCCCCC(CCCCCCCC1CC1CCCCCCCC)N(C)CC(C)(C)SSC(C)(C)CN(C)C(CCCCCCCCC)CCCCCCCC1CC1CCCCCCCC] N,N'-(disulfanediylbis(2-methylpropane-2,1-diyl))bis(N-methyl-1-(2-octylcyclopropyl)heptadecan-8-amine) |

TABLE 1-continued
| Exemplary ionizable lipids of Formula (A) | |
|---|---|
| Lipid No. | Structure and Name |
| 26 | 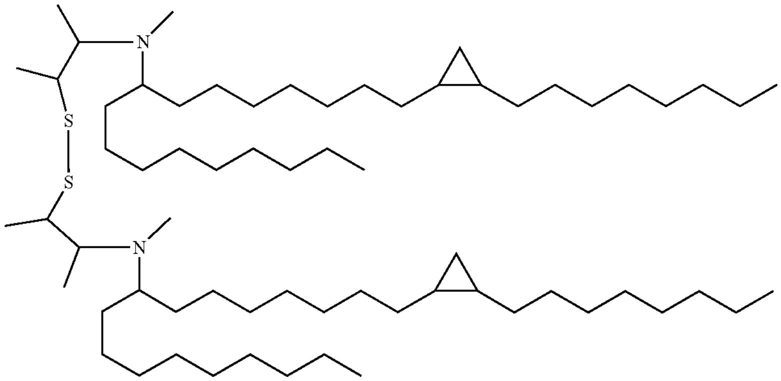 [SMILES: CCCCCCCCCC(CCCCCCCC1CC1CCCCCCCC)N(C)C(C)C(C)SSC(C)C(C)N(C)C(CCCCCCCCC)CCCCCCCC1CC1CCCCCCCC] N,N'-(disulfanediylbis(butane-3,2-diyl))bis(N-methyl-1-(2-octylcyclopropyl)heptadecan-8-amine) |
| 27 | 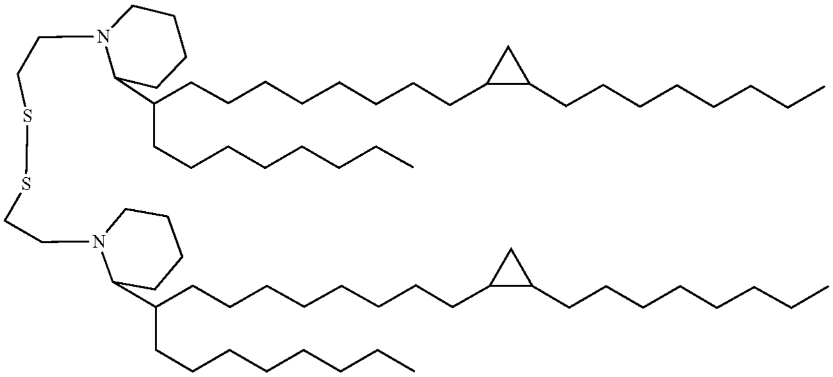 [SMILES: CCCCCCCCC1CC1CCCCCCCCC(CCCCCCCC)C1CCCCN1CCSSCCN1CCCCC1C(CCCCCCCC)CCCCCCCCC1CC1CCCCCCCC] 1,2-bis(2-(2-(1-(2-octylcyclopropyl)heptadecan-9-yl)piperidin-1-yl)ethyl)disulfane |
| 28 | 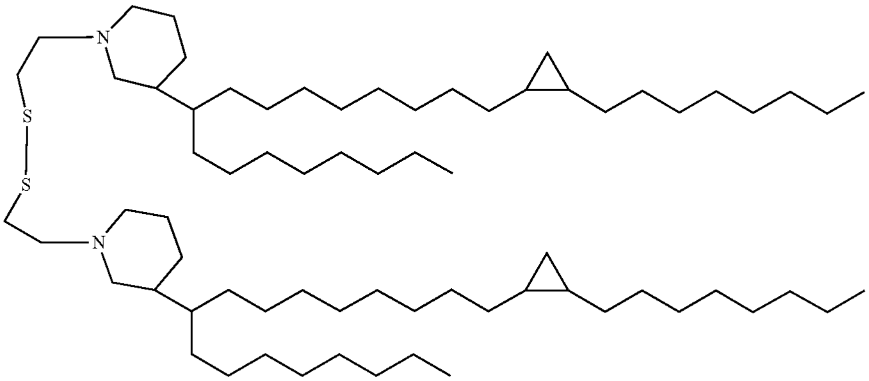 [SMILES: CCCCCCCCC(CCCCCCCCC1CC1CCCCCCCC)C1CCCN(CCSSCCN2CCCC(C(CCCCCCCC)CCCCCCCCC3CC3CCCCCCCC)C2)C1] 1,2-bis(2-(3-(1-(2-octylcyclopropyl)heptadecan-9-yl)piperidin-1-yl)ethyl)disulfane |

TABLE 1-continued
| Exemplary ionizable lipids of Formula (A) | |
|---|---|
| Lipid No. | Structure and Name |
| 29 | 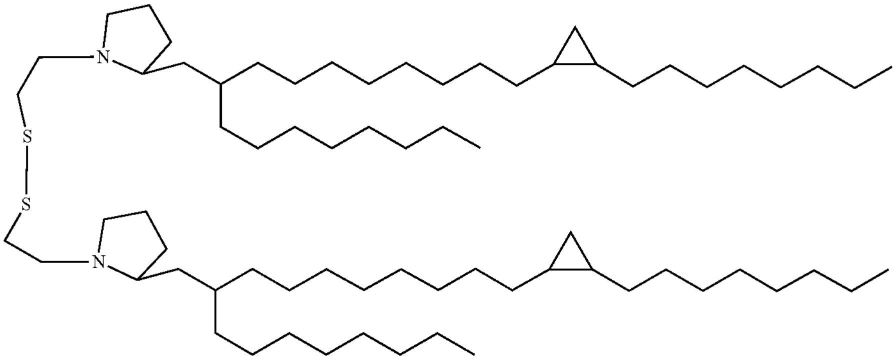 [SMILES: CCCCCCCCC(CCCCCCCCC1CC1CCCCCCCC)CC1CCCN1CCSSCCN1CCCC1CC(CCCCCCCC)CCCCCCCCC1CC1CCCCCCCC] 1,2-bis(2-(2-(2-octyl-10-(2-octylcyclopropyl)decyl)pyrrolidin-1-yl)ethyl)disulfane |
| 30 | 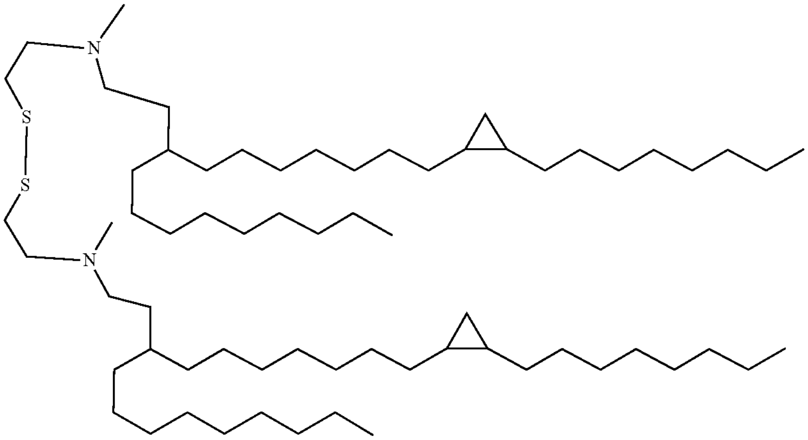 [SMILES: CCCCCCCCCC(CCCCCCCC1CC1CCCCCCCC)CCN(C)CCSSCCN(C)CCC(CCCCCCCCC)CCCCCCCC1CC1CCCCCCCC] N,N'-(disulfanediylbis(ethane-2,1-diyl))bis(N-methyl-3-(7-(2-octylcyclopropyl)heptyl)dodecan-1-amine) |
| 31 | 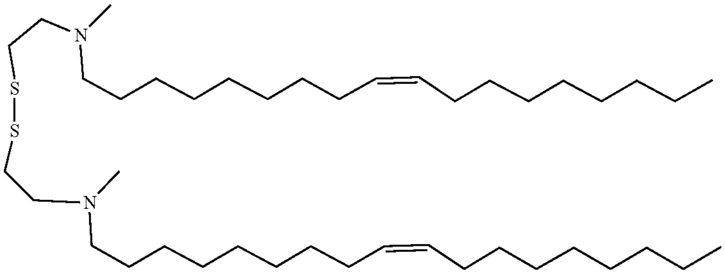 [SMILES: CCCCCCCC/C=C\CCCCCCCCN(C)CCSSCCN(C)CCCCCCCC/C=C\CCCCCCCC] (9Z,9'Z)-N,N'-(disulfanediylbis(ethane-2,1-diyl))bis(N-methyloctadec-9-en-1-amine) |

TABLE 1-continued

| Exemplary ionizable lipids of Formula (A) | |
|---|---|
| Lipid No. | Structure and Name |
| 32 | 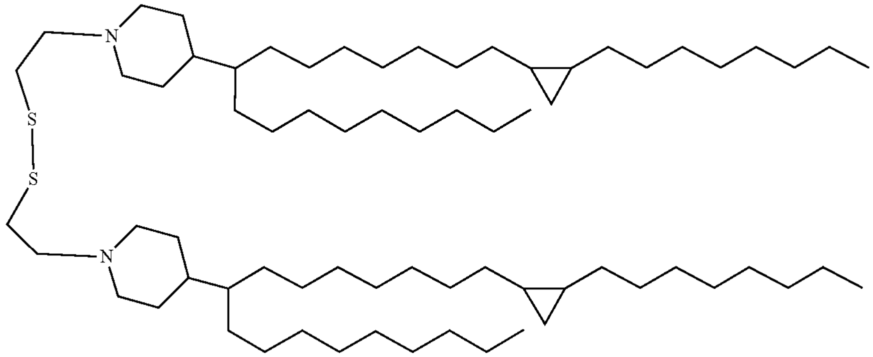 [SMILES: CCCCCCCCCC(CCCCCCCC1CC1CCCCCCCC)C1CCN(CCSSCCN2CCC(C(CCCCCCCCC)CCCCCCCC3CC3CCCCCCCC)CC2)CC1] 1,2-bis(2-(4-(1-(2-octylcyclopropyl)heptadecan-8-yl)piperidin-1-yl)ethyl)disulfane |
| 33 | 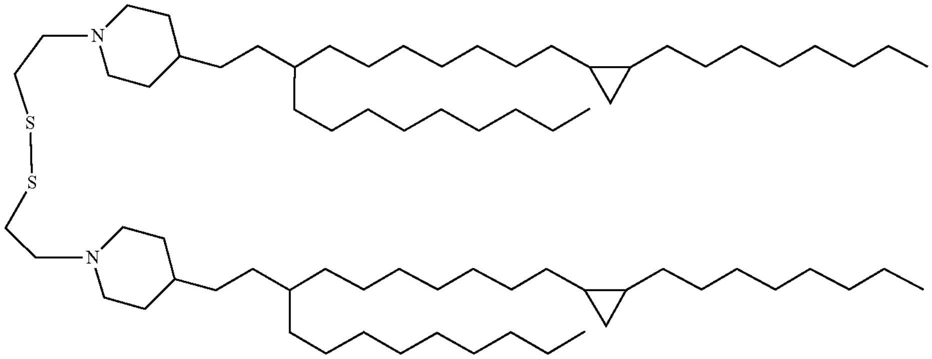 [SMILES: CCCCCCCCCC(CCCCCCCC1CC1CCCCCCCC)CCC1CCN(CCSSCCN2CCC(CCC(CCCCCCCCC)CCCCCCCC3CC3CCCCCCCC)CC2)CC1] 1,2-bis(2-(4-(3-(7-(2-octylcyclopropyl)heptyl)dodecyl)piperidin-1-yl)ethyl)disulfane |
| 34 | 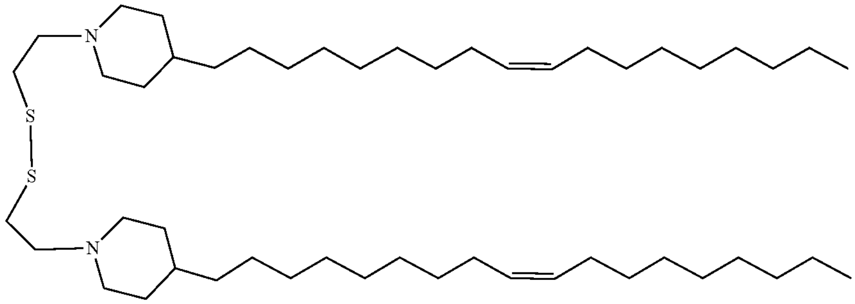 [SMILES: CCCCCCCC/C=C\CCCCCCCCC1CCN(CCSSCCN2CCC(CCCCCCCC/C=C\CCCCCCCC)CC2)CC1] 1,2-bis(2-(4-((Z)-octadec-9-en-1-yl)piperidin-1-yl)ethyl)disulfane |
| 35 | 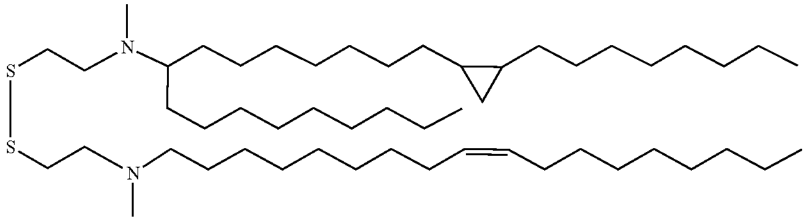 [SMILES: CCCCCCCC/C=C\CCCCCCCCN(C)CCSSCCN(C)C(CCCCCCCCC)CCCCCCCC1CC1CCCCCCCC] (Z)-N-methyl-N-(2-((2-(methyl(1-(2-octylcyclopropyl)heptadecan-8-yl)amino)ethyl)disulfaneyl)ethyl)octadec-9-en-1-amine |

TABLE 1-continued

| Exemplary ionizable lipids of Formula (A) | |
|---|---|
| Lipid No. | Structure and Name |
| 36 | 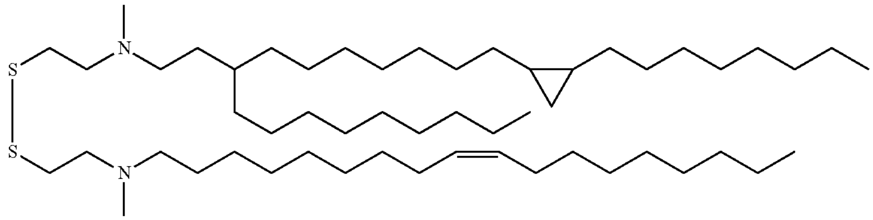 [SMILES: CCCCCCCC/C=C\CCCCCCCCN(C)CCSSCCN(C)CCC(CCCCCCCCC)CCCCCCCC1CC1CCCCCCCC] (Z)-N-methyl-N-(2-((2-(methyl(3-(7-(2-octylcyclopropyl)heptyl)dodecyl)amino)ethyl)disulfaneyl)ethyl)octadec-9-en-1-amine |
| 37 | 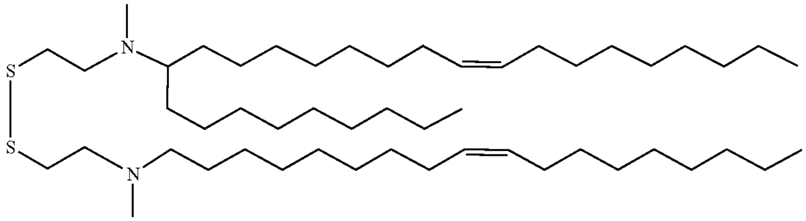 [SMILES: CCCCCCCC/C=C\CCCCCCCCN(C)CCSSCCN(C)C(CCCCCCC/C=C\CCCCCCCC)CCCCCCCCC] (Z)-N-methyl-N-(2-((2-(methyl((Z)-octadec-9-en-1-yl)amino)ethyl)disulfaneyl)ethyl)heptacos-18-en-10-amine |
| 38 | 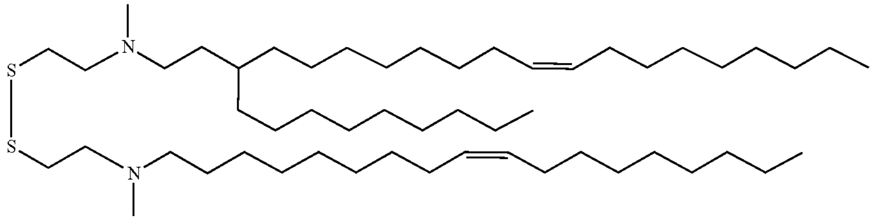 [SMILES: CCCCCCCC/C=C\CCCCCCCCN(C)CCSSCCN(C)CCC(CCCCCCC/C=C\CCCCCCCC)CCCCCCCCC] (Z)-N-methyl-N-(2-((2-(methyl((Z)-octadec-9-en-1-yl)amino)ethyl)disulfaneyl)ethyl)-3-nonylicos-11-en-1-amine |
| 39 | 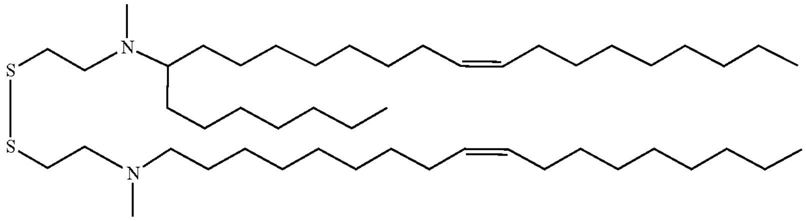 [SMILES: CCCCCCCC/C=C\CCCCCCCCN(C)CCSSCCN(C)C(CCCCCCC)CCCCCCC/C=C\CCCCCCCC] (Z)-N-methyl-N-(2-((2-(methyl((Z)-octadec-9-en-1-yl)amino)ethyl) disulfaneyl)ethyl)pentacos-16-en-8-amine |
| 40 | 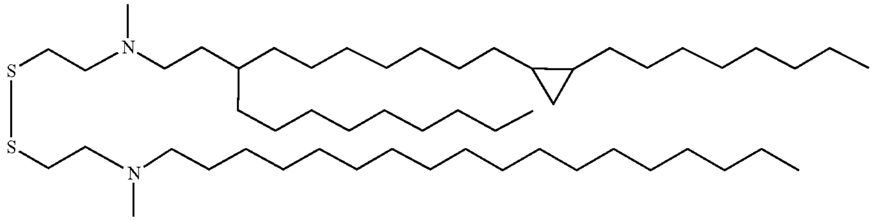 [SMILES: CCCCCCCCCCCCCCCCCCN(C)CCSSCCN(C)CCC(CCCCCCCCC)CCCCCCCC1CC1CCCCCCCC] N-methyl-N-(2-((2-(methyl(3-(7-(2-octylcyclopropyl)heptyl)dodecyl)amino)ethyl)disulfaneyl)ethyl)octadecan-1-amine |

TABLE 1-continued

| Lipid No. | Exemplary ionizable lipids of Formula (A) Structure and Name |
|---|---|
| 41 | 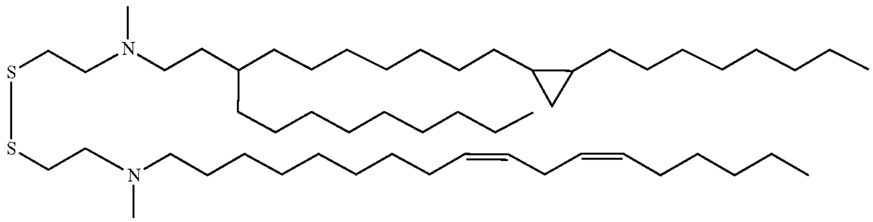 [SMILES: CCCCC/C=C\C/C=C\CCCCCCCCN(C)CCSSCCN(C)CCC(CCCCCCCCC)CCCCCCCC1CC1CCCCCCCC] (9Z,12Z)-N-methyl-N-(2-((2-(methyl(3-(7-(2-octylcyclopropyl)heptyl)dodecyl)amino)ethyl)disulfaneyl)ethyl)octadeca-9,12-dien-1-amine |
| 42 | 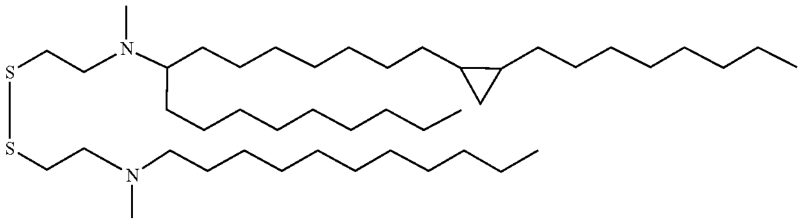 [SMILES: CCCCCCCCCCCN(C)CCSSCCN(C)C(CCCCCCCCC)CCCCCCCC1CC1CCCCCCCC] N-methyl-N-(2-((2-(methyl(undecyl)amino)ethyl)disulfaneyl)ethyl)-1-(2-octylcyclopropyl)heptadecan-8-amine |
| 43 | 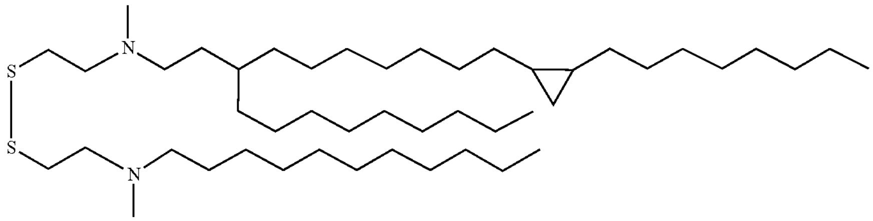 [SMILES: CCCCCCCCCCCN(C)CCSSCCN(C)CCC(CCCCCCCCC)CCCCCCCC1CC1CCCCCCCC] N-methyl-N-(2-((2-(methyl(undecyl)amino)ethyl)disulfaneyl)ethyl)-3-(7-(2-octylcyclopropyl)heptyl)dodecan-1-amine |
| 44 | 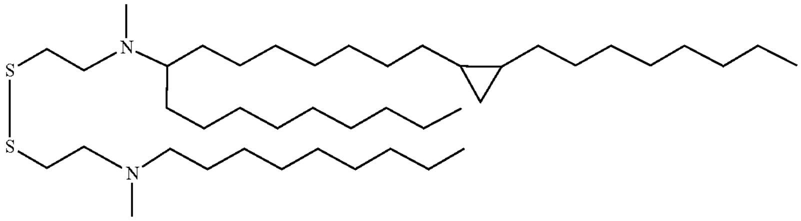 [SMILES: CCCCCCCCCC(CCCCCCCC1CC1CCCCCCCC)N(C)CCSSCCN(C)CCCCCCCCC] N-methyl-N-(2-((2-(methyl(nonyl)amino)ethyl)disulfaneyl)ethyl)-1-(2-octylcyclopropyl)heptadecan-8-amine |
| 45 | 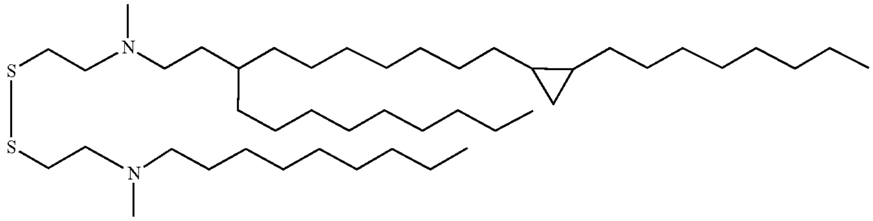 [SMILES: CCCCCCCCCC(CCCCCCCC1CC1CCCCCCCC)CCN(C)CCSSCCN(C)CCCCCCCCC] N-methyl-N-(2-((2-(methyl(nonyl)amino)ethyl)disulfaneyl)ethyl)-3-(7-(2-octylcyclopropyl)heptyl)dodecan-1-amine |

TABLE 1-continued

| Exemplary ionizable lipids of Formula (A) | |
|---|---|
| Lipid No. | Structure and Name |
| 46 | 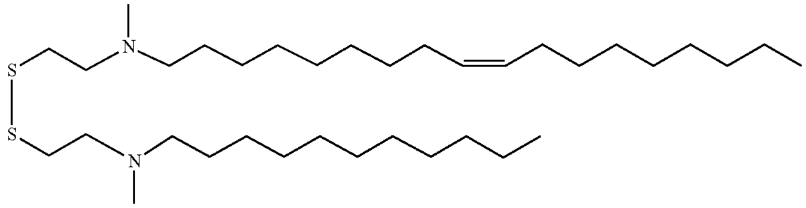 [SMILES: CCCCCCCC/C=C\CCCCCCCCN(C)CCSSCCN(C)CCCCCCCCCCC] (Z)-N-methyl-N-(2-((2-(methyl(undecyl)amino)ethyl)disulfaneyl)ethyl)octadec-9-en-1-amine |
| 47 | 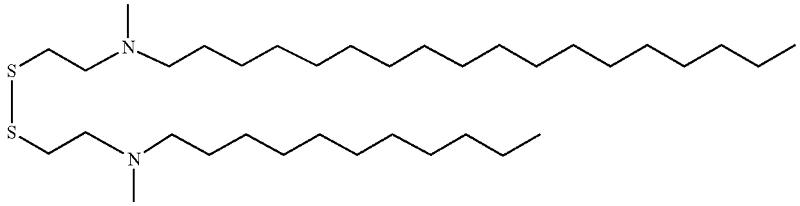 [SMILES: CCCCCCCCCCCCCCCCCCN(C)CCSSCCN(C)CCCCCCCCCCC] N-methyl-N-(2-((2-(methyl(undecyl)amino)ethyl)disulfaneyl)ethyl)octadecan-1-amine |
| 48 | 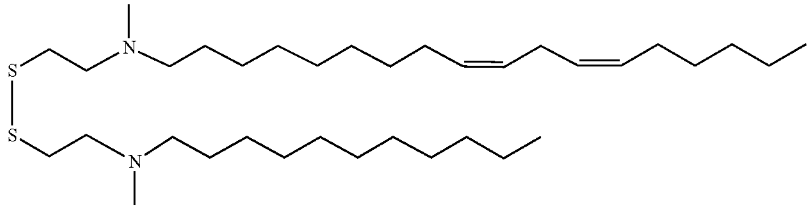 [SMILES: CCCCC/C=C\C/C=C\CCCCCCCCN(C)CCSSCCN(C)CCCCCCCCCCC] (9Z,12Z)-N-methyl-N-(2-((2-(methyl(undecyl)amino)ethyl)disulfaneyl)ethyl)octadeca-9,12-dien-1-amine |
| 49 | 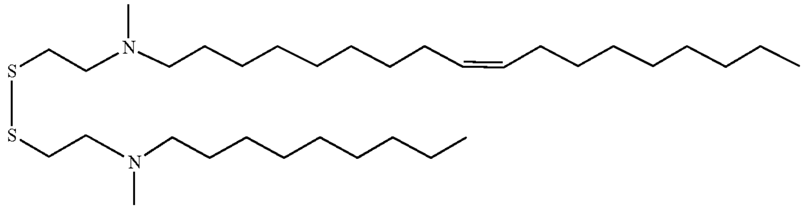 [SMILES: CCCCCCCC/C=C\CCCCCCCCN(C)CCSSCCN(C)CCCCCCCCC] (Z)-N-methyl-N-(2-((2-(methyl(nonyl)amino)ethyl)disulfaneyl)ethyl)octadec-9-en-1-amine |
| 50 | 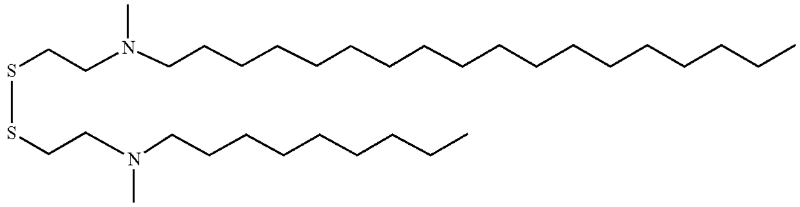 [SMILES: CCCCCCCCCCCCCCCCCCN(C)CCSSCCN(C)CCCCCCCCC] N-methyl-N-(2-((2-(methyl(nonyl)amino)ethyl)disulfaneyl)ethyl)octadecan-1-amine |

TABLE 1-continued

| Lipid No. | Exemplary ionizable lipids of Formula (A)<br>Structure and Name |
|---|---|
| 51 | 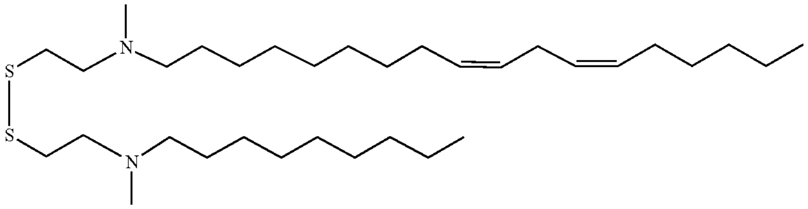 [SMILES: CCCCC/C=C\C/C=C\CCCCCCCCN(C)CCSSCCN(C)CCCCCCCCC]<br>(9Z,12Z)-N-methyl-N-(2-((2-(methyl(nonyl)amino)ethyl)disulfaneyl)ethyl)octadeca-9,12-dien-1-amine |

Formula (B)

In some embodiments, the ionizable lipid in the LNPs of the present disclosure is represented by Formula (B):

3 to 8, 3 to 7, 3 to 6, 3 to 5, 4 to 8, 4 to 7, 4 to 6, 5 to 8, 5 to 7, or 6 to 8, wherein the remaining variables are as described for Formula (B-1).

(B)

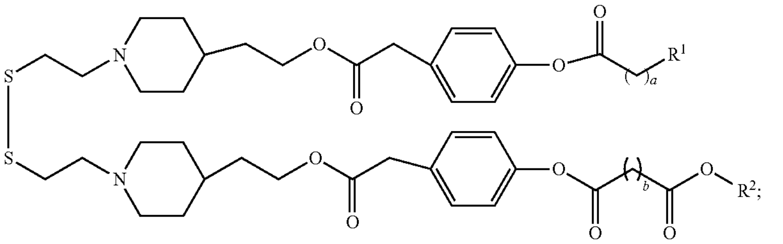

or a pharmaceutically acceptable salt thereof, wherein:

a is an integer ranging from 1 to 20 (e.g., a is 1, 2, 3, 4, 5, 6, 7, 8, 9, 10, 11, 12, 13, 14, 15, 16, 17, 18, 19, or 20);

b is an integer ranging from 2 to 10 (e.g., b is 2, 3, 4, 5, 6, 7, 8, 9, or 10);

$R^1$ is absent or is selected from ($C_2$-$C_{20}$)alkenyl, —C(O)O($C_2$-$C_{20}$)alkyl, and cyclopropyl substituted with ($C_2$-$C_{20}$)alkyl; and $R^2$ is ($C_2$-$C_{20}$)alkyl.

In a second embodiment of Formula (B), the ionizable lipid of Formula (B) is represented by Formula (B-1):

In a fourth embodiment of Formula (B), c in Formula (B-1) is 2, 3, 4, 5, 6, 7, or 8, wherein the remaining variables are as described for Formula (B), or the second or third embodiment of Formula (B). Alternatively, c and d in Formula (B-1) are each independently 1, 3, 5, or 7, wherein the remaining variables are as described for Formula (B), or the second or third embodiment of Formula (B).

In a fifth embodiment of Formula (B), d in the cationic lipid of Formula (B-1) is 2, 3, 4, 5, 6, 7, or 8, wherein the remaining variables are as described for Formula (B), or the second, third or fourth embodiments of Formula (B). Alternatively, at least one of c and d in Formula (B-1) is 7, (B-1)

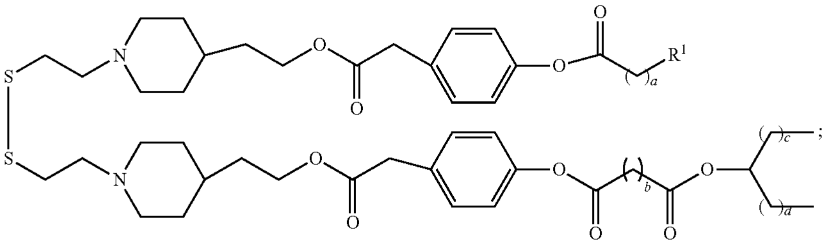

or a pharmaceutically acceptable salt thereof, wherein c and d are each independently integers ranging from 1 to 8 (e.g., 1, 2, 3, 4, 5, 6, 7, or 8), and wherein the remaining variables are as described for Formula (B).

In a third embodiment of Formula (B), c and d in Formula (B-1) are each independently integers ranging from 2 to 8, wherein the remaining variables are as described for Formula (B), or the second, third or fourth embodiments of Formula (B).

In a sixth embodiment of Formula (B), the ionizable lipid of Formula (B) or Formula (B-1) is represented by Formula (B-2):

(B-2)

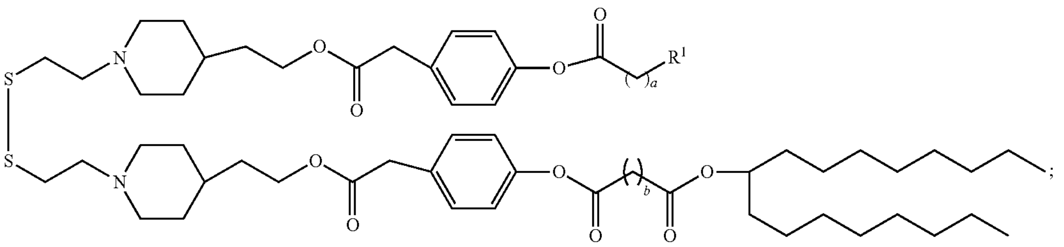

or a pharmaceutically acceptable salt thereof, wherein the remaining variables are as described for Formula (B) or Formula (B-1).

In a seventh embodiment of Formula (B), b in Formula (B), (B-1), or (B-2) is an integer ranging from 3 to 9, wherein the remaining variables are as described for Formula (B), or the second, third, fourth, fifth or sixth embodiments of Formula (B). Alternatively, b in Formula (B), (B-1), or (B-2) is an integer ranging from 3 to 8, 3 to 7, 3 to 6, 3 to 5, 4 to 9, 4 to 8, 4 to 7, 4 to 6, 5 to 9, 5 to 8, 5 to 7, 6 to 9, 6 to 8, or 7 to 9, wherein the remaining variables are as described for Formula (B), or the second, third, fourth, fifth or sixth embodiments of Formula (B). Alternatively, b in Formula (B), (B-1), or (B-2) is 3, 4, 5, 6, 7, 8, or 9, wherein the remaining variables are as described for Formula (B), or the second, third, fourth, fifth or sixth embodiments of Formula (B).

In an eighth embodiment of Formula (B), a in Formula (B), (B-1), or (B-2) is an integer ranging from 2 to 18, wherein the remaining variables are as described for Formula (B), or the second, third, fourth, fifth, sixth or seventh embodiment of Formula (B). Alternatively, a in Formula (B), (B-1), or (B-2) is an integer ranging from 2 to 18, 2 to 17, 2 to 16, 2 to 15, 2 to 14, 2 to 13, 2 to 12, 2 to 11, 2 to 10, 2 to 9, 2 to 8, 2 to 7, 2 to 6, 2 to 5, 2 to 4, 3 to 18, 3 to 17, 3 to 16, 3 to 15, 3 to 14, 3 to 13, 3 to 12, 3 to 11, 3 to 10, 3 to 9, 3 to 8, 3 to 7, 3 to 6, 3 to 5, 4 to 18, 4 to 17, 4 to 16, 4 to 15, 4 to 14, 4 to 13, 4 to 12, 4 to 11, 4 to 10, 4 to 9, 4 to 8, 4 to 7, 4 to 6, 5 to 18, 5 to 17, 5 to 16, 5 to 15, 5 to 14, 5 to 13, 5 to 12, 5 to 11, 5 to 10, 5 to 9, 25 to 8, 5 to 7, 6 to 18, 6 to 17, 6 to 16, 6 to 15, 6 to 14, 6 to 13, 6 to 12, 6 to 11, 6 to 10, 6 to 9, 6 to 8, 7 to 18, 7 to 17, 7 to 16, 7 to 15, 7 to 14, 7 to 13, 7 to 12, 7 to 11, 7 to 10, 7 to 9, 8 to 18, 8 to 17, 8 to 16, 8 to 15, 8 to 14, 8 to 13, 8 to 12, 8 to 11, 8 to 10, 9 to 18, 9 to 17, 9 to 16, 9 to 15, 9 to 14, 9 to 13, 9 to 12, 9 to 11, 10 to 18, 10 to 17, 10 to 16, 10 to 15, 10 to 14, 10 to 13, 11 to 18, 11 to 17, 11 to 16, 11 to 15, 11 to 14, 11 to 13, 12 to 18, 12 to 17, 12 to 16, 12 to 15, 12 to 14, 13 to 18, 13 to 17, 13 to 16, 13 to 15, 14 to 18, 14 to 17, 14 to 16, 15 to 18, 15 to 17, or 16 to 18, wherein the remaining variables are as described for Formula (B), or the second, third, fourth, fifth, sixth or seventh embodiment of Formula (B). Alternatively, a in Formula (B), (B-1), or (B-2) is 2, 3, 4, 5, 6, 7, 8, 9, 10, 11, 12, 13, 14, 15, 16, 17, or 18, wherein the remaining variables are as described for Formula (B), or the second, third, fourth, fifth, sixth or seventh embodiment of Formula (B).

In a ninth embodiment of Formula (B), $R^1$ in Formula (B), Formula (B-1), or Formula (B-2) is absent or is selected from ($C_5$-$C_{15}$)alkenyl, —C(O)O($C_4$-$C_{15}$)alkyl, and cyclopropyl substituted with ($C_4$-$C_{16}$)alkyl, wherein the remaining variables are as described for Formula (B), or the second, third, fourth, fifth, sixth, seventh or eighth embodiments of Formula (B). Alternatively, $R^1$ in Formula (B), Formula (B-1), or Formula (B-2) is absent or is selected from ($C_5$-$C_{15}$)alkenyl, —C(O)O($C_4$-$C_{16}$)alkyl, and cyclopropyl substituted with ($C_4$-$C_{16}$)alkyl, wherein the remaining variables are as described for Formula (B), or the second, third, fourth, fifth, sixth, seventh or eighth embodiments of Formula (B). Alternatively, $R^1$ in Formula (B), Formula (B-1), or Formula (B-2) is absent or is selected from ($C_5$-$C_{12}$) alkenyl, —C(O)O($C_4$-$C_{12}$)alkyl, and cyclopropyl substituted with ($C_4$-$C_{12}$)alkyl, wherein the remaining variables are as described for Formula (B), or the second, third, fourth, fifth, sixth, seventh or eighth embodiments of Formula (B). In another alternative, $R^1$ in the cationic lipid of Formula (B), Formula (B-1), or Formula (B-2) is absent or is selected from ($C_5$-$C_{10}$)alkenyl, —C(O)O($C_4$-$C_{10}$)alkyl, and cyclopropyl substituted with ($C_4$-$C_{10}$)alkyl, wherein the remaining variables are as described for Formula (B), or the second, third, fourth, fifth, sixth, seventh or eighth embodiments of Formula (B).

In a tenth embodiment of Formula (B), $R^1$ is $C_{10}$ alkenyl, wherein the remaining variables are as described for Formula (B), or the second, third, fourth, fifth, sixth, seventh or eighth embodiments of Formula (B).

In an eleventh embodiment of Formula (B), the alkyl in C(O)O($C_2$-$C_{20}$)alkyl, —C(O)O($C_4$-$C_{15}$)alkyl, —C(O)O($C_4$-$C_{12}$)alkyl, or —C(O)O($C_4$-$C_{10}$)alkyl of $R^1$ in Formula (B), Formula (B-1), or Formula (B-2) is an unbranched alkyl, wherein the remaining variables are as described for Formula (B), or the second, third, fourth, fifth, sixth, seventh, eighth or ninth embodiments of Formula (B). In one embodiment, $R^1$ is —C(O)O($C_9$ alkyl). Alternatively, the alkyl in —C(O)O($C_4$-$C_{18}$)alkyl, —C(O)O($C_4$-$C_{12}$)alkyl, or —C(O)O($C_4$-$C_{10}$)alkyl of $R^1$ in Formula (B), Formula (B-1), or Formula (B-2) is a branched alkyl, wherein the remaining variables are as described for Formula (B), Formula (B-1), or Formula (B-2), or the second, third, fourth, fifth, sixth, seventh, eighth or ninth embodiments of Formula (B). In one embodiment, $R^1$ is —C(O)O($C_{17}$ alkyl), wherein the remaining variables are as described for Formula (B), Formula (B-1), or Formula (B-2), or the second, third, fourth, fifth, sixth, seventh, eighth or ninth embodiments of Formula (B).

In a twelfth embodiment of Formula (B), $R^1$ in Formula (B), Formula (B-1), or Formula (B-2) is selected from any group listed in Table 2 below, wherein the wavy bond in each of the groups indicates the point of attachment of the group to the rest of the ionizable lipid molecule, and wherein the remaining variables are as described for Formula (B), Formula (B-1), or Formula (B-2), or the second, third, fourth, fifth, sixth, seventh or eighth embodiments of Formula (B). The present disclosure further contemplates the combination of any one of the $R^1$ groups in Table 2 with any one of the $R^2$ groups in Table 3 in Formula (B), wherein the remaining variables are as described for Formula (B), Formula (B-1), or Formula (B-2), or the second, third, fourth, fifth, sixth, seventh or eighth embodiments of Formula (B).

TABLE 2

| Exemplary $R^1$ groups in Formula (B), Formula (B-1), or Formula (B-2) |
| --- |
| 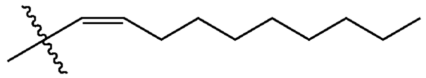 [SMILES: */C=C\CCCCCCCC] |
| 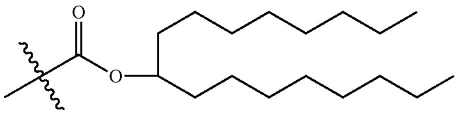 [SMILES: *C(=O)OC(CCCCCCCC)CCCCCCCC] |
| 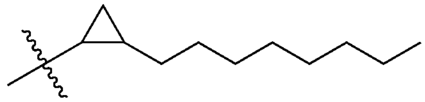 [SMILES: *C1CC1CCCCCCCC] |
| 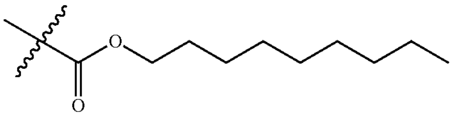 [SMILES: *C(=O)OCCCCCCCCC] |
| 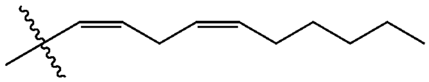 [SMILES: */C=C\C/C=C\CCCCC] |

In a thirteenth embodiment, $R^2$ in Formula (B) or a pharmaceutically acceptable salt thereof is selected from any group listed in Table 3 below, wherein the wavy bond in each of the groups indicates the point of attachment of the group to the rest of the ionizable lipid molecule, and wherein the remaining variables are as described for Formula (B), Formula (B-1), or Formula (B-2), or the second, third, fourth, fifth, sixth, seventh or eighth, ninth, tenth, eleventh or twelfth embodiments of Formula (B).

TABLE 3

| Exemplary $R^2$ groups in Formula (B) |
| --- |
| 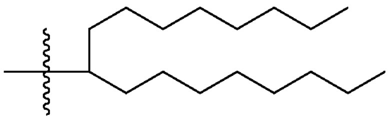 [SMILES: *C(CCCCCCCC)CCCCCCCC] |
| 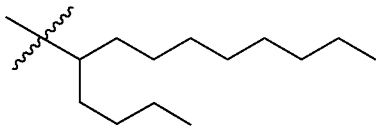 [SMILES: *C(CCCC)CCCCCCCC] |
| 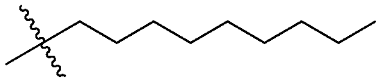 [SMILES: *CCCCCCCCC] |
| 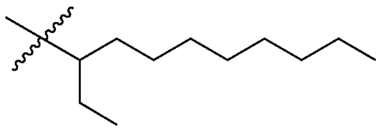 [SMILES: *C(CC)CCCCCCCC] |
| 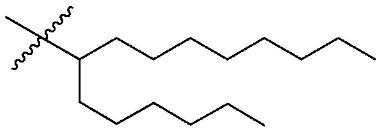 [SMILES: *C(CCCCCC)CCCCCCCC] |

Table 4 below provides specific examples of ionizable lipids of Formula (B). Pharmaceutically acceptable salts as well as ionized and neutral forms are also included.

TABLE 4
Exemplary ionizable lipids of Formula (B), (B-1), or (B-2)
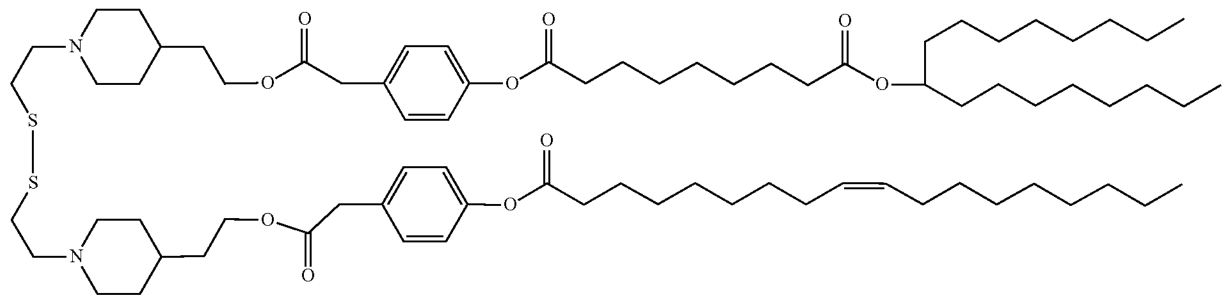 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]
Lipid 52
1-(heptadecan-9-yl) 9-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) nonanedioate
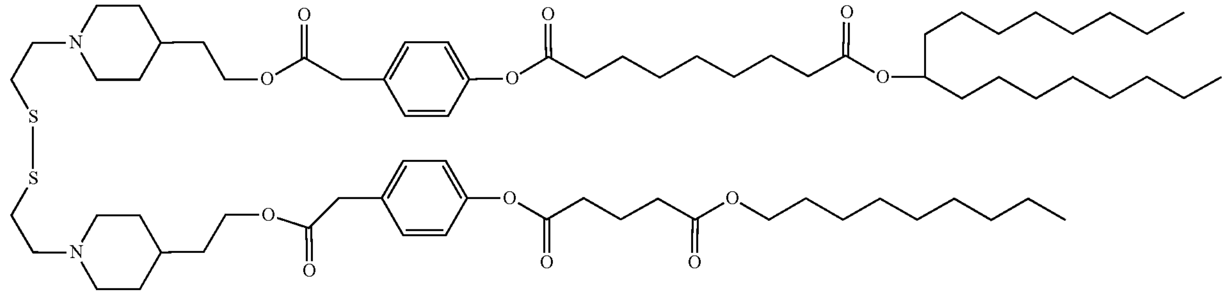 [SMILES: CCCCCCCCCOC(=O)CCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]
Lipid 53
1-(heptadecan-9-yl) 9-(4-(2-(2-(1-(2-((2-(4-(2-(2-(4-((5-(nonyloxy)-5-oxopentanoyl)oxy)phenyl)acetoxy)ethyl) piperidin-1-yl)ethyl)disulfaneyl)ethyl) piperidin-4-yl)ethoxy)-2-oxoethyl)phenyl) nonanedioate TABLE 4-continued

| Exemplary ionizable lipids of Formula (B), (B-1), or (B-2) |
| --- |
| 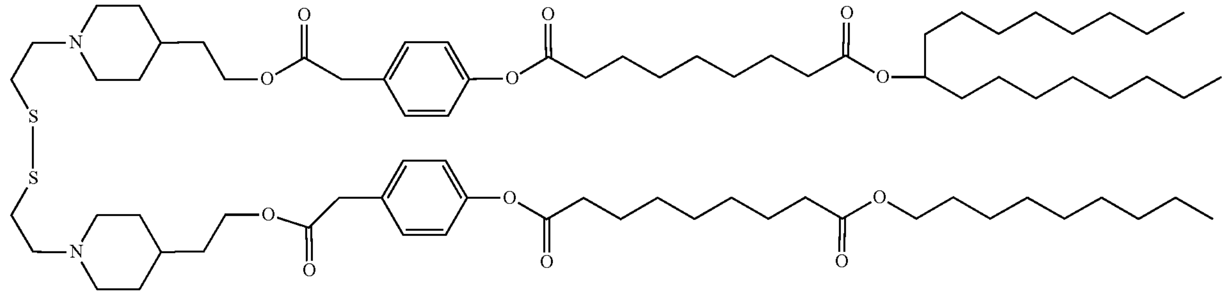 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1] Lipid 54 1-(heptadecan-9-yl) 9-(4-(2-(2-(1-(2-((2-(4-(2-(2-(4-((9-(nonyloxy)-9-oxononanoyl)oxy)phenyl)acetoxy)ethyl)piperidin-1-yl)ethyl)disulfaneyl)ethyl)piperidin-4-yl)ethoxy)-2-oxoethyl)phenyl) nonanedioate |
| 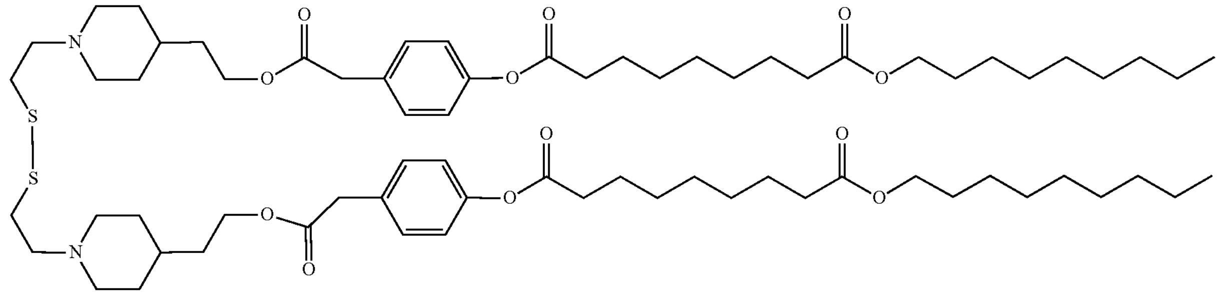 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCCCC(=O)OCCCCCCCCC)cc4)CC3)CC2)cc1] Lipid 55 1-(heptadecan-9-yl) 9-(4-(2-(2-(1-(2-((2-(4-(2-(2-(4-((5-(nonyloxy)-5-oxopentanoyl)oxy)phenyl)acetoxy)ethyl) piperidin-1-yl)ethyl)disulfaneyl)ethyl)piperidin-4-yl)ethoxy)-2-oxoethyl)phenyl) nonanedioate |

TABLE 4-continued

| Exemplary ionizable lipids of Formula (B), (B-1), or (B-2) |
| --- |
| 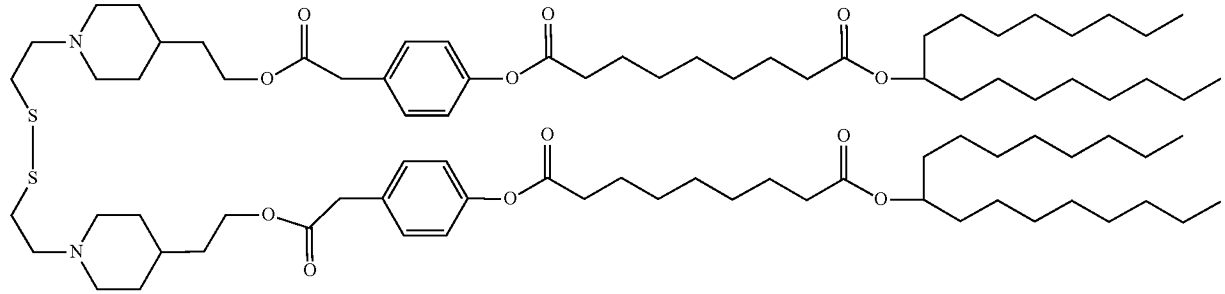 [SMILES: CCCCCCCCC(CCCCCCCC)OC(=O)CCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]<br>Lipid 56<br>O'1,O1-((((((disulfanediylbis(ethane-2,1-diyl))bis(piperidine-1,4-diyl))bis(ethane-2,1-diyl))bis(oxy))bis(2-oxoethane-2,1-diyl))bis(4,1-phenylene)) 9,9'-di(heptadecan-9-yl) di(nonanedioate) |
| 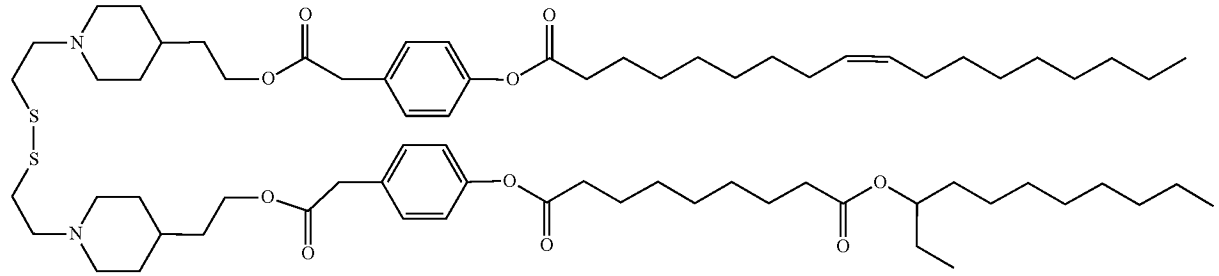 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCCC(=O)OC(CC)CCCCCCCC)cc4)CC3)CC2)cc1]<br>Lipid 57<br>1-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(undecan-3-yl) nonanedioate |

TABLE 4-continued

| Exemplary ionizable lipids of Formula (B), (B-1), or (B-2) |
| --- |
| 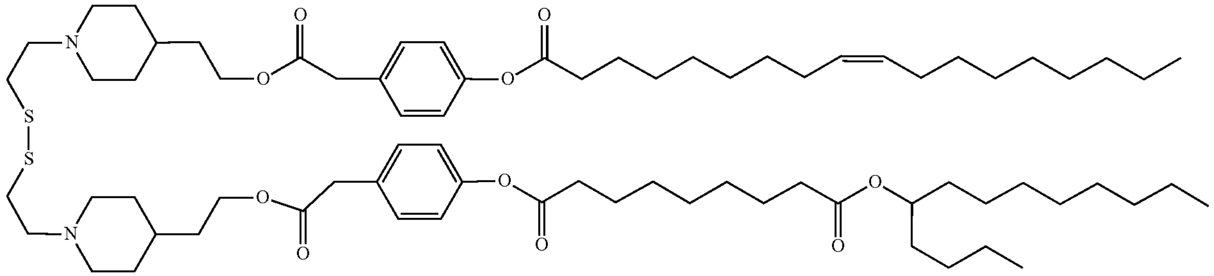 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCCC(=O)OC(CCCC)CCCCCCCC)cc4)CC3)CC2)cc1]<br>Lipid 58<br>1-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(tridecan-5-yl) nonanedioate |
| 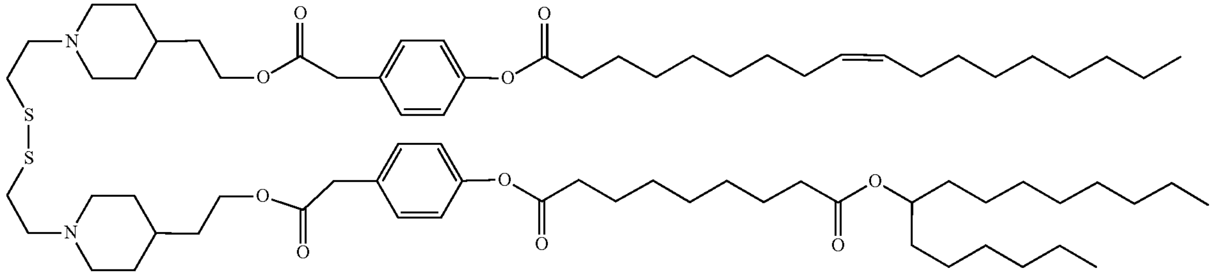 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCCC(=O)OC(CCCCCC)CCCCCCCC)cc4)CC3)CC2)cc1]<br>Lipid 59<br>1-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(pentadecan-7-yl) nonanedioate |

TABLE 4-continued

| Exemplary ionizable lipids of Formula (B), (B-1), or (B-2) |
| --- |
| 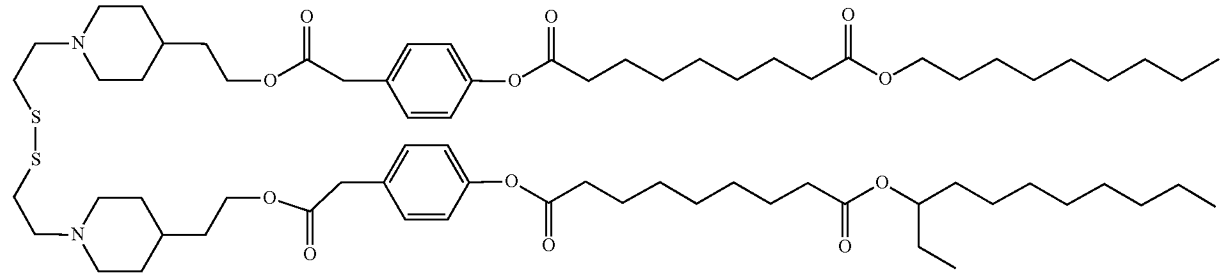 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCCCC(=O)OC(CC)CCCCCCCC)cc4)CC3)CC2)cc1] |
| Lipid 60<br>1-nonyl 9-(4-(2-oxo-2-(2-(1-(2-((2-(4-(2-(2-(4-((9-oxo-9-(undecan-3-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate |
| 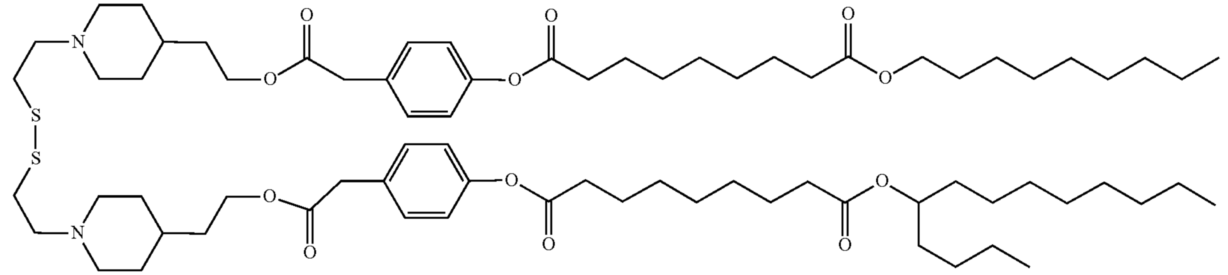 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCCCC(=O)OC(CCCC)CCCCCCCC)cc4)CC3)CC2)cc1] |
| Lipid 61<br>1-nonyl 9-(4-(2-oxo-2-(2-(1-(2-((2-(4-(2-(2-(4-((9-oxo-9-(tridecan-5-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate |

TABLE 4-continued

Exemplary ionizable lipids of Formula (B), (B-1), or (B-2)

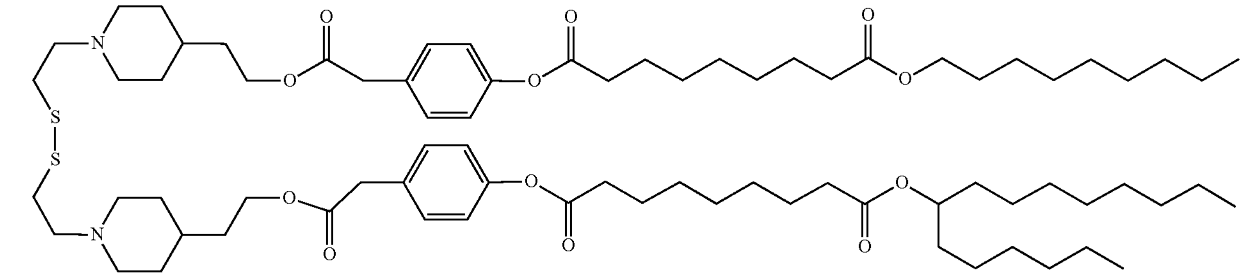 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCCCC(=O)OC(CCCCCC)CCCCCCCC)cc4)CC3)CC2)cc1]

Lipid 62
1-nonyl 9-(4-(2-oxo-2-(2-(1-(2-((2-(4-(2-(2-(4-((9-oxo-9-(pentadecan-7-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate

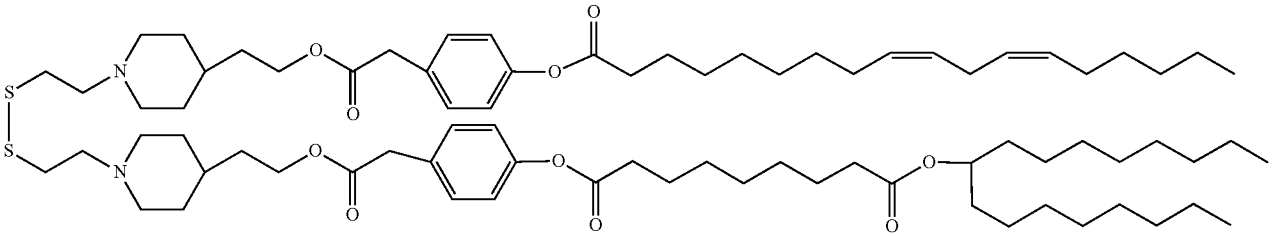 [SMILES: CCCCC/C=C\C/C=C\CCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

Lipid 63
1-(heptadecan-9-yl) 9-(4-(2-(2-(1-(2-((2-(4-(2-(2-(4-(((9Z,12Z)-octadeca-9,12-dienoyl)oxy)phenyl)acetoxy)ethyl)piperidin-1-yl)ethyl)disulfaneyl)ethyl)piperidin-4-yl)ethoxy)-2-oxoethyl)phenyl) nonanedioate

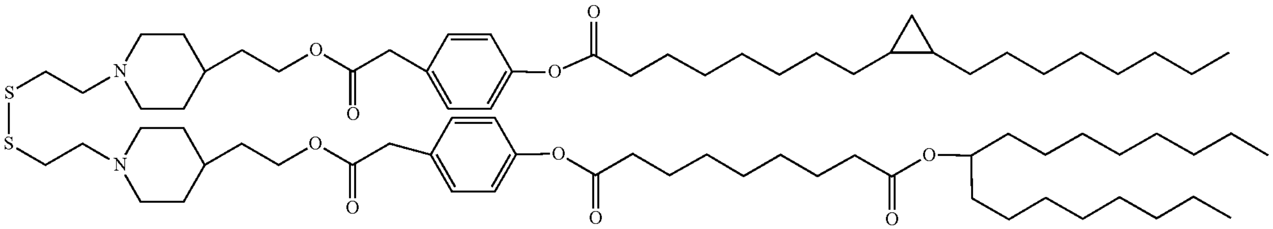 [SMILES: CCCCCCCCC(CCCCCCCC)OC(=O)CCCCCCCC(=O)Oc1ccc(CC(=O)OCCC2CCN(CCSSCCN3CCC(CCOC(=O)Cc4ccc(OC(=O)CCCCCCCC5CC5CCCCCCCC)cc4)CC3)CC2)cc1]

Lipid 64
1-(heptadecan-9-yl) 9-(4-(2-(2-(1-(2-((2-(4-(2-(2-(4-((8-(2-octylcyclopropyl)octanoyl)oxy)phenyl)acetoxy)ethyl)piperidin-1-yl)ethyl)disulfaneyl)ethyl)piperidin-4-yl)ethoxy)-2-oxoethyl)phenyl) nonanedioate TABLE 4-continued Exemplary ionizable lipids of Formula (B), (B-1), or (B-2)

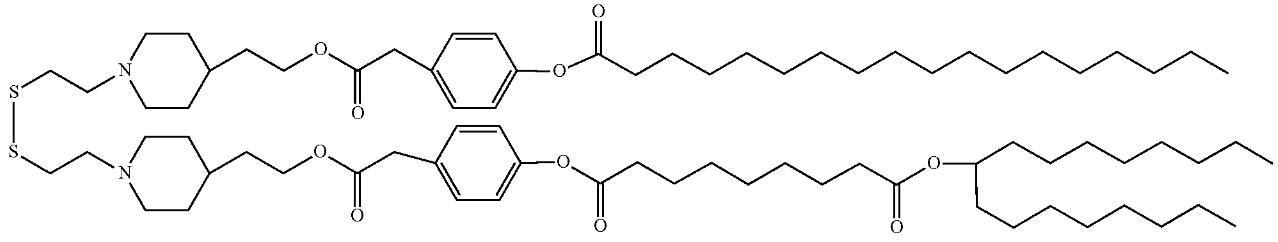 [SMILES: CCCCCCCCCCCCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

Lipid 65
1-(heptadecan-9-yl) 9-(4-(2-oxo-2-(2-(1-(2-((2-(4-(2-(2-(4-(stearoyloxy)phenyl)acetoxy)ethyl)piperidin-1-yl)ethyl)disulfaneyl)ethyl)piperidin-4-yl)ethoxy)ethyl)phenyl) nonanedioate

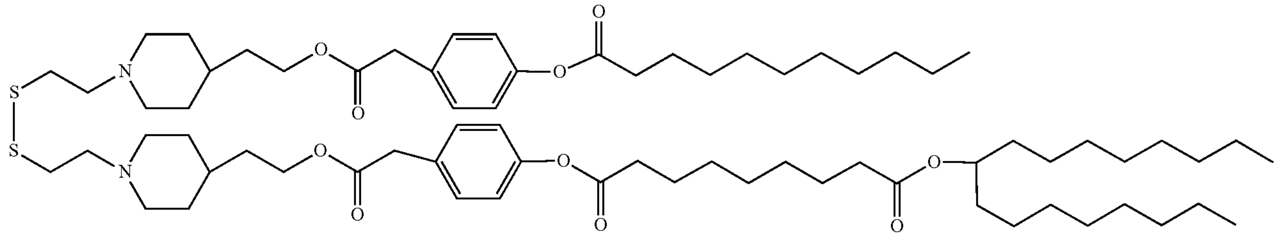 [SMILES: CCCCCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

Lipid 66
1-(heptadecan-9-yl) 9-(4-(2-oxo-2-(2-(1-(2-((2-(4-(2-(2-(4-(undecanoyloxy)phenyl)acetoxy)ethyl)piperidin-1-yl)ethyl)disulfaneyl)ethyl)piperidin-4-yl)ethoxy)ethyl)phenyl) nonanedioate

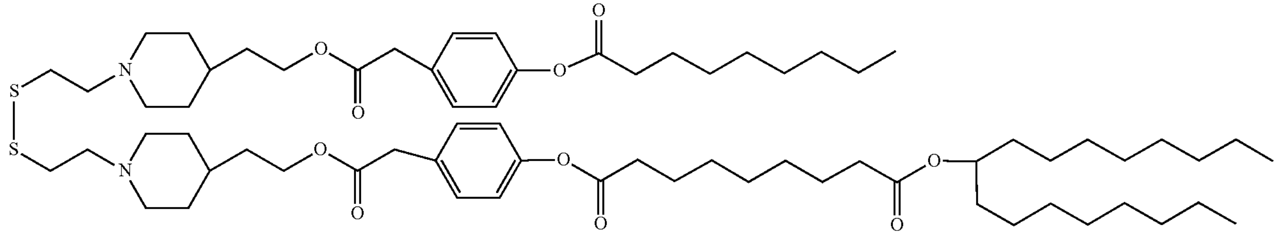 [SMILES: CCCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

Lipid 67
1-(heptadecan-9-yl) 9-(4-(2-(2-(1-(2-((2-(4-(2-(2-(4-(nonanoyloxy)phenyl)acetoxy)ethyl)piperidin-1-yl)ethyl)disulfaneyl)ethyl)piperidin-4-yl)ethoxy)-2-oxoethyl)phenyl) nonanedioate TABLE 4-continued Exemplary ionizable lipids of Formula (B), (B-1), or (B-2)

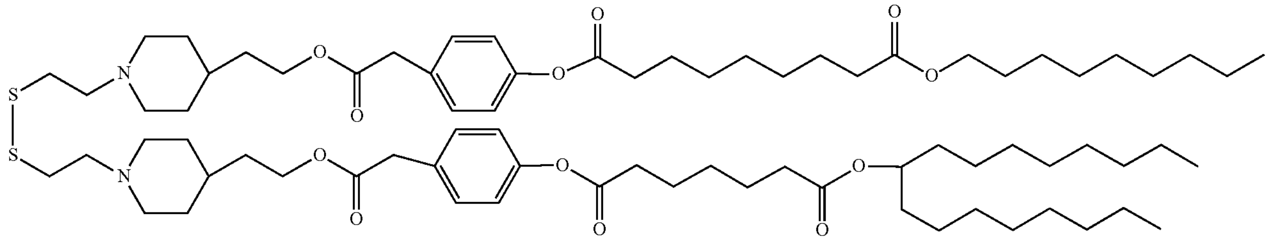 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCC(=O)OC(CCCCCCCC)CCCCCCCC)cc4)CC3)CC2)cc1]

Lipid 68
1-nonyl 9-(4-(2-(2-(1-(2-((2-(4-(2-(2-(4-((9-((3-octylundecyl)oxy)-9-oxononanoyl)oxy)phenyl)acetoxy)ethyl)piperidin-1-yl)ethyl)disulfaneyl)ethyl)piperidin-4-yl)ethoxy)-2-oxoethyl)phenyl) nonanedioate

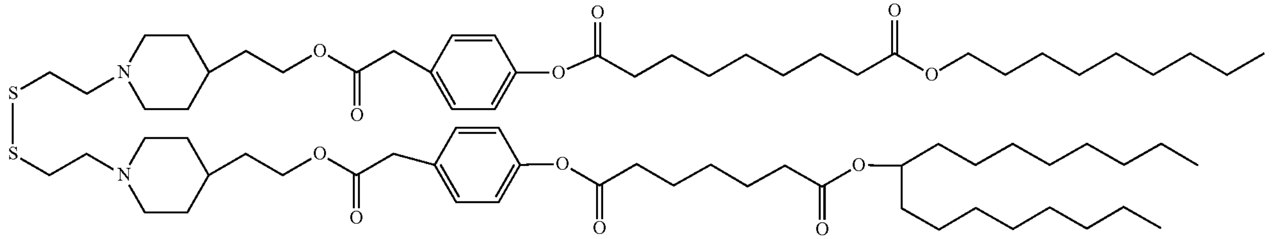 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCC(=O)OC(CCCCCCCC)CCCCCCCC)cc4)CC3)CC2)cc1]

Lipid 69
1-(4-(2-(2-(1-(2-((2-(4-(2-(2-(4-((7-(heptadecan-9-yloxy)-7-oxoheptanoyl)oxy)phenyl)acetoxy)ethyl)piperidin-1-yl)ethyl)disulfaneyl)ethyl)piperidin-4-yl)ethoxy)-2-oxoethyl)phenyl) 9-nonyl nonanedioate

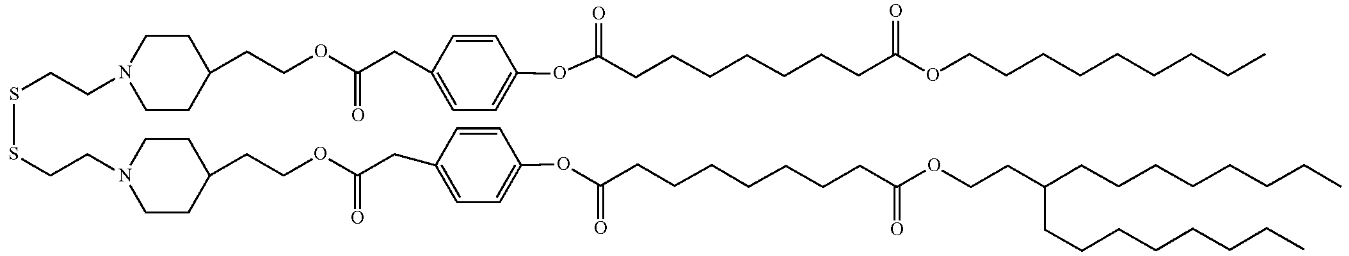 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCCCC(=O)OCCC(CCCCCCCC)CCCCCCCC)cc4)CC3)CC2)cc1]

Lipid 70
1-nonyl 9-(4-(2-(2-(1-(2-((2-(4-(2-(2-(4-((9-((3-octylundecyl)oxy)-9-oxononanoyl)oxy)phenyl)acetoxy)ethyl)piperidin-1-yl)ethyl)disulfaneyl)ethyl)piperidin-4-yl)ethoxy)-2-oxoethyl)phenyl) nonanedioate TABLE 4-continued
| Exemplary ionizable lipids of Formula (B), (B-1), or (B-2) |
| --- |
| 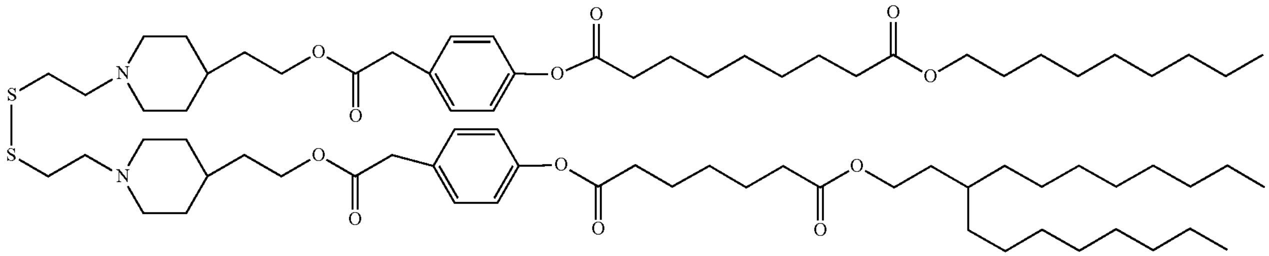 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCC(=O)OCCC(CCCCCCCC)CCCCCCCC)cc4)CC3)CC2)cc1]<br>Lipid 71<br>1-nonyl 9-(4-(2-(2-(1-(2-((2-(4-(2-(2-(4-((7-((3-octylundecyl)oxy)-7-oxoheptanoyl)oxy)phenyl)acetoxy)ethyl)piperidin-1-yl)ethyl)disulfaneyl)ethyl)piperidin-4-yl)ethoxy)-2-oxoethyl)phenyl) nonanedioate |

Formula (C)

In some embodiments, the ionizable lipid in the LNPs of the present disclosure are represented by Formula (C):

(C)

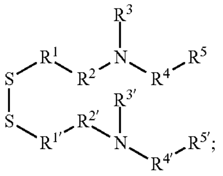

or a pharmaceutically acceptable salt thereof, wherein:

$R^1$ and $R^{1'}$ are each independently $(C_1-C_6)$alkylene optionally substituted with one or more groups selected from $R^a$;

$R^2$ and $R^{2'}$ are each independently $(C_1-C_2)$alkylene;

$R^3$ and $R^{3'}$ are each independently $(C_1-C_6)$alkyl optionally substituted with one or more groups selected from $R^b$;

or alternatively, $R^2$ and $R^3$ and/or $R^{2'}$ and $R^{3'}$ are taken together with their intervening N atom to form a 4- to 7-membered heterocyclyl;

$R^4$ and $R^{4'}$ are each a $(C_2-C_6)$alkylene interrupted by —C(O)O—;

$R^5$ and $R^{5'}$ are each independently a $(C_2-C_{30})$alkyl or $(C_2-C_{30})$alkenyl, each of which are optionally interrupted with —C(O)O— or $(C_3-C_6)$cycloalkyl; and $R^a$ and $R^b$ are each halo or cyano.

In a second embodiment of Formula (C), $R^1$ and $R^1$ are each independently $(C_1-C_6)$alkylene, wherein the remaining variables are as described above for Formula (C). Alternatively, $R^1$ and $R^{1'}$ are each independently $(C_1-C_3)$alkylene, wherein the remaining variables are as described above for Formula (C).

In a third embodiment of Formula (C), the ionizable lipid of the Formula (C) is represented by Formula (C-1):

(C-1)

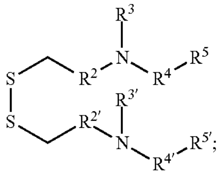

or a pharmaceutically acceptable salt thereof, wherein $R^2$ and $R^{2'}$, $R^3$ and $R^{3'}$, $R^4$ and $R^{4'}$ and $R^5$ and $R^{5'}$ are as described above for Formula (C) or the second embodiment of Formula (C).

In a fourth embodiment, the ionizable lipid of Formula (C) is represented by Formula (C-2) or Formula (C-3):

(C-2)

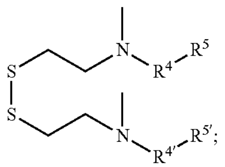

or

-continued (C-3)

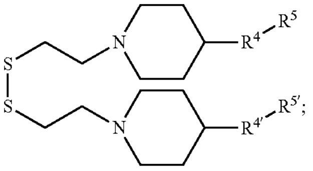

or a pharmaceutically acceptable salt thereof, wherein $R^4$ and $R^{4'}$ and $R^5$ and $R^{5'}$ are as described above for Formula (C).

In a fifth embodiment of Formula (C), the ionizable lipid of Formula (C) is represented by Formula (C-4) or (C-5):

(C-4)

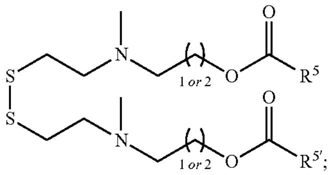

or (C-5)

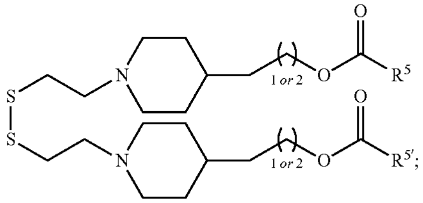

or a pharmaceutically acceptable salt thereof, wherein $R^5$ and $R^{5'}$ are as described above for Formula (C).

In a sixth embodiment of Formula (C), the ionizable lipid of Formula (C) is represented by Formula (C-6), (C-7), (C-8), or (C-9):

(C-6)

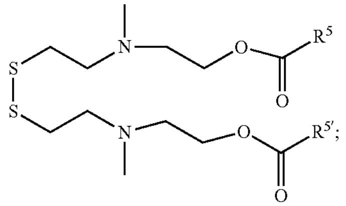

(C-7)

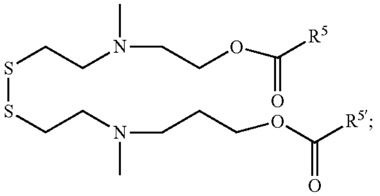

(C-8)

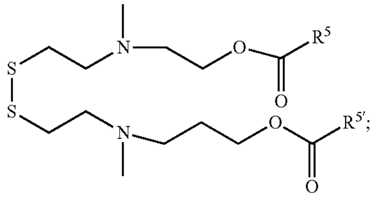

or

-continued (C-9)

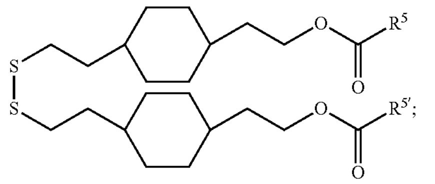

or a pharmaceutically acceptable salt thereof, wherein $R^5$ and $R^{5'}$ are as described above for Formula (XV).

In a seventh embodiment of Formula (C), at least one of $R^5$ and $R^{5'}$ in Formula (C), (C-1), (C-2), (C-3), (C-4), (C-5), (C-6), (C-7), (C-8), or (C-9) is a branched alkyl or branched alkenyl, and the remaining variables are as described above for Formula (C) or the second embodiment of Formula (C). Alternatively, one of $R^5$ and $R^{5'}$ in Formula (C), (C-1), (C-2), (C-3), (C-4), (C-5), (C-6), (C-7), (C-8), or (C-9) is a branched alkyl or branched alkenyl, and the remaining variables are as described above for Formula (C) or the second embodiment of Formula (C). Alternatively, $R^5$ in Formula (C), (C-1), (C-2), (C-3), (C-4), (C-5), (C-6), (C-7), (C-8), or (C-9) is a branched alkyl or branched alkenyl, and the remaining variables are as described above for Formula (C) or the second embodiment of Formula (C). Alternatively, $R^{5'}$ in Formula (C), (C-1), (C-2), (C-3), (C-4), (C-5), (C-6), (C-7), (C-8), or (C-9) is a branched alkyl or branched alkenyl, and the remaining variables are as described above for Formula (C) or the second embodiment of Formula (C).

In an eighth embodiment of Formula (C), $R^5$ in Formula (C), (C-1), (C-2), (C-3), (C-4), (C-5), (C-6), (C-7), (C-8), or (C-9) is a $(C_6\text{-}C_{26})$alkyl or $(C_6\text{-}C_{26})$alkenyl, each of which are optionally interrupted with —C(O)O— or $(C_3\text{-}C_6)$cycloalkyl, and the remaining variables are as described above for Formula (C) or the second embodiment of Formula (C). Alternatively, $R^5$ in Formula (C), (C-1), (C-2), (C-3), (C-4), (C-5), (C-6), (C-7), (C-8), or (C-9) is a $(C_6\text{-}C_{26})$alkyl or $(C_6\text{-}C_{26})$alkenyl, each of which are optionally interrupted with —C(O)O— or $(C_3\text{-}C_5)$cycloalkyl, and the remaining variables are as described above for Formula (C) or the second embodiment of Formula (C). Alternatively, $R^5$ in Formula (C), (C-1), (C-2), (C-3), (C-4), (C-5), (C-6), (C-7), (C-8), or (C-9) is a $(C_7\text{-}C_{26})$alkyl or $(C_7\text{-}C_{26})$alkenyl, each of which are optionally interrupted with —C(O)O— or $(C_3\text{-}C_5)$cycloalkyl, and the remaining variables are as described above for Formula (C) or the second embodiment of Formula (C). Alternatively, $R^5$ in Formula (C), (C-1), (C-2), (C-3), (C-4), (C-5), (C-6), (C-7), (C-8), or (C-9) is a $(C_5\text{-}C_{26})$alkyl or $(C_5\text{-}C_{26})$alkenyl, each of which are optionally interrupted with —C(O)O— or $(C_3\text{-}C_5)$cycloalkyl, and the remaining variables are as described above for Formula (C) or the second embodiment of Formula (C). Alternatively, $R^5$ in Formula (C), (C-1), (C-2), (C-3), (C-4), (C-5), (C-6), (C-7), (C-8), or (C-9) is a $(C_6\text{-}C_{24})$alkyl or $(C_6\text{-}C_{24})$alkenyl, each of which are optionally interrupted with —C(O)O— or cyclopropyl, and the remaining variables are as described above for Formula (C) or the second embodiment of Formula (C). Alternatively, $R^5$ in Formula (C), (C-1), (C-2), (C-3), (C-4), (C-5), (C-6), (C-7), (C-8), or (C-9) is a $(C_5\text{-}C_{24})$alkyl or $(C_5\text{-}C_{24})$alkenyl, wherein said $(C_5\text{-}C_{24})$alkyl is optionally interrupted with —C(O)O— or cyclopropyl, and the remaining variables are as described above for Formula (C) or the second embodiment of Formula (C). Alternatively, $R^5$ in Formula (C), (C-1), (C-2), (C-3), (C-4), (C-5), (C-6), (C-7), (C-8), or (C-9) is a $(C_5\text{-}C_{10})$alkyl, and the remaining variables are as described above for Formula (C) or the second embodiment of Formula (C). Alternatively, $R^5$ in Formula (C), (C-1), (C-2), (C-3), (C-4), (C-5), (C-6), (C-7), (C-8), or (C-9) is a $(C_{14}\text{-}C_{16})$alkyl interrupted with cyclopropyl, and the remaining variables are as described above for Formula (C) or the second embodiment of Formula (C). Alternatively, $R^5$ in Formula (C), (C-1), (C-2), (C-3), (C-4), (C-5), (C-6), (C-7), (C-8), or (C-9) is a $(C_{10}\text{-}C_{24})$alkyl interrupted with —C(O)O—, and the remaining variables are as described above for Formula (C) or the second embodiment of Formula (C). Alternatively, $R^5$ in Formula (C), (C-1), (C-2), (C-3), (C-4), (C-5), (C-6), (C-7), (C-8), or (C-9) is a $(C_{16}\text{-}C_{18})$alkenyl, and the remaining variables are as described above for Formula (C) or the second embodiment of Formula (C). Alternatively, $R^5$ in Formula (C), (C-1), (C-2), (C-3), (C-4), (C-5), (C-6), (C-7), (C-8), or (C-9) is $-(CH_2)_3C(O)O(CH_2)_8CH_3$, $-(CH_2)_5C(O)O(CH_2)_5CH_3$, $-(CH_2)_7C(O)O(CH_2)_8CH_3$, $-(CH_2)_7C(O)OCH[(CH_2)_7CH_3]_2$, $-(CH_2)_7\text{-}C_3H_6-(CH_2)_7CH_3$, $-(CH_2)_7CH_3$, $-(CH_2)_9CH_3$, $-(CH_2)_{16}CH_3$, $-(CH_2)_7CH{=}CH(CH_2)_7CH_3$, or $-(CH_2)_7CH{=}CHCH_2CH{=}CH(CH_2)_4CH_3$, and the remaining variables are as described above for Formula (C) or the second embodiment of Formula (C).

In a ninth embodiment, $R^{5'}$ in Formula (C), (C-1), (C-2), (C-3), (C-4), (C-5), (C-6), (C-7), (C-8), or (C-9) is a $(C_{15}\text{-}C_{28})$alkyl interrupted with —C(O)O—, and the remaining variables are as described above for Formula (C) or the second or eighth embodiments of Formula (C). Alternatively, $R^{5'}$ in Formula (C), (C-1), (C-2), (C-3), (C-4), (C-5), (C-6), (C-7), (C-8), or (C-9) is a $(C_{17}\text{-}C_{28})$alkyl interrupted with —C(O)O—, and the remaining variables are as described above for Formula (C) or the second or eighth embodiments of Formula (C). Alternatively, $R^{5'}$ in Formula (C), (C-1), (C-2), (C-3), (C-4), (C-5), (C-6), (C-7), (C-8), or (C-9) is a $(C_{19}\text{-}C_{28})$alkyl interrupted with —C(O)O—, and the remaining variables are as described above for Formula (C) or the second or eighth embodiments of Formula (C). Alternatively, $R^{5'}$ in Formula (C), (C-1), (C-2), (C-3), (C-4), (C-5), (C-6), (C-7), (C-8), or (C-9) is a $(C_{17}\text{-}C_{26})$alkyl interrupted with —C(O)O—, and the remaining variables are as described above for Formula (C) or the second or eighth embodiments of Formula (C). Alternatively, $R^{5'}$ in Formula (C), (C-1), (C-2), (C-3), (C-4), (C-5), (C-6), (C-7), (C-8), or (C-9) is a $(C_{19}\text{-}C_{26})$alkyl interrupted with —C(O)O—, and the remaining variables are as described above for Formula (C) or the second or eighth embodiments of Formula (C). Alternatively, $R^{5'}$ in Formula (C), (C-1), (C-2), (C-3), (C-4), (C-5), (C-6), (C-7), (C-8), or (C-9) is a $(C_{20}\text{-}C_{26})$alkyl interrupted with —C(O)O—, and the remaining variables are as described above for Formula (C) or the second or eighth embodiments of Formula (C). Alternatively, $R^{5'}$ is a $(C_{22}\text{-}C_{24})$alkyl interrupted with —C(O)O—, and the remaining variables are as described above for Formula (C) or the second or eighth embodiments of Formula (C). Alternatively, $R^{5'}$ is $-(CH_2)_5C(O)OCH[(CH_2)_7CH_3]2$, $-(CH_2)_7C(O)OCH[(CH_2)_7CH_3]_2$, $-(CH_2)_5C(O)OCH(CH_2)_2[(CH_2)_7CH_3]_2$, or $-(CH_2)_7C(O)OCH(CH_2)_2[(CH_2)_7CH_3]_2$, and the remaining variables are as described above for Formula (C) or the second or eighth embodiments of Formula (C).

In some embodiments, the ionizable lipid of Formula (C), (C-1), (C-3), (C-3), (C-4), (C-5), (C-7), (C-8), or (C-9) may be selected from any of the lipids listed in Table 5 below, or pharmaceutically acceptable salts thereof.

TABLE 5

| Exemplary ionizable lipids of Formula (C), (C-1), (C-2), (C-3), (C-4), (C-5), (C-6), (C-7), (C-8), or (C-9) | |
|---|---|
| Lipid No. | Lipid Structure and Name |
| 72 | 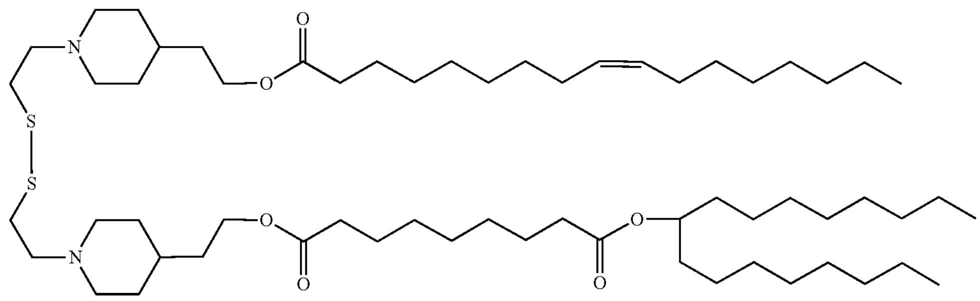 (Z)-1-(2-(1-(2-((2-(4-(2-(heptadec-9-enoyloxy)ethyl)piperidin-1-yl)ethyl)disulfaneyl)ethyl)piperidin-4-yl)ethyl) 9-(heptadecan-9-yl) nonanedioate |
| 73 | 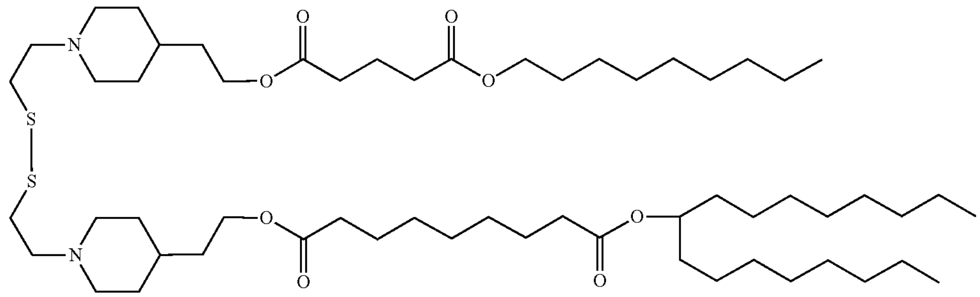 1-(heptadecan-9-yl) 9-(2-(1-(2-((2-(4-(2-((5-(nonyloxy)-5-oxopentanoyl)oxy)ethyl)piperidin-1-yl)ethyl)disulfaneyl)ethyl)piperidin-4-yl)ethyl) nonanedioate |
| 74 | 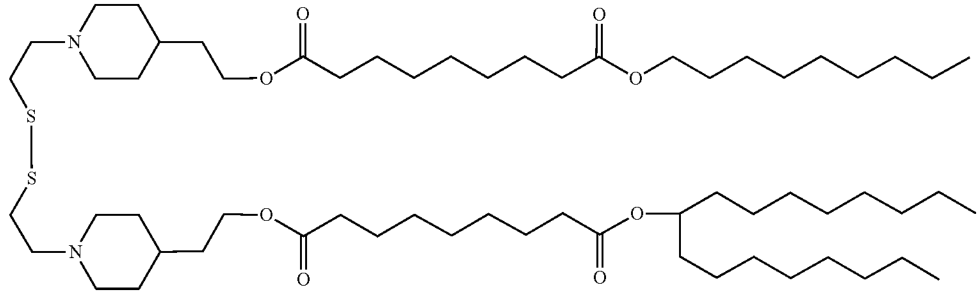 1-(heptadecan-9-yl) 9-(2-(1-(2-((2-(4-(2-((9-(nonyloxy)-9-oxononanoyl)oxy)ethyl)piperidin-1-yl)ethyl)disulfaneyl)ethyl)piperidin-4-yl)ethyl) nonanedioate |
| 75 | 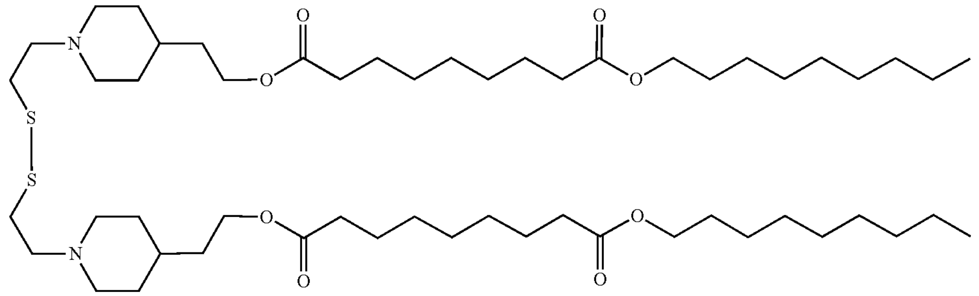 O'1,O1-(((disulfanediylbis(ethane-2,1-diyl))bis(piperidine-1,4-diyl))bis(ethane-2,1-diyl)) 9,9'-dinonyl di(nonanedioate) |

TABLE 5-continued

| Exemplary ionizable lipids of Formula (C), (C-1), (C-2), (C-3), (C-4), (C-5), (C-6), (C-7), (C-8), or (C-9) | |
|---|---|
| Lipid No. | Lipid Structure and Name |
| 76 | 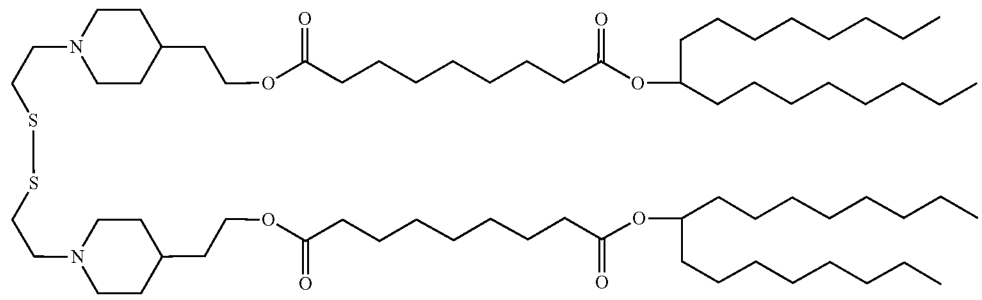 O'1,O1-(((disulfanediylbis(ethane-2,1-diyl))bis(piperidine-1,4-diyl))bis(ethane-2,1-diyl)) 9,9'-di(heptadecan-9-yl) di(nonanedioate) |

Formula (D)

In some embodiments, the ionizable lipid, e.g., cationic lipid, in the LNPs of the present disclosure is represented by Formula (D):

(D)

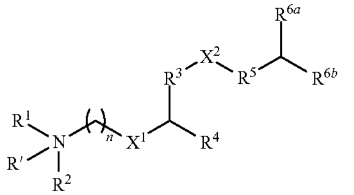

or a pharmaceutically acceptable salt thereof, wherein:

R' is absent, hydrogen, or $C_1$-$C_6$ alkyl; provided that when R' is hydrogen or $C_1$-$C_6$ alkyl, the nitrogen atom to which R', $R^1$, and $R^2$ are all attached is positively charged;

$R^1$ and $R^2$ are each independently hydrogen, $C_1$-$C_6$ alkyl, or $C_2$-$C_6$ alkenyl;

$R^3$ is $C_1$-$C_{12}$ alkylene or $C_2$-$C_{12}$ alkenylene;

$R^4$ is $C_1$-$C_{18}$ unbranched alkyl, $C_2$-$C_{18}$ unbranched alkenyl, or

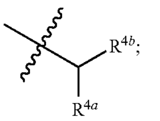

wherein:

$R^{4a}$ and $R^{4b}$ are each independently $C_1$-$C_{16}$ unbranched alkyl or $C_2$-$C_{16}$ unbranched alkenyl;

$R^5$ is absent, $C_1$-$C_8$ alkylene, or $C_2$-$C_8$ alkenylene;

$R^{6a}$ and $R^{6b}$ are each independently $C_7$-$C_{16}$ alkyl or $C_7$-$C_{16}$ alkenyl; provided that the total number of carbon atoms in $R^{6a}$ and $R^{6b}$ as combined is greater than 15;

$X^1$ and $X^2$ are each independently —OC(=O)—, —SC(=O)—, —OC(=S)—, —C(=O)O—, —C(=O)S—, —S—S—, —C($R^a$)=N—, —N=C($R^a$)—, —C($R^a$)=NO—, —O—N=C($R^a$)—, —C(=O)N$R^a$—, —N$R^a$C(=O)—, —N$R^a$C(=O)N$R^a$—, —OC(=O)O—, —OSi($R^a$)$_2$O—, —C(=O)(C$R^a_2$)C(=O)O—, or OC(=O)(C$R^a_2$)C(=O)—; wherein:

$R^a$, for each occurrence, is independently hydrogen or $C_1$-$C_6$ alkyl; and n is an integer selected from 1, 2, 3, 4, 5, and 6.

In a second embodiment of Formula (D), $X^1$ and $X^2$ are the same; and all other remaining variables are as described for Formula (C).

In a third embodiment of Formula (D), $X^1$ and $X^2$ are each independently —OC(=O)—, —SC(=O)—, —OC(=S)—, —C(=O)O—, —C(=O)S—, or —S—S—; or $X^1$ and $X^2$ are each independently —C(=O)O—, —C(=O)S—, or —S—S—; or $X^1$ and $X^2$ are each independently —C(=O)O— or —S—S—; and all other remaining variables are as described for Formula (D) or the second embodiment of Formula (D).

In a fourth embodiment of Formula (D), the ionizable lipid, e.g., cationic lipid, in the LNPs of the present disclosure, is represented by Formula (D-1):

(D-1)

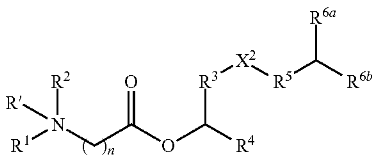

or a pharmaceutically acceptable salt thereof, wherein n is an integer selected from 1, 2, 3, and 4; and all other remaining variables are as described for Formula (D) or the second or third embodiments of Formula (D).

In a fifth embodiment of Formula (D), the ionizable lipid, e.g., cationic lipid, in the LNPs of the present disclosure, is represented by Formula (D-2):

(D-2)

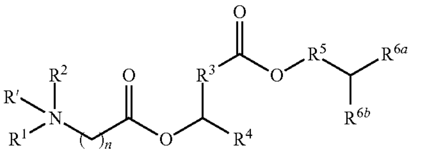

or a pharmaceutically acceptable salt thereof, wherein n is an integer selected from 1, 2, and 3; and all other remaining variables are as described for Formula (D) or the second or third embodiments of Formula (D).

In a sixth embodiment of Formula (D), the ionizable lipid, e.g., cationic lipid, in the LNPs of the present disclosure is represented by Formula (D-3):

(D-3)

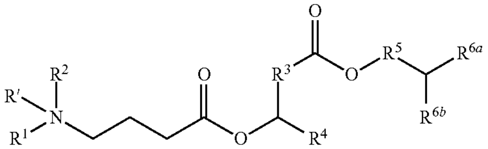

or a pharmaceutically acceptable salt thereof; and all other remaining variables are as described for Formula (D) or the second or third embodiments of Formula (D).

In a seventh embodiment of Formula (D), in the ionizable lipid, e.g., cationic lipid, according to Formula (D), Formula (D-1), Formula (D-2), Formula (D-3), or the second or third embodiments of Formula (D), $R^1$ and $R^2$ are each independently hydrogen, $C_1$-$C_6$ alkyl or $C_2$-$C_6$ alkenyl, or $C_1$-$C_5$ alkyl or $C_2$-$C_5$ alkenyl, or $C_1$-$C_4$ alkyl or $C_2$-$C_4$ alkenyl, or $C_6$ alkyl, or $C_5$ alkyl, or $C_4$ alkyl, or $C_3$ alkyl, or $C_2$ alkyl, or $C_1$ alkyl, or $C_6$ alkenyl, or $C_5$ alkenyl, or $C_4$ alkenyl, or $C_3$ alkenyl, or $C_2$ alkenyl; and all other remaining variables are as described for Formula (D), Formula (D-1), Formula (D-2), Formula (D-3) or the second or third embodiments of Formula (D).

In an eighth embodiment of Formula (D), the ionizable lipid, e.g., cationic lipid, in the LNPs of the present disclosure is represented by Formula (D-4):

(D-4)

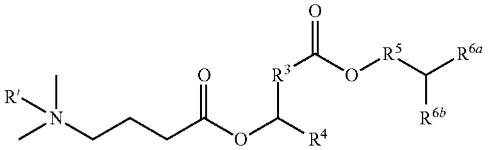

or a pharmaceutically acceptable salt thereof; and all other remaining variables are as described for Formula (D), Formula (D-1), Formula (D-2), Formula (D-3) or the second, third or seventh embodiments of Formula (D).

In a ninth embodiment of Formula (D), in the ionizable lipid, e.g., cationic lipid, according to Formula (D), Formula (D-1), Formula (D-2), Formula (D-3), Formula (D-4) or the second, third or seventh embodiments of Formula (D), $R^3$ is $C_1$-$C_9$ alkylene or $C_2$-$C_9$ alkenylene, $C_1$-$C_7$ alkylene or $C_2$-$C_7$ alkenylene, $C_1$-$C_5$ alkylene or $C_2$-$C_5$ alkenylene, or $C_2$-$C_8$ alkylene or $C_2$-$C_8$ alkenylene, or $C_3$-$C_7$ alkylene or $C_3$-$C_7$ alkenylene, or $C_5$-$C_7$ alkylene or $C_5$-$C_7$ alkenylene; or $R^3$ is $C_{12}$ alkylene, $C_{11}$ alkylene, $C_{10}$ alkylene, $C_9$ alkylene, or $C_8$ alkylene, or $C_7$ alkylene, or $C_6$ alkylene, or $C_5$ alkylene, or $C_4$ alkylene, or $C_3$ alkylene, or $C_2$ alkylene, or $C_1$ alkylene, or $C_{12}$ alkenylene, $C_{11}$ alkenylene, $C_{10}$ alkenylene, $C_9$ alkenylene, or $C_8$ alkenylene, or $C_7$ alkenylene, or $C_6$ alkenylene, or $C_5$ alkenylene, or $C_4$ alkenylene, or $C_3$ alkenylene, or $C_2$ alkenylene; and all other remaining variables are as described for Formula (D), Formula (D-1), Formula (D-2), Formula (D-3), Formula (D-4) or the second, third or seventh embodiments of Formula (D).

In a tenth embodiment of Formula (D), in the ionizable lipid, e.g., cationic lipid, according to Formula (D), Formula (D-1), Formula (D-2), Formula (D-3), Formula (D-4) or the second, third or seventh embodiments of Formula (D), $R^5$ is absent, $C_1$-$C_6$ alkylene, or $C_2$-$C_6$ alkenylene; or $R^5$ is absent, $C_1$-$C_4$ alkylene, or $C_2$-$C_4$ alkenylene; or $R^5$ is absent; or $R^5$ is $C_8$ alkylene, $C_7$ alkylene, $C_6$ alkylene, $C_5$ alkylene, $C_4$ alkylene, $C_3$ alkylene, $C_2$ alkylene, $C_1$ alkylene, $C_8$ alkenylene, $C_7$ alkenylene, $C_6$ alkenylene, $C_5$ alkenylene, $C_4$ alkenylene, $C_3$ alkenylene, or $C_2$ alkenylene; and all other remaining variables are as described for Formula (D), Formula (D-1), Formula (D-2), Formula (D-3), Formula (D-4) or the second, third, seventh, or ninth embodiments of Formula (D).

In an eleventh embodiment of Formula (D), in the ionizable lipid, e.g., cationic lipid, according to Formula (D), Formula (D-1), Formula (D-2), Formula (D-3), Formula (D-4) or the second, third, seventh, ninth or tenth embodiments of Formula (D), $R^4$ is $C_1$-$C_{14}$ unbranched alkyl, $C_2$-$C_{14}$ unbranched alkenyl, or

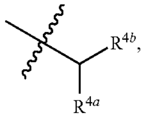

wherein $R^{4a}$ and $R^{4b}$ are each independently $C_1$-$C_{12}$ unbranched alkyl or $C_2$-$C_{12}$ unbranched alkenyl; or $R^4$ is $C_2$-$C_{12}$ unbranched alkyl or $C_2$-$C_{12}$ unbranched alkenyl; or $R^4$ is $C_5$-$C_7$ unbranched alkyl or $C_5$-$C_7$ unbranched alkenyl; or $R^4$ is $C_{16}$ unbranched alkyl, $C_{15}$ unbranched alkyl, $C_{14}$ unbranched alkyl, $C_{13}$ unbranched alkyl, $C_{12}$ unbranched alkyl, $C_{11}$ unbranched alkyl, $C_{10}$ unbranched alkyl, $C_9$ unbranched alkyl, $C_8$ unbranched alkyl, $C_7$ unbranched alkyl, $C_6$ unbranched alkyl, $C_5$ unbranched alkyl, $C_4$ unbranched alkyl, $C_3$ unbranched alkyl, $C_2$ unbranched alkyl, $C_1$ unbranched alkyl, $C_{16}$ unbranched alkenyl, $C_{15}$ unbranched alkenyl, $C_{14}$ unbranched alkenyl, $C_{13}$ unbranched alkenyl, $C_{12}$ unbranched alkenyl, $C_{11}$ unbranched alkenyl, $C_{10}$ unbranched alkenyl, $C_9$ unbranched alkenyl, $C_8$ unbranched alkenyl, $C_7$ unbranched alkenyl, $C_6$ unbranched alkenyl, $C_5$ unbranched alkenyl, $C_4$ unbranched alkenyl, $C_3$ unbranched alkenyl, or $C_2$ alkenyl; or $R^4$ is

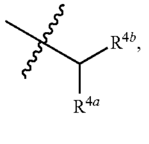

wherein $R^{4a}$ and $R^{4b}$ are each independently $C_2$-$C_{10}$ unbranched alkyl or $C_2$-$C_{10}$ unbranched alkenyl; or $R^4$ is

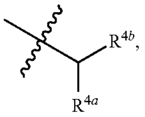

wherein $R^{4a}$ and $R^{4b}$ are each independently $C_{16}$ unbranched alkyl, $C_{15}$ unbranched alkyl, $C_{14}$ unbranched alkyl, $C_{13}$ unbranched alkyl, $C_{12}$ unbranched alkyl, $C_{11}$ unbranched alkyl, $C_{10}$ unbranched alkyl, $C_9$ unbranched alkyl, $C_8$ unbranched alkyl, $C_7$ unbranched alkyl, $C_6$ unbranched alkyl, $C_5$ unbranched alkyl, $C_4$ unbranched alkyl, $C_3$ unbranched alkyl, $C_2$ alkyl, $C_1$ alkyl, $C_{16}$ unbranched alkenyl, $C_{15}$ unbranched alkenyl, $C_{14}$ unbranched alkenyl, $C_{13}$ unbranched alkenyl, $C_{12}$ unbranched alkenyl, $C_{11}$ unbranched alkenyl, $C_{10}$ unbranched alkenyl, $C_9$ unbranched alkenyl, $C_8$ unbranched alkenyl, $C_7$ unbranched alkenyl, $C_6$ unbranched alkenyl, $C_5$ unbranched alkenyl, $C_4$ unbranched alkenyl, $C_3$ unbranched alkenyl, or $C_2$ alkenyl; and all other remaining variables are as described for Formula (D), Formula (D-1), Formula (D-2), Formula (D-3), Formula (D-4) or the second, third, seventh, ninth or tenth embodiments of Formula (D).

In a twelfth embodiment, in the ionizable lipid, e.g., cationic lipid, according to Formula (D), Formula (D-1), Formula (D-2), Formula (D-3), Formula (D-4), or the second, third, seventh, ninth, tenth or eleventh embodiments of Formula (D), $R^{6a}$ and $R^{6b}$ are each independently $C_6$-$C_{14}$ alkyl or $C_6$-$C_{14}$ alkenyl; or $R^{6a}$ and $R^{6b}$ are each independently $C_5$-$C_{12}$alkyl or $C_8$-$C_{12}$ alkenyl; or $R^{6a}$ and $R^{6b}$ are each independently $C_{16}$ alkyl, $C_{15}$ alkyl, $C_{14}$ alkyl, $C_{13}$ alkyl, $C_{12}$ alkyl, $C_{11}$ alkyl, $C_{10}$ alkyl, $C_9$ alkyl, $C_8$ alkyl, $C_7$ alkyl, $C_{16}$ alkenyl, $C_{15}$ alkenyl, $C_{14}$ alkenyl, $C_{13}$ alkenyl, $C_{12}$ alkenyl, $C_{11}$ alkenyl, $C_{10}$ alkenyl, $C_9$ alkenyl, $C_8$ alkenyl, or $C_7$ alkenyl; provided that the total number of carbon atoms in $R^{6a}$ and $R^{6b}$ as combined is greater than 15; and all other remaining variables are as described for Formula (D), Formula (D-1), Formula (D-2), Formula (D-3), Formula (D-4), or the second, third, seventh, ninth, tenth or eleventh embodiments of Formula (D).

In a thirteenth embodiment of Formula (D), in the ionizable lipid, e.g., cationic lipid, according to Formula (D), Formula (D-1), Formula (D-2), Formula (D-3), Formula (D-4), or the second, third, seventh, ninth, tenth, eleventh or twelfth embodiments of Formula (D), or a pharmaceutically acceptable salt thereof, $R^{6a}$ and $R^{6b}$ contain an equal number of carbon atoms with each other; or $R^{6a}$ and $R^{6b}$ are the same; or $R^{6a}$ and $R^{6b}$ are both $C_{16}$ alkyl, $C_{15}$ alkyl, $C_{14}$ alkyl, $C_{13}$ alkyl, $C_{12}$ alkyl, $C_{11}$ alkyl, $C_{10}$ alkyl, $C_9$ alkyl, $C_8$ alkyl, $C_7$ alkyl, $C_{16}$ alkenyl, $C_{15}$ alkenyl, $C_{14}$ alkenyl, $C_{13}$ alkenyl, $C_{12}$ alkenyl, $C_{11}$ alkenyl, $C_{10}$ alkenyl, $C_9$ alkenyl, $C_8$ alkenyl, or $C_7$ alkenyl; provided that the total number of carbon atoms in $R^{6a}$ and $R^{6b}$ as combined is greater than 15; and all other remaining variables are as described for Formula (D), Formula (D-1), Formula (D-2), Formula (D-3), Formula (D-4) or the second, third, seventh, ninth, tenth, eleventh or twelfth embodiments of Formula (D).

In a fourteenth embodiment of Formula (D), in the ionizable lipid, e.g., cationic lipid, according to Formula (D), Formula (D-1), Formula (D-2), Formula (D-3), Formula (D-4), or the second, third, seventh, ninth, tenth, eleventh, twelfth or thirteenth embodiments of Formula (D), $R^{6a}$ and $R^{6b}$ as defined in any one of the preceding embodiments each contain a different number of carbon atoms with each other; or the number of carbon atoms $R^{6a}$ and $R^{6b}$ differs by one or two carbon atoms; or the number of carbon atoms $R^{6a}$ and $R^{6b}$ differs by one carbon atom; or $R^{6a}$ is $C_7$ alkyl and $R^{6a}$ is $C_8$ alkyl, $R^{6a}$ is $C_8$ alkyl and $R^{6a}$ is $C_7$ alkyl, $R^{6a}$ is $C_8$ alkyl and $R^{6a}$ is $C_9$ alkyl, $R^{6a}$ is $C_9$ alkyl and $R^{6a}$ is $C_8$ alkyl, $R^{6a}$ is $C_9$ alkyl and $R^{6a}$ is $C_{10}$ alkyl, $R^{6a}$ is $C_{10}$ alkyl and $R^{6a}$ is $C_9$ alkyl, $R^{6a}$ is $C_{10}$ alkyl and $R^{6a}$ is $C_{11}$ alkyl, $R^{6a}$ is $C_{11}$ alkyl and $R^{6a}$ is $C_{10}$ alkyl, $R^{6a}$ is $C_{11}$ alkyl and $R^{6a}$ is $C_{12}$ alkyl, $R^{6a}$ is $C_{12}$ alkyl and $R^{6a}$ is $C_{11}$ alkyl, $R^{6a}$ is $C_7$ alkyl and $R^{6a}$ is $C_9$ alkyl, $R^{6a}$ is $C_9$ alkyl and $R^{6a}$ is $C_7$ alkyl, $R^{6a}$ is $C_8$ alkyl and $R^{6a}$ is $C_{10}$ alkyl, $R^{6a}$ is $C_{10}$ alkyl and $R^{6a}$ is $C_8$ alkyl, $R^{6a}$ is $C_9$ alkyl and $R^{6a}$ is $C_{11}$ alkyl, $R^{6a}$ is $C_{11}$ alkyl and $R^{6a}$ is $C_9$ alkyl, $R^{6a}$ is $C_{10}$ alkyl and $R^{6a}$ is $C_{12}$ alkyl, $R^{6a}$ is $C_{12}$ alkyl and $R^{6a}$ is $C_{10}$ alkyl, $R^{6a}$ is $C_{11}$ alkyl and $R^{6a}$ is $C_{13}$ alkyl, or $R^{6a}$ is $C_{13}$ alkyl and $R^{6a}$ is $C_{11}$ alkyl, etc.; and all other remaining variables are as described for Formula I, Formula II, Formula III, Formula IV, Formula V, or the second, third, seventh, ninth, tenth, eleventh, twelfth or thirteenth embodiments of Formula (D).

In a fifteenth embodiment of Formula (D), $R^4$ is $C_1$-$C_{16}$ unbranched alkyl, $C_2$-$C_{16}$ unbranched alkenyl, or

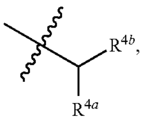

wherein $R^{4a}$ and $R^{4b}$ are as described above for the second, third, fourth, fifth, sixth, seventh, eighth, ninth, tenth, eleventh, twelfth, thirteenth or fourteenth embodiments of Formula (D).

In one embodiment, the ionizable lipid, e.g., cationic lipid, of the present disclosure or the ionizable lipid of Formula (D), Formula (D-1), Formula (D-2), Formula (D-3), or Formula (D-4) is any one lipid selected from the lipids listed in Table 6 below, or a pharmaceutically acceptable salt thereof:

TABLE 6

| Lipid No. | Lipid Structure and Name |
| --- | --- |
| Exemplary lipids of Formula (D), Formula (D-1), Formula (D-2), Formula (D-3) or Formula (D-4) | |
| 77 | 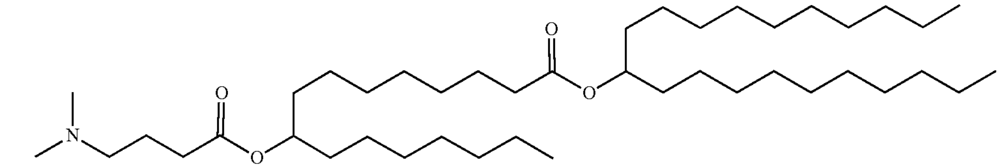 [SMILES: CCCCCCCCCCC(CCCCCCCCCC)OC(=O)CCCCCCCC(CCCCCCC)OC(=O)CCCN(C)C] henicosan-11-yl 9-((4-(dimethylamino)butanoyl)oxy)hexadecanoate |
| 78 | 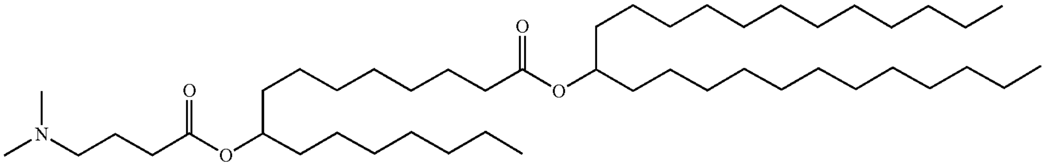 [SMILES: CCCCCCCCCCCCC(CCCCCCCCCCCC)OC(=O)CCCCCCCC(CCCCCCC)OC(=O)CCCN(C)C] pentacosan-13-yl 9-((4-(dimethylamino)butanoyl)oxy)hexadecanoate |
| 79 | 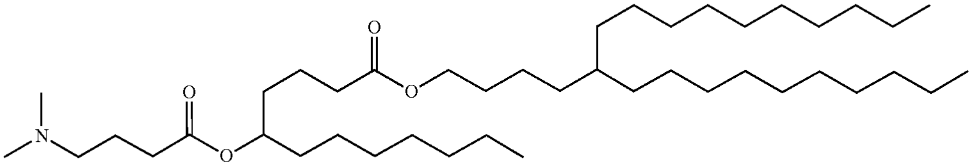 [SMILES: CCCCCCCCCCC(CCCCCCCCCC)CCCCOC(=O)CCCC(CCCCCCC)OC(=O)CCCN(C)C] 5-decylpentadecyl 5-((4-(dimethylamino)butanoyl)oxy)dodecanoate |
| 80 | 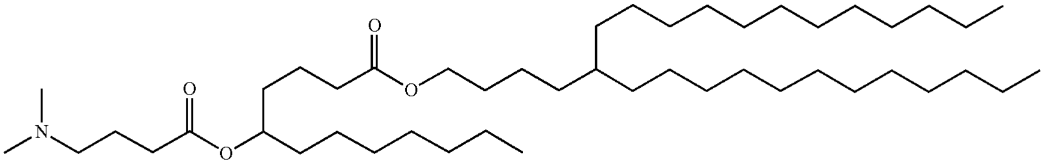 [SMILES: CCCCCCCCCCCCC(CCCCCCCCCCCC)CCCCOC(=O)CCCC(CCCCCCC)OC(=O)CCCN(C)C] 5-dodecylheptadecyl 5-((4-(dimethylamino)butanoyl)oxy)dodecanoate |
| 81 | 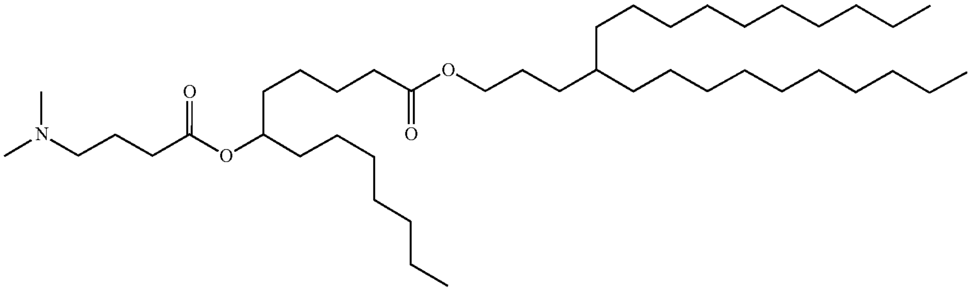 [SMILES: CCCCCCCCCCC(CCCCCCCCCC)CCCOC(=O)CCCCC(CCCCCCC)OC(=O)CCCN(C)C] 4-decyltetradecyl 6-((4-(dimethylamino)butanoyl)oxy)tridecanoate |
| 82 | 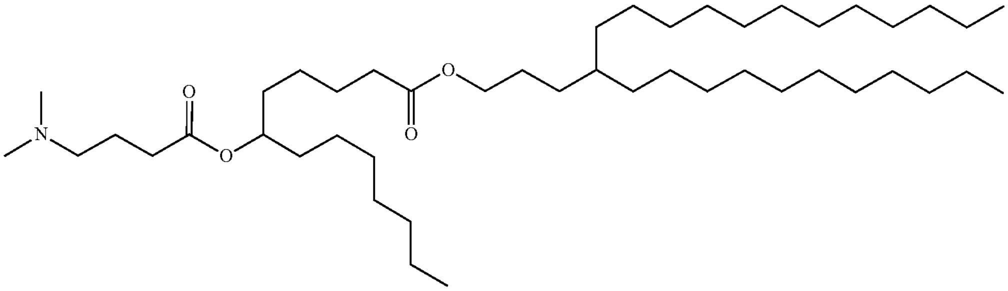 [SMILES: CCCCCCCCCCCCC(CCCCCCCCCCC)CCCOC(=O)CCCCC(CCCCCCC)OC(=O)CCCN(C)C] 4-dodecylhexadecyl 6-((4-(dimethylamino)butanoyl)oxy)tridecanoate |

TABLE 6-continued

Exemplary lipids of Formula (D), Formula (D-1), Formula (D-2), Formula (D-3) or Formula (D-4)

| Lipid No. | Lipid Structure and Name |
|---|---|
| 83 | 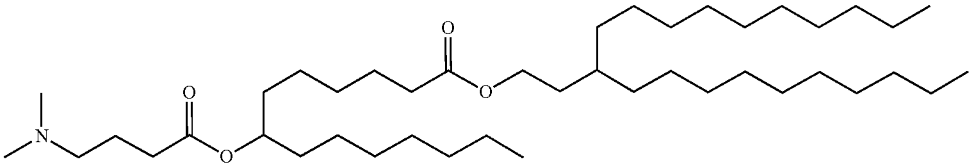 [SMILES: CCCCCCCCCCC(CCCCCCCCCC)CCOC(=O)CCCCCC(CCCCCCC)OC(=O)CCCN(C)C] 3-decyltridecyl 7-((4-(dimethylamino)butanoyl)oxy)tetradecanoate |
| 84 | 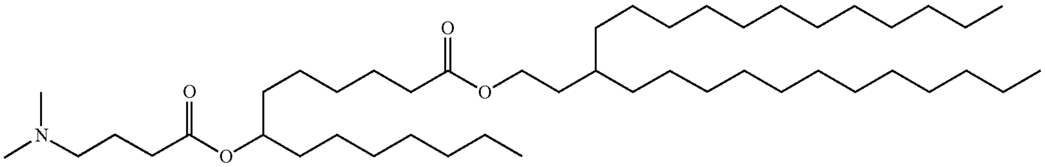 [SMILES: CCCCCCCCCCCCC(CCCCCCCCCCCC)CCOC(=O)CCCCCC(CCCCCCC)OC(=O)CCCN(C)C] 3-dodecylpentadecyl 7-((4-(dimethylamino)butanoyl)oxy)tetradecanoate |
| 85 | 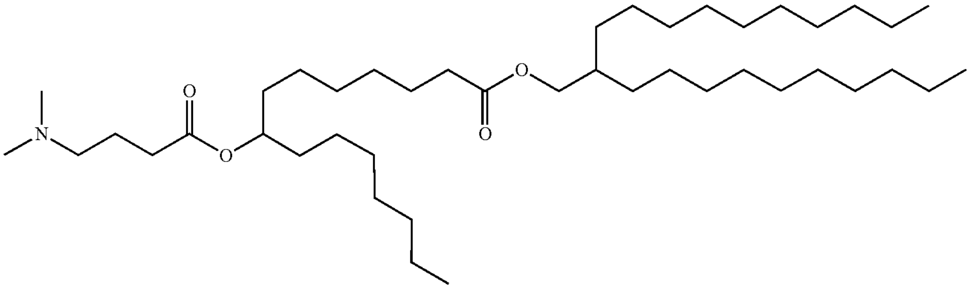 [SMILES: CCCCCCCCCCC(CCCCCCCCCC)COC(=O)CCCCCCC(CCCCCCC)OC(=O)CCCN(C)C] 2-decyldodecyl 8-((4-(dimethylamino)butanoyl)oxy)pentadecanoate |
| 86 | 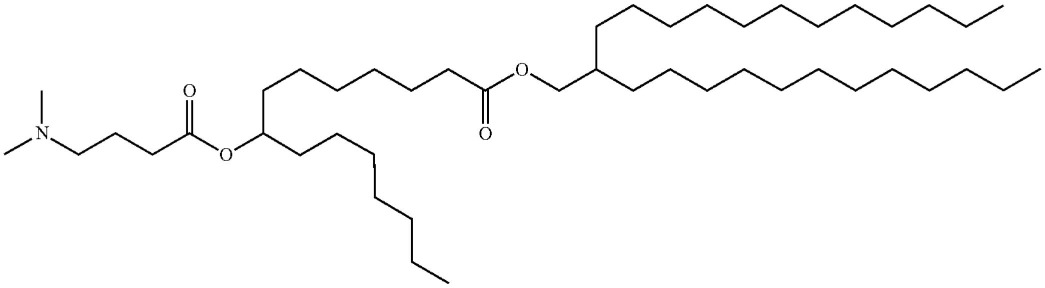 [SMILES: CCCCCCCCCCCCC(CCCCCCCCCCCC)COC(=O)CCCCCCC(CCCCCCC)OC(=O)CCCN(C)C] 2-dodecyltetradecyl 8-((4-(dimethylamino)butanoyl)oxy)pentadecanoate |
| 87 | 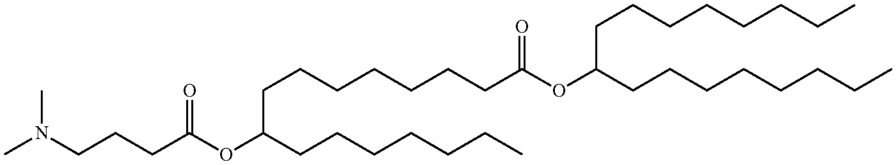 [SMILES: CCCCCCCCC(CCCCCCCC)OC(=O)CCCCCCCC(CCCCCCC)OC(=O)CCCN(C)C] heptadecan-9-yl 9-((4-(dimethylamino)butanoyl)oxy)hexadecanoate |
| 88 | 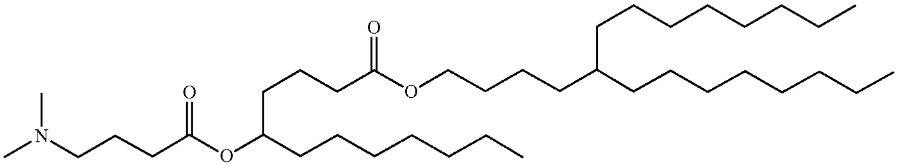 [SMILES: CCCCCCCCC(CCCCCCCC)CCCCOC(=O)CCCC(CCCCCCC)OC(=O)CCCN(C)C] 5-octyltridecyl 5-((4-(dimethylamino)butanoyl)oxy)dodecanoate |

TABLE 6-continued

| Exemplary lipids of Formula (D), Formula (D-1), Formula (D-2), Formula (D-3) or Formula (D-4) | |
|---|---|
| Lipid No. | Lipid Structure and Name |
| 89 | 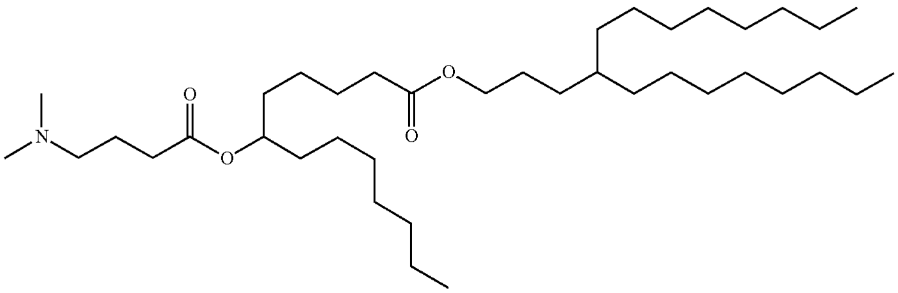 [SMILES: CCCCCCCCC(CCCCCCCC)CCCOC(=O)CCCCC(CCCCCCC)OC(=O)CCCN(C)C]<br>4-octyldodecyl 6-((4-(dimethylamino)butanoyl)oxy)tridecanoate |
| 91 | 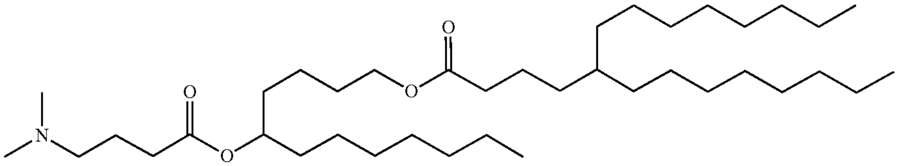 [SMILES: CCCCCCCCC(CCCCCCCC)CCCC(=O)OCCCCC(CCCCCCC)OC(=O)CCCN(C)C]<br>3-octylundecyl 7-((4-(dimethylamino)butanoyl)oxy)tetradecanoate |
| 92 | 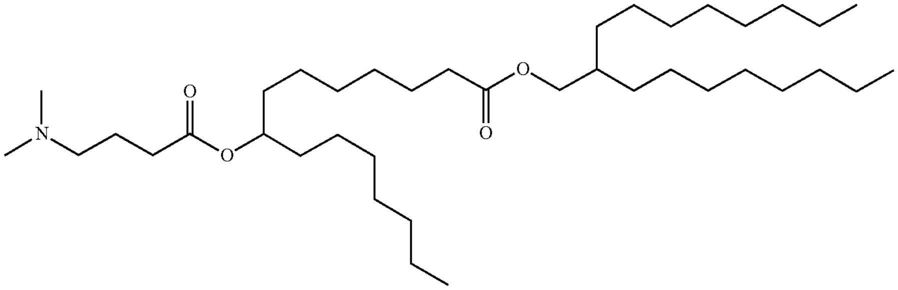 [SMILES: CCCCCCCCC(CCCCCCCC)COC(=O)CCCCCCC(CCCCCCC)OC(=O)CCCN(C)C]<br>2-octyldecyl 8-((4-(dimethylamino)butanoyl)oxy)pentadecanoate |
| 93 | 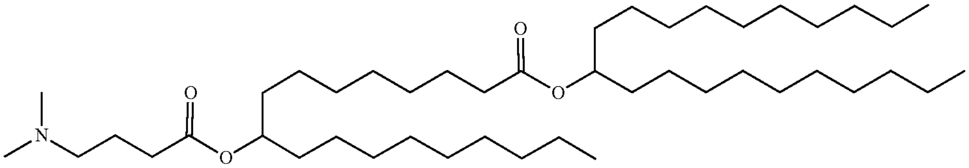 [SMILES: CCCCCCCCCCC(CCCCCCCCCC)OC(=O)CCCCCCCC(CCCCCCCCC)OC(=O)CCCN(C)C]<br>henicosan-11-yl 9-((4-(dimethylamino)butanoyl)oxy)octadecanoate |
| 94 | 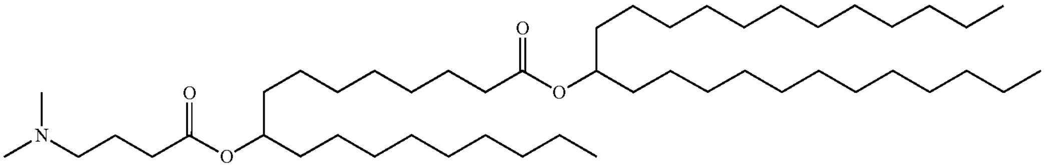 [SMILES: CCCCCCCCCCCCC(CCCCCCCCCCCC)OC(=O)CCCCCCCC(CCCCCCCCC)OC(=O)CCCN(C)C]<br>pentacosan-13-yl 9-((4-(dimethylamino)butanoyl)oxy)octadecanoate |
| 95 | 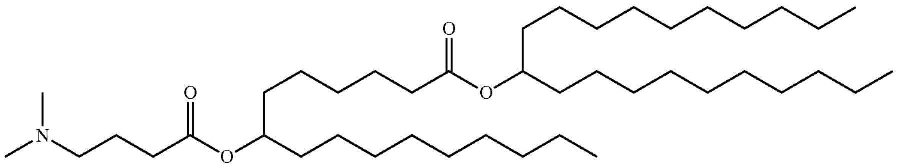 [SMILES: CCCCCCCCCCC(CCCCCCCCCC)OC(=O)CCCCCC(CCCCCCCCC)OC(=O)CCCN(C)C]<br>henicosan-11-yl 7-((4-(dimethylamino)butanoyl)oxy)hexadecanoate |

TABLE 6-continued

| Lipid No. | Exemplary lipids of Formula (D), Formula (D-1), Formula (D-2), Formula (D-3) or Formula (D-4)<br>Lipid Structure and Name |
|---|---|
| 96 | 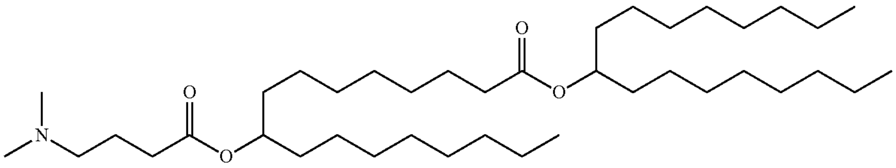 [SMILES: CCCCCCCCC(CCCCCCCC)OC(=O)CCCCCCCC(CCCCCCCC)OC(=O)CCCN(C)C]<br>heptadecan-9-yl 9-((4-(dimethylamino)butanoyl)oxy)heptadecanoate |
| 97 | 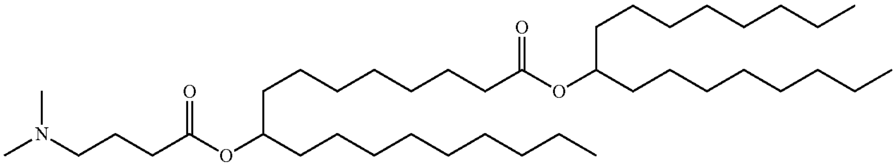 [SMILES: CCCCCCCCCC(CCCCCCCC(=O)OC(CCCCCCCC)CCCCCCCC)OC(=O)CCCN(C)C]<br>heptadecan-9-yl 9-((4-(dimethylamino)butanoyl)oxy)octadecanoate |
| 98 | 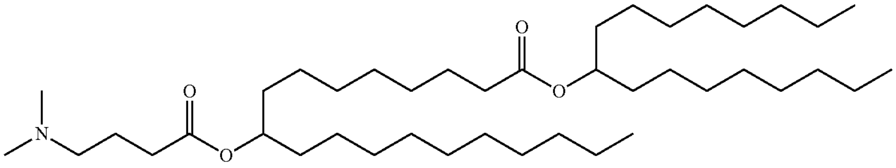 [SMILES: CCCCCCCCCCC(CCCCCCCC(=O)OC(CCCCCCCC)CCCCCCCC)OC(=O)CCCN(C)C]<br>heptadecan-9-yl 9-((4-(dimethylamino)butanoyl)oxy)nonadecanoate |
| 99 | 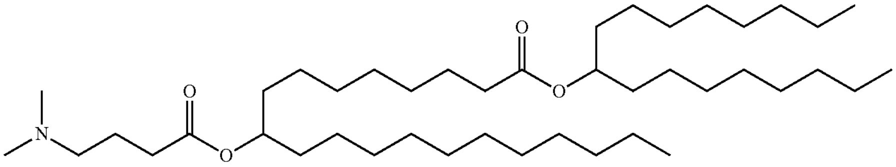 [SMILES: CCCCCCCCCCCC(CCCCCCCC(=O)OC(CCCCCCCC)CCCCCCCC)OC(=O)CCCN(C)C]<br>heptadecan-9-yl 9-((4-(dimethylamino)butanoyl)oxy)icosanoate |
| 100 | 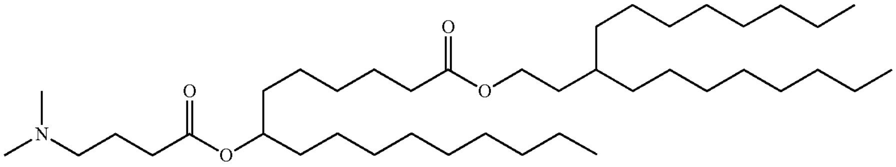 [SMILES: CCCCCCCCCC(CCCCCC(=O)OCCC(CCCCCCCC)CCCCCCCC)OC(=O)CCCN(C)C]<br>3-octylundecyl 7-((4-(dimethylamino)butanoyl)oxy)hexadecanoate |
| 101 | 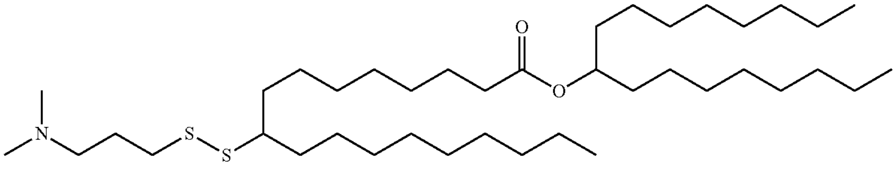 [SMILES: CCCCCCCCCC(CCCCCCCC(=O)OC(CCCCCCCC)CCCCCCCC)SSCCCN(C)C]<br>heptadecan-9-yl 9-((3-(dimethylamino)propyl)disulfaneyl)octadecanoate |
| 113 | 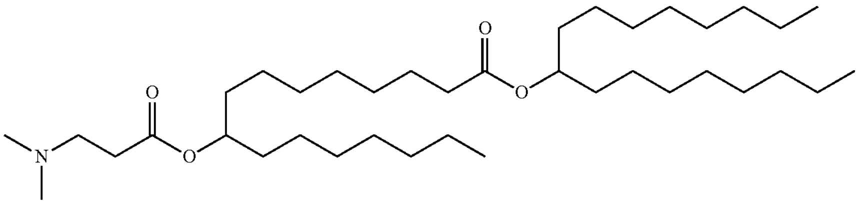 [SMILES: CCCCCCCCC(CCCCCCCC)OC(=O)CCCCCCCC(CCCCCCC)OC(=O)CCN(C)C] |

TABLE 6-continued
| Lipid No. | Lipid Structure and Name |
|---|---|
| | Exemplary lipids of Formula (D), Formula (D-1), Formula (D-2), Formula (D-3) or Formula (D-4) |
| 114 | 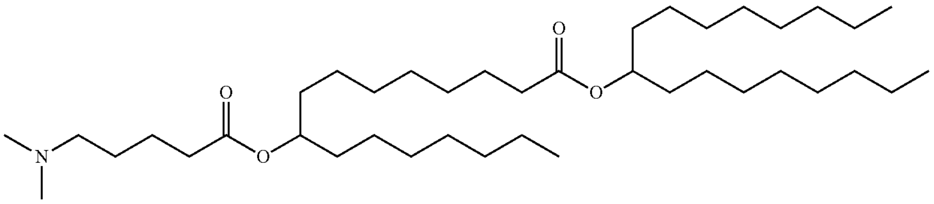 [SMILES: CCCCCCCCC(CCCCCCCC)OC(=O)CCCCCCCC(CCCCCCC)OC(=O)CCCCN(C)C] |
| 115 | 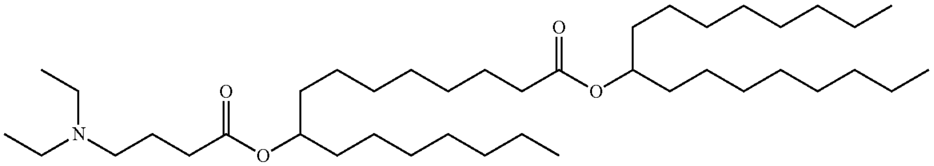 [SMILES: CCCCCCCCC(CCCCCCCC)OC(=O)CCCCCCCC(CCCCCCC)OC(=O)CCCN(CC)CC] |
| 116 | 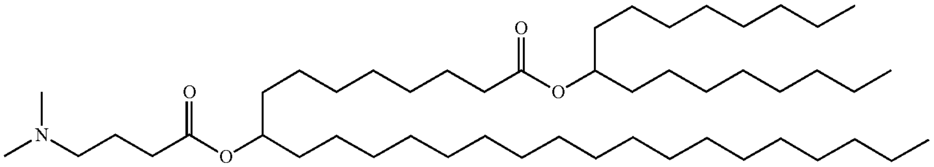 [SMILES: CCCCCCCCCCCCCCCCCCC(CCCCCCCC(=O)OC(CCCCCCCC)CCCCCCCC)OC(=O)CCCN(C)C] |
| 117 | 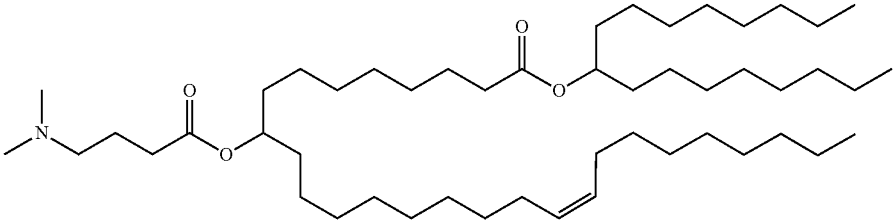 [SMILES: CCCCCCCC/C=C\CCCCCCCCC(CCCCCCCC(=O)OC(CCCCCCCC)CCCCCCCC)OC(=O)CCCN(C)C] |
| 118 | 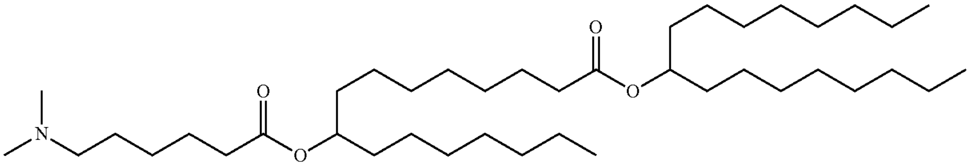 [SMILES: CCCCCCCCC(CCCCCCCC)OC(=O)CCCCCCCC(CCCCCCC)OC(=O)CCCCCN(C)C] |
| 119 | 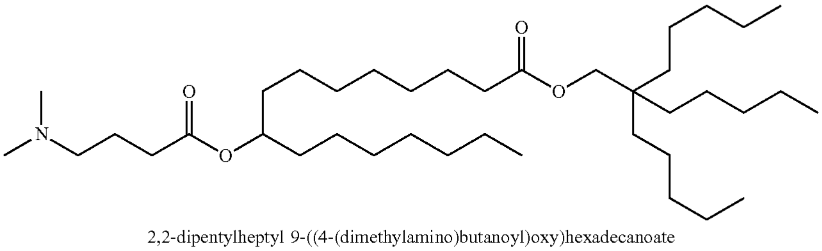 2,2-dipentylheptyl 9-((4-(dimethylamino)butanoyl)oxy)hexadecanoate |

In one embodiment, the ionizable lipid in the LNPs of the present disclosure comprises Lipid No. 87:

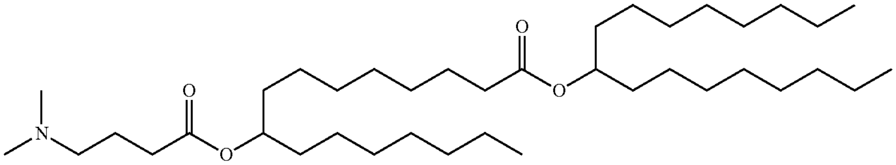

heptadecan-9-yl 9-((4-(dimethylamino)butanoyl)oxy)hexadecanoate or a pharmaceutically acceptable salt or ester thereof, or a deuterated analogue thereof.

In one embodiment, the ionizable lipid in the LNPs of the stealth lipid nanoparticles may be Lipid 119, as shown above. The chemical name is 2,2-dipentylheptyl 9-((4-(dimethylamino) butanoyl)oxy)hexadecanoate. In another embodiment, the ionizable lipid in the LNPs of the present disclosure comprises Lipid No. 119:

Lipid No. 119:

In one embodiment, the ionizable lipid in the LNPs of the present disclosure comprises Lipid No. 119: 2,2-dipentylheptyl 9-((4-(dimethylamino)butanoyl)oxy)hexadecanoate

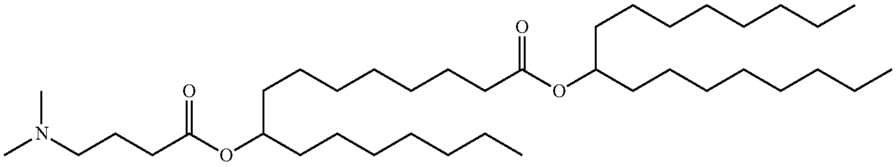

heptadecan-9-yl 9-((4-(dimethylamino)butanoyl)oxy)hexadecanoate or a pharmaceutically acceptable salt or ester thereof, or a deuterated analogue thereof.

Formula (E)

In some embodiments, the ionizable lipid, e.g., cationic lipid, in the LNPs of the present disclosure is represented by Formula (D):

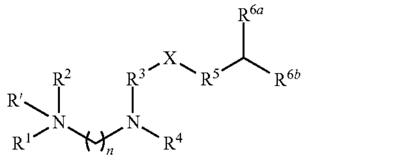

(E)

or a pharmaceutically acceptable salt thereof, wherein:

R' is absent, hydrogen, or $C_1$-$C_3$ alkyl; provided that when R' is hydrogen or $C_1$-$C_3$ alkyl, the nitrogen atom to which R', $R^1$, and $R^2$ are all attached is positively charged;

$R^1$ and $R^2$ are each independently hydrogen or $C_1$-$C_3$ alkyl;

$R^3$ is $C_3$-$C_{10}$ alkylene or $C_3$-$C_{10}$ alkenylene;

$R^4$ is $C_1$-$C_{16}$ unbranched alkyl, $C_2$-$C_{16}$ unbranched alkenyl, or $R_4$;

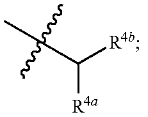

wherein:

$R^{4a}$ and $R^{4b}$ are each independently $C_1$-$C_{16}$ unbranched alkyl or $C_2$-$C_{16}$ unbranched alkenyl;

$R^5$ is absent, $C_1$-$C_6$ alkylene, or $C_2$-$C_6$ alkenylene;

$R^{6a}$ and $R^{6b}$ are each independently $C_7$-$C_{14}$ alkyl or $C_7$-$C_{14}$ alkenyl;

X is —OC(═O)—, —SC(═O)—, —OC(═S)—, —C(═O)O—, —C(═O)S—, —S—S—, —C($R^a$)═N—, —N═C($R^a$)—, —C($R^a$)═NO—, —O—N═C($R^a$)—, —C(═O)N$R^a$—, —N$R^a$C(═O)—, —N$R^a$C(═O)N$R^a$—, —OC(═O)O—, —OSi($R^a$)$_2$O—, —C(═O)(C$R^a_2$)C(═O)O—, or OC(═O)(C$R^a_2$)C(═O)—; wherein:

$R^a$, for each occurrence, is independently hydrogen or $C_1$-$C_6$ alkyl; and n is an integer selected from 1, 2, 3, 4, 5, and 6.

In a second embodiment of Formula (E), in the ionizable lipid, e.g., cationic lipid, according to the first embodiment, or a pharmaceutically acceptable salt thereof, X is —OC(═O)—, —SC(═O)—, —OC(═S)—, —C(═O)O—, —C(═O)S—, or —S—S—; and all other remaining variables are as described for Formula I or the first embodiment.

In a third embodiment of Formula (E), the ionizable lipid, e.g., cationic lipid, in the LNPs of the present disclosure is represented by Formula (E-1):

(E-1)

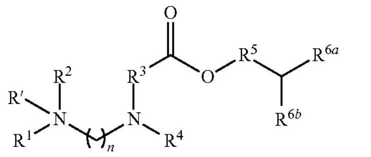

or a pharmaceutically acceptable salt thereof, wherein n is an integer selected from 1, 2, 3, and 4; and all other remaining variables are as described for Formula (E) or the second embodiment of Formula (E). Alternatively, n is an integer selected from 1, 2, and 3; and all other remaining variables are as described for Formula (E) or the second embodiment of Formula (E).

In a fourth embodiment of Formula (E), the ionizable lipid, e.g., cationic lipid, in the LNPs of the present disclosure is represented by Formula (E-2):

(E-2)

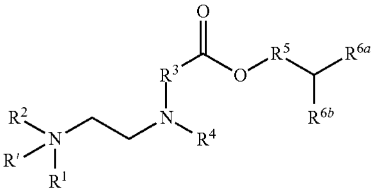

or a pharmaceutically acceptable salt thereof; and all other remaining variables are as described for Formula (E), Formula (E-1) or the second embodiment of Formula (E).

In a fifth embodiment of Formula (E), in the ionizable lipid, e.g., cationic lipid, in the LNPs of the present disclosure, $R^1$ and $R^2$ are each independently hydrogen or $C_1$-$C_2$ alkyl, or $C_2$-$C_3$ alkenyl; or R', $R^1$, and $R^2$ are each independently hydrogen, $C_1$-$C_2$ alkyl; and all other remaining variables are as described for Formula (E), Formula (E-1) or the second embodiment of Formula (E).

In a sixth embodiment of Formula (E), the ionizable lipid, e.g., cationic lipid, in the LNPs of the present disclosure is represented by Formula (E-3):

(E-3)

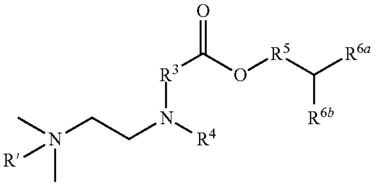

or a pharmaceutically acceptable salt thereof; and all other remaining variables are as described for Formula (E), Formula (E-1), Formula (E-2) or the second or fifth embodiments of Formula (E).

In a seventh embodiment of Formula (E), in the ionizable lipid, e.g., cationic lipid, according to Formula (E), Formula (E-1), Formula (E-2), Formula (E-3) or the second or firth embodiments of Formula (E), $R^5$ is absent or $C_1$-$C_8$ alkylene; or $R^5$ is absent, $C_1$-$C_6$ alkylene, or $C_2$-$C_6$ alkenylene; or $R^5$ is absent, $C_1$-$C_4$ alkylene, or $C_2$-$C_4$ alkenylene; or $R^5$ is absent; or $R^5$ is $C_8$ alkylene, $C_7$ alkylene, $C_6$ alkylene, $C_5$ alkylene, $C_4$ alkylene, $C_3$ alkylene, $C_2$ alkylene, $C_1$ alkylene, $C_8$ alkenylene, $C_7$ alkenylene, $C_6$ alkenylene, $C_5$ alkenylene, $C_4$ alkenylene, $C_3$ alkenylene, or $C_2$ alkenylene; and all other remaining variables are as described for Formula (E), Formula (E-1), Formula (E-2), Formula (E-3) or the second or fifth embodiments of Formula (E).

In an eighth embodiment of Formula (E), the ionizable lipid, e.g., cationic lipid, in the LNPs of the present disclosure is represented by Formula (E-4):

(E-4)

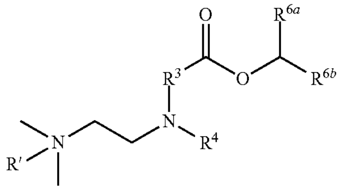

or a pharmaceutically acceptable salt thereof; and all other remaining variables are as described for Formula (E), Formula (E-1), Formula (E-2), Formula (E-3) or the second, fifth or seventh embodiments of Formula (E).

In a ninth embodiment, in the ionizable lipid, e.g., cationic lipid, according to Formula (E), Formula (E-1), Formula (E-2), Formula (E-3), Formula (E-4) or the second, fifth or seventh embodiments of Formula (E), or a pharmaceutically acceptable salt thereof, $R^4$ is $C_1$-$C_{14}$ unbranched

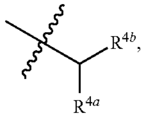

alkyl, $C_2$-$C_{14}$ unbranched alkenyl, or, wherein $R^{4a}$ and $R^{4b}$ are each independently $C_1$-$C_{12}$ unbranched alkyl or $C_2$-$C_{12}$ unbranched alkenyl; or $R^4$ is $C_2$-$C_{12}$ unbranched alkyl or $C_2$-$C_{12}$ unbranched alkenyl; or $R^4$ is $C_5$-$C_{12}$ unbranched alkyl or $C_5$-$C_{12}$ unbranched alkenyl; or $R^4$ is $C_{16}$ unbranched alkyl, $C_{15}$ unbranched alkyl, $C_{14}$ unbranched alkyl, $C_{13}$ unbranched alkyl, $C_{12}$ unbranched alkyl, $C_{11}$ unbranched alkyl, $C_{10}$ unbranched alkyl, $C_9$ unbranched alkyl, $C_8$ unbranched alkyl, $C_7$ unbranched alkyl, $C_6$ unbranched alkyl, $C_5$ unbranched alkyl, $C_4$ unbranched alkyl, $C_3$ unbranched alkyl, $C_2$ unbranched alkyl, $C_1$ unbranched alkyl, $C_{16}$ unbranched alkenyl, $C_{15}$ unbranched alkenyl, $C_{14}$ unbranched alkenyl, $C_{13}$ unbranched alkenyl, $C_{12}$ unbranched alkenyl, $C_{11}$ unbranched alkenyl, $C_{10}$ unbranched alkenyl, $C_9$ unbranched alkenyl, $C_8$ unbranched alkenyl, $C_7$ unbranched alkenyl, $C_6$ unbranched alkenyl, $C_5$ unbranched alkenyl, $C_4$ unbranched alkenyl, $C_3$ unbranched alkenyl, or $C_2$ alkenyl; or $R^4$ is

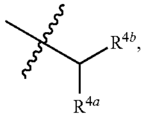

wherein $R^{4a}$ and $R^{4b}$ are each independently $C_2$-$C_{10}$ unbranched alkyl or $C_2$-$C_{10}$ unbranched alkenyl; or $R^4$ is

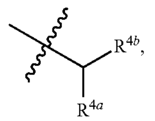

wherein $R^{4a}$ and $R^{4b}$ are each independently $C_{16}$ unbranched alkyl, $C_{15}$ unbranched alkyl, $C_{14}$ unbranched alkyl, $C_{13}$ unbranched alkyl, $C_{12}$ unbranched alkyl, $C_{11}$ unbranched alkyl, $C_{10}$ unbranched alkyl, $C_9$ unbranched alkyl, $C_8$ unbranched alkyl, $C_7$ unbranched alkyl, $C_6$ unbranched alkyl, $C_5$ unbranched alkyl, $C_4$ unbranched alkyl, $C_3$ unbranched alkyl, $C_2$ alkyl, $C_1$ alkyl, $C_{16}$ unbranched alkenyl, Cis unbranched alkenyl, $C_{14}$ unbranched alkenyl, $C_{13}$ unbranched alkenyl, $C_{12}$ unbranched alkenyl, $C_{11}$ unbranched alkenyl, $C_{10}$ unbranched alkenyl, $C_9$ unbranched alkenyl, $C_8$ unbranched alkenyl, $C_7$ unbranched alkenyl, $C_6$ unbranched alkenyl, $C_5$ unbranched alkenyl, $C_4$ unbranched alkenyl, $C_3$ unbranched alkenyl, or $C_2$ alkenyl; and all other remaining variables are as described for Formula (E), Formula (E-1), Formula (E-2), Formula (E-3), Formula (E-4) or the second, fifth or seventh embodiments of Formula (E).

In a tenth embodiment, in the ionizable lipid, e.g., cationic lipid, according to Formula (E), Formula (E-1), Formula (E-2), Formula (E-3), Formula (E-4) or the second, fifth, seventh or ninth embodiments of Formula (E), $R^3$ is $C_3$-$C_5$ alkylene or $C_3$-$C_5$ alkenylene, $C_3$-$C_7$ alkylene or $C_3$-$C_7$ alkenylene, or $C_3$-$C_5$ alkylene or $C_3$-$C_5$ alkenylene, or $R^3$ is $C_8$ alkylene, or $C_7$ alkylene, or $C_6$ alkylene, or $C_5$ alkylene, or $C_4$ alkylene, or $C_3$ alkylene, or $C_1$ alkylene, or $C_8$ alkenylene, or $C_7$ alkenylene, or $C_6$ alkenylene, or $C_5$ alkenylene, or $C_4$ alkenylene, or $C_3$ alkenylene; and all other remaining variables are as described for Formula (E), Formula (E-1), Formula (E-2), Formula (E-3), Formula (E-4) or the second, fifth, seventh or ninth embodiments of Formula (E).

In an eleventh embodiment, in the ionizable lipid, e.g., cationic lipid, according to Formula (E), Formula (E-1), Formula (E-2), Formula (E-3), Formula (E-4) or the second, fifth, seventh, ninth or tenth embodiments of Formula (E), $R^{6a}$ and $R^{6b}$ are each independently $C_7$-$C_{12}$ alkyl or $C_7$-$C_{12}$ alkenyl; or $R^{6a}$ and $R^{6b}$ are each independently $C_5$-$C_{10}$ alkyl or $C_5$-$C_{10}$ alkenyl; or $R^{6a}$ and $R^{6b}$ are each independently $C_{12}$ alkyl, $C_{11}$ alkyl, $C_{10}$ alkyl, $C_9$ alkyl, $C_8$ alkyl, $C_7$ alkyl, $C_{12}$ alkenyl, $C_{11}$ alkenyl, $C_{10}$ alkenyl, $C_9$ alkenyl, $C_8$ alkenyl, or $C_7$ alkenyl; and all other remaining variables are as described for Formula (E), Formula (E-1), Formula (E-2), Formula (E-3), Formula (E-4) or the second, fifth, seventh, ninth or tenth embodiments of Formula (E).

In a twelfth embodiment, in the ionizable lipid, e.g., cationic lipid, according to Formula (E), Formula (E-1), Formula (E-2), Formula (E-3), Formula (E-4) or the second, fifth, seventh, ninth, tenth or eleventh embodiments of Formula (E), $R^{6a}$ and $R^{6b}$ contain an equal number of carbon atoms with each other; or $R^{6a}$ and $R^{6b}$ are the same; or $R^{6a}$ and $R^{6b}$ are both $C_{12}$ alkyl, $C_{11}$ alkyl, $C_{10}$ alkyl, $C_9$ alkyl, $C_8$ alkyl, $C_7$ alkyl, $C_{12}$ alkenyl, $C_{11}$ alkenyl, $C_{10}$ alkenyl, $C_9$ alkenyl, $C_8$ alkenyl, or $C_7$ alkenyl; and all other remaining variables are as described for Formula (E), Formula (E-1), Formula (E-2), Formula (E-3), Formula (E-4) or the second, fifth, seventh, ninth, tenth or eleventh embodiments of Formula (E).

In a thirteenth embodiment, in the ionizable lipid, e.g., cationic lipid, according to Formula (E), Formula (E-1), Formula (E-2), Formula (E-3), Formula (E-4), $R^{6a}$ and $R^{6b}$ as defined in any one of the preceding embodiments each contain a different number of carbon atoms with each other; or the number of carbon atoms $R^{6a}$ and $R^{6b}$ differs by one or two carbon atoms; or the number of carbon atoms $R^{6a}$ and $R^{6b}$ differs by one carbon atom; or $R^{6a}$ is $C_7$ alkyl and $R^{6a}$ is $C_8$ alkyl, $R^{6a}$ is $C_8$ alkyl and $R^{6a}$ is $C_7$ alkyl, $R^{6a}$ is $C_8$ alkyl and $R^{6a}$ is $C_9$ alkyl, $R^{6a}$ is $C_9$ alkyl and $R^{6a}$ is $C_8$ alkyl, $R^{6a}$ is $C_9$ alkyl and $R^{6a}$ is $C_{10}$ alkyl, $R^{6a}$ is $C_{10}$ alkyl and $R^{6a}$ is $C_9$ alkyl, $R^{6a}$ is $C_{10}$ alkyl and $R^{6a}$ is $C_{11}$ alkyl, $R^{6a}$ is $C_{11}$ alkyl and $R^{6a}$ is $C_{10}$ alkyl, $R^{6a}$ is $C_{11}$ alkyl and $R^{6a}$ is $C_{12}$ alkyl, $R^{6a}$ is $C_{12}$ alkyl and $R^{6a}$ is $C_{11}$ alkyl, $R^{6a}$ is $C_7$ alkyl and $R^{6a}$ is $C_9$ alkyl, $R^{6a}$ is $C_9$ alkyl and $R^{6a}$ is $C_7$ alkyl, $R^{6a}$ is $C_8$ alkyl and $R^{6a}$ is $C_{10}$ alkyl, $R^{6a}$ is $C_{10}$ alkyl and $R^{6a}$ is $C_8$ alkyl, $R^{6a}$ is $C_9$ alkyl and $R^{6a}$ is $C_{11}$ alkyl, $R^{6a}$ is $C_{11}$ alkyl and $R^{6a}$ is $C_9$ alkyl, $R^{6a}$ is $C_{10}$ alkyl and $R^{6a}$ is $C_{12}$ alkyl, $R^{6a}$ is $C_{12}$ alkyl and $R^{6a}$ is $C_{10}$ alkyl, etc.; and all other remaining variables are as described for Formula (E), Formula (E-1), Formula (E-2), Formula (E-3), Formula (E-4) or the second, fifth, seventh, ninth, tenth, eleventh or twelfth embodiments of Formula (E).

In a fourteenth embodiment, in the ionizable lipid, e.g., cationic lipid, according to Formula (E), Formula (E-1), Formula (E-2), Formula (E-3), Formula (E-4) or the second, fifth, seventh, ninth, tenth, eleventh, twelfth or thirteenth embodiments of Formula (E), R' is absent; and all other remaining variables are as described for Formula (E), Formula (E-1), Formula (E-2), Formula (E-3), Formula (E-4) or the second, fifth, seventh, ninth, tenth, eleventh, twelfth or thirteenth embodiments of Formula (E).

In one embodiment, the ionizable lipid, e.g., cationic lipid, in the LNPs of the present disclosure or the cationic lipid of Formula (E), Formula (E-1), Formula (E-2), Formula (E-3), Formula (E-4) is any one lipid selected from the lipids in Table 7 or a pharmaceutically acceptable salt thereof:

TABLE 7

| Exemplary lipids of Formula (E), Formula (E-1), Formula (E-2), Formula (E-3), Formula (E-4) | |
|---|---|
| Lipid No. | Lipid Structure and Name |
| 102 | 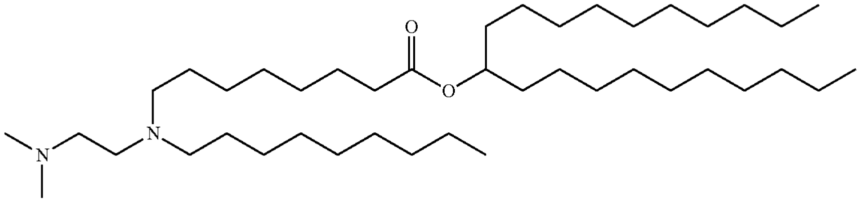 [SMILES: CCCCCCCCCCC(CCCCCCCCCC)OC(=O)CCCCCCCN(CCCCCCCCC)CCN(C)C] henicosan-11-yl 8-((2-(dimethylamino)ethyl)(nonyl)amino)octanoate |

TABLE 7-continued

Exemplary lipids of Formula (E), Formula (E-1), Formula (E-2), Formula (E-3), Formula (E-4)

| Lipid No. | Lipid Structure and Name |
|---|---|
| 103 | 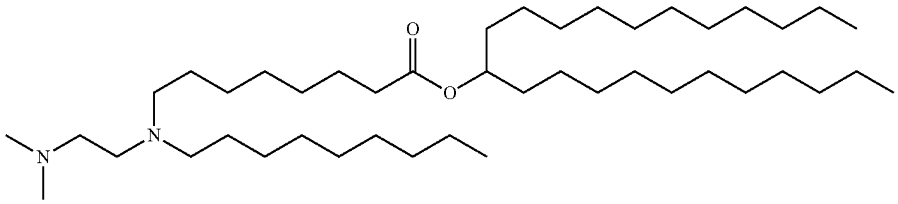 [SMILES: CCCCCCCCCCCC(CCCCCCCCCCC)OC(=O)CCCCCCCN(CCCCCCCCC)CCN(C)C] tricosan-12-yl 8-((2-(dimethylamino)ethyl)(nonyl)amino)octanoate |
| 104 | 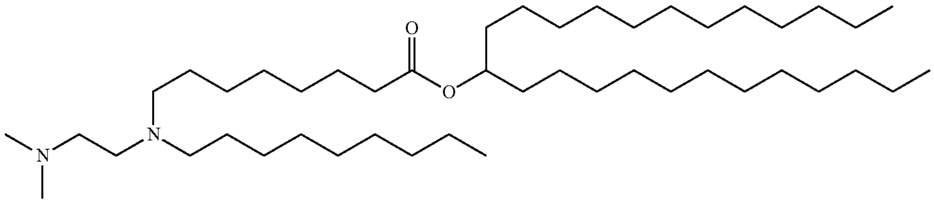 [SMILES: CCCCCCCCCCCCC(CCCCCCCCCCCC)OC(=O)CCCCCCCN(CCCCCCCCC)CCN(C)C] pentacosan-13-yl 8-((2-(dimethylamino)ethyl)(nonyl)amino)octanoate |
| 105 | 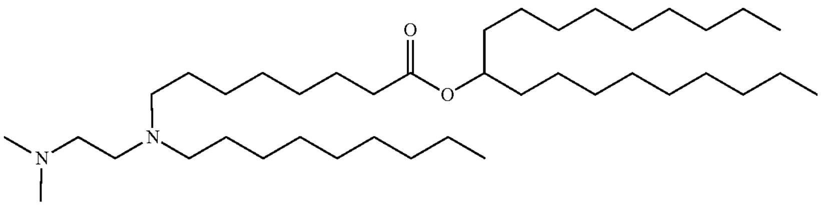 [SMILES: CCCCCCCCCC(CCCCCCCCC)OC(=O)CCCCCCCN(CCCCCCCCC)CCN(C)C] nonadecan-10-yl 8-((2-(dimethylamino)ethyl)(nonyl)amino)octanoate |
| 106 | 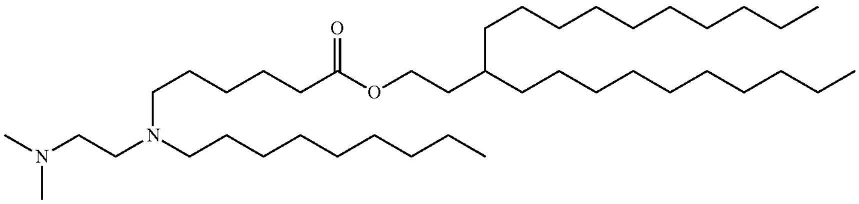 [SMILES: CCCCCCCCCCC(CCCCCCCCCC)CCOC(=O)CCCCCN(CCCCCCCCC)CCN(C)C] 3-decyltridecyl 6-((2-(dimethylamino)ethyl)(nonyl)amino)hexanoate |
| 107 | 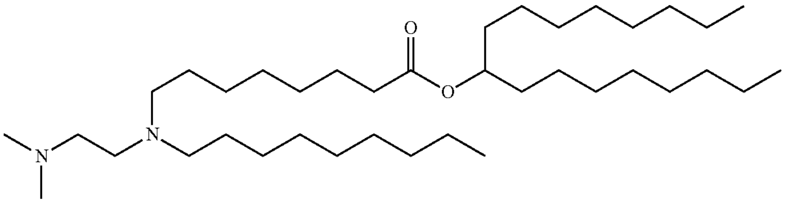 [SMILES: CCCCCCCCCN(CCCCCCCC(=O)OC(CCCCCCCC)CCCCCCCC)CCN(C)C] heptadecan-9-yl 8-((2-(dimethylamino)ethyl)(nonyl)amino)octanoate |
| 108 | 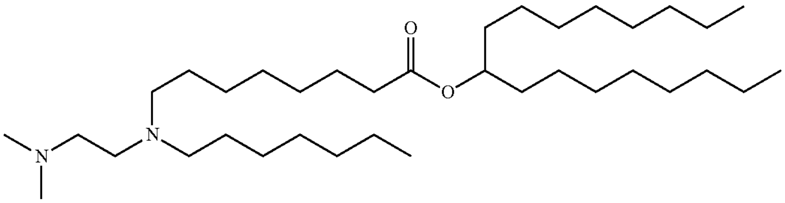 [SMILES: CCCCCCCCC(CCCCCCCC)OC(=O)CCCCCCCN(CCCCCCC)CCN(C)C] heptadecan-9-yl 8-((2-(dimethylamino)ethyl)(heptyl)amino)octanoate |

TABLE 7-continued

| Exemplary lipids of Formula (E), Formula (E-1), Formula (E-2), Formula (E-3), Formula (E-4) | |
|---|---|
| Lipid No. | Lipid Structure and Name |
| 109 | 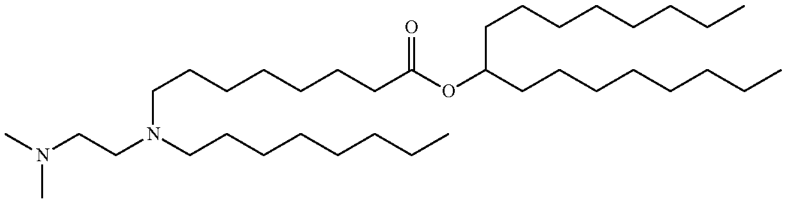 [SMILES: CCCCCCCCC(CCCCCCCC)OC(=O)CCCCCCCN(CCCCCCCC)CCN(C)C] heptadecan-9-yl 8-((2-(dimethylamino)ethyl)(octyl)amino)octanoate |
| 110 | 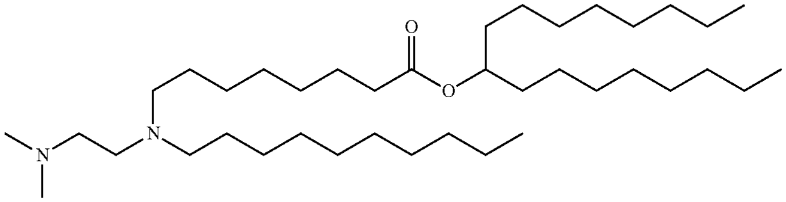 [SMILES: CCCCCCCCCCN(CCCCCCCC(=O)OC(CCCCCCCC)CCCCCCCC)CCN(C)C] heptadecan-9-yl 8-(decyl(2-(dimethylamino)ethyl)amino)octanoate |
| 111 | 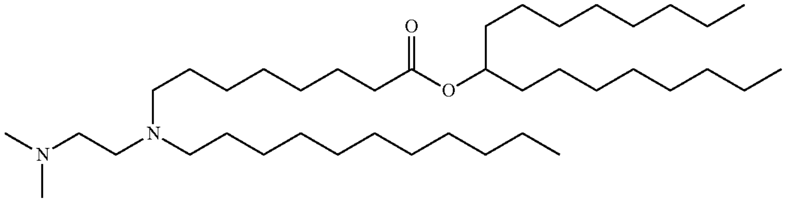 [SMILES: CCCCCCCCCCCN(CCCCCCCC(=O)OC(CCCCCCCC)CCCCCCCC)CCN(C)C] heptadecan-9-yl 8-((2-(dimethylamino)ethyl)(undecyl)amino)octanoate |
| 112 | 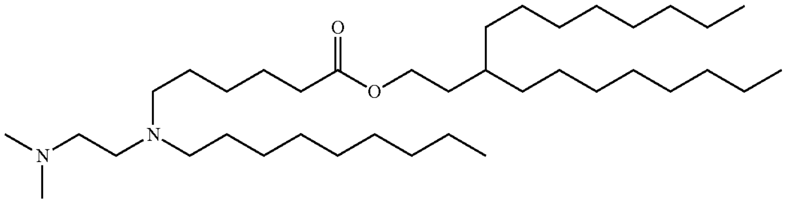 [SMILES: CCCCCCCCCN(CCCCCC(=O)OCCC(CCCCCCCC)CCCCCCCC)CCN(C)C] 3-octylundecyl 6-((2-(dimethylamino)ethyl)(nonyl)amino)hexanoate |

Specific examples are provided in the exemplification section below and are included as part of the cationic or ionizable lipids described herein. Pharmaceutically acceptable salts as well as neutral forms are also included.

Cleavable Lipids

In some embodiments, the LNPs provided by the present disclosure comprise an ionizable lipid that is also a cleavable lipid. As used herein, the term "cleavable lipid", which may be used interchangeably with the term "SS-cleavable lipid" refers to an ionizable lipid comprising a disulfide bond ("SS"). The SS in the cleavable lipid is a cleavable unit. In one embodiment, a cleavable lipid comprises an amine, e.g., a tertiary amine, and a disulfide bond. In this cleavable lipid, an amine can become protonated in an acidic compartment (e.g., an endosome or a lysosome), leading to LNP destabilization, and the cleavable lipid can become cleaved in a reductive environment (e.g., the cytoplasm). Cleavable lipids also include pH-activated lipid-like materials, such as ss-OP lipids, ssPalm lipids, ss-M lipids, ss-E lipids, ss-EC lipids, ss-LC lipids and ss-OC lipids, etc.

According to some embodiments, SS-cleavable lipids are described in International Patent Application Publication No. WO2019188867, incorporated by reference in its entirety herein.

In one embodiment, a cleavable lipid may comprise three components: an amine head group, a linker group, and a hydrophobic tail(s). In one embodiment, the cleavable lipid comprises one or more phenyl ester bonds, one of more tertiary amino groups, and a disulfide bond. The tertiary amine groups provide pH responsiveness and induce endosomal escape, the phenyl ester bonds enhance the degradability of the structure (self-degradability), and the disulfide bond becomes cleaved in a reductive environment.

In one embodiment, the cleavable lipid is an ss-OP lipid. In one embodiment, an ss-OP lipid comprises the structure of Lipid A shown below:

Lipid A

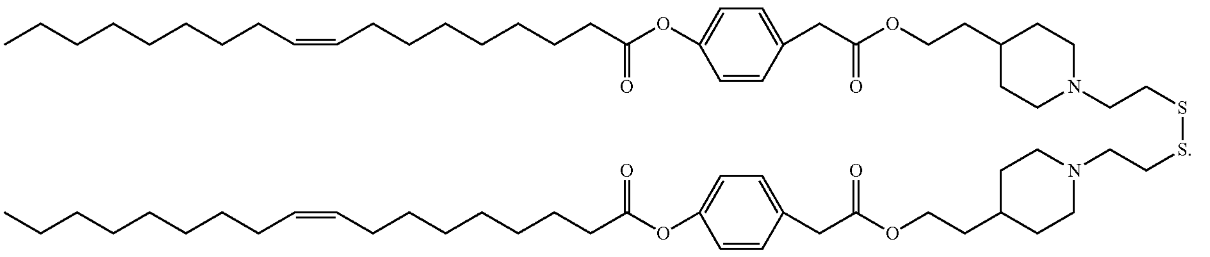

In one embodiment, the SS-cleavable lipid is an SS-cleavable and pH-activated lipid-like material (ssPalm). ssPalm lipids are well known in the art. For example, see Togashi et al., *Journal of Controlled Release,* 279 (2018) 262-270, the entire contents of which are incorporated herein by reference. In one embodiment, the ssPalm is an ssPalmM lipid comprising the structure of Lipid B shown below:

Lipid B

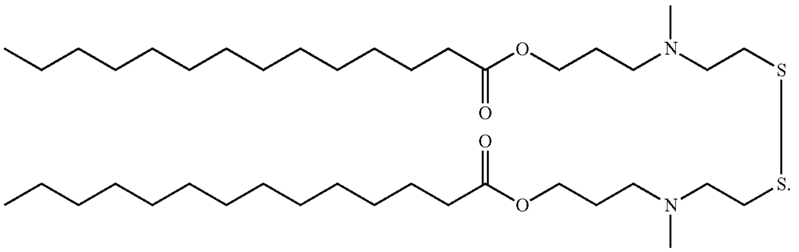

In one embodiment, the ssPalmE lipid is a ssPalmE-P4-$C_2$ lipid comprising the structure of Lipid C below:

Lipid C

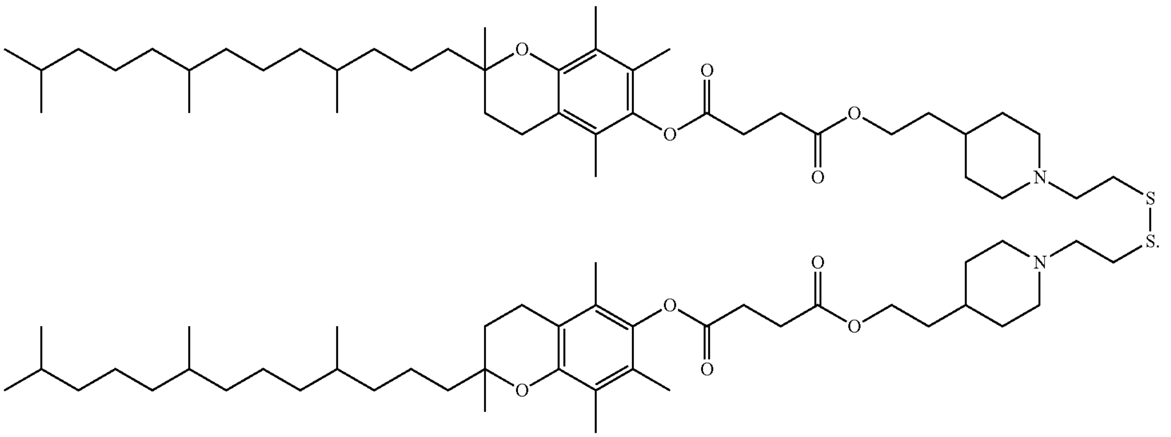

In one embodiment, the ssPalmE lipid is a ssPalmE-Paz4-$C_2$ lipid comprising the structure of Lipid D below:

Lipid D

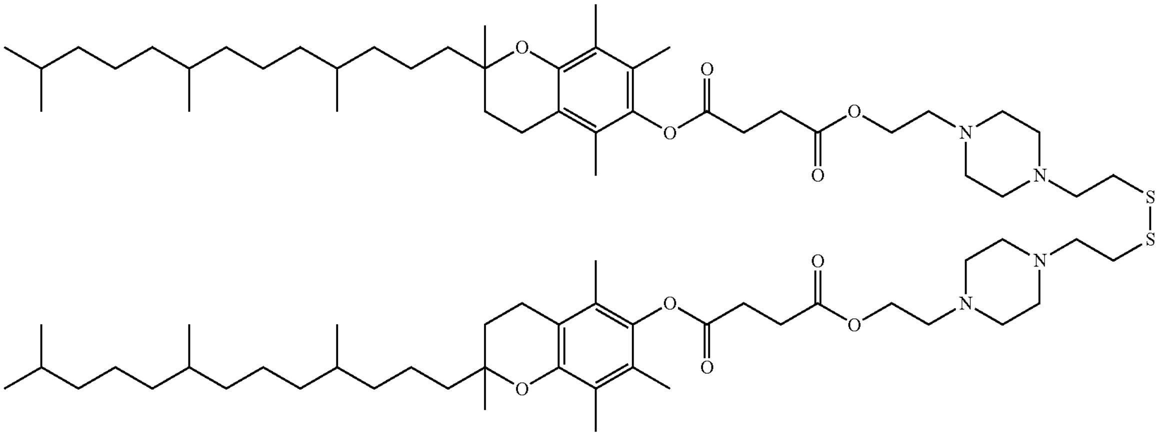

In one embodiment, the cleavable lipid is an ss-M lipid. In one embodiment, an ss-M lipid comprises the structure shown in Lipid E below:

Lipid E

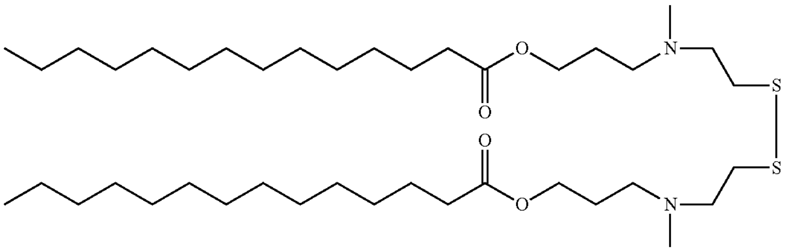

In one embodiment, the cleavable lipid is an ss-E lipid. In one embodiment, an ss-E lipid comprises the structure shown in Lipid F below:

Lipid F

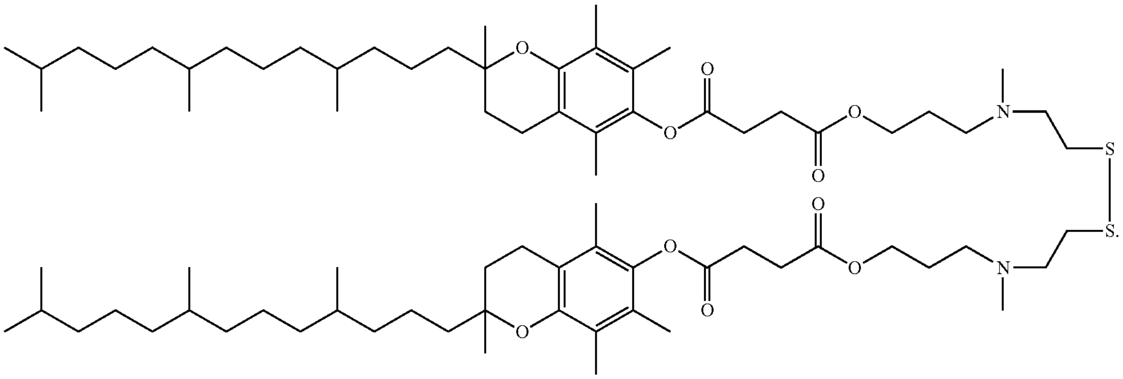

In one embodiment, the cleavable lipid is an ss-EC lipid. In one embodiment, an ss-EC lipid comprises the structure shown for Lipid G below:

Lipid G

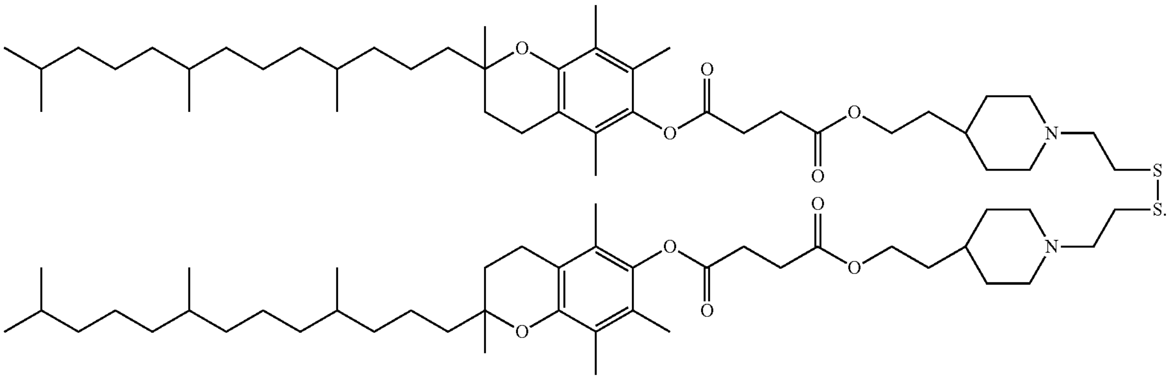

In one embodiment, the cleavable lipid is an ss-LC lipid. In one embodiment, an ss-LC lipid comprises the structure shown for Lipid H below:

Lipid H

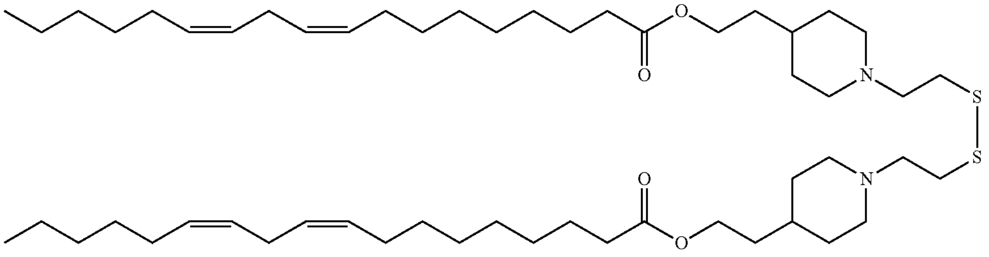

In one embodiment, the cleavable lipid is an ss-OC lipid. In one embodiment, an ss-OC lipid comprises the structure shown for Lipid J below:

Lipid J

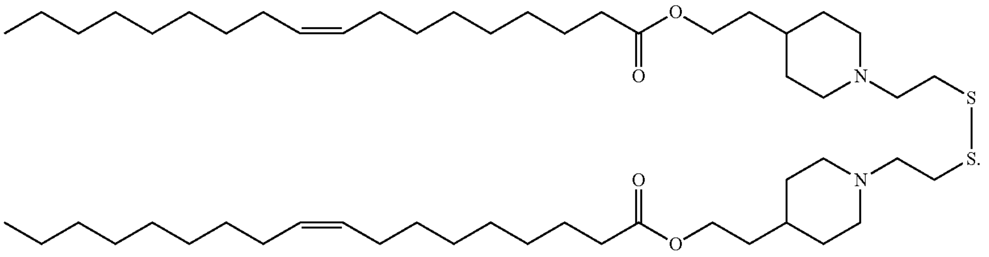

Other Lipids

In some embodiments, the ionizable lipid in the LNPs of the present disclosure is selected from the group consisting of N-[1-(2,3-dioleyloxy)propyl]-N,N,N-trimethylammonium chloride (DOTMA); N-[1-(2,3-dioleoyloxy)propyl]-N,N,N-trimethylammonium chloride (DOTAP); 1,2-dioleoyl-sn-glycero-3-ethylphosphocholine (DOEPC); 1,2-dilauroyl-sn-glycero-3-ethylphosphocholine (DLEPC); 1,2-dimyristoyl-sn-glycero-3-ethylphosphocholine (DMEPC); 1,2-dimyristoleoyl-sn-glycero-3-ethylphosphocholine (14:1), N1-[2-((1S)-1-[(3-aminopropyl)amino]-4-[di(3-amino-propyl) aminolbutylcarboxamidoiethyl]-3,4-di[oleyloxy]-benzamide (MVL5); Dioctadecylamido-glycylspermine (DOGS); 3b-[N—(N',N'-dimethylaminoethyl)carbamoyl] cholesterol (DC-Chol); Dioctadecyldimethylammonium Bromide (DDAB); a Saint lipid (e.g., SAINT-2, N-methyl-4-(dioleyl)methylpyridinium); 1,2-dimyristyloxypropyl-3-dimethylhydroxyethylammonium bromide (DMRIE); 1,2-dioleoyl-3-dimethyl-hydroxyethyl ammonium bromide (DORIE); 1,2-dioleoyloxypropyl-3-dimethylhydroxyethyl ammonium chloride (DORI); Di-alkylated Amino Acid (DILA2) (e.g., C18:1-norArg-C16); Dioleyldimethylammonium chloride (DODAC); 1-palmitoyl-2-oleoyl-sn-glycero-3-ethylphosphocholine (POEPC); and 1,2-dimyristoleoyl-sn-glycero-3-ethylphosphocholine (MOEPC). In some variations, the condensing agent, e.g. a cationic lipid, is a lipid such as, e.g., Dioctadecyldimethylammonium bromide (DDAB), 1,2-dilinoleyloxy-3-dimethylaminopropane (DLinDMA), 2,2-dilinoleyl-4-(2-dimethylaminoethyl)-[1,3]-dioxolane (DLin-KC2-DMA), heptatriaconta-6,9,28,31-tetraen-19-yl-4-(dimethylamino)butanoate (DLin-MC3-

DMA), 1,2-Dioleoyloxy-3-dimethylaminopropane (DODAP), 1,2-Dioleyloxy-3-dimethylaminopropane (DODMA), Morpholinocholesterol (Mo-CHOL), (R)-5-(dimethylamino)pentane-1,2-diyl dioleate hydrochloride (DODAPen-$C_1$), (R)-5-guanidinopentane-1,2-diyl dioleate hydrochloride (DOPen-G), and (R)-N,N,N-trimethyl-4,5-bis (oleoyloxy)pentan-1-aminium chloride (DOTAPen).

In some embodiments, the ionizable lipid in the LNP of the present disclosure is represented by the following structure:

(MC3)

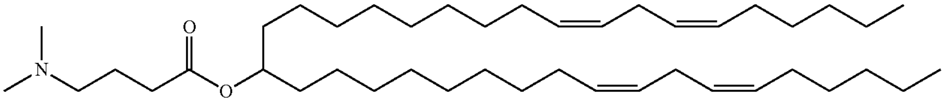

, (L319)

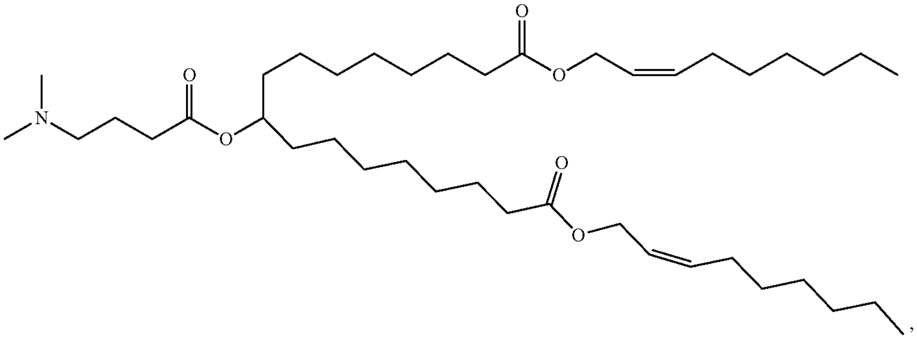

, (L369)

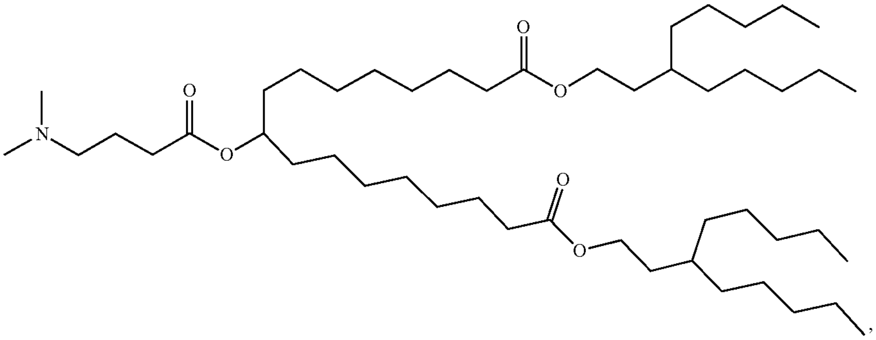

,

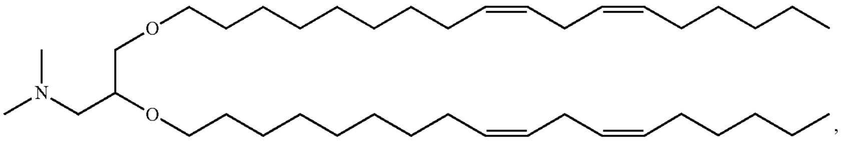

,

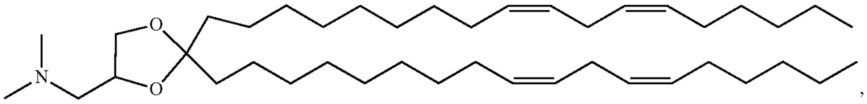

, (SM102)

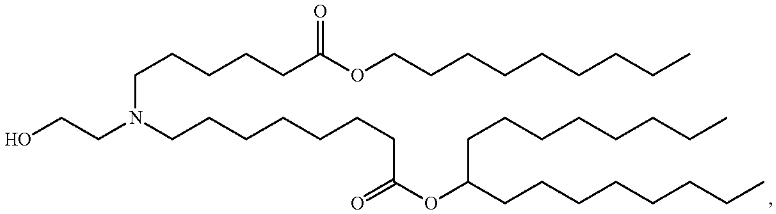

,

-continued

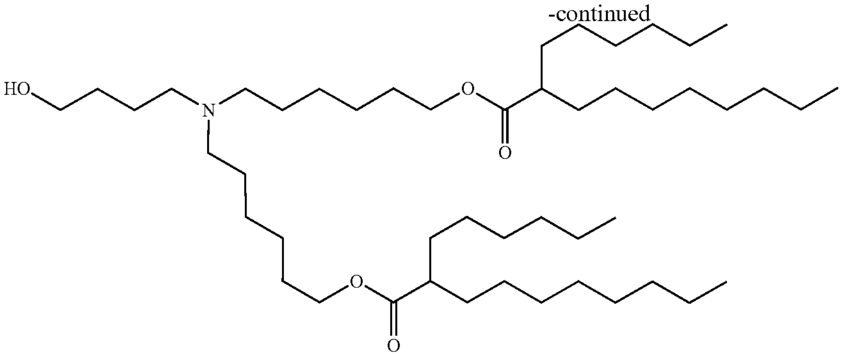

,

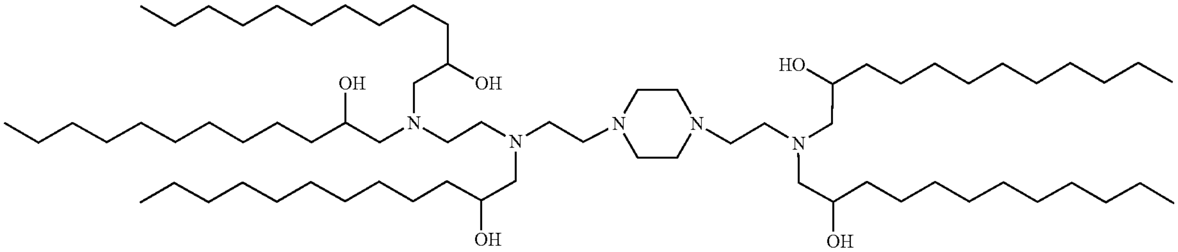

,

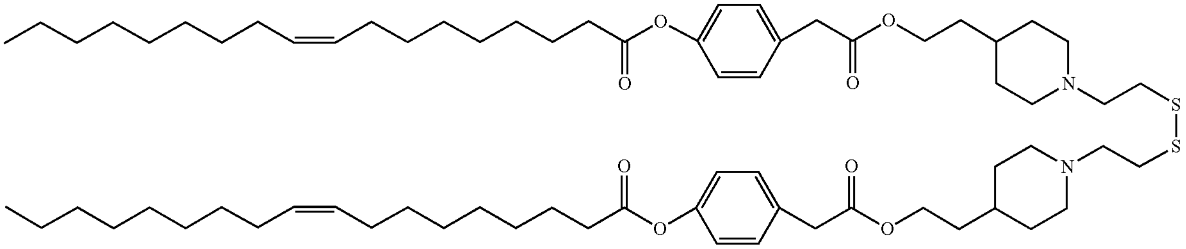

,

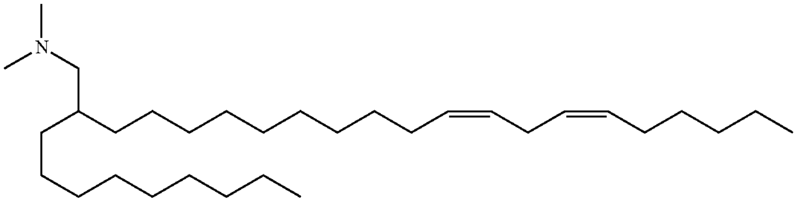

, or (LP01)

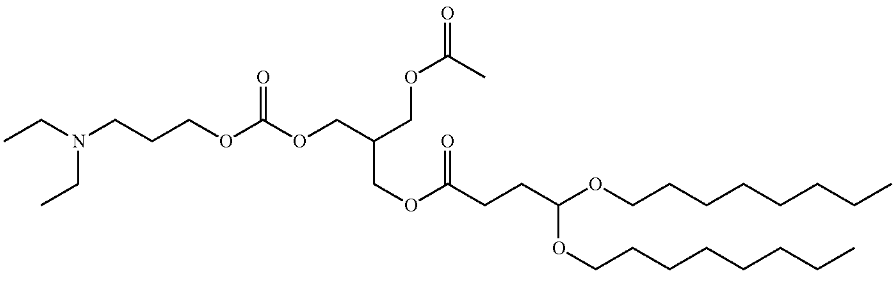

or a pharmaceutically acceptable salt or ester thereof, or a deuterated analogue thereof.

B. Structural Lipids, e.g., Sterols

In some embodiments, the LNPs provided by the present disclosure comprise a structural lipid. Without wishing to be bound by a specific theory, it is believed that a structural lipid, when present in an LNP, contributes to membrane integrity and stability of the LNP.

In some embodiments, the structural lipid is a sterol, e.g., cholesterol, or a derivative thereof. In one embodiment, the structural lipid is cholesterol. In another embodiment, the structural lipid is a derivative of cholesterol. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In some embodiments, the cholesterol derivative is a polar analogue such as cholesteryl-(4'-hydroxy)-butyl ether. In some embodiments, cholesterol derivative is cholestryl hemisuccinate (CHEMS).

Exemplary cholesterol derivatives are described in International Patent Application Publication No. WO2009/127060 and U.S. Patent Application Publication No. US2010/0130588, contents of both of which are incorporated herein by reference in their entirety.

In some embodiments, the sterol in the LNPs of the present disclosure is selected from the group consisting of cholesterol, beta-sitosterol, stigmasterol, beta-sitostanol, campesterol, brassicasterol, and derivatives thereof, and any combination thereof. In one embodiment, the sterol is cholesterol. In another embodiment, the sterol is beta-sitosterol.

In some embodiments, the structural lipid constitutes about 20 mol % to about 45 mol % of the total lipid present in the LNP. In some embodiments, the structural lipid constitutes about 25 mol % to about 45 mol % of the total lipid content of the LNP. In some embodiments, the structural lipid constitutes about 30 to about 45% of the total lipid present in the LNP. In some embodiments, the structural lipid constitutes about 30 mol % to about 40 mol % of the total lipid present in the LNP. In some embodiments, such a component is about 40 mol % of the total lipid present in the LNP. In some embodiments, the structural lipid, e.g., a sterol, constitutes about 20 mol % to about 45 mol % of the total lipid present in the LNP. In some embodiments, the structural lipid, e.g., a sterol, constitutes about 30 mol % to about 40 mol % of the total lipid present in the LNP. In some embodiments, the structural lipid, e.g., a sterol, constitutes about 35 mol % to about 40 mol % of the total lipid present in the LNP and the average LNP size is about 60 nm to about 80 nm in diameter.

In some embodiments, the structural lipid is cholesterol and constitutes about 30 mol % to about 45 mol % of the total lipid present in the LNP. In some embodiments, the structural lipid is cholesterol and constitutes about 35 mol % to about 45 mol % of the total lipid present in the LNP. In some embodiments, the structural lipid is cholesterol and constitutes about 40 mol % to about 45 mol % of the total lipid present in the LNP. In some embodiments, the structural lipid is cholesterol and constitutes about 40 mol % of the total lipid present in the LNP. In some embodiments, the structural lipid is cholesterol and constitutes about 45 mol % of the total lipid present in the LNP. In some embodiments, the structural lipid is cholesterol and constitutes about 40 mol % to about 45 mol % of the total lipid present in the LNP, wherein the encapsulation efficiency ("Enc. Eff.") of TNA is greater than 95% and/or the average size of the LNP ranges about 70 nm to 90 nm in diameter.

C. Helper Lipids

In some embodiments, the LNPs provided by the present disclosure do not comprise a helper lipid. In some embodiments, the LNPs provided by the present disclosure comprise a helper lipid.

In some embodiments, the helper lipid is DSPC, a salt or an ester thereof, or a deuterated analogue of any of the foregoing. In some embodiments, the helper lipid is DOPE, or a salt or an ester thereof, or a deuterated analogue of any of the foregoing. In some embodiments, the helper lipid is ceramide, a salt or an ester thereof, or a deuterated analogue of any of the foregoing.

As used herein, the term "salt" means a pharmaceutically acceptable salt of a helper lipid including both acid and base addition salts. A salt of a helper lipid retains the biological effectiveness and properties of the free acid forms or free base forms of the helper lipid.

As used herein, the term "ester" when referring to a helper lipid means an ester of a helper lipid. As a non-limiting example, a hydroxyl group of the helper lipid may be linked to an organic acid such as phosphoric acid or carboxylic acid via the process of esterification to form an ester (e.g., a carboxylate or a phosphate) of a helper lipid.

As used herein, a "deuterated analogue" when referring to a helper lipid means an analogue of a helper lipid where any one or more hydrogen atoms of the helper lipid are substituted with deuterium.

In some embodiments, an LNP of the present disclosure does not contain or comprise a helper lipid (e.g., distearoylphosphatidylcholine (DSPC), 1,2-dioleoyl-sn-glycero-3-phosphocholine (DOPC), or 1,2-dioleoyl-sn-glycero-3-phosphoethanolamine (DOPE).

In some embodiments, the helper lipid (e.g., ceramide of this disclosure constitutes about 2 mol % to about 40 mol % of the total lipid present in the LNP, or about 5 mol % to about 40 mol %, or about 5 mol % to about 35 mol %, or about 5 mol % to about 30 mol %, or about 5 mol % to about 25 mol %, or about 5 mol % to about 20 mol %, or about 5 mol % to about 15 mol %, or 10 mol % to about 40 mol %, or about 10 mol % to about 35 mol %, or about 10 mol % to about 30 mol %, or about 10 mol % to about 25 mol %, or about 10 mol % to about 20 mol %, or 15 mol % to about 40 mol %, or about 15 mol % to about 35 mol %, or about 15 mol % to about 30 mol %, or about 15 mol % to about 25 mol %, or about 15 mol % to about 20 mol %, or 20 mol % to about 40 mol %, or about 20 mol % to about 35 mol %, or about 20 mol % to about 30 mol %, or about 20 mol % to about 25 mol %, or 25 mol % to about 40 mol %, or about 25 mol % to about 35 mol %, or about 25 mol % to about 30 mol %, or 30 mol % to about 40 mol %, or about 30 mol % to about 35 mol %, or about 35 mol % to about 40 mol %, or about 5 mol %, or about 10 mol %, or about 15 mol %, or about 20%, or about 25 mol %, or about 30 mol %, or about 35 mol %, or about 40 mol %. In some embodiments, the helper lipid (e.g., DSPC, DOPE, ceramide, etc.) constitutes about 10% mol to about 20 mol % of the total lipid present in the LNP and such LNP having about 10% mol to about 20 mol % of the total lipid present in the LNP demonstrate overall increased tolerability (e.g., as demonstrated in body weight loss profiles in a subject and reduced cytokine response), as compared to the LNP comprising less than 10% of the same helper lipid.

D. Lipid-Anchored Polymers

In some embodiments, the LNPs provided by the present disclosure comprise at least one type of lipid-anchored polymer, e.g., a first lipid-anchored polymer. As used herein, the term "lipid-anchored polymer" refers to a molecule comprising a lipid moiety covalently attached to a polymer, e.g., via a linker. In other words, a lipid-anchored polymer may comprise a hydrophilic polymer and a lipid-linker. Without wishing to be bound by a specific theory, it is believed that a lipid-anchored polymer can inhibit aggregation of LNPs and provide steric stabilization and increase blood half-life ($t_{1/2}$) of LNP in vivo as disclosed herein. In some embodiments, the LNPs provided by the present disclosure comprise two lipid-anchored polymers, i.e., a first lipid-anchored polymer and a second lipid-anchored polymer.

Lipid Moieties in Lipid-Anchored Polymers

More specifically, in one embodiment, a lipid-anchored polymer, e.g., a first lipid-anchored polymer in accordance with the present disclosure comprises:

(i) a polymer;

(ii) a lipid moiety comprising at least one hydrophobic tail (which may be linear or branched); and (iii) optionally a linker connecting the polymer to the lipid moiety;

wherein the at least one hydrophobic tail (which may be linear or branched) comprises 18 to 22 carbon atoms in a single aliphatic chain backbone, e.g., 18, 19, 20, 21, or 22 carbon atoms in a single aliphatic chain backbone. In one embodiment, the lipid-anchored polymer, e.g., a first lipid-anchored polymer comprises a lipid moiety comprising a single or two hydrophobic tails, wherein the single or two hydrophobic tails each comprise 18 to 22 carbon atoms in a single aliphatic chain backbone, e.g., 18, 19, 20, 21, or 22 carbon atoms in a single aliphatic chain backbone.

The terms "lipid-linker," "linker-lipid", or "linker-lipid moiety," as used herein, refer to a lipid moiety comprising at least two hydrophobic tails, e.g., two hydrophobic tails, covalently attached to a linker. In some embodiments, the linker-lipid moiety may be a part of a lipid-anchored polymer.

In one embodiment, the at least one (e.g., single or two) hydrophobic tail is a fatty acid (saturated or unsaturated). Non-limiting examples of the at least one (e.g., single or two) hydrophobic tail comprising 18 to 22 carbon atoms in a single aliphatic chain backbone include lauric acid, octadecylamine, stearic acid, arachidic acid, sapienic acid, oleic acid, elaidic acid, vaccenic acid, linoleic acid, linoelaidic acid, α-linolenic acid, arachidonic acid, eicosapentaenoic acid, and a derivative thereof.

The term "derivative," when used herein in reference to hydrophobic tails in a lipid-anchored polymer, refers to a hydrophobic tail that has been modified as compared to the original or native hydrophobic tail. In some embodiments, the derivative contains one or more of the following modifications as compared to the original or native hydrophobic tail: a) carboxylate group has been replaced with an amine group, an amide group, an ether group, or a carbonate group; b) one or more points of saturation, e.g., double bonds, have been introduced into (e.g., via dehydrogenation) the hydrophobic tail; c) one or more points of saturation, e.g., double bonds, have been removed from (e.g., via hydrogenation) the hydrophobic tail; and d) configuration of one or more double bonds, if present, has been changed, e.g., from a cis configuration to a trans configuration, or from a trans configuration to a cis configuration. The derivative contains the same number of carbon atoms as its original or native hydrophobic tail.

As used herein the term "a single aliphatic chain backbone" when referring to a hydrophobic tail in a lipid-anchored polymer refers the main linear aliphatic chain or carbon chain, i.e., the longest continuous linear aliphatic chain or carbon chain. For example, the alkyl chain below that has several branching points contains 18 carbon atoms in a single aliphatic chain backbone, i.e., the longest continuous linear alkyl chain contains 18 carbon atoms. Note that the one or two carbon atoms (all indicated with *) in the several branching points are not included in the carbon atom count in the single aliphatic chain backbone.

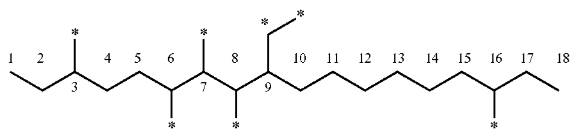 [SMILES: *CC(CCCCCCC(*)CC)C(*)C(*)C(*)CCC(*)CC]

In one embodiment, a lipid-anchored polymer or a first lipid-anchored polymer in accordance with the present disclosure comprises:

(i) a polymer;

(ii) a lipid moiety comprising at least two hydrophobic tails (which may be linear or branched); and (iii) optionally a linker connecting the polymer to the lipid moiety;

wherein the at least two hydrophobic tails (which may be linear or branched) comprise 18 to 22 carbon atoms in a single aliphatic chain backbone, e.g., 18, 19, 20, 21, or 22 carbon atoms in a single aliphatic chain backbone. In one embodiment, the lipid-anchored polymer or first lipid-anchored polymer comprises a lipid moiety comprising two hydrophobic tails, wherein the two hydrophobic tails each independently comprise 18 to 22 carbon atoms in a single aliphatic chain backbone, e.g., 18, 19, 20, 21, or 22 carbon atoms in a single aliphatic chain backbone. In one embodiment, the two hydrophobic tails each comprise 18 carbon atoms in a single aliphatic chain backbone. In one embodiment, the two hydrophobic tails each comprise 19 carbon atoms in a single aliphatic chain backbone. In one embodiment, the two hydrophobic tails each comprise 20 carbon atoms in a single aliphatic chain backbone.

In one embodiment, the at least two hydrophobic tails (e.g., two) are each a fatty acid. Non-limiting examples of the at least two hydrophobic tails comprising 18 to 22 carbon atoms in a single aliphatic chain backbone include octadecylamine, stearic acid, arachidic acid, sapienic acid, oleic acid, elaidic acid, vaccenic acid, linoleic acid, linoelaidic acid, α-linolenic acid, arachidonic acid, eicosapentaenoic acid, and a derivative thereof.

(i) Linkers in Lipid-Anchored Polymers

In some embodiments, in a lipid-anchored polymer of the present disclosure, a lipid moiety is covalently attached to a polymer optionally via a linker (the lipid moiety and/or the lipid moiety with the linker are collectively referred to as "lipid-linker" or "linker-lipid moiety" as used herein). In some embodiments, the linker in the lipid-anchored polymer of the present disclosure is a glycerol linker, a phosphate linker, an ether linker, an amide linker, an amine linker, a peptide linker, a phosphoethanolamine linker, a phosphocholine linker, or any combination thereof. In some embodiments, the linker in the lipid-anchored polymer in the LNPs of the present disclosure a glycerol linker. Accordingly, in some embodiments, the lipid-anchored polymer in the LNPs of the present disclosure is a glycerolipid, wherein the glycerolipid comprises glycerol as a linker and one or more two lipid moieties as described above, e.g., distearoyl-rac-glycerol (DSG).

In some embodiments, the linker in the lipid-anchored polymer in the LNPs of the present disclosure is a phosphate linker. Accordingly, in some embodiments, the lipid-anchored polymer in the LNPs of the present disclosure is a phospholipid, wherein the phospholipid comprises a phosphate group as a linker and one or more lipid moieties as described above.

In some embodiments, the lipid-anchored polymer in an LNP of the present disclosure is both a glycerolipid and a phospholipid, such as 1,2-distearoyl-sn-glycero-3-phosphoethanolamine (DSPE).

In another embodiment, the first lipid-anchored polymer is DSPE-polysarcosine (pSar) as shown below:

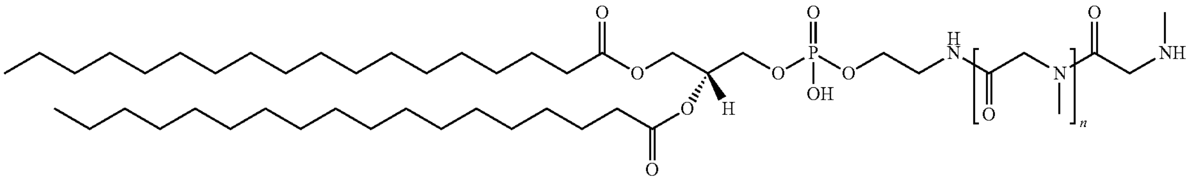

Polysarcosine is a polypeptoid-lipid conjugate based on the amino acid sarcosine (pSar). The pSar is an alternative hydrophilic polymer to PEG. The molecular weight of pSar varies with the varying lengths of the polymeric chain and may be useful in tuning physical properties of LNPs such as particle size, morphology and internal structure. Different sizes of pSar include pSar 20, pSar 25, pSar 45 and pSar 50 with molecular weights varying from 1800 to about 5,000 daltons.

In some embodiments, the first lipid-anchored polymer comprises a linker-lipid moiety (i.e., with one or more hydrophobic tails containing 18 to 22 carbon atoms in a single aliphatic chain) selected from the group consisting of 1,2-distearoyl-sn-glycero-3-phosphoethanolamine (DSPE), 1,2-dielaidoyl-sn-phosphatidylethanolamine (DEPE), 1-stearoyl-2-oleoyl-sn-glycero-3-phosphoethanolamine (SOPE), 1,2-dioleoyl-sn-glycero-3-phosphoglycerol (DOPG), 1,2-dielaidoyl-sn-glycero-3-phosphoethanolamine (18-1-trans PE), 1,2-dioleoyl-sn-glycero-3-phospho-L-serine (DOPS), dioctadecylamine (DODA), distearoyl-rac-glycerol (DSG), 1,2 dioleoyl-sn-glycero-3-phosphoethanolamine (DOPE), and combinations and derivatives thereof.

As used herein, the term "derivative" when used in reference to a linker-lipid moiety means a linker-lipid moiety containing one or more of the following modifications: a) a phosphatidylethanolamine (PE) head group, if present, is modified to convert an amino group into a methylamino group or a dimethylamino group; b) the modified linker-lipid moiety comprises one or more additional functional groups or moieties, such as —OH, —$OCH_3$, —$NH_2$, a maleimide, an azide or a cyclooctyne such as dibenzocyclooctyne (DBCO).

In one embodiment, the first lipid-anchored polymer comprises a linker-lipid moiety (i.e., with one or more hydrophobic tails containing 18 to 22 carbon atoms in a single aliphatic chain) selected from the group consisting of DSPE, DEPE, SOPE, DOPG, 18-1-trans PE, DOPS, DSG, DODA, DOPE, a derivative thereof, and a combination of any of the foregoing.

(ii) Polymers in Lipid-Anchored Polymers

In some embodiments, the polymer comprised in the lipid-anchored polymer is a hydrophilic polymer. In some embodiments, the polymer is selected from the group consisting of polyethylene (PE), polypropylene (PP), polyethylene glycol (PEG), polyglycerol (PG), polyvinyl alcohol (PVOH), polysarcosine (pSar), and a combination thereof. In one embodiment, the polymer is selected from the group consisting of polyethylene glycol (PEG), polyglycerol (PG), polysarcosine (pSar), poly(2-methacryloyloxyethyl phosphorylcholine) (PMPC), and a combination thereof. In one embodiment, the polymer is polyethylene glycol (PEG).

In one embodiment, the polymer is polyethylene glycol (PEG) or PEG derivative. In another embodiment, the polymer is polyglycerol (PG) or PG derivative. In yet another embodiment, the polymer is polysarcosine (pSar). In yet another embodiment, the polymer is poly(2-methacryloyloxyethyl phosphorylcholine) (PMPC).

In some embodiments, the polymer in the lipid-anchored polymer has a molecular weight of about 5000 Da or less, e.g., about 4500 Da or less, about 4000 Da or less, about 3500 Da or less, about 3200 Da or less, about 3000 Da or less, about 2500 Da or less, about 2000 Da or less, about 1500 Da or less, about 1000 Da or less, about 500 Da or less, about 100 Da or less or about 50 Da or less. In some embodiments, the polymer in the lipid-anchored polymer has an average molecular weight of about 20 Da to about 100 Da, about 50 Da to about 500 Da, about 500 Da to about 2000 Da, about 1000 Da to about 5000 Da, e.g., about 2000 Da to about 5000 Da, about 1000 Da to about 3000 Da, about 1500 Da to about 2500 Da, about 2000 Da to about 4000 Da or about 2000 Da to about 5000 Da. In some embodiments, the polymer in the lipid-anchored polymer has an average molecular weight of about 1000 Da, about 1500 Da, about 2000 Da, about 2500 Da, about 3000 Da, about 3200 Da, about 3300 Da, about 3350 Da, about 3400 Da, about 3500 Da, about 4000 Da, about 4500 Da or about 5000 Da. In some embodiments, the polymer in the lipid-anchored polymer has an average molecular weight of about 2000 Da. In some embodiments, the polymer in the lipid-anchored polymer has an average molecular weight of about 2000 Da. In some embodiments, the polymer in the lipid-anchored polymer has an average molecular weight of about 3200 Da to about 3500 Da. In some embodiments, the polymer in the lipid-anchored polymer has an average molecular weight of about 3300 Da. In some embodiments, the polymer in the lipid-anchored polymer has an average molecular weight of about 3350 Da. In some embodiments, the polymer in the lipid-anchored polymer has an average molecular weight of about 3400 Da. In some embodiments, the polymer in the lipid-anchored polymer has an average molecular weight of about 3500 Da.

(iii) Ratio of Molecular Weights of Lipophilic Polymers Between the First and Second Lipid-Anchored Polymers In certain embodiments it is advantageous for the second lipid-anchored when conjugated to a targeting moiety such as an antibody or other binding moiety to project above the surface of the LNP as represented by the outer reach of the first lipid anchor polymer. Extending the reach of the targeting moiety prevents any steric interference between the targeting moiety conjugated to the second lipid polymer and the hydrophilic polymer of the first lipid-anchored polymer. Comparing the molecular weights of the two hydrophilic polymers is a convenient way to make sure the functions of the two lipid-anchored polymers do not interfere with one another. In one embodiment the molecular weight of the hydrophilic polymer attached to the second lipid-anchored polymer is greater than the molecular weight of the hydrophilic polymer attached to the first lipid-anchored polymer.

In another embodiment the molecular weight of the hydrophilic polymer attached to the second lipid-anchored polymer is at least 10% greater to 200% greater than the molecular weight of the hydrophilic polymer attached to the first lipid-anchored polymer. In another embodiment the molecular weight of the hydrophilic polymer attached to the second lipid-anchored polymer is at least 10% greater to 150% greater than the molecular weight of the hydrophilic polymer attached to the first lipid-anchored polymer. In another embodiment the molecular weight of the hydrophilic polymer attached to the second lipid-anchored polymer is at least 10% greater to 100% greater than the molecular weight of the hydrophilic polymer attached to the first lipid-anchored polymer. In another embodiment the molecular weight of the hydrophilic polymer attached to the second lipid-anchored polymer is at least 10% greater to 80% greater than the molecular weight of the hydrophilic polymer attached to the first lipid-anchored polymer. In another embodiment the molecular weight of the hydrophilic polymer attached to the second lipid-anchored polymer is at least 10% greater to 70% greater than the molecular weight of the hydrophilic polymer attached to the first lipid-anchored polymer.

In another embodiment the molecular weight of the hydrophilic polymer attached to the second lipid-anchored polymer is at least 10% greater than the molecular weight of the hydrophilic polymer attached to the first lipid-anchored polymer. In another embodiment the molecular weight of the hydrophilic polymer attached to the second lipid-anchored polymer is at least 15% greater than the molecular weight of the hydrophilic polymer attached to the first lipid-anchored polymer. In another embodiment the molecular weight of the hydrophilic polymer attached to the second lipid-anchored polymer is at least 20% greater than the molecular weight of the hydrophilic polymer attached to the first lipid-anchored polymer. In another embodiment the molecular weight of the hydrophilic polymer attached to the second lipid-anchored polymer is at least 25% greater than the molecular weight of the hydrophilic polymer attached to the first lipid-anchored polymer. In another embodiment the molecular weight of the hydrophilic polymer attached to the second lipid-anchored polymer is at least 30% greater than the molecular weight of the hydrophilic polymer attached to the first lipid-anchored polymer. In another embodiment the molecular weight of the hydrophilic polymer attached to the second lipid-anchored polymer is at least 35% greater than the molecular weight of the hydrophilic polymer attached to the first lipid-anchored polymer. In another embodiment the molecular weight of the hydrophilic polymer attached to the second lipid-anchored polymer is at least 40% greater than the molecular weight of the hydrophilic polymer attached to the first lipid-anchored polymer. In another embodiment the molecular weight of the hydrophilic polymer attached to the second lipid-anchored polymer is at least 45% greater than the molecular weight of the hydrophilic polymer attached to the first lipid-anchored polymer. In another embodiment the molecular weight of the hydrophilic polymer attached to the second lipid-anchored polymer is at least 50% greater than the molecular weight of the hydrophilic polymer attached to the first lipid-anchored polymer. In another embodiment the molecular weight of the hydrophilic polymer attached to the second lipid-anchored polymer is at least 55% greater than the molecular weight of the hydrophilic polymer attached to the first lipid-anchored polymer. In another embodiment the molecular weight of the hydrophilic polymer attached to the second lipid-anchored polymer is at least 60% greater than the molecular weight of the hydrophilic polymer attached to the first lipid-anchored polymer. In one embodiment the molecular weight of the hydrophilic polymer attached to the second lipid-anchored polymer is at least 70% greater than the molecular weight of the hydrophilic polymer attached to the first lipid-anchored polymer. In another embodiment the molecular weight of the hydrophilic polymer attached to the second lipid-anchored polymer is at least 70%, at least 80%, at least 90%, at least 100%, at least 110%, at least 120%, at least 130%, at least 140%, at least 150%, at least 160%, at least 170%, at least 180%, at least 190%, or at least 200%, greater than the molecular weight of the hydrophilic polymer attached to the first lipid-anchored polymer. It is understandable that there may be certain targeting moieties with less sensitivity to the steric qualities of the first lipid polymer and therefore in some circumstances the molecular weight of the hydrophilic polymer attached to the second lipid-anchored polymer is at least 20% or at least 30% or at least 40% greater than the molecular weight of the hydrophilic polymer attached to the first lipid-anchored polymer.

(iv) Targeting Moiety and Second Lipid-Anchored Polymer

In some embodiments, an LNP of the present disclosure further comprises one or more targeting moieties. The targeting moiety targets the LNP for delivery to a specific cell type or a tissue in a subject, e.g., liver, bone marrow, spleen, blood, etc. In some embodiments, the targeting moiety is capable of binding to specific cell types e.g., hepatocytes, T-cells, B cells, NK cells, dendritic cells, or CD34+ cells (e.g., hematopoietic stem cells (HSCs), hematopoietic progenitor cells (HSPC)), etc. In some embodiments, the one or more targeting moieties are conjugated to a second lipid-anchored polymer. In some embodiments, the one or more targeting moieties conjugated to the second lipid-anchored polymer can be an antibody, or an antigen-binding fragment thereof.

The antibodies may be intact monoclonal or polyclonal antibodies, and immunologically active fragments (e.g., a Fab or $(Fab)_2$ fragment), an antibody heavy chain, an antibody light chain, humanized antibodies, a genetically engineered single chain Fv (scFv) molecule, or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art. In one embodiment the targeting moiety is an antibody or an antibody fragment, e.g., an antibody or an antibody fragment that is capable of specifically binding to an antigen present on the surface of a cell. In one embodiment the antibody or an antibody fragment is a monoclonal antibody (mAb), a single chain variable fragment (scFv), a heavy chain antibody (hcAb), a nanobody (Nb), a heavy-chain-only immunoglobulin (HCIg), an immunoglobulin new antigen receptor (IgNAR), variable domain of immunoglobulin new antigen receptor (VNAR), a single-domain antibody, or a variable heavy chain-only antibody (VHH). In one embodiment, the antibody target moiety is scFv. In another embodiment, the antibody targeting moiety is IgG. In yet another embodiment, the antibody targeting moiety is VHH (e.g., nanobody). In some embodiments, the targeting moiety is an antibody directed to an epitope present on a target cell. In some embodiments, the target cell is selected from the group consisting of T cell, B cell, NK cell, dendritic cell, hematopoietic stem cell, neuronal cell, and hepatocyte. In some embodiments, the target cell is the T cell. In some embodiments, the antibody targeting moiety binds an epitope of T cell receptor (TCR), CD3, CD4, CD5, CD6, CD7, CD8, CD9, CD10, CD11, CD19, CD21, CD28, or PD-1.

In some embodiments, it may be advantageous to have more than one targeting moiety conjugated to different subpopulations of the second lipid-anchored polymer. In this way two or more different targeting moieties such as antibodies or antibody derivatives could be conjugated to portions of the second lipid-anchored polymer. This would confer more than one binding specificity to the stealth LNP or provide a form of bispecific binding character to the stealth LNP. Having more than one binding specificity could also increase cell binding through the avidity effect of two or more binding specificities. Alternatively, bispecific antibodies could be used directly and conjugated to the second lipid-anchored polymer. Where two or more targeting moieties are used, they could be conjugated in a mixed reaction containing both targeting moieties or the two targeting moieties could be conjugated separately in two or more conjugation reactions and mixed together at some desired proportion of antibody 1 to antibody 2 or however many targeting moieties are desired, Increasing the valency of an antibody is of interest as it enhances the functional affinity of that antibody due to the avidity effect. In some embodiments the targeting moiety is a bispecific antibody or diabody or other bispecific format available to combine two different antibody binding domains into a single fusion protein. Multiple dual antibody formats are known in the art such as DVD-Ig, CODV-Ig. See U.S. Pat. Nos. 9,221,917 and 11,179,934.

Genetic engineering has been used with increasing frequency to design, modify, and produce antibodies or antibody derivatives with a desired set of binding properties and effector functions. A variety of recombinant methods have been developed for efficient production of BsAbs, both as antibody fragments (Carter et al., 1995, J. Hematother. 4(5): 463-70; Pluckthum et al., 1997. *Immunotechnology* 3(2): 83-105; Todorovska et al., 2001, *J. Immunol. Methods* 248(1-2): 47-66) and full-length IgG formats (Carter, 2001, *J. Immunol. Methods* 2481-2): 7-15).

Combining two different scFvs results in BsAb formats with minimal molecular mass, termed sc-BsAbs or Ta-scFvs (Mack et al. 1995. *Proc. Natl. Acad. Sci. U.S.A*, 92(15): 7021-25; Mallender et al., 1994, *J. Boil. Chem.* 269(1): 199-206). BsAbs have been constructed by genetically fusing two scFvs to a dimerization functionality such as a leucine zipper (Kostelny et al. 1992, *J Immunol.* 148(5): 1547-53; de Kruif #et al., 1996. *J Biol. Chem.* 271(13): 7630-34).

Diabodies are small bivalent and bispecific antibody fragments. The fragments comprise a $V_H$ connected to a $V_L$ on the same polypeptide chain, by using a linker that is too short (less than 12 amino acid residues) to allow pairing between the two domains on the same chain. The domains are forced to pair intermolecularly with the complementary domains of another chain and create two antigen-binding sites. These dimeric antibody fragments, or "diabodies" are bivalent and bispecific (Holliger et al., 1993, *Proc. Natl. Acad. Sci, U.S.A.* 90(14): 6444-48). Diabodies are similar in size to a Fab fragment. Polypeptide chains of $V_H$ and $V_L$ domains joined with a linker of between 3 and 12 amino acid residues form predominantly dimers (diabodies), whereas with a linker of between 0 and 2 amino acid residues, trimers (triabodies) and tetramers (tetrabodies) predominate. In addition to the linker length, the exact pattern of oligomerization seems to depend on the composition as well as the orientation of the variable domains (Hudson et al., 1999, *J. Immunol. Methods* 231(1-2): 177-89).

Although sc-BsAb and diabody-based constructs display interesting clinical potential, it was shown that such non-covalently associated molecules are not sufficiently stable under physiological conditions. The overall stability of a scFv fragment depends on the intrinsic stability of the VL and VH domain as well as on the stability of the domain interface. Insufficient stability of the VH-VL interface of scFv fragments has often been suggested as a main cause of irreversible scFv inactivation, since transient opening of the interface, which would be allowed by the peptide linker, exposes hydrophobic patches that favor aggregation and therefore instability and poor production yield (Worn et al., 2001, J. Mol. Biol. 305(5): 989-1010).

In some other embodiments, the targeting moiety is a ligand (e.g., oligosaccharides) capable of binding to a receptor present on a target cell. In one embodiment, the targeting moiety is capable of binding to the asialoglycoprotein receptor (ASGPR), i.e., hepatocyte-specific ASGPR. In one embodiment, the targeting moiety comprises an N-acetylgalactosamine molecule (GalNAc) or a GalNAc derivative thereof. As used herein, a "GalNAc derivative" refers to a modified GalNAc molecule or a conjugate of one or more GalNAc molecules (modified or unmodified) covalently linked to, for example, a lipid-anchored polymer as defined herein. In one embodiment, the targeting moiety is a tri-antennary or tri-valent GalNAc conjugate (i.e., GalNAc3) which is a ligand conjugate having three GalNAc molecules or three GalNAc derivatives. In one embodiment, the targeting moiety is a tri-antennary GalNAc represented by the following structural formula:

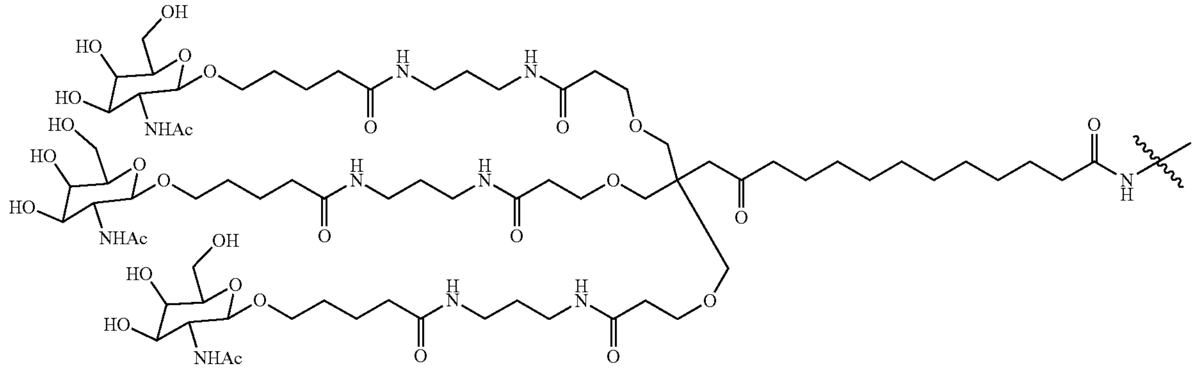 [SMILES: *NC(=O)CCCCCCCCCCC(=O)CC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

In one embodiment, the targeting moiety is a tetra-antennary GalNAc conjugate. In one embodiment, the targeting moiety is a tetra-antennary or tetra-valent GalNAc conjugate (i.e., GalNAc4) which is a ligand having four GalNAc molecules or four GalNAc derivatives.

In some other embodiments, the targeting moiety is a protein or peptide ligand of a receptor present on a target cell. In one embodiment, the targeting moiety is capable of binding to low-density lipoprotein receptors (LDLRs), e.g., hepatocyte-specific LDLRs. In one embodiment, the targeting moiety comprises an apoliprotein E (ApoE) protein, an ApoE polypeptide (or peptide), an apoliprotein B (ApoB) protein, an ApoB polypeptide (or peptide), a fragment of any of the foregoing, or a derivative of any of the foregoing. In one embodiment, the ApoE polypeptide, ApoB polypeptide, or a fragment thereof is a ApoE polypeptide, ApoB polypeptide, or a fragment thereof as disclosed in International Patent Application Publication No. WO2022/261101, which is incorporated herein by reference in its entirety. In one embodiment, the ApoE protein is a modified ApoE protein and the ApoB protein is a modified ApoB protein. In one embodiment, the ApoE protein has an amino acid sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98, or at least about 99% sequence identity to the following amino acid sequence: MKVEQAVETEPEPELRQQTEWQSGQRWELAL-GRFWDYLRWVQTLSEQVQEELLSSQVTQE LRALM-DETMKELKAYKSELEEQLTPVAEETRARLSKEL-QAAQARLGADMEDVCGRLVQYR GEVQAML-GQSTEELRVRLASHLRKLRKRLLRDADDLQKR-LAVYQAGAREGAERGLSAIRER LGPLVEQGRVR (SEQ ID NO: 1). In one embodiment, the ApoE protein comprises, or consists of, the amino acid sequence set forth in SEQ ID NO: 1. In one embodiment, the ApoE protein has an amino acid sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98, or at least about 99% sequence identity to the following amino acid sequence: MKVEQAVETEPEPELRQQTEWQSGQR-WELALGRFWDYLRWVQTLSEQVQEELLSSQVTQE LRALMDETMKELKAYKSELEEQLTPVAEETRARL-SKELQAAQARLGADMEDVCGRLVQYR GEVQA-MLGQSTEELRVRLASHLRKLRKRLLRDADDLQKR-LAVYQAGAREGAERGLSAIRER LGPLVEQGRV-RHHHHHH (SEQ ID NO: 2). In one embodiment, the ApoE protein comprises the amino acid sequence set forth in SEQ ID NO: 2. In one embodiment, the ApoE protein consists of the amino acid sequence set forth in SEQ ID NO: 2. In one embodiment, the ApoE protein has an amino acid sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98, or at least about 99% sequence identity to the following amino acid sequence: MKVEQAVETEPEPELRQQTEWQSGQRWELAL-GRFWDYLRWVQTLSEQVQEELLSSQVTQE LRALM-DETMKELKAYKSELEEQLTPVAEETRARLSKEL-QAAQARLGADMEDVSGRLVQYR GEVQAMLGQ-STEELRVRLASHLRKLRKRLLRDADDLQKRLAVY-QAGAREGAERGLSAIRER LGPLVEQGRVR (SEQ ID NO: 3). In one embodiment, the ApoE protein comprises, or consists of, the amino acid sequence set forth in SEQ ID NO: 3. In one embodiment, the ApoE protein has an amino acid sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98, or at least about 99% sequence identity to the following amino acid sequence: MKVEQAVETEPEPELRQQTEWQSGQRWELAL-GRFWDYLRWVQTLSEQVQEELLSSQVTQE LRALM-DETMKELKAYKSELEEQLTPVAEETRARLSKEL-QAAQARLGADMEDVSGRLVQYR GEVQAMLG-QSTEELRVRLASHLRKLRKRLLRDADDLQKR-LAVYQAGAREGAERGLSAIRER LGPLVEQGRV-RHHHHHHGGSSGSGC (SEQ ID NO: 4). In one embodiment, the ApoE protein comprises the amino acid sequence set forth in SEQ ID NO: 4. In one embodiment, the ApoE protein consists of the amino acid sequence set forth in SEQ ID NO: 4.

In some other embodiments, the targeting moiety is a scFv or VHH antibody fragment.

In one embodiment, the targeting moiety is an scFv that recognizes and binds to CD117. One scFv example includes L80-CD117. The full scFv-FLAG is tagged with an extra c-terminal cys residue, the L80-CD117 VH polypeptide sequence is as follows:

```
                                             (SEQ ID NO: 11)
QVQLKQSGAELVRPGASVKLSCKASGYTFTDYYINWVKQRPGQGLEWIA

RIYPGSGNTYYNEKFKGKATLTAEKSSSTAYMQLSSLTSEDSAVYFCAR

GVYYFDYWGQGTTLTVSS
```

The L80-CD117 VL polypeptide sequence is as follows:

```
                                             (SEQ ID NO: 12)
DIVMTQSQKFMSTSVGDRVSVTCKASQNVRTNVAWYQQKPGQSPKALIY

SASYRYSGVPDRFTGSGSGTDFTLTISNVQSEDLADYFCQQYNSYPRTF

GGGTKLEIKR
```

In one embodiment, the targeting moiety is an scFv. One example includes L95-CD117. The full L95-CD117 scFv-FLAG is tagged with an extra c-terminal cys residue, the full scFv polypeptide sequence is as follows:

```
                                             (SEQ ID NO: 13)
QVQLVQSGAEVKKPGSSVKVSCKASGGTFSSYAISWVRQAPGQGLEWMG

GIIPMSGRTTYAQKFQGRVTITADESTSTAYMELSSLRSEDTAVYYCAR

DYGPEAPDYGQSTSYFWYYAFDPWGQGTLVTVSSGGGGSGGGGSGGGGS

GGGGDIELTQPPSVSVSPGQTASITCSGDNIPSYFVHWYQQKPGQAPVL

VIYDDNDRPSGIPERFSGSNSGNTATLTISGTQAEDEADYYCSSWDQDT

VVFGGGTKLTVLGGGGSGGGGSDYKDDDDKGGGGSC
```

The L95-CD117 VH polypeptide sequence only is shown below:

(SEQ ID NO: 14)
QVQLVQSGAEVKKPGSSVKVSCKASGGTFSSYAISWVRQAPGQGLEWMG

GIIPMSGRTTYAQKFQGRVTITADESTSTAYMELSSLRSEDTAVYYCAR

DYGPEAPDYGQSTSYFWYYAFDPWGQGTLVTVSS

The L95-CD117 VL polypeptide sequence only is as follows:

(SEQ ID NO: 15)
DIELTQPPSVSVSPGQTASITCSGDNIPSYFVHWYQQKPGQAPVLVIYD

DNDRPSGIPERFSGSNSGNTATLTISGTQAEDEADYYCSSWDQDTVVFG

GGTKLTVL

In some embodiments, the sequences of CD45 ligands were identified that showed lower affinity binding (Kd>10 nM) but surprisingly good LNP delivery in primary HSPCs post-conjugation. In one embodiment the targeting moieties are antibodies modified to scFv fragments that recognize and bind CD45. In one embodiment, the CD45 scFv is known as L111-CD45 and has the following polypeptide sequences in the full scFv and separately in the VH and VL.

The full L111-CD45 scFv-FLAG, tagged with an extra c-terminal cys residue, polypeptide sequence is as follows:

(SEQ ID NO: 16)
DIQMTQSPSFLSASVGDRVTINCKASQNINKYLDWYQQKHGEAPKLLIH

YTNNLHTGIPSRFSGSGSGTDYTLTISSLQPEDVATYFCLQHSSRWTFG

GGTKLELKGGGGSGGGGSGGGGSGGGGEVQLVESGGDLVQPGRSLKLSC

IASGFTFTNFWMTWIRQVSGKGLEWVASISSSGGSIYYPDSVKDRFTIS

RDNAKNTLYLQMNSLRSEDTATYYCVKLHYYSGGGDAWGQGTSVTVSSG

GGGSGGGGSDYKDDDDKGGGGSC

The L111-CD45 VH polypeptide sequence only is as follows:

(SEQ ID NO: 17)
EVQLVESGGDLVQPGRSLKLSCIASGFTFTNFWMTWIRQVSGKGLEWVA

SISSSGGSIYYPDSVKDRFTISRDNAKNTLYLQMNSLRSEDTATYYCVK

LHYYSGGGDAWGQGTSVTVSS

L111-CD45 VL polypeptide sequence only is as follows:

(SEQ ID NO: 18)
DIQMTQSPSFLSASVGDRVTINCKASQNINKYLDWYQQKHGEAPKLLIH

YTNNLHTGIPSRFSGSGSGTDYTLTISSLQPEDVATYFCLQHSSRWTFG

GGTKLELK

In another embodiment the targeting moiety is an scFv known as L112-CD45 and binds to CD45 on HSC cells. The full L112-CD45 is an scFv-FLAG, tagged with an extra C-terminal cys residue, and the polypeptide sequence for L112-CD45 is as follows:

(SEQ ID NO: 19)
EVQLVESGGDLVQPGRSLKLSCVASGFTFNNYWMTWIRQVPGKGLEWVA

SISSSGGSIYYPDSVKDRFTISRDNAKNTLFLQMNSLRSEDTATYYCAR

LYYYSGGGDAWGQGTSVTVSSGGGGSGGGGSGGGGSGGGGDIQMTQSPS

FLSASVGDRVTIICKASQDINKYLDWYQQKLGEAPKLLIYNTNNLHTGI

PSRFSGSGSGTDYTLTISSLQPEDVATYFCLQHISRWTFGGGTKLELKG

GGGSGGGGSDYKDDDDKGGGGSC

L112-CD45 VH sequence only:

(SEQ ID NO: 20)
EVQLVESGGDLVQPGRSLKLSCVASGFTFNNYWMTWIRQVPGKGLEWVA

SISSSGGSIYYPDSVKDRFTISRDNAKNTLFLQMNSLRSEDTATYYCAR

LYYYSGGGDAWGQGTSVTVSS

L112-CD45 VL sequence only:

(SEQ ID NO: 21)
DIQMTQSPSFLSASVGDRVTIICKASQDINKYLDWYQQKLGEAPKLLIY

NTNNLHTGIPSRFSGSGSGTDYTLTISSLQPEDVATYFCLQHISRWTFG

GGTKLELK

In another embodiment, the targeting moiety is known as L122-CD45 and is an scFv recognizing and binding to CD45.

The full L122-CD45 is an scFv-FLAG and is tagged with an extra c-terminal cys residue, and the polypeptide sequence is shown as follows:

(SEQ ID NO: 22)
EVKLLESGGGLVQPGGSLKLSCAASGFDFSRYWMSWVRQAPGKGLEWIG

EINPTSSTINFTPSLKDKVFISRDNAKNTLYLQMSKVRSEDTALYYCAR

GNYYRYGDAMDYWGQGTSVTVSSAKGGGGSGGGGSGGGGSGGGGSDIAL

TQSPASLAVSLGQRATISCRASKSVSTSGYSYLHWYQQKPGQPPKLLIY

LASNLESGVPARFSGSGSGTDFTLNIHPVEEEDAATYYCQHSRELPFTF

GSGTKLEIKGGGGSGGGGSDYKDDDDKGGGGSC

The L122-CD45 VH polypeptide sequence only is as follows:

(SEQ ID NO: 23)
EVKLLESGGGLVQPGGSLKLSCAASGFDFSRYWMSWVRQAPGKGLEWIG

EINPTSSTINFTPSLKDKVFISRDNAKNTLYLQMSKVRSEDTALYYCAR

GNYYRYGDAMDYWGQGTSVTVSSAK

The L122-CD45 VL polypeptide sequence only is shown below:

(SEQ ID NO: 24)
DIALTQSPASLAVSLGQRATISCRASKSVSTSGYSYLHWYQQKPGQPPK

LLIYLASNLESGVPARFSGSGSGTDFTLNIHPVEEEDAATYYCQHSREL

PFTFGSGTKLEIK

In another embodiment, the targeting moiety is an scFv known as L81-CD117. The full L81-CD117 scFv-FLAG, is tagged with an extra c-terminal cys residue, and the polypeptide sequence is as follows:

(SEQ ID NO: 25)
QVQLKQSGAELVRPGASVKLSCKASGYTFTDYYINWVKQRPGQGLEWIA
RIYPGSGNTYYNEKFKGKATLTAEKSSSTAYMQLSSLTSEDSAVYFCAR
GVYYFDYWGQGTTLTVSSGGGGSGGGGSGGGGSGGGGDIVMTQSQKFMS
TSVGDRVSVTCKASQNVRTNVAWYQQKPGQSPKALIYSASYRYSGVPDR
FTGSGSGTDFTLTISNVQSEDLADYFCQQYNSYPRTFGGGTKLEIKRGG
GGSGGGGSDYKDDDDKGGGGSC

The L81-CD117 VH polypeptide sequence only is shown below:

(SEQ ID NO: 26)
QVQLKQSGAELVRPGASVKLSCKASGYTFTDYYINWVKQRPGQGLEWIA
RIYPGSGNTYYNEKFKGKATLTAEKSSSTAYMQLSSLTSEDSAVYFCAR
GVYYFDYWGQGTTLTVSS

The L81-CD117 VL polypeptide sequence only is shown as follows:

(SEQ ID NO: 27)
DIVMTQSQKFMSTSVGDRVSVTCKASQNVRTNVAWYQQKPGQSPKALIY
SASYRYSGVPDRFTGSGSGTDFTLTISNVQSEDLADYFCQQYNSYPRTF
GGGTKLEIKR

In another embodiment, the targeting moiety is an scFv that recognizes and binds CD117, known as L86-CD117. The full scFv-FLAG is tagged with an extra c-terminal cys residue, the full scFv polypeptide sequence is shown below:

(SEQ ID NO: 28)
DIQMTQSPSSLSASVGDRVTITCRSSQGIRSDLGWYQQKPGKAPKLLIY
DASNLETGVPSRFSGSGSGTDFTLTISSLQPEDFATYYCQQANGFPLTF
GGGTKVEIKGGGGSGGGGSGGGGSGGGGSEVQLVQSGAEVKKPGESLKI
SCKGSGYSFTNYWIGWVRQMPGKGLEWMAIINPRDSDTRYRPSFQGQVT
ISADKSISTAYLQWSSLKASDTAMYYCARHGRGYEGYEGAFDIWGQGTL
VTVSSGGGGSGGGGSDYKDDDDKGGGGSC

The L86-CD117 VH polypeptide sequence only is shown below:

(SEQ ID NO: 29)
EVQLVQSGAEVKKPGESLKISCKGSGYSFTNYWIGWVRQMPGKGLEWMA
IINPRDSDTRYRPSFQGQVTISADKSISTAYLQWSSLKASDTAMYYCAR
HGRGYEGYEGAFDIWGQGTLVTVSS

The L86-CD117 VL polypeptide sequence only is shown below:

(SEQ ID NO: 30)
DIQMTQSPSSLSASVGDRVTITCRSSQGIRSDLGWYQQKPGKAPKLLIY
DASNLETGVPSRFSGSGSGTDFTLTISSLQPEDFATYYCQQANGFPLTF
GGGTKVEIK

In another embodiment, the targeting moiety is an scFv that recognizes and binds CD117 known as L088-CD117. The full scFv-FLAG is tagged with a c-terminal cys residue, the full scFv polypeptide sequence is shown below:

(SEQ ID NO: 31)
DIQMTQSPSSLSASVGDRVTITCRASQGIGSALAWYQQKPGKAPKLLIY
DASNLETGVPSRFSGSGSGTDFTLTISSLQPEDFATYYCQQLNGYPLTF
GQGTRLEIKGGGGSGGGGSGGGGSGGGGSEVQLVQSGAEVKKPGESLKI
SCKGSGYRFTTSWIGWVRQMPGKGLEWMGIIYPGDSDTRYSPSFQGQVT
ISADKSISTAYLQWSSLKASDTAMYYCARHGLGYNGYEGAFDIWGQGTL
VTVSSGGGGSGGGGSDYKDDDDKGGGGSC

The L088-CD117 VH polypeptide sequence only is shown below:

(SEQ ID NO: 32)
EVQLVQSGAEVKKPGESLKISCKGSGYRFTTSWIGWVRQMPGKGLEWMG
IIYPGDSDTRYSPSFQGQVTISADKSISTAYLQWSSLKASDTAMYYCAR
HGLGYNGYEGAFDIWGQGTLVTVSS

The L088-CD117 VL polypeptide sequence only is as follows:

(SEQ ID NO: 33)
DIQMTQSPSSLSASVGDRVTITCRASQGIGSALAWYQQKPGKAPKLLIY
DASNLETGVPSRFSGSGSGTDFTLTISSLQPEDFATYYCQQLNGYPLTF
GQGTRLEIK

As used herein, the term “sequence identity” refers to the ratio of the number of identical amino acids between the 2 aligned sequences over the aligned length, expressed as a percentage. In some embodiments, the 2 aligned sequences are identical in length, i.e., have the same number of amino acids.

In one embodiment, the targeting moiety in an LNP of the present disclosure is an ApoE protein conjugate in an ApoB protein conjugate, which is a conjugate of one or more ApoE and/or ApoB protein molecules (native or modified) or a fragment thereof covalently linked to, for example, a lipid-anchored polymer as defined herein. In one embodiment, the targeting moiety in an LNP of the present disclosure is an ApoE polypeptide conjugate in an ApoB polypeptide conjugate, which is a conjugate of one or more ApoE and/or ApoB polypeptide molecules or a fragment thereof covalently linked to, for example, a lipid-anchored polymer as defined herein.

In one embodiment, the LNP of the present disclosure comprises a second lipid-anchored polymer and the targeting moiety as defined herein (e.g., mAb, IgG, scFv, VHH, GalNAc, ApoE protein or peptide, ApoB protein or peptide)

is conjugated to the second lipid-anchored polymer. The second lipid-anchored polymer is structurally similar to the first lipid-anchored polymer in that the second lipid-anchored polymer also contains a lipid moiety comprising a hydrophobic fatty acid tail with a single aliphatic chain backbone of $C_{18}$-$C_{22}$ covalently attached to a polymer via a linker. In one embodiment, the second lipid-anchored polymer comprises a lipid-linker moiety selected from the group consisting of 1,2-distearoyl-sn-glycero-3-phosphoethanolamine (DSPE), 1,2-dielaidoyl-sn-phosphatidylethanolamine (DEPE), 1-stearoyl-2-oleoyl-sn-glycero-3-phosphoethanolamine (SOPE), 1,2-dioleoyl-sn-glycero-3-phosphoglycerol (DOPG), 1,2-dielaidoyl-sn-glycero-3-phosphoethanolamine (18-1-trans PE), 1,2-dioleoyl-sn-glycero-3-phospho-L-serine (DOPS), dioctadecylamine (DODA), distearoyl-rac-glycerol (DSG), 1,2-dioleoyl-sn-glycero-3-phosphoethanolamine (DOPE), and combinations and derivatives thereof. According to some embodiments of any of the above aspects and embodiments, the second lipid-linker is selected from the group consisting of DSPE, DEPE, SOPE, DOPG, 18-1-trans PE, DOPS, DSG, DODA, DOPE, and a derivative thereof or any combinations thereof.

A lipid-anchored polymer of the present disclosure may also comprise a reactive species. In some embodiments, the reactive species is conjugated to the polymer in the lipid-anchored polymer. The reactive species present in a lipid-anchored polymer of the present disclosure may be used for conjugation, e.g., to a targeting moiety which has been functionalized with a complementary reactive species, i.e., a reactive species capable of reacting with the reactive species comprised in the lipid-anchored polymer of the present disclosure. In some embodiments, the reactive species conjugated to the lipid-anchored polymer of the present disclosure may be a thiol reagent, a maleimide reagent, or click chemistry reagent, e.g., a reagent selected from the group consisting of an alkyne reagent, such as a dibenzocyclooctyne (DBCO) reagent, a transcyclooctene (TCO) reagent, a tetrazine (TZ) reagent and an azide (AZ) reagent.

In one embodiment, the antibody or fragment thereof, e.g., IgG, scFv, VHH, is covalently linked to a lipid-anchored polymer (e.g., second lipid-anchored polymer) via strain promoted alkyne-azide cycloaddition (SPAAC) chemistry, such as via an azide-modified lipid-anchored polymer (e.g., DSG-PEG2000-azide, DSPE-PEG2000-azide, DSG-PEG3400-azide, DSPE-PEG3400-azide, DSG-PEG5000-azide, DSPE-PEG5000-azide; DODA-PG46-azide) and a dibenzocyclooctyne (DBCO)-functionalized scFv, VHH, IgG or a fragment thereof.

In an exemplary embodiment, the second lipid-anchored polymer conjugated to a targeting moiety is represented by the following structure:

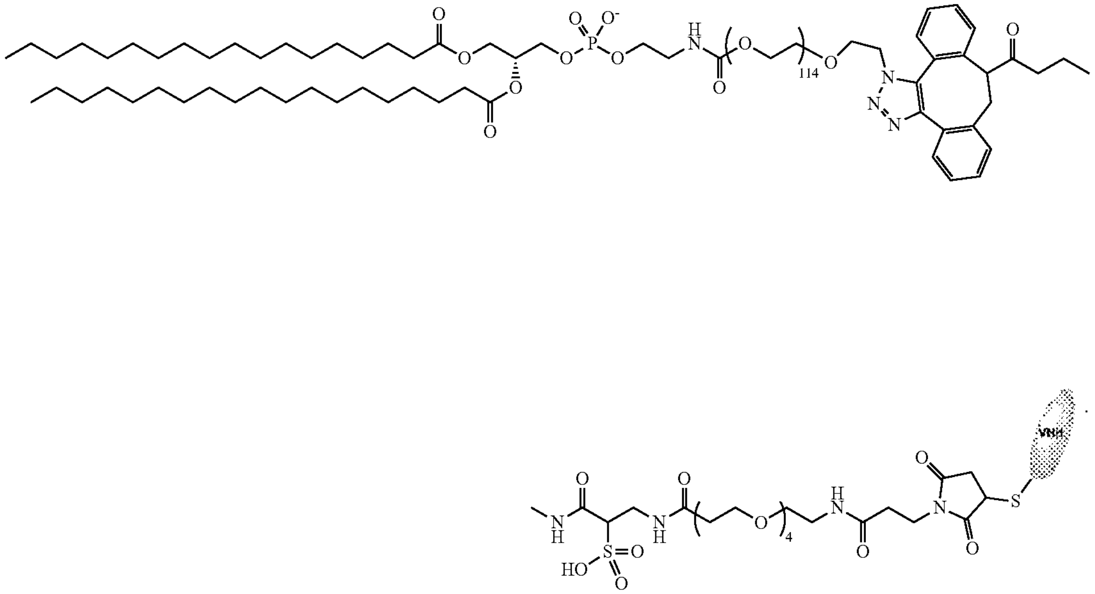

In another exemplary embodiment, the second lipid-anchored polymer conjugated to a targeting moiety is represented by the following structure:

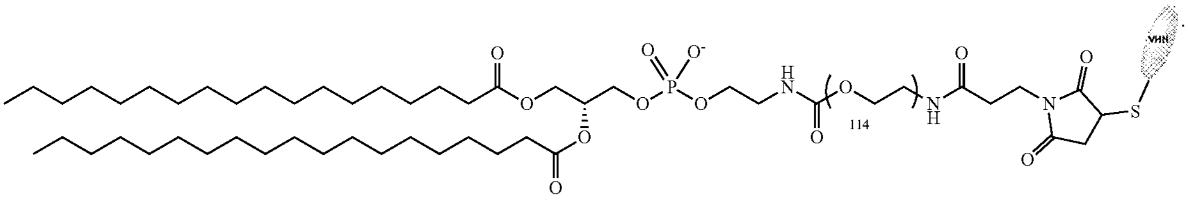

In another exemplary embodiment, the second lipid-anchored polymer conjugated to a targeting moiety is represented by the following structure:

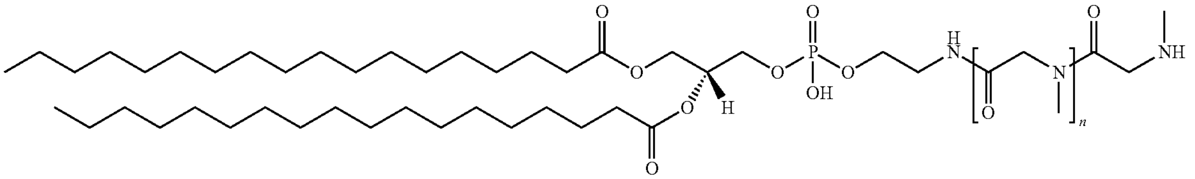

DSPE-pSar: 1,2-distearoyl-sn-glycero-3-phosohoethanolamine-N-Polysarcosine

In one embodiment, the ApoE protein, ApoB protein, ApoE polypeptide, ApoB polypeptide, or a fragment thereof, is covalently linked to a lipid-anchored polymer (e.g., second lipid-anchored polymer) via strain promoted alkyne-azide cycloaddition (SPAAC) chemistry, such as via an azide-modified lipid-anchored polymer (e.g., DSG-PEG2000-azide, DSPE-PEG2000-azide, DSG-PEG3400-azide, DSPE-PEG3400-azide, DSG-PEG5000-azide, DSPE-PEG5000-azide, DODA-PG-azide) and a dibenzocyclooctyne (DBCO)-functionalized ApoE protein, ApoB protein, ApoE polypeptide, ApoB polypeptide, or a fragment thereof.

In some embodiments, the LNPs of the present disclosure may comprise a first lipid-anchored polymer and a second lipid-anchored polymer. For example, the LNPs of the present disclosure may comprise a first lipid-anchored polymer that does not comprise a targeting moiety, and a second type of lipid-anchored polymer that comprises a targeting moiety, such as scFv, VHH, GalNAc, ApoE protein/peptide, ApoB protein/peptide. For example, the LNPs of the present disclosure may comprise DSG-PEG2000 modified to comprise an additional $OCH_3$ group (DSG-PEG2000-OMe) as a first lipid-anchored polymer and DSPE-PEG2000-scFv as a second lipid-anchored polymer.

In one specific embodiment, the first lipid-anchored polymer is the polymer-conjugated lipid of the present disclosure, e.g., DODA-PG34, DODA-PG45, DODA-PG46, or DODA-PG58. For example, the LNPs of the present disclosure may comprise DODA-PG45 as a first lipid-anchored polymer and DSPE-PEG2000-scFv as the second lipid-anchored polymer.

In some embodiments, the LNPs of the present disclosure may comprise a first lipid-anchored polymer and a second lipid-anchored polymer, wherein the second lipid-anchored polymer comprises a targeting moiety. In some embodiments, the second lipid-anchored polymer comprises a lipid-linker moiety selected from the group consisting of DSPE, DSG, DODA, DPG, DOPE, and a derivative of thereof. In some embodiments, the first lipid-anchored polymer is any lipid-anchored polymer as described hereinabove.

In some embodiments, the LNPs of the present disclosure may comprise a first lipid-anchored polymer and a second lipid-anchored polymer, wherein the second lipid-anchored polymer comprises a targeting moiety, and the first lipid-anchored polymer and the second lipid-anchored polymer are the same in their lipid-linkers but different in their hydrophilic polymers.

In some embodiments, the LNPs of the present disclosure may comprise a first lipid-anchored polymer and a second lipid-anchored polymer, wherein the second lipid-anchored polymer comprises a targeting moiety, and the first lipid-anchored polymer and the second lipid-anchored polymer are different in their lipid-linker as shown below:

- DSG-PEG (the first lipid-anchored polymer) and DSPE-PEG (the second lipid-anchored polymer);
- DSPE-PEG (the first lipid-anchored polymer) and DSG-PEG (the second lipid-anchored polymer);
- DODA-PG (the first lipid-anchored polymer) and DSPE-PEG (the second lipid-anchored polymer);
- DPG-PEG (the first lipid-anchored polymer) and DSPE-PEG (the second lipid-anchored polymer);
- DODA-PG (the first lipid-anchored polymer) and DSG-PEG (the second lipid-anchored polymer);
- DPG-PEG (the first lipid-anchored polymer) and DSG-PEG (the second lipid-anchored polymer); and
- DPG-PEG (the first lipid-anchored polymer) and DODA-PG (the second lipid-anchored polymer).

In some embodiments, the LNPs of the present disclosure may comprise a first lipid-anchored polymer and a second lipid-anchored polymer, wherein the second lipid-anchored polymer comprises a targeting moiety, and the first lipid-anchored polymer and the second lipid-anchored polymer are the same lipid-anchored polymers and are selected from one of the following combinations:

- DSG-PEG (the first lipid-anchored polymer) and DSG-PEG (the second lipid-anchored polymer);
- DSPE-PEG (the first lipid-anchored polymer) and DSPE-PEG (the second lipid-anchored polymer);
- DODA-PG (the first lipid-anchored polymer) and DODA-PG (the second lipid-anchored polymer); and
- DPG-PEG (the first lipid-anchored polymer) and DPG-PEG (the second lipid-anchored polymer).

In some embodiments, the targeting moiety is conjugated to a DSPE-anchored polymer. In some embodiments, the DSPE-anchored polymer is DSPE-PEG or a derivative thereof.

In some embodiments, the targeting moiety is conjugated to a DSG-anchored polymer. In some embodiments, the DSG-anchored polymer is DSG-PEG or a derivative thereof.

In some embodiments, the LNPs provided by the present disclosure comprise a therapeutic nucleic acid (TNA); an ionizable lipid; helper lipid (e.g., DSPC, DOPE, ceramide); cholesterol; DODA-PG; and DSPE-PEG-IgG. In some embodiments, the LNPs provided by the present disclosure consist essentially of a therapeutic nucleic acid (TNA); an ionizable lipid; helper lipid (e.g., DSPC, DOPE, ceramide); cholesterol; DODA-PG; and DSPE-PEG-IgG. In some embodiments, the LNPs provided by the present disclosure consist of a therapeutic nucleic acid (TNA); an Ionizable lipid; helper lipid (e.g., DSPC, DOPE, ceramide); cholesterol; DODA-PG; and DSPE-PEG-IgG.

In some embodiments, the LNPs provided by the present disclosure comprise a therapeutic nucleic acid (TNA); an ionizable lipid; helper lipid (e.g., DSPC, DOPE, ceramide); cholesterol; DODA-PG; and DSPE-PEG-VHH. In some embodiments, the LNPs provided by the present disclosure consist essentially of a therapeutic nucleic acid (TNA); an ionizable lipid; helper lipid (e.g., DSPC, DOPE, ceramide); cholesterol; DODA-PG; and DSPE-PEG-VHH. In some embodiments, the LNPs provided by the present disclosure consist of a therapeutic nucleic acid (TNA); an ionizable lipid; helper lipid (e.g., DSPC, DOPE, ceramide); cholesterol; DODA-PG; and DSPE-PEG-VHH.

In some embodiments, the LNPs provided by the present disclosure comprise a therapeutic nucleic acid (TNA); an ionizable lipid; helper lipid (e.g., DSPC, DOPE, ceramide); cholesterol; DODA-PG; and DODA-PG-scFv. In some embodiments, the LNPs provided by the present disclosure consist essentially of a therapeutic nucleic acid (TNA); an ionizable lipid; helper lipid (e.g., DSPC, DOPE, ceramide); cholesterol; DODA-PG; and DODA-PG-scFv. In some embodiments, the LNPs provided by the present disclosure consist of a therapeutic nucleic acid (TNA); an ionizable lipid; helper lipid (e.g., DSPC, DOPE, ceramide); cholesterol; DODA-PG; and DODA-PG-scFv.

In some embodiments, the LNPs provided by the present disclosure comprise a therapeutic nucleic acid (TNA); an ionizable lipid; helper lipid (e.g., DSPC, DOPE, ceramide); cholesterol; DODA-PG; and DODA-PG-VHH. In some embodiments, the LNPs provided by the present disclosure consist essentially of a therapeutic nucleic acid (TNA); an ionizable lipid; helper lipid (e.g., DSPC, DOPE, ceramide); cholesterol; and DODA-PG; and DODA-PG-VHH. In some embodiments, the LNPs provided by the present disclosure consist of a therapeutic nucleic acid (TNA); an ionizable lipid; helper lipid (e.g., DSPC, DOPE, ceramide); cholesterol; DODA-PG; and DODA-PG-VHH.

In some embodiments, the LNPs provided by the present disclosure comprise a therapeutic nucleic acid (TNA); an ionizable lipid; helper lipid (e.g., DSPC, DOPE, ceramide); cholesterol; and DODA-PG46 (i.e., polyglycerol having an average of 46 glycerol repeating units). In some embodiments, the LNPs provided by the present disclosure consist essentially of a therapeutic nucleic acid (TNA); an ionizable lipid; helper lipid (e.g., DSPC, DOPE, ceramide); cholesterol; and bis-DODA-PG46 (e.g., d18:1/2:0 or d14:1/2:0). In some embodiments, the LNPs provided by the present disclosure consist of a therapeutic nucleic acid (TNA); an ionizable lipid; helper lipid (e.g., DSPC, DOPE, ceramide); cholesterol; and DODA-PG46.

In some embodiments, the LNPs provided by the present disclosure comprise a therapeutic nucleic acid (TNA); an ionizable lipid; helper lipid (e.g., DSPC, DOPE, ceramide); cholesterol; and DODA-PG34 (i.e., polyglycerol having an average of 34 glycerol units). In some embodiments, the LNPs provided by the present disclosure consist essentially of a therapeutic nucleic acid (TNA); an ionizable lipid; helper lipid (e.g., DSPC, DOPE, ceramide); cholesterol; and DODA-PG34. In some embodiments, the LNPs provided by the present disclosure consist of a therapeutic nucleic acid (TNA); an ionizable lipid; helper lipid (e.g., DSPC, DOPE, ceramide); cholesterol; and DODA-PG34.

In some embodiments, the LNPs provided by the present disclosure comprise a therapeutic nucleic acid (TNA); an ionizable lipid; helper lipid (e.g., DSPC, DOPE, ceramide); cholesterol; DODA-PG46; and DODA-PG46-VHH. In some embodiments, the LNPs provided by the present disclosure consist essentially of a therapeutic nucleic acid (TNA); an ionizable lipid; helper lipid (e.g., DSPC, DOPE, ceramide); cholesterol; DODA-PG46; and DODA-PG46-VHH. In some embodiments, the LNPs provided by the present disclosure consist of a therapeutic nucleic acid (TNA); an ionizable lipid; helper lipid (e.g., DSPC, DOPE, ceramide); cholesterol; DODA-PG46; and DODA-PG46-VHH.

In some embodiments, the LNPs provided by the present disclosure comprise a therapeutic nucleic acid (TNA); an ionizable lipid; helper lipid (e.g., DSPC, DOPE, ceramide); cholesterol; DODA-PG46; and DODA-PG46-scFv. In some embodiments, the LNPs provided by the present disclosure consist essentially of a therapeutic nucleic acid (TNA); an ionizable lipid; helper lipid (e.g., DSPC, DOPE, ceramide); cholesterol; DODA-PG46; and DODA-PG46-scFv. In some embodiments, the LNPs provided by the present disclosure consist of a therapeutic nucleic acid (TNA); an ionizable lipid; helper lipid (e.g., DSPC, DOPE, ceramide); cholesterol; DODA-PG46; and DODA-PG46-scFv.

In some embodiments, the LNPs provided by the present disclosure comprise a therapeutic nucleic acid (TNA); an ionizable lipid; helper lipid (e.g., DSPC, DOPE, ceramide); cholesterol; DSG-PEG2000-OMe; and DODA-PG-VHH. In some embodiments, the LNPs provided by the present disclosure consist essentially of a therapeutic nucleic acid (TNA); an ionizable lipid; helper lipid (e.g., DSPC, DOPE, ceramide); cholesterol; DSG-PEG2000-OMe; and DODA-PG-VHH. In some embodiments, the LNPs provided by the present disclosure consist of a therapeutic nucleic acid (TNA); an ionizable lipid; helper lipid (e.g., DSPC, DOPE, ceramide); cholesterol; DSG-PEG2000-OMe; and DODA-PG-VHH.

In some embodiments, the LNPs provided by the present disclosure comprise a therapeutic nucleic acid (TNA); an ionizable lipid; helper lipid (e.g., DSPC, DOPE, ceramide); cholesterol; DSG-PEG2000-OH; and DODA-PG-VHH. In some embodiments, the LNPs provided by the present disclosure consist essentially of a therapeutic nucleic acid (TNA); an ionizable lipid; helper lipid (e.g., DSPC, DOPE, ceramide); cholesterol; DSG-PEG2000-OH; and DODA-PG-VHH. In some embodiments, the LNPs provided by the present disclosure consist of a therapeutic nucleic acid (TNA); an ionizable lipid; helper lipid (e.g., DSPC, DOPE, ceramide); cholesterol; DSG-PEG2000-OH; and DODA-PG-VHH.

In some embodiments, the LNPs provided by the present disclosure comprise a therapeutic nucleic acid (TNA); an ionizable lipid; helper lipid (e.g., DSPC, DOPE, ceramide); cholesterol; and DSG-PEG2000-OMe. In some embodiments, the LNPs provided by the present disclosure consist essentially of a therapeutic nucleic acid (TNA); an ionizable lipid; helper lipid (e.g., DSPC, DOPE, ceramide); cholesterol; and DSG-PEG2000-OMe. In some embodiments, the LNPs provided by the present disclosure consist of a therapeutic nucleic acid (TNA); an ionizable lipid; helper lipid (e.g., DSPC, DOPE, ceramide); cholesterol; DSG-PEG2000-OMe; and DSPE-PEG2000-VHH.

In some embodiments, the LNPs provided by the present disclosure comprise a therapeutic nucleic acid (TNA); an ionizable lipid; helper lipid (e.g., DSPC, DOPE, ceramide); cholesterol; and DSG-PEG2000-OH. In some embodiments, the LNPs provided by the present disclosure consist essentially of a therapeutic nucleic acid (TNA); an ionizable lipid; helper lipid (e.g., DSPC, DOPE, ceramide); cholesterol; DSG-PEG2000-OH; and DSPE-PEG2000-VHH. In some embodiments, the LNPs provided by the present disclosure consist of a therapeutic nucleic acid (TNA); an ionizable lipid; helper lipid (e.g., DSPC, DOPE, ceramide) cholesterol; DSG-PEG2000-OH; and DSPE-PEG2000-VHH.

In some embodiments, the LNPs provided by the present disclosure comprise a therapeutic nucleic acid (TNA); an ionizable lipid; helper lipid (e.g., DSPC, DOPE, ceramide); cholesterol; DSG-PEG2000-OMe and DSPE-PEG2000-scFv. In some embodiments, the LNPs provided by the present disclosure consist essentially of a therapeutic nucleic acid (TNA); an ionizable lipid; helper lipid (e.g., DSPC, DOPE, ceramide); cholesterol; DSG-PEG2000-OMe and DSPE-PEG2000-scFv. In some embodiments, the LNPs provided by the present disclosure consist of a therapeutic nucleic acid (TNA); an ionizable lipid; helper lipid (e.g., DSPC, DOPE, ceramide); cholesterol; DSG-PEG2000-OMe and DSPE-PEG2000-scFv.

In some embodiments, the LNPs provided by the present disclosure comprise a therapeutic nucleic acid (TNA); an ionizable lipid; helper lipid (e.g., DSPC, DOPE, ceramide); cholesterol; DSG-PEG2000-OH and DSPE-PEG2000-scFv. In some embodiments, the LNPs provided by the present disclosure consist essentially of a therapeutic nucleic acid (TNA); an ionizable lipid; helper lipid (e.g., DSPC, DOPE, ceramide); cholesterol; DSG-PEG2000-OH and DSPE-PEG2000-scFv. In some embodiments, the LNPs provided by the present disclosure consist of a therapeutic nucleic acid (TNA); an ionizable lipid; helper lipid (e.g., DSPC, DOPE, ceramide); cholesterol; DSG-PEG2000-OH and DSPE-PEG2000-scFv.

In some embodiments, the LNPs provided by the present disclosure comprise a therapeutic nucleic acid (TNA); an ionizable lipid; helper lipid (e.g., DSPC, DOPE, ceramide); cholesterol; bis-DSG-PEG2000 and DSPE-PEG2000-scFv. In some embodiments, the LNPs provided by the present disclosure consist essentially of a therapeutic nucleic acid (TNA); an ionizable lipid; helper lipid (e.g., DSPC, DOPE, ceramide); cholesterol; bis-DSG-PEG2000 and DSPE-PEG2000-scFv. In some embodiments, the LNPs provided by the present disclosure consist of a therapeutic nucleic acid (TNA); an ionizable lipid; helper lipid (e.g., DSPC, DOPE, ceramide); cholesterol; bis-DSG-PEG2000 and DSPE-PEG2000-scFv.

In some embodiments, the LNPs provided by the present disclosure comprise a therapeutic nucleic acid (TNA); an ionizable lipid; helper lipid (e.g., DSPC, DOPE, ceramide); cholesterol; DODA-PG and DSPE-PEG-scFv. In some embodiments, the LNPs provided by the present disclosure consist essentially of a therapeutic nucleic acid (TNA); an ionizable lipid; helper lipid (e.g., DSPC, DOPE, ceramide); cholesterol; DODA-PG45 and DSPE-PEG2000-scFv. In some embodiments, the LNPs provided by the present disclosure consist of a therapeutic nucleic acid (TNA); an ionizable lipid; helper lipid (e.g., DSPC, DOPE, ceramide); cholesterol; DODA-PG45 and DSPE-PEG2000-scFv.

In some embodiments, the lipid-anchored polymers (first and second lipid-anchored polymers in combination) constitute about 0.1 mol % to about 20 mol % of the total lipid present in the LNP. In some embodiments, the lipid-anchored polymers constitute about 0.5 mol % to about 10 mol % present in the LNP. In some embodiments, the lipid-anchored polymers constitute about 1 mol % to about 10 mol % present in the LNP. In some embodiments, the lipid-anchored polymers constitute about 2 mol % to about 10 mol % present in the LNP. In some embodiments, the lipid-anchored polymers constitute more than about 2 mol % (e.g., 2.1 mol %, 2.2 mol %, 2.3 mol %, 2.4 mol %, 2.5 mol %, 2.6 mol %, 2.7 mol %, 2.8 mol %, 2.9 mol %, 3.0 mol %) to about 10 mol % present in the LNP. In some embodiments, the lipid-anchored polymers constitute about 3 mol % to about 8 mol % present in the LNP. In some embodiments, the lipid-anchored polymers constitute about 3 mol % to about 7 mol % present in the LNP. In some embodiments, the lipid-anchored polymers constitute about 3 mol % to about 5 mol % present in the LNP. In some embodiments, the lipid-anchored polymers constitute about 2 mol % to about 4 mol % present in the LNP. In some embodiments, the lipid-anchored polymers constitute about 2% to about 3% present in the LNP. In some embodiments, the lipid-anchored polymers constitute about 2 mol % present in the LNP. In some embodiments, the lipid-anchored polymers constitute about 2.5 mol % present in the LNP. In some embodiments, the lipid-anchored polymers constitute about 3 mol % present in the LNP. In some embodiments, the lipid-anchored polymers constitute about 3.5 mol % present in the LNP. In some embodiments, the lipid-anchored polymers constitute about 4 mol % present in the LNP. In some embodiments, the lipid-anchored polymers constitute about 5 mol % present in the LNP. In some embodiments, the lipid-anchored polymers constitute about 6 mol % present in the LNP. In some embodiments, the lipid-anchored polymers constitute about 7 mol % present in the LNP. In some embodiments, the lipid-anchored polymers constitute about 8 mol % present in the LNP. In some embodiments, the lipid-anchored polymers constitute about 9 mol % present in the LNP. In some embodiments, the lipid-anchored polymers constitute about 10 mol % present in the LNP.

In some embodiments, the first lipid-anchored polymer is present at about 0.1 mol % to about 10 mol % of the total lipid present in the LNP, or about 0.2 mol % to about 8 mol %, or about 0.2 mol % to about 7 mol %, or about 0.2% mol % to about 5 mol %, or about 0.3 mol to about 4 mol %, or about 0.4 mol % to about 4 mol %, or about 0.5 mol % to about 5 mol %, or about 0.5 mol % to about 4 mol %, or about 0.5 mol % to about 3.5 mol %, or about 0.5 mol % to about 3 mol %, or about 0.7 mol % to about 5 mol %, or about 0.7 mol % to about 4 mol %, or about 0.7 mol % to about 3.5 mol %, or about 0.7 mol % to about 3 mol %, or about 1 mol % to about 5 mol %, or about 1 mol % to about 4 mol %, or about 1 mol % to about 3.5 mol %, or about 1 mol % to about 3 mol %, or about 1.5 mol % to about 5 mol %, or about 1.5 mol % to about 4 mol %, or about 1.5 mol % to about 3.5 mol %, or about 1.5 mol % to about 3 mol %, or about 2 mol % to about 5 mol %, or about 2 mol % to about 4 mol %, or about 2 mol % to about 3.5 mol %, or about 2 mol % to about 3 mol %, or about 2.5 mol % to about 5 mol %, or about 2.5 mol % to about 4 mol %, or about 2.5 mol % to about 3.5 mol %, or about 2.5 mol % to about 3 mol %, or about 3 mol % to about 5 mol %, or about 3 mol % to about 4.5 mol % or about 3 mol % to about 4 mol %, or about 3 mol % to about 3.5 mol %, or about 3.5 mol % to about 5 mol %, or about 3.5 mol % to about 4.5 mol % or about 3.5 mol % to about 4 mol % or about 3 mol % to about 7 mol %.

In some embodiments, the second lipid-anchored polymer, if present, is present at about 0.01 mol % to about 5 mol % of the total lipid present in the LNP. In some embodiments, the second lipid-anchored polymer, if present, is present at about 0.01 mol % to about 4 mol % of the total lipid present in the LNP. In some embodiments, the second lipid-anchored polymer, if present, is present at about 0.01 mol % to about 3 mol % of the total lipid present in the LNP. In some embodiments, the second lipid-anchored polymer, if present, is present at about 0.01 mol % to about 2.5 mol % of the total lipid present in the LNP. In some embodiments, the second lipid-anchored polymer, if present, is present at about 0.01 mol % to about 2 mol % of the total lipid present in the LNP. In some embodiments, the second lipid-anchored polymer, if present, is present at about 0.01 mol % to about 1 mol % of the total lipid present in the LNP. In some embodiments, the second lipid-anchored polymer, if present, is present at about 0.01 mol % to about 0.5 mol % of the total lipid present in the LNP. In some embodiments, the second lipid-anchored polymer, if present, is present at about 0.01 mol % to about 0.25 mol % of the total lipid present in the LNP. In some embodiments, the second lipid-anchored polymer, if present, is present at about 0.01 mol % to about 0.2 mol % of the total lipid present in the LNP. In some embodiments, the second lipid-anchored polymer, if present, is present at about 0.01 mol % to about 0.1 mol % of the total lipid present in the LNP. In some embodiments, the second lipid-anchored polymer, if present, is present at about 0.05 mol % to about 0.15 mol % of the total lipid present in the LNP.

In some embodiments, the second lipid-anchored polymer, if present, is present at about 0.005 mol % to about 5 mol % of the total lipid present in the LNP, or about 0.005 mol % to about 3 mol %, or about 0.005 mol % to about 2 mol %, or about 0.005 mol % to about 1 mol %, or about 0.005 mol % to about 0.5 mol %, or about 0.01 mol % to about 3 mol %, or about 0.01 mol % to about 2 mol %, or about 0.01 mol % to about 1 mol %, or about 0.01 mol % to about 0.5 mol %, or about 0.025 mol % to about 3 mol %, or about 0.025 mol % to about 2 mol %, or about 0.025 mol % to about 1 mol %, or about 0.025 mol % to about 0.5 mol %, or about 0.05 mol % to about 3 mol %, or about 0.05 mol % to about 2 mol %, or about 0.05 mol % to about 1 mol %, or about 0.05 mol % to about 0.5 mol %, or about 0.01 mol % to about 0.4 mol %, or about 0.01 mol % to about 0.3 mol %, or about 0.01 mol % to about 0.25 mol %, or about 0.01 mol % to about 0.2 mol %, or about 0.01 mol % to about 0.1 mol %, or about 0.025 mol % to about 0.4 mol %, or about 0.025 mol % to about 0.3 mol %, or about 0.025 mol % to about 0.25 mol %, or about 0.025 mol % to about 0.2 mol %, or about 0.025 mol % to about 0.1 mol %, or about 0.05 mol % to about 0.4 mol %, or about 0.05 mol % to about 0.3 mol %, or about 0.05 mol % to about 0.25 mol %, or about 0.05 mol % to about 0.2 mol %, or about 0.05 mol % to about 0.1 mol %.

In some embodiments, the second lipid-anchored polymer is present at about 0.01 mol %. In some embodiments, the second lipid-anchored polymer is present at about 0.05 mol %. In some embodiments, the second lipid-anchored polymer is present at about 0.06 mol %. In some embodiments, the second lipid-anchored polymer is present at about 0.08 mol %. In some embodiments, the second lipid-anchored polymer is present at about 0.5 mol %. In some embodiments, the second lipid-anchored polymer is present at about 0.1 mol %. In some embodiments, the second lipid-anchored polymer is present at about 0.2 mol %. In some embodiments, the second lipid-anchored polymer is present at about 0.3 mol %. In some embodiments, the second lipid-anchored polymer is present at about 0.4 mol %. In some embodiments, the second lipid-anchored polymer is present at about 0.1 mol % to about 0.4 mol %. In some embodiments, the second lipid-anchored polymer is present at about 0.1 mol % to about 0.3 mol %. In some embodiments, the second lipid-anchored polymer is present at about 0.15 mol % to about 0.25 mol %.

Lipid nanoparticles (LNPs) comprising ceDNA are disclosed in International Patent Application No. PCT/US2018/050042, filed on Sep. 7, 2018, which is incorporated herein in its entirety and envisioned for use in the methods and compositions as disclosed therein.

The size of LNPs can be determined by quasi-elastic light scattering using a Malvern Zetasizer Nano ZS (Malvern, UK). In some embodiments, LNPs of the present disclosure have a mean diameter as determined by light scattering of less than about 90 nm, e.g., less than about 80 nm or less than about 75 nm. According to some embodiments, LNPs of the present disclosure have a mean diameter as determined by light scattering of between about 50 nm and about 75 nm or between about 50 nm and about 70 nm.

The pKa of formulated ionizable or cationic lipids can be correlated with the effectiveness of the LNPs for delivery of nucleic acids (see Jayaraman et al., Angewandte Chemie, International Edition (2012), 51(34), 8529-8533; Semple et al., Nature Biotechnology 28, 172-176 (2010), both of which are incorporated by reference in their entireties). In one embodiment, the pKa of each cationic lipid is determined in lipid nanoparticles using an assay based on fluorescence of 6,P-toluidinylnaphthalene-2-sulfonate (TNS). LNPs in PBS at a concentration of 0.4 mM total lipid can be prepared using the in-line process as described herein and elsewhere. TNS can be prepared as a 100 mM stock solution in distilled water. Vesicles can be diluted to 24 mM lipid in 2 mL of buffered solutions containing, 10 mM HEPES, 10 mM MES, 10 mM ammonium acetate, 130 mM NaCl, where the pH ranges from 2.5 to 11. An aliquot of the TNS solution can be added to give a final concentration of 1 mM and following vortex mixing fluorescence intensity is measured at room temperature in a SLM Aminco Series 2 Luminescence Spectrophotometer using excitation and emission wavelengths of 321 nm and 445 nm. A sigmoidal best fit analysis can be applied to the fluorescence data and the pKa is measured as the pH giving rise to half-maximal fluorescence intensity.

In one embodiment, relative activity can be determined by measuring luciferase expression in the liver 4 hours following administration via tail vein injection. The activity is compared at a dose of 0.3 and 1.0 mg ceDNA/kg and expressed as ng luciferase/g liver measured 4 hours after administration.

Without limitations, LNP of the present disclosure includes a lipid formulation that can be used to deliver a capsid-free, non-viral DNA vector to a target site of interest (e.g., cell, tissue, organ, and the like). Generally, the LNP comprises capsid-free, non-viral DNA vector and a cationic lipid or a salt thereof.

Yet further exemplary lipid-anchored polymers include N-(Carbonyl-methoxypolyethyleneglycoln)-1,2-dimyristoyl-sn-glycero-3-phosphoethanolamine ($DMPE-PEG_n$, where n is 350, 500, 750, 1000 or 2000), N-(Carbonyl-methoxypolyethyleneglycoln)-1,2-distearoyl-sn-glycero-3-phosphoethanolamine ($DSPE-PEG_n$, where n is 350, 500, 750, 1000 or 2000), DSPE-polyglycerin-cyclohexyl-carboxylic acid, DSPE-polyglycelin-2-methylglutar-carboxylic acid, 1,2-Distearoyl-sn-Glycero-3-Phosphoethanolamine (DSPE) conjugated Polyethylene Glycol (DSPE-PEG-OH), or polyethylene glycol-distearoyl glycerol (PEG-DSG). In some examples of $DMPE-PEG_n$, where n is 350, 500, 750, 1000 or 2000, the PEG-lipid is N-(Carbonyl-methoxypolyethyleneglycol 2000)-1,2-dimyristoyl-sn-glycero-3-phosphoethanolamine (DMPE-PEG 2,000). In some examples of $DSPE-PEG_n$. where n is 350, 500, 750, 1000 or 2000, the PEG-lipid is N-(Carbonyl-methoxypolyethyleneglycol 2000)-1,2-distearoyl-sn-glycero-3-phosphoethanolamine (DSPE-PEG 2,000). In some embodiments, the PEG-lipid is DSPE-PEG-OH. In some embodiments, the PEG-lipid is PEG-DMG having two $C_{14}$ hydrophobic tails and PEG2000.

E. Density of Targeting Moieties Conjugated to Second Lipid-Anchored Polymer

In another embodiment of the present disclosure, the stealth LNP displays approximately 5, 10, 15, 20, 25, 30, 35, 40, 42, 45, 50, 52, 55, 60, 65, 70, 75, 80, 85, 90, 95, 100, 105, 110, 115, 120, 125, 126, 130, 135, 140, 145, 150, 155, 160, 165, 168, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 340, 345, 350, 355, 360, 365, 370, 375, 380, 385, 390, 390, 395, or 400 targeting moieties per LNP.

In another embodiment, the stealth LNP displays at least 5 targeting moieties, at least 10 targeting moieties, at least 15 targeting moieties, at least 20 targeting moieties, at least 25 targeting moieties, at least 30 targeting moieties, at least 35 targeting moieties, at least 40 targeting moieties, at least 45 targeting moieties, at least 50 targeting moieties, at least 55 targeting moieties, at least 60 targeting moieties, at least 65 targeting moieties, at least 70 targeting moieties, at least 75 targeting moieties, at least 80 targeting moieties, at least 85 targeting moieties, at least 90 targeting moieties, at least 95 targeting moieties, at least 100 targeting moieties, at least 110 targeting moieties, at least 120 targeting moieties, at least 130 targeting moieties, at least 140 targeting moieties, at least 150 targeting moieties, at least 160 targeting moieties, at least 170 targeting moieties, at least 180 targeting moieties, at least 190 targeting moieties, at least 200 targeting moieties, at least 210 targeting moieties, at least 220 targeting moieties, at least 230 targeting moieties, at least 240 targeting moieties, at least 250 targeting moieties per LNP, at least 260 targeting moieties, at least 270 targeting moieties, at least 280 targeting moieties, at least 290 targeting moieties, at least 300 targeting moieties per LNP, at least 310 targeting moieties per LNP, at least 320 targeting moieties per LNP, at least 330 targeting moieties per LNP, at least 340 targeting moieties per LNP, at least 350 targeting moieties per LNP, at least 360 targeting moieties per LNP, at least 370 targeting moieties per LNP, at least 380 targeting moieties per LNP, at least 390 targeting moieties per LNP, or at least 400 targeting moieties per LNP.

In another embodiment, the stealth LNP displays fewer than 400 targeting moieties, fewer than 390 targeting moieties, fewer than 380 targeting moieties, fewer than 370 targeting moieties, fewer than 360 targeting moieties, fewer than 350 targeting moieties, fewer than 340 targeting moieties, fewer than 330 targeting moieties, fewer than 320 targeting moieties, fewer than 310 targeting moieties, fewer than 300 targeting moieties, fewer than 290 targeting moieties, fewer than 280 targeting moieties, fewer than 270 targeting moieties, fewer than 260 targeting moieties, fewer than 250 targeting moieties, fewer than 240 targeting moieties, fewer than 230 targeting moieties, fewer than 220 targeting moieties, fewer than 210 targeting moieties, fewer than 200 targeting moieties, fewer than 190 targeting moieties, fewer than 180 targeting moieties, fewer than 170 targeting moieties, fewer than 160 targeting moieties, fewer than 150 targeting moieties, fewer than 140 targeting moieties, fewer than 130 targeting moieties, fewer than 120 targeting moieties, fewer than 110 targeting moieties, fewer than 100 targeting moieties, fewer than 95 targeting moieties, fewer than 90 targeting moieties, fewer than 85 targeting moieties, fewer than 80 targeting moieties, fewer than 75 targeting moieties, fewer than 70 targeting moieties, fewer than 65 targeting moieties, fewer than 60 targeting moieties, fewer than 55 targeting moieties, fewer than 50 targeting moieties, fewer than 45 targeting moieties, fewer than 40 targeting moieties, fewer than 35 targeting moieties, fewer than 30 targeting moieties, fewer than 25 targeting moieties, fewer than 20 targeting moieties, fewer than 15 targeting moieties, or fewer than 10 targeting moieties per LNP.

In another embodiment, the stealth LNP displays about 5-400 targeting moieties, about 10-390 targeting moieties, about 20-380 targeting moieties, about 30-370 targeting moieties, about 40-360 targeting moieties, about 50-350 targeting moieties, about 60-340 targeting moieties, about 70-330 targeting moieties, about 80-320 targeting moieties, about 90-310 targeting moieties, about 100-300 targeting moieties, about 110-290 targeting moieties, about 120-280 targeting moieties, about 130-270 targeting moieties, about 140-260 targeting moieties, about 150-250 targeting moieties, about 160-249 targeting moieties, about 170-230 targeting moieties, about 180-220 targeting moieties, about 195-215 targeting moieties, or about 200-210 targeting moieties per LNP.

In another embodiment, the stealth LNP displays about 5-50 targeting moieties, about 50-100 targeting moieties, about 100-150 targeting moieties, about 150-200 targeting moieties, about 200-250 targeting moieties, about 250-300 targeting moieties, about 300-350 targeting moieties, or about 350-400 targeting moieties.

In another embodiment, the stealth LNP displays about 5-100 targeting moieties, about 100-200 targeting moieties, about 200-300 targeting moieties, or about 300-400 targeting moieties per LNP.

In another embodiment, the stealth LNP displays about 5-20 targeting moieties, about 20-40 targeting moieties, about 40-60 targeting moieties, about 60-80 targeting moieties, about 80-100 targeting moieties, about 100-120 targeting moieties, about 120-140 targeting moieties, about 140-160 targeting moieties, about 160-180 targeting moieties, about 180-200 targeting moieties, about 200-220 targeting moieties, about 220-240 targeting moieties, about 240-260 targeting moieties, about 260-280 targeting moieties, about 280-300 targeting moieties, about 200-320 targeting moieties, about 320-340 targeting moieties, about 340-360 targeting moieties, about 360-380 targeting moieties, or about 380-400 targeting moieties per LNP.

In another embodiment, the stealth LNP displays about 5-10 targeting moieties, about 10-20 targeting moieties, about 20-30 targeting moieties, about 30-40 targeting moieties, about 40-50 targeting moieties, about 50-60 targeting moieties, about 60-70 targeting moieties, about 70-80 targeting moieties, about 80-90 targeting moieties, about 90-100 targeting moieties, about 100-110 targeting moieties, about 110-120 targeting moieties, about 120-130 targeting moieties, about 130-140 targeting moieties, about 140-150 targeting moieties, about 150-160 targeting moieties, about 160-170 targeting moieties, about 170-180 targeting moieties, about 180-190 targeting moieties, about 190-200 targeting moieties, about 210-220 targeting moieties, about 220-230 targeting moieties, about 230-240 targeting moieties, about 240-250 targeting moieties, about 250-260 targeting moieties, about 260-270 targeting moieties, about 270-280 targeting moieties, about 280-290 targeting moieties, about 290-300 targeting moieties, about 300-310 targeting moieties, about 310-320 targeting moieties, about 320-330 targeting moieties, about 330-340 targeting moieties, about 340-350 targeting moieties, about 350-360 targeting moieties, about 360-370 targeting moieties, about 370-380 targeting moieties, about 380-390 targeting moieties, or about 390-400 targeting moieties per LNP.

In another embodiment, the stealth LNP displays about 60-250 scFv targeting moieties, about 70-200 scFv targeting moieties, about 80-150 scFv targeting moieties, about 84-125 scFv targeting moieties per LNP. In another embodiment, the stealth LNP displays about 84 or about 125 scFv targeting moieties per LNP.

In another embodiment, the stealth LNP displays about 20-400 VHH targeting moieties, about 30-350 VHH targeting moieties, about 40-300 VHH targeting moieties, about 50-250 VHH targeting moieties, about 52-210 VHH targeting moieties per LNP. In another embodiment, the stealth LNP displays about 52, 104 or 210 VHH targeting moieties per LNP.

III. Therapeutic Nucleic Acids (TNAs)

The LNPs provided by the present disclosure also comprise one or more therapeutic nucleic acids (TNAs). Illustrative therapeutic nucleic acids in the LNPs of the present disclosure can include, but are not limited to, minigenes, plasmids, minicircles, small interfering RNA (siRNA), microRNA (miRNA), antisense oligonucleotides (ASO), ribozymes, closed ended double stranded DNA (e.g., ceDNA, ssDNA, CELiD, linear covalently closed DNA ("ministring"), Doggybone™, protelomere closed ended DNA, or dumbbell linear DNA), dicer-substrate dsRNA, small hairpin RNA (shRNA), asymmetrical interfering RNA (aiRNA), mRNA, tRNA, rRNA, gRNA, and DNA viral vectors, viral RNA vector, and any combination thereof.

In any of the aspects and embodiments provided herein, the therapeutic nucleic acid can be a therapeutic DNA. Said therapeutic DNA can be ceDNA or a ssDNA. CELiD, linear covalently closed DNA ("ministring" or otherwise), Doggybone™, protelomere closed ended DNA, dumbbell linear DNA, minigenes, plasmids, or minicircles.

In one embodiment, the therapeutic nucleic acid is a therapeutic RNA. siRNA or miRNA that can downregulate the intracellular levels of specific proteins through a process called RNA interference (RNAi) are also contemplated by the present disclosure to be nucleic acid therapeutics.

After siRNA or miRNA is introduced into the cytoplasm of a host cell, these double-stranded RNA constructs can bind to a protein called RISC. The sense strand of the siRNA or miRNA is removed by the RISC complex. The RISC complex, when combined with the complementary mRNA, cleaves the mRNA and releases the cut strands. RNAi is by inducing specific destruction of mRNA that results in down-regulation of a corresponding protein.

Antisense oligonucleotides (ASO) and ribozymes that inhibit mRNA translation into protein can be nucleic acid therapeutics. For antisense constructs, these single stranded deoxy nucleic acids have a complementary sequence to the sequence of the target protein mRNA, and capable of binding to the mRNA by Watson-Crick base pairing. This binding prevents translation of a target mRNA, and/or triggers rNaseH degradation of the mRNA transcript. As a result, the antisense oligonucleotide has increased specificity of action (i.e., down-regulation of a specific disease-related protein).

In any of the aspects and embodiments provided herein, the therapeutic nucleic acid can be a therapeutic RNA. The therapeutic RNA can be messenger RNA (mRNA) encoding a protein or peptide, an inhibitor of mRNA translation, agent of RNA interference (RNAi), catalytically active RNA molecule (ribozyme), transfer RNA (tRNA), an RNA that binds an mRNA transcript (ASO), protein or other molecular ligand (aptamer), or a guide RNA (gRNA). In any of the methods provided herein, the agent of RNAi can be a double-stranded RNA, single-stranded RNA, microRNA, short interfering RNA, short hairpin RNA, or a triplex-forming oligonucleotide. In one embodiment, the TNA is mRNA.

A. Single Stranded DNA (ssDNA)

As described herein, the present disclosure encompasses synthetic single-stranded (ssDNA) molecules. According to some aspects, the disclosure provides a single stranded deoxyribonucleic acid (ssDNA) molecule comprising at least one nucleic acid sequence of interest flanked by at least one stem-loop structure at the 3' and/or 5' end. According to some embodiments, the ssDNA molecule comprises at least one stem-loop structure at 3' end. According to some embodiments, the ssDNA molecule comprises at least one stem-loop structure a 5' end. The present disclosure further encompasses ssDNA molecules described in International Patent Application Serial No. PCT/US2023/081990, filed on Dec. 1, 2023, which is incorporated herein by reference.

i. 3' End Stem-Loop Structure of ssDNA

As described herein, according to some aspects, the disclosure provides a ssDNA molecule comprising at least one nucleic acid sequence of interest flanked by at least one stem-loop structure at the 3' end. As described herein, the stem structure comprises a partial DNA duplex (e.g., with a free 3' —OH group) to prime replication or transcription. The partial DNA duplex functions, in part, to hold the stem-loop structure together.

According to some embodiments, the partial DNA duplex comprises between 4-1500 nucleotides, for example between 4-10 nucleotides, between 4-25 nucleotides, between 4-50 nucleotides, between 4-100 nucleotides, between 4-200 nucleotides, between 4-300 nucleotides, between 4-400 nucleotides, between 20-25 nucleotides, between 20-50 nucleotides, between 20-100 nucleotides, between 20-200 nucleotides, between 20-300 nucleotides, between 20-400 nucleotides, between 20-500 nucleotides, between 50-100 nucleotides, between 50-200 nucleotides, between 50-300 nucleotides, between 50-400 nucleotides, between 50-500 nucleotides, 150-200 nucleotides, between 150-300 nucleotides, between 150-400 nucleotides, between 150-500 nucleotides, between 200-300 nucleotides, between 200-400 nucleotides, between 200-500 nucleotides, between 250-300 nucleotides, between 250-400 nucleotides, between 250-500 nucleotides, between 300-400 nucleotides, between 300-500 nucleotides, between 350-400 nucleotides, between 350-500 nucleotides, between 400-500 nucleotides, between 450-500 nucleotides, between 500-550 nucleotides, between 550-600 nucleotides, between 600-650 nucleotides, between 650-700 nucleotides, between 700-750 nucleotides, between 750-800 nucleotides, between 800-850 nucleotides, between 850-900 nucleotides, between 900-950 nucleotides, between 950-1000 nucleotides, between 1000-1100 nucleotides, between 1100-1200 nucleotides, between 1200-1300 nucleotides, between 1300-1400 nucleotides, or between 1400-1500 nucleotides, and at least one loop on the 3' end. According to some embodiments, the DNA duplex comprises at least 4, 5, 6, 7, 8, 9, 10, 20, 30, 40, 50, 60, 70, 80, 90, 100, 150, 200, 250, 300, 350, 400, 450 500, 500, 600, 650, 700, 750, 800, 850, 900, 950, 1000, 1050, 1100, 1150, 1200, 1250, 1300, 1350, 1400, 1450, or 1500 nucleotides, and at least one loop on the 3' end.

According to some embodiments, the loop structure at the 3' end comprises a minimum of between 3-500 unbound nucleotides, for example between 3-450 nucleotides, between 3-400 nucleotides, between 3-350 nucleotides, between 3-300 nucleotides, between 3-250 nucleotides, between 3-200 nucleotides, between 3-150 nucleotides, between 3-100 nucleotides, between 3-90 nucleotides, between 3-80 nucleotides, between 3-70 nucleotides, between 3-60 nucleotides, between 3-50 nucleotides, between 3-40 nucleotides, between 3-30 nucleotides, between 3-20 nucleotides, between 3-10 nucleotides, between 3-5 nucleotides, between 10-450 nucleotides, between 10-400 nucleotides, between 10-350 nucleotides, between 10-300 nucleotides, between 10-250 nucleotides, between 10-200 nucleotides, between 10-150 nucleotides, between 10-100 nucleotides, between 10-90 nucleotides, between 10-80 nucleotides, between 10-70 nucleotides, between 10-60 nucleotides, between 10-50 nucleotides, between 10-40 nucleotides, between 10-30 nucleotides, between 10-20 nucleotides, between 50-450 nucleotides, between 50-400 nucleotides, between 50-350 nucleotides, between 50-300 nucleotides, between 50-250 nucleotides, between 50-200 nucleotides, between 50-150 nucleotides, between 50-100 nucleotides, between 50-90 nucleotides, between 50-80 nucleotides, between 50-70 nucleotides, between 50-60 nucleotides, between 100-450 nucleotides, between 100-400 nucleotides, between 100-350 nucleotides, between 100-300 nucleotides, between 100-250 nucleotides, between 100-200 nucleotides, between 150-450 nucleotides, between 150-400 nucleotides, between 150-350 nucleotides, between 150-300 nucleotides, between 150-250 nucleotides, between 150-200 nucleotides, between 200-450 nucleotides, between 200-400 nucleotides, between 200-350 nucleotides, between 200-300 nucleotides, between 200-250 nucleotides, between 250-450 nucleotides, between 250-400 nucleotides, between 250-350 nucleotides, between 250-300 nucleotides, between 300-450 nucleotides, between 300-400 nucleotides, between 300-350 nucleotides, between 350-450 nucleotides, between 350-400 nucleotides, or between 400-450 nucleotides.

According to some embodiments, the stem portion of the stem-loop is 4-500 nucleotides in length and the loop portion of the stem-loop is 3-500 nucleotides in length. According to some embodiments, the stem portion of the stem-loop is 4-50 nucleotides in length and the loop portion of the stem-loop is 3-50 nucleotides in length. According to some embodiments, the stem portion of the stem-loop is 4-20 nucleotides in length and the loop portion of the stem-loop is 3-20 nucleotides in length. According to some embodiments, the stem portion of the stem-loop is 4-10 nucleotides in length and the loop portion of the stem-loop is 3-10 nucleotides in length.

According to some embodiments, the loop further comprises one or more nucleic acids or that are used to stabilize the ends. According to other embodiments, the loop further comprises one or more nucleic acids that may be employed in therapeutic methods. According to other embodiments, the loop further comprises one or more nucleic acids that may be employed in diagnostic methods. According to other embodiments, the loop further comprises one or more nucleic acids that that may be employed for research purposes.

According to some embodiments, the minimal nucleic acid structure that is necessary at the 3' end of the ssDNA is any structure that loops back on itself, i.e., a hairpin structure. However, it is to be understood that a variety of structures are envisioned at the 3' end, as long as there is at least one stem and one loop. For example, in some embodiments, the ssDNA described herein may comprise at least one stem-loop structure at the 3' end. In some embodiments, the ssDNA may comprise at least at least two stem-loop structures at the 3' end. In some embodiments, the ssDNA may comprise at least at least three stem-loop structures at the 3' end. In some embodiments, the ssDNA may comprise at least at four stem-loop structures at the 3' end. In some embodiments, the ssDNA may comprise at least at least five stem-loop structures at the 3' end.

According to some embodiments, the nucleotides at the 3' end form a cruciform DNA structure. A DNA cruciform structure can be formed when both strands form a stem-loop structure at the same location in the molecule and comprises a four-way junction and two closed hairpin-shaped points.

According to some embodiments, the nucleotides at the 3' end form a hairpin DNA structure. Hairpin loop structures in nucleic acids consist of a base-paired stem structure and a loop sequence with unpaired or non-Watson-Crick-paired nucleotides.

According to some embodiments, the nucleotides at the 3' end form a hammerhead DNA structure, made up of three base paired helices, separated by short linkers of conserved sequence.

According to some embodiments, the nucleotides at the 3' end form a quadraplex DNA structure. G-quadruplexes are four-stranded DNA secondary structures (G4s) that form from certain guanine-rich sequences.

According to some embodiments, the nucleotides at the 3' end form a bulged DNA structure.

According to some embodiments, the nucleotides at the 3' end form a multibranched loop.

According to some embodiments, the nucleotides at the 3' end do not form a 2 stem-loop structure. In one embodiment, the nucleotides at the 3' end do not form an AAV ITR structure.

According to some embodiments, the at least one stem-loop structure at the 3' end does not comprise the A, A', D, and D' regions that would be present in a wild-type AAV ITR.

According to some embodiments, the at least one stem-loop structure at the 3' end does not comprise the A, A', B, B', C, C', D, and D' regions that would be present in a wild-type AAV ITR.

According to some embodiments, the at least one stem-loop structure at the 3' end does not comprise a rep binding element (RBE) that would be present in a wild-type ITR. According to some embodiments, the at least one stem-loop structure at the 3' end does not comprise a terminal resolution site (trs) that would be present in a wild-type ITR. According to some embodiments, the at least one stem loop structure at the 3' end is devoid of any viral capsid protein coding sequences.

According to some embodiments, the stem structure at the 3' end comprises one or more nucleotides that are modified to be exonuclease resistant. According to some embodiments, the stem structure at the 3' end comprises two or more, 3 or more, 4 or more, 5 or more, 6 or more, 7 or more, 8 or more, 9 or more, 10 or more, or 20 or more nucleotides that are modified to be exonuclease resistant.

According to some embodiments, the stem structure at the 3' end comprises one or more phosphorothioate-modified nucleotides. According to some embodiments, the stem structure at the 3' end comprises about 4 to about 10 phosphorothioate-modified nucleotides, e.g., about 4 to about 5, about 4 to about 6, about 4 to about 7, about 4 to about 8, about 4 to about 9, about 4 to about 10, about 5 to about 6, about 5 to about 7, about 5 to about 8, about 5 to about 9, about 5 to about 10, about 6 to about 7, about 6 to about 8, about 6 to about 9, about 6 to about 10, about 7 to about 8, about 7 to about 9, about 7 to about 10, about 8 to about 9, about 8 to about 10 or about 9 to about 10.

According to some embodiments, the stem structure comprises more than 10 phosphorothioate-modified nucleotides.

According to some embodiments, the phosphorothioate-modified nucleotides are located adjacent to each other.

According to some embodiments, the one or more phosphorothioate-modified nucleotides of the 3' end are resistant to exonuclease degradation. Boranophosphate modified DNA is also resistant to nuclease degradation and may be considered as an alternative to phosphorothioate modification.

According to further embodiments, the stem structure may comprise at least one functional moiety. In one embodiment, the at least one functional moiety is an aptamer sequence. In further embodiments, the aptamer sequence has a high binding affinity to a nuclear localized protein.

According to some embodiments, the nucleotides in the loop are chemically modified with functional groups in order to alter their properties.

According to some embodiments, the loop further comprises one or more aptamers. According to some embodiments, the aptamer is identified from the Apta-index database of aptamers available to the public (aptagen.com/apta-index).

According to some embodiments, the loop further comprises one or more synthetic ribozymes.

According to some embodiments, the loop further comprises one or more antisense oligonucleotides (ASOs).

According to some embodiments, the loop further comprises one or more short-interfering RNAs (siRNAs).

According to some embodiments, the loop further comprises one or more antiviral nucleoside analogues (ANAs).

According to some embodiments, the loop further comprises one or more triplex forming oligonucleotides.

According to some embodiments, the loop further comprises one or more gRNAs or gDNAs.

According to some embodiments, the loop further comprises one or more molecular probes, for example nucleic acid based fluorescent probes.

According to some embodiments, "click" azide-alkyne cycloaddition (Kolb et al., Angew. Chem. Int. Ed. Engl. 2001, 40, 2004-2021) is used to modify the nucleotides in the loop. Click chemistry was developed to join together organic molecules under mild conditions in the presence of a diverse range of functional groups. Most click-mediated modifications are performed on the nitrogenous bases by introducing novel base analogues, attaching fluorophores or isotopic elements for molecular imaging, forming interstrand linkages between oligonucleotides, and for the bioconjugation of molecules. The best example of click chemistry is the $Cu^I$ catalyzed version of Huisgen's [3+2]azide-alkyne cycloaddition reaction (Angew. Chem., Int. Ed. 1963, 2, 633-645), discovered independently by Sharpless and Meldal (the CuAAC reaction) (Angew. Chem., Int. Ed. 2002, 41, 2596-2599).

According to some embodiments, the introduction of active amino or thiol groups into synthesized oligonucleotides provides acceptors for, e.g., subsequent chemical fluorescent labeling.

According to some embodiments, the stem-loop structure may comprise alternative or modified nucleotides, including, but not limited to, ribonucleic acids (RNA), peptide-nucleic acids (PNA), locked nucleic acids (LNA). According to some embodiments, the loop portion of the stem-loop structure may comprise a chemical structure that does not comprise nucleic acids.

ii. 5' End Stem-Loop Structure of ssDNA

As described herein, according to some aspects, the disclosure provides a ssDNA molecule comprising at least one nucleic acid sequence of interest flanked by at least one stem-loop structure at the 3' end, as set forth in detail above. According to some embodiments, the ssDNA molecule further comprises a 5' end, comprising at least one stem-loop structure. According to some embodiments, the DNA structure at the 5' end is the same as the DNA structure at the 3' end. According to some embodiments, the DNA structure at the 5' end is different from the DNA structure at the 3' end.

For example, in some embodiments, the ssDNA described herein may comprise at least one stem-loop structure at the 5' end. According to some embodiments, ssDNA may comprise at least at least two stem-loop structures at the 5' end. According to some embodiments, the ssDNA may comprise at least at least three stem-loop structures at the 5' end. According to some embodiments, the ssDNA may comprise at least at least four stem-loop structures at the 5' end. According to some embodiments, the ssDNA may comprise at least at least five stem-loop structures at the 5' end.

According to some embodiments, the nucleotides at the 5' end form a cruciform DNA structure.

According to some embodiments, the nucleotides at the 5' end form a hairpin structure.

According to some embodiments, the nucleotides at the 5' end form a hammerhead structure.

According to some embodiments, the nucleotides at the 5' end form a quadraplex structure.

According to some embodiments, the nucleotides at the 5' end form a bulging structure.

According to some embodiments, the nucleotides at the 5' end form a multibranched loop.

According to some embodiments, the nucleotides at the 5' end do not form a 2 stem-loop structure. In one embodiment, the nucleotides at the 5' end do not form an AAV ITR structure.

According to some embodiments, at least one stem-loop structure at the 5' end does not comprise the A, A', D, and D' regions that would be present in a wild-type AAV ITR.

According to some embodiments, the at least one stem-loop structure at the 5' end does not comprise the A, A', B, B', C, C', D, and D' regions that would be present in a wild-type AAV ITR.

According to some embodiments, at least one stem-loop structure at the 5' end does not comprise a rep binding element (RBE) that would be present in a wild-type ITR. According to some embodiments, at least one stem-loop structure at the 5' end does not comprise a terminal resolution site (trs) that would be present in a wild-type ITR. According to some embodiments, the at least one stem loop structure at the 5' end is devoid of any viral capsid protein coding sequences.

According to some embodiments, the stem structure at the 5' end comprises one or more nucleotides that are modified to be exonuclease resistant. According to some embodiments, the stem structure at the 5' end comprises two or more, 3 or more, 4 or more, 5 or more, 6 or more, 7 or more, 8 or more, 9 or more, 10 or more, or 20 or more nucleotides that are modified to be exonuclease resistant.

According to some embodiments, the stem structure comprises one or more phosphorothioate-modified nucleotides. According to some embodiments, the stem structure comprises about 4 to about 10 phosphorothioate-modified nucleotides, e.g., about 4 to about 5, about 4 to about 6, about 4 to about 7, about 4 to about 8, about 4 to about 9, about 4 to about 10, about 5 to about 6, about 5 to about 7, about 5 to about 8, about 5 to about 9, about 5 to about 10, about 6 to about 7, about 6 to about 8, about 6 to about 9, about 6 to about 10, about 7 to about 8, about 7 to about 9, about 7 to about 10, about 8 to about 9, about 8 to about 10 or about 9 to about 10. According to some embodiments, the stem structure comprises more than 10 phosphorothioate-modified nucleotides.

According to some embodiments, the phosphorothioate-modified nucleotides are located adjacent to each other. According to some embodiments, the one or more phosphorothioate-modified nucleotides of the are resistant to exonuclease degradation.

According to some embodiments, the loop further comprises one or more nucleic acids or that are used to stabilize the ends. According to other embodiments, the loop further comprises one or more nucleic acids that may be employed in therapeutic methods. According to other embodiments, the loop further comprises one or more nucleic acids that may be employed in diagnostic methods. According to other embodiments, the loop further comprises one or more nucleic acids that that may be employed for research purposes.

According to some embodiments, the nucleotides in the loop are chemically modified with functional groups in order to alter their properties.

According to some embodiments, the loop further comprises one or more aptamers.

According to some embodiments, the aptamer is identified from the Apta-index database of aptamers available to the public (aptagen.com/apta-index).

According to some embodiments, the loop further comprises one or more synthetic ribozymes.

According to some embodiments, the loop further comprises one or more antisense oligonucleotides (ASOs).

According to some embodiments, the loop further comprises one or more short-interfering RNAs (siRNAs).

According to some embodiments, the loop further comprises one or more antiviral nucleoside analogues (ANAs).

According to some embodiments, the loop further comprises one or more triplex forming oligonucleotides.

According to some embodiments, the loop further comprises one or more gRNAs or gDNAs.

According to some embodiments, the loop further comprises one or more molecular probes, for example nucleic acid based fluorescent probes.

According to some embodiments, "click" azide-alkyne cycloaddition (Kolb et al., Angew. Chem. Int. Ed. Engl. 2001, 40, 2004-2021) is used to modify the nucleotides in the loop. Click chemistry was developed to join together organic molecules under mild conditions in the presence of a diverse range of functional groups. Most click-mediated modifications are performed on the nitrogenous bases by introducing novel base analogues, attaching fluorophores or isotopic elements for molecular imaging, forming inter-strand linkages between oligonucleotides, and for the bioconjugation of molecules. The best example of click chemistry is the $Cu^{I}$ catalyzed version of Huisgen's [3+2]azide-alkyne cycloaddition reaction (Angew. Chem., Int. Ed. 1963, 2, 633-645), discovered independently by Sharpless and Meldal (the CuAAC reaction) (Angew. Chem., Int. Ed. 2002, 41, 2596-2599).

According to some embodiments, the introduction of active amino or thiol groups into synthesized oligonucleotides provides acceptors for, e.g., subsequent chemical fluorescent labeling.

According to some embodiments, the stem-loop structure may comprise alternative or modified nucleotides, including, but not limited to, ribonucleic acids (RNA), peptide-nucleic acids (PNA), locked nucleic acids (LNA). According to some embodiments, the loop portion of the stem-loop structure may comprise a chemical structure that does not comprise nucleic acids.

The single-stranded DNA (ssDNA) molecules described herein have no packaging constraints imposed by the limiting space within the viral capsid. This permits the insertion of one or more genetic elements, e.g., a single-stranded enhancer, a single-stranded intron, a single-stranded post-transcriptional regulatory element, a single-stranded poly-adenylation signal, and a single-stranded regulatory switch, large transgenes, multiple transgenes etc.

According to some embodiments, the nucleic acid sequence of interest further comprises at least one single-stranded promoter linked to the at least one nucleic acid sequence of interest.

In other aspects of the disclosure, the single-stranded transgene cassettes find use in gene editing applications, as described in more detail herein.

According to some embodiments, the nucleic acid sequence of interest (also referred to as a transgene herein) encodes a protein that is either absent, inactive, or insufficient activity in the recipient subject or a gene that encodes a protein having a desired biological or a therapeutic effect. The transgene can encode a gene product that can function to correct the expression of a defective gene or transcript. In principle, the expression cassette can include any gene that encodes a protein, polypeptide or RNA that is either reduced or absent due to a mutation or which conveys a therapeutic benefit when overexpressed is considered to be within the scope of the disclosure.

The nucleic acid sequence of interest can comprise any sequence that is useful for treating a disease or disorder in a subject. A ssDNA molecule can be used to deliver and express any gene of interest in the subject, which includes but are not limited to, nucleic acids encoding polypeptides, or non-coding nucleic acids (e.g., RNAi, miRs etc.), as well as exogenous genes and nucleotide sequences, including virus sequences in a subjects' genome, e.g., HIV virus sequences and the like.

In some embodiments, ssDNA molecules disclosed herein are used for therapeutic purposes (e.g., for medical, diagnostic, or veterinary uses). In certain embodiments, ssDNA molecules are useful to express any gene of interest in the subject, which includes one or more polypeptides, peptides, ribozymes, peptide nucleic acids, siRNAs, RNAis, antisense oligonucleotides, antisense polynucleotides, or RNAs (coding or non-coding; e.g., siRNAs, shRNAs, micro-RNAs, mRNA or gRNA, and their antisense counterparts (e.g., antagoMiR), antibodies, antigen binding fragments, or any combination thereof.

Sequences can be codon optimized for the target host cell. As used herein, the term "codon optimized" or "codon optimization" refers to the process of modifying a nucleic acid sequence for enhanced expression in the cells of the vertebrate of interest, e.g., mouse or human, by replacing at least one, more than one, or a significant number of codons of the native sequence (e.g., a prokaryotic sequence) with codons that are more frequently or most frequently used in the genes of that vertebrate. Various species exhibit particular bias for certain codons of a particular amino acid. Typically, codon optimization does not alter the amino acid sequence of the original translated protein. Optimized codons can be determined using e.g., Aptagen's GENE-FORGE® codon optimization and custom gene synthesis platform (Aptagen, Inc., 2190 Fox Mill Rd. Suite 300, Herndon, Va. 20171) or another publicly available database.

In some embodiments, a transgene expressed by the ssDNA molecules is a therapeutic gene. In some embodiments, a therapeutic gene is an antibody, or antibody fragment, or antigen-binding fragment thereof, e.g., a neutralizing antibody or antibody fragment and the like.

In particular, a therapeutic gene is one or more therapeutic agent(s), including, but not limited to, for example, protein(s), polypeptide(s), peptide(s), enzyme(s), antibodies, antigen binding fragments, as well as variants, and/or active fragments thereof, for use in the treatment, prophylaxis, and/or amelioration of one or more symptoms of a disease, dysfunction, injury, and/or disorder. Exemplary therapeutic genes are described herein in the section entitled "Method of Treatment".

According to any of the above aspects and embodiments, the ssDNA molecules are synthetically produced.

According to any of the above aspects and embodiments, the ssDNA molecules are devoid of any viral capsid protein coding sequences.

According to any of the above aspects the DNA is peptide nucleic acid (PNA) are synthetic mimics of DNA.

As described herein, the present disclosure relates to single-stranded (ssDNA) molecules. In some aspects, the ssDNA molecules are, e.g., synthetic AAV vectors, e.g., single-stranded (ss) synthetic AAV vectors, produced from double stranded closed-ended DNA comprising phosphorothioate (PS) bonds. The PS bond substitutes a sulfur atom for non-bridging oxygen in the phosphate backbone of an oligonucleotide. Advantageously, this modification renders the internucleotide linkage resistant to nuclease degradation and provides accuracy for targeting of the exonuclease.

In some aspects, the disclosure provides a single-stranded transgene cassette comprising at least one single-stranded transgene and at least one inverted terminal repeat (ITR) comprising one or more phosphorothioate-modified nucleotides. According to some embodiments, a ssDNA molecule comprises a first ITR and an optional second ITR; wherein at least one of the first ITR and the optional second ITR comprises one or more phosphorothioate-modified nucleotides. In further embodiments, the ssDNA molecule comprises a 3' terminal fragment that comprises a terminal resolution site (trs) sequence.

According to some aspects, the disclosure provides an isolated, linear, and single-stranded DNA (ssDNA) molecule comprising a single-stranded transgene cassette comprising at least one single-stranded transgene; and a first inverted terminal repeat (ITR) and a second ITR that each flanks the at least one single-stranded transgene cassette; wherein at least one of the first ITR and the second ITR comprises one or more phosphorothioate-modified nucleotides.

As described in more detail herein, the ssDNA molecule is synthetically produced in vitro from dsDNA comprising phosphorothioate (PS) bonds ("starting material") by removing one DNA strand from a specific nicking site and to a PS bonded site of the dsDNA. According to further embodiments, the ssDNA molecule is synthetically produced in vitro in a cell-free environment.

According to some embodiments, it is a feature of the present disclosure that the 3' terminal portion of the double stranded DNA molecule (starting material) comprises a nickase recognition sequence. In one embodiment, the 3' terminal portion of the dsDNA molecule comprises the sequence 5'-CCAA-3'. In some embodiments the 3' terminal portion of the dsDNA molecule comprises any one or more of the sequences shown in Table 8 below. Further, since these are unique sequences after a double stranded ceDNA with special engineered nick sites has been nicked by a nicking endonuclease as shown in the table, resultant ssDNA molecules also comprise any one or more of the sequences shown in Table 8 below in its 3' terminal fragment.

TABLE 8

| Sequence | Nicking Endonuclease |
|---|---|
| 5'-CCAA-3' | (Nb.BtsI) (Nb.BsrDI) (Nt.CviPII) |
| 5'-CCAAGC-3' | (Nb.BbvCI) |
| 5'-CCAACC-3' | (Nt.BbvCI) |
| 5'-CCAAGAGTCNNNN-3' | (Nt.BstNBI)-N can be A, G, C, or T |
| 5'-CCAAG-3' | (Nb.BsmI) |
| 5'-CCAAC-3' | (Nb.BssSI) |
| 5'-CCAAGGATCNNNN-3' | (Nt.AlwI) |
| 5'-CCAAGTCTCN-3' | (Nt.BsmAI) |
| 5'-CCAAGCTCTTCN-3' (SEQ ID NO: 9) | (Nt.BspQI) |

According to some embodiments, the 3' terminal fragment of the ssDNA molecule comprises a terminal residue that is hydroxylated (—OH) such that it enables polymerase activity once the ssDNA is transported to the nucleus of a host cell in which the ssDNA get convert to regenerated dsDNA that is capable of being expressed.

According to some embodiments, the ssDNA molecule comprises a 3' terminal fragment that comprises a terminal resolution site (trs) sequence.

The ssDNA molecule described herein is capable of being transported across the nuclear membrane from the cytosol into the nucleus of a host cell and reached upon by host cell DNA polymerase to generate a double stranded DNA ("regenerated dsDNA) for expression of the transgene in the host cell. Accordingly, in some embodiments, the terminal residue that is hydroxylated (—OH) in the ssDNA molecule is critical to be responsive towards DNA polymerase activity inside the nucleus of a host cell. According to further embodiments, the DNA polymerase generates a dsDNA molecule.

Importantly, the ssDNA molecule does not activate or minimally activates an innate immune pathway inside a host cell. As used herein the term "the innate immune response" refers to the cellular pathways that respond to pathogen associated molecular patterns and activate a defense response through the RIG-I-like receptors, the toll-like receptors, or other pathogen associated molecular pattern receptors to activate interferon, NF-kappa-B, STAT, IRF and other response pathways that protect against pathogen infection. According to some embodiments, the innate immune pathway may be the cGAS/STING pathway, the TLR9 pathway, an inflammasome-mediated pathway, or a combination thereof. Indicators of the activation of the innate immune response include increased expression and/or phosphorylation of IRF family members, increased expression of the RIG-I like receptors, and increased expression of interferons and/or chemokines.

According to some embodiments, the single-stranded transgene cassette further comprises at least one single-stranded promoter operably linked to the at least one single-stranded transgene; and the dsDNA molecule comprises a regenerated double-stranded expression cassette comprising at least one regenerated double-stranded transgene and at least one double-stranded promoter operably linked to the regenerated double-stranded transgene to control expression of the at least one regenerated double-stranded transgene. The double-stranded expression cassette is capable of being expressed in a host cell, for example a host cell in vivo. In some embodiments, the double-stranded expression cassette is capable of being expressed into at least one therapeutic protein or a fragment thereof.

In further embodiments, the single-stranded transgene cassette further comprises one or more genetic elements selected from the group consisting of a single-stranded enhancer, a single-stranded intron, a single-stranded post-transcriptional regulatory element, a single-stranded poly-adenylation signal, and a single-stranded regulatory switch.

In other aspects of the disclosure, the single-stranded transgene cassettes find use in gene editing applications.

Accordingly, in some embodiments, the at least one single-stranded transgene cassette is a promoterless transgene cassette; and the dsDNA molecule comprises at least one regenerated promoterless double-stranded transgene. In some embodiments, at least one regenerated promoterless double-stranded transgene is capable of being inserted at a target locus in the genome of a host cell. In further embodiments, the at least one regenerated promoterless double-stranded transgene is capable of being inserted at a target locus in the genome of a host cell in vivo. In some embodiments, the at least one regenerated promoterless double-stranded transgene is capable of being inserted at the target locus to replace or to supplement at least one target gene. In other embodiments, at least one regenerated promoterless double-stranded transgene is capable of being inserted at the target locus via homology-directed recombination (HDR) or microhomology-mediated end joining (MMEJ). In other further embodiments, the at least one single-stranded transgene is a single-stranded donor sequence; and the single-stranded transgene cassette further comprises a single-stranded 5' homology arm and a single-stranded 3' homology arm flanking the single-stranded donor sequence. The single-stranded 5' homology arm and the single-stranded 3' homology arm are each between about 10 to 2000 nt in length, for example about 100 to 2000 nt in length or about 1000 to 2000 nt in length, or about 10 to 1000 nt in length, for example about 100 to 1000 nt in length or about 10 to 500 nt in length, about 50 to 500 nt in length or about 100 to 500 nt in length, about 10 to 50 nt in length, about 50 to 500 nt in length or about 500 to 1000 nt in length, about 500 to 1500 nt in length, about 1500 to 2000 nt in length, about 2 to 1000 nt in length, about 2 to 500 nt in length, about 2 to 100 nt in length, or about 2 to 50 nt in length. In some embodiments, at least one regenerated promoterless double-stranded transgene is capable of being inserted at the target locus via non-homology end joining (NHEJ). In some embodiments, the at least one single-stranded transgene is a single-stranded donor sequence; and the single-stranded transgene cassette is devoid of a single-stranded 5' homology arm and a single-stranded 3' homology arm. In other embodiments, the single-stranded transgene cassette is cleavable and further comprises at least a first single-stranded guide RNA (gRNA) target sequence (TS); at least a first single-stranded protospacer adjacent motif (PAM); at least a second single-stranded gRNA TS; and at least a second single-stranded PAM.

As described in more detail herein, in some embodiments, the ssDNA molecule described herein is synthetically produced from the dsDNA construct by a method comprising a) contacting the dsDNA construct with one or more nicking endonucleases that nick one of the single strands of the dsDNA construct at one or more nick sites; and b) contacting the dsDNA construct with an exonuclease capable of removing nucleotides from the nicked strand of the dsDNA construct to thereby produce the ssDNA molecule.

ssDNA molecules are further described in PCT Publication No. WO 2024/119017 and PCT Application No. PCT/US2024/032649, filed on Jun. 5, 2024, the entire contents of which are incorporated herein by reference.

B. Closed-Ended DNA (ceDNA) Vectors

In some embodiments, LNPs provided by the present disclosure comprise a therapeutic nucleic acid, wherein the therapeutic nucleic acid is a closed-ended DNA (ceDNA).

In some embodiments, the TNA comprises closed-ended linear duplexed (ceDNA) vectors that can express a transgene (e.g., a therapeutic nucleic acid (TNA)). The ceDNA vectors as described herein have no packaging constraints imposed by the limiting space within the viral capsid. ceDNA vectors represent a viable eukaryotically-produced alternative to prokaryote-produced plasmid DNA vectors, as opposed to encapsulated AAV genomes. This permits the insertion of control elements, e.g., regulatory switches as disclosed herein, large transgenes, multiple transgenes etc.

ceDNA vectors preferably have a linear and continuous structure rather than a non-continuous structure. The linear and continuous structure is believed to be more stable from attack by cellular endonucleases, as well as less likely to be recombined and cause mutagenesis. Thus, a ceDNA vector in the linear and continuous structure is a preferred embodiment. The continuous, linear, single strand intramolecular duplex ceDNA vector can have covalently bound terminal ends, without sequences encoding AAV capsid proteins. These ceDNA vectors are structurally distinct from plasmids (including ceDNA plasmids described herein), which are circular duplex nucleic acid molecules of bacterial origin. The complimentary strands of plasmids may be separated following denaturation to produce two nucleic acid molecules, whereas in contrast, ceDNA vectors, while having complimentary strands, are a single DNA molecule and therefore even if denatured, it is likely to remain a single molecule. In some embodiments, ceDNA vectors can be produced without DNA base methylation of prokaryotic type, unlike plasmids. Therefore, the ceDNA vectors and ceDNA-plasmids are different both in term of structure (in particular, linear versus circular) and also in view of the methods used for producing and purifying these different objects, and also in view of their DNA methylation which is of prokaryotic type for ceDNA-plasmids and of eukaryotic type for the ceDNA vector.

Provided herein are non-viral, capsid-free ceDNA molecules with covalently closed ends (ceDNA). These non-viral capsid free ceDNA molecules can be produced in permissive host cells from an expression construct (e.g., a ceDNA-plasmid, a ceDNA-bacmid, a ceDNA-baculovirus, or an integrated cell-line) containing a heterologous gene (e.g., a transgene, in particular a therapeutic transgene) positioned between two different inverted terminal repeat (ITR) sequences, where the ITRs are different with respect to each other. In some embodiments, one of the ITRs is modified by deletion, insertion, and/or substitution as compared to a wild-type ITR sequence (e.g., AAV ITR); and at least one of the ITRs comprises a functional terminal resolution site (trs) and a Rep binding site. The ceDNA vector is preferably duplex, e.g., self-complementary, over at least a portion of the molecule, such as the expression cassette (e.g., ceDNA is not a double stranded circular molecule). The ceDNA vector has covalently closed ends, and thus is resistant to exonuclease digestion (e.g., exonuclease I or exonuclease III), for over an hour at 37° C.

In one aspect, a ceDNA vector comprises, in the 5' to 3' direction: a first adeno-associated virus (AAV) inverted terminal repeat (ITR), a nucleotide sequence of interest (for example an expression cassette as described herein) and a second AAV ITR. In one embodiment, the first ITR (5' ITR) and the second ITR (3' ITR) are asymmetric with respect to each other—that is, they have a different 3D-spatial configuration from one another. As an exemplary embodiment, the first ITR can be a wild-type ITR and the second ITR can be a mutated or modified ITR, or vice versa, where the first ITR can be a mutated or modified ITR and the second ITR a wild-type ITR. In one embodiment, the first ITR and the second ITR are both modified but are different sequences, or have different modifications, or are not identical modified ITRs, and have different 3D spatial configurations. Stated differently, a ceDNA vector with asymmetric ITRs have ITRs where any changes in one ITR relative to the WT-ITR are not reflected in the other ITR; or alternatively, where the asymmetric ITRs have a the modified asymmetric ITR pair can have a different sequence and different three-dimensional shape with respect to each other.

In one embodiment, a ceDNA vector comprises, in the 5' to 3' direction: a first adeno-associated virus (AAV) inverted terminal repeat (ITR), a nucleotide sequence of interest (for example an expression cassette as described herein) and a second AAV ITR, where the first ITR (5' ITR) and the second ITR (3' ITR) are symmetric, or substantially symmetrical with respect to each other—that is, a ceDNA vector can comprise ITR sequences that have a symmetrical three-dimensional spatial organization such that their structure is the same shape in geometrical space, or have the same A, C-C' and B-B' loops in 3D space. In such an embodiment, a symmetrical ITR pair, or substantially symmetrical ITR pair can be modified ITRs (e.g., mod-ITRs) that are not wild-type ITRs. A mod-ITR pair can have the same sequence which has one or more modifications from wild-type ITR and are reverse complements (inverted) of each other. In one embodiment, a modified ITR pair are substantially symmetrical as defined herein, that is, the modified ITR pair can have a different sequence but have corresponding or the same symmetrical three-dimensional shape. In some embodiments, the symmetrical ITRs, or substantially symmetrical ITRs can be wild type ITRs (WT-ITRs) as described herein. That is, both ITRs have a wild-type sequence from the same AAV serotype. In some other embodiments, the two wild-type ITRs can be from different AAV serotypes. For example, one WT-ITR can be from one AAV serotype, and the other WT-ITR can be from a different AAV serotype. In such an embodiment, a WT-ITR pair are substantially symmetrical as defined herein, that is, they can have one or more conservative nucleotide modification while still retaining the symmetrical three-dimensional spatial organization.

The wild-type or mutated or otherwise modified ITR sequences provided herein represent DNA sequences included in the expression construct (e.g., ceDNA-plasmid, ceDNA Bacmid, ceDNA-baculovirus) for production of the ceDNA vector. Thus, ITR sequences actually contained in the ceDNA vector produced from the ceDNA-plasmid or other expression construct may or may not be identical to the ITR sequences provided herein as a result of naturally occurring changes taking place during the production process (e.g., replication error).

In one embodiment, a ceDNA vector in the LNPs of the present disclosure comprising the expression cassette with a transgene which is a therapeutic nucleic acid sequence, can be operatively linked to one or more regulatory sequence(s) that allows or controls expression of the transgene. In one embodiment, the polynucleotide comprises a first ITR sequence and a second ITR sequence, wherein the nucleotide sequence of interest is flanked by the first and second ITR sequences, and the first and second ITR sequences are asymmetrical relative to each other, or symmetrical relative to each other.

In one embodiment, an expression cassette is located between two ITRs in the following order with one or more of: a promoter operably linked to a transgene, a posttranscriptional regulatory element, and a polyadenylation and termination signal. In one embodiment, the promoter is regulatable inducible or repressible. The promoter can be any sequence that facilitates the transcription of the transgene. In one embodiment the promoter is a CAG promoter, or variation thereof. The posttranscriptional regulatory element is a sequence that modulates expression of the transgene, as a non-limiting example, any sequence that creates a tertiary structure that enhances expression of the transgene which is a therapeutic nucleic acid sequence.

In one embodiment, the posttranscriptional regulatory element comprises WPRE. In one embodiment, the polyadenylation and termination signal comprise BGHpolyA. Any cis regulatory element known in the art, or combination thereof, can be additionally used e.g., SV40 late polyA signal upstream enhancer sequence (USE), or other posttranscriptional processing elements including, but not limited to, the thymidine kinase gene of herpes simplex virus, or hepatitis B virus (HBV). In one embodiment, the expression cassette length in the 5' to 3' direction is greater than the maximum length known to be encapsidated in an AAV virion. In one embodiment, the length is greater than 4.6 kb, or greater than 5 kb, or greater than 6 kb, or greater than 7 kb. Various expression cassettes are exemplified herein.

In one embodiment, the expression cassette can comprise more than 4000 nucleotides, 5000 nucleotides, 10,000 nucleotides or 20,000 nucleotides, or 30,000 nucleotides, or 40,000 nucleotides or 50,000 nucleotides, or any range between about 4000-10,000 nucleotides or 10,000-50,000 nucleotides, or more than 50,000 nucleotides. In some embodiments, the expression cassette can comprise a transgene which is a therapeutic nucleic acid sequence in the range of 500 to 50,000 nucleotides in length. In one embodiment, the expression cassette can comprise a transgene which is a therapeutic nucleic acid sequence in the range of 500 to 75,000 nucleotides in length. In one embodiment, the expression cassette can comprise a transgene which is a therapeutic nucleic acid sequence in the range of 500 to 10,000 nucleotides in length. In one embodiment, the expression cassette can comprise a transgene which is a therapeutic nucleic acid sequence in the range of 1000 to 10,000 nucleotides in length. In one embodiment, the expression cassette can comprise a transgene which is a therapeutic nucleic acid sequence in the range of 500 to 5,000 nucleotides in length. The ceDNA vectors do not have the size limitations of encapsidated AAV vectors, and thus enable delivery of a large-size expression cassette to the host. In one embodiment, the ceDNA vector is devoid of prokaryote-specific methylation.

In one embodiment, the rigid therapeutic nucleic acid can be a plasmid.

In one embodiment, the ceDNA vectors disclosed herein are used for therapeutic purposes (e.g., for medical, diagnostic, or veterinary uses) or immunogenic polypeptides.

The expression cassette can comprise any transgene which is a therapeutic nucleic acid sequence. In certain embodiments, the ceDNA vector comprises any gene of interest in the subject, which includes protein, enzyme, one or more polypeptides, peptides, ribozymes, peptide nucleic acids, siRNAs, gRNA, mRNA, RNAis, antisense oligonucleotides, antisense polynucleotides, antibodies, antigen binding fragments, or any combination thereof.

In one embodiment, the ceDNA expression cassette can include, for example, an expressible exogenous sequence (e.g., open reading frame) that encodes a protein that is either absent, inactive, or insufficient activity in the recipient subject or a gene that encodes a protein having a desired biological or a therapeutic effect. In one embodiment, the exogenous sequence such as a donor sequence can encode a gene product that can function to correct the expression of a defective gene or transcript. In one embodiment, the expression cassette can also encode corrective DNA strands, encode polypeptides, sense or antisense oligonucleotides, or RNAs (coding or non-coding; e.g., siRNAs, shRNAs, micro-RNAs, and their antisense counterparts (e.g., antagoMiR). In one embodiment, expression cassettes can include an exogenous sequence that encodes a reporter protein to be used for experimental or diagnostic purposes, such as β-lactamase, β-galactosidase (LacZ), alkaline phosphatase, thymidine kinase, green fluorescent protein (GFP), chloramphenicol acetyltransferase (CAT), luciferase, and others well known in the art.

Accordingly, the expression cassette can include any gene that encodes a protein, polypeptide or RNA that is either reduced or absent due to a mutation or which conveys a therapeutic benefit when overexpressed is considered to be within the scope of the disclosure. The ceDNA vector may comprise a template or donor nucleotide sequence used as a correcting DNA strand to be inserted after a double-strand break (or nick) provided by a nuclease. The ceDNA vector may include a template nucleotide sequence used as a correcting DNA strand to be inserted after a double-strand break (or nick) provided by a guided RNA nuclease, meganuclease, or zinc finger nuclease.

IV. Preparation of Lipid Nanoparticles (LNPs)

Lipid nanoparticles (LNPs) can form spontaneously upon mixing of a therapeutic nucleic acid (e.g., ceDNA, ssDNA, synthetic AAV, etc., as described herein) and a pharmaceutically acceptable excipient that comprises a lipid.

Generally, LNPs can be formed by any method known in the art. For example, the LNPs can be prepared by the methods described, for example, in US2013/0037977, US2010/0015218, US2013/0156845, US2013/0164400, US2012/0225129, and US2010/0130588, content of each of which is incorporated herein by reference in its entirety. In some embodiments, LNPs can be prepared using a continuous mixing method, a direct dilution process, or an in-line dilution process. The processes and apparatuses for preparing lipid nanoparticles using direct dilution and in-line dilution processes are described in US2007/0042031, the content of which is incorporated herein by reference in its entirety. The processes and apparatuses for preparing lipid nanoparticles using step-wise dilution processes are described in US2004/0142025, the content of which is incorporated herein by reference in its entirety.

According to some embodiments, the disclosure provides for an LNP comprising a DNA vector, including a ceDNA vector, ssDNA vector, or synthetic AAV, as described herein and an ionizable lipid. For example, a lipid nanoparticle formulation that is made and loaded with therapeutic nucleic acid like ceDNA obtained by the process as disclosed in International Patent Application No. PCT/US2018/050042, filed on Sep. 7, 2018, which is incorporated by reference in its entirety herein. This can be accomplished by high energy mixing of ethanolic lipids with aqueous ceDNA, ssDNA or mRNA at low pH which protonates the ionizable lipid and provides favorable energetics for synthetic AAV/lipid association and nucleation of particles. The particles can be further stabilized through aqueous dilution and removal of the organic solvent. The particles can be concentrated to the desired level.

Generally, the lipid particles are prepared at a total lipid to synthetic ceDNA, ssDNA or mRNA (mass or weight) ratio of from about 10:1 to 30:1. In some embodiments, the lipid to ssDNA molecule or the dsDNA construct ratio (mass/mass ratio; w/w ratio) can be in the range of from about 1:1 to about 25:1, from about 10:1 to about 14:1, from about 3:1 to about 15:1, from about 4:1 to about 10:1, from about 5:1 to about 9:1, or about 6:1 to about 9:1. The amounts of lipids and synthetic ceDNA, ssDNA or mRNA can be adjusted to provide a desired N/P ratio, for example, N/P ratio of 3, 4, 5, 6, 7, 8, 9, 10 or higher. Generally, the lipid particle formulation's overall lipid content can range from about 5 mg/ml to about 30 mg/mL.

The ionizable lipid is typically employed to condense the nucleic acid cargo at low pH and to drive membrane association and fusogenicity. Generally, ionizable lipids are lipids comprising at least one amino group that is positively charged or becomes protonated under acidic conditions, for example at pH of 6.5 or lower.

In one embodiment, the LNPs can be prepared by an impinging jet process. Generally, the particles are formed by mixing lipids dissolved in alcohol (e.g., ethanol) with ceDNA, ssDNA or mRNA dissolved in a buffer, e.g., a citrate buffer, a sodium acetate buffer, a sodium acetate and magnesium chloride buffer, a malic acid buffer, a malic acid and sodium chloride buffer, or a sodium citrate and sodium chloride buffer. The mixing ratio of lipids to ceDNA, ssDNA or mRNA can be about 45-55% lipid and about 65-45% ceDNA, ssDNA or mRNA.

The lipid solution can contain an ionizable lipid, a ceramide, a lipid-anchored polymer and a sterol (e.g., cholesterol) at a total lipid concentration of 5-30 mg/mL, more likely 5-15 mg/mL, most likely 9-12 mg/mL in an alcohol, e.g., in ethanol. In the lipid solution, mol ratio of the lipids can range from about 25-98% for the cationic lipid, preferably about 35-65%; about 0-15% for the non-ionic lipid, preferably about 0-12%; about 0-15% for the PEG or PEG conjugated lipid molecule, preferably about 1-6%; and about 0-75% for the sterol, preferably about 30-50%.

The ceDNA solution can comprise the ceDNA at a concentration range from 0.3 to 1.0 mg/mL, preferably 0.3-0.9 mg/mL in buffered solution, with pH in the range of 3.5-5.

For forming the LNPs, in one exemplary but nonlimiting embodiment, the two liquids are heated to a temperature in the range of about 15-40° C., preferably about 30-40° C., and then mixed, for example, in an impinging jet mixer, instantly forming the LNP. The mixing flow rate can range from 10-600 mL/min. The tube ID can have a range from 0.25 to 1.0 mm and a total flow rate from 10-600 mL/min. The combination of flow rate and tubing ID can have the effect of controlling the particle size of the LNPs between 30 and 200 nm. The solution can then be mixed with a buffered solution at a higher pH with a mixing ratio in the range of 1:1 to 1:3 vol:vol, preferably about 1:2 vol:vol. If needed this buffered solution can be at a temperature in the range of 15-40° C. or 30-40° C. The mixed LNPs can then undergo an anion exchange filtration step. Prior to the anion exchange, the mixed LNPs can be incubated for a period of time, for example 30 mins to 2 hours. The temperature during incubation can be in the range of 15-40° C. or 30-40° C. After incubating the solution is filtered through a filter, such as a 0.8 μm filter, containing an anion exchange separation step. This process can use tubing IDs ranging from 1 mm ID to 5 mm ID and a flow rate from 10 to 2000 m/min.

After formation, the LNPs can be concentrated and diafiltered via an ultrafiltration process where the alcohol is removed and the buffer is exchanged for the final buffer solution, for example, phosphate buffered saline (PBS) at about pH 7, e.g., about pH 6.9, about pH 7.0, about pH 7.1, about pH 7.2, about pH 7.3, or about pH 7.4.

The ultrafiltration process can use a tangential flow filtration format (TFF) using a membrane nominal molecular weight cutoff range from 30-500 kD. The membrane format is hollow fiber or flat sheet cassette. The TFF processes with the proper molecular weight cutoff can retain the LNP in the retentate and the filtrate or permeate contains the alcohol; citrate buffer and final buffer wastes. The TFF process is a multiple step process with an initial concentration to a ceDNA concentration of 1-3 mg/mL. Following concentration, the LNPs solution is diafiltered against the final buffer for 10-20 volumes to remove the alcohol and perform buffer exchange. The material can then be concentrated an additional 1-3-fold. The concentrated LNP solution can be sterile filtered.

Targeting Moieties

The present disclosure provides bispecific stealth targeting lipid nanoparticles (LNPs) and LNP compositions (e.g., pharmaceutical compositions) comprising a therapeutic nucleic acid (TNA), e.g., a gene expression vector or a gene/base editing template, such as closed-ended double stranded DNA (ceDNA), single stranded DNA (ssDNA), siRNA, or messenger RNA (mRNA), wherein the LNP comprises an ionizable lipid; with or without a "helper" lipid; a structural lipid, e.g., a sterol; and one or more types of lipid-anchored polymers comprising a polymer (e.g., PEG or polyglycerol), a lipid moiety with at least one hydrophobic tail with 16-22 carbon atoms in a single aliphatic chain backbone and a linker connecting the polymer to the lipid moiety. Moreover, the disclosed bispecific LNP compositions can further comprise two or more targeting moieties such as single chain fragment variable region (scFv) and/or single domain antibody (VHH) linked to the LNP, wherein each scFv or VHH is specific for an antigen present on the surface of a cell (e.g., an HSC, a tumor cell, T-cell, B-cell, NK cell, etc.), thereby increasing the targeting specificity of the stealth LNP to a desired tissue or cell-type. The bispecific stealth targeting LNP compositions described herein advantageously provide efficient covalent conjugation with minimal or no unexpected effects on blood pharmacokinetics (PK), particle size and stability as compared to unconjugated stealth LNPs. It is a finding of the present disclosure that DBCO mediated conjugation (via "Click chemistry") or maleimide conjugation (via thiol—maleimide reaction) between each targeting moiety (e.g., scFv or VHH) and the lipid-anchored polymer present on the surface of the stealth LNP resulted in robust linkages that maintained the physiochemical characteristics of the bispecific stealth LNPs, and the resultant stealth LNPs comprising two or more targeting moieties effectively demonstrated highly increased specificity and targeting efficiency to a desired cell-type in vivo.

The present disclosure also provides a bispecific stealth LNP composition comprising a lipid-anchored polymer (i.e., second and third lipid-anchored polymers) comprising a reactive species (e.g., maleimide, azide, etc.) capable of reacting with a targeting moiety functionalized with thiol (—SH) or dibenzocyclooctyne (DBCO) reactive species, respectively, such that the stealth LNP encapsulating a TNA can be readily reacted with the targeting moiety having a specificity to a desired target.

Targeting moieties may be conjugated to LNPs via the lipid-anchored polymers described herein using any of a variety of conjugation methods known in the art. In one embodiment, an LNP comprises lipid-anchored polymers comprising a single type of reactive moiety (e.g., maleimide), and both targeting moieties comprise the same type of reactive moiety (e.g., thiol) that reacts with the reactive moiety on the lipid-anchored polymers to create a covalent linkage. In another embodiment, an LNP comprises lipid-anchored polymers with two different types of reactive moieties (e.g., maleimide and DBCO), while the two targeting moieties each comprise the two different corresponding reactive moieties (e.g., thiol and azide).

V. Chimeric Antigen Receptor (CAR) T Cells

The present disclosure contemplates the use of stealth targeting LNPs and TNA of the present disclosure in CAR T-therapy. According to some embodiments, the disclosure provides stealth targeting pharmaceutical compositions comprising stealth targeting LNPs encapsulating one or more TNA (ceDNA, ssDNA, siRNA, and/or mRNA) that target T cell at increased levels of efficiency in vivo or ex vivo to transform immune effector cells (e.g., T cells, B cells, dendritic cells, or NK cells) and to express a CAR wherein the CAR T cell exhibits an antitumor property. The immune effector cells (e.g., T cells, B cells, or NK cells) provided herein can be genetically modified, e.g., by transfection or transduction, to express a ceDNA, ssDNA, or mRNA encoding a CAR described herein.

According to some embodiments, the present disclosure encompasses a recombinant DNA construct comprising sequences encoding a CAR, wherein the CAR comprises an antigen binding domain (e.g., antibody or antibody fragment, TCR or TCR fragment) that binds specifically to a cancer associated antigen described herein, wherein the sequence of the antigen binding domain is contiguous with and in the same reading frame as a nucleic acid sequence encoding an intracellular signaling domain. The intracellular signaling domain can comprise a costimulatory signaling domain and/or a primary signaling domain, e.g., a zeta chain. The costimulatory signaling domain refers to a portion of the CAR comprising at least a portion of the intracellular domain of a costimulatory molecule.

According to some embodiments, an exemplary CAR construct comprises an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), and an intracellular stimulatory domain (e.g., an intracellular stimulatory domain described herein). In some aspects, an exemplary ceDNA encoding a CAR comprises an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), an intracellular costimulatory signaling domain (e.g., a costimulatory signaling domain described herein) and/or an intracellular primary signaling domain (e.g., a primary signaling domain described herein).

According to some embodiments, the present disclosure encompasses a recombinant nucleic acid construct comprising a ceDNA, ssDNA or mRNA encoding a CAR, wherein the ceDNA, ssDNA or mRNA comprises the nucleic acid sequence encoding an antigen binding domain, e.g., described herein, that is contiguous with and in the same reading frame as a nucleic acid sequence encoding an intracellular signaling domain.

According to some embodiments, the present disclosure encompasses a recombinant nucleic acid construct comprising a ceDNA, ssDNA or mRNA encoding a CAR, wherein the ceDNA comprises a nucleic acid sequence encoding an antigen binding domain, wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, e.g., CD3-zeta, CD28, CD27, 4-1BB, and the like. In some instances, the CAR can comprise any combination of CD3-zeta, CD28, 4-1BB, and the like.

The nucleic acid sequences coding for the desired molecules can be obtained using recombinant methods known in the art, such as, for example by screening libraries from cells expressing the nucleic acid molecule, by deriving the nucleic acid molecule from a vector known to include the same, or by isolating directly from cells and tissues containing the same, using standard techniques. Alternatively, the ceDNA, ssDNA or mRNA of interest can be produced synthetically, rather than cloned.

The present disclosure includes AAV, retroviral and lentiviral vector constructs expressing a CAR that can be directly transduced into a cell.

The present disclosure also includes an RNA construct that can be encapsulated into LNP disclosed herein. A method for generating mRNA for use in transfection involves in vitro transcription (IVT) of a template with specially designed primers, followed by polyA addition, to produce a construct containing 5' and 3' untranslated sequence "UT") (e.g., a 3' and/or 5' "UTR", as described herein), a 5' cap (e.g., a 5' cap described herein) and/or Internal Ribosome Entry Site (IRES) (e.g., an IRES described herein), the nucleic acid to be expressed, and a polyA tail, typically 50-2000 bases in length. RNA so produced can efficiently transfect different kinds of cells.

According to some embodiments, the template includes sequences for the CAR. In an embodiment, an RNA CAR vector is transduced into a cell, e.g., a T cell or a NK cell, by electroporation.

A. Antigen Binding Domains

According to some aspects, the CAR-mediated T-cell response can be directed to an antigen of interest by way of engineering an antigen binding domain that specifically binds a desired antigen into the CAR using ceDNA, ssDNA or mRNA as described herein.

According to some aspects, the portion of the CAR comprising the antigen binding domain comprises an antigen binding domain that targets a tumor antigen, e.g., a tumor antigen described herein.

According to some embodiments, the CAR of the disclosure comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Thus, examples of ceil surface markers that may act as ligands for the antigen moiety domain in the CAR of the disclosure include those associated with viral, bacterial and parasitic infections, autoimmune disease and cancer cells.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, e.g., single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

Tumor antigens are proteins that are produced by tumor cells that elicit an immune response, particularly T-cell mediated immune responses. The selection of the antigen binding moiety of the disclosure will depend on the particular type of cancer to be treated, Tumor antigens are well known in the art and include, for example, a glioma-associated antigen, carcinoembryonic antigen (CEA), β-human chorionic gonadotropin (HCG), alpha-fetoprotein (AFP), lectin-reactive AFP, thyroglobulin, RAGE-1, MN-CA IX, human telomerase reverse transcriptase, RU1, RU2 (AS), intestinal carboxylesterase, mut hsp70-2, M-CSF, prostase, prostate-specific antigen (PSA), PAP, NY-ESO-1, LAGE-1a, p53, prostein, PSMA, Her2/neu, survivin, telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

According to some embodiments, the tumor antigen comprises one or more antigenic cancer epitopes associated with a malignant tumor. Malignant tumors express a number of proteins that can serve as target antigens for an immune attack. For example, these molecules include but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen encompassed by the present disclosure may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond, or they may be antigens that are normally present at extremely low levels on normal cells, but which are expressed at much higher levels on tumor cells.

Non-limiting examples of TSA or TAA antigens include, but are not limited, the following: Differentiation antigens such as MART-1/MelanA (MART-1), g100(Pme117), tyrosinase, TRP-1, TRP-2 and tumor-specific multilineage antigens such as MAGE-1, MAGE-3, BAGE, GAGE-1, GAGE-2, pi5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, 1GH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA19-9, CA72-4, CAM17.1, NuMa, K-ras, beta-Catenin, CDK4, Mum-1, p15, p16, 43-9F, 5T4(791Tgp72) alpha-fetoprotein, beta-HCG, BCA225, BTAA, CA 125, CA 15-3\CA 27.29\BCAA, CA 195, CA 242, CA-50, CAM43, CD68\I, CO-029, FGF-5, G250, Ga733VEpCAM, HTgp-175, M344, MA-50, MG7-Ag, MOV18, NB/70K, NY-CO-1, RCAS1, SDCCAG16, TA-90\Mac-2 binding protein A, cyclophilin C-associated protein, TAAL6, TAG72, TLP, and TPS.

In a preferred embodiment, the antigen binding moiety portion of the CAR targets an antigen that includes but is not limited to CD19, CD20, CD22, ROR 1, Mesothelin, CD33/IL3R$^{a}$, c-Met, PSMA, Glycolipid F77, EGFRvIII, GD-2, NY-ESO-1 TCR, MAGE A3 TCR, and the like.

Depending on the desired antigen to be targeted, the CAR of the disclosure can be engineered to include the appropriate antigen bind moiety that is specific to the desired antigen target.

According to some embodiments, the antigen binding domain is a multi-specific antibody molecule (e.g., a bispecific or trispecific antibody). According to some embodiments, the multi-specific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. Protocols for generating multi-specific antibody molecules are known in the art.

B. Transmembrane Domain

According to some embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In some aspects, the transmembrane domain is one that is associated with one of the other domains of the CAR e.g., According to some embodiments, the transmembrane domain may be from the same protein that the signaling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In some aspects, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

The transmembrane domain may be derived either from a natural or from a recombinant source. Where the source is natural, the domain may be derived from any membrane-bound or transmembrane protein. In some aspects, the transmembrane domain is capable of signaling to the intracellular domain(s) whenever the CAR has bound to a target. A transmembrane domain of particular use in this disclosure may include at least the transmembrane region(s) of e.g., the alpha, beta or zeta chain of the T-cell receptor, CD28, CD27, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R alpha, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C.

According to some embodiments, the transmembrane domain can be attached to the extracellular region of the CAR, e.g., the antigen binding domain of the CAR, via a hinge, e.g., a hinge from a human protein. For example, according to some embodiments, the hinge can be a human Ig (immunoglobulin) hinge (e.g., an IgG4 hinge, an IgD hinge), a GS linker (e.g., a GS linker described herein), a KIR2DS2 hinge or a CD8a hinge.

According to some embodiments, the transmembrane domain may be recombinant, in which case it will comprise predominantly hydrophobic residues such as leucine and valine. In some aspects, a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in some aspects, the linker comprises the amino acid sequence of GGGGSGGGGS (SEQ ID NO: 10).

C. Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

According to some embodiments, exemplary intracellular signaling domains for use in the CAR of the disclosure include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

According to some embodiments, examples of ITAM containing primary intracellular signaling domains that are of particular use in the disclosure include those of CD3 zeta, common FcR gamma (FCER1G), Fe gamma Rlla, FcR beta (Fc Epsilon Rib), CD3 gamma, CD3 delta, CD3 epsilon, CD79a, CD79b, DAP10, and DAP12. According to some embodiments, a CAR of the disclosure comprises an intracellular signaling domain, e.g., a primary signaling domain of CD3-zeta.

According to some embodiments, a primary signaling domain comprises a modified ITAM domain, e.g., a mutated ITAM domain which has altered (e.g., increased or decreased) activity as compared to the native ITAM domain. According to some embodiments, a primary signaling domain comprises a modified ITAM-containing primary intracellular signaling domain, e.g., an optimized and/or truncated ITAM-containing primary intracellular signaling domain. According to some embodiments, a primary signaling domain comprises one, two, three, four or more ITAM motifs.

According to some embodiments, the intracellular signaling domain of the CAR can comprise the CD3-zeta signaling domain by itself, or it can be combined with any other desired intracellular signaling domain(s) useful in the context of a CAR of the disclosure. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. For example, CD27 co-stimulation has been demonstrated to enhance expansion, effector function, and survival of human CART cells in vitro and augments human T cell persistence and antitumor activity in vivo (Song et al. Blood. 2012; 119(3):696-706). Further examples of such costimulatory molecules include CDS, ICAM-1, GITR, BAFFR, HVEM (LIGHTR), SLAMF7, NKp80 (KLRF1, NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), NKG2D, CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

According to some embodiments, the intracellular signaling sequences within the cytoplasmic portion of the CAR of the disclosure may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. According to some embodiments, a glycine-serine doublet can be used as a suitable linker. According to some embodiments, a single amino acid, e.g., an alanine, a glycine, can be used as a suitable linker.

According to some embodiments, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. According to some embodiments, the intracellular signaling domain comprises two costimulatory signaling domains. In some embodiments, the linker molecule is a glycine residue. In some embodiments, the linker is an alanine residue.

According to some embodiments, the intracellular signaling domain is designed to comprise the signaling domain of CD3-zeta and the signaling domain of CD28. In some aspects, the intracellular signaling domain is designed to comprise the signaling domain of CD3-zeta and the signaling domain of 4-1BB. According to some embodiments, the intracellular signaling domain is designed to comprise the signaling domain of CD3-zeta and the signaling domain of CD27.

According to some embodiments, the CAR-expressing cell described herein can further comprise a second CAR, e.g., a second CAR that includes a different antigen binding domain, e.g., to the same target or a different target (e.g., a target other than a cancer associated antigen described herein or a different cancer associated antigen described herein). According to some embodiments, the second CAR includes an antigen binding domain to a target expressed the same cancer cell type as the cancer associated antigen. According to some embodiments, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. While not wishing to be bound by theory, placement of a costimulatory signaling domain, e.g., 4-1BB, CD28, CD27 or OX-40, onto the first CAR, and the primary signaling domain, e.g., CD3 zeta, on the second CAR can limit the CAR activity to cells where both targets are expressed. According to some embodiments, the CAR expressing cell comprises a first cancer associated antigen CAR that includes an antigen binding domain that binds a target antigen described herein, a transmembrane domain and a costimulatory domain and a second CAR that targets a different target antigen (e.g., an antigen expressed on that same cancer cell type as the first target antigen) and includes an antigen binding domain, a transmembrane domain and a primary signaling domain. In another embodiment, the CAR expressing cell comprises a first CAR that includes an antigen binding domain that binds a target antigen described herein, a transmembrane domain and a primary signaling domain and a second CAR that targets an antigen other than the first target antigen (e.g., an antigen expressed on the same cancer cell type as the first target antigen) and includes an antigen binding domain to the antigen, a transmembrane domain and a costimulatory signaling domain.

VI. Sources of T Cells

Prior to expansion and genetic modification or other modification, a source of cells, e.g., T cells, can be obtained from a subject. A "subject" is intended to include living organisms in which an immune response can be elicited (e.g., mammals). Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present disclosure, immune effector cells, e.g., T cells, can be obtained from a unit of blood collected from a subject using any number of techniques known to the skilled artisan, such as FICOLL™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In some aspects, the cells collected by apheresis may be washed to remove the plasma fraction and, optionally, to place the cells in an appropriate buffer or media for subsequent processing steps. According to some embodiments, the cells are washed with phosphate buffered saline (PBS). In an alternative embodiment, the wash solution lacks calcium and may lack magnesium or may lack many if not all divalent cations. Sources of T cells, isolation of T cells, enrichment of a T cell population and activation and expansion of T cells are described in International Publication No. WO2012079000, incorporated by reference in its entirety herein.

Also contemplated in the context of the disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. According to some embodiments a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, Cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immune, 73:316-321, 1991; Bterer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as O T3 or CAMPATH. In another embodiment, the cells are isolated prior to and can be frozen for later use for treatment following B-cell ablative therapy such as agents that react with CD20, e.g., Rituxan.

In a further embodiment, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative ceil types include T cells, B cells, dendritic cells, and other cells of the immune system.

A. Activation and Expansion of T Cells

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, a population of immune effector cells may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9): 13191328, 1999; Garland. et al., J. Immunol Meth. 227(1-2):53-63, 1999).

B. Activity Assays

Once a CAR is constructed, various assays can be used to evaluate the activity of the molecule, such as but not limited to, the ability to expand T cells following antigen stimulation, sustain T cell expansion in the absence of re-stimulation, and anti-cancer activities in appropriate animal models. Assays to evaluate the effects of a CAR are described in further detail below.

Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of CD4+ and CD8+ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of CAR+ T cells following antigen stimulation can be measured by flow cytometry. For example, a mixture of CD4+ and CD8+ T cells are stimulated with anti-CD3/anti-CD28 artificial APCs followed by transduction with lentiviral vectors expressing GFP under the control of the promoters to be analyzed. Exemplary promoters include the CMV IE gene, EF-1, ubiquitin C, or phosphoglycerokinase (PGK) promoters. GFP fluorescence is evaluated on day 6 of culture in the CD4+ and/or CD8+ T cell subsets by flow cytometry. See, e.g., Milone et al., Molecular Therapy 17(8): 1453-1464 (2009).

Sustained CAR+ T cell expansion in the absence of re-stimulation can also be measured. See, e.g., Milone et al., Molecular Therapy 17(8): 1453-1464 (2009).

Assessment of cell proliferation and cytokine production can be performed as previously described in, e.g., Milone et al., Molecular Therapy 17(8): 1453-1464 (2009).

Cytotoxicity can be assessed by a standard 51Cr-release assay. See, e.g., Milone et al., Molecular Therapy 17(8): 1453-1464 (2009), or by standard degranulation assays, as described in Example 5. For example, RNA CAR T cells co-expressing a CAR and one or more costimulatory molecules are incubated with target cells expressing the antigen targeted by the CAR. By way of example, a mesothelin-targeting CAR expressing T cells which also express one or more co-stimulatory molecules are incubated with mesothelin-expressing target cells (K-meso, SKOV3) and mesothelin-negative cells (K562) and evaluated for CD 107a exposure in a degranulation assay.

VII. Hematopoietic Stem Cells (HSCs)

In one embodiment, the bispecific LNP of the disclosure comprises two or more targeting moieties, wherein each targeting moiety binds to a different hematopoietic stem or progenitor cell (HSPC) antigen or a different hematopoietic stem cell (HSC) antigen. In one embodiment, the HSC antigen is selected from the group consisting of CD45, CD46, CD135, CD90, CD117, and CD133. In one embodiment, the HSC antigen is CD45. In one embodiment, the HSC antigen is CD46. In one embodiment, the HSC antigen is CD135. In one embodiment, the HSC antigen is CD90. In one embodiment, the HSC antigen is CD117. In one embodiment, the HSC antigen is CD133. In other embodiments, an HSC antigen is selected from the group consisting of ADAM8, ADAM28, ADGRE2, ASCT1, ASCT2, CALHN2, CD7, CD33, CD34, CD37, CD43, CD44, CD45, CD46, CD49f, CD71, CD79A, CD79B, CD84, CD90, CD105, CD110, CD117, CD123, CD126, CD131, CD133, CD146, CD164, CD184, CD244, CD300f, CD300LF, CD370, CSF3R, CSMD2, EFNA3, EPHB2, FASLG, GPI-80, GPR183, IGSF8, ITGA3, LAIR1, LILRA2, PTAFR, SELL, SLC2A5, TNFRSF8, and VCAM1.

In some embodiments, a bispecific LNP of the disclosure includes two targeting moieties that bind to different antigens on the same HSPC or HSC cell. For example, in one embodiment, a bispecific LNP of the disclosure include one targeting moiety that binds to an abundant but slow-internalizing HSPC or HSC antigen (e.g., CD45), and one targeting moiety that binds to a less abundant but faster-internalizing antigen (e.g., CDC117 or CD135). Such a bispecific LNP may take advantage of both antigens to provide improved nucleic acid cargo expression.

As used herein, the term "hematopoietic stem cell" or "HSC" refers to a stem cell that gives rise to all the blood cell types of the three hematopoietic lineages, erythroid, lymphoid, and myeloid. These cell types include the myeloid (monocytes and macrophages, neutrophils, basophils, eosinophils, erythrocytes, megakaryocytes/platelets, dendritic cells), and the lymphoid lineages (T-cells, B-cells, NK-cells). In one embodiment, the term "hematopoietic stem cell" or "HSC" refers to a stem cell that has the following cell surface markers: CD34+, CD59+, Thy1/CD90+, CD38lo/−, and C-kit/CD117+. In one embodiment, the term "hematopoietic stem cell" or "HSC" refers to a stem cell that is at least CD34+. In one embodiment, the term "hematopoietic stem cell" or "HSC" refers to a stem cell that is at least CD38lo/−. In one embodiment, the term "hematopoietic stem cell" or "HSC" refers to a stem cell that is at least CD34+ and CD38lo/−. In one embodiment, the term "hematopoietic stem cell" or "HSC" refers to a stem cell that is at least lin−. In one embodiment, the term "hematopoietic stem cell" or "HSC" refers to a stem cell that is at least CD34+ and lin−. In one embodiment, the term "hematopoietic stem cell" or "HSC" refers to a stem cell that is at least CD34+, CD38lo/−and lin−. In one embodiment, the term "hematopoietic stem cell" or "HSC" refers to a stem cell that is at least CD34+ and C-kit/CD117+. In one embodiment, the term "hematopoietic stem cell" or "HSC" refers to a stem cell that is at least CD34+, CD38lo/− and C-kit/CD117+. In another embodiment, as used herein, the term "hematopoietic stem cell" or "HSC" includes hematopoietic stem and progenitor cells (HSPC). As used herein, the term "HSPC" refers to a population of cells of hematopoietic origin that includes hematopoietic stem and progenitor cells. Both HSCs and HSPCs express the cell surface marker CD34, but progenitors also express CD38, while HSCs do not.

In one embodiment, as used herein, the term "a progenitor cell" refers to refer to an immature or undifferentiated cell that has the potential later on to mature (differentiate) into a specific cell type, for example, a blood cell, a skin cell, a bone cell, or a hair cells. A progenitor cell also can proliferate to make more progenitor cells that are similarly immature or undifferentiated.

Cells of the disclosure can be autologous/autogenic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells of the disclosure are allogeneic.

An "isolated cell" refers to a cell that has been obtained from an in vivo tissue or organ and is substantially free of extracellular matrix.

VIII. Therapeutic Applications

The present disclosure provides a variety of therapeutic methods using stealth targeting LNPs encapsulating TNA (e.g., ceDNA, ssDNA and/or mRNA that can transform T cells in vivo or ex vivo that express a chimeric antigen receptor (CAR).

According to some embodiments, the disclosure provides a method for inhibiting the proliferation or reducing a cell population expressing a disease-associated antigen by contacting a population of cells expressing the disease-associated antigen with CAR T cell described herein that binds to the disease-associated antigen. According to some embodiments, the cells are cancer cells.

The efficacy of the CAR T cell described herein can be tested using art-recognized animal models for the particular indication of interest. For example, in the context of cancer, established cancer mouse models are widely available for the particular cancer of interest.

In another embodiment, the disclosure provides methods for preventing, treating and/or managing a disorder associated with cells expressing a disease-associated antigen by administering to a subject in need a CAR T cell as described herein that binds to the disease-associated antigen-expressing cell. According to some embodiments, the subject is a human.

In another embodiment, the disclosure provides methods for preventing relapse of cancer associated with cells expressing a particular tumor antigen by administering to a subject in need thereof a CAR T cell as described herein that binds to the tumor antigen-expressing cell. In another embodiment, the methods comprise administering to the subject in need thereof an effective amount of a CAR T cell as described herein that binds to the disease-associated antigen-expressing cell in combination with an effective amount of another therapy.

In another embodiment, the disclosure provides a method of inhibiting growth of a cell expressing a tumor antigen by contacting the tumor cell with a CAR T cell as described herein such that the CAR T cell is activated in response to the antigen and targets the cancer cell, wherein the growth of the tumor is inhibited.

In another embodiment, the disclosure provides a method of treating a proliferative disease (e.g., cancer) by administering to a subject a CAR T cell as described herein, such that the cancer is treated in the subject. As used herein, the term "cancer" is meant to include all types of cancerous growths or oncogenic processes, metastatic tissues or malignantly transformed cells, tissues, or organs, irrespective of histopathologic type or stage of invasiveness. Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. According to some embodiments, the cancer is a melanoma, e.g., an advanced stage melanoma. Metastatic lesions of the aforementioned cancers can also be treated or prevented using the methods and compositions of the disclosure. Examples of other cancers that can be treated include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin Disease, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

According to some embodiments, the cancer associated with expression of a cancer associate antigen as described herein is a hematological cancer. In some aspects, the hematological cancer is a leukemia or a lymphoma. In some aspects, a cancer associated with expression of a cancer associate antigen as described herein includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of a cancer associate antigen as described herein include, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with a cancer associate antigen as described herein expression include, but not limited to, e.g., atypical and/or non-classical cancers, malignancies, precancerous conditions or proliferative diseases associated with expression of a cancer associate antigen as described herein.

In another embodiment, the disclosure provides a method of treating a precancerous condition by administering to a subject a CAR T cell as described herein, such that the precancerous condition is treated in the subject.

In another embodiment, the disclosure provides a method of treating a non-cancer indication by administering to a subject a CAR T cell as described herein, such that the non-cancer indication is treated in the subject. Non-limiting examples of non-cancer indications include inflammatory disorders, autoimmune disorders, parasitic, viral, bacterial, fungal or other infections.

According to some embodiments, the CAR T cells described herein are a vaccine for ex vivo immunization and/or in vivo therapy in a mammal (e.g., a human). Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

Procedures for ex vivo expansion of hematopoietic stem and progenitor cells are described, for example, in U.S. Pat. No. 5,199,942, incorporated herein by reference, can be applied to the cells of the present disclosure. Other suitable methods are known in the art therefore the present disclosure is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as Flt3-L, IL-1, IL-3 and c-kit ligand, can be used for culturing and expansion of the cells.

In addition to providing a cell-based vaccine for ex vivo immunization, the present disclosure also provides compositions and methods for in vivo immunization to elicit an immune response directed against an antigen in a patient.

According to some embodiments, the cells activated and expanded as described herein may be utilized in the treatment and prevention of diseases that arise in individuals who are immunocompromised. In certain aspects, the cells of the disclosure are used in the treatment of patients at risk for developing diseases, disorders and conditions associated with the expression of a disease-associated antigen. Thus, the present disclosure provides methods for the treatment or prevention of diseases, disorders and conditions associated with expression of a disease-associated antigen comprising administering to a subject in need thereof, a therapeutically effective amount of the CAR T cells of the disclosure, which bind cells expressing the disease-associated antigen.

IX. Pharmaceutical Compositions and Formulations

The present disclosure contemplates pharmaceutical compositions comprising a lipid nanoparticle (LNP) as described herein.

The present disclosure also contemplates pharmaceutical compositions comprising cells, e.g., a CAR T cell or population of CAR T cells. According to some embodiments, the pharmaceutical composition may further comprise one or more immunosuppressants described herein.

Pharmaceutical compositions of the present disclosure comprise an LNP, or a CAR T cell, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are formulated for intravenous administration.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

The precise amount of the compositions of the present disclosure to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319: 1676, 1988). The optimal dosage and treatment regime for a particular patient can readily be determined by one skilled in the art of medicine by monitoring the patient for signs of disease and adjusting the treatment accordingly.

According to some embodiments, it may be desired to administer activated T cells to a subject and then subsequently redraw blood (or have an apheresis performed), activate T cells therefrom according to the present disclosure, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

Administration of the compositions may be carried out in any convenient manner, including by aerosol inhalation, injection, ingestion, transfusion, implantation or transplantation. The compositions may be administered to a patient transarterially, subcutaneously, intradermally, intratumorally, intranodally, intramedullary, intramuscularly, by intravenous (i.v.) injection, or intraperitoneally. According to some embodiments, the compositions are administered to a patient by intradermal or subcutaneous injection. According to some embodiments, the compositions are administered by i.v. injection. According to some embodiments, the compositions are injected directly into a tumor, lymph node, or site of infection.

According to some embodiments, cells activated and expanded using the methods described herein, or other methods known in the art where T cells are expanded to therapeutic levels, are administered to a patient in conjunction with (e.g., before, simultaneously or following) any number of relevant treatment modalities including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further aspects, the T cells of the disclosure may be used in a treatment regimen in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present disclosure are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some aspects, the cell compositions of the present disclosure are administered following B-cell ablative therapy such as agents that react with CD20, e.g., Rituxan. For example, According to some embodiments, subjects may undergo standard treatment with high dose chemotherapy followed by peripheral blood stem cell transplantation. In certain embodiments, following the transplant, subjects receive an infusion of the expanded immune cells of the present disclosure. In an additional embodiment, expanded cells are administered before or following surgery.

In some embodiments, a pharmaceutical composition may comprise a lipid particle as a carrier. Such a lipid formulation can be used to deliver an immunomodulatory active agent (immunosuppressants, such as TKIs) and/or a nucleic acid therapeutics, to a target site of interest (e.g., cell, tissue, organ, and the like). In preferred embodiments, lipid particles can be a therapeutic nucleic acid containing lipid particle, which is typically formed from a cationic lipid, a non-cationic lipid, and optionally a conjugated lipid that prevents aggregation of the particles.

In some embodiments, the lipid particles are provided with full encapsulation, partial encapsulation of the therapeutic nucleic acid and/or an immunosuppressant. In a preferred embodiment, the nucleic acid therapeutics is fully encapsulated in the lipid particles to form a nucleic acid containing lipid particle that can optionally include any of the immunosuppressants of the present disclosure if the nucleic acid therapeutics and the immunosuppressant are to be co-formulated and administered to a subject simultaneously. In some embodiments, the immunosuppressants and/or the nucleic acid may be encapsulated within the lipid portion of the particle, thereby protecting it from enzymatic degradation. In some other embodiments, the lipid particles comprising a therapeutic nucleic acid and/or an immunosuppressant typically have a mean diameter of from about 20 nm to about 100 nm, 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm to ensure effective delivery. Nucleic acid containing lipid particles and their method of preparation are disclosed in, e.g., PCT/US18/50042, U.S. Patent Publication Nos. 20040142025 and 20070042031, the disclosures of which are herein incorporated by reference in their entirety for all purposes.

In some embodiments, a liquid pharmaceutical composition comprising a therapeutic nucleic acid and/or immunosuppressant of the present disclosure may be formulated in lipid particles. In some embodiments, the lipid particle comprising a therapeutic nucleic acid can be formed from a cationic lipid. In some other embodiments, the lipid particle comprising a therapeutic nucleic acid can be formed from non-cationic lipid. In a preferred embodiment, the lipid particle of the disclosure is a nucleic acid containing lipid particle, which is formed from a cationic lipid comprising a therapeutic nucleic acid selected from the group consisting of mRNA, antisense RNA and oligonucleotide, ribozymes, aptamer, interfering RNAs (RNAi), Dicer-substrate dsRNA, small hairpin RNA (shRNA), asymmetrical interfering RNA (aiRNA), microRNA (miRNA), minicircle DNA, minigene, viral DNA (e.g., Lentiviral or AAV genome) or non-viral synthetic DNA vectors, closed-ended linear duplex DNA (ceDNA/CELiD), plasmids, bacmids, Doggybone™ DNA vectors, minimalistic immunological-defined gene expression (MIDGE)-vector, nonviral ministring DNA vector (linear-covalently closed DNA vector), single stranded DNA (ssDNA), or dumbbell-shaped DNA minimal vector ("dumbbell DNA").

X. Methods of Treatment

In some aspects, the present disclosure provides methods of treating a disorder in a subject that comprise administering to the subject an effective amount of a bispecific LNP of the disclosure of the pharmaceutical composition comprising the bispecific LNP of the disclosure. In some embodiments, the disorder is a genetic disorder.

As used herein, the term "genetic disease" or "genetic disorder" refers to a disease, partially or completely, directly or indirectly, caused by one or more abnormalities in the genome, including and especially a condition that is present from birth. The abnormality may be a mutation, an insertion or a deletion in a gene. The abnormality may affect the coding sequence of the gene or its regulatory sequence.

Provided herein are methods for treating genetic disorders by administering the bispecific LNP of the disclosure or the pharmaceutical composition comprising bispecific LNPs of the disclosure. There are a number of inherited diseases in which defective genes are known, and typically fall into two classes: deficiency states, usually of enzymes, which are generally inherited in a recessive manner, and unbalanced states, which may involve regulatory or structural proteins, and which are typically but not always inherited in a dominant manner. For deficiency state diseases, the bispecific LNPs and LNP compositions of the disclosure can be used to deliver transgenes to bring a normal gene into affected tissues for replacement therapy, as well, in some embodiments of any of the aspects and embodiments herein, to create animal models for the disease using antisense mutations.

For unbalanced disease states, the bispecific LNPs and LNP compositions of the disclosure can be used to create a disease state in a model system, which could then be used in efforts to counteract the disease state. Thus, the bispecific LNPs or LNP compositions of the disclosure and methods disclosed herein permit the treatment of genetic diseases. As used herein, a disease state is treated by partially or wholly remedying the deficiency or imbalance that causes the disease or makes it more severe.

In general, the bispecific LNPs and LNP compositions of the disclosure can be used to deliver any transgene in accordance with the description above to treat, prevent, or ameliorate the symptoms associated with any disorder related to gene expression. Illustrative disease states include, but are not-limited to: cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Hurler's disease, adenosine deaminase deficiency, metabolic defects, retinal degenerative diseases (and other diseases of the eye), mitochondriopathies (e.g., Leber's hereditary optic neuropathy (LHON), Leigh syndrome, and subacute sclerosing encephalopathy), myopathies (e.g., facioscapulohumeral myopathy (FSHD) and cardiomyopathies), diseases of solid organs (e.g., brain, liver, kidney, heart), and the like. In some embodiments of any of the aspects and embodiments herein, the ceDNA vectors as disclosed herein can be advantageously used in the treatment of individuals with metabolic disorders (e.g., ornithine transcarbamylase deficiency).

In one embodiment of any of the aspects or embodiments herein, the LNPs of the disclosure or the pharmaceutical compositions comprising the bispecific LNPs of the disclosure can be used to treat, ameliorate, and/or prevent a disease or disorder caused by mutation in a gene or gene product. Exemplary diseases or disorders that can be treated with the bispecific LNPs or the LNP compositions of the disclosure include, but are not limited to, metabolic diseases or disorders (e.g., Fabry disease, Gaucher disease, phenylketonuria (PKU), glycogen storage disease); urea cycle diseases or disorders (e.g., ornithine transcarbamylase (OTC) deficiency); lysosomal storage diseases or disorders (e.g., metachromatic leukodystrophy (MLD), mucopolysaccharidosis Type II (MPSII; Hunter syndrome)); liver diseases or disorders (e.g., progressive familial intrahepatic cholestasis (PFIC); blood diseases or disorders (e.g., hemophilia A and B, thalassemia, and anemia); cancers and tumors, and genetic diseases or disorders (e.g., cystic fibrosis).

In one embodiment, the bispecific LNPs or LNP compositions of the disclosure may be employed to deliver a heterologous nucleotide sequence in situations in which it is desirable to regulate the level of transgene expression (e.g., transgenes encoding hormones or growth factors).

In one embodiment of any of the aspects or embodiments herein, the LNPs or LNP compositions of the disclosure can be used to correct an abnormal level and/or function of a gene product (e.g., an absence of, or a defect in, a protein) that results in the disease or disorder. The LNPs or LNP compositions of the disclosure can produce a functional protein and/or modify levels of the protein to alleviate or reduce symptoms resulting from, or confer benefit to, a particular disease or disorder caused by the absence or a defect in the protein. For example, treatment of OTC deficiency can be achieved by producing functional OTC enzyme; treatment of hemophilia A and B can be achieved by modifying levels of Factor VIII, Factor IX, and Factor X; treatment of PKU can be achieved by modifying levels of phenylalanine hydroxylase enzyme; treatment of Fabry or Gaucher disease can be achieved by producing functional alpha galactosidase or beta glucocerebrosidase, respectively; treatment of MFD or MPSII can be achieved by producing functional arylsulfatase A or iduronate-2-sulfatase, respectively; treatment of cystic fibrosis can be achieved by producing functional cystic fibrosis transmembrane conductance regulator; treatment of glycogen storage disease can be achieved by restoring functional G6Pase enzyme function; and treatment of PFIC can be achieved by producing functional ATP8B1, ABCB11, ABCB4, or TJP2 genes.

In some embodiments, the bispecific LNPs or LNP compositions of the disclosure can be used to provide a DNA-based therapeutic to a cell in vitro or in vivo. Examples of DNA-based therapeutics include, but are not limited to, minicircle DNA, minigene, viral DNA (e.g., Lentiviral or AAV genome) or non-viral synthetic DNA vectors, closed-ended linear duplex DNA (ceDNA/CELiD), plasmids, bacmids, Doggybone™ DNA vectors, minimalistic immunological-defined gene expression (MIDGE)-vector, nonviral ministring DNA vector (linear-covalently closed DNA vector), or dumbbell-shaped DNA minimal vector ("dumbbell DNA").

In one embodiment of any of the aspects or embodiments herein, exemplary transgenes encoded by ceDNA in the bispecific LNPs or LNP compositions of the disclosure include, but are not limited to: X, lysosomal enzymes (e.g., hexosaminidase A, associated with Tay-Sachs disease, or iduronate sulfatase, associated, with Hunter Syndrome/MPS II), erythropoietin, angiostatin, endostatin, superoxide dismutase, globin, leptin, catalase, tyrosine hydroxylase, as well as cytokines (e.g., a interferon, β-interferon, interferon-γ, interleukin-2, interleukin-4, interleukin 12, granulocyte-macrophage colony stimulating factor, lymphotoxin, and the like), peptide growth factors and hormones (e.g., somatotropin, insulin, insulin-like growth factors 1 and 2, platelet derived growth factor (PDGF), epidermal growth factor (EGF), fibroblast growth factor (FGF), nerve growth factor (NGF), neurotrophic factor-3 and 4, brain-derived neurotrophic factor (BDNF), glial derived growth factor (GDNF), transforming growth factor-α and -β, and the like), receptors (e.g., tumor necrosis factor receptor). In some exemplary embodiments, the transgene encodes a monoclonal antibody specific to one or more desired targets. In some exemplary embodiments, more than one transgene is encoded by the ceDNA vector. In some exemplary embodiments, the transgene encodes a fusion protein comprising two different polypeptides of interest. In some embodiments of any of the aspects and embodiments herein, the transgene encodes an antibody, including a full-length antibody or antibody fragment, as defined herein. In some embodiments of any of the aspects and embodiments herein, the antibody is an antigen-binding domain or an immunoglobulin variable domain sequence, as that is defined herein. Other illustrative transgene sequences encode suicide gene products (thymidine kinase, cytosine deaminase, diphtheria toxin, cytochrome P450, deoxycytidine kinase, and tumor necrosis factor), proteins conferring resistance to a drug used in cancer therapy, and tumor suppressor gene products.

In one embodiment of any of the aspects or embodiments herein, this disclosure provides a method of providing anti-tumor immunity in a subject, the method comprising administering to the subject an effective amount of any embodiment of a bispecific LNP contemplated herein or any embodiment of a pharmaceutical composition comprising an LNP contemplated herein. Furthermore, this disclosure provides a method of treating a subject having a disease, disorder or condition associated with an elevated expression of a tumor antigen, the method comprising administering to the subject an effective amount of any embodiment of a bispecific LNP contemplated herein or any embodiment of a pharmaceutical composition comprising an LNP contemplated herein. In some embodiments, the TNA is retained in the spleen for at least about 6 hours, or at least about 9 hours, or at least about 12 hours, or at least about 15 hours, or at least about 18 hours, or at least about 21 hours, or at least about 24 hours, or at least about 27 hours, or at least about 30 hours, or at least about 33 hours, or at least about 36 hours after dosing of an LNP of this disclosure, for example, via intravenous or intratumoral administration. In some embodiments, the amount (i.e., number of copies) of the TNA at the start of a 12, 18, or 24-hour time window post-dosing and the amount of the TNA at the end of the time window are within the same order of magnitude (e.g., $10^{-7}$ copies, $10^{-6}$ copies, $10^{-5}$ copies, $10^{-4}$ copies, $10^{-3}$ copies, $10^{-2}$ copies, $10^{-1}$ copies, $10^{0}$ copies, $10^{1}$ copies, $10^{2}$ copies, $10^{3}$ copies, etc. or any other suitable therapeutic levels). In other words, there is minimal reduction in concentrations of the TNA in the spleen within a 12, 18, or 24-hour time window post-dosing. In some embodiments, the TNA is a messenger RNA (mRNA).

Examples of solid tumors treatable with a bispecific LNP disclosed herein or a pharmaceutical composition comprising the same include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. According to some embodiments, the tumor or cancer is a melanoma, e.g., an advanced stage melanoma. Metastatic lesions of the aforementioned cancers can also be treated or prevented using the methods and compositions of the disclosure. Examples of other solid tumors or cancers that can be treated include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In further embodiments, the present disclosure provides a method of treating a blood disease, disorder or condition in a subject, the method comprising administering to the subject an effective amount of any embodiment of a bispecific LNP contemplated herein or any embodiment of a pharmaceutical composition comprising a bispecific LNP contemplated herein. Non-limiting examples of the blood disease, disorder or condition include acute myeloid leukemia (AML), acute lymphoblastic leukemia (ALL), chronic lymphocytic leukemia (CLL), chronic myelogenous leukemia (CML), Hodgkin lymphoma (HL), multiple myeloma, a myelodysplastic syndrome (MDS), non-Hodgkin lymphoma (NHL), adrenoleukodystrophy (ALD), Hurler syndrome, Krabbe disease (Globoid-cell leukodystrophy or GLD), metachromatic leukodystrophy (MLD), severe aplastic anemia (SAA), severe combined immunodeficiency (SCID), sickle cell disease (SCD), thalassemia, Wiskott-Aldrich syndrome, Diamond-Blackfan anemia, essential thrombocytosis, Fanconi anemia, hemophagocytic lymphohistiscytosis (HLH), juvenile myelomonocytic leukemia (JMML), myelofibrosis, polycythemia vera, and a combination thereof. In some embodiments, the TNA is a messenger RNA (mRNA). In some embodiments, the TNA is retained in the bone marrow for at least about 6 hours, or at least about 9 hours, or at least about 12 hours, or at least about 15 hours, or at least about 18 hours, or at least about 21 hours, or at least about 24 hours, or at least about 27 hours, or at least about 30 hours, or at least about 33 hours, or at least about 36 hours after dosing of an LNP of this disclosure, for example, via intravenous or intratumoral administration. In some embodiments, the amount (i.e. number of copies) of the TNA at the start of a 12, 18, or 24-hour time window post-dosing and the number of the TNA at the end of the time window are within the same order of magnitude (e.g., $10^{-7}$ copies, $10^{-6}$ copies, $10^{-5}$ copies, $10^{-4}$ copies, $10^{-3}$ copies, $10^{-2}$ copies, $10^{-1}$ copies, $10^{0}$ copies, $10^{1}$ copies, $10^{2}$ copies, $10^{3}$ copies, etc. or any other suitable therapeutic levels) or are reduced for less than one order of magnitude. In other words, there is minimal or insignificant reduction in concentrations of the TNA in the bone marrow within a 12, 18, or 24-hour time window post-dosing. In some embodiments, the TNA is a messenger RNA (mRNA).

A. Administration

In some embodiments, a bispecific LNP or an LNP composition of the disclosure can be administered to an organism for transduction of cells in vivo. In some embodiments, a bispecific LNP or an LNP composition of the disclosure can be administered to an organism for transduction of cells ex vivo.

Generally, administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route. Exemplary modes of administration of an LNP or an LNP composition of the disclosure include oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye, skeletal muscle, cardiac muscle, diaphragm muscle or brain).

Administration of the bispecific LNP or LNP compositions of the disclosure can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye. The most suitable route in any given case will depend on the nature and severity of the condition being treated, ameliorated, and/or prevented and on the nature of the particular ceDNA LNP that is being used. Additionally, ceDNA permits one to administer more than one transgene in a single vector, or multiple ceDNA vectors (e.g., a ceDNA cocktail).

In one embodiment of any of the aspects or embodiments herein, the bispecific LNPs or LNP compositions of the disclosure can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

In some embodiments, the bispecific LNPs of the disclosure or the pharmaceutical compositions comprising the bispecific LNPs of the disclosure, when administered to a subject, is characterized by a lower immunogenicity than a reference LNP or a pharmaceutical composition comprising a reference LNP. In some embodiments, the immunogenicity of the bispecific LNP of the disclosure or the pharmaceutical composition comprising the LNP of the disclosure may be measured by measuring levels of one or more proinflammatory cytokines. Accordingly, in some embodiments, the bispecific LNPs of the disclosure or the pharmaceutical compositions comprising the bispecific LNPs of the disclosure, when administered to a subject, elicits a lower pro-inflammatory cytokine response than a reference LNP or a pharmaceutical composition comprising a reference LNP. The term "elicits a lower pro-inflammatory cytokine response than a reference LNP or a pharmaceutical composition comprising a reference LNP", as used herein, means that the bispecific LNP of the disclosure or the pharmaceutical composition comprising the LNP of the disclosure, when administered to a subject, causes a smaller increase in the levels of one or more pro-inflammatory cytokines as compared to a reference LNP or a pharmaceutical composition comprising a reference LNP. Exemplary pro-inflammatory cytokines include, but are not limited to, granulocyte colony stimulating factor (G-CSF), interleukin 1 alpha (IL-1α), interleukin 1 beta (IL-1β), interleukin 6 (IL-6), interleukin 8 (IL-8 or CXCL8), interleukin 11 (IL-11), interleukin 17 (IL-17), interleukin 18 (IL-18), interferon α (IFN-α), interferon β (IFN-β), interferon γ (IFN-γ), C—X—C motif chemokine ligand 10 (CXCL10 or IP-10), monocyte chemoattractant protein 1 (MCP-1), CD40L, CCL2, CCL3, CCL4, CCL5, CCL11, tumor necrosis factor α (TNF-α), and combinations thereof.

In some embodiments, a subject may be administered one or more immunosuppressants (or derivative or salt thereof) and one or more nucleic acid therapeutics concomitantly. For example, the method may comprise administering to a subject an immunosuppressant and a nucleic acid therapeutic as two separate formulations but concomitantly. In another example, the method may comprise simultaneously administering to a subject an immunosuppressant and a therapeutic nucleic acid in one formulation, thereby the immunosuppressant and the therapeutic nucleic acid can be administered to a subject at the same time.

In some embodiment, a subject may be administered one or more immunosuppressants (or derivative or salt thereof) and one or more therapeutic nucleic acid sequentially. For example, the immunosuppressant may be administered prior to, at the same time, or subsequent to administration of a pharmaceutical composition comprising stealth targeting LNPs and therapeutic nucleic acid disclosed herein. For example, a subject may be administered a therapeutically effective dose of an immunosuppressant, and subsequently administered a therapeutic nucleic acid.

In cases of sequential administration, there may be a delay period between administration of the one or more immunosuppressant and the pharmaceutical composition comprising stealth targeting LNPs and therapeutic nucleic acid disclosed herein. For example, the immunosuppressant may be administered hours, days, or weeks prior to administration of the TNA (e.g., at least 30 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least about 2 days, at least about 3 days, at least about 4 days, at least about 5 days, at least about 6 days, at least about 1 week, at least about 2 weeks, at least about 3 weeks, and at least about 4 weeks prior to the administration of a therapeutic nucleic acid). In some embodiments, an immunosuppressant may be administered about thirty (30) minutes prior to the administration of a pharmaceutical composition comprising stealth targeting LNPs and therapeutic nucleic acid. In some embodiments, an immunosuppressant may be administered about one (1) hour prior to the administration of a therapeutic nucleic acid. In some embodiments, an immunosuppressant can be administered about two (2) hours prior to the administration of a therapeutic nucleic acid. In some embodiments, an immunosuppressant can be administered about three (3) hours prior to the administration of a therapeutic nucleic acid. In some embodiments, an immunosuppressant can be administered about four (4) hours prior to the administration of a therapeutic nucleic acid. In some embodiments, an immunosuppressant can be administered about five (5) hours prior to the administration of a therapeutic nucleic acid. In some embodiments, an immunosuppressant can be administered about six (6) hours prior to the administration of a therapeutic nucleic acid. In some embodiments, an immunosuppressant can be administered about seven (7) hours prior to the administration of a therapeutic nucleic acid. In some embodiments, an immunosuppressant can be administered about eight (8) hours prior to the administration of a therapeutic nucleic acid. In some embodiments, an immunosuppressant can be administered about nine (9) hours prior to the administration of a therapeutic nucleic acid. In some embodiments, an immunosuppressant can be administered about ten (10) hours prior to the administration of a therapeutic nucleic acid.

According to some embodiments, an immunosuppressant is administered no more than about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or 24 hours before the administration of a therapeutic nucleic acid. In some embodiments, an immunosuppressant can be administered no more than about 1 day, about 2 days, about 3 days, about 4 days, about 6 days, or about 7 days before the administration of a therapeutic nucleic acid.

In some embodiments, an immunosuppressant can be administered about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or 24 hours after the administration of a therapeutic nucleic acid. In some embodiments, an immunosuppressant can be administered about 1 day, about 2 days, about 3 days, about 4 days, about 6 days, or about 7 days after the administration of a therapeutic nucleic acid.

According to some embodiments, an immunosuppressant is administered no more than about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or 24 hours after the administration of a therapeutic nucleic acid. In some embodiments, an immunosuppressant can be administered no more than about 1 day, about 2 days, about 3 days, about 4 days, about 6 days, or about 7 days after the administration of a therapeutic nucleic acid.

In some embodiments, one or more immunosuppressants can be administered multiple times before, concurrently with, and/or after the administration of a therapeutic nucleic acid.

In some embodiments, a therapeutic nucleic acid can be administered and re-dosed multiple times in conjunction with one or more immunosuppressant disclosed herein. For example, the therapeutic nucleic acid can be administered on day 0 with one or more immunosuppressants that is administered before, after or at the same time with the administration of the therapeutic nucleic acid in a first dosing regimen. Following the initial treatment at day 0, a second dosing (re-dose) can be performed in about 1 week, about 2 weeks, about 3 weeks, about 4 weeks, about 5 weeks, about 6 weeks, about 7 weeks, about 8 weeks, or about 3 months, about 4 months, about 5 months, about 6 months, about 7 months, about 8 months, about 9 months, about 10 months, about 11 months, or about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 21 years, about 22 years, about 23 years, about 24 years, about 25 years, about 26 years, about 27 years, about 28 years, about 29 years, about 30 years, about 31 years, about 32 years, about 33 years, about 34 years, about 35 years, about 36 years, about 37 years, about 38 years, about 39 years, about 40 years, about 41 years, about 42 years, about 43 years, about 44 years, about 45 years, about 46 years, about 47 years, about 48 years, about 49 years or about 50 years after the initial treatment with the therapeutic nucleic acid, preferably with one or more immunosuppressants disclosed herein.

The immunosuppressants of the current disclosure may be administered by any of the accepted modes of administration, for example, by cutaneous, oral, topical, intradermal, intrathecal, intravenous, subcutaneous, intramuscular, intratumoral, intra-articular, intraspinal or spinal, nasal, epidural, rectal, vaginal, or transdermal/transmucosal routes. The most suitable route will depend on the nature and severity of the disorder and condition of the subject. Subcutaneous, oral, intradermal, intravenous and percutaneous administration can be routes for the immunosuppressants of this disclosure. Sublingual administration may be a route of administration for the immunosuppressants of this disclosure. Intravenous administration may be a route of administration for the immunosuppressants of this disclosure. In one particular example, the immunosuppressants provided herein may be administered to a subject orally.

In some embodiments, the immunosuppressant and the LNP and nucleic acid therapeutics are each formulated in a stealth targeting LNP of the present disclosure. Such a pharmaceutical composition in a stealth targeting LNP can be pharmaceutically acceptable excipient or carrier, e.g., for oral delivery, injection, infusion, subcutaneous delivery, intramuscular delivery, intraperitoneal delivery, intrathecal delivery, intratumoral delivery, sublingual delivery, or other method described herein. A pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile.

According to one embodiment, a pharmaceutical composition comprising stealth targeting LNPs encapsulating TNA can be efficiently delivered to specific tissue or cell type of interest to treat a disease, disorder, condition, or syndrome. TNA can be expressed in the target cell in an amount sufficient to treat or ameliorate one or more symptoms of the disease. TNA can be a nucleotide encoding a therapeutic protein, e.g., an antibody, an enzyme, a coagulation factor, a transcription factor, a replication factor, a growth factor, a hormone, or a fusion protein, or an inhibitory nucleotide, e.g., an siRNA or antisense oligonucleotide. According to one embodiment of any of the aspects and embodiments herein, the at least one therapeutic protein is useful for treating a genetic disorder selected from the group consisting of sickle cell disease, melanoma, hemophilia A (clotting factor VIII (FVIII) deficiency) and hemophilia B (clotting factor IX (FIX) deficiency), cystic fibrosis (CFTR), familial hypercholesterolemia (LDL receptor defect), hepatoblastoma, Wilson disease, phenylketonuria (PKU), congenital hepatic porphyria, inherited disorders of hepatic metabolism, Lesch-Nyhan syndrome, thalassaemias, xeroderma pigmentosum, Fanconi anemia, retinitis pigmentosa, ataxia telangiectasia, Bloom syndrome, retinoblastoma, mucopolysaccharide storage diseases (e.g., Hurler syndrome (MPS Type I), Scheie syndrome (MPS Type I S), Hurler-Scheie syndrome (MPS Type I H-S), Hunter syndrome (MPS Type II), Sanfilippo Types A, B, C, and D (MPS Types III A, B, C, and D), Morquio Types A and B (MPS IVA and MPS IVB), Maroteaux-Lamy syndrome (MPS Type VI), Sly syndrome (MPS Type VII), hyaluronidase deficiency (MPS Type IX)), Niemann-Pick Disease Types A/B, C1 and C2, Fabry disease, Schindler disease, GM2-gangliosidosis Type II (Sandhoff Disease), Tay-Sachs disease, Metachromatic Leukodystrophy, Krabbe disease, Mucolipidosis Type I, II/III and IV, Sialidosis Types I and II, Glycogen Storage disease Types I and II (Pompe disease), Gaucher disease Types I, II and III, cystinosis, Batten disease, Aspartylglucosaminuria, Salla disease, Danon disease (LAMP-2 deficiency), Lysosomal Acid Lipase (LAL) deficiency, neuronal ceroid lipofuscinoses (CLN1-8, INCL, and LINCL), sphingolipidoses, galactosialidosis, amyotrophic lateral sclerosis (ALS), Parkinson's disease, Alzheimer's disease, Huntington's disease, spinocerebellar ataxia, spinal muscular atrophy, Friedreich's ataxia, Duchenne muscular dystrophy (DMD), Becker muscular dystrophies (BMD), dystrophic epidermolysis bullosa (DEB), ectonucleotide pyrophosphatase 1 deficiency, generalized arterial calcification of infancy (GACI), Leber Congenital Amaurosis, Stargardt macular dystrophy (ABCA4), ornithine transcarbamylase (OTC) deficiency, Usher syndrome, alpha-1 antitrypsin deficiency, progressive familial intrahepatic cholestasis (PFIC) type I (ATP8B1 deficiency), type II (ABCB11), type III (ABCB4), or type IV (TJP2), and Cathepsin A deficiency.

Other diseases, disorders, conditions, and syndromes that may be treated using a ctLNP described herein (e.g., an HSC-targeted ctLNP), include, but are not limited to, Sickle Cell Disease (SCD), Thalassemia, Pyruvate Kinase Deficiency (PKD), G6PD deficiency, Hereditary elliptocytosis, Familial Thrombocytosis, Polycythemia vera, Erythropoietic protoporphyria, Leukocyte Adhesion Deficiency, Hereditary spherocytosis, Paroxysmal noctunal hemoglobinuria (PNH), Red cell aplasia, HFE-related hemochromatosis, Diamond Blackfan Amenia, Fanconi Anemia, Hemophagocytic Lymphohistiocytosis, Thrombocytopenia Absent Radius (TAR) syndrome, Myelodysplastic Syndromes (MDS), Histiocytosis, Chronic Granulomatous Disease (CGD), Leukocytes Adhesion Deficiency (LAD), Myoloperoxidase Deficiency, Neutropenia, Glanzmann's Thrombasthenia, Bernard-Soulier Syndrome, Gray Platelet Syndrome, Storage Pool Deficiency, Hemoglobin E disease, Hemoglobin C disease, Hereditary stomatocytosis, Hereditary persistence of fetal hemoglobin (HPFH), Southeast Asian ovalocytosis, Rh-null disease, and Shwachman-Diamond Syndrome (SBDS). In some embodiments, the ctLNPs described herein may be used to produce a therapeutic protein (e.g., a secreted therapeutic protein) in an HSC cell to treat a disease such as Hemophilia A, Hemophilia B, Gaucher disease, Fabry disease, MPS Types I and II, and other diseases described above.

XI. Kits

The present disclosure provides pharmaceutical compositions, as well as therapeutic kits that include a stealth LNP comprising TNA (ceDNA, ssDNA, and/or mRNA), ionizable lipid, helper lipid (e.g., DSPC), sterol, first lipid-anchored polymer, and second lipid-anchored polymer, wherein the second lipid-anchored polymer is functionalized with a reactive species such as azide or maleimide that can be readily reacted with its conjugation partner on a targeting moiety (e.g., thiol (—SH) or DBCO moiety functionalized in scFv, VHH, or IgG) formulated with one or more additional ingredients, or prepared with one or more instructions for their use. The pharmaceutical compositions and therapeutic kits of the present disclosure may further comprise a targeting moiety that has increased affinity to a target (e.g., an epitope such as CD3, 4, 5, 6, 7, 8, 9, 10, 11, TCR, and PD-1 of T-cell; or a receptor such ASGPR and LDLR).

EXAMPLES

Example 1. Stealth Targeting LNP

The present disclosure provides stealth targeting lipid nanoparticles (LNPs) and LNP compositions (e.g., pharmaceutical compositions) comprising a therapeutic nucleic acid (TNA), e.g., a gene expression vector or a gene/base editing template, such as closed-ended double stranded DNA (ceDNA), single stranded DNA (ssDNA), or messenger RNA (mRNA), wherein the LNP comprises an ionizable lipid; with or without a "helper" lipid; a structural lipid, e.g., a sterol; and one or more types of lipid-anchored polymers comprising a polymer (e.g., PEG or polyglycerol), a lipid moiety with at least one hydrophobic tail with 16-22 carbon atoms in a single aliphatic chain backbone and a linker connecting the polymer to the lipid moiety. The LNPs disclosed herein provide surprising and unexpected properties as compared to known LNPs. For example, the helper lipid, if present, functions to increase the fusogenicity of the lipid bilayer of the LNP and to facilitate endosomal escape; the structural lipid of the LNP contributes to membrane integrity and stability of the LNP; and the lipid-anchored polymer of the LNP can inhibit aggregation of LNPs and provide steric stabilization (e.g., enhancing the stealth property of overall LNP characteristic in the circulation (e.g., the blood compartment) by minimizing interactions between opsonins present in the blood and the surface of the LNP). Moreover, the disclosed LNP compositions can further comprise a targeting moiety such as a single chain fragment variable region (scFv) and/or single domain antibody (VHH) linked to the LNP, wherein the scFv or VHH is specific for an antigen present on the surface of a cell (e.g., a tumor cell, T-cell, B-cell, NK cell, etc.), thereby increasing the targeting specificity of the stealth LNP to a desired tissue or cell-type. The stealth targeting LNP compositions described herein advantageously provide efficient covalent conjugation with minimal or no unexpected effects on blood pharmacokinetics (PK), particle size and stability as compared to unconjugated stealth LNPs. It is a finding of the present disclosure that DBCO mediated conjugation (via "Click chemistry") or maleimide conjugation (via thiol—maleimide reaction) between the targeting moiety (e.g., scFv or VHH) and the lipid-anchored polymer present on the surface of the stealth LNP resulted in robust linkages that maintained the physiochemical characteristics of the stealth LNPs and the resultant stealth LNPs comprising a targeting moiety effectively demonstrated highly increased specificity and targeting efficiency to a desired cell-type in vivo.

The present disclosure also provides a stealth LNP composition comprising a lipid-anchored polymer (i.e., second lipid-anchored polymer) comprising a reactive species (e.g., maleimide, azide, etc.) capable of reacting with a targeting moiety functionalized with thiol (—SH) or dibenzocyclooctyne (DBCO) reactive species, respectively such that the stealth LNP encapsulating a TNA can be readily reacted with the targeting moiety having a specificity to a desired target.

Figure 2:
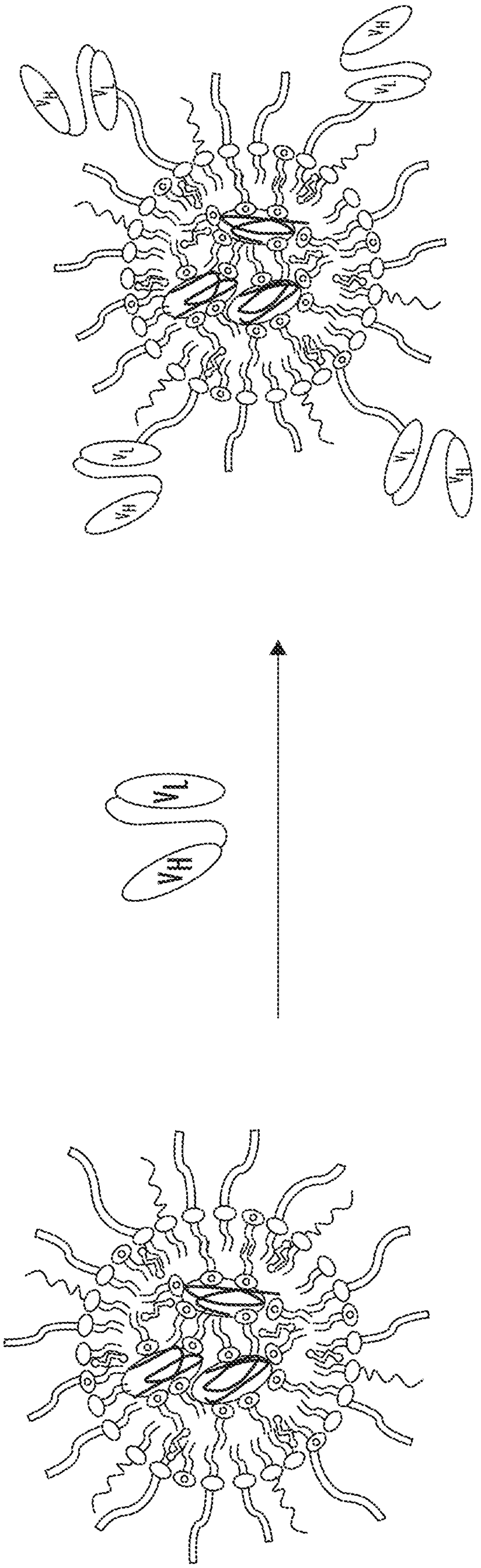
FIG. 2 illustrates a stealth LNP having an ScFv conjugated to the surface of the LNP where the conjugated scFv is able to project into the biological milieu and target the LNP to a particular surface antigen on a predetermined cell target.

Example 2. PK Profiles of Stealth Targeted LNP Versus Non-Targeted Stealth and Non-Stealth MRNA LNPs in Various Species In this example the conjugation of various targeting moieties such as an ScFv were conjugated to the surfaces of a series of Stealth LNPs through conjugation to lipid-anchored polymer and the pK/pD profiles were determined. The Stealth LNPs are illustrated in FIG. 1. FIG. 2 illustrates a stealth LNP having an ScFv conjugated to the surface of the LNP where it is able to project into the biological milieu and target the LNP to a particular surface antigen on a predetermined cell target.

Many different targeting moieties can be used to direct the stealth LNPs to specific surface antigens of different cell types. For example, the targeting moiety may be an antibody or an antibody fragment, e.g., an antibody or an antibody fragment that is capable of specifically binding to an antigen present on the surface of a cell. In addition, the antibody or an antibody fragment could be a monoclonal antibody (mAb), a single chain variable fragment (scFv), a heavy chain antibody (hcAb), a nanobody (Nb), a heavy-chain-only immunoglobulin (HCIg), an immunoglobulin new antigen receptor (IgNAR), variable domain of immunoglobulin new antigen receptor (VNAR), a single-domain antibody, or a variable heavy chain-only antibody (VHH). In this example, scFv was employed as a targeting moiety and its targeting specificity was demonstrated as the principle.

Figure 3:
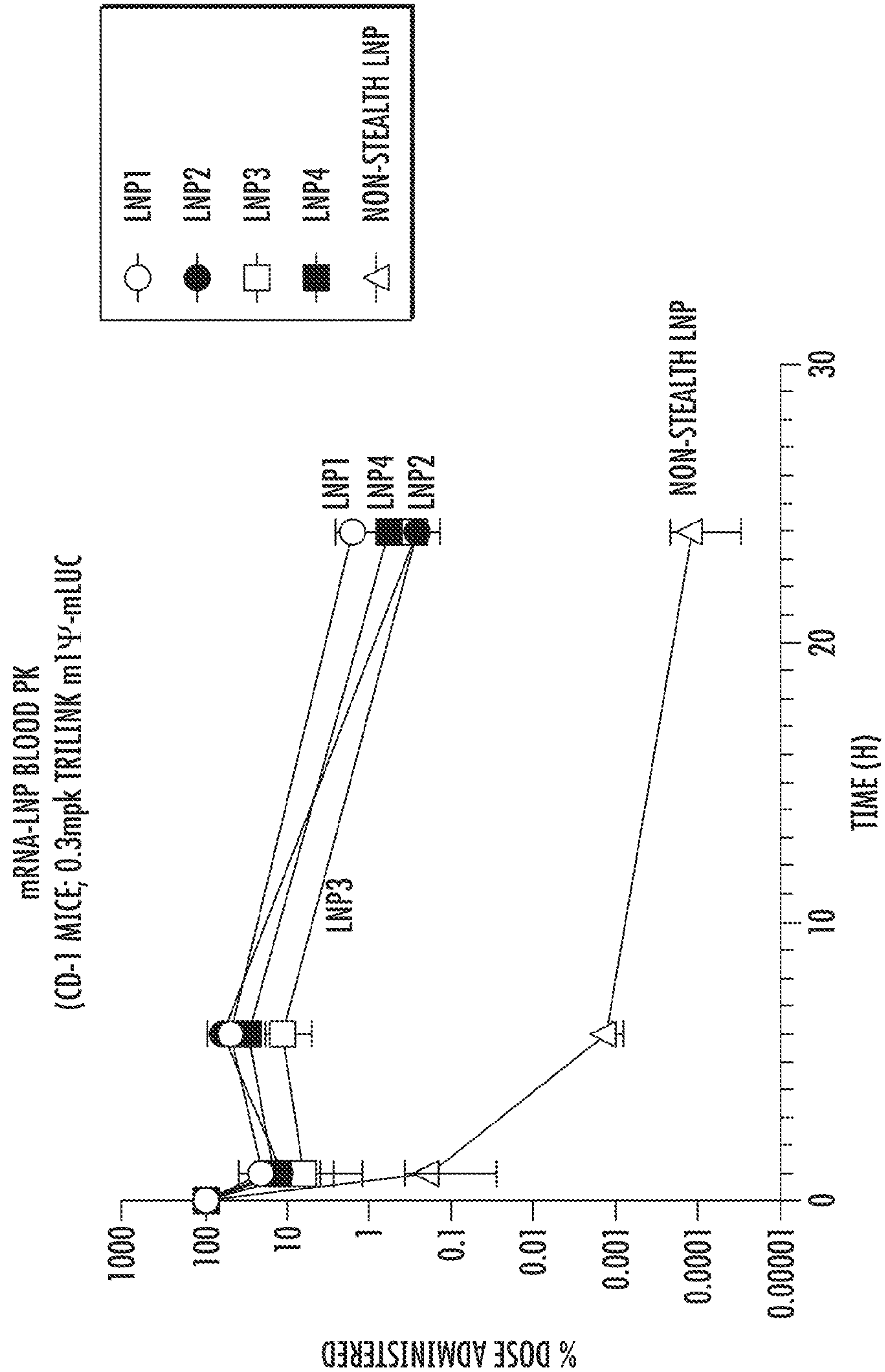
FIG. 3 is a graph that shows unconjugated stealth LNPs maintained 4-5 orders of magnitude higher blood concentrations of mRNA when administered to CD-1 mice compared to non-stealth LNPs loaded with the same mRNA at 0.3 mpk Trilink m1Ψ-mLuc.

FIG. 3 shows unconjugated stealth LNPs maintained 4-5 orders of magnitude higher blood concentrations of mRNA when administered to CD-1 mice compared to non-stealth LNPs loaded with the same mRNA at 0.3 mpk Trilink m1Φ-mLuc. In this experiment, blood concentrations of the mRNA payload were measured using qPCR out to 24 hours. The 4 stealth LNPs loaded with an mRNA maintained between 10-60% payload doses in blood at 6 hours, whereas the non-stealth standard LNP exhibited only 0.001% of the dose still present in the blood at 6 hours.

Figure 4A:
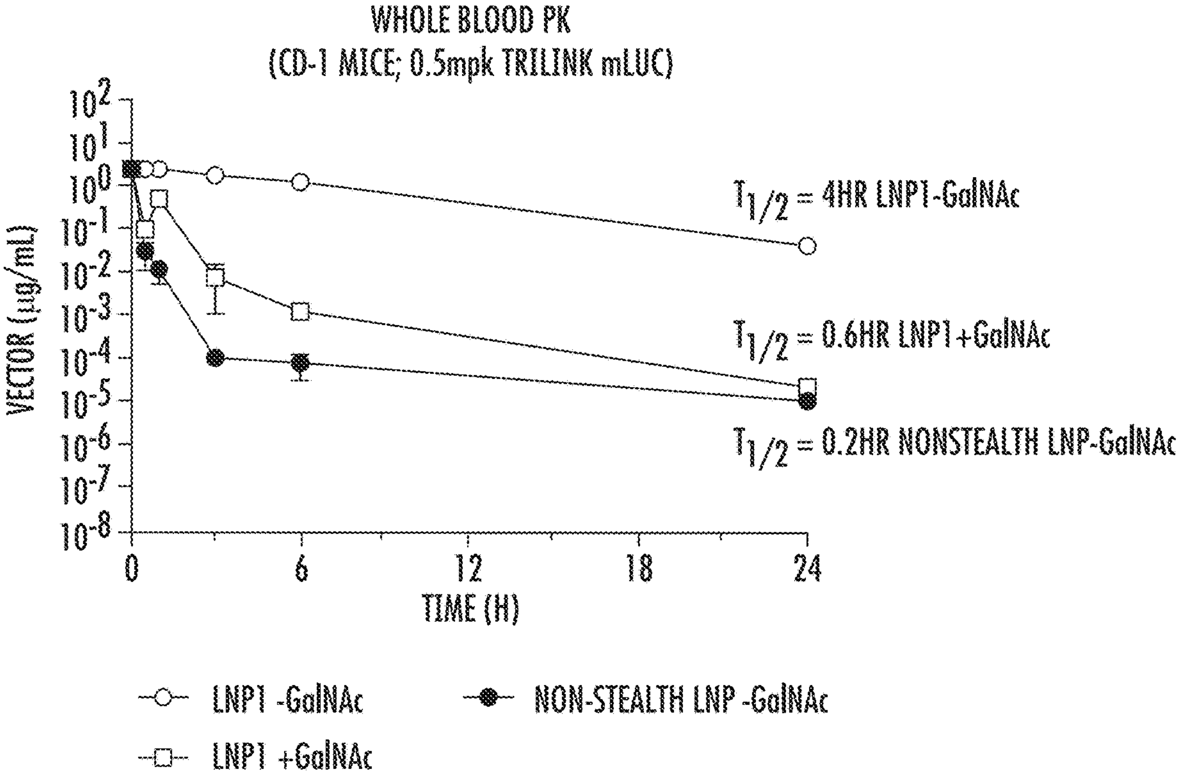
FIG. 4A and FIG. 4B are graphs that show the whole blood PK of a non-stealth LNP without a targeting moiety (minus GalNAc) versus the whole blood PK of two stealth LNPs, one with a GalNAc targeting moiety and one without GalNAc targeting moiety in CD-1 mice.
Figure 4B:
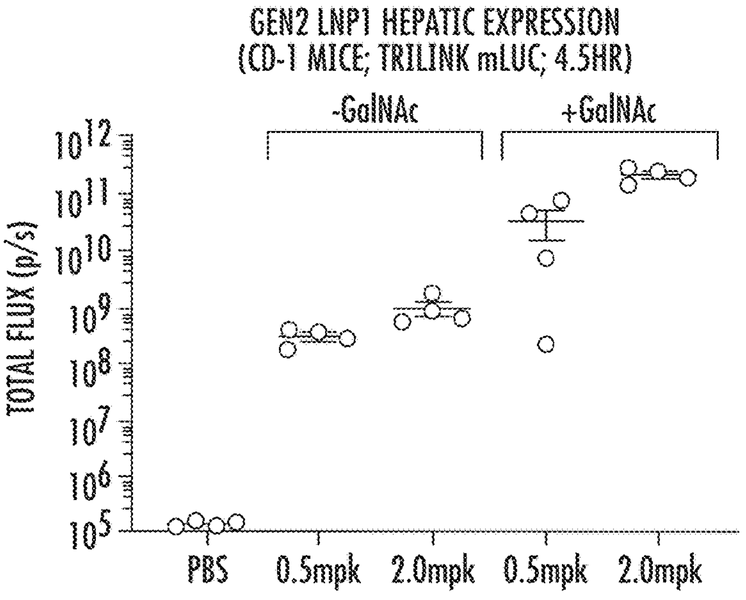

FIG. 4A shows the whole blood PK of a non-stealth LNP without a targeting moiety (minus GalNAc) versus the whole blood PK of two stealth LNPs, one with a GalNAc targeting moiety and one without GalNAc targeting moiety. The right side of FIG. 4B shows that there was a 100× increase in hepatic expression of a sample mRNA payload by using a GalNAc conjugated targeting moiety to the stealth LNP (LNP1). In this example, all test articles were well tolerated with nearly all cytokines investigated (IFNα, IFNγ, IL18, IL6, TNFα, IP10) at or below LOQ at up to 2 mpk. The stealth mRNA-LNP1s without GalNAc showed blood half-life ($t_{1/2}$) of 4 hr; the stealth mRNA-LNP1 with GalNAc targeting moiety showed $t_{1/2}$ of 0.6 hr, whereas the non-stealth LNP without GalNAc exhibited $t_{1/2}$ of 0.2 hr.

Figure 5A:
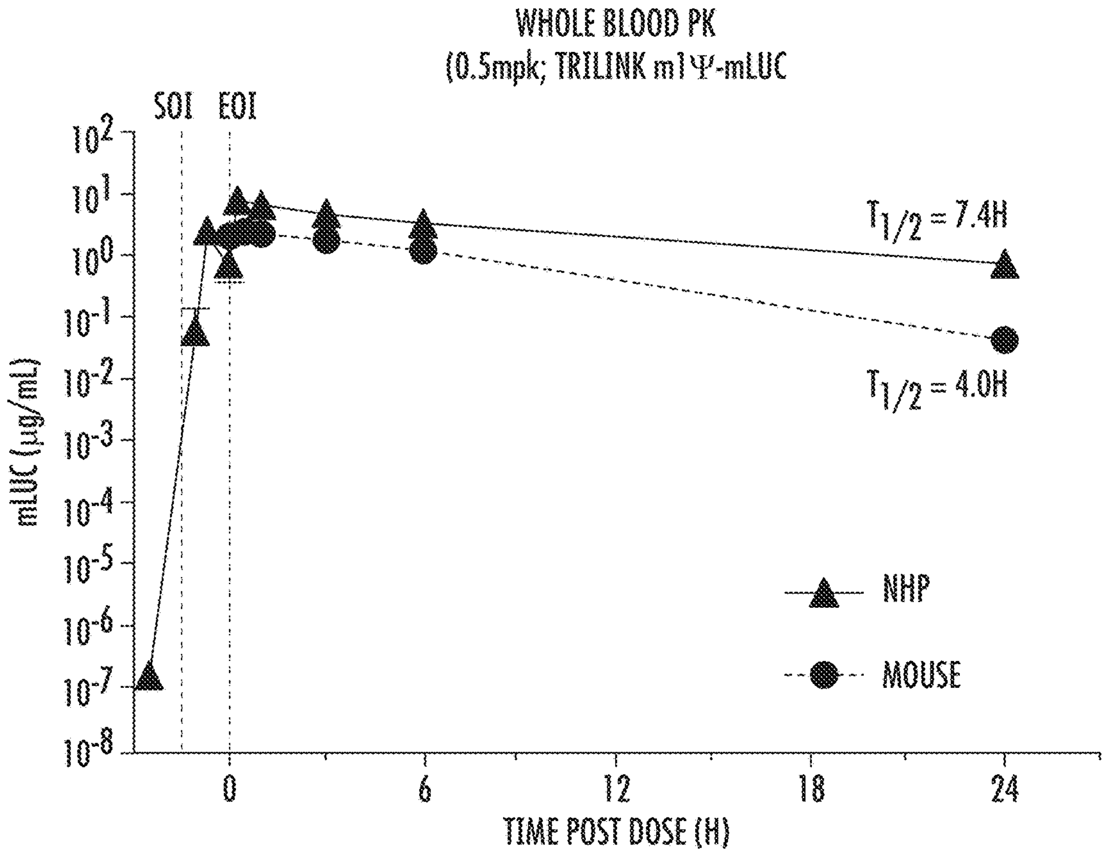
FIGS. 5A and 5B are graphs that show that the extended pharmacokinetics (PK) profiles of stealth LNPs were maintained in non-human primates (NHP) as was also observed in mice.
Figure 5B:
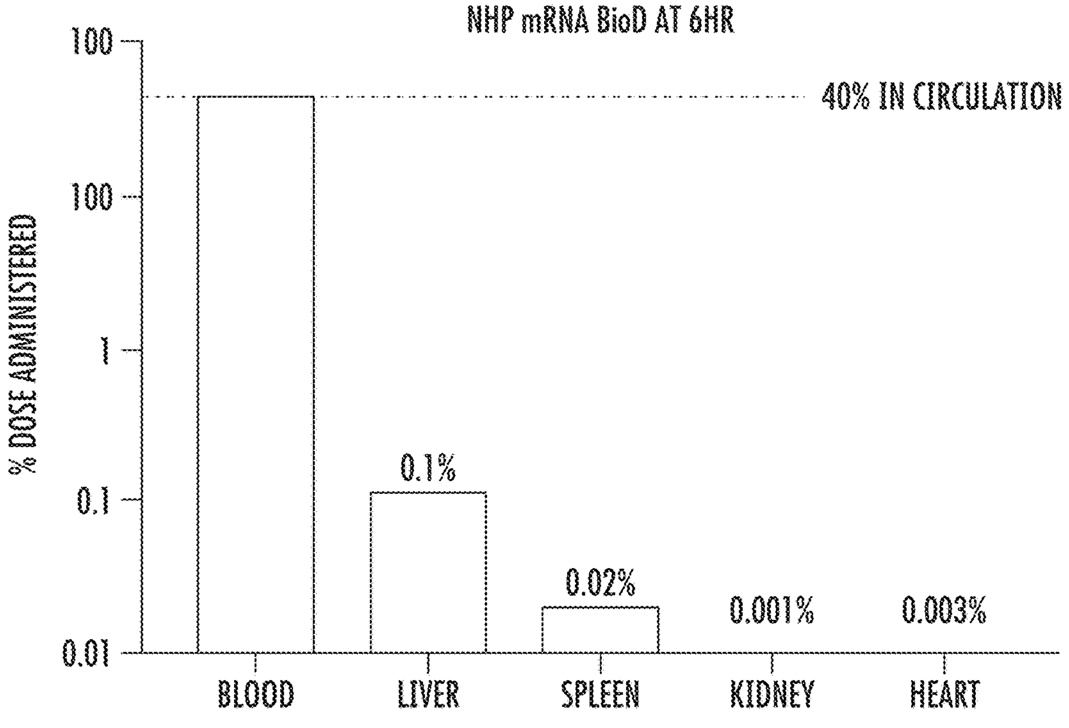

The extended pharmacokinetics (PK) profiles of stealth LNPs were maintained in non-human primates (NHPs), just as in mice (FIG. 5A). FIG. 5A shows whole blood PK of stealth LNPs with mRNA cargo containing 0.3 mpk Trilink m1Φ-mLuc. In this example, all cytokines investigated, including IFNα, IFNγ, IL18, IL6, TNFα, and IP10, were at or below LOQ in both mice and NHPs. These mRNA-LNP1 showed $t_{1/2}$ of 7.4 hr in NHPs and 4.0 hr in mice. These times represent consistent, extended exposures in these two species. In a separate NHP study, the long circulating half-life of stealth LNPs and very low off-target delivery to the liver and spleen were demonstrated (FIG. 5B).

Figure 6:
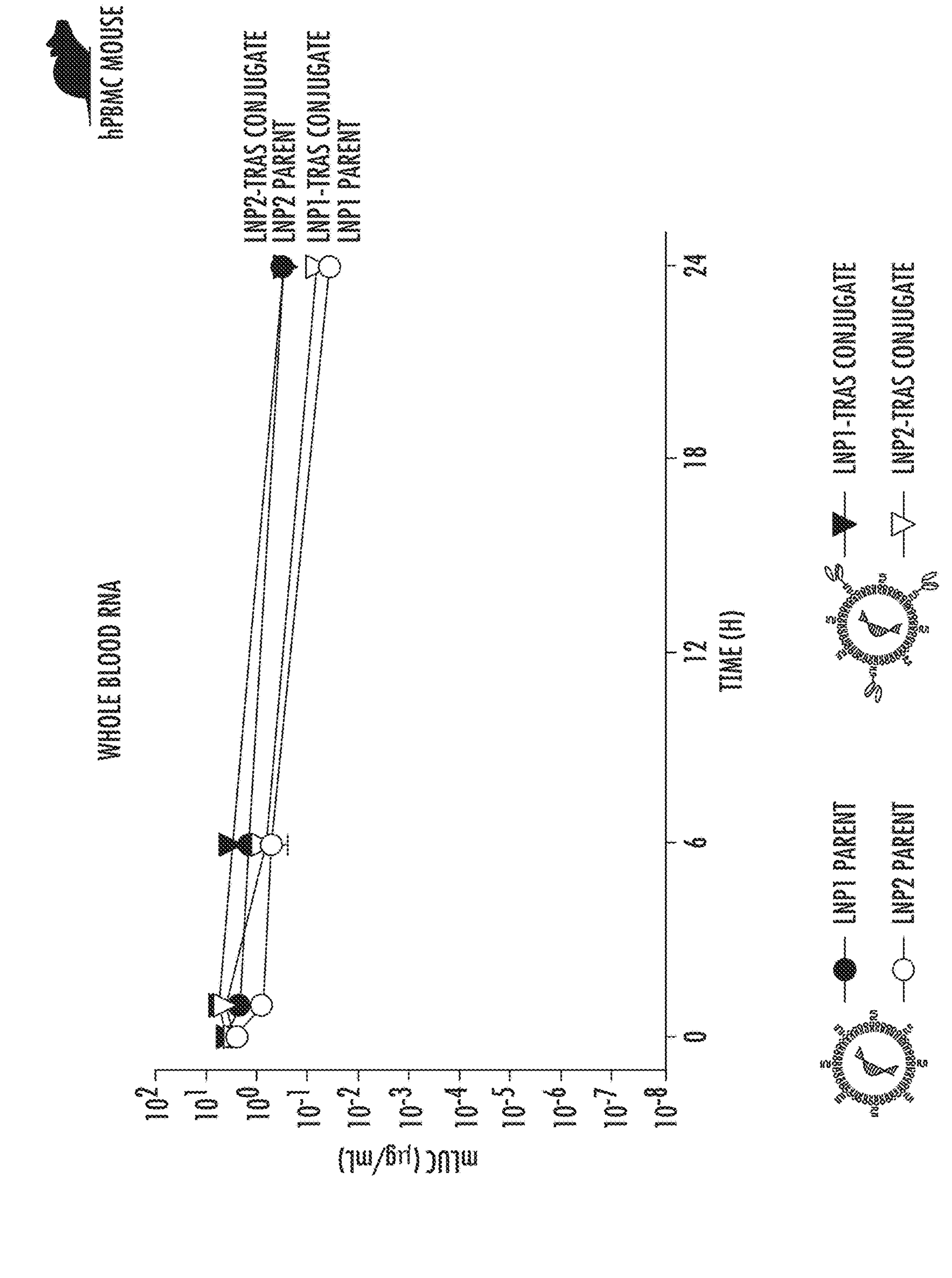
FIG. 6 is a graph that shows the targeting moiety such as scFv had no negative effect on the stealth LNP in its prolonged blood circulation in the absence of a matching antigen for the targeting moiety.

Humanized PBMC engrafted mice were selected to study the pharmacology of stealth mRNA loaded LNPs with a negative control targeting moiety (trastuzumab) conjugated to the stealth LNP versus stealth LNP with no targeting moiety. FIG. 6 shows the targeting moiety such as scFv had virtually no negative effect on the stealth LNP blood circulation in the absence of a matching antigen for the targeting moiety. In FIG. 6, it is clear that all 4 mRNA-LNPs displayed a very consistent PK over 24 hours in humanized mice.

Figure 7:
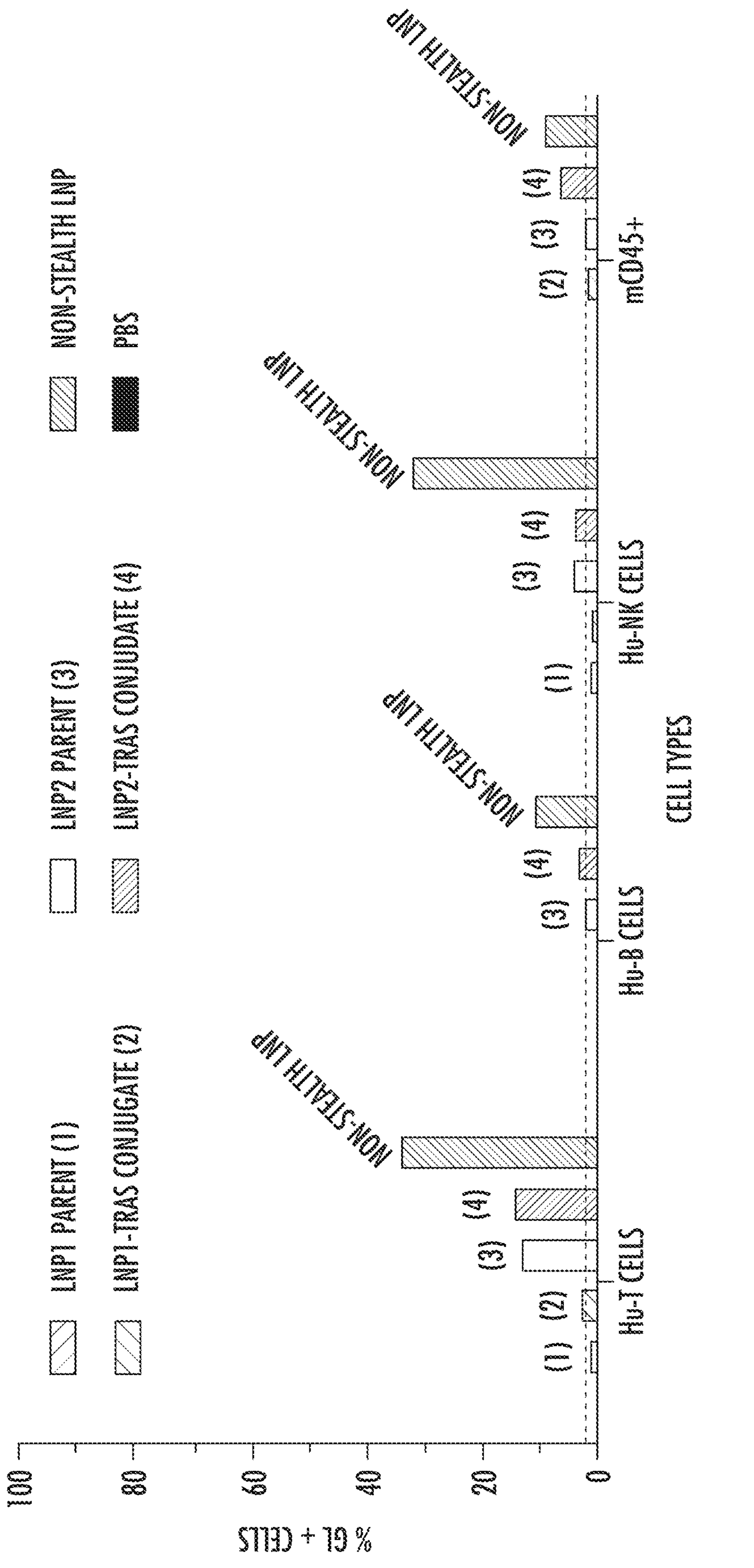
FIG. 7 is a graph that shows that the stealth LNPs consistently exhibited less uptake by human T cells, B cells, NK cells and CD45+ cells as compared to that of the non-stealth LNPs measured in hPBMC engrafted mice.

The stealth LNPs consistently exhibited less uptake by human T cells, B cells, NK cells and CD45+ cells as compared to that of the non-stealth LNPs measured in hPBMC engrafted mice (FIG. 7). As shown in FIG. 7, untargeted stealth LNPs showed no non-specific uptake. Similarly, stealth LNPs conjugated to negative control antibody trastuzumab also showed no non-specific uptake. The non-stealth LNP was the only LNP form that demonstrated a significant amount of non-specific entry into human T-cells, B cells, and NK cells in humanized PBMC engrafted mice (FIG. 7).

In sum, stealthy LNP1 and LNP2 showed less uptake into non-targeted cell populations even in the presence of a non-targeting scFv conjugated to the LNP (trastuzumab conjugate). The PK profile for stealth LNPs were validated in murine and NHP models. The precision of hepatic targeting and subsequent expression of a protein was also demonstrated in both mice and NHP. In addition, the tolerability of mRNA-ctLNP in vivo was also demonstrated. The stealth profile of the stealth LNP of the present disclosure was not affected by the addition of a targeting moiety (e.g., scFv). Finally, it was demonstrated that stealth LNPs did not undergo nonspecific entry into T cell in vitro and in vivo.

Example 3. Stealth LNPs Targeted Human T-Cells Using Targeting Moieties

In this example, the general applicability of conjugating targeting moieties to stealth LNPs was demonstrated. As shown in Table 9 below, 25 different antibody derived anti-T-cell binding targeting moieties were created and tested for suitability of creating T-cell targeting stealth LNPs. In summary, 12 anti-CD3 targeting moieties were engineered as either VHH (2) or scFv (10); 4 anti-CD5 targeting moieties were engineered as scFv; 3 anti-CD6 targeting moieties were engineered as scFv; 6 anti-CD7 targeting moieties were engineered as scFv. Initially, the targeting moieties contained HIS tags for use in purification and detection. The yields varied from as low as 1.84 mg to as high as 51 mg.

TABLE 9

| | Target | Format | ID | Library Nomenclature |
|---|---|---|---|---|
| 1 | CD3 | VHH | CD3-001 | huCD3_60E11-VHH-TagC |
| 2 | CD3 | VHH | CD3-002 | huCD3_117G03-VHH-TagC |
| 3 | CD3 | scFv | CD3-003 | huCD3_acapatamab_scFv-TagC |
| 4 | CD3 | scFv | CD3-004 | huCD3_acmaucabtagene-UCHT1_scFv-TagC |
| 5 | CD3 | scFv | CD3-007 | huCD3_H1.30_L1.47_scFv-TagC |
| 6 | CD3 | scFv | CD3-008 | huCD3_nivatrotamab_scFv-TagC |
| 7 | CD3 | scFv | CD3-009 | huCD3_solitomab_scFv-TagC |
| 8 | CD3 | scFv | CD3-010 | huCD3_Tebentafusp_scFv-TagC |
| 9 | CD3 | scFv | CD3-013 | huCD3_teplizumab_VL-GS4-VH-TagC |
| 10 | CD3 | scFv | CD3-014 | huCD3_teplizumab_VH-GS4-VL-TagC |
| 11 | CD3 | scFv | CD3-015 | huCD3_teclistamab talquetamab_VL-GS4-VH-TagC |
| 12 | CD3 | scFv | CD3-016 | huCD3_teclistamab talquetamab_VH-GS4-VL-TagC |
| 13 | | | | |
| 14 | CD5 | scFv | CD5-001 | huCD5_5D7CD5-XC2339_scFv-TagC |
| 15 | CD5 | scFv | CD5-008 | huCD5_BaylorCD5CAR-H65mod_scFv14-TagC |
| 16 | CD5 | scFv | CD5-009 | huCD5_Cd5A_VH-GKPGS4-VL-TagC |
| 17 | CD5 | scFv | CD5-010 | huCD5_Cd5B-XC2340_scFv-TagC |
| 18 | | | | |
| 19 | CD6 | scFv | CD6-003 | huCD6_CD6CAR-scFvop-TagC |
| 20 | CD6 | scFv | CD6-004 | huCD6_Itolizumab_VH-GS4-VL-TagC |
| 21 | CD6 | scFv | CD6-005 | huCD6_Itolizumab_VL-GS4-VH-TagC |
| 22 | | | | |
| 23 | CD7 | scFv | CD7-001 | huCD7_7CAR8_scFv-TagC |
| 24 | CD7 | scFv | CD7-004 | huCD7_G09_VH-GS4-VL-TagC |
| 25 | CD7 | scFv | CD7-005 | huCD7_G09_VL-GS4-VH-TagC |
| 26 | CD7 | scFv | CD7-006 | huCD7_UCART7_scFv-TagC |
| 27 | CD7 | VHH | CD7-007 | huCD7_Vhh6-TagC |
| 28 | CD7 | VHH | CD7-008 | huCD7_Vhh10-TagC |

Figure 8:
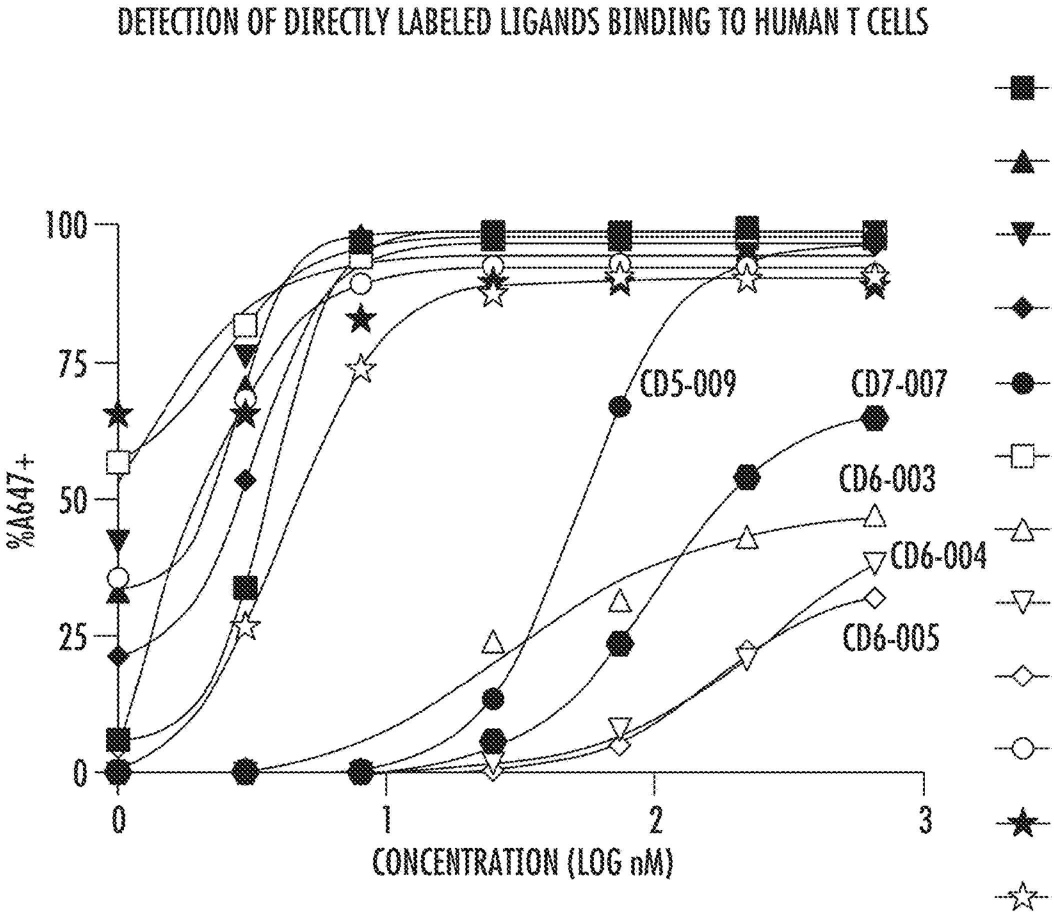
FIG. 8 is a graph that depicts specific targeting capacity of scFv to human T cells.

Many of these binding moieties were directly conjugated to stealth LNPs as described above (thiol-maleimide chemistry) and were shown to specifically target and bind human T cells. See FIG. 8. As shown in FIG. 8, the majority of those tested displayed very strong specific targeting of the LNPs to human T-cells through binding to known T cell surface antigens such as CD3, CD5, CD6 or CD7.

Figure 9A:
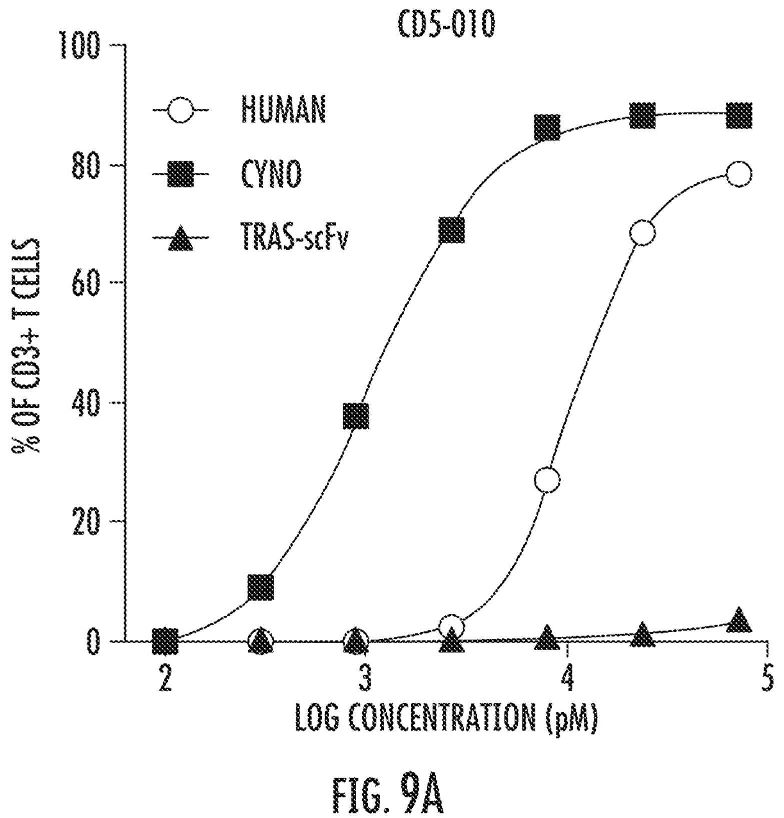
FIG. 9A and FIG. 9B are graphs that show a comparison of two stealth LNP with scFv conjugation for binding to either human or cyno T cells.
Figure 9B:
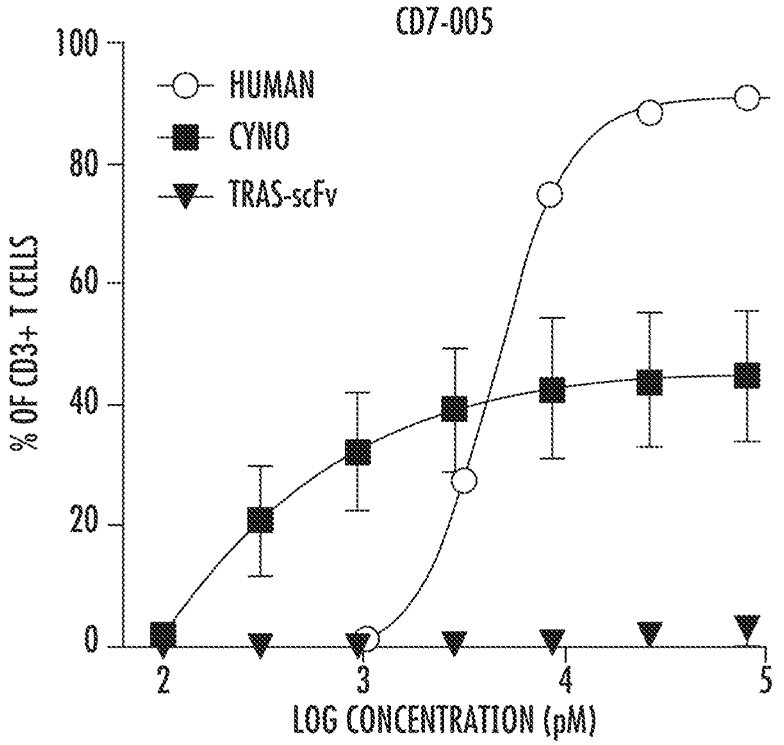

A comparison of two of the antibody conjugated stealth LNPs for binding to either human or cyno T cells was performed. See FIG. 9A and FIG. 9B. As shown in FIGS. 9A and 9B, the binding of anti-CD5 (FIG. 9A) and anti-CD7 (FIG. 9B) conjugated cell targeting LNPs to human and cyno versions of CD5 and CD7 varied due to differences in homology between the proteins in these two species. However, the stealth T-cell targeting LNPs did bind to T cells from both human and cyno NHPs.

Example 4. Conjugation of Targeting Moieties to Stealth LNPs

Figure 10:
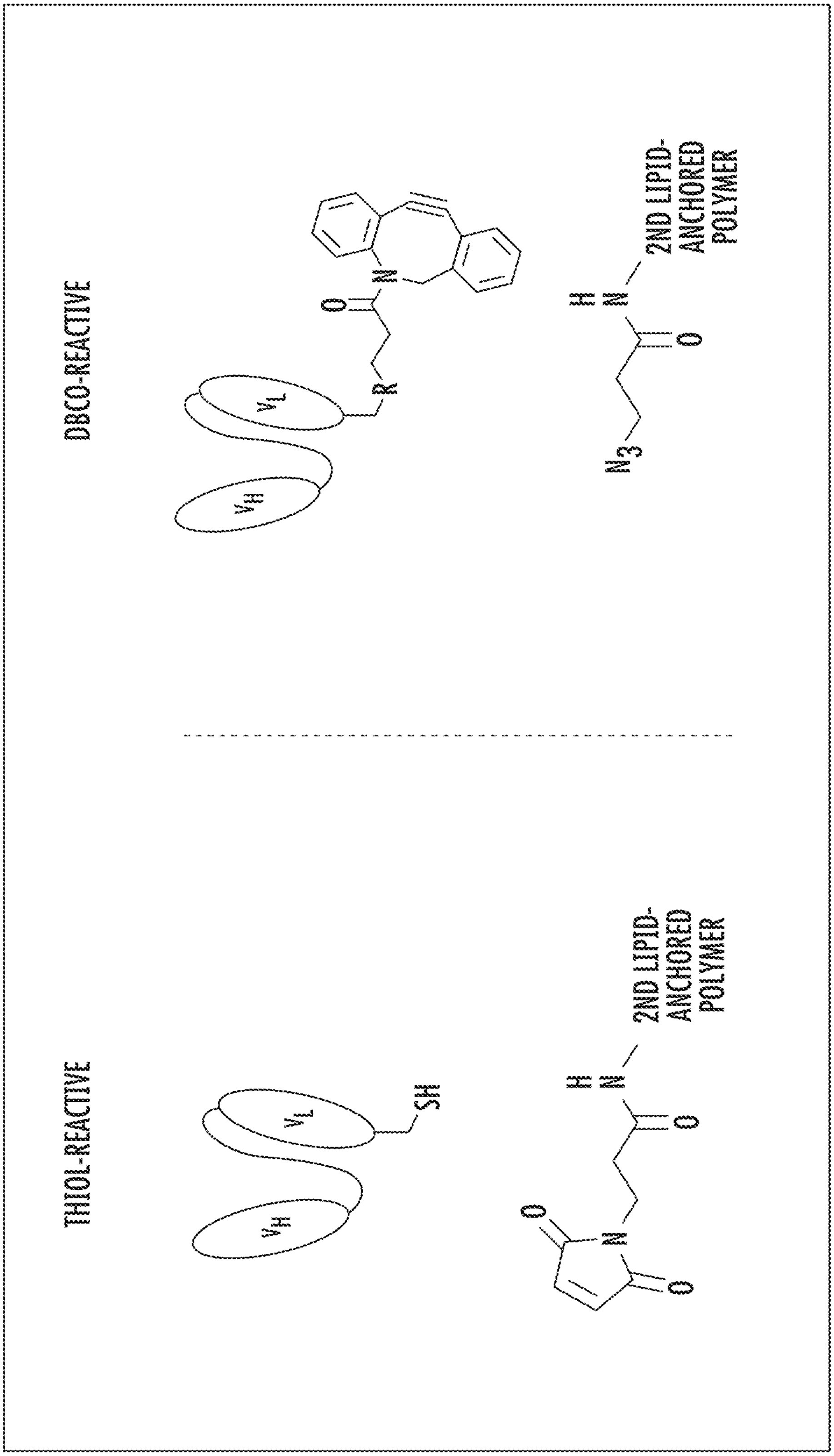
FIG. 10 depicts a conjugation schematic diagram for binding (targeting) moieties to stealth LNPs (e.g., maleimide, thiol, azide, DBCO reagents).

The conjugation of binding moieties to stealth LNPs was accomplished through various chemical linking methods. See FIG. 10. Examples include use of a thiol reactive species and DBCO reactive chemistries, and are discussed in more detail below and shown in FIG. 10:

Maleimide Conjugation:

This example describes the preparation of an LNP-conjugated to a protein ligand of interest, which requires the inclusion of an additional cysteine residue (not in the native protein sequence). The protein ligand of interest was initially reduced with 10 molar equivalents of TCEP for 30 minutes at 23° C. After reduction, the TCEP was removed using a Zeba spin column. The reduced ligand was then incubated with LNP's formulated with DSPE-PEG5k-Maleimide using a mole percentage of 0.5%, for 3 hours at 23° C. The ratio of ligand to DSPE-PEG5k-Maleimide varied from 0.3 down to 0.02. SDS-PAGE and LCMS were used to confirm that the conjugation occurred and to what extent. LNP conjugates were then evaluated using DLS to obtain any changes in size (z-average) or PDI along with a ribogreen assay to evaluate differences in the encapsulation efficiency.

SPAAC Conjugation:

This example describes the preparation of an LNP-conjugated to a protein ligand of interest, which requires the inclusion of an additional cysteine residue (not in the native protein sequence). The protein ligand of interest was initially reduced with 10 molar equivalents of TCEP for 30 minutes at 23° C. After reduction, the TCEP was removed using a Zeba spin column. The reduced ligand was then incubated with 10 molar equivalents of Sulfo DBCO-PEG4-Maleimide for 3 hours at 23° C. The excess DBCO reagent was then removed using a Zeba spin column. The extent of labelling and overall protein purity was confirmed using a UPLC-QTOF.

The DBCO labelled protein was then incubated with LNP's formulated with DSPE-PEG5k-N3 using a mole percentage of 0.5%, for 16 hours at 23° C. The ratio of ligand to DSPE-PEG5k-N3 varied from 0.3 down to 0.02. SDS-PAGE and LCMS were used to confirm that the conjugation occurred and to what extent. LNP conjugates were then evaluated using DLS to obtain any changes in size (z-average) or PDI along with a ribogreen assay to evaluate differences in the encapsulation efficiency.

Figure 11:
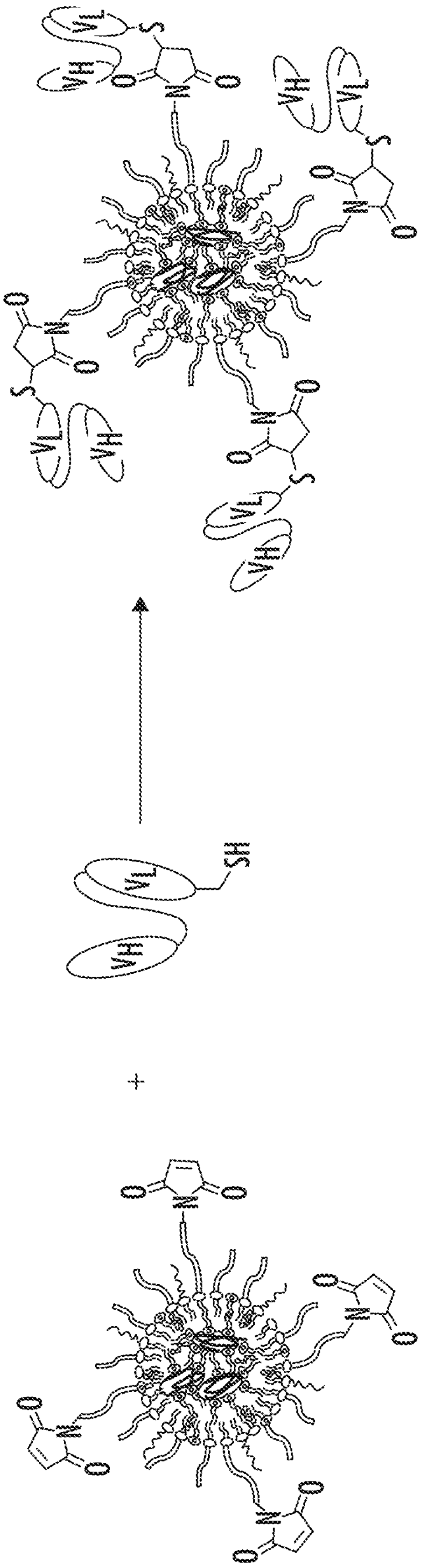
FIG. 11 is a schematic that shows conjugation of a binding moiety to a stealth LNP affected the LNP diameter by at least the amount that the antibody species extends from the parental surface of the LNP.
Figure 12:
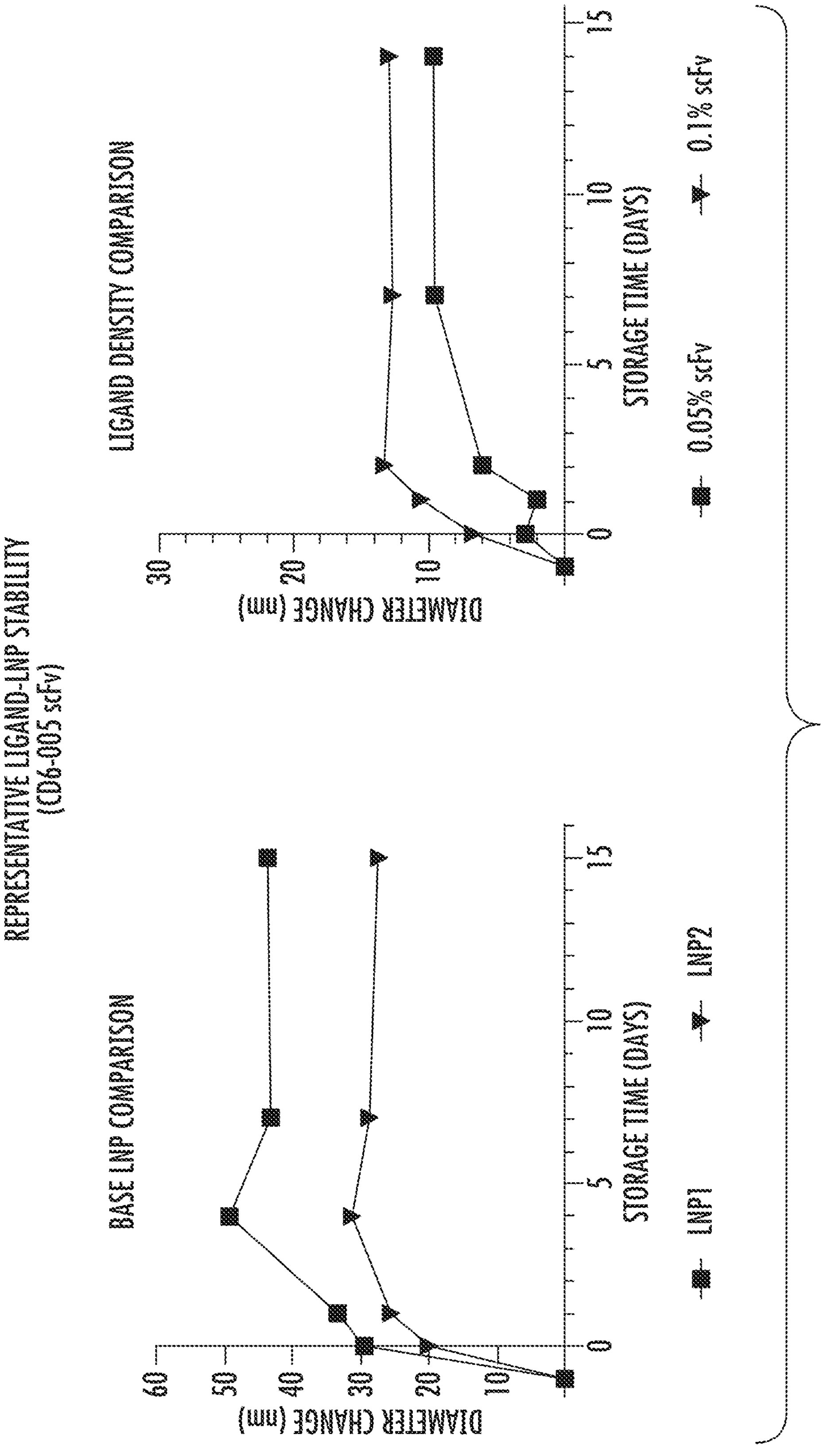
FIG. 12 is a panel of graphs that demonstrate that 0.05% to 0.1% scFv ligand density were optimal to minimize LNP size expansion after 15 days in storage. (In some embodiments herein, the targeting moiety is also referred to as a ligand.)

One important note is that conjugation of a binding moiety to a stealth LNP affected the LNP diameter by at least the amount that the antibody species extends from the parental surface of the LNP. See FIG. 11 and FIG. 12. Important design considerations are base composition of the genetic cargo, ligand density and the ligand modification site to allow for enhanced ligand stability, presentation and effective ligand targeting and binding. See FIG. 11 and FIG. 12. In the example shown in FIG. 11, 0.05% to 0.1% scFv ligand density were optimal to minimize LNP size expansion after 15 days in storage.

The Thiol-Maleimide conjugation efficiencies were measured for 18 of the 25 antibodies and antibody derivatives in Table 9 using mRNA green lantern cargo and it remained greater than 80% in most cases except where competing cysteine disulfides were present (data not shown). Simultaneously, the encapsulation efficiency remained at least 93% for all constructs tested.

Figure 13:
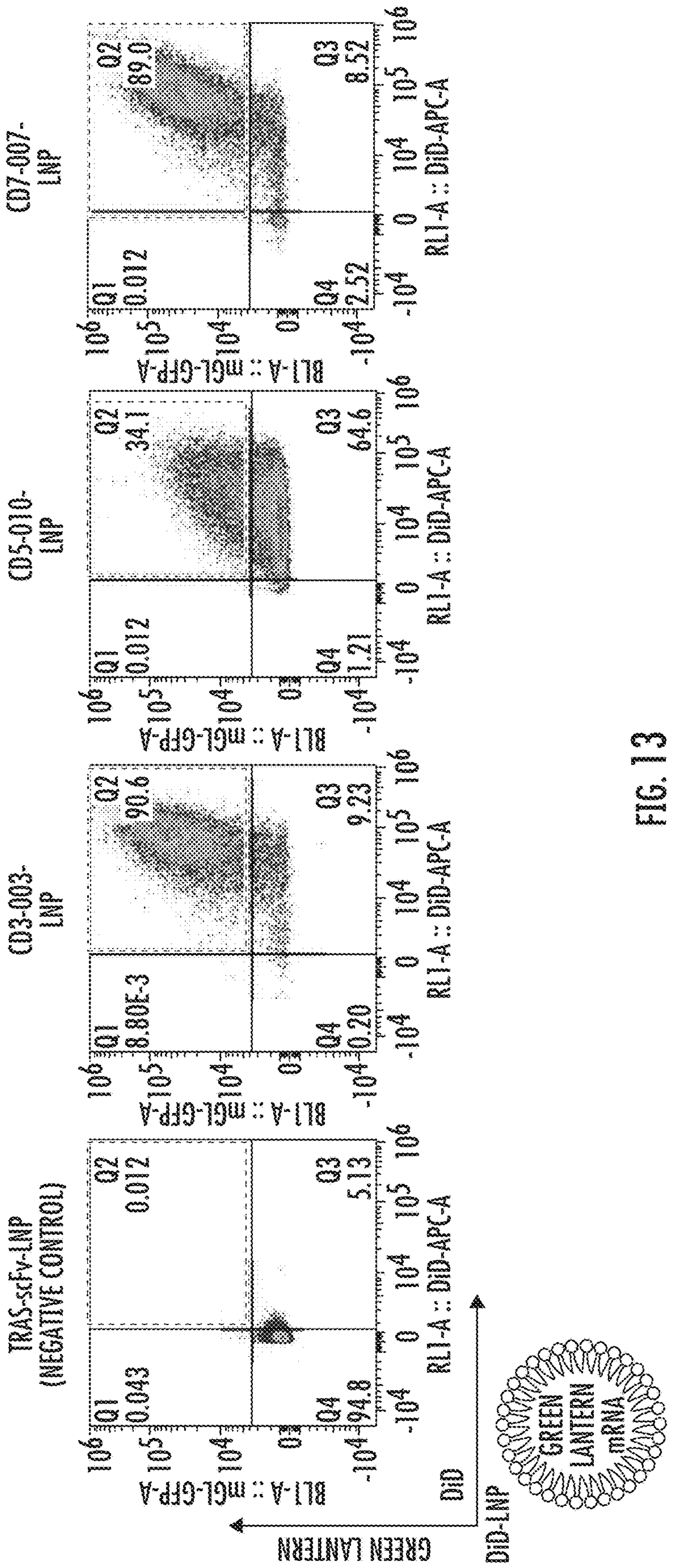
FIG. 13 is a panel of flow cytometry results that show human T cells activated in vitro with anti-CD3, anti-CD28 and excess recombinant IL-2. Flow cytometry results demonstrated that human T-cells were successfully targeted by anti-CD3, anti-CD5 and anti-CD7 conjugated stealth LNPs encapsulating mRNA cargo. Human T cells were activated for 3 days with anti-CD3/28 & IL2 prior to incubation with serum-opsonized LNPs.

Example 5. Flow Cytometry Using Primary Human T-cells Targeted by Conjugated LNPs with mRNA Cargo In this example, human T cells were activated in vitro with anti-CD3, anti-CD28 and excess recombinant IL-2 (FIG. 13). As shown in FIG. 13, flow cytometry results demonstrated that human T-cells were successfully targeted by anti-CD3, anti-CD5 and anti-CD7 conjugated stealth LNPs encapsulating mRNA cargo. In this experiment the lipophilic tracer DiD was used to track the LNP (x-axis), and mRNA expression was revealed by green lantern florescence (y-axis). As shown, the cargo was taken up by the targeted human T-cells and cargo mRNA was successfully expressed in the cytoplasm of the targeted human T-cells. It is noted that the targeted cells expressing CD3 did not induce rapid death in vitro because of the presence of excess IL-2 supplemented in the cell culture growth medium. In contrast, in vivo anti-CD3 LNP induced rapid death of human T cells in humanized mice (in vivo) as expected and discussed below and shown in FIG. 19.

Figure 14:
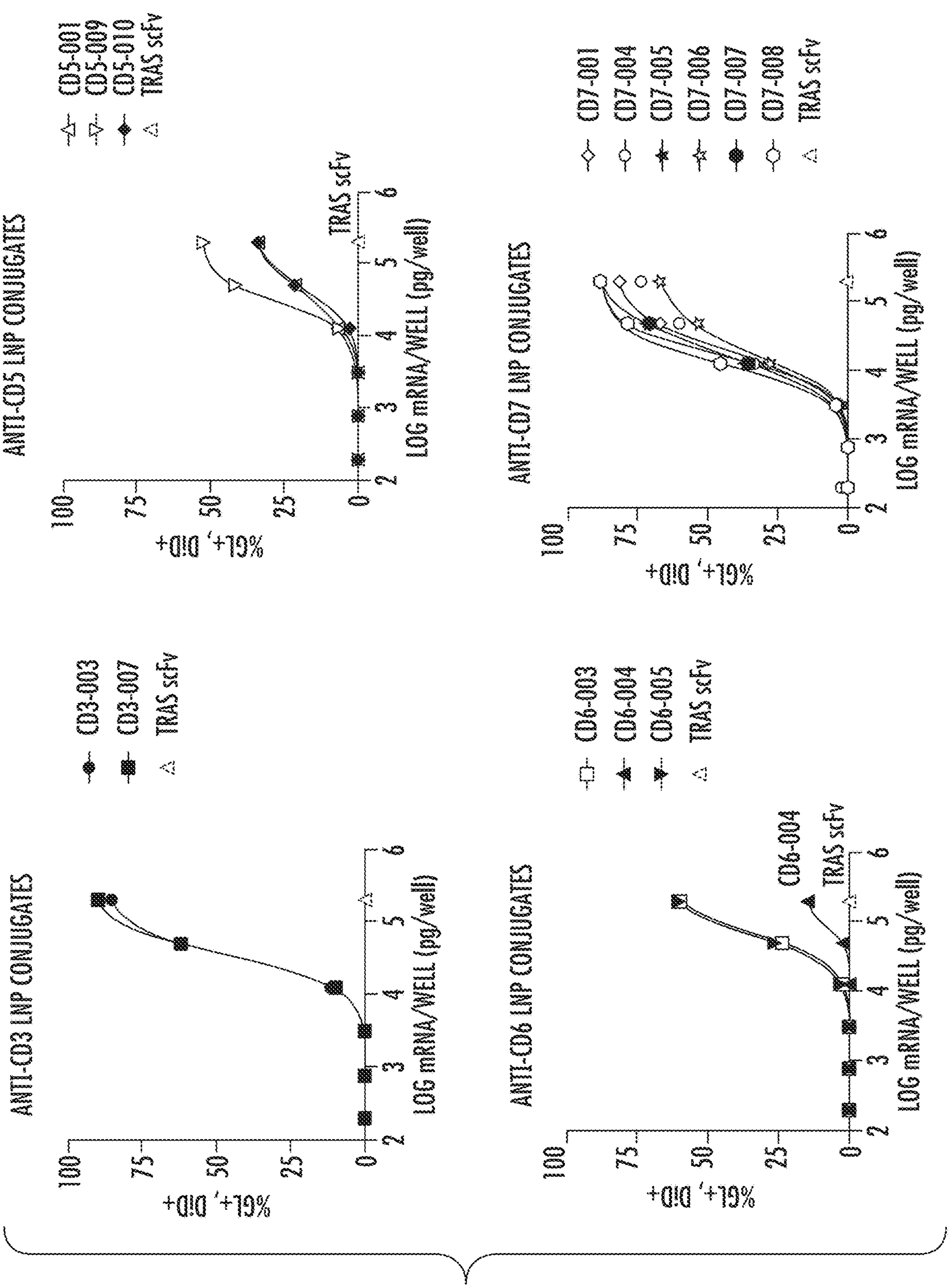
FIG. 14 is a panel of graphs that show that the stealth LNP with anti-CD3 scFv, anti-CD5 scFv, anti-CD6 scFv, anti-CD7 scFv and trastuzumab (anti-Her) all exhibited dose dependent binding, uptake and mRNA cargo expression. Anti-HER2 Ab was included as a negative control because HER2 is not found on these cells and confirmed that even non-targeted LNPs remain stealthy.

A large number of the ligand conjugates in Table 9 were screened at a targeted 0.1 mol % density against activated human primary T-cells from 2 donors (FIG. 14) and it was found that most displayed robust uptake and expression across a range of doses and across all selected antigens of interest. FIG. 14 shows that the stealth LNP with anti-CD3 scFv, anti-CD5 scFv, anti-CD6 scFv, anti-CD7 scFv and trastuzumab (anti-Her) all exhibited dose dependent binding, uptake and mRNA cargo expression. Importantly, anti-HER2 (trastuzumab scFv) was included as a negative control in each experiment, because HER2 is not found on these cells, and confirmed that even non-targeted LNPs remain stealthy.

Figure 15:
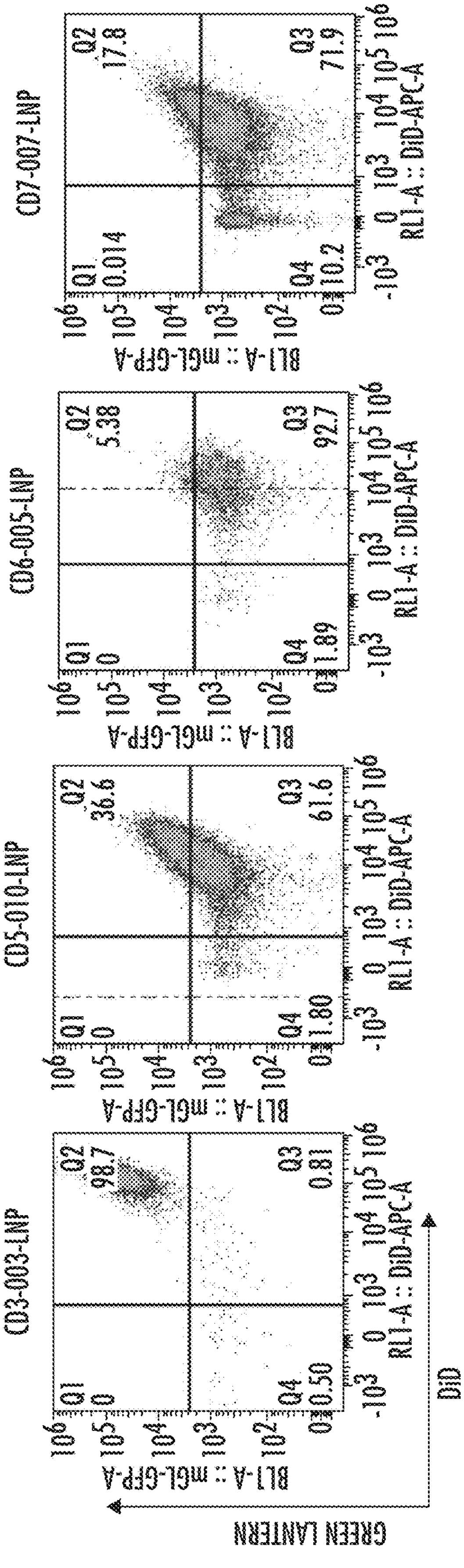
FIG. 15 is a panel of flow cytometry results that demonstrate that stealth targeting LNPs with anti-CD3-scFv, anti-CD5-scFv, anti-CD6 scFv and anti-CD7 scFv exhibited clear binding and were taken up by resting primary human T-cells, but expression of the cargo was reduced.
Figure 16:
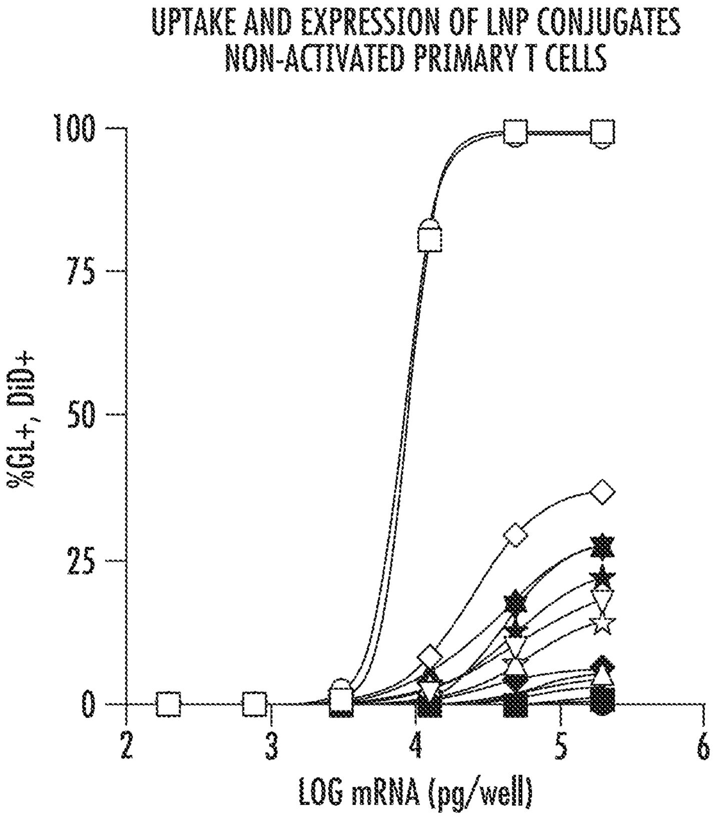
FIG. 16 is a graph that shows that much less mRNA was detected in the non-activated T-cells versus the anti-CD3 LNPs, which were self-activating the T-cells as they were attaching and entering the cell.

The data in FIG. 15 demonstrated that stealth targeting LNPs with anti-CD3-scFv, anti-CD5-scFv, anti-CD6 scFv and anti-CD7 scFv clearly bound and were taken up by resting primary human T-cells but expression of the cargo was reduced. See FIG. 15. However, the increased expression seen with anti-CD3 LNP was likely due to the ability of anti-CD3 to directly activate the resting cells to an activated state and thus also show enhanced expression of the cargo over this time span and under in vitro conditions. These observations are confirmed in FIG. 16 showing that much less mRNA was detected in the non-activated cells versus the anti-CD3 LNPs which were self-activating the T-cells as they were attaching and entering the cell.

Figure 17:
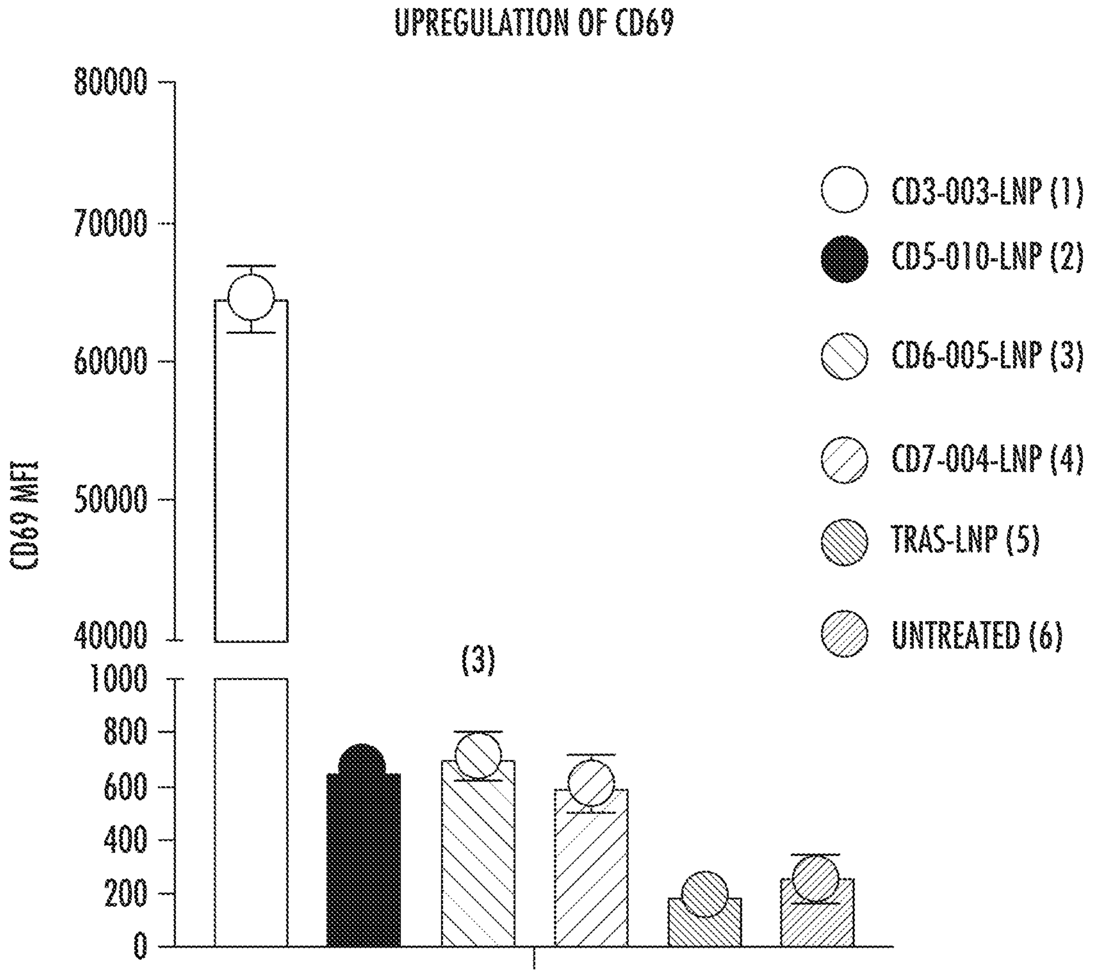
FIG. 17 is a graph that depicts anti-CD3 LNPs activated T cells as they bound and entered the cells during an overnight incubation with primary human T-cells in vitro. CD69 is a marker for early T cell activation. A 40-fold higher activation of T-cells was observed in the presence of anti-CD3 LNP as compared to that of anti-CD5 LNP, anti-CD6 LNP, or anti-CD7 LNP.

FIG. 17 verifies the observation that anti-CD3 LNPs were activating T cells as they bound and entered the cell during an overnight incubation with primary human T-cells. CD69 is a marker for early T cell activation, and it was 40-fold higher in the presence of anti-CD3 LNP than for anti-CD5 LNP, anti-CD6 LNP anti-CD7 LNP. This activation of T-cells by anti-CD3 LNPs produced cytokine storms and cell death when the experiment was carried out in vivo. See FIG. 19. Trastuzumab-LNPs were even lower than untreated (FIG. 16).

Figure 18:
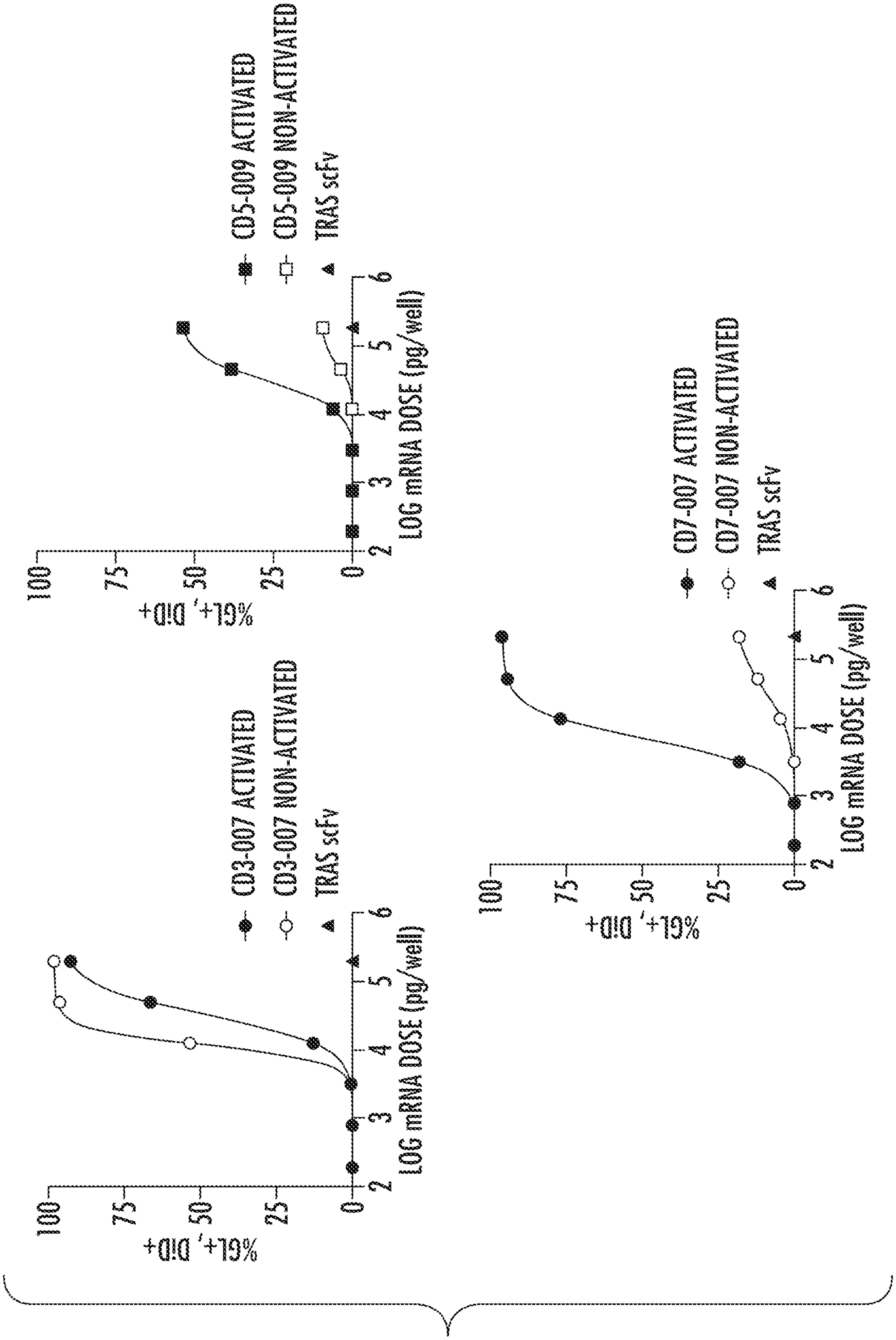
FIG. 18 shows results where conjugations were prepared with the maleimide conjugation protocol described in the Examples, and the conjugated LNPs were incubated with resting and activated T-cells. The graphs show the % of DiD uptake on the Y-axis and green lantern mRNA expression on the X-axis. Data was highly repeatable across two donors.

In this experiment the conjugations were prepared with the maleimide conjugation protocol discussed above and the conjugated LNPs were incubated with resting and activated T-cells. See FIG. 18. In each case the graphs represent % of DiD uptake on the Y-axis and the green lantern mRNA expression on the X-axis. Here again the anti-CD3 LNP activated the non-activated T cells and resulted in much greater green lantern expression. See left panel of FIG. 18. It is noted that the encapsulation efficiency was maintained above 95% after conjugation and that all conjugation efficiencies were above 90%.

Figure 19:
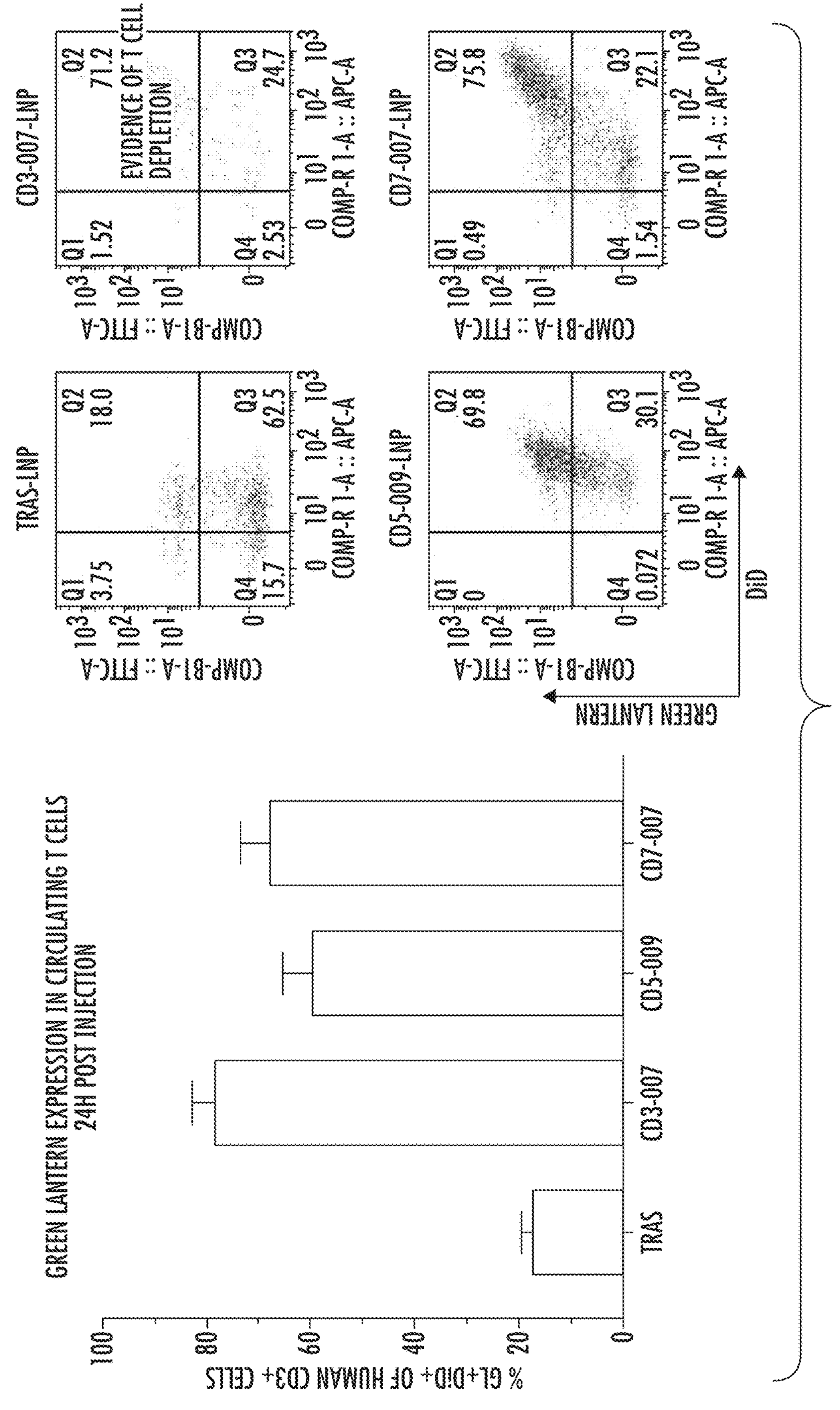
FIG. 19 shows the results from an experiment where T-cell targeting LNPs were compared for their ability target, bind, enter and express their mRNA cargo into human T-cells in humanized mice.

Example 6. In Vivo Use of T-Cell Targeting LNPs and Expression of mRNA Cargo In this experiment T-cell targeting LNPs were compared for their ability to target, bind, enter and express their mRNA cargo into human T-cells in humanized mice (FIG. 19). The anti-CD3 LNPs highly activated the T-cells in vivo and produced cell death in the process. The negative control trastuzumab LNP did not show any sign of expression of the cargo as expected. However, the targeting LNPs constructed using anti-CD5 and anti-CD7 produced T-cell targeting LNPs having a more optimal profile including cell targeting, combined with uptake and expression of the mRNA green lantern cargo (FIG. 19).

Example 7. T-cell Specific Delivery of LNP2-Anti-CD7 scFv

Figure 20:
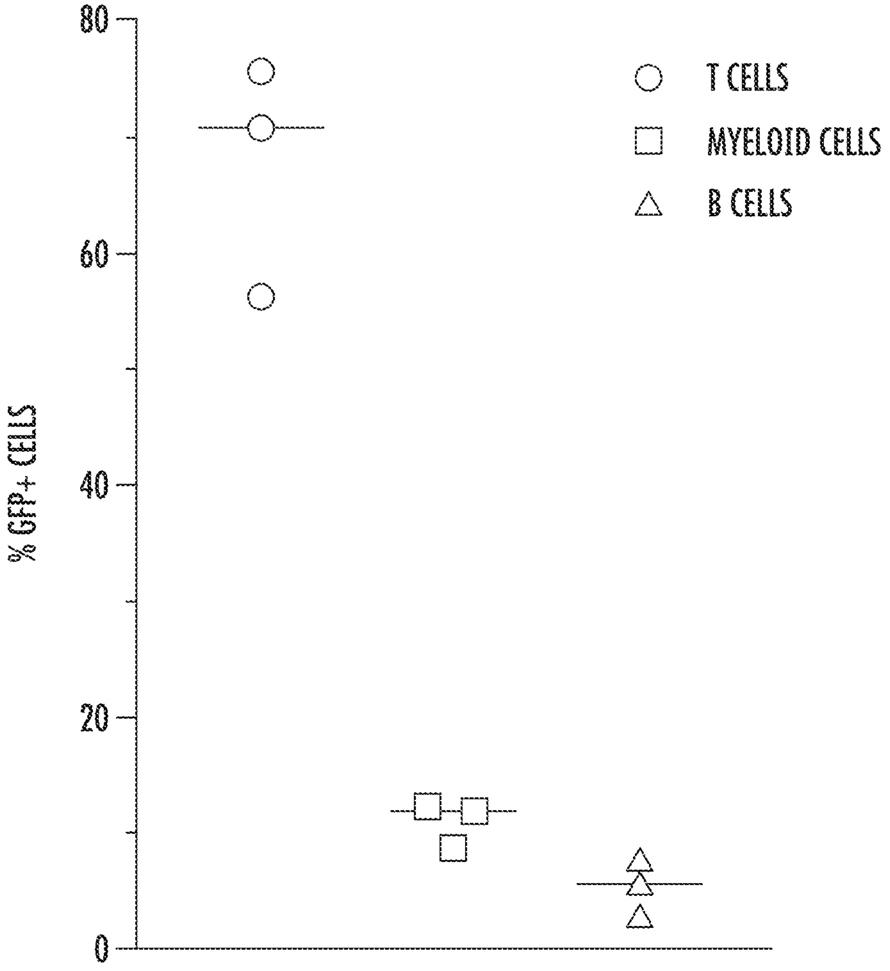
FIG. 20 shows results from an in vivo study where LNP2 conjugated to an anti-CD7 scFv displayed highly selective receptor-mediated uptake and expression of mRNA in humanized mice upon systemic administration.
Figure 21:
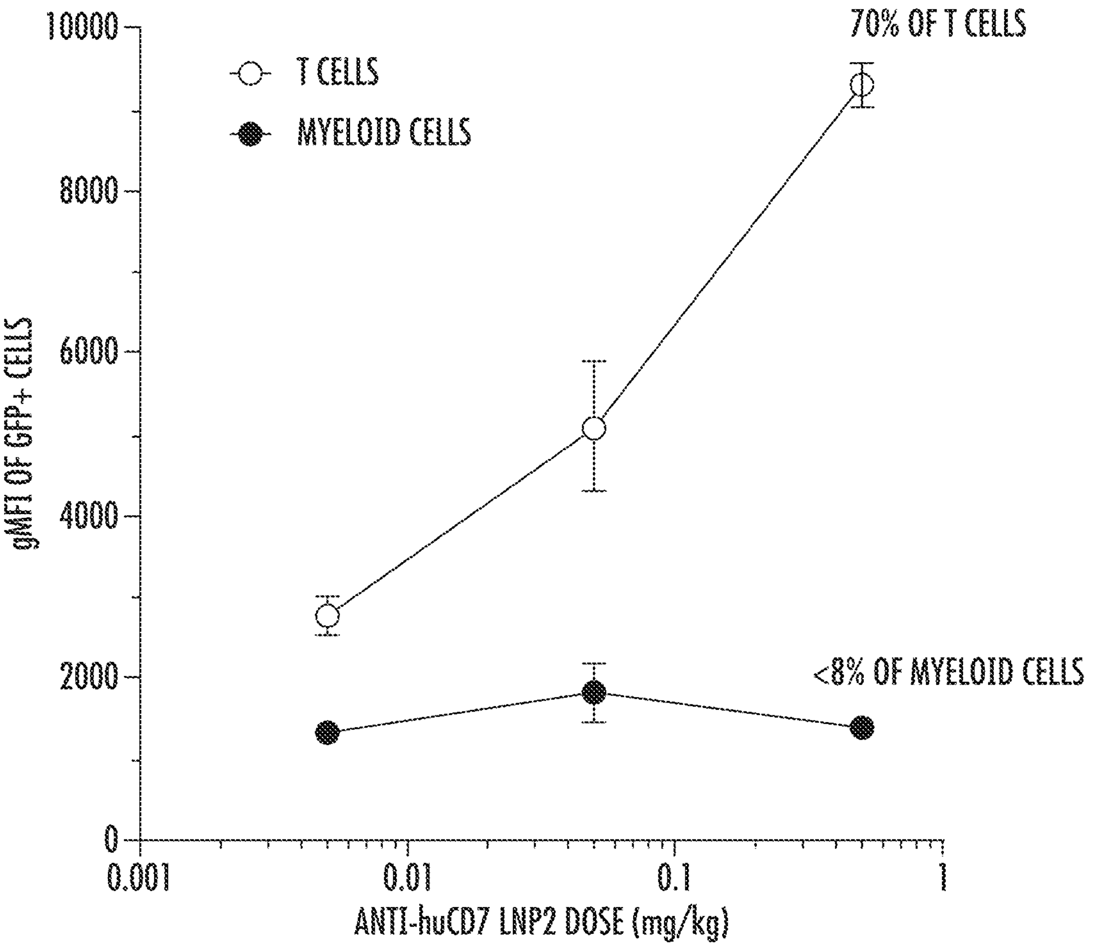
FIG. 21 shows dose dependent receptor-mediated delivery and expression of mRNA in vivo using humanized mice.

In this in vivo study, LNP2 conjugated to an anti-CD7 scFv (T-cell-specific) displayed highly selective receptor-mediated uptake and expression of mRNA in humanized mice upon systemic administration (FIG. 20). In addition, FIG. 20 shows that LNP2 targeted to T-cells exhibited minimal levels of off-target delivery to B-cells and other myeloid cells, thus confirming the efficacy of receptor-mediated delivery and uptake. In FIG. 21, the use of receptor-specific delivery through conjugated binding moieties such as scFv directed to T-cells (via CD7) produced highly selective delivery to T-cells, which successfully resulted in expression of mRNA in a dose dependent manner in vivo (FIG. 21).

Example 8. Blood pK Characteristics of Stealth Versus Non-Stealth LNPs within 30 Minutes of Administration to the Blood in CD-1 Mice The following study was performed in male CD-1 mice aged 3-5 weeks. Animals were dosed with dose of 1 mg/kg of LNP201, LNP202, and LNP203, all encapsulating ceDNA as cargo. These LNPs were formulated as described above and their particle sizes and encapsulation efficiency were measured and found to be consistent with previous results (e.g., the average particle size of <80 nm in diameter and 90% EE, respectively). Blood samples were collected through submandibular or tail vein nick at 0 h, 1 h, 3 h, 6 h, and 24 h post dose administration. Blood samples were stored at −80° C. in K2 EDTA tubes until analysis was performed to determine ceDNA levels (qPCR analysis was performed to determine ceDNA levels in blood).

TABLE 11

Formulations for pK Analysis over 30 minutes in Blood

| Test Article | Compositional Basis (mol %) |
|---|---|
| LNP201 | Lipid Z/DSPC/Chol/DSG-PEG2000-OH/DiD/DSPE-PEG5000-N3 (47.5/10.0/39.0/2.8/0.5/0.2) |
| LNP202 | Lipid 87/DSPC/Chol/DSG-PEG2000-OH/DiD/DSPE-PEG5000-N3 (47.5/10.0/39.0/2.8/0.5/0.2) |

TABLE 11-continued

| Formulations for pK Analysis over 30 minutes in Blood | |
|---|---|
| Test Article | Compositional Basis (mol %) |
| LNP203 (non-stealth reference LNP) | Lipid Z/DSPC/Chol/DMG-PE2000-OH (48.6/10.1/37.6/3.7) |

Figure 22:
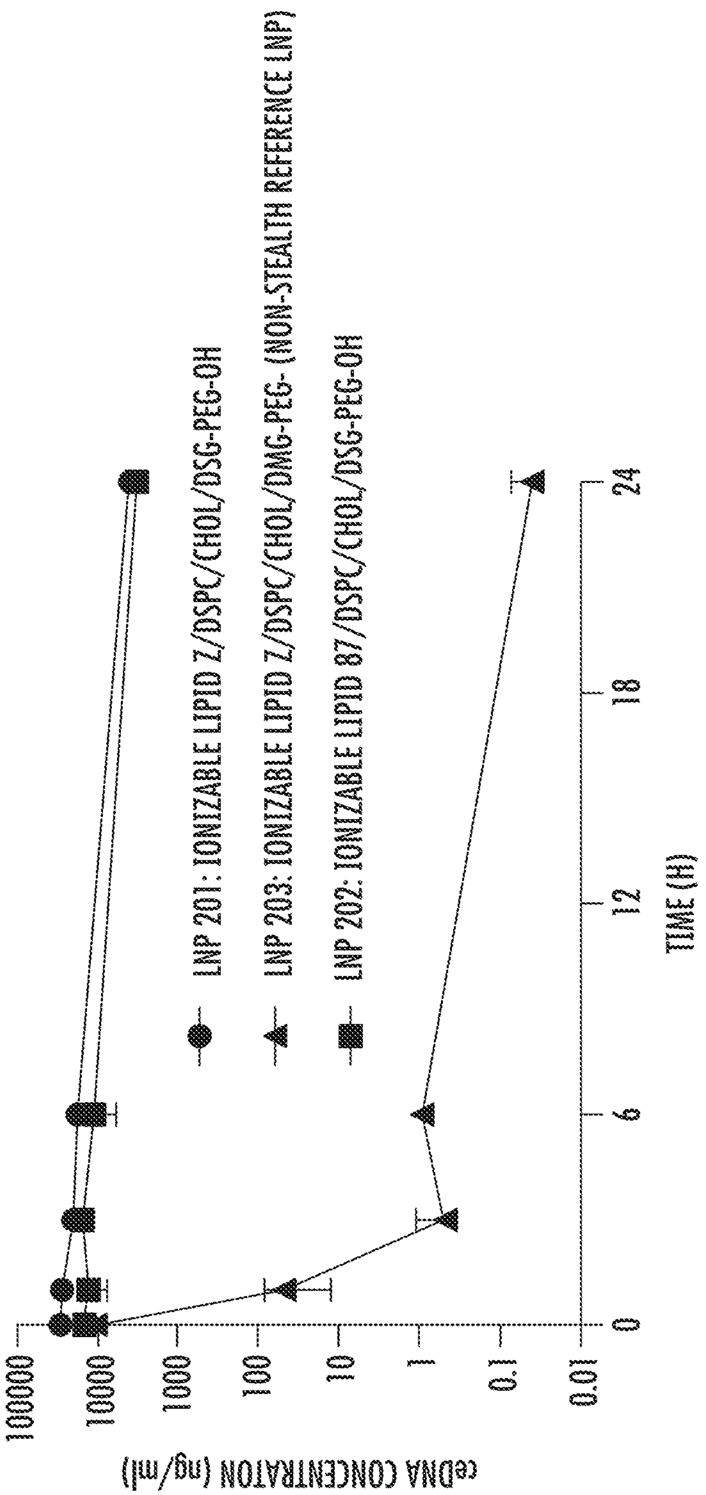
FIG. 22 depicts a chart quantifying, via qPCR, copies of ceDNA in the whole blood at 0 hour, 1 hour, 3 hours, 6 hours and 24 hours after dosing for CD-1 mice groups treated with LNP201, LNP202, and LNP203.

As shown in FIG. 22, LNP201 (ionizable Lipid Z, $t_{1/2}$=8.91) and LNP202 (ionizable Lipid 87, $t_{1/2}$=10.4) that contain C18 DSG-PEG as a lipid-anchored polymer exhibited much greater and extended blood half-life ($t_{1/2}$) as compared to that of the reference LNP, LNP203 ($t_{1/2}$=0.25 alpha phase), which comprises C14 DMG-PEG as lipid polymer. The detailed results are shown in Table 12 below and FIG. 22:

TABLE 12

| Blood pK Characteristics for Stealth versus Non-Stealth LNP in the first 3 hours of Blood Exposure as Measured by $t_{1/2}$ and AUC. | | |
|---|---|---|
| Formulation | Half-life (stealth/non-stealth) | AUC (hr*ng/ml) (stealth/non-stealth) |
| LNP201 (Stealth) | 8.91 (35.6-fold) | 311,000 (207-fold) |
| LNP202 (Stealth) | 10.4 (41.6-fold) | 193,000 (128-fold) |
| LNP203 non-Stealth | 0.25 (alpha) | 1500 |

For LNP203 and other non-stealth LNPs, 99.9% of the formulation is cleared from systemic circulation by 3 hours, hence only $t_{1/2}$ of the alpha phase (i.e., 0.25 $t_{1/2}$) is reported in Table 12. When the rapid clearance of 99.9% of the LNP for non-stealth LNP is considered, the ratios of the $t_{1/2}$ and AUC of stealth to non-stealth is very different than shown in the previous example. In this example, the biological effect of stealth versus non-stealth LNPs is much more pronounced. The ratio of the $t_{1/2}$ (hr) alpha phase is 35.6 for LNP201 versus LNP203. Similarly, the ratio of the $t_{1/2}$ (hr) alpha phase is 41.6 for LNP202 versus LNP203.

The effect on AUC was even more intense. The ratio of the AUC (hr*ng/ml) of the alpha phase is 207-fold for LNP201 versus LNP203. Similarly, the ratio of the AUC (hr*ng/ml) of the alpha phase is 128-fold for LNP202 versus LNP203. These data suggest that stealth LNPs comprising C18 lipid-anchored polymer, all formulated using the component ratios disclosed herein consistently exhibited stealth characteristics that are resistant to random off-target delivery to or biological uptake by non-target cells, while possessing average particle sizes effective for therapeutic uses (<80 nm in diameter).

Example 9. Effect of Increasing Lipid-Anchored Polymer Content on Stealth LNPs In this example, the effect of increasing the amount of lipid-anchored polymer into helper lipid containing stealth LNPs was explored. A series of LNPs containing from 1.5% and up to 7.0% lipid-anchored polymers were formulated as shown in Table 13 below:

TABLE 13

| Maximum Amount of Lipid-Anchored Polymers in Stealth LNPs | | | | |
|---|---|---|---|---|
| Lipid-Anchored Polymer | Lipid-Anchored Polymer mol % | | | |
| DSG-PEG2k-OMe | 1.5 | 3.0 | 5.0 | 7.0 |
| DODA-PG45 | 1.5 | 3.0 | 5.0 | 7.0 |
| DSPE-PCB1 | 1.5 | 3.0 | 5.0 | 7.0 |
| DSPE-PMPC | 1.5 | 3.0 | 5.0 | 7.0 |

Figure 23A:
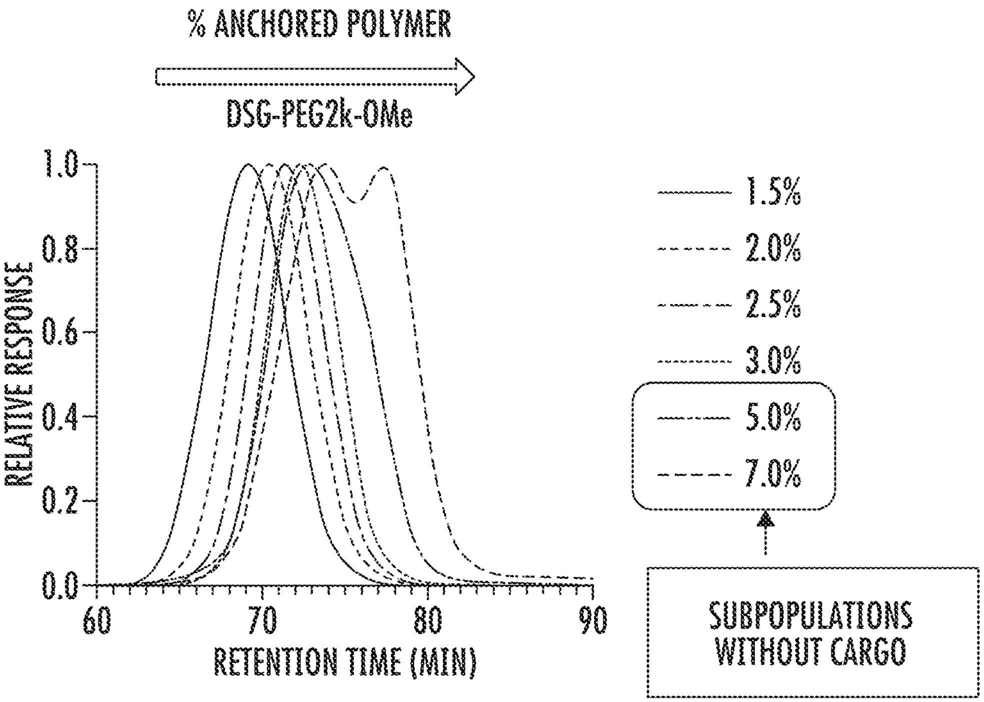
FIG. 23A depicts different retention times from HPLC-SEC readout for LNP formulations having incremental mol % of a first lipid-anchored polymer (i.e., LNPs having DSG-PEG2000-OMe at 1.5 mol %, 2 mol %, 2.5 mol %, 3 mol %, 5 mol %, and 7 mol %).
Figure 23B:
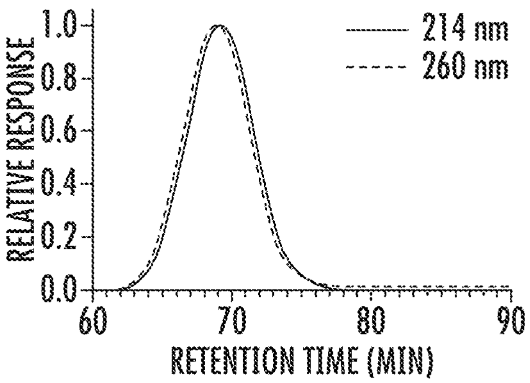
FIG. 23B depicts retention times for a LNP formulation having mol % of a lipid-anchored polymer (DSG-PEG2000-OMe) at 1.5 mol % (wavelength readout: 214 nm to track lipids and 260 nm to track nucleic acid cargo).
Figure 23C:
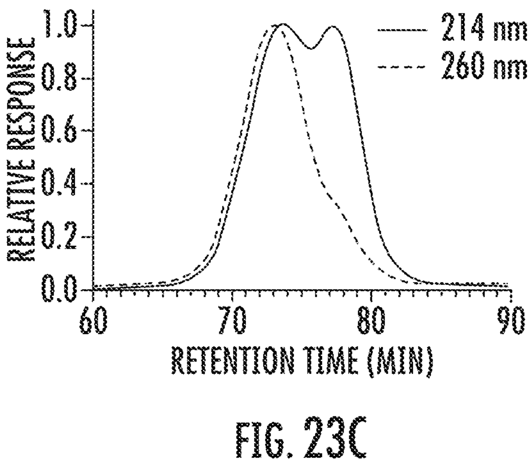
FIG. 23C depicts retention times for LNPs having mol % of a lipid-anchored polymer (DSG-PEG2000-OMe) at 7 mol % (wavelength readout: 214 nm to track lipids and 260 nm to track nucleic acid cargo).

The polymer composition was Lipid Z, DSPC (helper lipid), cholesterol, and 1.5-7.0% lipid-anchored polymer in 47.5:10:(35.5-41):1.5-7.0 mol % ratios or Lipid Z, DSPC, cholesterol, DiD, DSPE-PEG5000-N3, second lipid-anchored polymer in mol % ratios 47.5:10:(35.0-40.5): 0.5: 0.2:(1.3-6.8). Polymer hydrophilicity of the lipid-anchored polymers of Table 13 decreases as the list goes down the rows. The results showed that increasing polymer density up to 5 and 7 mol % significantly increased LNP thermal stability to elevated temperatures ranging from 20-80° C. As shown in FIG. 23A, using HPLC-SEC analysis of the listed LNPs, it was found that increasing the total lipid-anchored polymer content either with a first and second lipid-anchored polymer or any of the single lipid-anchored polymer of Table 13 greater than 5 mol % resulted in subpopulations of LNP particles without cargo encapsulated. FIG. 23B shows the uniform retention time of LNPs with cargo at 1.5 mol % lipid-anchored polymer (measured at 214 nm to track lipid and 260 nm to track nucleic acid cargo) and FIG. 23C shows the non-uniform retention time of LNPs with cargo at 7 mol % lipid-anchored polymer, suggesting that the presence of a subpopulation of LNPs without cargo at higher polymer mol % (e.g., 7%). Therefore, in the present disclosure, 1.5 mol %, 2 mol %, 2.5 mol %, 3 mol %, and up to 5 mol % of a lipid-anchored polymer was found to be an ideal target range for most stealth LNP formulations. See FIGS. 23A-C.

Example 10. Designing Stealthy and Targetable LNPs with Stability

A useful enhancement of the functionality of the stealth LNPs disclosed herein is to add the ability of the LNP first to evade rapid opsonization/destabilization and also to target the cargo to specific cells and tissues by adding a targeting moiety to the LNP through conjugation to, e.g., a lipid-anchored polymer. The goal was to first create stealthy LNPs by using between 3-5 mol % lipid-anchored polymer in combination with ionizable lipids (35-50 mol %), helper lipids (~10 mol %), and sterols (~30-40 mol %) where the LNP can be sufficiently stable, small, and stealthy to transport any cargo such as mRNA, dsDNA, ssDNA or other gene editing or gene silencing components. The basis of this design was that a combination of one or two lipid-anchored polymers can be divided into two primary functions. Those functions include first to provide stealth character to an LNP by avoiding rapid opsonization and remaining in blood circulation long enough for the second, and critically important targeting function to be carried out. This second function, which is a targeting function, should be achieved through a sub-population of the total lipid-anchored polymer content in mol % on the surface of the LNP. The targeting function occurs by inclusion of a conjugation moiety ("handle") to a subpopulation of the total lipid-anchored polymers ("second lipid-anchored polymer") which can be conjugated to a targeting moiety such as an scFv, VHH or one or more other specific binding ligand moieties. This disclosure provides such stealth LNPs with a first lipid-anchored polymer as the main driver of LNP stealth and stability through employing linker-lipid portion for the first anchored lipid that do not allow rapid dissociation and function to enable stealthiness (e.g., C18 DODA, C18 DSPE, C18 DSG, etc.). Next, this disclosure provides a second lipid-anchored polymer functionalized to contain a conjugation handle to conjugate a targeting moiety to the LNP. The population or subpopulation of lipid-anchored polymer conveying the targeting function can also contribute to the stealth characteristic of the LNP by carefully selecting a lipid component that resists rapid disassociation from the LNP surface.

In this example, stealth LNPs containing a second lipid polymer with a conjugation handle attached were formulated and the resulting size of the resulting LNP and % encapsulation of an mRNA cargo was measured.

The results in Table 14 show twenty working examples of formulated stealth LNPs with an azide conjugation handle covalently attached to a second lipid-anchored polymer and where all the LNPs encapsulate an mRNA cargo expressing luciferase. In Table 14, LNPs 301-310 do not include a helper lipid and thus contain a higher level (57.6%) of the ionizable lipid, which generally led to larger particle sizes as compared to corresponding LNPs having ~10 mol % helper lipid (e.g., DSPC, C2 ceramide, etc.). In Table 14, LNPs 311-320 contain 10% DSPC helper lipid and 47.5% of various ionizable lipids and 40 mol % of cholesterol. All of the LNP formulations Table 14, encapsulated the cargo in an acceptable manner. The vast majority of the formulated LNPs encapsulated the cargo with greater than 90% effectiveness. The particle size after formulation was acceptable in most cases (e.g., 60-80 nm in diameter) with only two formulations that had no helper lipid showing a size greater than 100 nm.

TABLE 14

Composition with Reactive Azide on Second Lipid-Anchored Polymer as Conjugation Handle

| LNP | Composition with Reactive Azide on Second Lipid-Anchored Polymer | Size (nm) | EE(%) |
|---|---|---|---|
| 301 | LIPID 87:Chol:DSG-PEG2000-OMe:DSPE-PEG5000-N3:DiD (57.6:39.45:2.4:0.5:0.05) | 85.3 | 92.0% |
| 302 | LIPID Z:Chol:DSG-PEG2000-OMe:DSPE-PEG5000-N3:DiD (57.6:39.45:2.4:0.5:0.05) | 101.8 | 93.7% |
| 303 | Lipid 58:Chol:DSG-PEG2000-OMe:DSPE-PEG5000-N3:DiD (57.6:39.45:2.4:0.5:0.05) | 101.4 | 93.1% |
| 304 | MC3:Chol:DSG-PEG2000-OMe:DSPE-PEG5000-N3:DiD (57.6:39.45:2.4:0.5:0.05) | 87.5 | 90.9% |
| 305 | L369:Chol:DSG-PEG2000-OMe:DSPE-PEG5000-N3:DiD (57.6:39.45:2.4:0.5:0.05) | 87.1 | 92.9% |
| 306 | LP01:Chol:DSG-PEG2000-OMe:DSPE-PEG5000-N3:DiD (57.6:39.45:2.4:0.5:0.05) | 78.6 | 96.0% |
| 307 | SM102:Chol:DSG-PEG2000-OMe:DSPE-PEG5000-N3:DiD (57.6:39.45:2.4:0.5:0.05) | 78.1 | 92.8% |
| 308 | DOTAP:Chol:DSG-PEG2000-OMe:DSPE-PEG5000-N3:DiD (57.6:39.45:2.4:0.5:0.05) | 64.1 | 98.8% |
| 309 | LIPID 81:Chol:DSG-PEG2000-OMe:DSPE-PEG5000-N3:DiD (57.6:39.45:2.4:0.5:0.05) | 88.8 | 94.2% |
| 310 | ALC-0315:Chol:DSG-PEG2000-Ome:DSPE-PEG5000-N3:DiD (57.6:39.45:2.4:0.5:0.05) | 88.4 | 89.2% |
| 311 | LIPID 87:DSPC:Chol:DSG-PEG2000-Ome:DSPE-PEG5000-N3:DiD (47.5:10:39.45:2.5:0.5:0.05) | 70.6 | 99.0% |
| 312 | Lipid Z:DSPC:Chol:DSG-PEG2000-Ome:DSPE-PEG5000-N3:DiD (47.5:10:39.45:2.5:0.5:0.05) | 67.7 | 99.0% |
| 313 | LIPID 58:DSPC:Chol:DSG-PEG2000-Ome:DSPE-PEG5000-N3:DiD (47.5:10:39.45:2.5:0.5:0.05) | 70.5 | 97.6% |
| 314 | MC3:DSPC:Chol:DSG-PEG2000-Ome:DSPE-PEG5000-N3:DiD (47.5:10:39.45:2.5:0.5:0.05) | 65.8 | 97.2% |
| 315 | L369:DSPC:Chol:DSG-PEG2000-Ome:DSPE-PEG5000-N3:DiD (47.5:10:39.45:2.5:0.5:0.05) | 68.5 | 99.2% |
| 316 | LP01:DSPC:Chol:DSG-PEG2000-Ome:DSPE-PEG5000-N3:DiD (47.5:10:39.45:2.5:0.5:0.05) | 68.9 | 98.0% |
| 317 | SM102:DSPC:Chol:DSG-PEG2000-Ome:DSPE-PEG5000-N3:DiD (47.5:10:39.45:2.5:0.5:0.05) | 63.9 | 99.3% |
| 318 | DOTAP:DSPC:Chol:DSG-PEG2000-Ome:DSPE-PEG5000-N3:DiD (47.5:10:39.45:2.5:0.5:0.05) | 74.8 | 99.9% |
| 319 | LIPID 81:DSPC:Chol:DSG-PEG2000-Ome:DSPE-PEG5000-N3:DiD (47.5:10:39.45:2.5:0.5:0.05) | 80.8 | 98.7% |
| 320 | ALC-0315:DSPC:Chol:DSG-PEG2000-Ome:DSPE-PEG5000-N3:DiD (47.5:10:39.45:2.5:0.5:0.05) | 62.8 | 96.9% |

Figure 24:
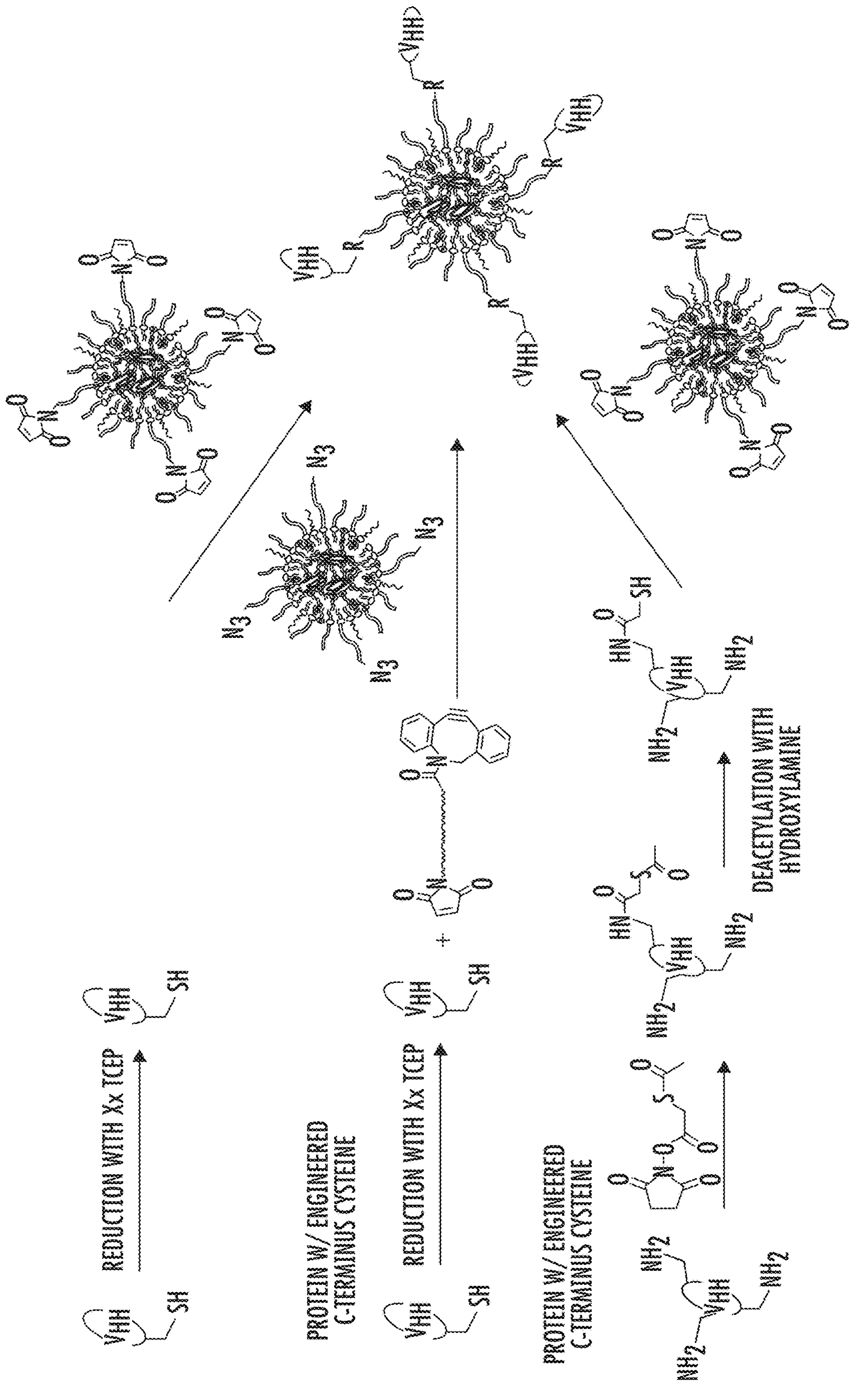
FIG. 24 depicts various conjugation chemistry schemes.

The maintenance of stealth characteristics for the LNPs of Table 14, which were functionalized with conjugation handles according to the scheme in FIG. 24 were evaluated by measuring the amount of shielding from opsonization in the HepaRG model system. Briefly, cryopreserved HepaRG cells were thawed and plated at 72 k/well in a 96-well format and incubated overnight at 37° C. The LNPs with DID were pre-treated with human serum to allow attachment of any human proteins facilitating opsonization. If particular LNPs are stealthy, they will be shielded from opsonization facilitating protein and if they were not stealthy and lacked sufficient shielding then opsonization was detected in the following steps. In the next step, the serum exposed LNPs were incubated with the hepatocytes for 1 hour. The cells were then washed 3 times and imaged for DID uptake or luminescence and viability.

The results were that serum opsonization drove minimal expression for the Stealth LNPs without helper lipid from Table 14 with azide conjugation handles attached. The minor exceptions were LNPs with ionizable lipid SM102, 10% helper lipid with maleimide conjugation handle that produced some opsonization based luciferase expression in HepaRG cells, but at much a lower level than the control LNP comprising DMG-PEG2000 lipid polymer (dissociable lipid polymer). In conclusion, most of ionizable lipids do not break stealth except in one case with SM102 in context of an LNP using a helper lipid and having a maleimide conjugation handle, and DOTAP in context of LNP without a helper lipid with an azide conjugation handle although DOTAP containing LNPs do not show any expression.

Example 11. Evaluate and Compare Effect of scFv Conjugation and Luciferase Expression on Stealth LNPs without Helper Lipids This example evaluated and compared the effect of scFv conjugation to the second lipid polymer on LNP uptake and cargo expression. The LNP formulations in Table 15 were evaluated and compared on the effect of scFv conjugation on LNP uptake and luciferase expression of stealth LNPs without helper lipids using various ionizable lipids in human primary hepatocytes. The cryopreserved primary human hepatocytes were plated in a 96-well format for 4 hours. The LNPs are pre-incubated in human serum for 30 minutes (pre-opsonization). Next 200 ng of DiD-LNPs were treated per well for 1 hr. Following 2 PBS washes, the plates were incubated overnight in complete media. The next day 20× water objective confocal imaging of DiD dye uptake and cell viability were performed.

The results indicated that scFv conjugation led to a significant increase in uptake of all tested stealth formulations as compared to the parental LNPs. The parental LNPs showed minimal uptake. Uptake of the standard LNP control was only slightly higher compared to parentals, which suggested that the LDLR pathway was not as active in these primary human hepatocytes.

TABLE 15

Stealth LNPs without helper lipid conjugated to hepatocyte specific scFv.

| LNP | Composition with Reactive Maleimide on Second Lipid-Anchored Polymer | *Size (nm) | EE(%) |
|---|---|---|---|
| 401 | Lipid 87:Chol:DSG-PEG2000-OMe:DSPE-PEG5000-Mal:DiD (57.6:39.45:2.4:0.5:0.05) | 81 | 88.20% |
| 402 | Lipid Z:Chol:DSG-PEG2000-OMe:DSPE-PEG5000-Mal:DiD (57.6:39.45:2.4:0.5:0.05) | 99.5 | 93.20% |
| 403 | Lipid 58:Chol:DSG-PEG2000-OMe:DSPE-PEG5000-Mal:DiD (57.6:39.45:2.4:0.5:0.05) | 100.2 | 91.00% |
| 404 | MC3:Chol:DSG-PEG2000-OMe:DSPE-PEG5000-Mal:DiD (57.6:39.45:2.4:0.5:0.05) | 81.3 | 91.40% |
| 405 | L369:Chol:DSG-PEG2000-OMe:DSPE-PEG5000-Mal:DiD (57.6:39.45:2.4:0.5:0.05) | 82.3 | 91.90% |
| 406 | LP01:Chol:DSG-PEG2000-OMe:DSPE-PEG5000-Mal:DiD (57.6:39.45:2.4:0.5:0.05) | 74.8 | 94.60% |
| 407 | SM102:Chol:DSG-PEG2000-OMe:DSPE-PEG5000-Mal:DiD (57.6:39.45:2.4:0.5:0.05) | 75.9 | 91.30% |
| 408 | Lipid Z:DSPC:Chol:DMG-PEG2000:DiD (47.5:10:40.15:2.3:0.05) | 66.1 | 98.70% |
| The Following LNPs 4099-416 have scFv conjugated to LNPs 401-408 above through the maleimide conjugate handle | | | |
| 409 | Lipid 87:Chol:DSG-PEG2000-OMe:DSPE-PEG5000-Mal:DiD (57.6:39.45:2.4:0.5:0.05) | 173.5 | 83.40% |
| 410 | Lipid Z:Chol:DSG-PEG2000-OMe:DSPE-PEG5000-Mal:DiD (57.6:39.45:2.4:0.5:0.05) | 197.3 | 84.50% |
| 411 | Lipid 58:Chol:DSG-PEG2000-OMe:DSPE-PEG5000-Mal:DiD (57.6:39.45:2.4:0.5:0.05) | 181.9 | 87.20% |
| 412 | MC3:Chol:DSG-PEG2000-OMe:DSPE-PEG5000-Mal:DiD (57.6:39.45:2.4:0.5:0.05) | 135.8 | 86.30% |
| 413 | L369:Chol:DSG-PEG2000-OMe:DSPE-PEG5000-Mal:DiD (57.6:39.45:2.4:0.5:0.05) | 152.4 | 86.70% |
| 414 | LP01:Chol:DSG-PEG2000-OMe:DSPE-PEG5000-Mal:DiD (57.6:39.45:2.4:0.5:0.05) | 139.8 | 89.60% |
| 415 | SM102:Chol:DSG-PEG2000-OMe:DSPE-PEG5000-Mal:DiD (57.6:39.45:2.4:0.5:0.05) | 219.2 | 83.00% |
| 416 | Lipid Z:DSPC:Chol:DSG-PEG2K-OMe:DSPE-PEG3.4K-GalNAc:DiD (47.5:10:39:2.5:0.5:0.5) | GalNAc Control | |

*LNP particle size (average size in diameter) measured after scFv conjugation

In conclusion, scFv conjugation to the stealth LNPs led to significant increase in uptake of all tested formulations as compared to parental LNPs having no scFv conjugates, regardless of ionizable lipid component in the LNPs. The conjugation of scFv to the LNPs resulted in a significant increase in LNP particle size as expected.

Figure 25:
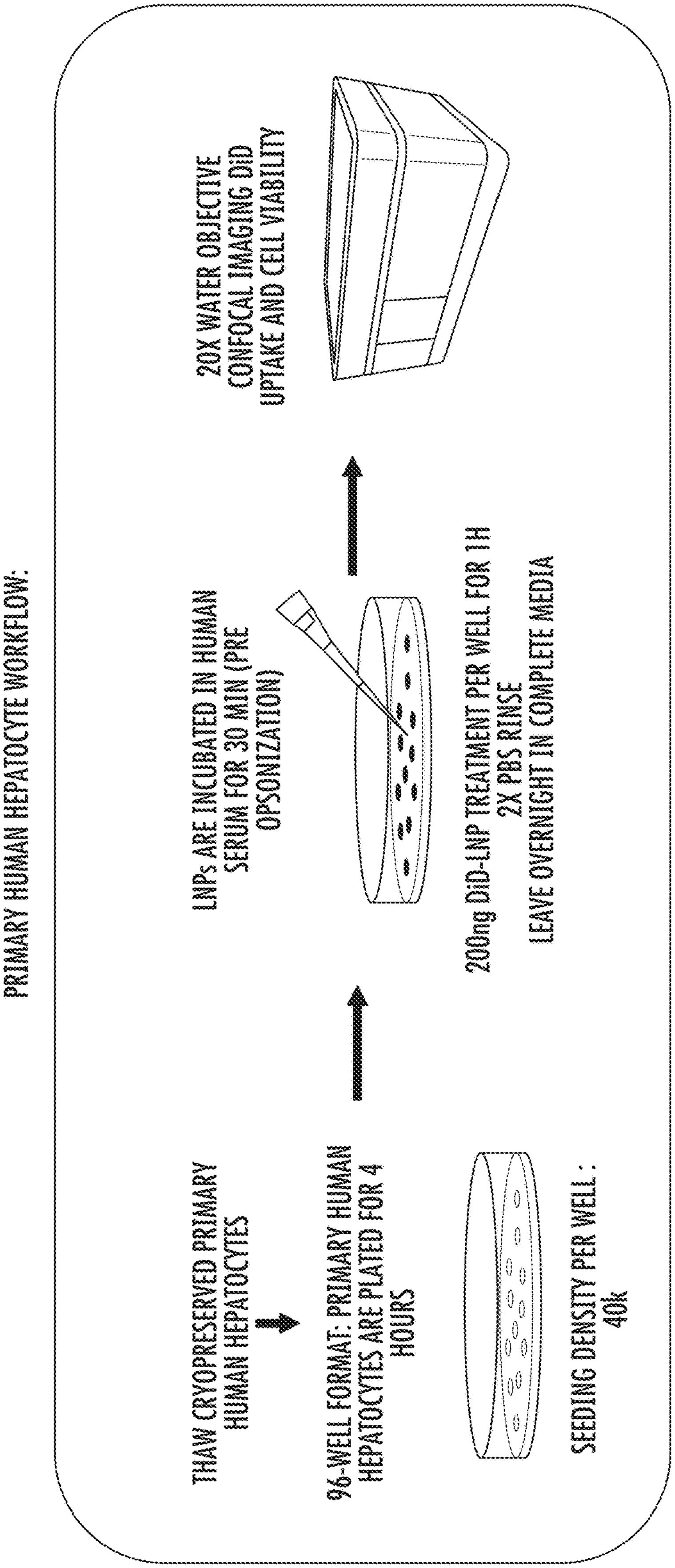
FIG. 25 depicts a workflow for using primary human hepatocytes to screen and compare various LNP formulations for the ability to enter cells, without an endocytosis inhibitor.
Figure 28:
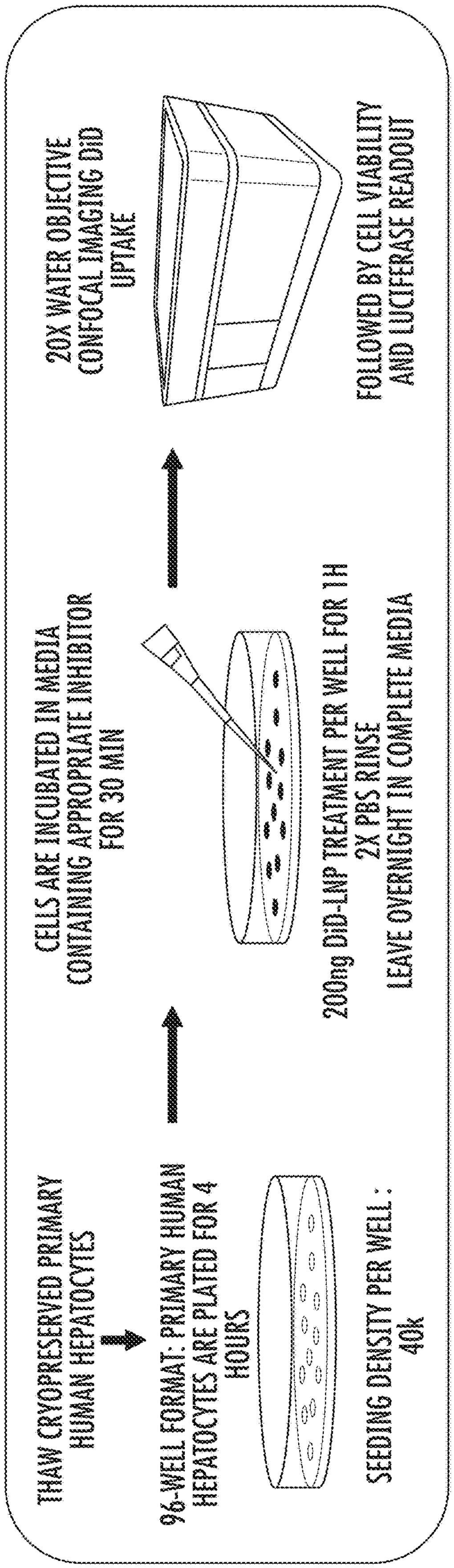
FIG. 28 depicts a workflow for using primary human hepatocytes to screen and compare various LNP formulations for their relative ability to enter cells, with an endocytosis inhibitor (DynGo-4a).

Example 12: Antibody Conjugation of the LNPs of the Present Disclosure Leads to Significant Increase in Uptake and Expression as Compared to the Parental LNPs, Regardless of Ionizable Lipid This example compared DiD uptake and mRNA luciferase expression in primary human hepatocytes of the LNPs of the present disclosure, with or without antibody conjugation (e.g., scFv, VHH, Fab, etc.), using the protocols as shown in FIG. 25 (without an endocytosis inhibitor) and FIG. 28 (with an endocytosis inhibitor). The aim of the study using the protocol as shown in FIG. 25 was to ensure that uptake and expression of conjugated LNPs with varying ionizable lipids was clathrin-mediated by using an endocytosis inhibitor. The media containing an endocytosis inhibitor was incomplete (no BSA or transferrin) media with 100 μM of DynGo-4a (Dynamin (endocytosis) inhibitor).

TABLE 16

Physicochemical properties of LNP formulations having mRNA-luciferase cargo

| LNP Formulation | Lipids and Molar Ratios | Average Diameter (nm) | Encapsulation Efficiency (%) |
|---|---|---|---|
| 175 | Ionizable Lipid 87:Chol:DSG-PEG2000-OMe:DSPE-PEG5000-Mal:DiD (57.6:39.45:2.4:0.5:0.05) | 81.0 | 88.2 |
| 178 | MC3:Chol:DSG-PEG2000-OMe:DSPE-PEG5000-Mal:DiD (57.6:39.45:2.4:0.5:0.05) | 81.3 | 91.4 |
| 179 | L369:Chol:DSG-PEG2000-OMe:DSPE-PEG5000-Mal:DiD (57.6:39.45:2.4:0.5:0.05) | 82.3 | 91.9 |
| 180 | LP01:Chol:DSG-PEG2000-OMe:DSPE-PEG5000-Mal:DiD (57.6:39.45:2.4:0.5:0.05) | 74.8 | 94.6 |
| 181 | SM102:Chol:DSG-PEG2000-OMe:DSPE-PEG5000-Mal:DiD (57.6:39.45:2.4:0.5:0.05) | 75.9 | 91.3 |
| Control LNP 183 | Ionizable Lipid Z:DSPC:Chol:DMG-PEG2000:DiD (47.5:10:40.15:2.3:0.05) | 66.1 | 98.7 |
| 175 + Antibody conjugation | Ionizable Lipid 87:Chol:DSG-PEG2000-OMe:DSPE-PEG5000-maleimide:Did (57.6:39.45:2.4:0.5:0.05) | 173.5 | 83.4 |
| 178 + Antibody conjugation | MC3:Chol:DSG-PEG2000-OMe:DSPE-PEG5000-Mal:DiD (57.6:39.45:2.4:0.5:0.05) | 135.8 | 86.3 |
| 179 + Antibody conjugation | L369:Chol:DSG-PEG2000-OMe:DSPE-PEG5000-Mal:DiD (57.6:39.45:2.4:0.5:0.05) | 152.4 | 86.7 |
| 180 + Antibody conjugation | LP01:Chol:DSG-PEG2000-OMe:DSPE-PEG5000-Mal:DiD (57.6:39.45:2.4:0.5:0.05) | 139.8 | 89.6 |
| 181 + Antibody conjugation | SM102:Chol:DSG-PEG2000-OMe:DSPE-PEG5000-Mal:DiD (57.6:39.45:2.4:0.5:0.05) | 219.2 | 53.0 |
| Control LNP 868 | Ionizable Lipid Z:DSPC:Chol:DSG-PEG2K-OMe:DSPE-PEG3.4K-GalNAc:DiD (47.5:10:39:2.5:0.5:0.5) | | |

Figure 26A:
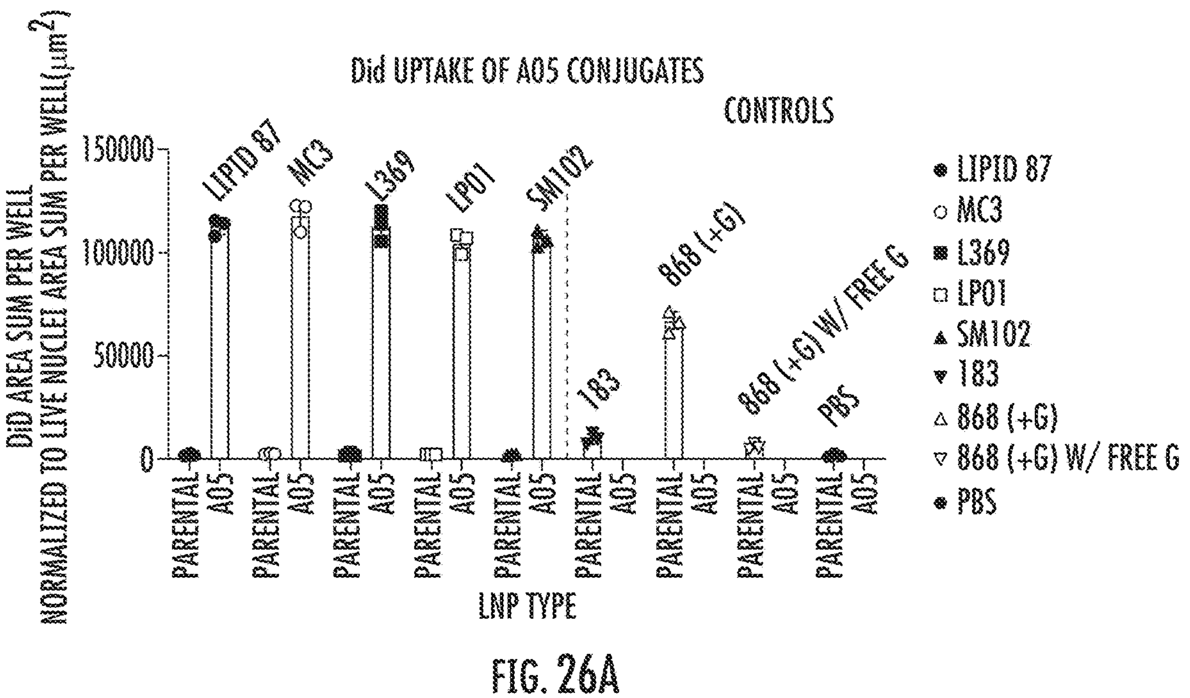
FIGS. 26A and 26B show the results of a screening study of the LNP formulations of the present disclosure with antibody (VHH: "A05") conjugation for targeting hepatic ASGPR1 protein, for their relative ability to gain entry into primary human hepatocytes after 24 hours, according to the workflow as depicted in FIG. 25.
Figure 26B:
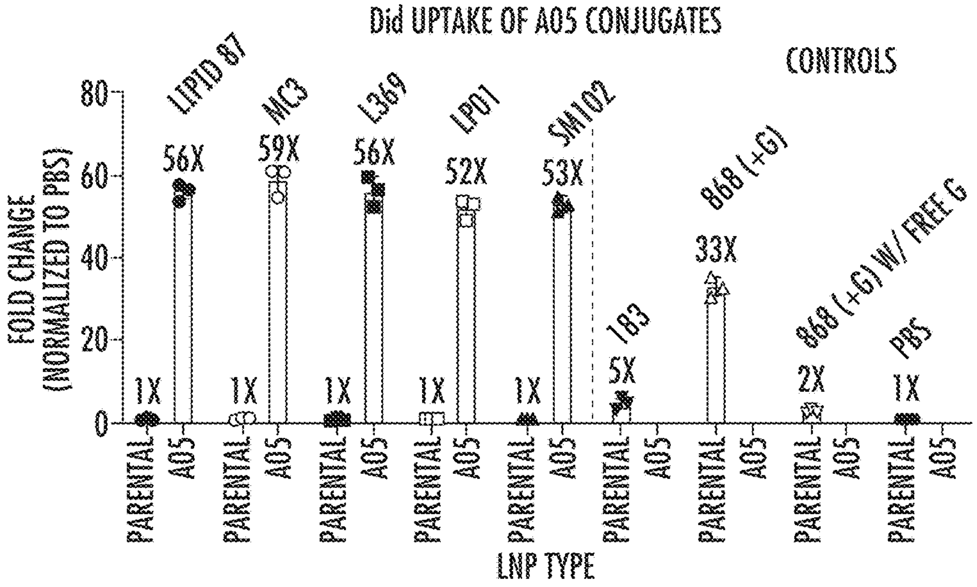

Referring to FIGS. 26A and 26B and Table 16, antibody (VHH; "A05") conjugation for targeting hepatic ASGPR1 protein led to significant increase in LNP uptake compared to the parental LNPs of the present disclosure without antibody conjugation, and regardless of the identity of the ionizable lipid.

Figure 27A:
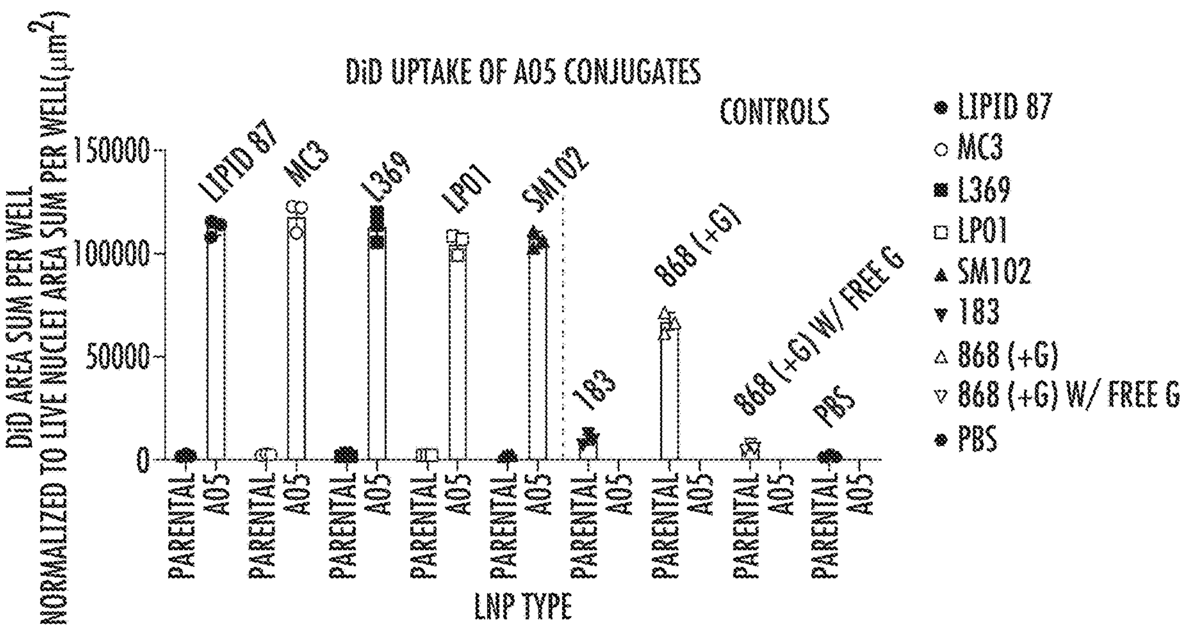
FIGS. 27A and 27B show the results of a screening study of the LNP formulations of the present disclosure with antibody (VHH: "A05") conjugation for targeting hepatic ASGPR1 protein, for their relative ability to express mLuc and rLuc cargo, according to the workflow as depicted in FIG. 25.
Figure 27B:
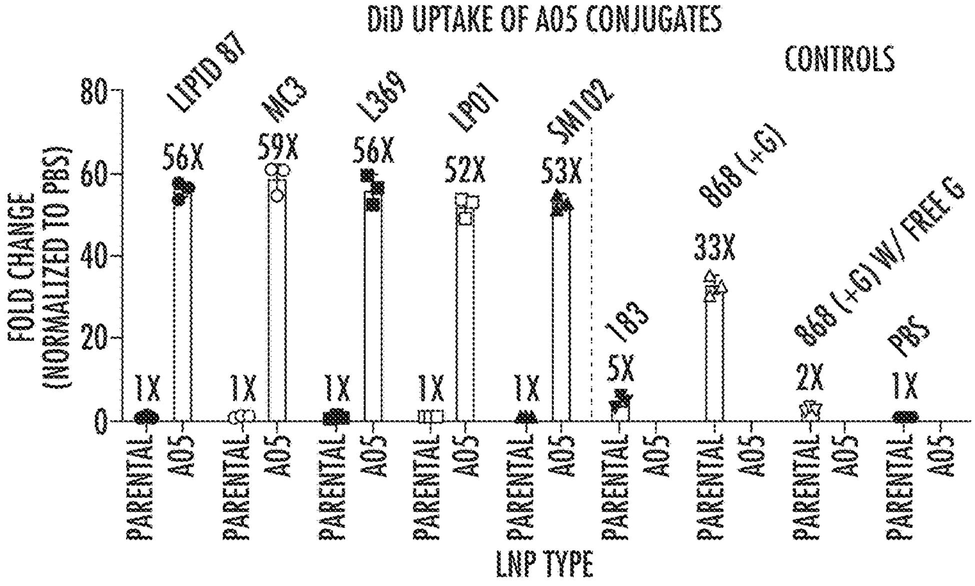

Referring to FIGS. 27A and 27B and Table 16, antibody (VHH; "A05") conjugation for targeting hepatic ASGPR1 protein led to minimal increase in luciferase expression as compared to the parental LNPs of the present disclosure without antibody conjugation. Parental (unconjugated) LNP formulations of the present disclosure and Control LNP 183 showed minimal luciferase expression. LNPs formulated with ionizable lipids MC3 and LPO1 showed equivalent uptake but very low expression suggesting that these ionizable lipids adversely affect endosomal escape.

Figure 29A:
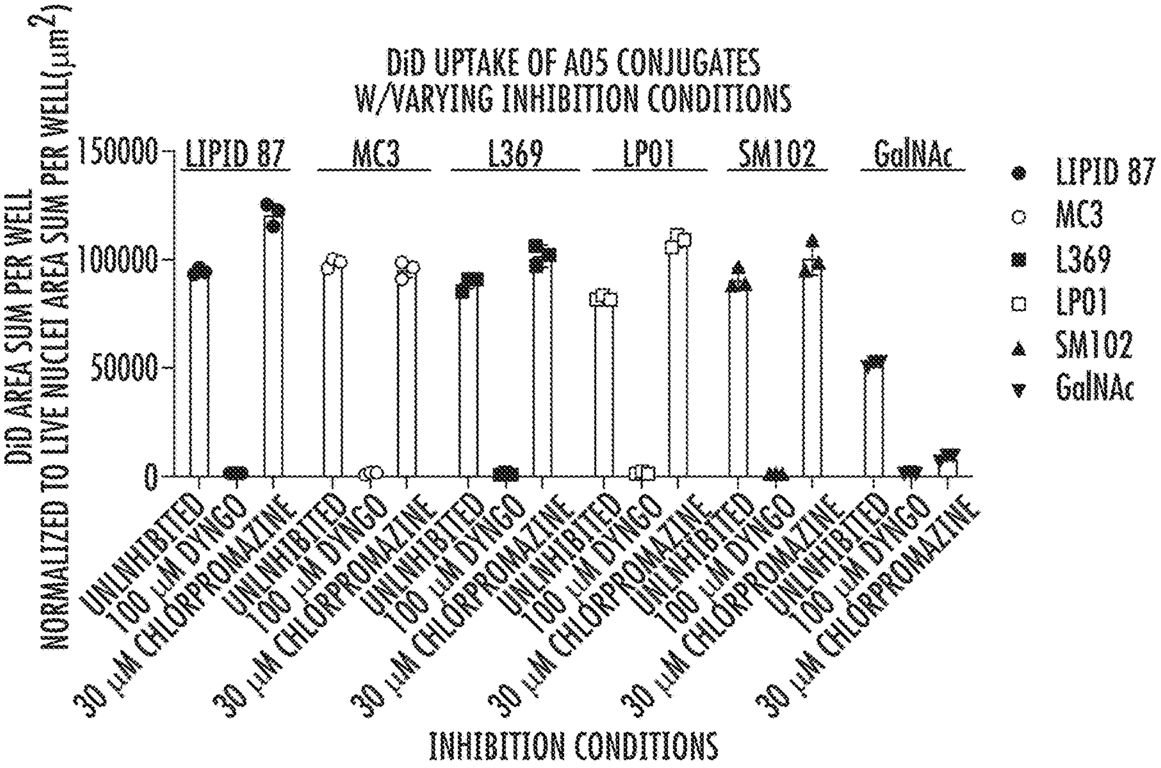
FIGS. 29A and 29B show the results of a screening study of the LNP formulations of the present disclosure with antibody (VHH ("A05") and scFv) conjugation for targeting hepatic ASGPR1 protein, for their relative ability to gain entry into primary human hepatocytes after 24 hours, according to the workflow as depicted in FIG. 28.
Figure 29B:
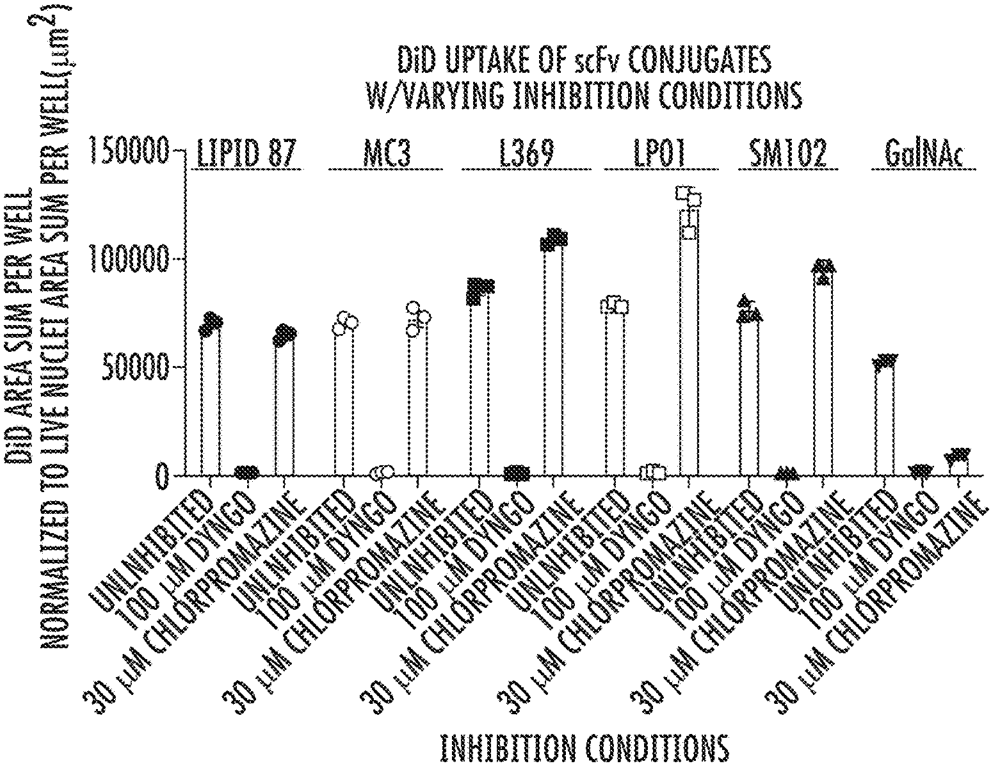

Referring to FIGS. 29A and 29B and Table 16, for both VHH ("A05") and scFv conjugates (for targeting hepatic ASGPR1 protein) of the LNP formulations of the present disclosure, co-incubation with an endocytosis inhibitor resulted in complete inhibition of uptake in all ionizable lipids.

Figure 30A:
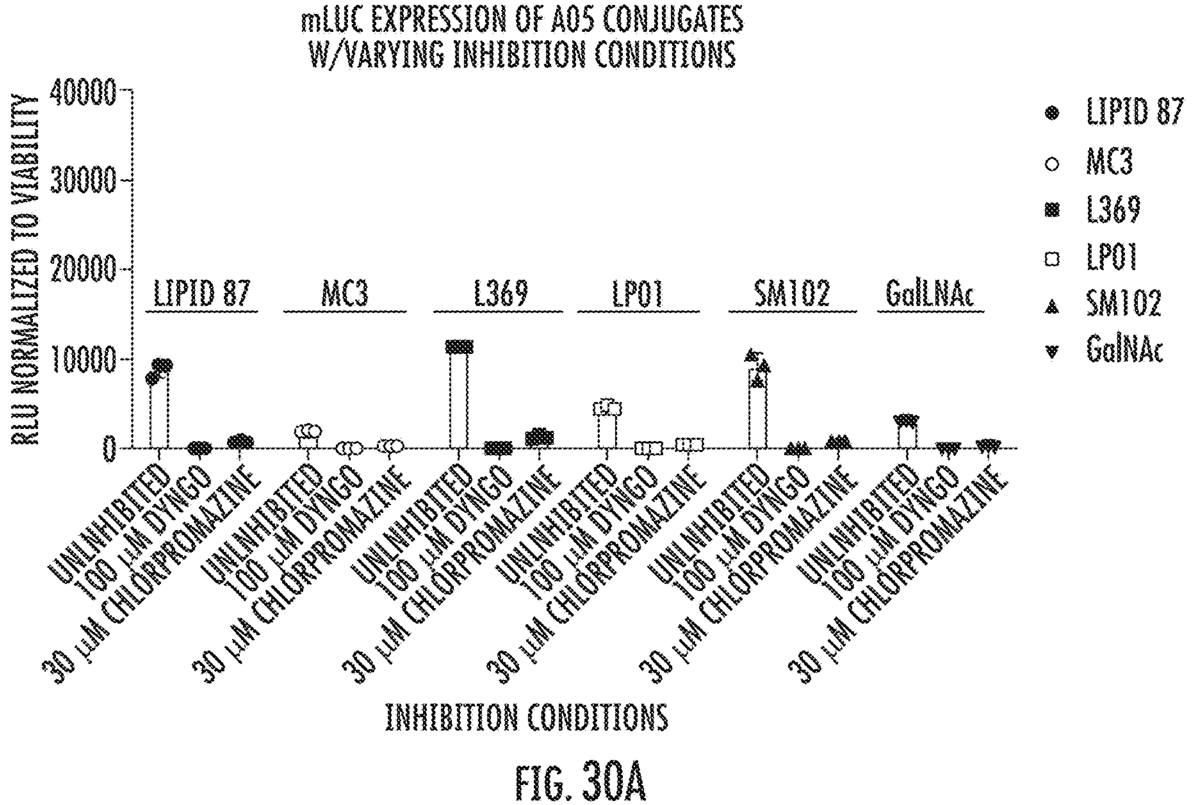
FIGS. 30A and 30B show the results of a screening study of the LNP formulations of the present disclosure with antibody (VHH ("A05") and scFv) conjugation for targeting hepatic ASGPR1 protein, for their relative ability to express mLuc cargo, with varying inhibition conditions, according to the workflow as depicted in FIG. 28.
Figure 30B:
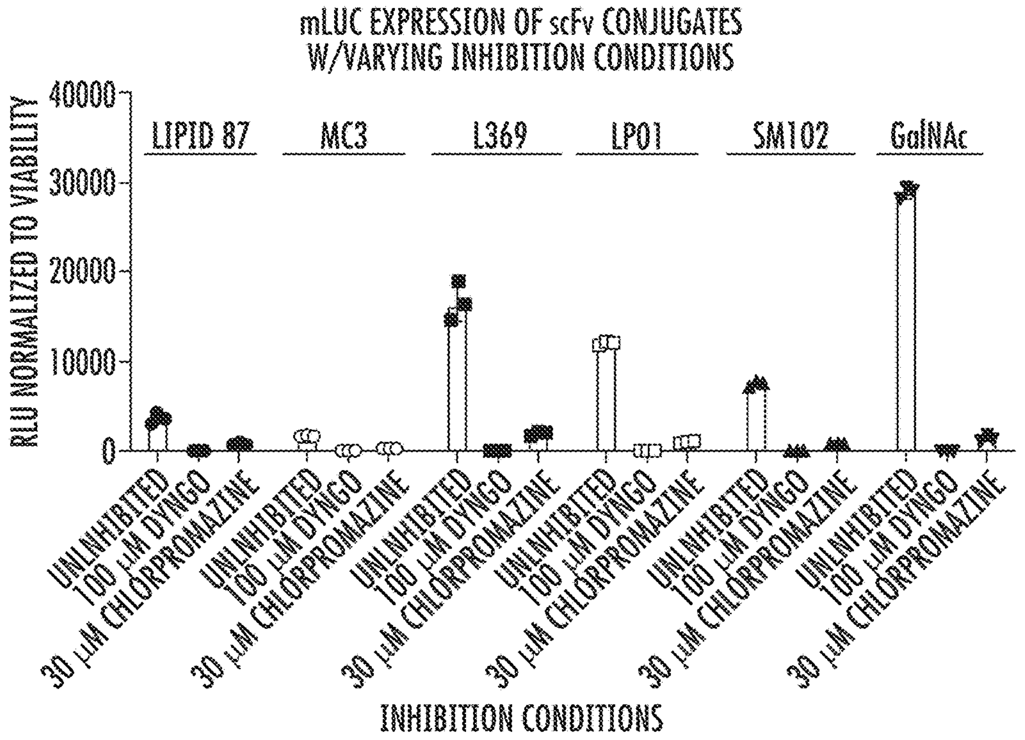

Referring to FIGS. 30A and 30B and Table 16, for both VHH ("A05") and scFv conjugates (for targeting hepatic ASGPR1 protein) of the LNP formulations of the present disclosure, co-incubation with an endocytosis inhibitor resulted in complete inhibition of mRNA cargo expression in all ionizable lipids.

TABLE 17

Physicochemical properties of LNP formulations having mRNA-luciferase cargo

| LNP Formulation | Lipids and Molar Ratios | Average Diameter (nm) | Encapsulation Efficiency (%) |
|---|---|---|---|
| 225 | Ionizable Lipid 87:Chol:DSG-PEG2000-OMe:DSPE-PEG5000-N3:DiD (57.6:39.45:2.4:0.5:0.05) | 85.3 | 92.0 |
| 228 | MC3:Chol:DSG-PEG2000-OMe:DSPE-PEG5000-N3:DiD (57.6:39.45:2.4:0.5:0.05) | 87.5 | 90.9 |
| 229 | L369:Chol:DSG-PEG2000-OMe:DSPE-PEG5000-N3:DiD (57.6:39.45:2.4:0.5:0.05) | 87.1 | 92.9 |
| 230 | LP01:Chol:DSG-PEG2000-OMe:DSPE-PEG5000-N3:DiD (57.6:39.45:2.4:0.5:0.05) | 78.6 | 96.0 |
| 231 | SM102:Chol:DSG-PEG2000-OMe:DSPE-PEG5000-N3:DiD (57.6:39.45:2.4:0.5:0.05) | 78.1 | 92.8 |
| 232 | DOTAP:Chol:DSG-PEG2000-OMe:DSPE-PEG5000-N3:DiD (57.6:39.45:2.4:0.5:0.05) | 64.1 | 98.8 |
| 233 | Ionizable Lipid 81:Chol:DSG-PEG2000-OMe:DSPE-PEG5000-N3:DiD (57.6:39.45:2.4:0.5:0.05) | 88.8 | 94.2 |
| 225 + Antibody conjugation | Ionizable Lipid 87:Chol:DSG-PEG2000-OMe:DSPE-PEG5000-N3:DiD (57.6:39.45:2.4:0.5:0.05) | 92.1 | 88.2 |
| 228 + Antibody conjugation | MC3:Chol:DSG-PEG2000-OMe:DSPE-PEG5000-N3:DiD (57.6:39.45:2.4:0.5:0.05) | 120.9 | 87.4 |
| 229 + Antibody conjugation | L369:Chol:DSG-PEG2000-OMe:DSPE-PEG5000-N3:DiD (57.6:39.45:2.4:0.5:0.05) | 158.5 | 88.1 |
| 230 + Antibody conjugation | LP01:Chol:DSG-PEG2000-OMe:DSPE-PEG5000-N3:DiD (57.6:39.45:2.4:0.5:0.05) | 121.8 | 90.5 |
| 231 + Antibody conjugation | SM102:Chol:DSG-PEG2000-OMe:DSPE-PEG5000-N3:DiD (57.6:39.45:2.4:0.5:0.05) | 110.9 | 84.0 |
| 232 + Antibody conjugation | DOTAP:Chol:DSG-PEG2000-OMe:DSPE-PEG5000-N3:DiD (57.6:39.45:2.4:0.5:0.05) | 127.1 | 95.4 |
| 233 + Antibody conjugation | Ionizable Lipid 81:Chol:DSG-PEG2000-OMe:DSPE-PEG5000-N3:DiD (57.6:39.45:2.4:0.5:0.05) | 101.0 | 88.9 |
| Control Lipid 183 | Ionizable Lipid Z:DSPC:Chol:DMG-PEG2000:DiD (47.5:10:40.15:2.3:0.05) | 66.1 | 98.7 |
| GalNAc Control Lipid 261 | Ionizable Lipid Z:DSPC:Chol:DSG-PEG2K-OMe:DSPE-PEG3.4K-GalNAc:DiD (47.5:10:39:2.5:0.5:0.5) | | |

Figure 31A:
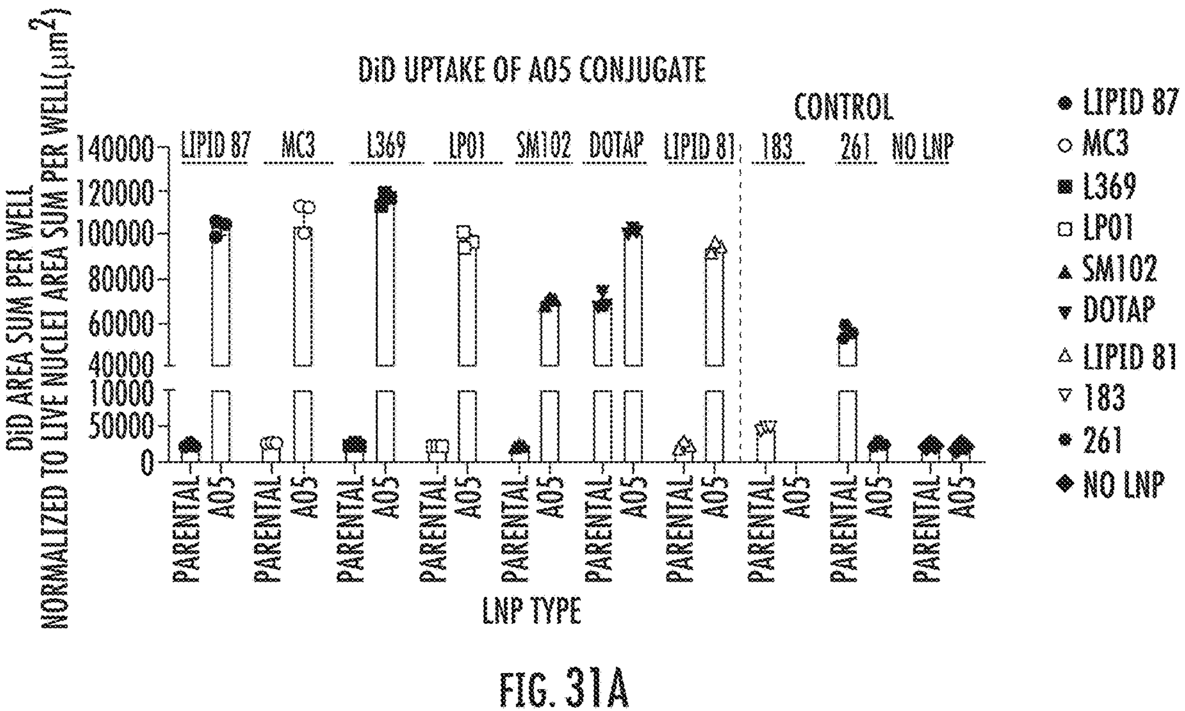
FIGS. 31A and 31B show the results of a screening study of the LNP formulations of the present disclosure with antibody (VHH: "A05") conjugation for targeting hepatic ASGPR1 protein, for their relative ability to gain entry into primary human hepatocytes after 24 hours, according to the workflow as depicted in FIG. 28.
Figure 31B:
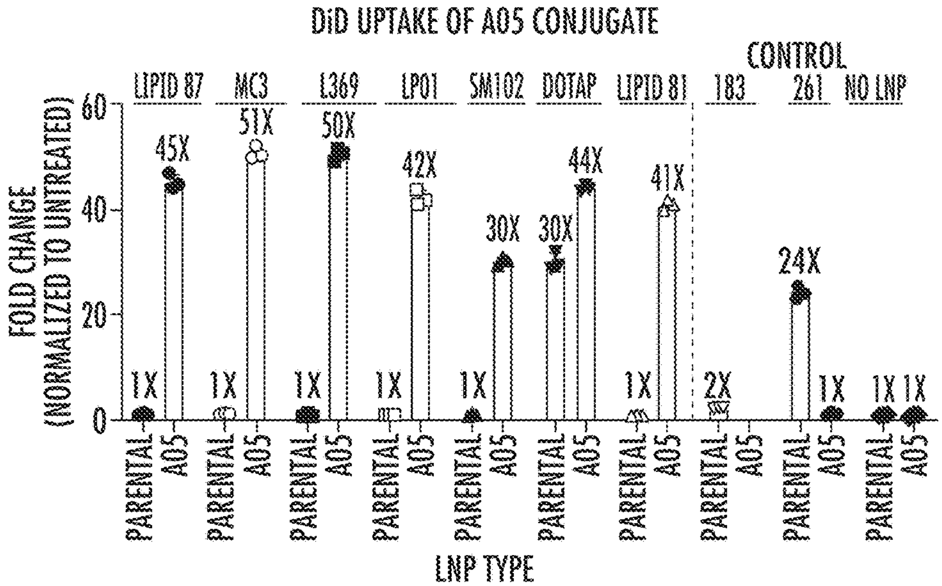

Referring to FIGS. 31A and 31B and Table 17, antibody (VHH; "A05") conjugation for targeting hepatic ASGPR1 protein led to higher levels of uptake compared to the parental LNPs of the present disclosure without antibody conjugation, and regardless of the identity of the ionizable lipid, as well as when compared to Control LNPs 183 and 261.

Figure 32A:
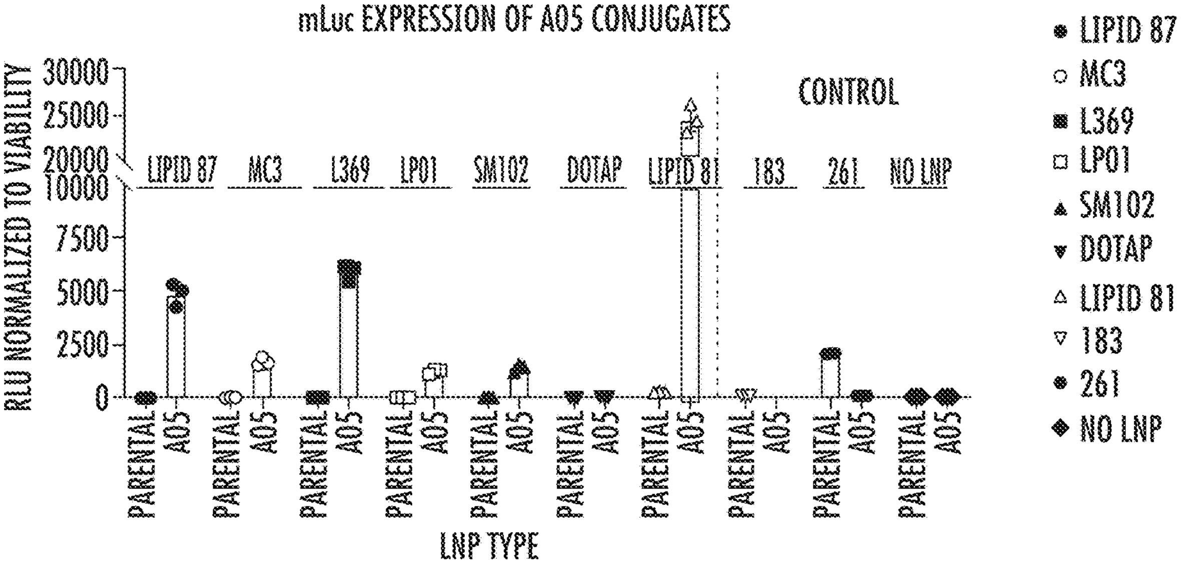
FIGS. 32A and 32B show the results of a screening study of the LNP formulations of the present disclosure with antibody (VHH) conjugation for targeting hepatic ASGPR1 protein, for their relative ability to express mLuc and rLuc cargo, according to the workflow as depicted in FIG. 28.
Figure 32B:
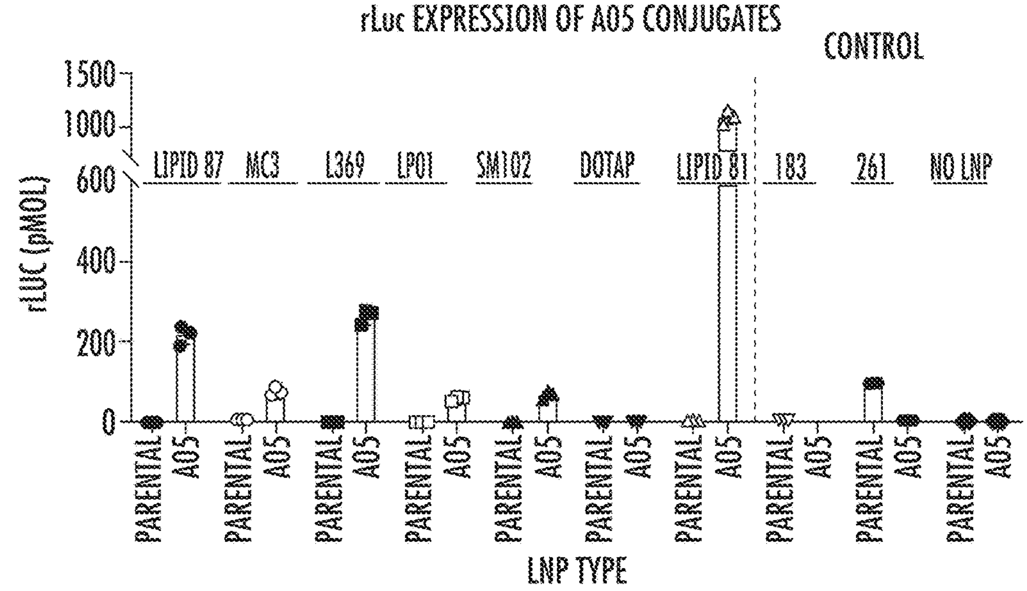
Figure 33A:
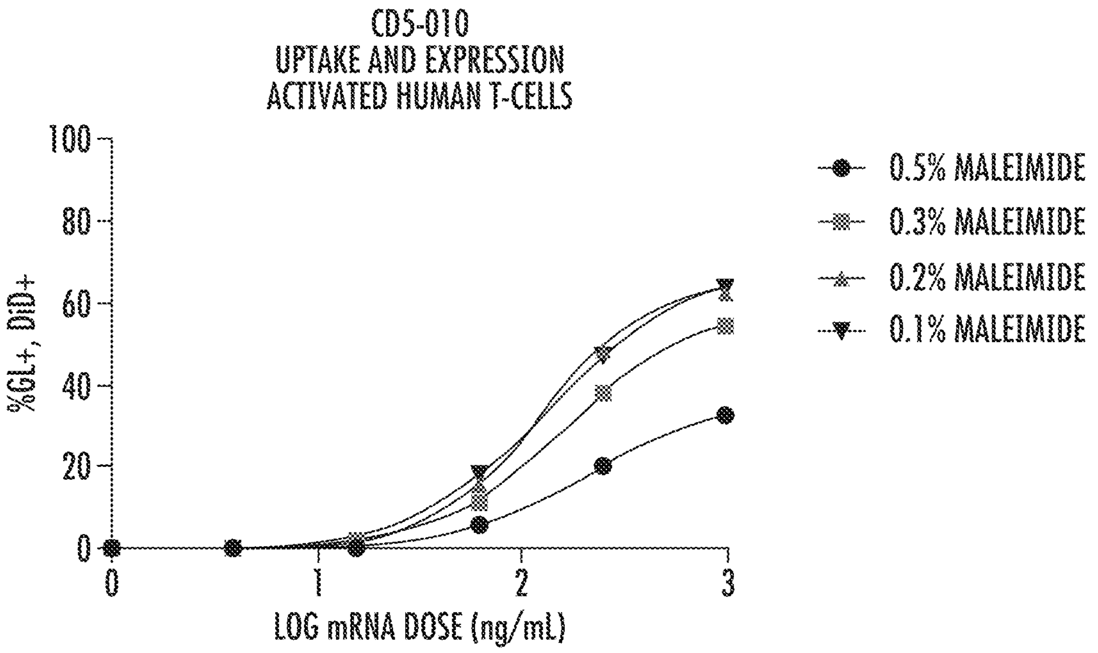
FIGS. 33A and 33B show CD5 uptake and expression in activated human T cells (FIG. 33A) and in non-activated human T cells (FIG. 33B).
Figure 33B:
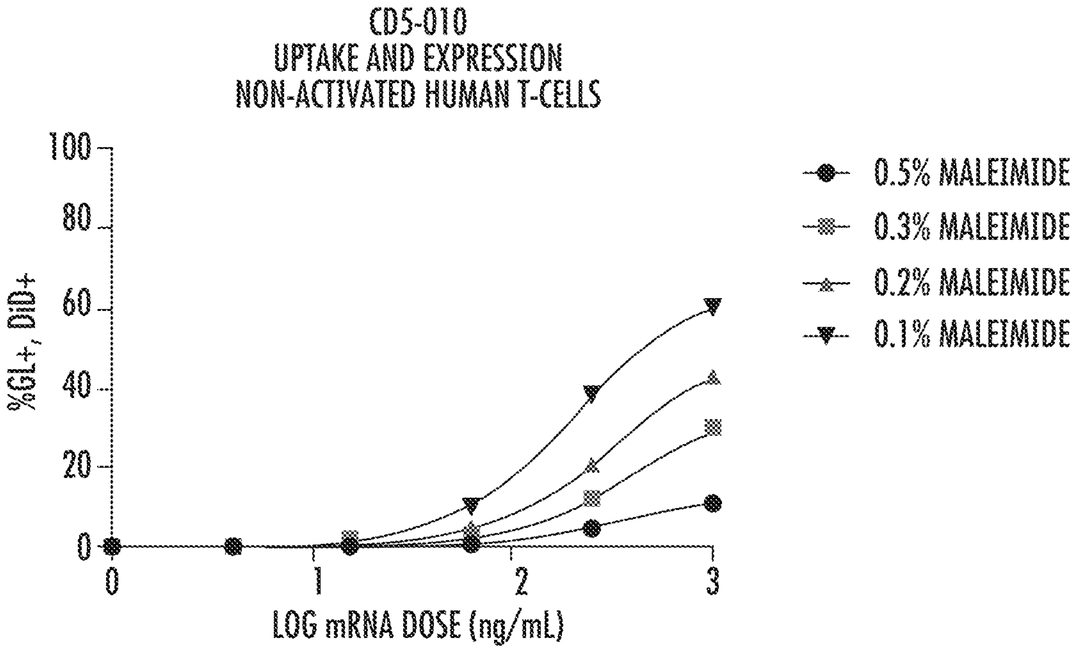
Figure 34A:
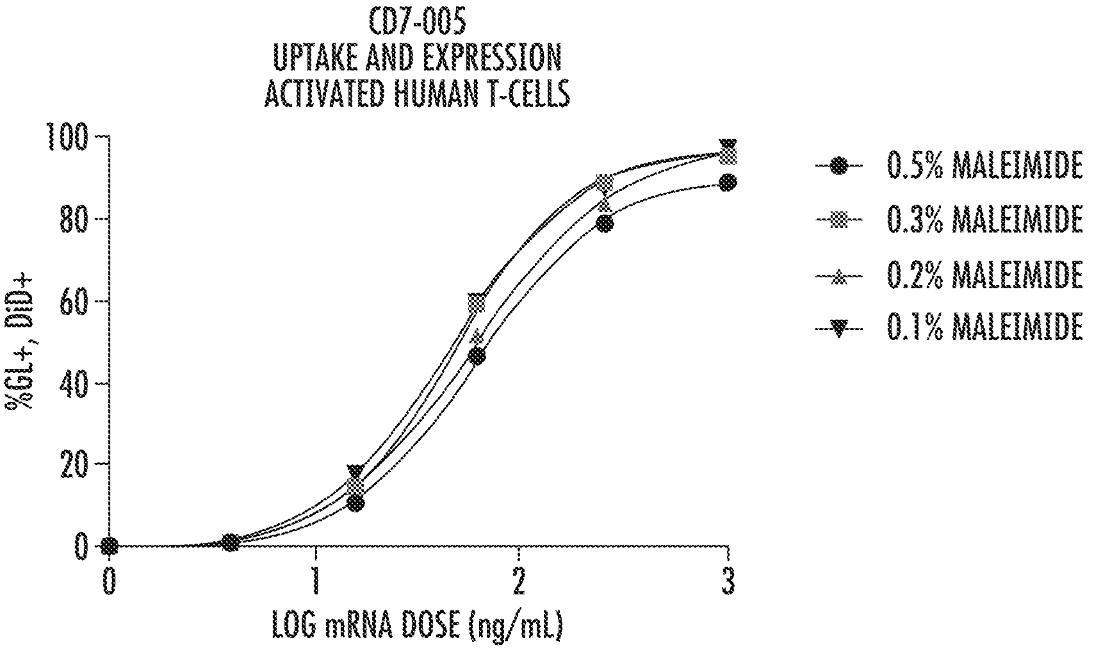
FIGS. 34A and 34B show CD7 uptake and expression in activated human T cells (FIG. 34A) and in non-activated human T cells (FIG. 34B).
Figure 34B:
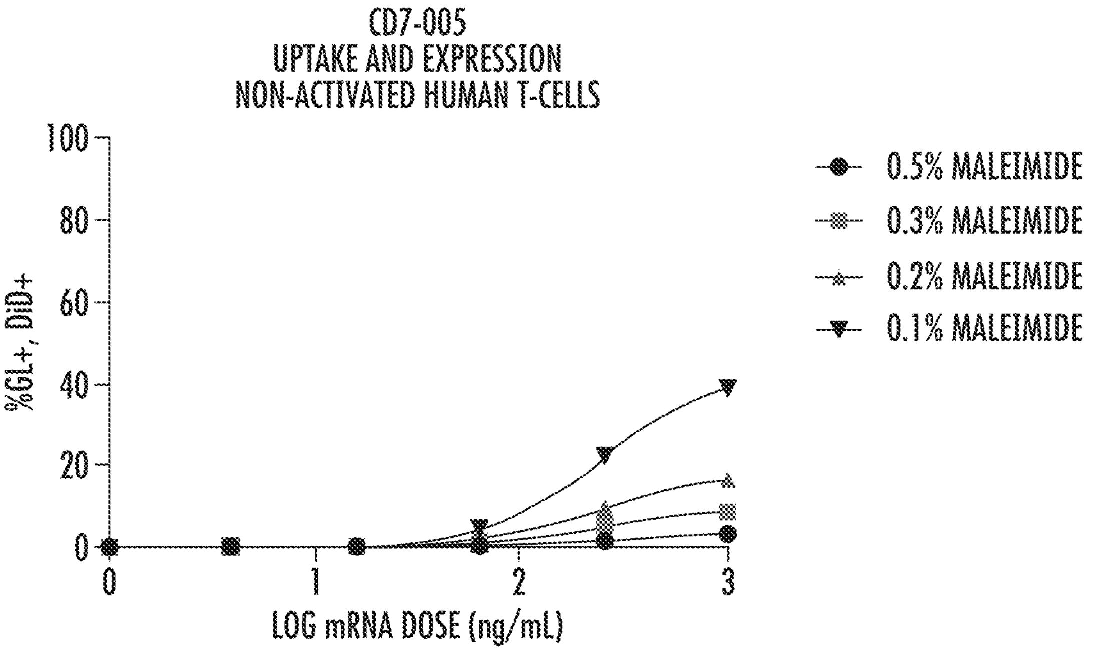

Referring to FIGS. 32A and 32B and Table 17, antibody (VHH; "A05") conjugation for targeting hepatic ASGPR1 protein leads to higher levels of expression of mLuc and rLuc luciferase cargo compared to the parental LNPs of the present disclosure without antibody conjugation, except for DOTAP.

Example 13: Effect of Second Lipid-Anchored Polymer Concentration on LNP Uptake and mRNA Expression DiD uptake and mRNA luciferase expression were compared in activated and non-activated human T-cells using LNPs with varying concentrations of second lipid-anchored polymer conjugated to antibodies via maleimide linkage. LNPs were formulated as described above and comprised Lipid 87:DSPC:Chol:DiD:DSG-PEG2000-OMe:DSPE-PEG5000-maleimide-antibody wherein the mol % of the four components was 47.5:10:39:0.5, the mol % of DSPE-PEG5000-maleimide-antibody (anti-CD5 or anti-CD7) was 0.5%, 0.3%, 0.2%, or 0.1%, and the DSG-PEG2000-OMe comprised the remainder.

As shown in FIG. 33A, FIG. 33B, FIG. 34A, and FIG. 34B, LNPs comprising lower concentrations of second lipid-anchored polymer conjugated to antibodies via maleimide linkage (for example, 0.1%, 0.2%, and 0.3%) surprisingly exhibited higher degree of DiD and Green lantern double positive cells than LNPs with higher concentrations of second lipid-anchored polymer conjugated to antibodies such as 0.5% for both CD5 and CD7 targets.

Example 14: Detectable T Cell Targeting at Very Low Ligand Density

Figure 35A:
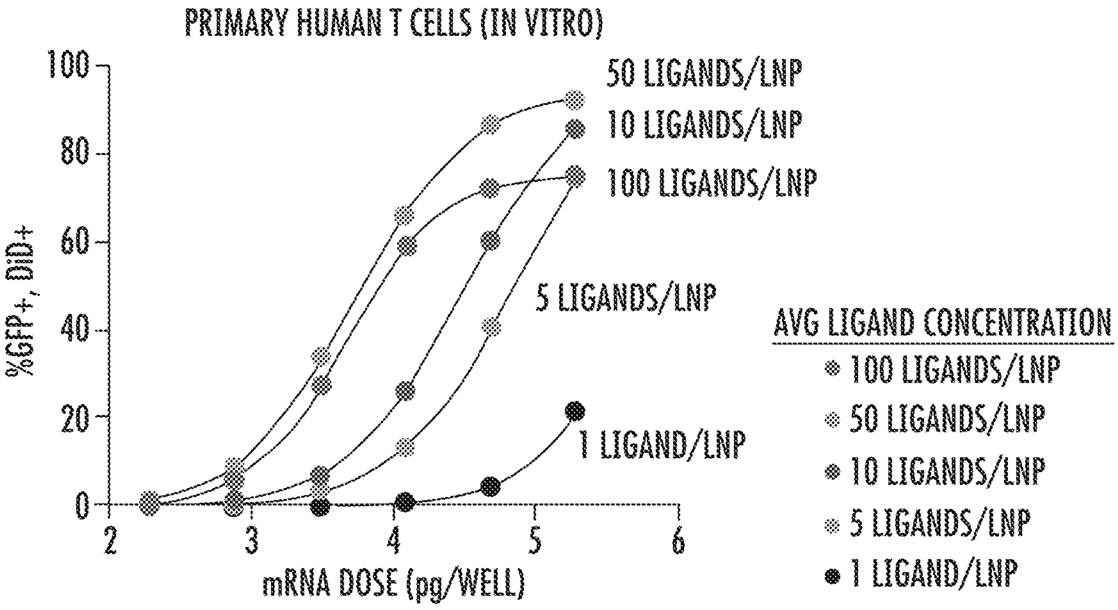
FIGS. 35A and 35B show T cell targeting at low ligand densities on primary human T cells in vitro (FIG. 35A) and in vivo (FIG. 35B).
Figure 35B:
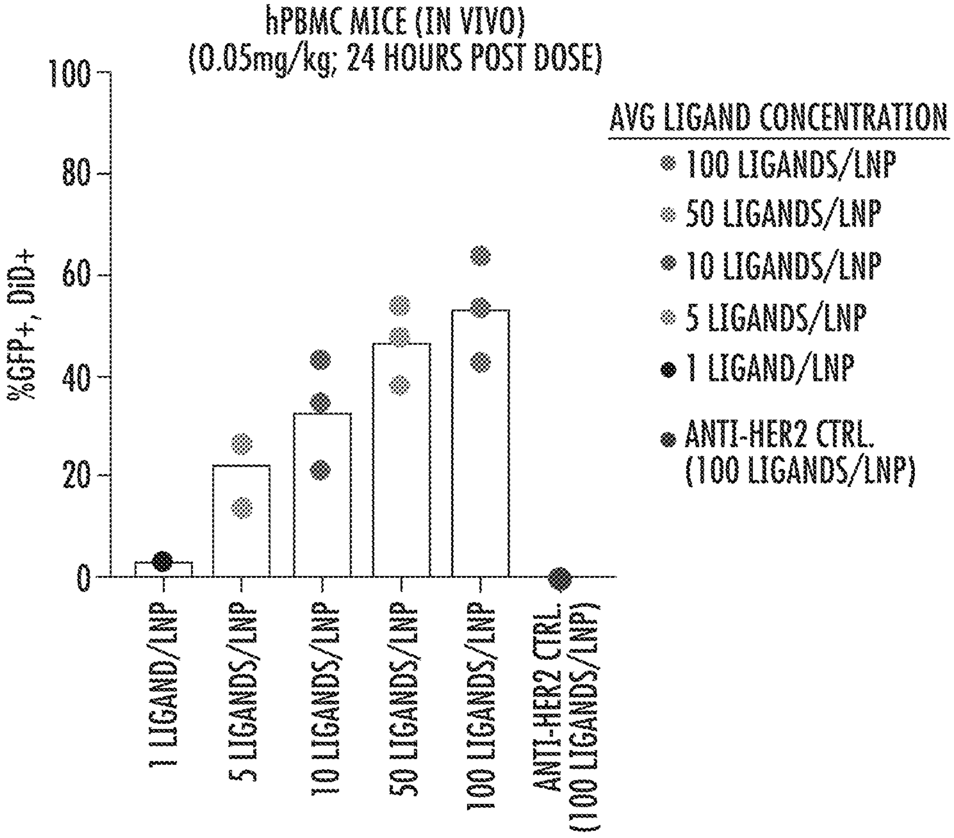

This example approximated the ability of stealth cell targeting lipid nanoparticles of the present disclosure to target primary human T cells in vitro and in vivo at very low densities of cell targeting moieties conjugated to the second lipid polymer per LNP surface. LNPs were formulated as described above and comprised Lipid 87:DSPC:Chol:DiD:DSG-PEG2000-OMe:DSPE-PEG5000-maleimide wherein the mol % of the four components was 47.5:10:39:0.5:2.5:0.5 mole %. The mol % of DSPE-PEG5000-maleimide was 0.5 mol %. The quantity of binding ligands to DSPE-PEG5000-maleimide was varied by changing the antibody concentration during the conjugation reaction. The antibody was either anti-CD5 or anti-CD7 and anti-Her2 was used as a negative control. FIG. 35A shows T cell targeting was observable and measurable down as low as 5 ligands per LNP. At the higher numbers of ligands per LNP, the targeting seemed to saturate. See FIG. 35A where the difference between 50 and 100 ligands per LNP was similar. The in vivo data is shown in FIG. 35B. The response was effective down to 5 ligands per LNP and targeting increased from 5, 10, 50, 100 ligands per LNP. See FIG. 35B. The estimated average ligands/LNP was based on calculations of total particle count, material input, and conjugation efficiency.

Example 15: Increasing the Length of the DSPE-PEG-N3 Used for Conjugation of a Targeting Moiety Leads to a Significant Increase in Uptake and Expression as Compared to the Parental LNP and a Non-Targeted scFv Conjugate This example compared DiD uptake and mRNA luciferase expression in primary mouse hepatocytes of the LNPs of the present disclosure (see Table 18 below), with or without targeting antibody conjugation (e.g., scFv, VHH, Fab, etc.). Briefly the protocol was as follows: Freshly isolated primary mouse hepatocytes were plated at 35,000 cells/well in collagen coated plates. Next, waiting 3½ hours after plating, the cells were treated with the LNPs with the following dosage scheme (10 ng per well for the DiD uptake, 200 ng per well for the luciferase expression). One hour after treatment, both plates were washed of all remaining LNP and placed in an incubator overnight. The following morning, both plates were given 80 μL of fresh maintenance media and placed in the incubator for an additional 30 minutes. One plate was then imaged on a Phenix imager, where the relative DiD Spot Intensity was normalized to Nuclei per well to evaluate the amount of uptake into the hepatocytes. The other plate was used to measure cell viability and then treated with OneStep Luciferase reagent to quantify the amount of luciferase protein expressed.

The aim of the study was to investigate the impact of DSPE-PEG-N3 polymer length on uptake and luciferase expression in primary mouse hepatocytes.

Figure 36A:
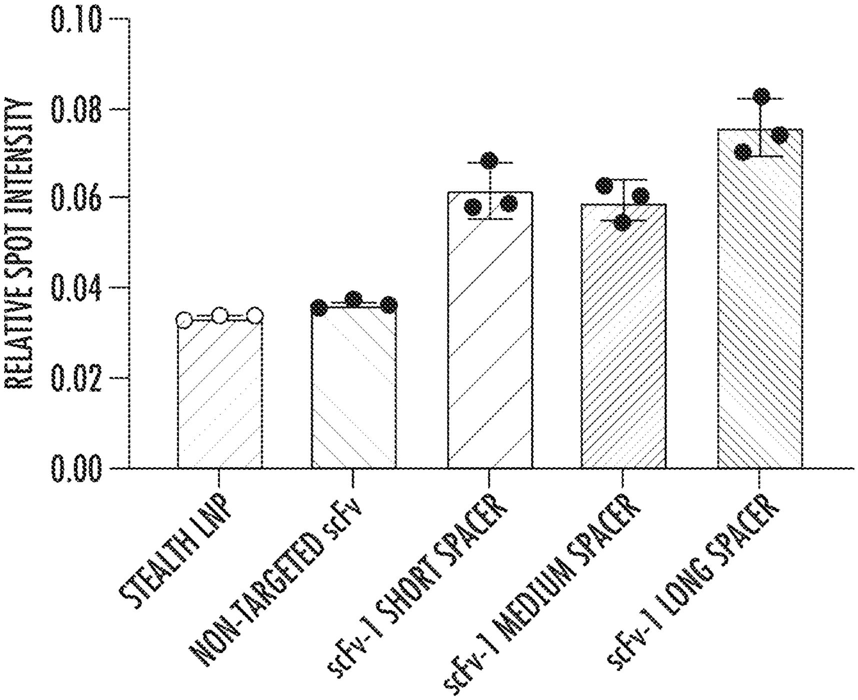
FIG. 36A shows cell-targeted (ctLNP) uptake into primary mouse hepatocytes as monitored by DiD.
Figure 36B:
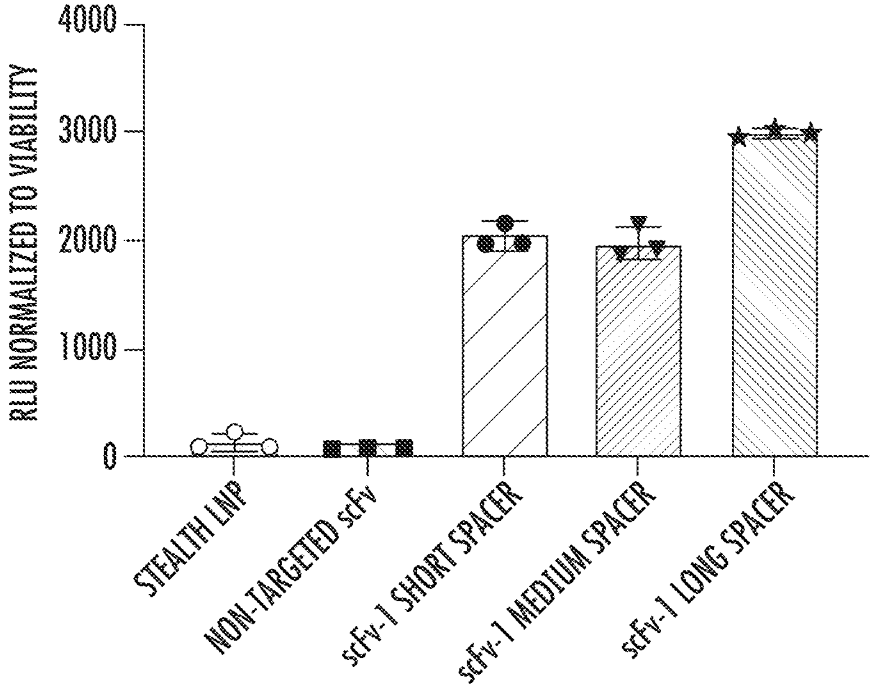
FIG. 36B shows ctLNP mRNA expression in primary mouse hepatocytes as monitored by luciferase activity.
Figure 36C:
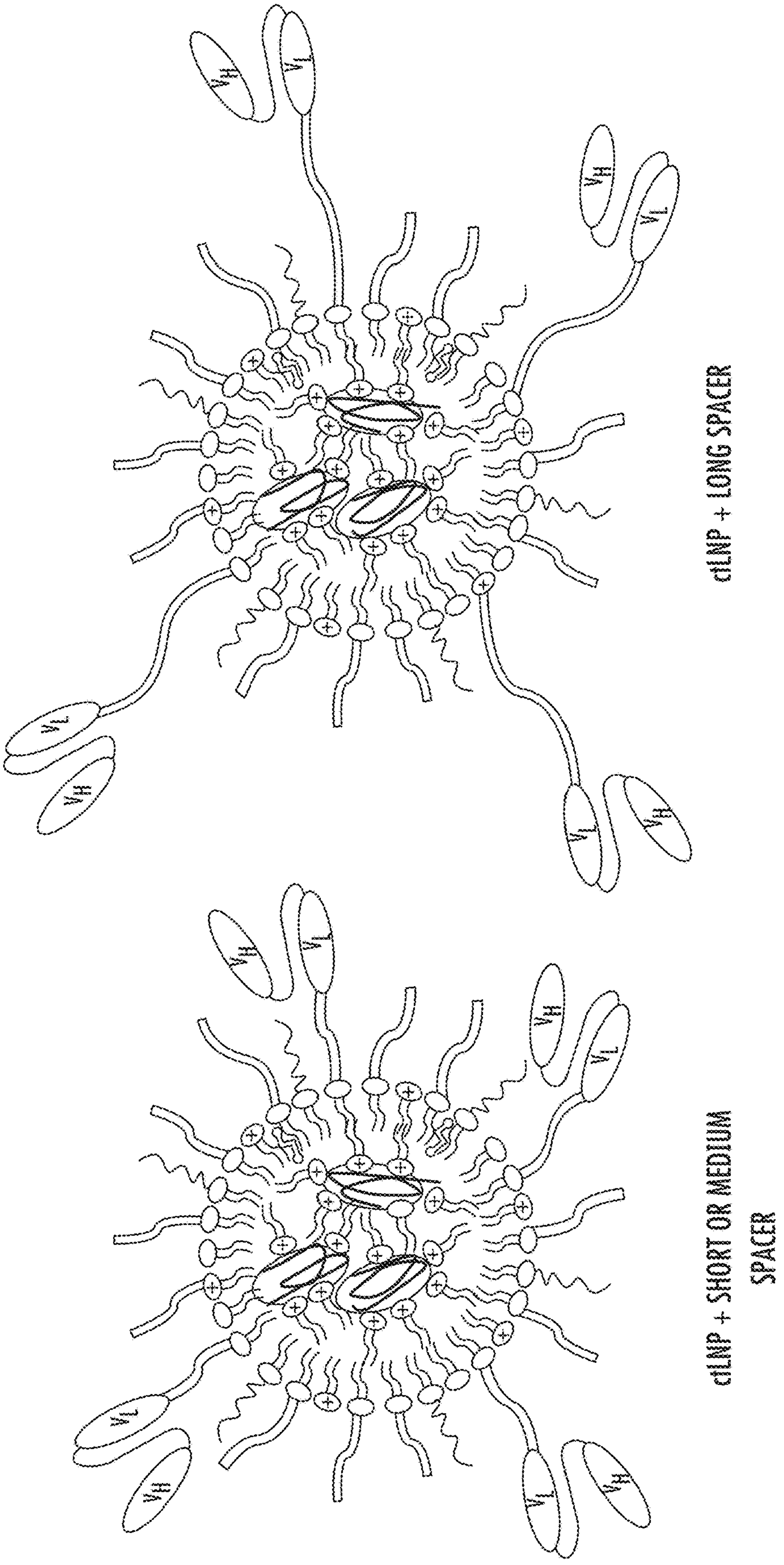
FIG. 36C shows the advantage of having the targeting moiety conjugated to the second lipid-anchored polymer where the molecular weight of the hydrophilic polymer is greater in the second lipid-anchored polymer than in the first.

Referring to FIG. 36A and Table 18 conjugation of targeting ASGPR1 protein led to a significantly higher amount of uptake into primary mouse hepatocytes when compared to the stealth LNP or after conjugation to a negative control anti-Her2 scFv targeting protein (Her2 not expressed on primary hepatocytes). Additionally, conjugates made using DSPE-PEG2000-N3 and DSPE-PEG3400-N3 showed a comparable amount of uptake, while those made with DSPE-PEG5000-N3 showed a significantly higher amount of uptake. See FIG. 36B. Referring to FIG. 36B and Table 18, these observations demonstrated targeted delivery through ASGPR1 and that conjugates made from the longer DSPE-PEG5000-N3 showed elevated levels of activity compared to all other samples with shorter polymer lengths for the second lipid-anchored polymer. These results lead to the conclusion that extending the conjugated antibody as shown in FIG. 36C or other targeting moiety further above the surface of the first lipid-anchored polymer of PEG2000-OMe or PEG3400-OMe provides less steric hindrance or greater antibody mobility needed for target binding (FIG. 36C).

It has become clear it is advantageous for the second lipid-anchored polymer when conjugated to a targeting moiety such as a VHH or other binding moiety to project above the surface of the LNP as represented by the outer reach of the first lipid anchor polymer. Extending the reach of the targeting moiety prevents any steric interference between the targeting moiety conjugated to the second lipid polymer and the hydrophilic polymer of the first lipid-anchored polymer. See FIG. 36C. Comparing the molecular weights of the two hydrophilic polymers is a convenient way to make sure the functions of the two lipid-anchored polymers do not interfere with one another. In one embodiment the molecular weight of the hydrophilic polymer attached to the second lipid-anchored polymer is at least 50% greater than the molecular weight of the hydrophilic polymer attached to the first lipid-anchored polymer. In another embodiment the molecular weight of the hydrophilic polymer attached to the second lipid-anchored polymer is at least 60% greater than the molecular weight of the hydrophilic polymer attached to the first lipid-anchored polymer. In one embodiment the molecular weight of the hydrophilic polymer attached to the second lipid-anchored polymer is at least 70% greater than the molecular weight of the hydrophilic polymer attached to the first lipid-anchored polymer. In another embodiment the molecular weight of the hydrophilic polymer attached to the second lipid-anchored polymer is at least 70%, at least 80%, at least 90%, or at least 100% greater or more than the molecular weight of the hydrophilic polymer attached to the first lipid-anchored polymer. It is understandable that there may be certain targeting moieties with less sensitivity to the steric qualities of the first lipid polymer and therefore in some circumstances the molecular weight of the hydrophilic polymer attached to the second lipid-anchored polymer is at least 20% or at least 30% or at least 40% greater than the molecular weight of the hydrophilic polymer attached to the first lipid-anchored polymer and still is able to function without too much steric hindrance. See FIG. 36C.

TABLE 18

Effect of length of 2nd lipid-anchored polymer conjugated to targeting moiety on target binding.

| LNP Formulation | Lipids and Molar Ratios | Average Diameter (nm) | Encapsulation Efficiency (%) |
|---|---|---|---|
| Stealth | Lipid Z:DSPC:Chol:DSG-PEG2000-OMe:DSPE-PEG2000-OH:DiD (47.5:10:39:2.5:0.5:0.5) | 71.4 | 96.2 |
| Short | Lipid Z:DSPC:Chol:DSG-PEG2000-OMe:DSPE-PEG2000-N3:DiD (47.5:10:39:2.5:0.5:0.5) | 73.6 | 97.1 |
| Medium | Lipid Z:DSPC:Chol:DSG-PEG2000-OMe:DSPE-PEG3400-N3:DiD (47.5:10:39:2.5:0.5:0.5) | 95.8 | 95.1 |
| Long | Lipid Z:DSPC:Chol:DSG-PEG2000-OMe:DSPE-PEG5000-N3:DiD (47.5:10:39:2.5:0.5:0.5) | 80.6 | 94.3 |
| Stealth | Lipid Z:DSPC:Chol:DSG-PEG2000-OMe:DSPE-PEG2000-OH:DiD (47.5:10:39:2.5:0.5:0.5) | 71.4 | 96.2 |
| Short | Lipid Z:DSPC:Chol:DSG-PEG2000-OMe:DSPE-PEG2000-N3:DiD (47.5:10:39:2.5:0.5:0.5) | 73.6 | 97.1 |
| Medium | Lipid Z:DSPC:Chol:DSG-PEG2000-OMe:DSPE-PEG3400-N3:DiD (47.5:10:39:2.5:0.5:0.5) | 95.8 | 95.1 |
| Long | Lipid Z:DSPC:Chol:DSG-PEG2000-OMe:DSPE-PEG5000-N3:DiD (47.5:10:39:2.5:0.5:0.5) | 80.6 | 94.3 |

Example 16: VHH and scFv Exhibit Superior Efficiency in LNP Targeting

Figure 37A:
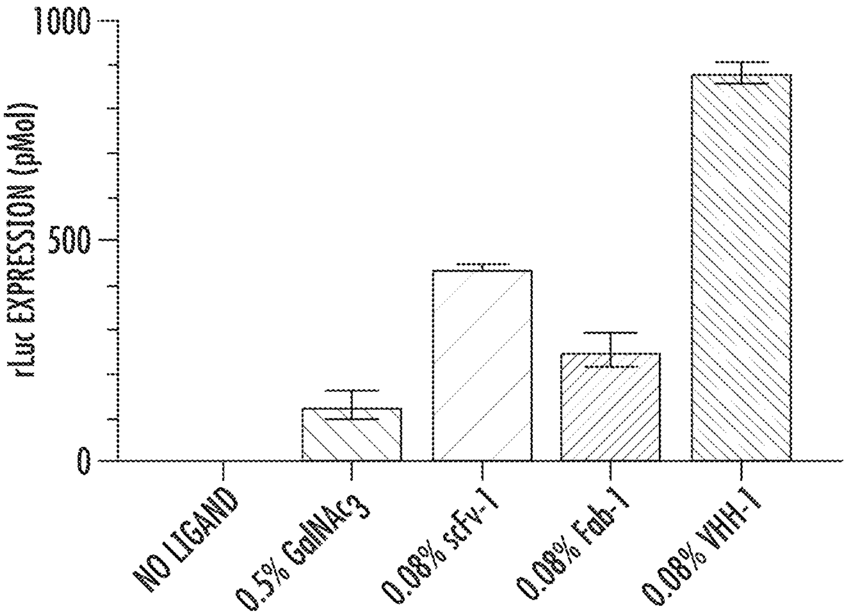
FIG. 37A depicts cellular expression from cells targeted by the different targeting moieties (tri N-acetylgalactosamine ($GalNAc_3$), an Fab antibody fragment, an scFv, and a VHH-1) at ligand densities at 0.08% for the antibodies and 0.5% for $GalNAc_3$.

As shown in FIG. 37A, the four targeting moieties were tested (an N-acetylgalactosamine, an Fab antibody fragment, a single chain scFv, and a VHH-1) at ligand densities at 0.08% for the antibodies and 0.5% for GalNAc3. As shown in FIG. 37A, ASGPR targeting LNPs with VHH nanobody exhibited the highest efficiency in delivering a luciferase construct to cells at 0.08%, followed by the ASGPR targeting LNPs with scFv.

Figure 37B:
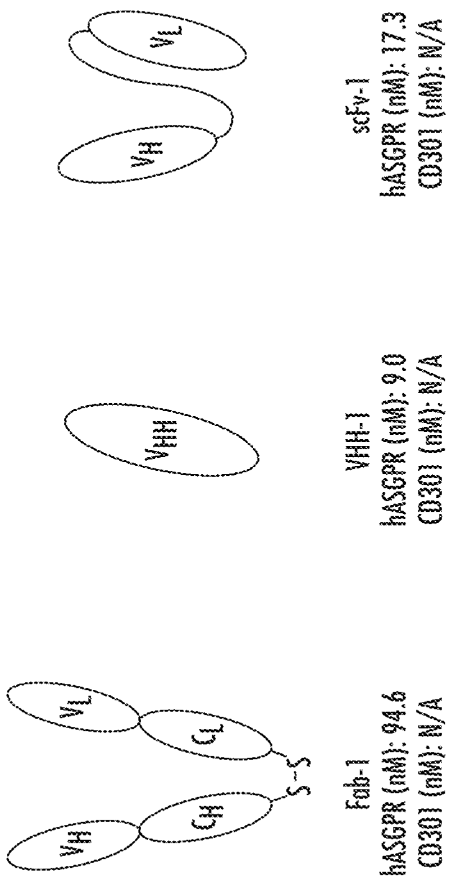
FIG. 37B depicts a VHH nanobody produces a targeting moiety with the highest affinity.
Figure 37B:
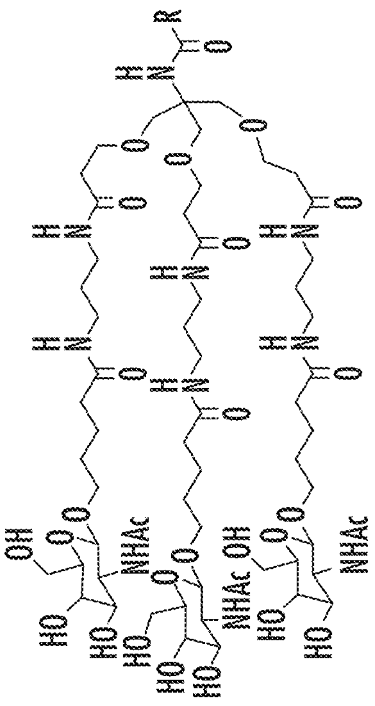

Example 17: Comparing Multiple Targeting Ligand Formats with Varying Affinities to ASGPR and Off-Target Receptors In this example, multiple targeting ligand formats with varying affinities to ASGPR and off target receptors were compared. As shown in FIG. 37B, the VHH-1 and scFv formats were highly superior to the Fab and GalNAc3. With respect binding to ASGPR, dissociation constants (Kd) were approximately 30.7 nM, 94.6 nM, 9.0 mM, and 17.3 nM, for GalNAc, Fab-1, VHH-1, and scFv-1, respectively. The GalNAc3 targeting moiety required a higher concentration of ligand conjugation to produce an inferior targeting moiety. The Fab-1 conjugates while benefiting from avidity also showed a high degree of over modification and were excluded. The high degree of over modification refers to modifying each Fab with more than 1 SATA molecule leading to multiple points of PEG-Mal conjugation during the final phase of ctLNP formulation and conjugation.

Figure 38A:
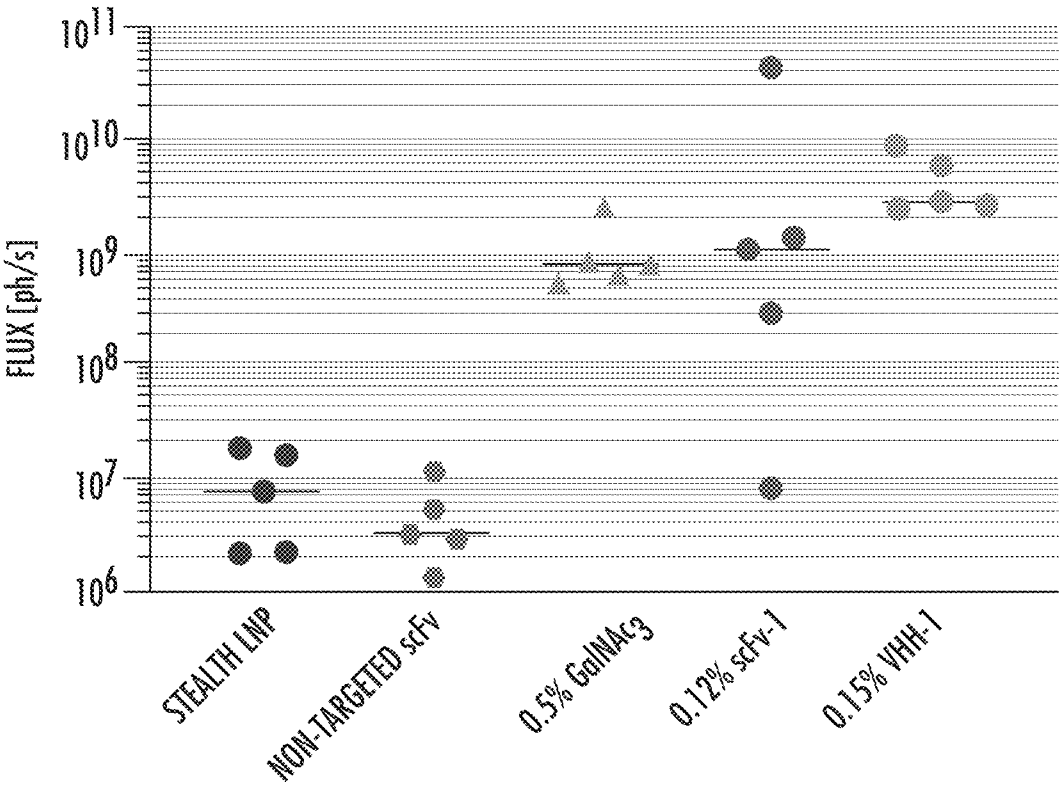
FIG. 38A shows that use of a VHH ligand led to a 0.4 log enhancement in potency over $GalNAc_3$. In some embodiments herein, the targeting moiety is also referred to as a ligand.
Figure 38B:
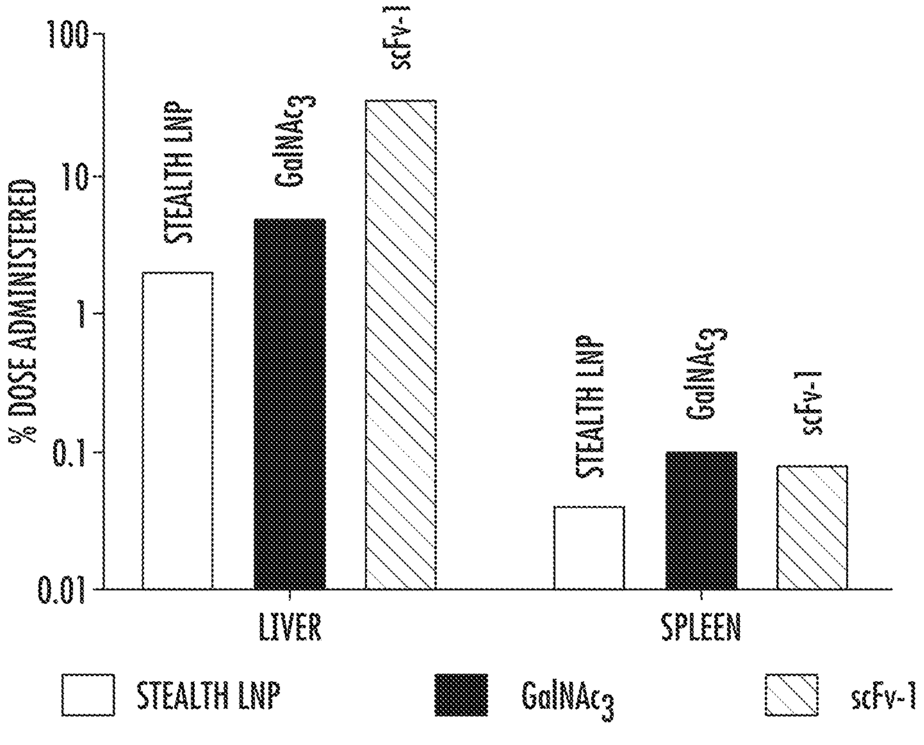
FIG. 38B shows that use of scFv targeting ligand results in delivery of approximately 7 times more cargo to the liver at 1 hour.

Example 18: ASGPR Targeting Using scFv or VHH Show Higher Liver Expression than when Using GalNAc3 in Mice As shown in FIGS. 38A and 38B, when ApoE −/− mice are injected with 1.0 mg/kg i.v. Luc ceDNA and IVIS analysis was performed 7 days later. FIG. 38A and FIG. 38B shows that use of a VHH ligand led to a 0.4 log enhancement in potency over GalNAc3 at a much lower coupling concentration. Similarly, use of scFv targeting ligand delivered approximately 7 times more cargo to the liver at 1 hour and at a much lower coupling concentration.

Figure 39A:
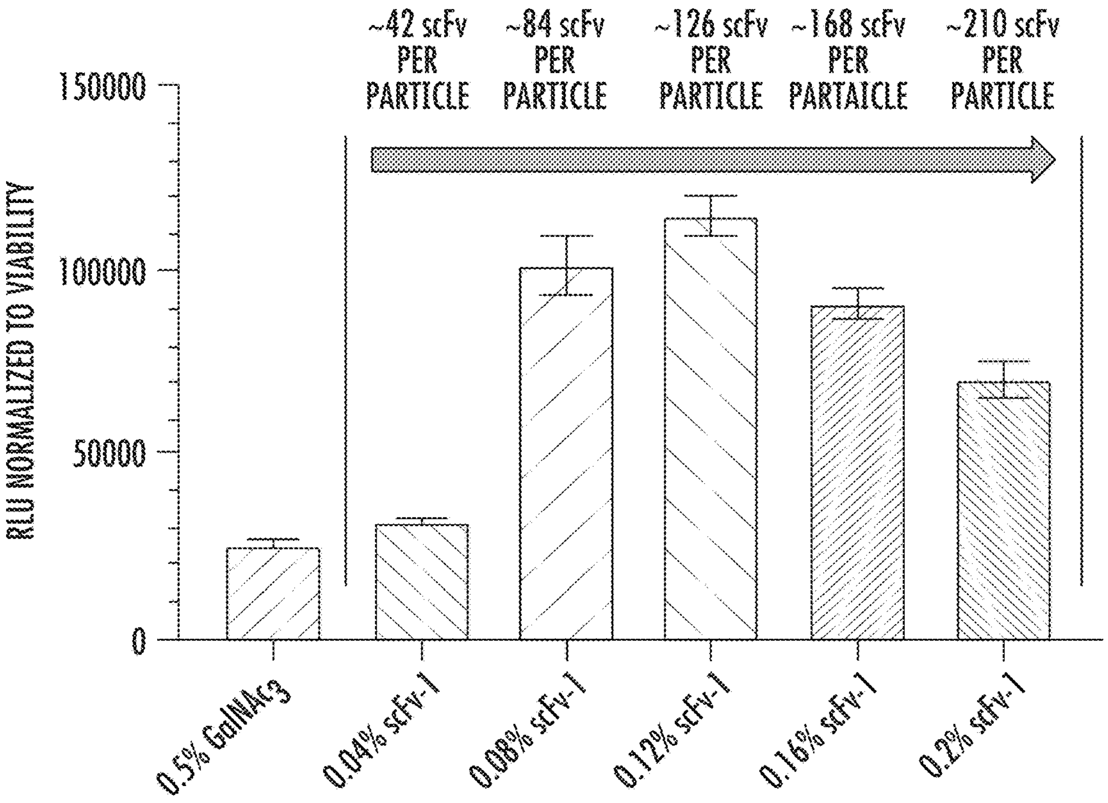
FIG. 39A shows that the optimal ligand density of scFv-1 was around approximately 84 to 210 targeting moieties per LNP particle, peaking at approximately 126 targeting moieties per particle.

Example 19: The Number of Ligands Per LNP can be Titrated for Optimal Expression In Vitro In this example, the number of maleimide linkers was used as a variable to evaluate the optimal ligand density. The ligand density can be manipulated by varying the maleimide concentration when conjugating maleimide to the second lipid-anchored polymer and by varying the concentration of the targeting moiety or targeting ligand when conjugating to maleimide. FIG. 39A shows that the optimal ligand density is 0.12% (125 ligands per particle) for scFv-1 in primary mouse hepatocytes. This particular experiment compared scFv-1 ligands per LNP particle from a low of 42 ligands per particle, 84 ligands per particle, 126 ligands per particle, 168 ligands per particle, and 210 ligands per particle, and found that 126 scFv-1 ligands per particle (0.12% scFv of FIG. 39A) to be the most efficient.

Figure 39B:
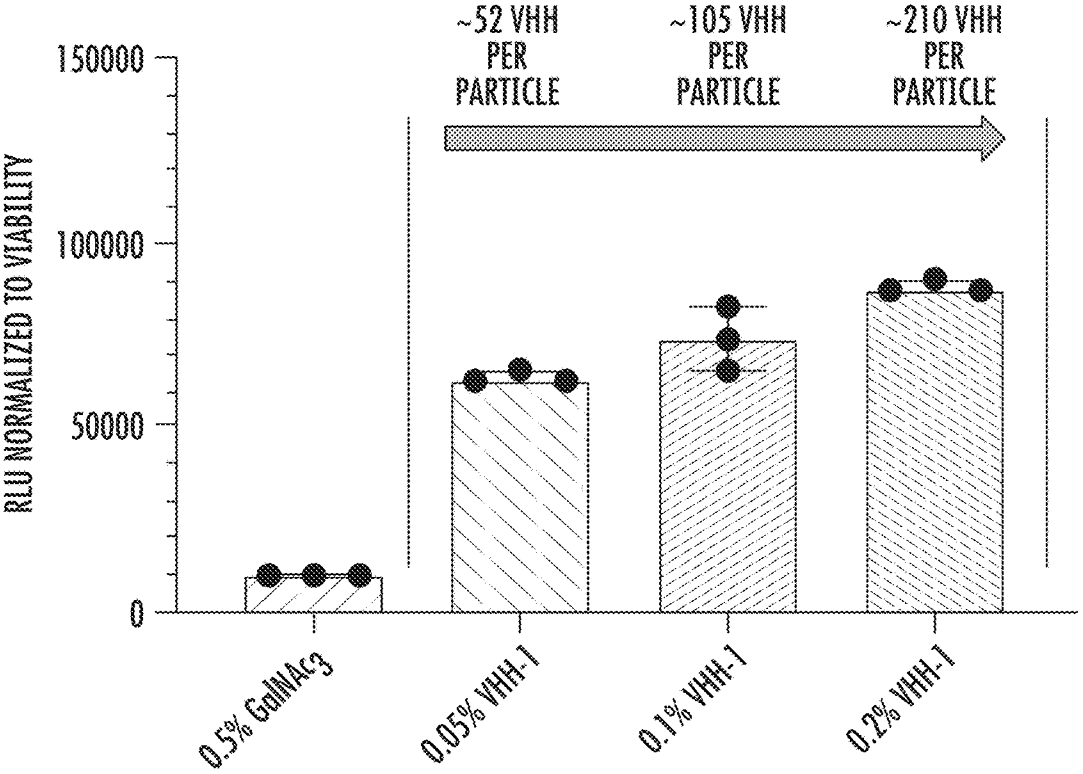
FIG. 39B shows that the optimal performance of ligand density of VHH-1 increased with greater ligand density with an optimal ligand density starting at 52 VHHs per particle, peaking at 210 VHHs per particle (the highest density tested).

When the ligand was the smaller format where VHH-1 targeting moiety and the conjugation was via maleimide, it was found that VHH targeting moieties performed better as ligand densities increased in vitro. FIG. 39B shows a comparison of LNPs with 52, 105 and 210 VHH-1 ligands per particle, indicating that higher ligand or targeting moiety densities (210 VHHs per particle or above) were more efficient than the lower densities tested.

Example 20: Comparing Multiple HSC-Targeting Ligand Formats with Varying Affinities to HSPC Surface Receptors In this example, data was generated using an in vitro model demonstrating selective delivery of ctLNPs to CD34+

Figure 40:
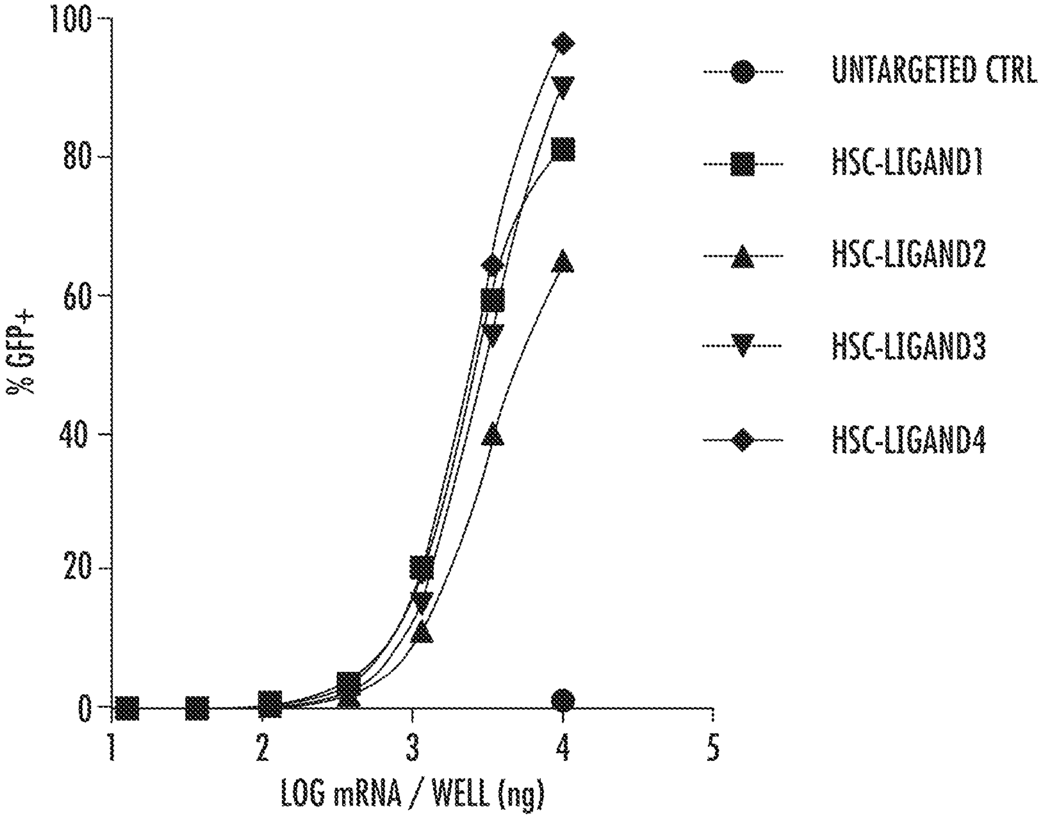
FIG. 40 shows an in vivo model demonstrating selective delivery of ctLNPs to CD34+ HSPCs obtained from umbilical cord blood using 4 different human antiCD45 antibodies (scFv) as targeting moieties.

HSPCs obtained from cord blood. Primary human CD34+ cells were isolated from umbilical cord blood (CB) mononuclear cells (MNCs) using positive immunomagnetic separation techniques. CD34 is expressed on hematopoietic stem and progenitor cells. See FIG. 40.

In this example, as shown by % Green Fluorescent Protein expression, all ligands performed very well. Ligand 4 was slightly superior, followed by ligand 3, then ligand 1, and finally, ligand 2. In this example, the ligands were 4 different scFvs to human CD45. The CT formulation was Lipid 87: DSPC:Chol:DSG-PEG2000-OMe:DSPE-PEG5000-Mal: DiD (47.5:10:39.45:2.5:0.5:0.05, all in mol %). The 4 different scFvs were conjugated to the parental LNP through DSPE-PEG5000-Mal (0.5 mol %) linkage. A more detailed explanation of maleimide conjugation can be found in Example 4 above.

Example 21: Maleimide Linker Chemistry Demonstrates Higher Activity Across Multiple Stealth LNPs with Both scFv-1 and VHH-1

Figure 41:
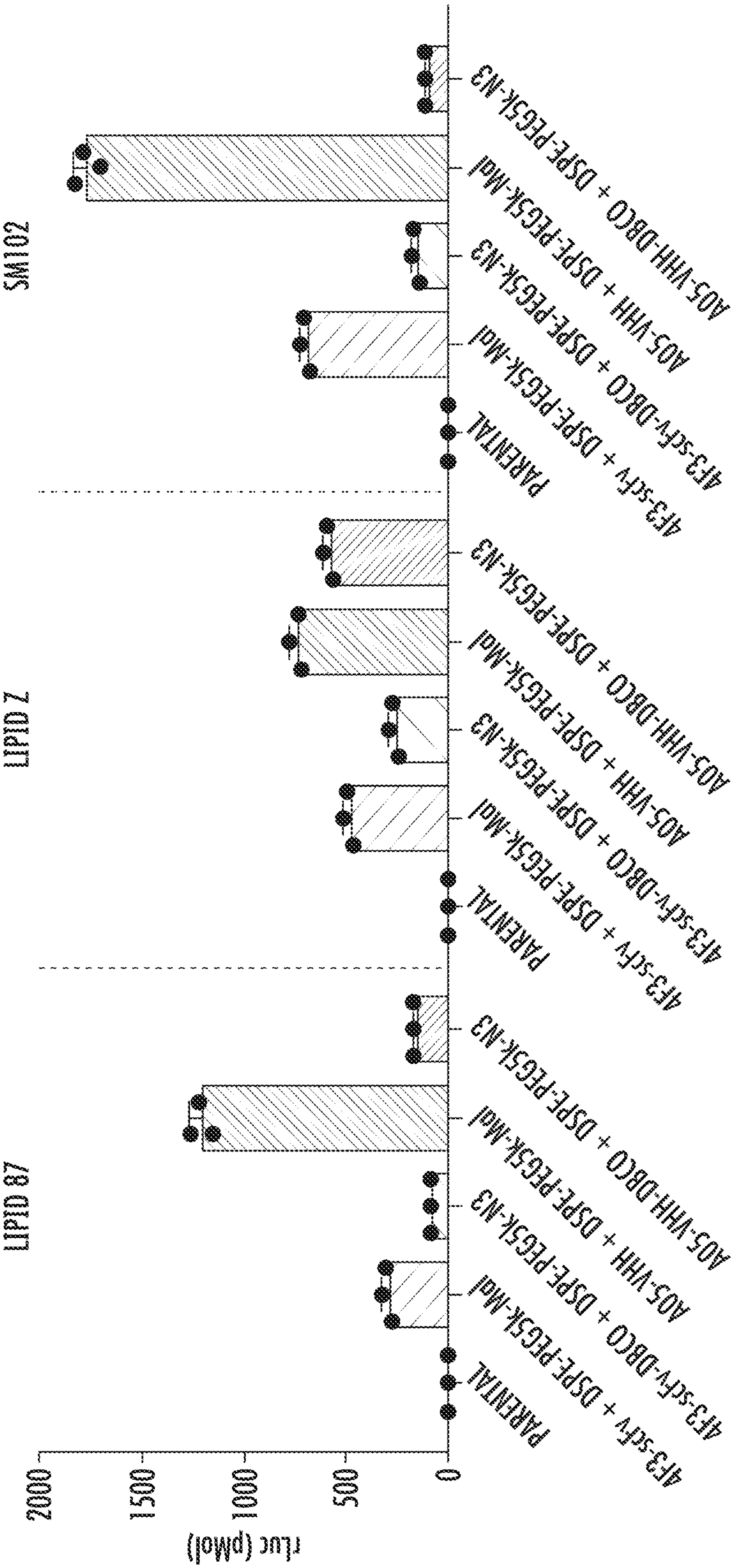
FIG. 41 shows the superiority of a maleimide linker as compared to an azide/DBCO linker attached to second lipid-anchored polymers for conjugating VHH antibodies in three different LNP formulations having different ionizable lipids.

FIG. 41 shows the evaluation of targeting moieties scFv and VHH when combined with either a maleimide linker or azide/DBCO linker. The maleimide linker was created using maleimide-thiol chemistry, where the free thiol was on the targeting moiety, and the maleimide was on the LNP. The azide linker was created using click chemistry, where dibenzocyclooctyne (DBCO) was attached to the targeting moiety, and the azide was on the LNP. See Example 10 and Table 14 above for this procedure. As shown in FIG. 41, it was found that the maleimide conjugated scFv (4F3) and VHH (A05) tested in three different ionizable lipid-containing LNPs consistently performed with increased efficiency in delivering a luciferase construct to cells, as compared to the azide/DBCO conjugated antibodies. Table 19 shows comparative properties and compositions of the parental and antibody conjugated LNPs used in this study.

TABLE 19

The physical characteristics of ctLNP compositions used in the maleimide v. azide comparison study.

| LNP | Sample ID FIG. 41 | $Z_{ave}$ Size (nm) | EE (%) | Ligand (%) | Lipid composition |
|---|---|---|---|---|---|
| 500 | 4F3-scFv + DSPE-PEG5k-Mal | 113.3 | 98 | 0 (Parental) | Lipid 87/DSPC/Chol/DSG-PEG2K/DSPE-PEG5k-Mal/DiD (47.5/10/39.45/2.5/0.5/0.05) |
| 501 | 4F3-scFv-DBCO + DSPE-PEG5k-N3 | 70.6 | 99 | 0 (Parental) | Lipid 87/DSPC/Chol/DSG-PEG2K/DSPE-PEG5k-N3/DiD (47.5/10/39.45/2.5/0.5/0.05) |
| 502 | A05-VHH + DSPE-PEG5k-Mal | 113.3 | 98 | 0 (Parental) | Lipid 87/DSPC/Chol/DSG-PEG2K/DSPE-PEG5k-Mal/DiD (47.5/10/39.45/2.5/0.5/0.05) |
| 503 | A05-VHH-DBCO + DSPE-PEG5k-N3 | 70.6 | 99 | 0 (Parental) | Lipid 87/DSPC/Chol/DSG-PEG2K/DSPE-PEG5k-N3/DiD (47.5/10/39.45/2.5/0.5/0.05) |
| 504 | 4F3-scFv + DSPE-PEG5k-Mal | 105.7 | 96 | 0.08 | Lipid 87/DSPC/Chol/DSG-PEG2K/DSPE-PEG5k-Mal/DiD (47.5/10/39.45/2.5/0.5/0.05) |
| 505 | 4F3-scFv-DBCO + DSPE-PEG5k-N3 | 70.2 | 95 | 0.08 | Lipid 87/DSPC/Chol/DSG-PEG2K/DSPE-PEG5k-N3/DiD (47.5/10/39.45/2.5/0.5/0.05) |
| 506 | A05-VHH + DSPE-PEG5k-Mal | 115.5 | 96 | 0.08 | Lipid 87/DSPC/Chol/DSG-PEG2K/DSPE-PEG5k-Mal/DiD (47.5/10/39.45/2.5/0.5/0.05) |
| 507 | A05-VHH-DBCO + DSPE-PEG5k-N3 | 70.9 | 95 | 0.08 | Lipid 87/DSPC/Chol/DSG-PEG2K/DSPE-PEG5k-N3/DiD (47.5/10/39.45/2.5/0.5/0.05) |
| 508 | 4F3-scFv + DSPE-PEG5k-Mal | 81.8 | 99 | 0 (Parental) | Lipid Z/DSPC/Chol/DSG-PEG2K/DSPE-PEG5k-Mal/DiD (47.5/10/39.45/2.5/0.5/0.05) |
| 509 | 4F3-scFv-DBCO + DSPE-PEG5k-N3 | 67.7 | 99 | 0 (Parental) | Lipid Z/DSPC/Chol/DSG-PEG2K/DSPE-PEG5k-N3/DiD (47.5/10/39.45/2.5/0.5/0.05) |
| 510 | A05-VHH + DSPE-PEG5k-Mal | 81.8 | 99 | 0 (Parental) | Lipid Z/DSPC/Chol/DSG-PEG2K/DSPE-PEG5k-Mal/DiD (47.5/10/39.45/2.5/0.5/0.05) |
| 511 | A05-VHH-DBCO + DSPE-PEG5k-N3 | 67.7 | 99 | 0 (Parental) | Lipid Z/DSPC/Chol/DSG-PEG2K/DSPE-PEG5k-N3/DiD (47.5/10/39.45/2.5/0.5/0.05) |
| 512 | 4F3-scFv + DSPE-PEG5k-Mal | 88.1 | 94 | 0.08 | Lipid Z/DSPC/Chol/DSG-PEG2K/DSPE-PEG5k-Mal/DiD (47.5/10/39.45/2.5/0.5/0.05) |
| 513 | 4F3-scFv-DBCO + DSPE-PEG5k-N3 | 68.7 | 92 | 0.08 | Lipid Z/DSPC/Chol/DSG-PEG2K/DSPE-PEG5k-N3/DiD (47.5/10/39.45/2.5/0.5/0.05) |
| 514 | A05-VHH + DSPE-PEG5k-Mal | 105.3 | 95 | 0.08 | Lipid Z/DSPC/Chol/DSG-PEG2K/DSPE-PEG5k-Mal/DiD (47.5/10/39.45/2.5/0.5/0.05) |
| 515 | A05-VHH-DBCO + DSPE-PEG5k-N3 | 69.5 | 93 | 0.08 | Lipid Z/DSPC/Chol/DSG-PEG2K/DSPE-PEG5k-N3/DiD (47.5/10/39.45/2.5/0.5/0.05) |
| 516 | 4F3-scFv + DSPE-PEG5k-Mal | 84.2 | 99 | 0 (Parental) | SM102/DSPC/Chol/DSG-PEG2K/DSPE-PEG5k-Mal/DiD (47.5/10/39.45/2.5/0.5/0.05) |
| 517 | 4F3-scFv-DBCO + DSPE-PEG5k-N3 | 63.7 | 99 | 0 (Parental) | SM102/DSPC/Chol/DSG-PEG2K/DSPE-PEG5k-N3/DiD (47.5/10/39.45/2.5/0.5/0.05) |
| 518 | A05-VHH + DSPE-PEG5k-Mal | 84.2 | 99 | 0 (Parental) | SM102/DSPC/Chol/DSG-PEG2K/DSPE-PEG5k-Mal/DiD (47.5/10/39.45/2.5/0.5/0.05) |
| 519 | A05-VHH-DBCO + DSPE-PEG5k-N3 | 63.7 | 99 | 0 (Parental) | SM102/DSPC/Chol/DSG-PEG2K/DSPE-PEG5k-N3/DiD (47.5/10/39.45/2.5/0.5/0.05) |
| 520 | 4F3-scFv + DSPE-PEG5k-Mal | 85.1 | 95 | 0.08 | SM102/DSPC/Chol/DSG-PEG2K/DSPE-PEG5k-Mal/DiD (47.5/10/39.45/2.5/0.5/0.05) |
| 521 | 4F3-scFv-DBCO + DSPE-PEG5k-N3 | 67.3 | 92 | 0.08 | SM102/DSPC/Chol/DSG-PEG2K/DSPE-PEG5k-N3/DiD (47.5/10/39.45/2.5/0.5/0.05) |
| 522 | A05-VHH + DSPE-PEG5k-Mal | 99.3 | 95 | 0.08 | SM102/DSPC/Chol/DSG-PEG2K/DSPE-PEG5k-Mal/DiD (47.5/10/39.45/2.5/0.5/0.05) |

TABLE 19-continued

The physical characteristics of ctLNP compositions used in the maleimide v. azide comparison study.

| LNP | Sample ID FIG. 41 | $Z_{ave}$ Size (nm) | EE (%) | Ligand (%) | Lipid composition |
|---|---|---|---|---|---|
| 523 | A05-VHH-DBCO + DSPE-PEG5k-N3 | 70.8 | 92 | 0.08 | SM102/DSPC/Chol/DSG-PEG2K/DSPE-PEG5k-N3/DiD (47.5/10/39.45/2.5/0.5/0.05) |

Example 22: Evaluation of Candidate Ligands for ctLNP Targeting of Hematopoietic Stem Cells (HSC)

Figure 42A:
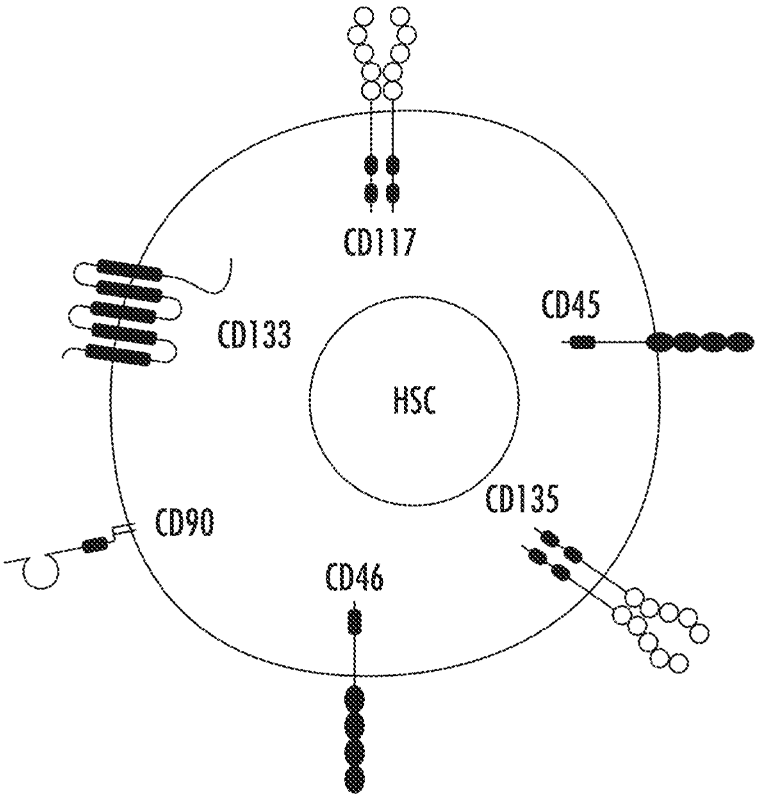
FIG. 42A shows six HSC antigens that meet the criteria to serve as candidates for inducing targeting moieties.
Figure 42B:
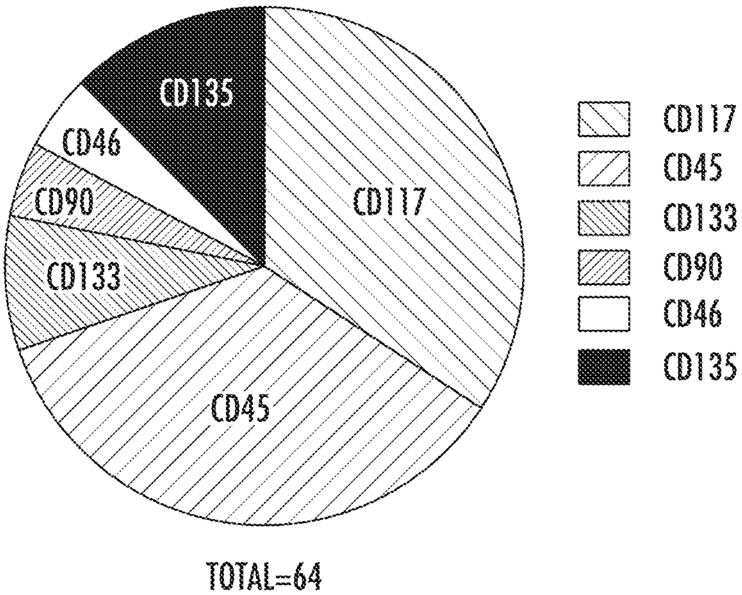
FIG. 42B is a pie chart of the total of 64 targeting moieties constructed from full-length antibodies and configured as scFv recognizing and binding CD117, CD45, CD135, CD46, CD90 or CD133.

This example focuses on selecting targeting moieties for HSC cells by using available antibodies as candidate ligands specific for antigens that were abundantly expressed on HSC cells. The following criteria were used to select HSC surface antigens and their associated candidate ligands. The antigen must be abundantly expressed on HSC cells and binding to the ligand must confer some degree of selectivity for HSCs over other cell types. The protein structure and the biological role of the surface antigen must be well characterized. The antigen must have shown a precedence for in vivo HSC targeting. Finally, there were available antibody sequences for use in investigating antibodies to the antigen for HSC targeting. FIG. 42A shows six antigens that satisfy the designated criteria, and they were as follows: CD117, CD45, CD135, CD46, CD90 and CD133. As shown in FIG. 42B, a total of 64 targeting moieties were constructed from full length antibodies and configured as scFv recognizing and binding CD117, CD45, CD135, CD46, CD90 or CD133 on HSCs. The 64 candidate targeting moieties were characterized for antigen binding to both human and cyno versions of the antigens, such that cynomolgus monkeys could be used as a proof-of-concept model.

Preparation of Candidate Ligands

Candidate targeting ligands ("targeting moieties") were expressed as single chain variable fragments (scFvs) in CHO cells with a C-terminal flag tag followed by an unpaired cysteine residue. Purification of ligands were performed using antiflag affinity resin columns and buffer exchanged into PBS. To expose unpaired C-terminal cysteines, dimers and cysteinylated ligands were reduced in TCEP (10× molar excess) for 1 hour at room temperature. Reduced proteins were purified and buffer exchanged into TBS with 1 mM EDTA using 7 kDa Zeba Spin columns before being frozen at −80° C. Protein concentration was quantified using a NanoDrop One (Thermo Scientific), reduction efficiency (quantified by monomer:dimer ratio) was quantified via SDS-PAGE under non-reducing conditions, and cysteinylation reduction and ligand over-reduction was characterized using an LCMS (Agilent 6530 Q-TOF).

Characterization of Candidate Ligand Affinities 20 nM His-tagged recombinant human receptors: CD117, CD45, CD46, CD133, and CD135, were immobilized onto nickel coated plates overnight at 4° C. in TBS buffer. Non-bound receptors were removed with three-washes of 1×TBS-T buffer. Blocking buffer was added to each well and incubated plate for 0.5 hr at room temperature with continuous shaking of 550 rpm. The plate was washed with 1×TBS-T. Serial dilutions of candidate ligands with concentrations ranged from 2 μM to 1 μM were added to each well and incubated for 1 hr at room temperature with continuous shaking of 550 rpm. After three washes of 1×TBS-T, horseradish peroxidase (HRP) enzyme liked FLAG antibody solution (1:200) was added to each well for 1 hr at room temperature with continuous shaking of 550 rpm. Chemiluminescent substrate was added and HRP enzymic activity was measured using an absorbance readout at 425 nm. The data was analyzed by non-linear regression to estimate binding affinity.

Figure 43:
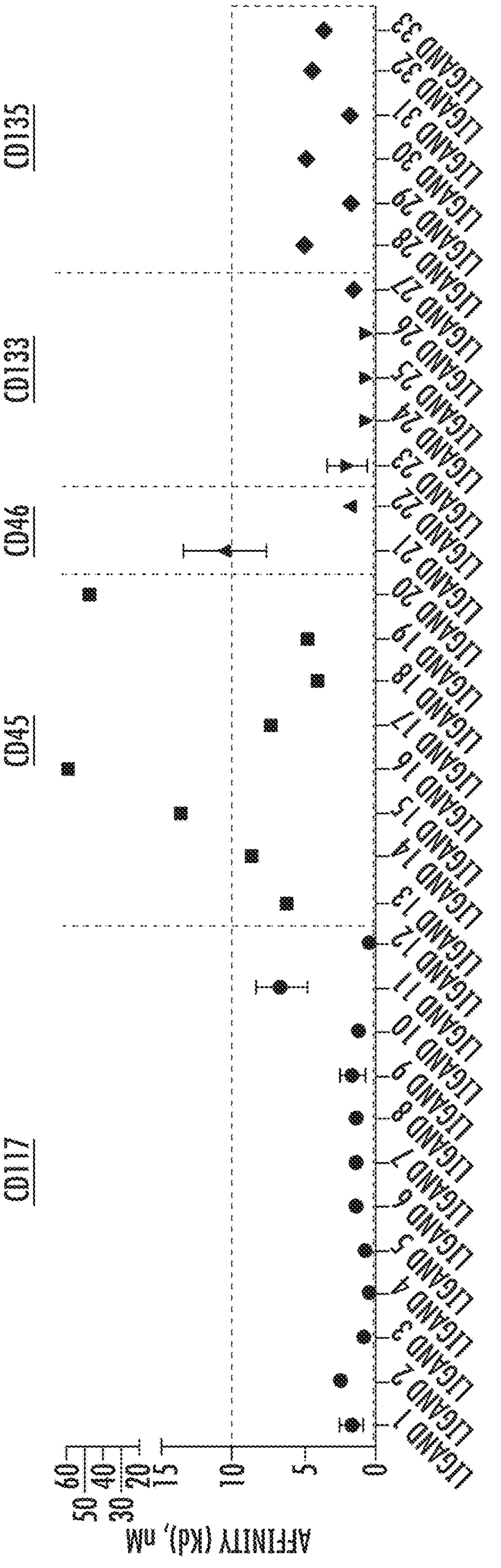
FIG. 43 is a plot of the affinity (Kd) for 29 of the Candidate ligands for the target were determined to be below 10 nm.

The affinity of the candidate ligands ranged from 0.5 nM to 60 nM. As shown in FIG. 43, the affinity (Kd) for 29 of the candidate ligands for the target were determined to be below 10 nm. There were 6 with a Kd lower than 1 nM and another 6 with Kd between 1 and 10 nM. See FIG. 43. Surprisingly, all but one of the anti-CD117 antibodies seemed to bind with affinity of less than 5 nM. However, it had an affinity of greater than 5 nM and lower than 10 nM. As shown in FIG. 43, eleven of twelve antibodies to CD117 maintained an affinity of close to or less than 1 nM.

Binding of Candidate Targeting Ligands to Both Human and Cyno Versions of the Antigen 20 nM His-tagged recombinant human or cynomolgus CD117 were immobilized onto nickel coated plates overnight at 4° C. in TBS buffer. Non-bound receptors were removed with three-washes of 1×TBS-T buffer. Blocking buffer was added to each well and incubated plate for 0.5 hr at room temperature with continuous shaking of 550 rpm. The plates were washed with 1×TBS-T. Serial dilutions of candidate ligands with concentrations ranged from 2 pM to 1 μM were added to each well and incubated for 1 hr at room temperature with continuous shaking of 550 rpm. After three washes of 1×TBS-T, horseradish peroxidase (HRP) enzyme liked FLAG antibody solution (1:200) was added to each well for 1 hr at room temperature with continuous shaking of 550 rpm. Chemiluminescent substrate was added and HRP enzymic activity was measured using an absorbance readout at 425 nm. The data was analyzed by non-linear regression to estimate binding affinity.

Figure 44:
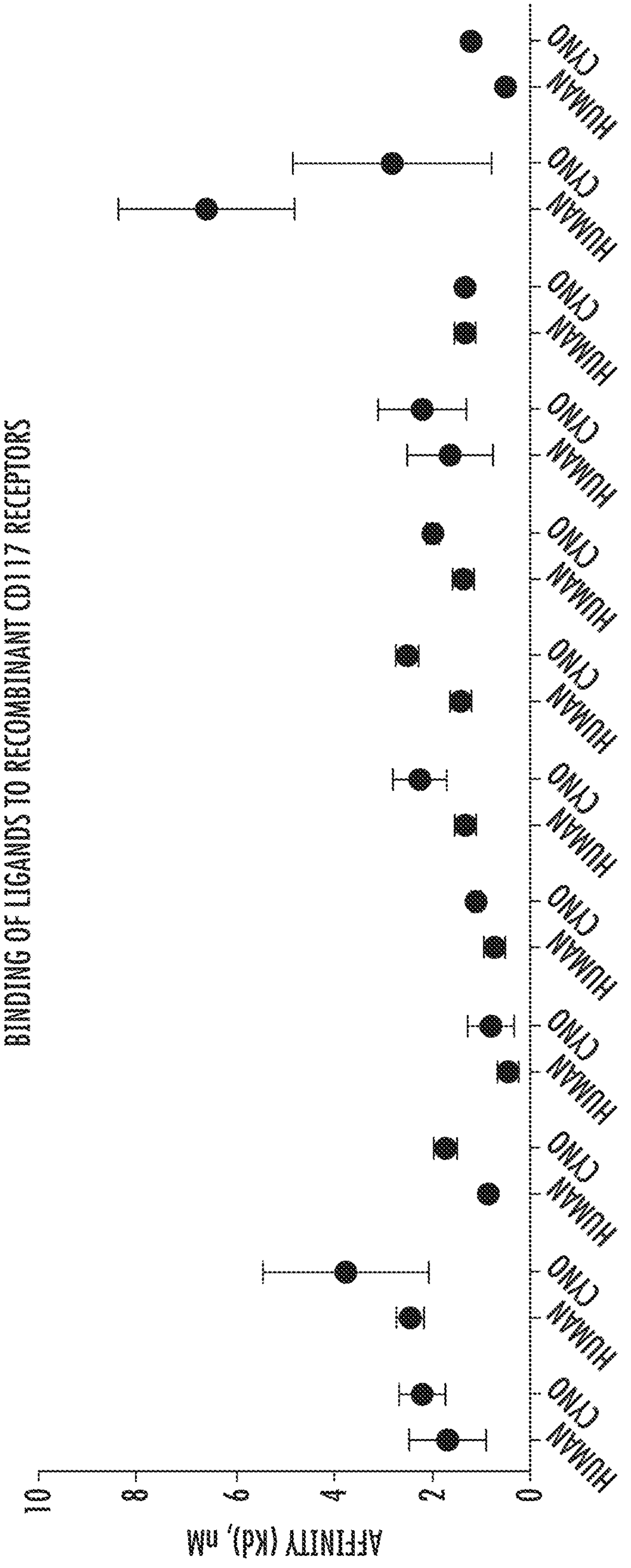
FIG. 44 is a plot of the CD117 antibodies and their binding to both human and cyno versions of CD117.

Many of the candidate targeting ligands maintained binding to Cyno forms of the human antigen. As shown in FIG. 44, the CD117 panel of antibodies were evaluated for binding to the cyno CD117. The antibodies to CD117 were particularly uniform in affinity for the target antigen. As shown in FIG. 44, all of the antibodies had an affinity for both cyno and human CD117 of less than 10 nM. Only one out of twelve showed a greater affinity for cyno antigen rather than human CD117.

Example 23: Conjugation of Targeting Moieties to LNPs to Create Stealth ctLNP Targeting Hematopoietic Stem Cells (HSC)

Figure 45:
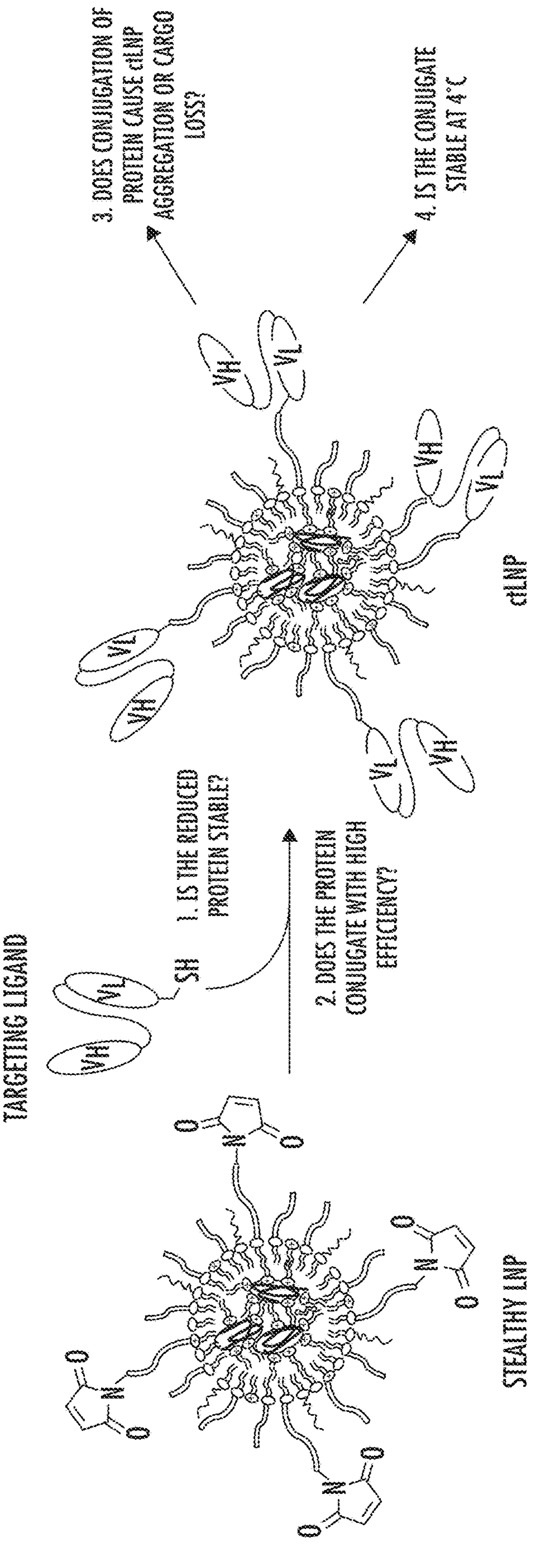
FIG. 45 is a schematic of the process for making stealth LNPs into stealth ctLNPs.

The process for making stealthy LNPs into stealth cell targeting LNPs (stealth LNPs or stealth ctLNPs) is shown schematically in FIG. 45. The process involves assessment of protein stability of the initial scFv after any modification of the candidate ligand by the addition of c-terminal cysteine residues and/or conversion into an scFv from IgG. Next, the conjugation to the second lipid polymer must occur with high efficiency. Once the conjugation is complete the ctLNP must be able to maintain the preloaded cargo without substantial aggregation. The final preliminary criteria is that the conjugated ctLNP must be stable at 4° C. These steps were carried out for a panel of antibodies as described below.

A set of candidate targeting ligands converted into scFv were evaluated in selection criteria as follows: first, candidate targeting ligands must have been stable to reduction for preparation to undergo conjugation to the maleimide which resides at the tip of the second lipid anchored polymer of the LNP. Candidates were evaluated for their reduction efficiency and those not reaching 80% or greater reduction efficiency failed. Next, the candidates were evaluated for conjugation efficiency and those not performing at near 100% efficiency failed. The effect of conjugation on LNP size must have been tolerable as measured by post-conjugation size growth. Candidates must have caused less than 50% size growth to be maintained. The conjugated targeting ligand (targeting moiety) could not interfere with encapsulation efficiency. The targeting moieties causing less than a 20% reduction in encapsulation efficiency were maintained and those causing a greater than 20% reduction failed. Finally, once the conjugated ctLNP was prepared it must have retained stability during 4° C. storage, candidates that showed 100% size growth during storage failed.

Once a modified candidate ligand was found suitable for incorporation into a ctLNP, there were multiple ways for a candidate to fail and thus only about 50% of candidates were found to be finally satisfactory after the ctLNP were evaluated using the following criteria: retention of antigen binding using octet or ELISA binding assays; displayed poor protein stability after modification and reduction; proved to be inefficient in the conjugation reaction or displayed excessive size growth after conjugation.

Conjugation of Candidate Ligands

Figure 46A:
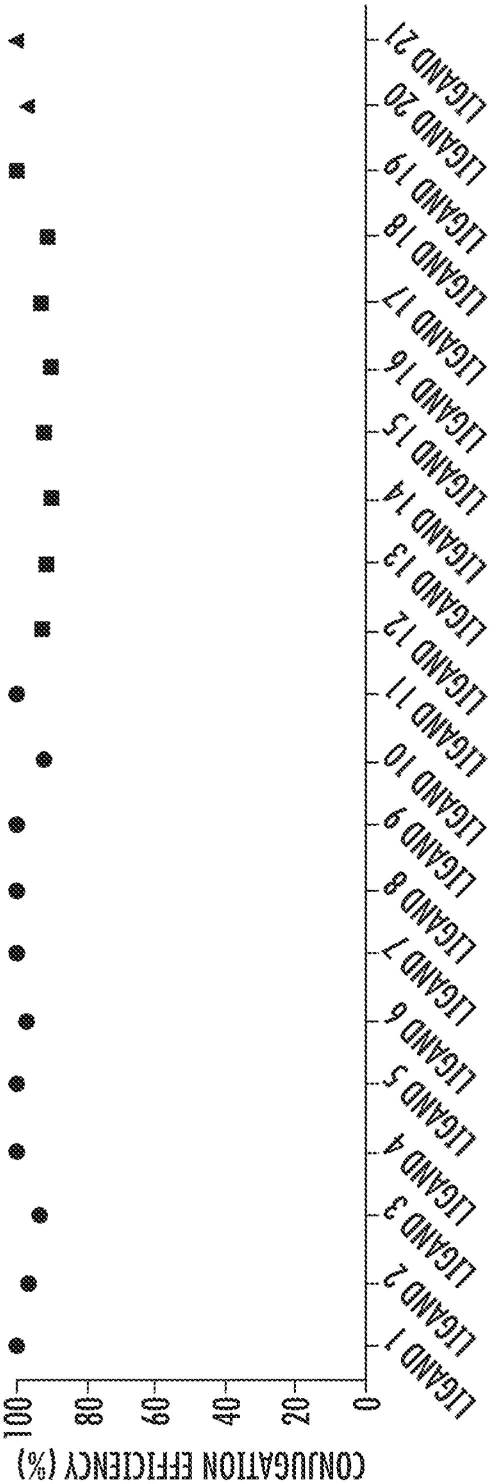
FIG. 46A is a graph showing the conjugation efficiencies obtained when the candidate ligands were conjugated to second lipid anchored polymers targeting HSCs
Figure 46B:
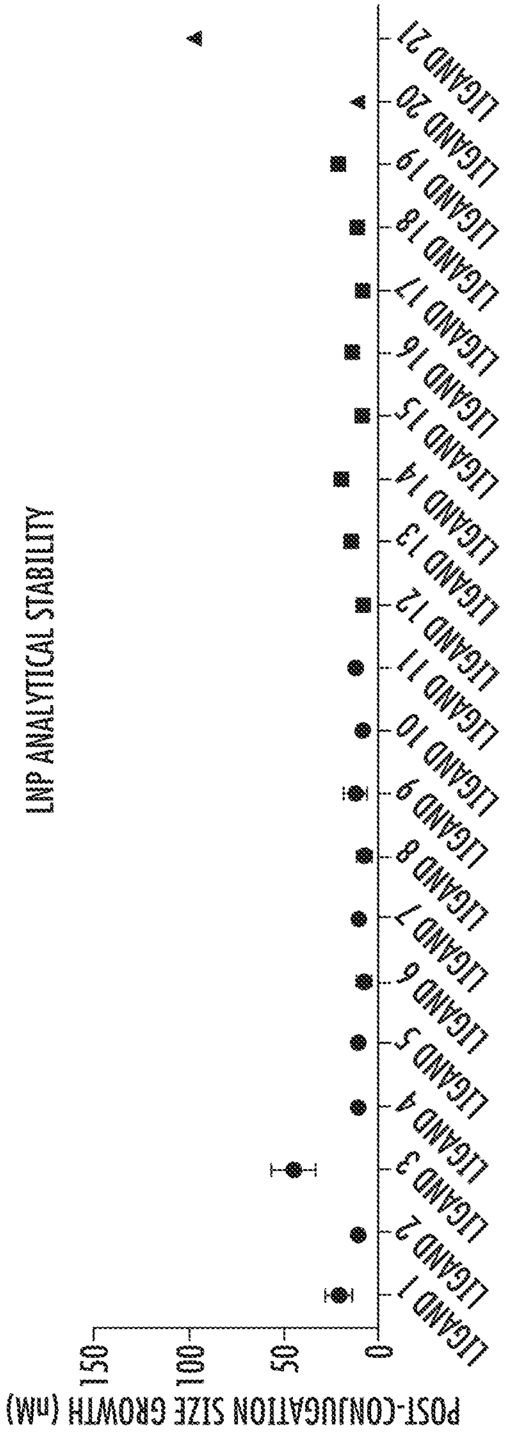
FIG. 46B is a graph showing post conjugation stability of the ctLNPs.

The candidate ligands were conjugated to second lipid anchored polymer to make ctLNPs targeting HSCs. In general, the conjugation efficiency was very high and as shown in FIG. 46A where all the candidate ligands conjugated at approximately 100%. The post conjugation stability of the ctLNPs was also quite uniform as shown in FIG. 46B, where only one of the conjugation reactions caused an almost 50% growth in LNP size. Most were of the order of about 10%. See FIG. 46B.

Conjugation efficiencies were calculated using SDS-PAGE. LNP-conjugates were diluted at a 1:1 ratio in SDS loading buffer, incubated at 80° C. for 5 minutes, and then run on a 10-20% Tricine Novex gel at 160V for 60 minutes. The gels were then stained using the eStain (Genscript L00657) and imaged using an iBright (FL1500) imaging system. The images were then analyzed using the iBright analysis software where the intensity of the bands was determined. The conjugation efficiency was then calculated using the following equation:

$$\frac{[\text{Conjugated Ligand}]}{[\text{Conjugated Ligand}]+[\text{Free Ligand}]}$$

Optimizing Binding Moieties Per LNP

Figure 47A:
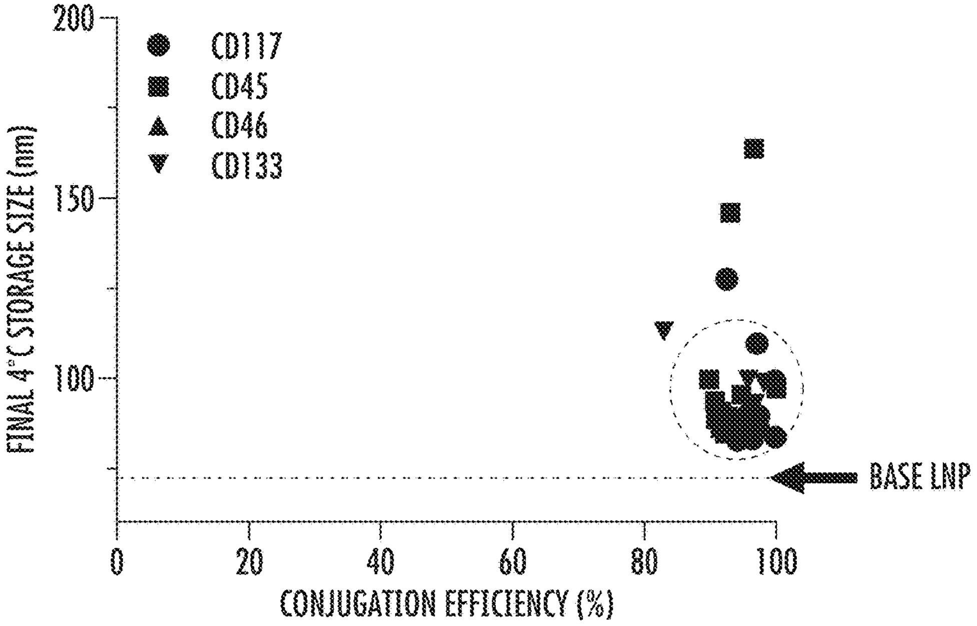
FIG. 47A is a graph showing the optimal stability of ctLNP was centered near 100 nm in LNP size.
Figure 47B:
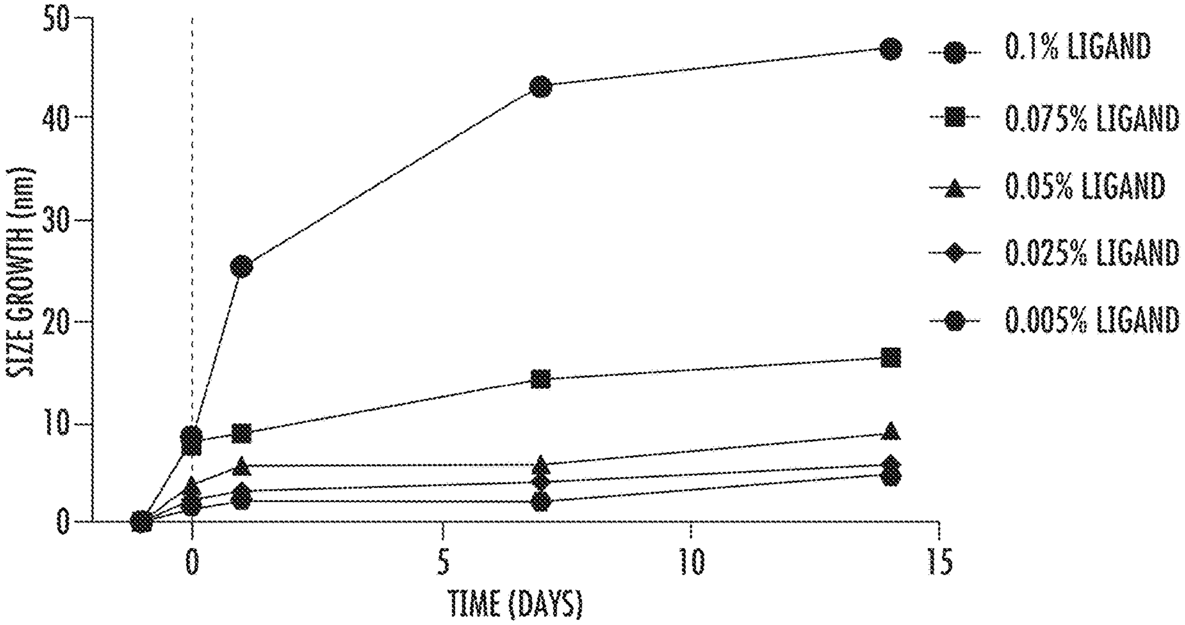
FIG. 47B is a graph showing how stability was achieved by reducing the number of ligands per LNP.

The selection process described above led to a set of optimized binding moieties for protein and LNP stability purposes. A final step remained to optimize the number of ligands on the surface to carry out binding and fusion in vivo with HSC target cells. FIG. 47A shows the ideal stability for this batch of binding moieties and ctLNPs was centered on about 100 nm LNP size. Another surprising result was that reducing the number of binding ligands per LNP resulted in improvements to overall ctLNP stability as shown in FIG. 47B, where LNP size was stabilized as the number of ligands was reduced.

Calculating the Number of Targeting or Candidate Ligands Per LNP

Parental LNPs were first run on the Agilent/Wyatt FFF-MALS system where the number of copies of mRNA per particle was calculated. Using this ratio, the targeted mole fraction of targeting ligand (referred to as [TL]), and the mole fraction of DSPE-PEG-Mal (referred to as [Mal]) it was then possible to calculate the number of ligands per particle using the following equation:

$$\frac{[\text{moles of } DSPE\text{-}PEG\text{-}Mal]}{[1 \text{ mol of cargo}]} \times \frac{[Mal]}{[TL]} \times [\#\text{ of } mRNA \text{ copies per } LNP]$$

Preparation of mRNA-ctLNPs mRNA-LNPs were prepared using a microfluidic mixer (nanoAssemblr Ignite+, Precision NanoSystems). A 3.4 mM stock of lipids in ethanol with a DMA-1-C7:DSPC:Chol:DSG-PEG2K-Ome:DiD:DSPE-PEG5k-Mal ratio of 47.5:10:39.45:2.5:0.05:0.5 and a 0.03 mg/mL stock of GFP mRNA (N1-methylpseudouridine modified, trilink) solubilized in 20 mM citrate buffer at pH 4 were mixed at a volumetric ratio of 3:1 aqueous to organic. The flow rate was maintained at 12 mL/min, with the first 0.35 μL and last 0.05 μL of mixed product being waste. All LNPs were made at an N:P ratio of 6. Mixed product was incubated at room temperature for 30 minutes prior to being dialyzed in a 10 kDa MWCO Slide-a-Lyzer cassette (Thermo Fisher) against PBS twice for 2 hours and against TBS overnight. LNP product was concentrated using 100 kDa MWCO Amicon centrifugal filters, diluted in 8.5% v/v sucrose, and frozen at −80° C. LNP concentration (based on cargo) was quantified using Ribogreen intercalating dye (Thermo Fisher) and size was quantified using plate-based DLS (Wyatt).

Candidate targeting ligands were expressed as single chain variable fragments (scFvs) in CHO cells with a C-terminal flag tag following by an unpaired cysteine residue to create candidate targeting moieties for conjugation to second lipid-anchored polymers. Purification of ligands was performed using anti-flag affinity resin columns and buffer exchanged into PBS. To expose unpaired C-terminal cysteines, dimers and cysteinylated ligands were reduced in TCEP (10× molar excess) for 1 hour at room temperature. Reduced proteins were purified and buffer exchanged into TBS with 1 mM EDTA using 7 kDa Zeba Spin columns before being frozen at −80° C. Protein concentration was quantified using a NanoDrop One (Thermo Scientific), reduction efficiency (quantified by monomer:dimer ratio) was quantified via SDS-PAGE under non-reducing conditions, and cysteinylation reduction and ligand over-reduction was characterized using an LCMS (Agilent 6530 Q-TOF).

mRNA-ctLNPs were prepared by mixing reduced ligands with LNPs at a 12.8 molar ratio (0.1 mol % of lipids conjugated) in TBS with 1 mM EDTA and 8.5% sucrose at a cargo concentration of 0.5 mg/mL for 2 hours at room temperature. Conjugation efficiency was assessed via SDS-PAGE under non-reducing conditions, stained with Coomassie blue, and quantified using densitometry to compare the band density ratio of ligand-lipid conjugates to free ligand (iBright, Thermo Fisher). ctLNP concentration (based on cargo) was quantified using Ribogreen intercalating dye (Thermo Fisher) and size was quantified using plate-based DLS (Wyatt). Size growth post ligand conjugation was quantified by comparing parental LNP size (without ligand) to ctLNP size (with ligand). ctLNPs were frozen at −80° C. on the same day as conjugation and used in vitro after one freeze/thaw cycle.

Example 24: Use of In Vitro Models to Select Final Candidates for Potential In Vivo ctLNP Targeting of Hematopoietic Stem Cells (HSC)

Figure 48A:
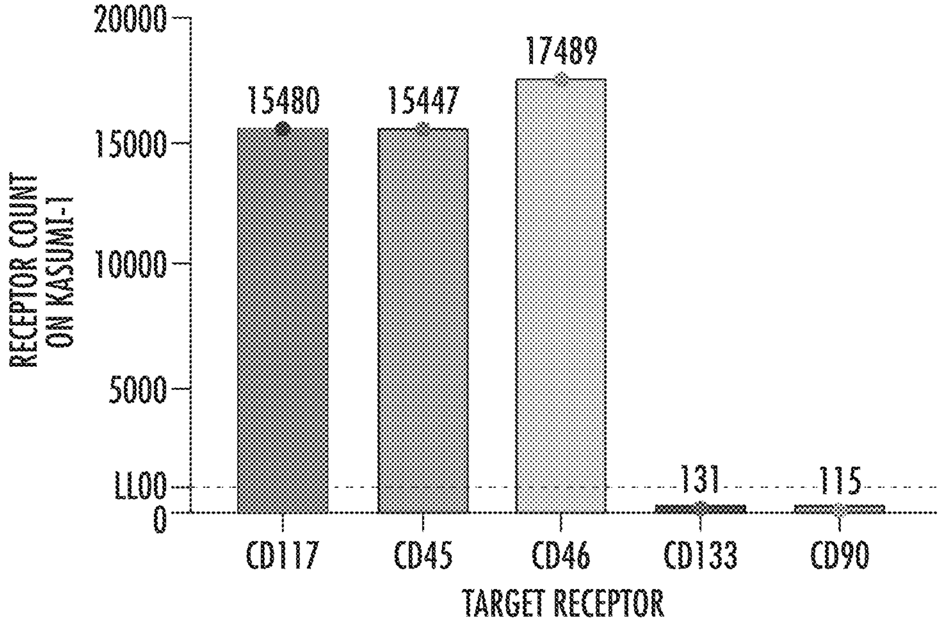
FIG. 48A is a graph showing antibodies to CD117, CD45, CD46 bind Kasumi cells but antibodies to CD133 and CD90 do not.
Figure 48B:
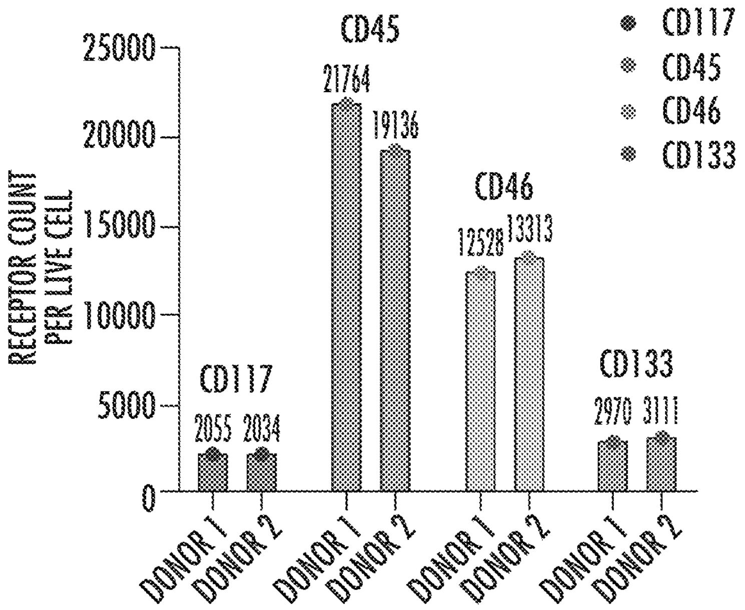
FIG. 48B is a graph depicting binding of antibodies to CD117, CD45, and CD46 to Kasumi-1 cells but not primary HSPC.

In this example, Kasumi-1 cells (FIG. 48A) and primary hematopoietic stem and progenitor cells (HSPCs) (FIG. 48B) from donors were used to eliminate binding moieties that had survived all previous screenings but were not likely suitable because of lack of expression of the target antigen on the in vivo cells of interest. For example, CD133 and CD117 antigens provided a series of acceptable targeting moieties but these antigens were not present in large numbers on primary HSPC cells (FIG. 48B). CD117 was present in suitable numbers on Kasumi-1 cells, which was misleading, because it was present at only 10% of that level on primary HSPC cells as shown in FIG. 48A and FIG. 48B.

Figure 49A:
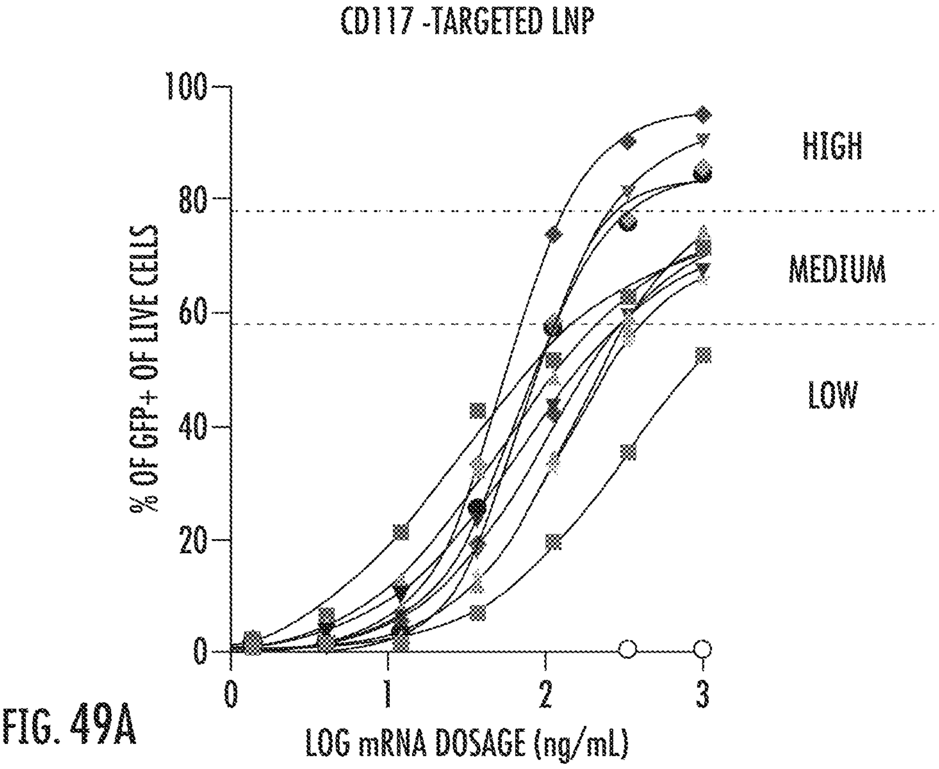
FIG. 49A is a graph showing a CD117 targeted LNP delivering mRNA encoding GFP to live cells and the resulting protein expression.
Figure 49B:
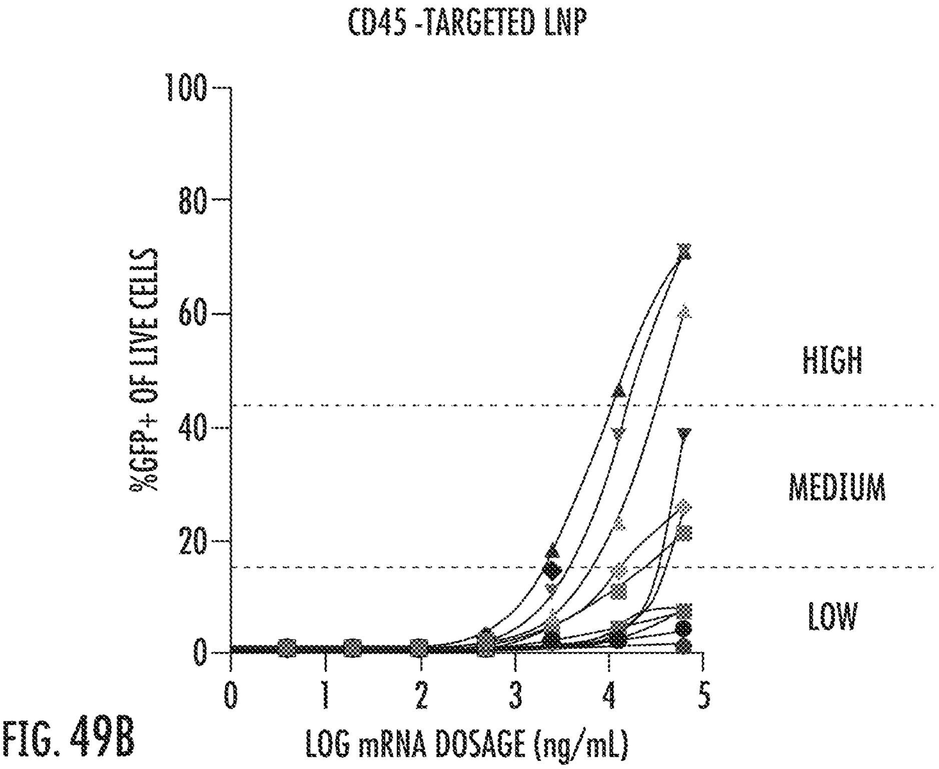
FIG. 49B is a graph showing a CD45 targeted LNP delivering mRNA encoding GFP to live cells and the resulting protein expression.
Figure 50A:
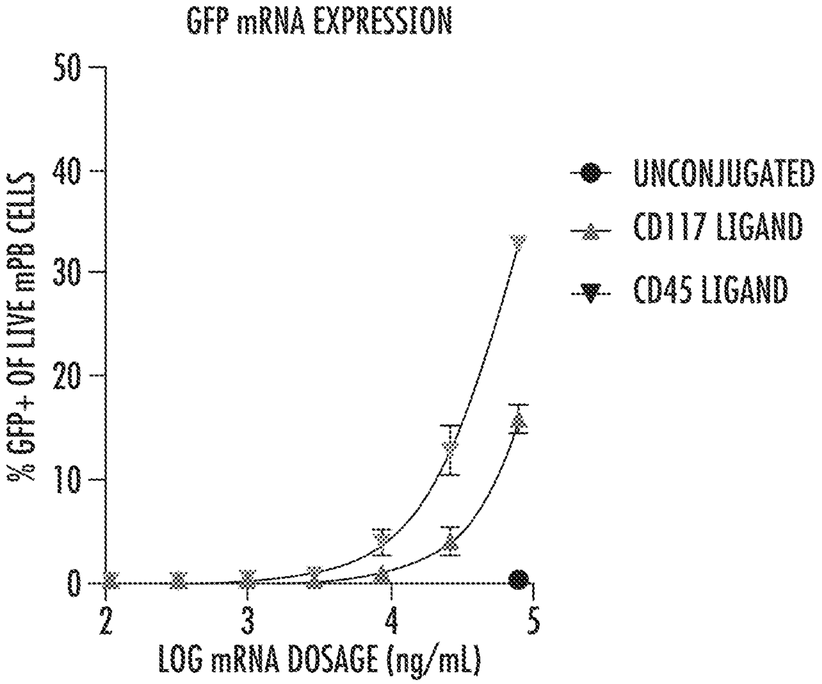
FIG. 50A is a graph showing GFP mRNA expression based on mRNA dosage (ng/mL) of unconjugated, CD117- and CD45-targeted delivery.
Figure 50B:
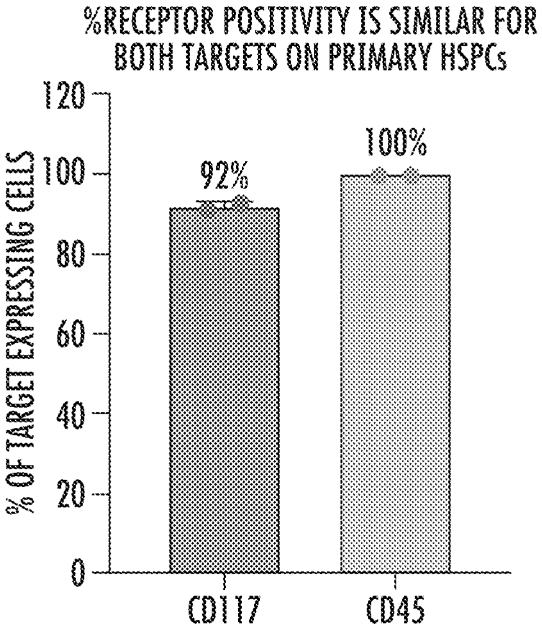
FIG. 50B is a graph showing percent receptor positivity is similar for CD117 and CD45 on primary HSPCs.
Figure 51A:
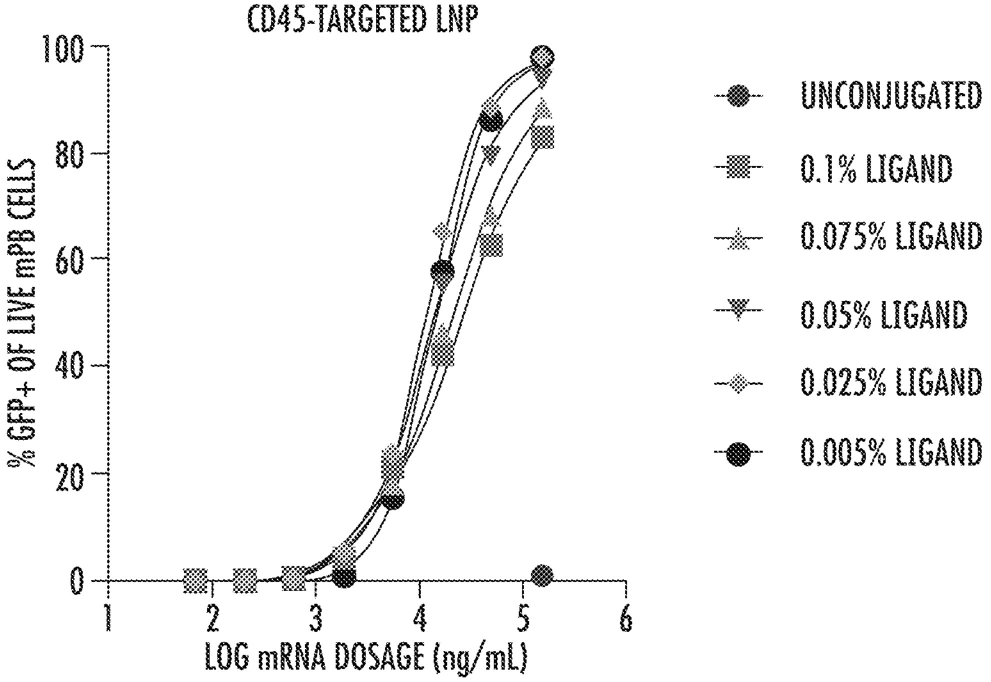
FIG. 51A depicts CD45 targeted delivery with various % of ligand.
Figure 51B:
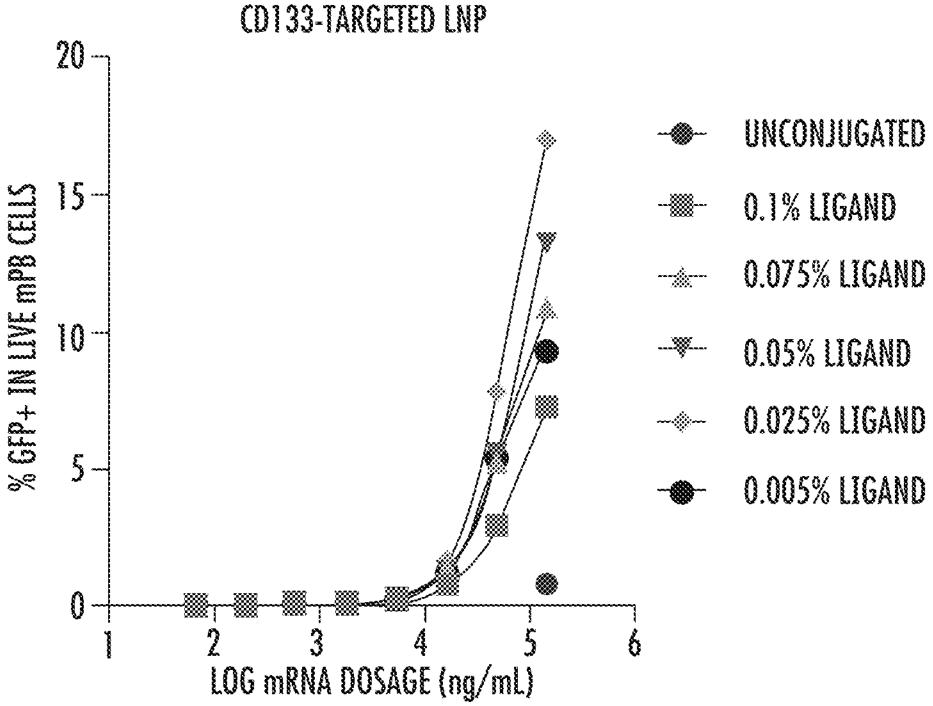
FIG. 51B depicts CD133 targeted delivery with various % of ligand.

Kasumi-1 cells can be used to narrow down cell-surface ligands for use in targeting HSPC cells. As shown in FIG. 49A, CD117 targeted LNP and FIG. 49B CD45 targeted LNP were able to deliver an antigen of interest as mRNA and induce expression. In this case, the antigen of interest was green fluorescent protein (GFP) and performance was determined by detecting GFP fluorescence. In this system, CD46 antibodies also produced effective targeting moieties for delivering mRNA to Kasumi-1 cells. Data not shown. The use of Kasumi-1 cells proved not predictive of behavior with HSPC cells because of a lack of receptors on HSPC cells (FIG. 48B). By some measures CD117 was predicted as a good target according to the number and quality of the antibodies induced to CD117 (FIG. 49A). In contrast, CD45 produced antibodies of very mixed quality as measured by affinity and mRNA delivery to Kasumi-1 cells in vitro (FIG. 49B). However, when the target cell was HSPC cells either from mobilized peripheral blood cells (mPB) cells as in FIG. 50A, primary hematopoietic stem and progenitor cells (HSPCs) as in FIG. 50B, and HSPCs from human cord blood in FIG. 40, CD45 targeted LNP were superior to CD117 targeted LNPs in many regards. CD45 induced the most varied group of antibodies based on affinity, but in the end, it provided superior scFv targeting ligands/moieties as shown in FIG. 51A. Another consistent and surprising finding was that less targeting ligand was often better than more in the final ctLNP as shown in FIG. 51B. However, this analysis was antigen and antibody dependent and must be optimized for each targeting moiety-cell antigen pair.

Cell Model Protocol

Two cell models were used to evaluate cell uptake of our cell targeting LNPs. Kasumi-1 cells and primary CD34+ human cord blood cells were plated in RPMI media supplemented with 10% FBS or IMDM media supplemented with 100 ng/mL of TPO, 100 ng/mL IL6, and 100 FLT3 ng/mL subsequently. Cells were treated with the various CD117 and CD45 targeted GFP mRNA containing LNPs for 48 hours with dosage ranges from 0.5 ng/mL to 60 μg/mL. Cells were washed of all remaining LNP and assessed for viability using Zombie Fixable Viability Kit according to the manufacturer's protocol. Percent GFP positive of live cells were measured using Attune Flow Cytometers.

Figure 52A:
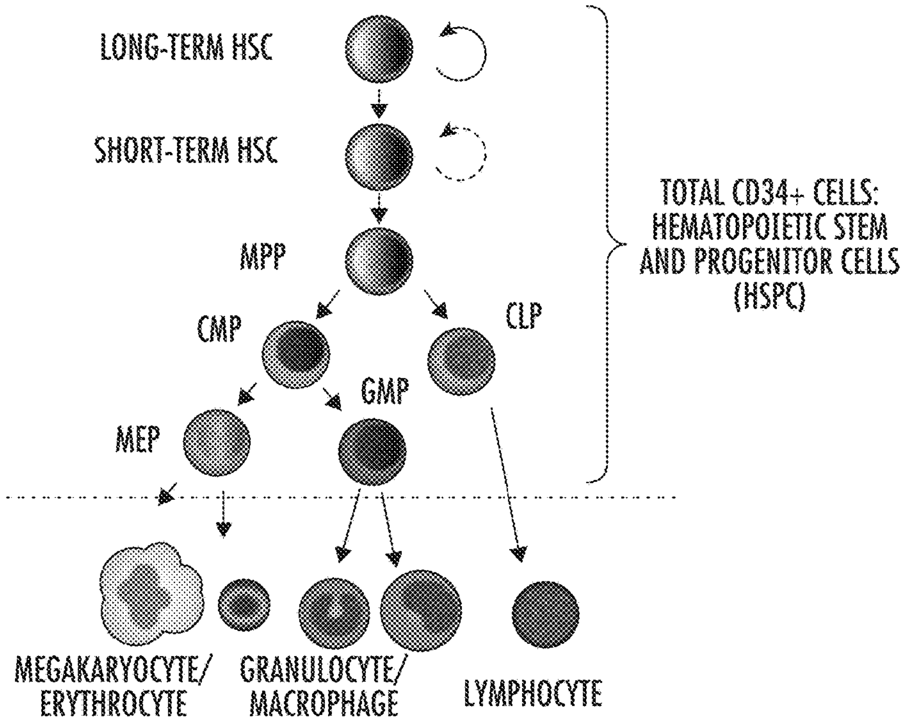
FIG. 52A shows targeted delivery of the cell lineage of CD34+ cells from HSCs down through maturation to megakaryocyte/erythrocytes, granulocyte/macrophage cells and lymphocytes correlates with relative receptor counts on surface of cells. The relative proportions of CD113, CD117, CD45 and CD46 remain similar on all cells within the lineage.
Figure 52B:
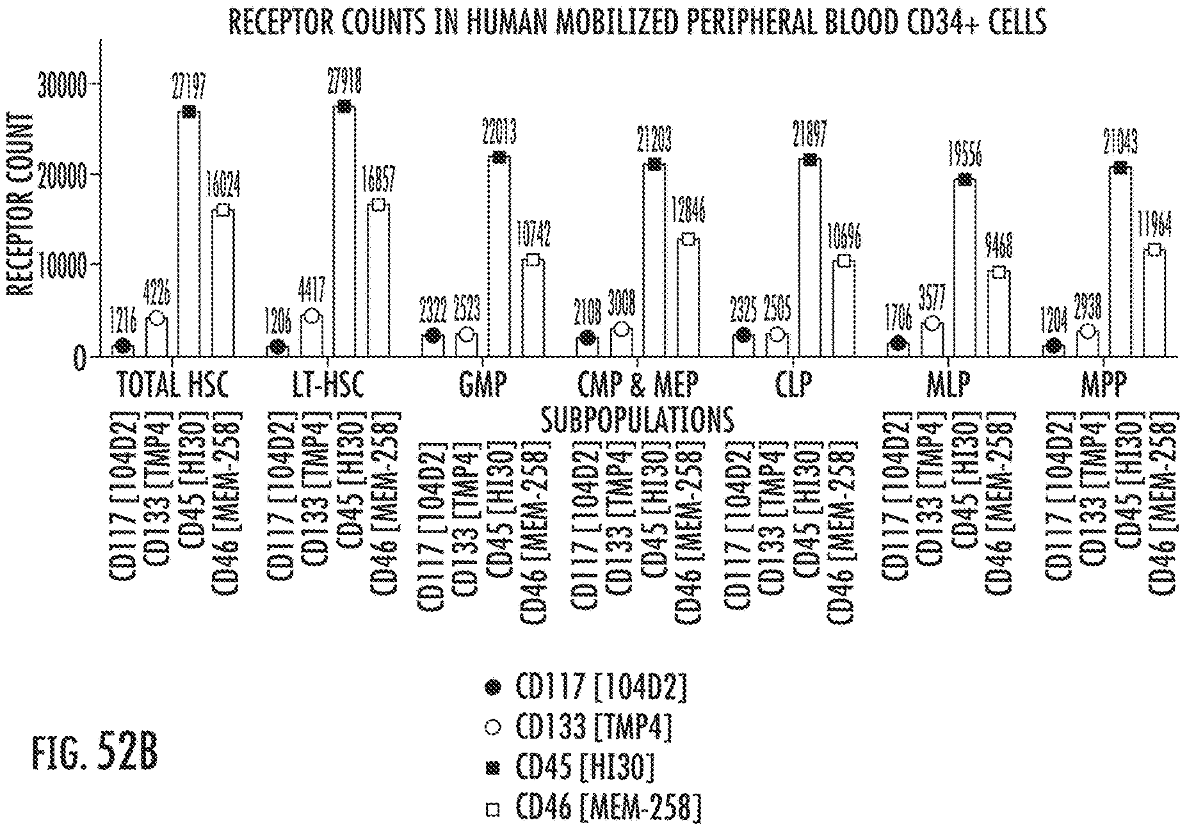
FIG. 52B is a graphical representation showing the relative amounts of CD117, CD133, CD45 and CD46 found on the surface of CD34+ cells in mobilized peripheral blood.
Figure 53:
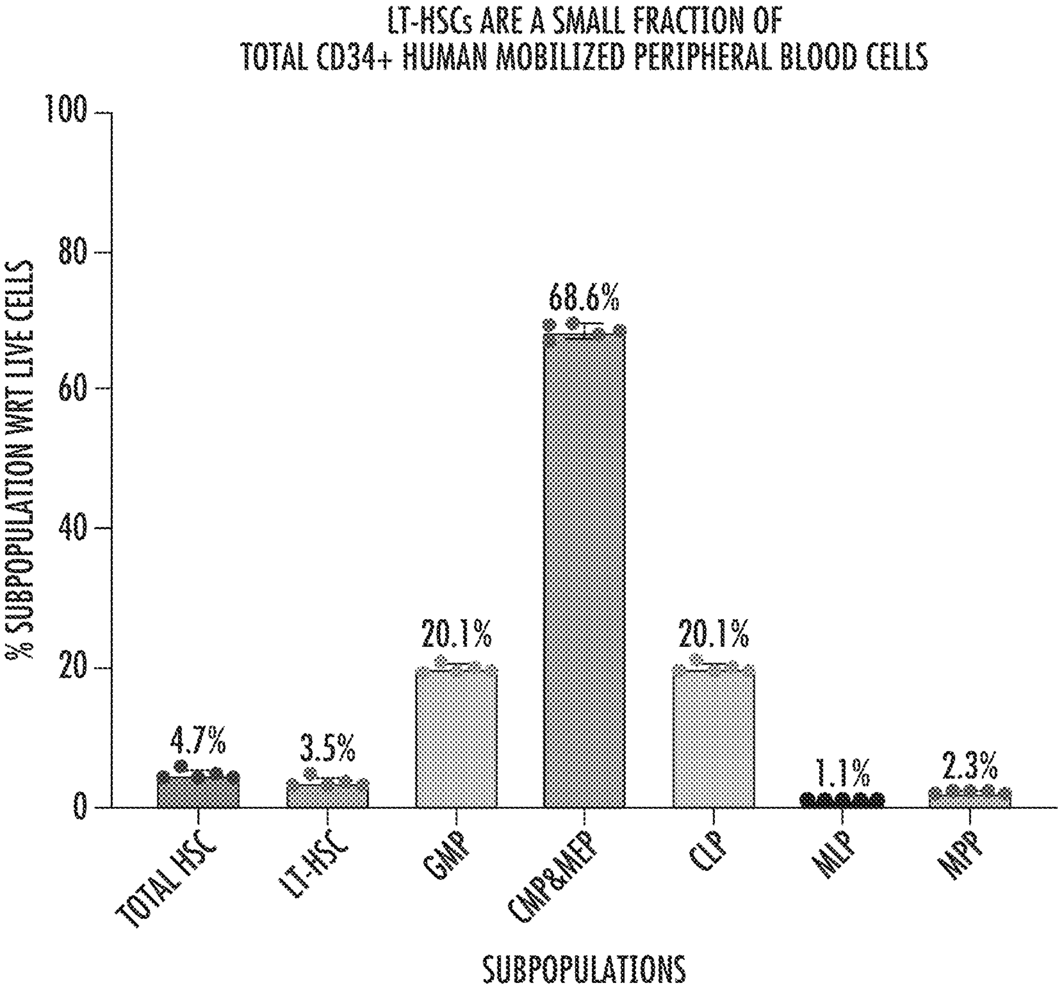
FIG. 53 is a graphical representation showing the subpopulations of CD34+ cells in which long-term HSC (LT-HSC) group constitutes 3.5% of total CD34+.

Example 25: Hematopoietic Stem and Progenitor Cells (HSPCs) are a Heterogenous Population, but Identified Target Receptors are Expressed at Similar Levels Across Subpopulations The total CD34+ cell population encompasses long-term HSCs, short-term HSCs, and progenitor cells MPP, CMP, GMP and CLP cell populations prior to their maturation into megakaryocyte/erythrocytes, granulocyte/macrophage cells and lymphocytes as shown in FIG. 52A. The targeting moieties created above to CD117, CD133, CD45 and CD46 indicate these receptor counts are present in similar proportions to the long term (LT)-HSC and the subpopulations of GMP, CMP&MEP, CLP, MLP and MPP cells. See FIG. 52B. Long-term-HSCs (LT-HSC) are a small proportion (3.5%) of the total CD34+ cells as shown in FIG. 53.

Example 26: Use of pSar as an Alternative Hydrophilic Polymer in Stealth LNPs

The hydrophilic polymer poly-sarcosine (pSar) may offer pharmaceutical advantages for the physical and immunological properties of LNPs for use in formulating stealth LNPs as compared to polyethyleneglycol (PEG). This example evaluated use of pSar20, pSAR50 and PEG as the first hydrophilic polymer with a first lipid linker (DSPE) in stealth LNPs. Table 20 shows comparative properties in formulations using various amounts (2, 3 or 4%) of PEG2K as compared to formulations using various amounts (2, 3 or 4%) pSAR20.

Figure 55:
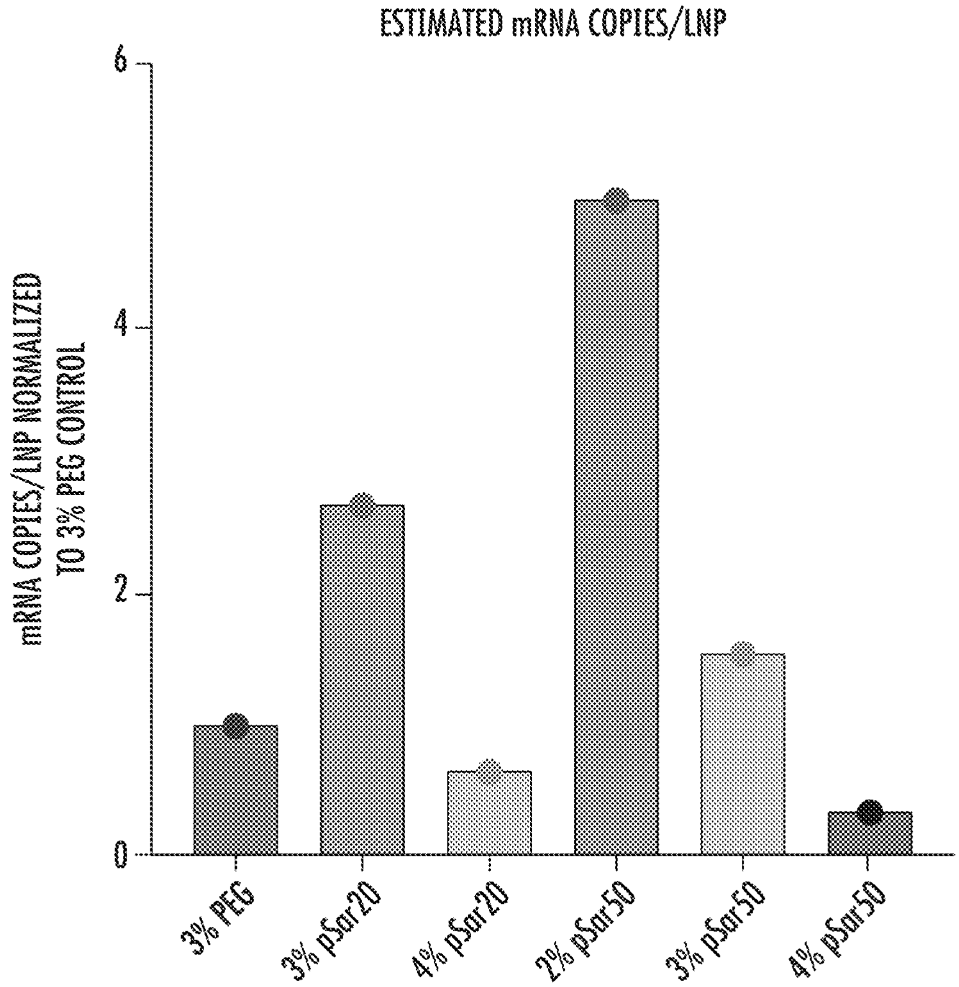
FIG. 55 is a graph showing the amount of mRNA contained within the ctLNP for different first lipid-anchored polymers. Here 2% DSPE-pSar50 loads more mRNA than either 3 or 4% DSPE-pSar50.

As shown in FIG. 55 and Table 21 below, where the IVIS expression of mRNA-ctLNPs was normalized to the parental LNPs for each polymer identity. The approximate 30-fold increase in targeted expression of the 3% PEG ctLNP over the parental 3% PEG LNP is known to possess a stealth profile by previous whole blood PK analysis. Similarly, the greater increase of 2% pSar50 to a 50-fold increase of the ctLNP over the parental 2% pSar50 LNP demonstrates an enhanced stealth profile for 2% pSAR50 LNP as compared to 3% PEG. Therefore, a lower mol % of lipid anchored polymer provides enhanced stealth characteristics. The test articles (TA) here were dosed at 0.05 mpk by mRNA concentration, with a total volume of 5 mL/kg of CD-1 mice.

Materials and Methods

LNP Formulation & Conjugation:

Firefly luciferase encoded mRNA was diluted in 20 mM sodium citrate buffer, to a mRNA concentration of 0.115 mg/mL. The lipids following the molar ratios described in the table below were dissolved in ethanol to a total lipid concentration of 7.96 mg/mL. A 3:1 ratio of aqueous mRNA solution and organic lipid solution (as described in the table below) were mixed using a microfluidic mixer to formulate the lipid nanoparticles (LNPs). The mixed LNPs were dialyzed against TBS saline solution using a 10 kDa dialysis membrane, and further concentrated using a 100 kDa ultracentrifugation filter. After a final sterile syringe filtration (0.2 μm), a filtered sucrose solution was added to 8.5% by volume. The LNP encapsulation efficiency and concentration of mRNA was measured using a Ribogreen intercalating dye, and the LNP size and PDI were measured using a dynamic light scattering (DLS) instrument.

The conjugation of a protein-based targeting ligand, directed to engage the ASGPR receptors of hepatic cells, was done as follows. mRNA-ctLNPs were prepared by mixing reduced ligands with LNPs at a 12.8 molar ratio (0.1 mol % of lipids conjugated) in TBS with 1 mM EDTA and 8.5% sucrose at a cargo concentration of 0.5 mg/mL for 2 hours at room temperature. Conjugation efficiency was assessed via SDS-PAGE under non-reducing conditions, stained with Coomassie blue, and quantified using densitometry to compare the band density ratio of ligand-lipid conjugates to free ligand (iBright, Thermo Fisher). ctLNP concentration (based on cargo) was quantified using Ribogreen intercalating dye (Thermo Fisher) and size was quantified using plate-based DLS (Wyatt). Size growth post ligand conjugation was quantified by comparing parental LNP size (without ligand) to ctLNP size (with ligand). ctLNPs were frozen at −80° C. on the same day as conjugation and used in vitro after one freeze/thaw cycle.

IVIS Method:

Whole-body luciferase bioluminescence was measured by In Vivo Imaging System (IVIS) 24 hours (D1) after dose administration via tail-vein IV injection into CD-1 mice. The total flux is recorded; represented as total photon count per second, across the region of interest, i.e., the liver measured by IVIS at day 1 (D1) for tested LNPs and PBS, a negative control injected with saline solution.

ctLNPs, an estimated number of mRNA copies per particle was calculated. The values for these were normalized to the PEG control LNP.

Figure 54:
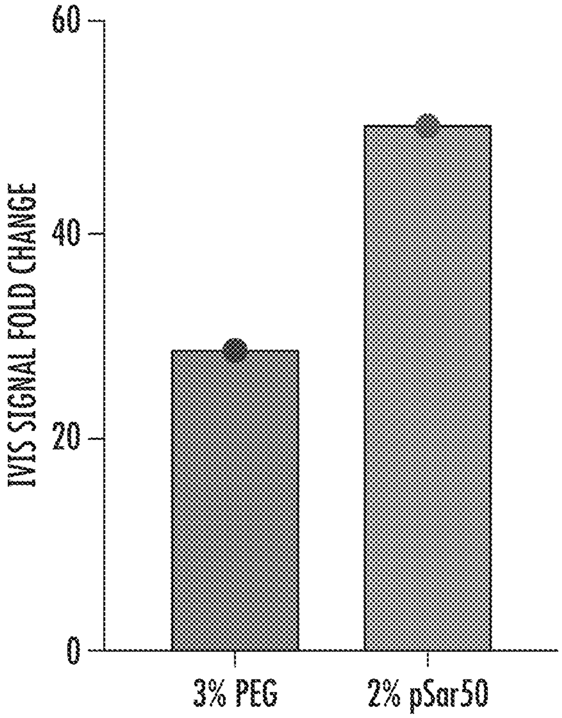
FIG. 54 is a graph comparing IVIS expression in mice treated with ctLNPs comprising 3% PEG as the first hydrophilic polymer in the first lipid-anchored polymer to mice treated with ctLNPs comprising 2% pSar50 as the first hydrophilic polymer in the first lipid-anchored polymer.
Figure 56A:
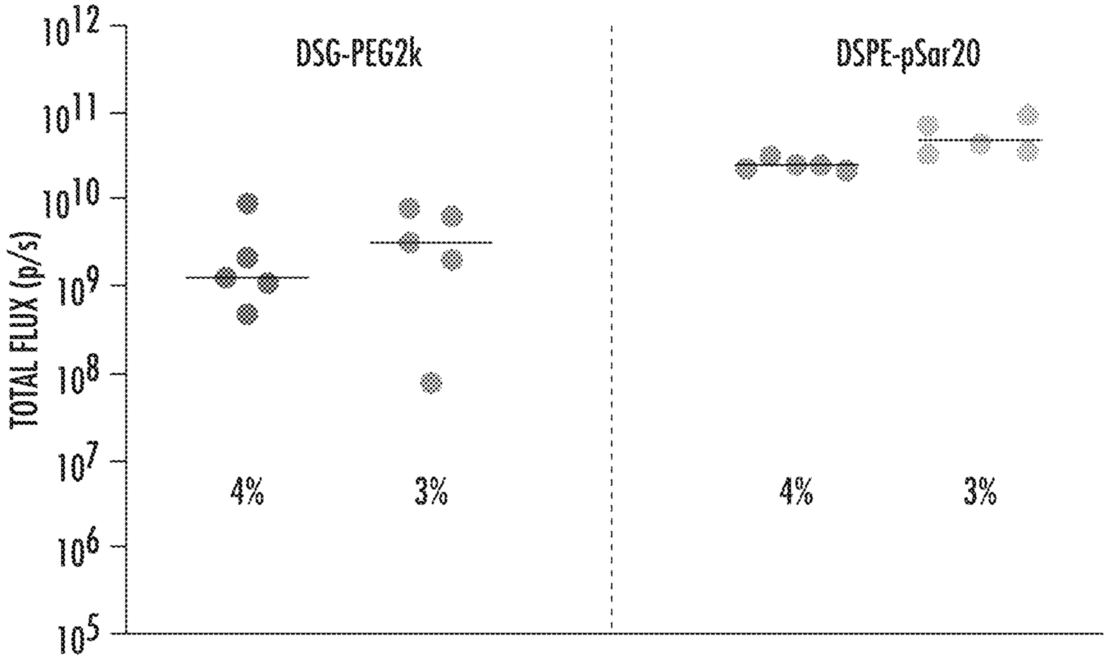
FIG. 56A is a graphical plot showing improved in vivo IVIS expression of Firefly luciferase (FLuc) in CD-1 mice with either 3% or 4% pSar20 compared to PEG2k at 3% or 4% as the first hydrophilic polymer in the first lipid anchored polymer in a ctLNP.
Figure 56B:
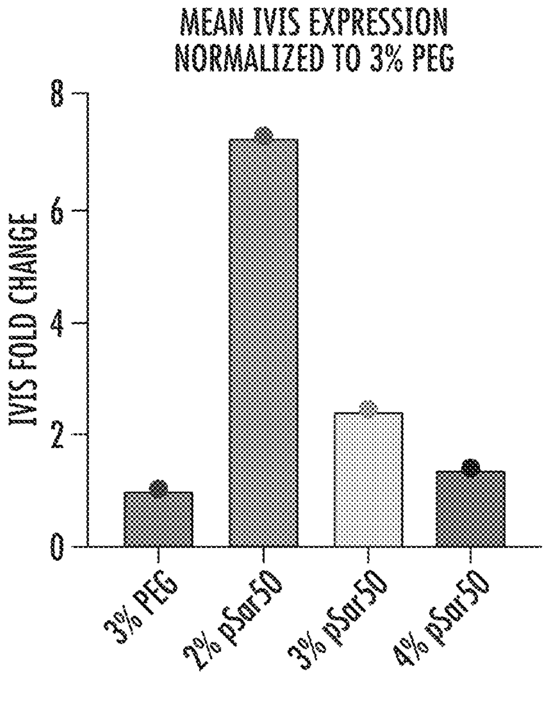
FIG. 56B is a graphical representation of improved expression with 2% and 3% pSar50 as the first hydrophilic polymer in the first hydrophilic polymer as compared to 3% PEG as the first hydrophilic polymer in the lipid-anchored polymer in an LNP.

As shown in FIG. 54, use of DSPE-pSar20 at 3% or DSPE-pSar50 at 2% as the first lipid anchored polymer has a significant benefit on stealthiness and there is also a benefit seen in the number of mRNA copies loaded per LNP (FIG. 55). As shown in FIG. 56A, the graph compares 3% DSG-PEG to 3 or 4% DSPE-pSAR20. In this case, 3% DSPE-pSar20 loads twice as many copies of mRNA as does 3% DSG-PEG2K. FIG. 56B compares the number of mRNA copies per LNP when using 2%, 3% or 4% DSPE-pSar50 as the first hydrophilic polymer as part of the first lipid-anchored polymer of a stealth lipid nanoparticle. The difference between 3% pSar20 and 3% PEG is greater than two-fold, but the difference between 2% pSar50 and 3% pSar50 is also surprising. In summary, 2% pSar50 has about 5 times higher mRNA copies per LNP compared to 3% PEG2K (FIG. 55). The copies of mRNA per LNP here are estimates from the molecular weight (MW) measurements made using FFF-MALS.

TABLE 20

Characteristics of ctLNPs used for mRNA cargo loading study

| LNP | Sample ID | $Z_{ave}$ Size (nm) | PDI | EE (%) | Ligand | Lipid composition |
|---|---|---|---|---|---|---|
| Parental LNP | 3% PEG | 77.2 | 0.107 | 93.1 | 0% | Lipid 87/DSPC/Chol/DSG-PEG2K/DSPE-PEG5k-Mal (47.5/10/39.5/2.5/0.5) |
| | 3% - pSar20 | 94.1 | 0.115 | 94.5 | | Lipid 87/DSPC/Chol/DSPE-pSar20/DSPE-PEG5k-Mal (47.5/10/39.5/2.5/0.5) |
| | 4% pSar20 | 94.1 | 0.115 | 94.5 | | Lipid 87/DSPC/Chol/DSPE-pSar20/DSPE-PEG5k-Mal (47.5/10/38.5/3.5/0.5) |
| | 2% pSar50 | 89.4 | 0.206 | 96 | | Lipid 87/DSPC/Chol/DSPE-pSar50/DSPE-PEG5k-Mal (47.5/10/40.5/1.5/0.5) |
| | 3% pSar50 | 80.2 | 0.097 | 93.7 | | Lipid 87/DSPC/Chol/DSPE-pSar50/DSPE-PEG5k-Mal (47.5/10/39.5/2.5/0.5) |
| | 4% pSar50 | 68.1 | 0.123 | 95.9 | | Lipid 87/DSPC/Chol/DSPE-pSar50/DSPE-PEG5k-Mal (47.5/10/38.5/3.5/0.5) |
| Conjugated ctLNP | 3% PEG | 81.1 | 0.115 | 92.7 | 0.1 mol % | Lipid 87/DSPC/Chol/DSG-PEG2K/DSPE-PEG5k-Mal (47.5/10/39.5/2.5/0.5) |
| | 3% pSar20 | 103.5 | 0.11 | 95.6 | | Lipid 87/DSPC/Chol/DSPE-pSar20/DSPE-PEG5k-Mal (47.5/10/39.5/2.5/0.5) |
| | 4% pSar20 | 94.6 | 0.128 | 96.7 | | Lipid 87/DSPC/Chol/DSPE-pSar20/DSPE-PEG5k-Mal (47.5/10/38.5/3.5/0.5) |
| | 2% pSar50 | 101.7 | 0.149 | 97.2 | | Lipid 87/DSPC/Chol/DSPE-pSar50/DSPE-PEG5k-Mal (47.5/10/40.5/1.5/0.5) |
| | 3% pSar50 | 88.7 | 0.114 | 94.5 | | Lipid 87/DSPC/Chol/DSPE-pSar50/DSPE-PEG5k-Mal (47.5/10/39.5/2.5/0.5) |
| | 4% pSar50 | 89.2 | 0.156 | 96.5 | | Lipid 87/DSPC/Chol/DSPE-pSar50/DSPE-PEG5k-Mal (47.5/10/38.5/3.5/0.5) |

FFF-MALS Method:

Field-flow fractionation (FFF) is used to separate the ctLNPs from any free mRNA. A short channel with a 400 μm spacer and a regenerated cellulose membrane (10 kDa) is used in a Wyatt Technology FFF instrument, at a 1 mL/min channel flow. The mRNA-ctLNPs are diluted to 0.1 mg/mL by mRNA concentration, of which 10 μL of sample is injected into the instrument. An initial focus injection is done at 25% of the channel position for 4 minutes. A gradient cross-flow of 0.5 m/min to 0 mL/min is applied over 10 minutes. The eluted ctLNPs were tested with the light scattering detector built into the instrument. Based on the experimentally obtained average molecular weight of the In Vivo Expression Comparing 3%, 4% pSar20, 2%, 3%, 4% pSar50 and 3% PEG2K As shown in FIG. 56A, there was improved in vivo IVIS expression of Firefly luciferase (FLuc) in CD-1 mice with either 3% or 4% pSar20 compared to PEG2K at 3% or 4% as the first hydrophilic polymer in the first lipid anchored polymer in ctLNP. FIG. 56B showed a similar trend of improved expression with 2%, 3% and 4% pSar50 over 3% PEG2K. However, while 3% and 4% pSar50 enhanced expression relative to 3% PEG2K, the enhancement was not nearly as much as 2% pSar50. See FIG. 56B. The test articles (TA) here were dosed at 0.05 mpk by mRNA concentration, with a total volume of 5 mL/kg of CD-1 mice.

TABLE 21

Effect of 2 mol % pSAR on Stealth Characteristics of ctLNPs

| Form. | Sample ID | $Z_{ave}$ Size (nm) | PDI | EE (%) | Ligand | Lipid composition |
|---|---|---|---|---|---|---|
| ctLNP | 4% PEG | 83.9 | 0.136 | 92.7% | 0.1 Mol % | Lipid 119/DSPC/Chol/DSG-PEG2K/DSPE-PEG5k-Mal (47.5/10/38.5/3.5/0.5) |
| | 3% PEG | 95.8 | 0.164 | 93.8% | | Lipid 119/DSPC/Chol/DSG-PEG2K/DSPE-PEG5k-Mal (47.5/10/39.5/2.5/0.5) |
| | 4% pSar20 | 92.3 | 0.127 | 85.5% | | Lipid 119/DSPC/Chol/DSPE-pSar20/DSPE-PEG5k-Mal (47.5/10/38.5/3.5/0.5) |
| | 3% pSar20 | 99.9 | 0.119 | 88.3% | | Lipid 119/DSPC/Chol/DSPE-pSar20/DSPE-PEG5k-Mal (47.5/10/39.5/2.5/0.5) |

Example 27: In Vivo Targeting of HSPCs and HSCs with ctLNPs

This example describes the use of a humanized mouse model to target CD45+CD34+ human hematopoietic stem and progenitor cells (HSPCs) and human CD45+CD34+ CD38− hematopoietic cells (HSCs) in vivo using targeted ctLNPs. Experiments used the NBSCW strain, an immunodeficient mouse strain that supports the engraftment of human hematopoietic stem cells without irradiation.

HSPCs were administered to NBSGW mice by intravenous injection (i.v.) into the lateral tail vein. This was followed immediately with i.v. injection of untargeted stealth LNPs and HSC-targeted ctLNPs at 0.1 mg/kg and 2.0 mg/kg (n=3 per group). Mice were euthanized 48 hours post-dose, and bone marrow was collected for flow cytometry analysis. LNP composition is described below in Table 22. All LNPs contained mRNA cargo encoding GFP.

TABLE 22

LNP composition for in vivo HSPC/HSC targeting study

| LNP | Formulation Type | $Z_{ave}$ (nm) | PDI | EE (%) | Ligand | Lipid composition |
|---|---|---|---|---|---|---|
| 391 | unconjugated, 0.5% mal, stealth LNP | 76.3 | 0.179 | 97.3 | None | Lipid 87/DSPC/Chol/DSG-PEG2k/DSPE-PEG5k-Mal/DID (47.5/10/39.45/2.5/0.5/0.05) |
| 392-148 | 0.1% mal, CD45-conjugated | 84.8 | 0.150 | 97.7 | 0.025% CD45 | Lipid 87/DSPC/Chol/DSG-PEG2k/DSPE-PEG5k-Mal/DID (47.5/10/39.45/2.9/0.1/0.05) |
| 391-160 | 0.5% mal, CD117-conjugated | 88.6 | 0.173 | 95.3 | 0.1% CD117 | Lipid 87/DSPC/Chol/DSG-PEG2k/DSPE-PEG5k-Mal/DID (47.5/10/39.45/2.5/0.5/0.05) |

Figure 57A:
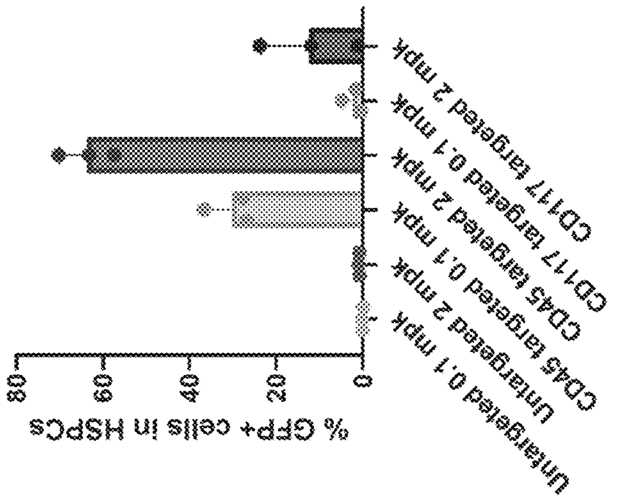
FIG. 57A is a graph showing in vivo targeting of HSPCs (huCD45+CD34+) in humanized NBSGW mice with ctLNPs carrying GFP-encoding mRNA cargo and HSC-targeting ligands CD45 or CD117, as a dosage of 0.0 mpk or 2 mpk.

As shown in FIG. 57A, ctLNPs conjugated to the HSC-specific ligands CD45 and CD117 demonstrated selective in vivo delivery to HSPC, as compared to unconjugated stealth LNPs, which showed little or no GFP expression.

Figure 57B:
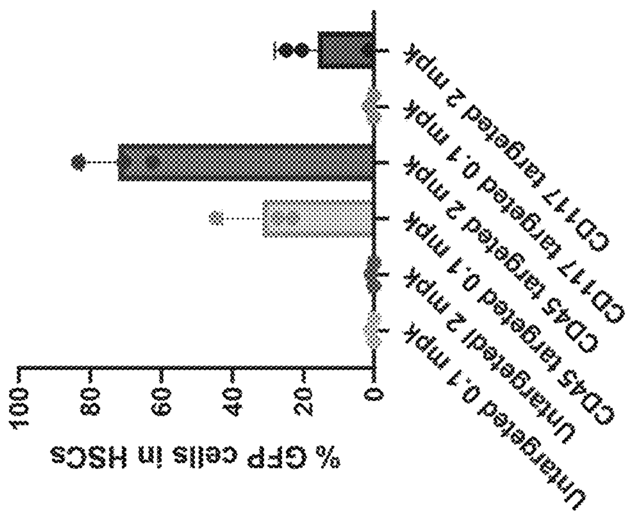
FIG. 57B is a graph showing in vivo targeting of HSCs (huCD45+CD34+CD38−) in humanized NBSGW mice with ctLNPs carrying GFP-encoding mRNA cargo and HSC-targeting ligands CD45 or CD117, as a dosage of 0.1 mpk or 2 mpk.

Further analysis identified the percentage of GFP-positive HSCs (huCD45+CD34+CD38−) in the bone marrow. Results were similar to those for HSPCs (FIG. 57B), which further demonstrated selective in vivo delivery to HSCs.

Example 28: Improved Targeting of HSPCs Using Bispecific LNP

This example describes the improved delivery of LNPs to HSPCs via the conjugation of two different ligands targeting different HSPC cell-surface antigens. LNPs were conjugated to ligands targeting CD117 (Formulation 427), CD45 (Formulations 428 and 429), or CD135 (Formulation 455) alone, or to combinations of CD45 and CD117 (Formulation 431) or CD45 and CD135 (Formulation 456). All LNPs carried GFP mRNA cargo.

Figure 58:
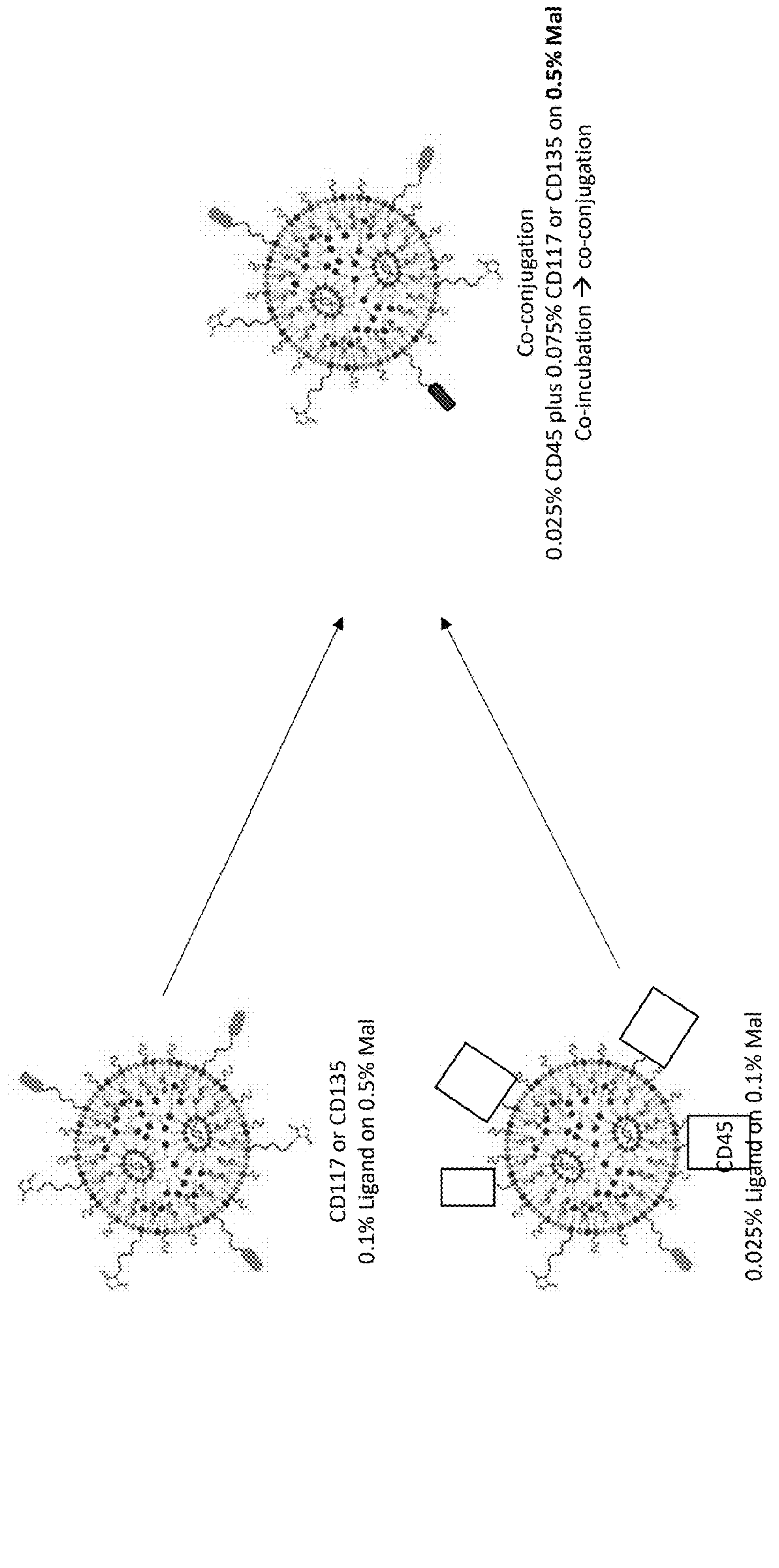
FIG. 58 shows schematic diagrams comparing bispecific LNPs to LNPs with single targeting ligands. LNPs comprised: 0.1% ligand on 0.5% maleimide (for single ligands CD117 or CD135; top left), 0.025% ligand on 0.1% maleimide (for single ligand CD45; bottom left), or 0.025% CD45 plus 0.75% CD117 or CD135 on 0.5% maleimide (for LNPs with two ligands; right).

Methods:

LNPs with unconjugated maleimide moieties were prepared as described below in Table 23. Separately, protein targeting ligands were treated to produce free (reduced) thiol groups on the terminal cysteine residues. The LNPs were then mixed with single ligands or mixtures of ligands as appropriate to produce LNPs with ligands conjugated via thiosuccinimide linkages. Schematic diagrams of the different LNPs are shown in FIG. 58. As shown in FIG. 58, LNPs comprised: 0.1%0 ligand on 0.5% maleimide (for single ligands CD117 or CD135; top left), 0.025% ligand on 0.1% maleimide (for single ligand CD45; bottom left), or 0.025% CD45 plus 0.75% CD117 or CD135 on 0.5% maleimide (for LNPs with two ligands; right).

Mobilized human peripheral blood (mPB) containing HSPCs was thawed the day prior to treatment. LNPs were diluted to 0.4 mg/mL in 8.5% sucrose prior to LNP treatment. Cells were treated with LNP doses of 10 μg, 5 μg, 2.5 μg, and 1 μg, for either 6 hours, 24 hours, or 48 hours. LNPs were titrated into wells in a well plate, and 100 μL of LNP/media was added to each well. 10 μL of cell suspension was added on top of the LNP dilution. The final cell count was 100 K cells per well. Plates were placed in a 37° C. 5% $CO_2$~incubator for 48 hours, after which cell suspensions were transferred to a fresh plate, cells were washed two times in PBS, and flow cytometry prep was started. Following washing, cells were stained with Zombie Violet™ Live/Dead Stain (Biolegendo®, San Diego, CA) for 15 minutes. Cells were then washed and fixed, and then run on an Attune Cytometer looking for DiD uptake and GFP expression.

TABLE 23

LNP composition for bispecific HSPC targeting

| LNP | Formulation Type | Zave (nm) | PDI | Conj. Eff. | EF | Lipid Composition |
|---|---|---|---|---|---|---|
| 427 | 0.075% CD117/ 0.5% Mal | 97.9 | 0.221 | 89.90% | 93.40% | Lipid 87:DSPC:Chol.:DSG-PEG2000-OMe:DSPE-PEG5000-Mal:DiD (47.5:10:39.45:2.5:0.5:0.05) |
| 428 | 0.025% CD45/ 0.5% Mal | 91 | 0.178 | 100.00% | 94.80% | Lipid 87:DSPC:Chol.:DSG-PEG2000-OMe:DSPE-PEG5000-Mal:DiD (47.5:10:39.45:2.5:0.5:0.05) |
| 429 | 0.025% CD45/ 0.1% Mal | 98.7 | 0.140 | 87.60% | 94.65% | Lipid 87:DSPC:Chol.:DSG-PEG2000-OMe:DSPE-PEG5000-Mal:DiD (47.5:10:39.45:2.9:0.1:0.05) |
| 431 | 0.075% CD117 + 0.025% CD45/ 0.5% Mal | 102.5 | 0.214 | 85.90% | 96.06% | Lipid 87:DSPC:Chol.:DSG-PEG2000-OMe:DSPE-PEG5000-Mal:DiD (47.5:10:39.45:2.5:0.5:0.05) |
| 455 | 0.075% CD135/ 0.5% Mal | 98.1 | 0.209 | 95.90% | 89.78% | Lipid 87:DSPC:Chol.:DSG-PEG2000-OMe:DSPE-PEG5000-Mal:DiD (47.5:10:39.45:2.5:0.5:0.05) |
| 456 | 0.075% CD135 + 0.025% CD45/ 0.5% Mal | 107.2 | 0.270 | 96.60% | 90.13% | Lipid 87:DSPC:Chol.:DSG-PEG2000-OMe:DSPE-PEG5000-Mal:DiD (47.5:10:39.45:2.5:0.5:0.05) |

Figure 59:
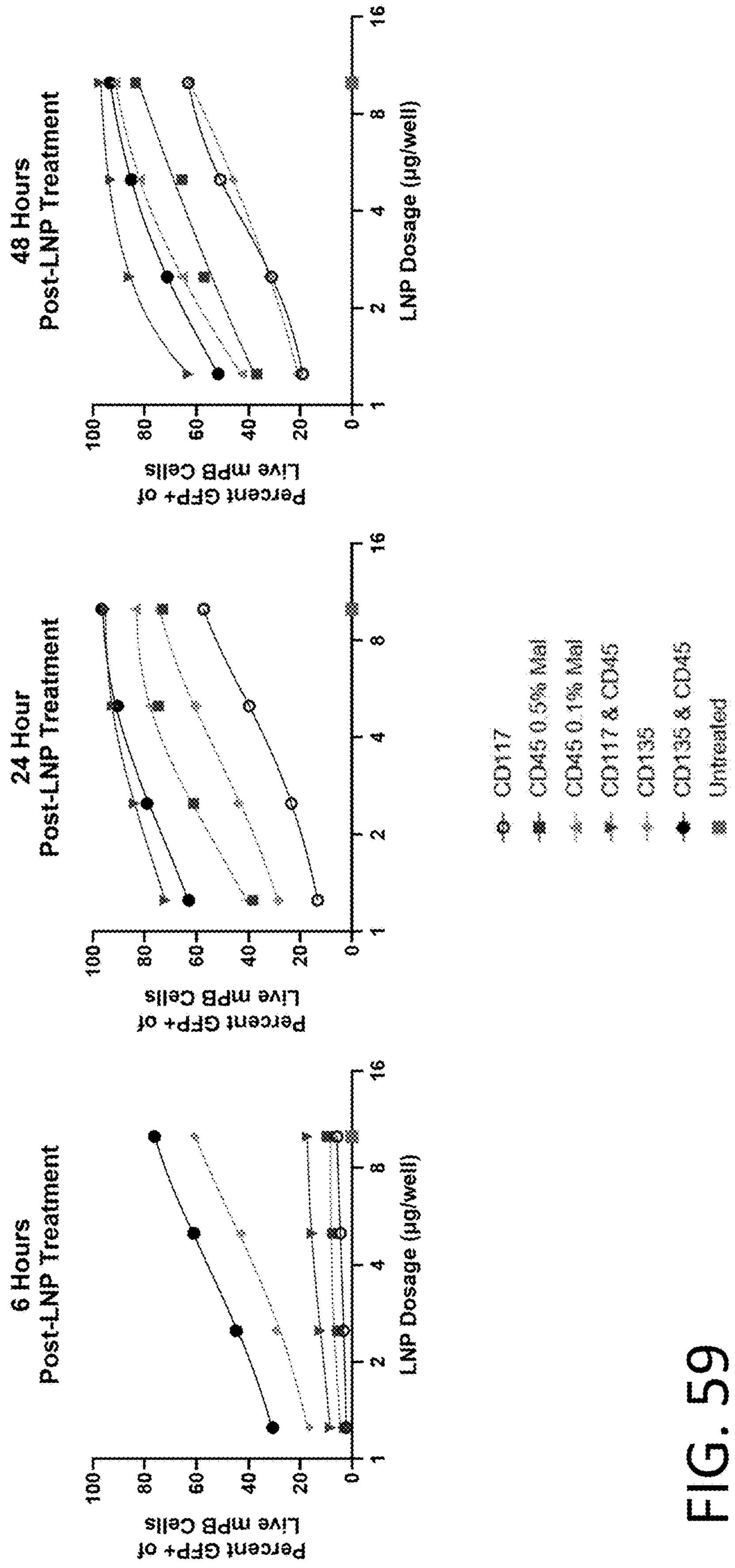
FIG. 59 shows graphs of GFP expression, as measured by the percentage of live GFP positive cells, for bispecific LNPs targeted to two different antigens (CD117/CD45 or CD135/CD45), as compared to LNPs targeting to CD45, CD117, or CD135 alone, across all three time points (6 hours, 24 hours, and 48 hours), at a range of LNP dosages, in primary human mobilized peripheral blood (mPB) cells.
Figure 60:
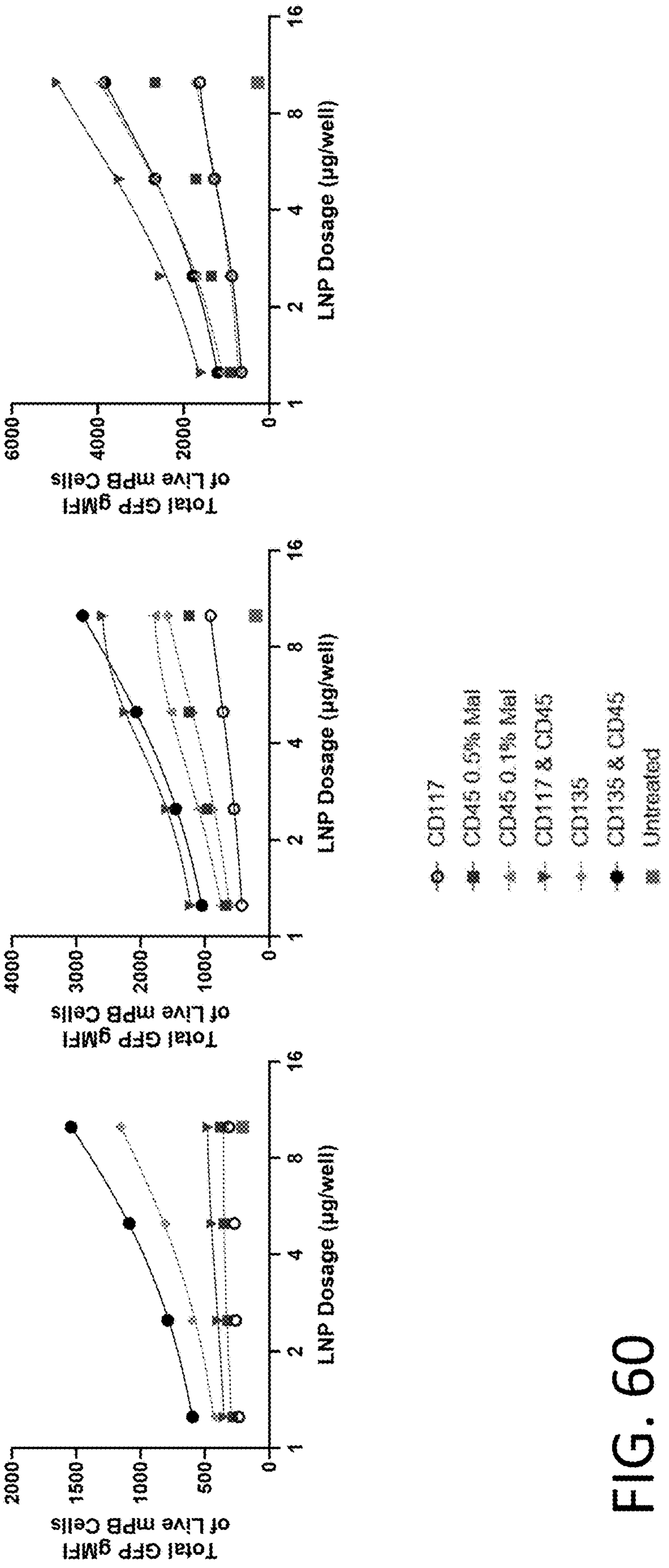
FIG. 60 shows graphs of GFP expression, as measured by total GFP gMFI (geometric mean fluorescence) of live cells, for bispecific LNPs targeted to two different antigens (CD117/CD45 or CD135/CD45), as compared to LNPs targeting to CD45, CD117, or CD135 alone, across all three time points (6 hours, 24 hours, and 48 hours), at a range of LNP dosages, in primary human mobilized peripheral blood (mPB) cells.
Figure 61:
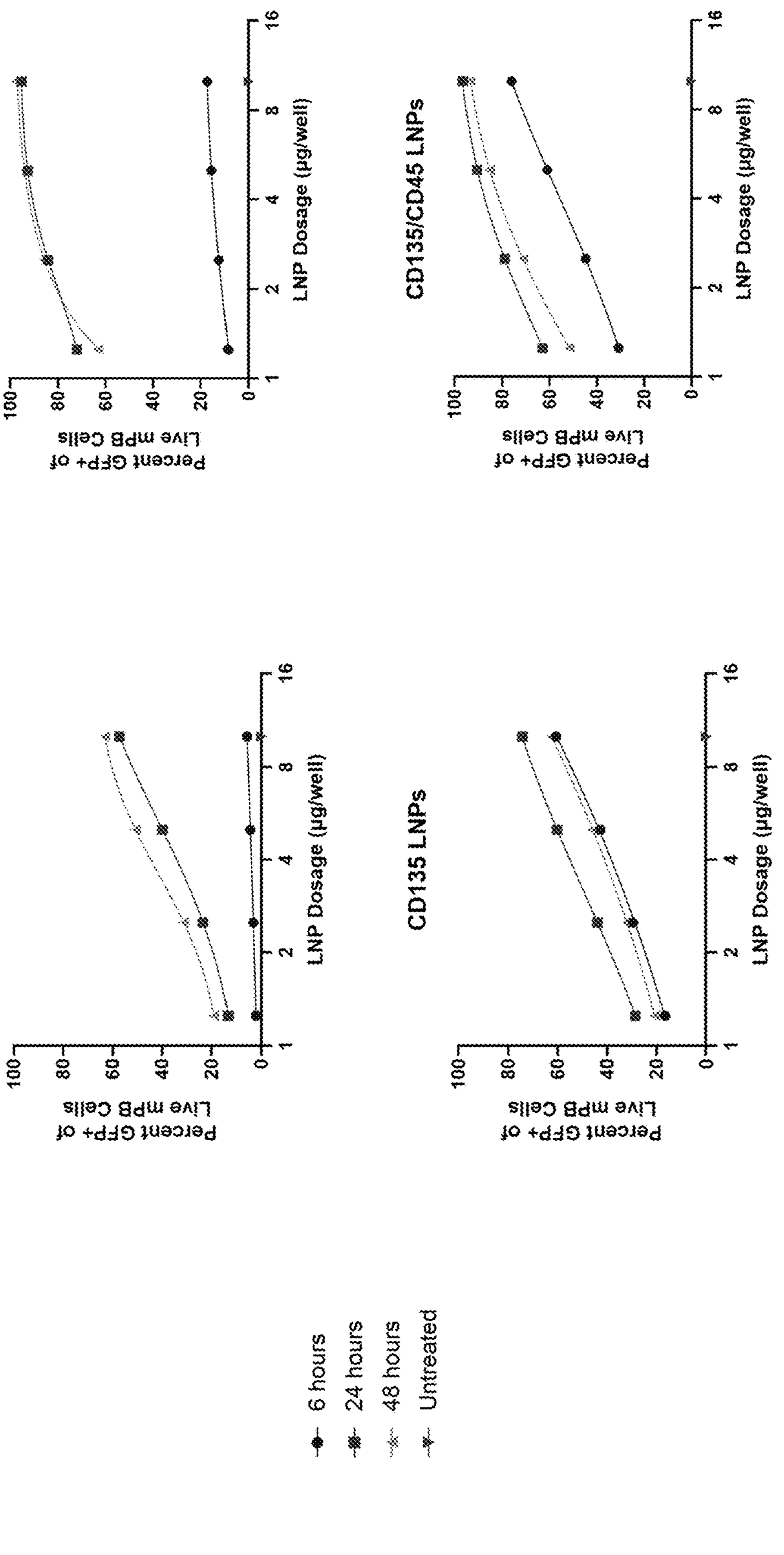
FIG. 61 shows graphs of GFP expression, as measured by percentage of GFP positive live cells, for each of the different bispecific or LNPs, as compared to LNPs targeting to CD45, CD117, or CD135 alone, at different time points and LNP dosages.
Figure 62:
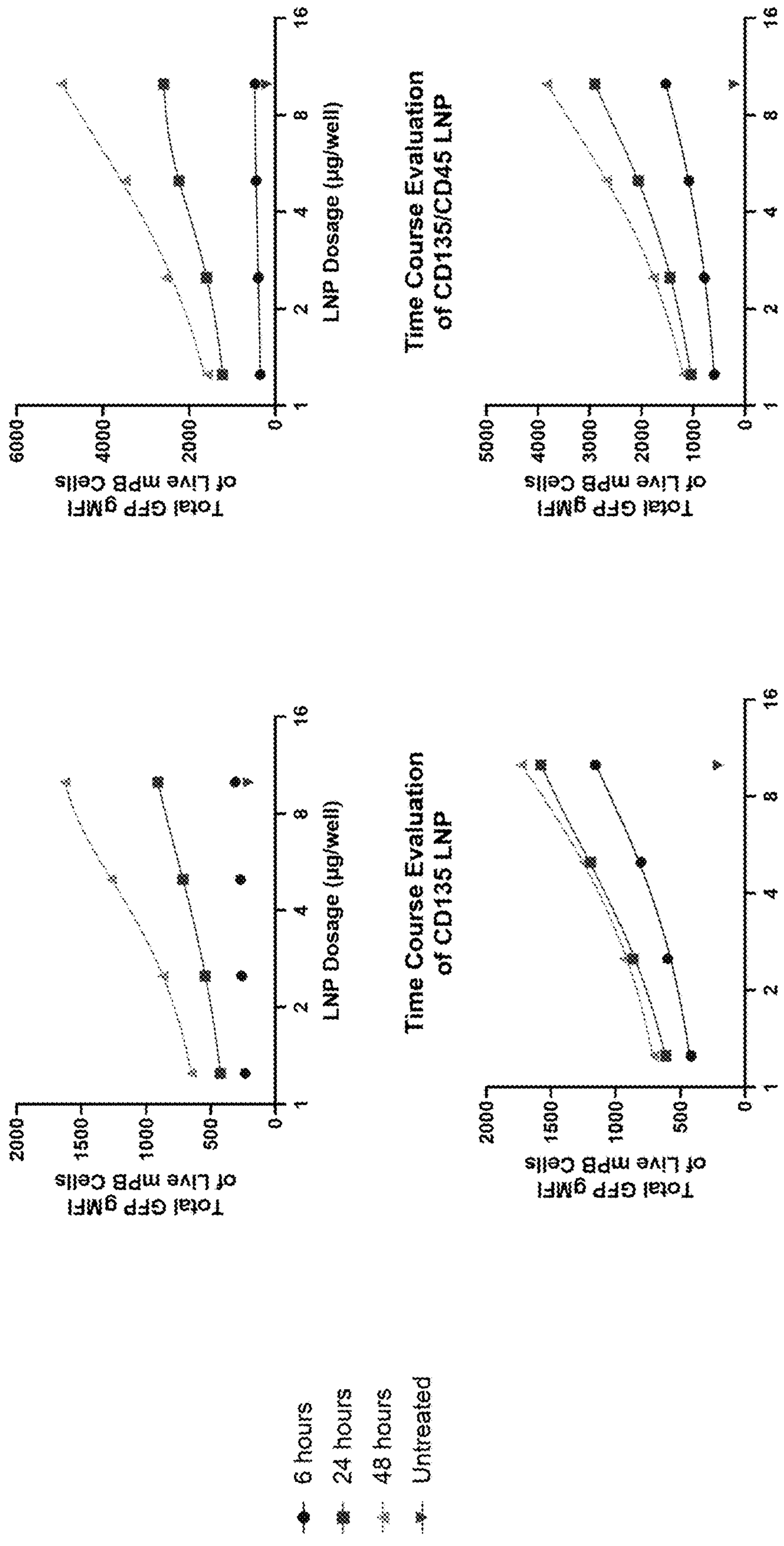
FIG. 62 shows graphs of GFP expression, as measured by total GFP gMFI, for each of the different bispecific or LNPs, as compared to LNPs targeting to CD45, CD117, or CD135 alone, at different time points and LNP dosages.
Figure 63:
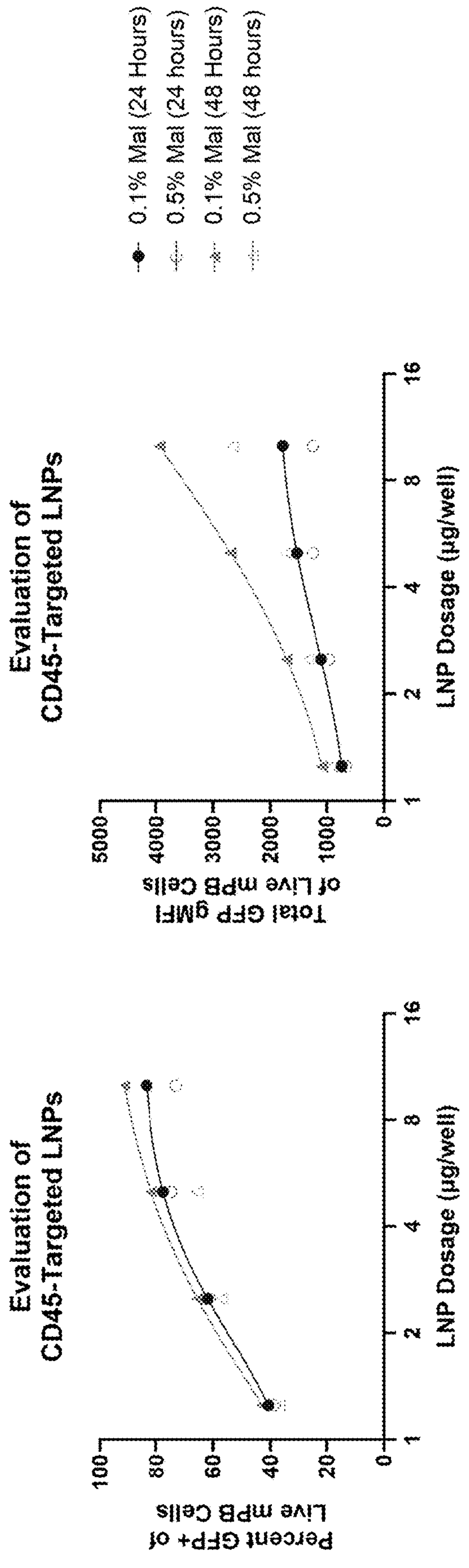
FIG. 63 shows an evaluation of CD45-targeted LNPs with different percentages of maleimide (0.1% vs 0.5%).

Results:

As shown in FIG. 59, bispecific LNPs targeted to two different antigens (CD117/CD45 or CD135/CD45) generally showed the highest GFP expression, as measured by the percentage of live GFP positive live cells, across all three time points (6 hours, 24 hours, and 48 hours). CD135/CD45 LNPs showed the highest expression at the earliest time point, while CD117/CD45 LNPs showed the best expression at later time point. As shown in FIG. 60, bispecific LNPs also showed the highest GFP expression, as measured by the total GFP gMFI (geometric mean fluorescence) of live cells, consistent with the results shown in FIG. 59. CD117/CD45 LNPs showed the highest expression for the later time points, while CD45/CD135 showed the highest expression for the earlier time point. FIG. 61 shows GFP expression, as measured by percentage of GFP positive live cells, for each of the different LNPs at different time points and LNP dosages. FIG. 62 shows GFP expression, as measured by total GFP gMFI, for each of the different LNPs at different time points and LNP dosages. FIG. 63 shows an evaluation of CD45-targeted LNPs with different percentages of maleimide (0.1% vs 0.5%). While CD45-targeted LNPs showed similar GFP positivity (percentage of GFP positive live cells) (left), LNPs with 0.1% maleimide showed a higher level of GFP expression (total GFP gMFI) (right).

The above results demonstrate that conjugation of two different ligands to the same LNP results in increased cell targeting and expression, as compared to LNPs conjugated to only a single ligand. Without being bound by theory, the improved targeting may be due to differing properties of the targeted cell-surface antigens. CD45 is more abundant on HSPCs and HSCs than CD117 and CD135, but CD117 and CD135 have faster internalization kinetics than CD45. Combining ligands that bind to both CD45 and CD117 or CD135 on a single LNP surprisingly confers the advantages of both ligands to provide improved cargo expression in target cells.

REFERENCES

All publications and references, including but not limited to patents and patent applications, cited in this specification and Examples herein are incorporated by reference in their entirety as if each individual publication or reference were specifically and individually indicated to be incorporated by reference herein as being fully set forth. Any patent application to which this application claims priority is also incorporated by reference herein in the manner described above for publications and references.

INFORMAL SEQUENCE LISTING

| SEQ ID NO | Name | Sequence |
|---|---|---|
| 1 | | MKVEQAVETEPEPELRQQTEWQSGQRWELALGRFWDYLRWVQTLSEQ VQEELLSSQVTQELRALMDETMKELKAYKSELEEQLTPVAEETRARLS KELQAAQARLGADMEDVCGRLVQYRGEVQAMLGQSTEELRVRLASHL RKLRKRLLRDADDLQKRLAVYQAGAREGAERGLSAIRERLGPLVEQGR VR |
| 2 | | MKVEQAVETEPEPELRQQTEWQSGQRWELALGRFWDYLRWVQTLSEQ VQEELLSSQVTQELRALMDETMKELKAYKSELEEQLTPVAEETRARLS KELQAAQARLGADMEDVCGRLVQYRGEVQAMLGQSTEELRVRLASHL RKLRKRLLRDADDLQKRLAVYQAGAREGAERGLSAIRERLGPLVEQGR VRHHHHHH |

-continued

| SEQ ID NO | Name | Sequence |
|---|---|---|
| 3 | | MKVEQAVETEPEPELRQQTEWQSGQRWELALGRFWDYLRWVQTLSEQ VQEELLSSQVTQELRALMDETMKELKAYKSELEEQLTPVAEETRARLS KELQAAQARLGADMEDVSGRLVQYRGEVQAMLGQSTEELRVRLASHL RKLRKRLLRDADDLQKRLAVYQAGAREGAERGLSAIRERLGPLVEQGR VR |
| 4 | | MKVEQAVETEPEPELRQQTEWQSGQRWELALGRFWDYLRWVQTLSEQ VQEELLSSQVTQELRALMDETMKELKAYKSELEEQLTPVAEETRARLS KELQAAQARLGADMEDVSGRLVQYRGEVQAMLGQSTEELRVRLASHL RKLRKRLLRDADDLQKRLAVYQAGAREGAERGLSAIRERLGPLVEQGR VRHHHHHHGGSSGSGC |
| 5 | | (Gly-Gly-Gly-Ser)n, where n is a positive integer equal to or greater than 1 |
| 6 | | (Gly4 Ser)4 |
| 7 | | (Gly4 Ser)3 |
| 8 | | GCGCGCTCGCTCGCTC |
| 9 | | CCAAGCTCTTCN |
| 10 | | GGGGSGGGGS |
| 11 | L80 CD117 VH | QVQLKQSGAELVRPGASVKLSCKASGYTFTDYYINWVKQRPGQGLEWIAR IYPGSGNTYYNEKFKGKATLTAEKSSSTAYMQLSSLTSEDSAVYFCARGVY YFDYWGQGTTLTVSS |
| 12 | L80 CD117 VL | DIVMTQSQKFMSTSVGDRVSVTCKASQNVRTNVAWYQQKPGQSPKALIYS ASYRYSGVPDRFTGSGSGTDFTLTISNVQSEDLADYFCQQYNSYPRTFGGGT KLEIKR |
| 13 | L95 CD117 Full scFv | QVQLVQSGAEVKKPGSSVKVSCKASGGTFSSYAISWVRQAPGQGLEWMGG IIPMSGRTTYAQKFQGRVTITADESTSTAYMELSSLRSEDTAVYYCARDYGPE APDYGQSTSYFWYYAFDPWGQGTLVTVSSGGGGSGGGGSGGGGSGGGGDIE LTQPPSVSVSPGQTASITCSGDNIPSYFVHWYQQKPGQAPVLVIYDDNDRPSGI PERFSGSNSGNTATLTISGTQAEDEADYYCSSWDQDTVVFGGGTKLTVLGGG GSGGGGSDYKDDDDKGGGGSC |
| 14 | L95 CD117 VH | QVQLVQSGAEVKKPGSSVKVSCKASGGTFSSYAISWVRQAPGQGLEWMGGII PMSGRTTYAQKFQGRVTITADESTSTAYMELSSLRSEDTAVYYCARDYGPEAP DYGQSTSYFWYYAFDPWGQGTLVTVSS |
| 15 | L95 CD45 VL | DIELTQPPSVSVSPGQTASITCSGDNIPSYFVHWYQQKPGQAPVLVIYDDNDR PSGIPERFSGSNSGNTATLTISGTQAEDEADYYCSSWDQDTVVFGGGTKLTVL |
| 16 | L111 scFv w/ C | DIQMTQSPSFLSASVGDRVTINCKASQNINKYLDWYQQKHGEAPKLLIHYTN NLHTGIPSRFSGSGSGTDYTLTISSLQPEDVATYFCLQHSSRWTFGGGTKLELK GGGGSGGGGSGGGGSGGGGEVQLVESGGDLVQPGRSLKLSCIASGFTFTNFW MTWIRQVSGKGLEWVASISSSGGSIYYPDSVKDRFTISRDNAKNTLYLQMNSL RSEDTATYYCVKLHYYSGGGDAWGQGTSVTVSSGGGGSGGGGSDYKDDDDK GGGGSC |
| 17 | L111 CD45 VH | EVQLVESGGDLVQPGRSLKLSCIASGFTFTNFWMTWIRQVSGKGLEWVASISSS GGSIYYPDSVKDRFTISRDNAKNTLYLQMNSLRSEDTATYYCVKLHYYSGGGD AWGQGTSVTVSS |
| 18 | L111 CD45 VL | DIQMTQSPSFLSASVGDRVTINCKASQNINKYLDWYQQKHGEAPKLLIHYTNN LHTGIPSRFSGSGSGTDYTLTISSLQPEDVATYFCLQHSSRWTFGGGTKLELK |
| 19 | L112 CD45 scFv | EVQLVESGGDLVQPGRSLKLSCVASGFTFNNYWMTWIRQVPGKGLEWVASI SSSGGSIYYPDSVKDRFTISRDNAKNTLFLQMNSLRSEDTATYYCARLYYYS GGGDAWGQGTSVTVSSGGGGSGGGGSGGGGSGGGGDIQMTQSPSFLSASVG DRVTIICKASQDINKYLDWYQQKLGEAPKLLIYNTNNLHTGIPSRFSGSGSGT DYTLTISSLQPEDVATYFCLQHISRWTFGGGTKLELKGGGGSGGGGSDYKDD DDKGGGGSC |
| 20 | L112 CD45 VH | EVQLVESGGDLVQPGRSLKLSCVASGFTFNNYWMTWIRQVPGKGLEWVAS ISSSGGSIYYPDSVKDRFTISRDNAKNTLFLQMNSLRSEDTATYYCARLYYY SGGGDAWGQGTSVTVSS |

-continued

| SEQ ID NO | Name | Sequence |
|---|---|---|
| 21 | L112 CD45 VL | DIQMTQSPSFLSASVGDRVTIICKASQDINKYLDWYQQKLGEAPKLLIYNTN NLHTGIPSRFSGSGSGTDYTLTISSLQPEDVATYFCLQHISRWTFGGGTKLELK |
| 22 | L122 CD45 scFv | EVKLLESGGGLVQPGGSLKLSCAASGFDFSRYWMSWVRQAPGKGLEWIGEIN PTSSTINFTPSLKDKVFISRDNAKNTLYLQMSKVRSEDTALYYCARGNYYRYG DAMDYWGQGTSVTVSSAKGGGGSGGGGSGGGGSGGGGSDIALTQSPASLAV SLGQRATISCRASKSVSTSGYSYLHWYQQKPGQPPKLLIYLASNLESGVPARFS GSGSGTDFTLNIHPVEEEDAATYYCQHSRELPFTFGSGTKLEIKGGGGSGGGGS DYKDDDDKGGGGSC |
| 23 | L122 CD45 VH | EVKLLESGGGLVQPGGSLKLSCAASGFDFSRYWMSWVRQAPGKGLEWIGEIN PTSSTINFTPSLKDKVFISRDNAKNTLYLQMSKVRSEDTALYYCARGNYYRYGD AMDYWGQGTSVTVSSAK |
| 24 | L122 CD45 VL | DIALTQSPASLAVSLGQRATISCRASKSVSTSGYSYLHWYQQKPGQPPKLLIY LASNLESGVPARFSGSGSGTDFTLNIHPVEEEDAATYYCQHSRELPFTFGSGTK LEIK |
| 25 | L81 CD117 scFv w C | QVQLKQSGAELVRPGASVKLSCKASGYTFTDYYINWVKQRPGQGLEWIARIY PGSGNTYYNEKFKGKATLTAEKSSSTAYMQLSSLTSEDSAVYFCARGVYYFD YWGQGTTLTVSSGGGGSGGGGSGGGGSGGGGDIVMTQSQKFMSTSVGDRVS VTCKASQNVRTNVAWYQQKPGQSPKALIYSASYRYSGVPDRFTGSGSGTDFT LTISNVQSEDLADYFCQQYNSYPRTFGGGTKLEIKRGGGGSGGGGSDYKDDDD KGGGGSC |
| 26 | L81 CD117 VH | QVQLKQSGAELVRPGASVKLSCKASGYTFTDYYINWVKQRPGQGLEWIARIY PGSGNTYYNEKFKGKATLTAEKSSSTAYMQLSSLTSEDSAVYFCARGVYYFDY WGQGTTLTVSS |
| 27 | L81 CD117 VL | DIVMTQSQKFMSTSVGDRVSVTCKASQNVRTNVAWYQQKPGQSPKALIYSAS YRYSGVPDRFTGSGSGTDFTLTISNVQSEDLADYFCQQYNSYPRTFGGGTKL EIKR |
| 28 | L86 CD45 scFv w C | DIQMTQSPSSLSASVGDRVTITCRSSQGIRSDLGWYQQKPGKAPKLLIYDASN LETGVPSRFSGSGSGTDFTLTISSLQPEDFATYYCQQANGFPLTFGGGTKVEIK GGGGSGGGGSGGGGSGGGGSEVQLVQSGAEVKKPGESLKISCKGSGYSFTN YWIGWVRQMPGKGLEWMAIINPRDSDTRYRPSFQGQVTISADKSISTAYLQW SSLKASDTAMYYCARHGRGYEGYEGAFDIWGQGTLVTVSSGGGGSGGGGSD YKDDDDKGGGGSC |
| 29 | L86 CD45 VH | EVQLVQSGAEVKKPGESLKISCKGSGYSFTNYWIGWVRQMPGKGLEWMAIIN PRDSDTRYRPSFQGQVTISADKSISTAYLQWSSLKASDTAMYYCARHGRGYE GYEGAFDIWGQGTLVTVSS |
| 30 | L86 CD45 VL | DIQMTQSPSSLSASVGDRVTITCRSSQGIRSDLGWYQQKPGKAPKLLIYDASNL ETGVPSRFSGSGSGTDFTLTISSLQPEDFATYYCQQANGFPLTFGGGTKVEIK |
| 31 | L88 CD117 scFv w C | DIQMTQSPSSLSASVGDRVTITCRASQGIGSALAWYQQKPGKAPKLLIYDASNL ETGVPSRFSGSGSGTDFTLTISSLQPEDFATYYCQQLNGYPLTFGQGTRLEIKG GGGSGGGGSGGGGSGGGGSEVQLVQSGAEVKKPGESLKISCKGSGYRFTTSWI GWVRQMPGKGLEWMGIIYPGDSDTRYSPSFQGQVTISADKSISTAYLQWSSLK ASDTAMYYCARHGLGYNGYEGAFDIWGQGTLVTVSSGGGGSGGGGSDYKDD DDKGGGGSC |
| 32 | L88 CD117 VH | EVQLVQSGAEVKKPGESLKISCKGSGYRFTTSWIGWVRQMPGKGLEWMGIIYP GDSDTRYSPSFQGQVTISADKSISTAYLQWSSLKASDTAMYYCARHGLGYNGY EGAFDIWGQGTLVTVSS |
| 33 | L88 CD117 VL | DIQMTQSPSSLSASVGDRVTITCRASQGIGSALAWYQQKPGKAPKLLIYDASNL ETGVPSRFSGSGSGTDFTLTISSLQPEDFATYYCQQLNGYPLTFGQGTRLEIK |

What is claimed is:

1. A stealth lipid nanoparticle (LNP) comprising:

(a) a therapeutic nucleic acid (TNA);

(b) an ionizable lipid;

(c) a sterol;

(d) a first lipid-anchored polymer comprising a first hydrophilic polymer and a first lipid-linker, wherein the first lipid-linker comprises a first lipid comprising at least two hydrophobic tails, and wherein each hydrophobic tail comprises a carbon chain having 18 carbon atoms ($C_{18}$);

(e) a second lipid-anchored polymer comprising a second hydrophilic polymer, a second lipid-linker, and a first reactive moiety conjugated to a first targeting moiety; wherein the second lipid-linker comprises a second lipid comprising at least two hydrophobic tails, wherein each hydrophobic tail comprises a carbon chain having 18 carbon atoms ($C_{18}$); and wherein the targeting moiety is a variable heavy chain-only antibody (VHH) or a single-chain antibody (scFv); and (f) a third lipid-anchored polymer comprising a third hydrophilic polymer, a third lipid-linker, and a second reactive moiety conjugated to a second targeting moiety; wherein the third lipid-linker comprises a third lipid comprising at least two hydrophobic tails, wherein each hydrophobic tail comprises a carbon chain having 18 carbon atoms ($C_{18}$); and wherein the second targeting moiety is a variable heavy chain-only antibody (VHH) or a single-chain antibody (scFv);

wherein the first targeting moiety and the second targeting moiety are different;

wherein the first targeting moiety and the second targeting moiety are each cell-type specific targeting moieties, wherein the cell-type is a hematopoietic stem cell (HSC), wherein the molecular weight of each of the second and third hydrophilic polymers is greater than the molecular weight of the first hydrophilic polymer;

wherein the first lipid-anchored polymer, the second lipid-anchored polymer, and the third lipid-anchored polymer are present at a combined molar percentage of about 2% to about 5%, and wherein the second lipid-anchored polymer and the third lipid-anchored polymer are present at a combined molar percentage of about 0.01% to about 0.5%; optionally wherein the stealth LNP comprises about 5 to 400 total targeting moieties.

2. The stealth LNP of claim 1, wherein the first hydrophilic polymer, the second hydrophilic polymer, and the third hydrophilic polymer are each independently.

3. The stealth LNP of claim 1, wherein the first hydrophilic polymer, the second hydrophilic polymer, and the third hydrophilic polymer are each independently polyethylene glycol (PEG).

4. The stealth LNP of claim 3, wherein:

each PEG is independently selected from the group consisting of PEG5000, PEG2000, PEG2000-OMe, PEG3000, PEG3000-OMe, PEG3400, PEG3400-OMe, and PEG5000-OMe;

the second and third hydrophilic polymers are PEG5000; and/or the first hydrophilic polymer is PEG2000.

5. The stealth LNP of claim 1, wherein:

the first hydrophilic polymer, the second hydrophilic polymer, and the third hydrophilic polymer are the same; or the second and third hydrophilic polymers are the same, and wherein the first hydrophilic polymer is different from the second and third hydrophilic polymers.

6. The stealth LNP of claim 1, wherein;

the second and third lipid-anchored polymers are present at a combined molar percentage of about 0.01% to about 0.3%;

the second and third lipid-anchored polymers are present at a combined molar percentage of about 0.05% to about 0.2%;

the second and third lipid-anchored polymers are present at a combined molar percentage of about 0.05% to about 0.1%;

the second and third lipid-anchored polymers are present at a combined molar percentage of about 0.08%;

the second and third lipid-anchored polymers are present at a combined molar percentage of about 0.08%;

the second and third lipid-anchored polymers are present at a combined molar percentage of about 0.1%;

the second and third lipid-anchored polymers are present at a combined molar percentage of about 0.2%;

the second and third lipid-anchored polymers are present at a combined molar percentage of about 0.3%;

the second and third lipid-anchored polymers are present at a combined molar percentage of about 0.4%;

the second and third lipid-anchored polymer are present at a combined molar percentage of about 0.5%;

the first, second, and third lipid-anchored polymers are present at a combined molar percentage of about 3%;

the first lipid-anchored polymer is present at a molar percentage of about 2% to about 3%; and/or the first lipid-anchored polymer is present at a molar percentage of about 2.5%.

7. The stealth LNP of claim 1, wherein;

the second and third lipid-linkers are the same;

the second and third lipid-linkers are the same, and the first lipid-linker is different from the second and third lipid-linkers; or the first, second, and third lipid-linkers are the same.

8. The stealth LNP of claim 1, wherein;

the first, second, and third lipid-linkers are each independently selected from the group consisting of 1,2-distearoyl-sn-glycero-3-phosphoethanolamine (DSPE), distearoyl-rac-glycerol (DSG), 1,2-dielaidoyl-sn-phosphatidylethanolamine (DEPE), 1-stearoyl-2-oleoyl-sn-glycero-3-phosphoethanolamine (SOPE), 1,2-dioleoyl-sn-glycero-3-phosphoglycerol (DOPG), 1,2-dielaidoyl-sn-glycero-3-phosphoethanolamine (18-1-trans PE), 1,2-dioleoyl-sn-glycero-3-phospho-L-serine (DOPS), dioctadecylamine (DODA), 1,2-dioleoyl-sn-glycero-3-phosphoethanolamine (DOPE), and combinations thereof; or the first, second, and third lipid-linkers are each independently selected from the group consisting of DSPE, DSG, DEPE, SOPE, DOPG, 18-1-trans PE, DOPS, DODA, DOPE, and combinations thereof.

9. The stealth LNP of claim 1, wherein the molecular weight of each of the second and third hydrophilic polymers is at least about 10%, 15%, 20%, 25%, 30%, 35%, 40%, 45%, 47%, 50%, 55%, 60%, 65%, 70%, 75%, 80%, 85%, 90%, 95%, 100%, 110%, 120%, 130%, 140%, 150%, 160%, 170%, 180%, 190%, 200% or more greater than the molecular weight of the first hydrophilic polymer.

10. The stealth LNP of claim 1, wherein;

the molecular weight of the first hydrophilic polymer is about 2000 Daltons (Da) to about 3400 Da; and/or the molecular weight of each of the second and third hydrophilic polymers is about 3400 Da to about 7000 Da.

11. The stealth LNP of claim 1, wherein each of the first targeting moiety and the second targeting moiety binds to a different HSC specific antigen.

12. The stealth LNP of claim 1, wherein;

each of the first and second targeting moieties independently binds to an antigen selected from the group consisting of CD45, CD46, CD135, CD90, CD117, CD133, ADAM8, ADAM28, ADGRE2, ASCT1, ASCT2, CALHN2, CD33, CD34, CD37, CD43, CD44, CD49f, CD71, CD79A, CD79B, CD84, CD105, CD110, CD123, CD126, CD131, CD133, CD146, CD164, CD184, CD244, CD300f, CD300LF, CD370, CSF3R, CSMD2, EFNA3, EPHB2, FASLG, GPI-80, GPR183, IGSF8, ITGA3, LAIR1, LILRA2, PTAFR, SELL, SLC2A5, TNFRSF8, and VCAM1;

at least one of the first and second targeting moieties binds to an antigen selected from the group consisting of CD45, CD117, and CD135;

the first targeting moiety binds to CD45;

the first targeting moiety binds CD45, and the second targeting moiety binds to CD117; and/or the first targeting moiety binds CD45, and the second targeting moiety binds to CD135.

13. The stealth LNP of claim 1, wherein the stealth LNP comprises a total of at least 5 targeting moieties, at least 10 targeting moieties, at least 15 targeting moieties, at least 20 targeting moieties, at least 25 targeting moieties, at least 30 targeting moieties, at least 35 targeting moieties, at least 40 targeting moieties, at least 42 targeting moieties, at least 45 targeting moieties, at least 50 targeting moieties, at least 52 targeting moieties, at least 55 targeting moieties, at least 60 targeting moieties, at least 65 targeting moieties, at least 70 targeting moieties, at least 75 targeting moieties, at least 80 targeting moieties, at least 84 targeting moieties, at least 85 targeting moieties, at least 90 targeting moieties, at least 95 targeting moieties, at least 100 targeting moieties, at least 104 targeting moieties, at least 110 targeting moieties, at least 120 targeting moieties, at least 124 targeting moieties, at least 126 targeting moieties, at least 130 targeting moieties, at least 140 targeting moieties, at least 150 targeting moieties, at least 156 targeting moieties, at least 160 targeting moieties, at least 168 targeting moieties, at least 170 targeting moieties, at least 180 targeting moieties, at least 190 targeting moieties, at least 200 targeting moieties, at least 208 targeting moieties, at least 210 targeting moieties, at least 220 targeting moieties, at least 230 targeting moieties, at least 240 targeting moieties, at least 250 targeting moieties, at least 260 targeting moieties, at least 270 targeting moieties, at least 280 targeting moieties, at least 290 targeting moieties, at least 300 targeting moieties, at least 310 targeting moieties, at least 320 targeting moieties, at least 330 targeting moieties, at least 340 targeting moieties, at least 350 targeting moieties, at least 360 targeting moieties, at least 370 targeting moieties, at least 380 targeting moieties, at least 390 targeting moieties, or at least 400 targeting moieties per LNP.

14. The stealth LNP of claim 1, wherein:

each targeting moiety is a VHH; or each targeting moiety is an scFv.

15. The stealth LNP of claim 14, wherein the stealth LNP comprises a total of about 20-400 VHH targeting moieties, about 30-350 VHH targeting moieties, about 40-300 VHH targeting moieties, about 50-250 VHH targeting moieties, or about 52-210 VHH targeting moieties per LNP.

16. The stealth LNP of claim 14, wherein the stealth LNP comprises a total of about 60-250 scFv targeting moieties, about 70-200 scFv targeting moieties, about 80-150 scFv targeting moieties, or about 84-125 scFv targeting moieties per LNP.

17. The stealth LNP of claim 1, wherein;

the first and second targeting moieties are present at a combined molar percentage of about 0.001% to about 0.1%;

the first and second targeting moieties are present at a combined molar percentage of about 0.1% of total lipid; or the first and second targeting moieties are present at a combined molar percentage of about 20% of the combined molar percentage of second and third lipid-anchored polymers.

18. The stealth LNP of claim 1, wherein the sterol is selected from the group consisting of cholesterol, beta-sitosterol, stigmasterol, beta-sitostanol, campesterol, brassicasterol, and combinations thereof.

19. The stealth LNP of claim 1, wherein:

the sterol is present at a molar percentage of about 35% to about 40%;

the sterol is present at a molar percentage of about 37% to about 40%; or the sterol is present at a molar percentage of about 39% to about 40%.

20. The stealth LNP of claim 1, wherein:

the ionizable lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), DLin-MC3-DMA, N-[1-(2,3-dioleyloxy) propyl]-N,N,N-trimethylammonium chloride (DOTMA), N-[1-(2,3-dioleoyloxy) propyl]-N,N,N-trimethylammonium chloride (DOTAP), 1,2-dioleoyl-sn-glycero-3-ethylphosphocholine (DOEPC), 1,2-dilauroyl-sn-glycero-3-ethylphosphocholine (DLEPC), 1,2-dimyristoyl-sn-glycero-3-ethylphosphocholine (DMEPC), 1,2-dimyristoleoyl-sn-glycero-3-ethylphosphocholine (14:1), N1-[2-((1S)-1-[(3-aminopropyl)amino]-4-[di(3-amino-propyl) aminolbutylcarboxamidoiethyl]-3,4-di[oleyloxy]-benzamide (MVL5), Dioctadecylamido-glycylspermine (DOGS), 3b-[N-(N',N'-dimethylaminoethyl) carbamoyl] cholesterol (DC-Chol), Dioctadecyldimethylammonium Bromide (DDAB), a Saint lipid, SAINT-2, N-methyl-4-(dioleyl)methylpyridinium), 1,2-dimyristyloxypropyl-3-dimethylhydroxyethylammonium bromide (DMRIE), 1,2-dioleoyl-3-dimethyl-hydroxyethyl ammonium bromide (DORIE), 1,2-dioleoyloxypropyl-3-dimethylhydroxyethyl ammonium chloride (DORI), Di-alkylated Amino Acid (DILA2), C18: 1-norArg-C16), Dioleyldimethylammonium chloride (DODAC), 1-palmitoyl-2-oleoyl-sn-glycero-3-ethylphosphocholine (POEPC), 1,2-dimyristoleoyl-sn-glycero-3-ethylphosphocholine (MOEPC), Dioctadecyldimethylammonium bromide (DDAB), 1,2-dilinoleyloxy-3-dimethylaminopropane (DLinDMA), 2,2-dilinoleyl-4-(2-dimethylaminoethyl)-[1,3]-dioxolane (DLin-KC2-DMA), heptatriaconta-6,9,28,31-tetraen-19-yl-4-(dimethylamino) butanoate (DLin-MC3-DMA), 1,2-Dioleoyloxy-3-dimethylaminopropane (DODAP), 1,2-Dioleyloxy-3-dimethylaminopropane (DODMA), Morpholinocholesterol (Mo-CHOL), (R)-5-(dimethylamino) pentane-1,2-diyl dioleate hydrochloride (DODAPen-C1), (R)-5-guanidinopentane-1,2-diyl dioleate hydrochloride (DOPen-G), and (R)-N,N,N-trimethyl-4,5-bis (oleoyloxy) pentan-1-aminium chloride (DOTAPen), SMA102, L369, L319, LP01, SS-cleavable lipid, and combinations and mixtures thereof;

the ionizable lipid is selected from the group consisting of the lipids set forth in Table 6, or a pharmaceutically acceptable salt thereof, or;

the ionizable lipid comprises Lipid No. 87 or a pharmaceutically acceptable salt or ester thereof, or a deuterated analogue thereof, or

LIPID 87

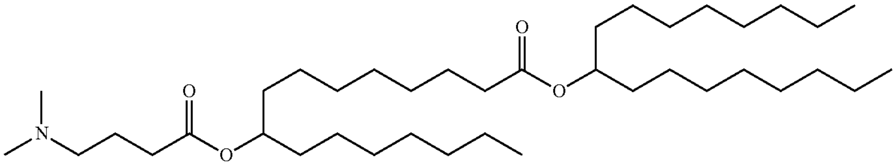 [SMILES: CCCCCCCCC(CCCCCCCC)OC(=O)CCCCCCCC(CCCCCCC)OC(=O)CCCN(C)C]

heptadecan-9-yl 9-((4-(dimethylamino)butanoyl)oxy)hexadecanoate; or the ionizable lipid comprises Lipid No. 119 or a pharmaceutically acceptable salt or ester thereof, or a deuterated analogue thereof, or

LIPID 119

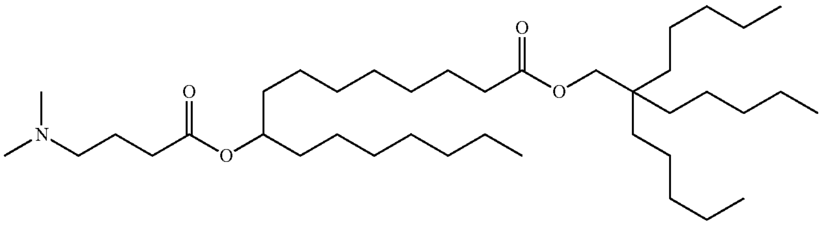 [SMILES: CCCCCCCC(CCCCCCCC(=O)OCC(CCCCC)(CCCCC)CCCCC)OC(=O)CCCN(C)C]

2,2-dipentylheptyl 9-((4-(dimethylamino)butanoyl)oxy) hexadecanoate.

21. The stealth LNP of claim 1, wherein the ionizable lipid is present at a molar percentage of about 40% to about 50%, or wherein the ionizable lipid is present at a molar percentage of about 45% to about 50%.

22. The stealth LNP of claim 1, further comprising a helper lipid.

23. The stealth LNP of claim 22, wherein:

the helper lipid is distearoylphosphatidylcholine (DSPC);

the helper lipid is selected from the group consisting of distearoyl-sn-glycero-phosphoethanolamine (DSPE), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoylo-leoylphosphatidylcholine (POPC), palmitoylo-leoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), monomethyl-phosphatidylethanolamine, dimethyl-phosphatidylethanolamine, 18-1-trans PE, 1-stearoyl-2-oleoyl-phosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoyl phosphatidylcholine (DMPC), dimyristoyl phosphatidylglycerol (DMPG), distearoylphosphatidylglycerol (DSPG), dierucoylphosphatidylcholine (DEPC), palmitoyloleyol-phosphatidylglycerol (POPG), dielaidoyl-phosphatidy-lethanolamine (DEPE), 1,2-dilauroyl-sn-glycero-3-phosphoethanolamine (DLPE); 1,2-diphytanoyl-sn-glycero-3-phosphoethanolamine (DPHyPE); lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidicacid, cerebrosides, dicetylphosphate, lysophosphatidylcholine, dilinoleoylphosphatidylcholine, DODA, ceramide, and combinations thereof; and/or the helper lipid is present at a molar percentage of about 10%.

24. The stealth LNP of claim 1, wherein;

the first and second reactive moieties are each independently selected from the group consisting of maleimide, thiol, azide, click chemistry reagent, and combinations thereof;

the first and second reactive moieties are both maleimide or both thiol;

the first reactive moiety is maleimide or thiol and the second reactive moiety is azide or DBCO;

the first and second reactive moieties are both azide, and wherein the third and fourth reactive moieties are both DBCO;

the first and second reactive moieties are both DBCO, and wherein the third and fourth reactive moieties are both azide; and/or neither of the first nor second reactive moiety is azide or DBCO.

25. The stealth LNP of claim 1, wherein the stealth LNP is present in an LNP composition comprising a plurality of LNPs having an average diameter of about 40 nm to about 120 nm.

26. The stealth LNP of claim 1, wherein the TNA encodes a therapeutic protein.

27. The stealth LNP of claim 1, wherein the TNA is selected from the group consisting of an mRNA, an siRNA, a synthetic ribozyme, an antisense RNA, and a gRNA.

28. The stealth LNP of claim 1, wherein the LNP has a half-life ($t_{1/2}$) in blood in vivo is between about 3 hours and about 48 hours or between about 4 hours and 48 hours.

29. A cell comprising the stealth LNP of claim 1, wherein the cell is a hematopoietic stem cell (HSC).

30. A pharmaceutical composition comprising the stealth LNP of claim 1.

* * * * *